US009988627B2

(12) United States Patent
Baryza et al.

(10) Patent No.: US 9,988,627 B2
(45) Date of Patent: Jun. 5, 2018

(54) FORMATS FOR ORGANIC COMPOUNDS FOR USE IN RNA INTERFERENCE

(71) Applicants: Jeremy Lee Baryza, Cambridge, MA (US); Marcel Blommers, Basel (CH); William Chutkow, Cambridge, MA (US); Cesar Fernandez, Basel (CH); Erin Geno, Cambridge, MA (US); Alvar Gossert, Basel (CH); Paulette Greenidge, Basel (CH); Dieter Huesken, Basel (CH); Juerg Hunziker, Basel (CH); Francois Jean-Charles Natt, Basel (CH); Anup Patnaik, Cambridge, MA (US); Andrew Patterson, Cambridge, MA (US); Jean-Michel Rene Rondeau, Basel (CH); Jan Weiler, Cambridge, MA (US); Meicheng Zhu, Cambridge, MA (US)

(72) Inventors: Jeremy Lee Baryza, Cambridge, MA (US); Marcel Blommers, Basel (CH); William Chutkow, Cambridge, MA (US); Cesar Fernandez, Basel (CH); Erin Geno, Cambridge, MA (US); Alvar Gossert, Basel (CH); Paulette Greenidge, Basel (CH); Dieter Huesken, Basel (CH); Juerg Hunziker, Basel (CH); Francois Jean-Charles Natt, Basel (CH); Anup Patnaik, Cambridge, MA (US); Andrew Patterson, Cambridge, MA (US); Jean-Michel Rene Rondeau, Basel (CH); Jan Weiler, Cambridge, MA (US); Meicheng Zhu, Cambridge, MA (US)

(73) Assignee: NOVARTIS AG, Basel (CH)

( * ) Notice: Subject to any disclaimer, the term of this patent is extended or adjusted under 35 U.S.C. 154(b) by 0 days. days.

(21) Appl. No.: 15/025,826

(22) PCT Filed: Oct. 6, 2014

(86) PCT No.: PCT/US2014/059301
§ 371 (c)(1),
(2) Date: Mar. 29, 2016

(87) PCT Pub. No.: WO2015/051366
PCT Pub. Date: Apr. 9, 2015

(65) Prior Publication Data
US 2016/0244756 A1 Aug. 25, 2016

Related U.S. Application Data

(60) Provisional application No. 61/886,748, filed on Oct. 4, 2013, provisional application No. 62/025,164, filed on Jul. 16, 2014.

(51) Int. Cl.
C12N 15/113 (2010.01)

(52) U.S. Cl.
CPC ........ C12N 15/113 (2013.01); C12N 2310/14 (2013.01); C12N 2310/317 (2013.01);
(Continued)

(58) Field of Classification Search
CPC .......... C12N 2310/14; C12N 2310/317; C12N 2310/321; C12N 2310/332
See application file for complete search history.

(56) References Cited

U.S. PATENT DOCUMENTS 3,687,808 A    8/1972  Merigan, Jr. et al.
4,469,863 A    9/1984  Ts'o et al.
(Continued)

FOREIGN PATENT DOCUMENTS

EP    1752536       2/2007
WO    1991/006309   5/1991
(Continued)

OTHER PUBLICATIONS

Bartel, D. P., "MicroRNAs: Target Recognition and Regulatory Functions," *Cell*, 136, (2009), pp. 215-233.
(Continued)

*Primary Examiner* — Brian A Whiteman
(74) *Attorney, Agent, or Firm* — Brinks Gilson & Lione

(57) ABSTRACT

The disclosure relates to compositions comprising a RNAi agent having a novel format including a spacer subunit. The disclosure relates to compositions comprising a RNAi agent having a novel format: an 18-mer format with at least one internal spacer. These RNAi agents comprise a first and a second 18-mer strand, wherein the first strand is 18 ribonucleotides or 18 total ribonucleotides and spacer subunit(s), and the second strand is 18 total ribonucleotides and spacer subunit(s), wherein: each spacer subunit consists of: (a) a phosphate or modified internucleoside linker and (b) a spacer; a spacer subunit can be at any position in the strand; the two strands form a duplex with at least one blunt end; and the 3 end of one or both strands terminates in a phosphate or modified internucleoside linker and further comprises, in 5 to 3 order: a second spacer; a second phosphate or modified internucleoside linker, and a 3 end cap. In various embodiments, the RNAi agents comprise a first and a second strand, wherein each strand is a 30-mer or shorter, the first strand comprises ribonucleotides, and the second strand comprises ribonucleotides and one or more spacer subunit(s), wherein: each spacer subunit consists of: (a) a phosphate or modified internucleoside linker and (b) a spacer; a spacer subunit can be at any position in the strand. In some embodiments, the 3 end of both strands further comprise, in 5 to 3 order: a second spacer; a second phosphate or modified internucleoside linker; and a 3 end cap. The two strands can have the same or different spacers, phosphates or modified internucleoside linkers, and/or 3 end
(Continued)

caps. The strands can be ribonucleotides, or, optionally, one or more nucleotide can be modified or substituted. Optionally, at least one nucleotide comprises a modified internucleoside linker. Optionally, the first two base-pairing nucleotides on the 3 end of the one or both strand are 2-MOE. Optionally, the RNAi agent can be modified on one or both 5 end. Optionally, the first or second strand is the sense strand, and the sense strand can comprise a 5 end cap which reduces the amount of the RNA interference mediated by this strand. Optionally, the RNAi agent is attached to a ligand. This format can be used to devise RNAi agents to a variety of different targets and sequences. The disclosure also relates to processes for making such compositions, and methods and uses of such compositions, e.g., to mediate RNA interference.

21 Claims, 33 Drawing Sheets

(52) U.S. Cl.
CPC .. *C12N 2310/321* (2013.01); *C12N 2310/322* (2013.01); *C12N 2310/332* (2013.01); *C12N 2310/341* (2013.01); *C12N 2310/351* (2013.01); *C12N 2310/3515* (2013.01)

(56) References Cited

U.S. PATENT DOCUMENTS

| | | | |
|---|---|---|---|
| 5,023,243 A | 6/1991 | Tullis | |
| 5,034,506 A | 7/1991 | Summerton et al. | |
| 5,134,066 A | 7/1992 | Rogers et al. | |
| 5,212,295 A | 5/1993 | Cook | |
| 5,214,134 A | 5/1993 | Weis et al. | |
| 5,216,141 A | 6/1993 | Benner | |
| 5,218,105 A | 6/1993 | Cook et al. | |
| 5,264,423 A | 11/1993 | Cohen et al. | |
| 5,264,562 A | 11/1993 | Matteucci | |
| 5,321,131 A | 6/1994 | Agrawal et al. | |
| 5,359,044 A | 10/1994 | Cook et al. | |
| 5,399,676 A | 3/1995 | Froehler | |
| 5,405,939 A | 4/1995 | Suhadolnik et al. | |
| 5,453,496 A | 9/1995 | Caruthers et al. | |
| 5,455,233 A | 10/1995 | Spielvogel et al. | |
| 5,459,255 A | 10/1995 | Cook et al. | |
| 5,466,677 A | 11/1995 | Baxter et al. | |
| 5,466,786 A | 11/1995 | Buhr et al. | |
| 5,470,967 A | 11/1995 | Huie et al. | |
| 5,489,677 A | 2/1996 | Sanghvi et al. | |
| 5,506,351 A | 4/1996 | McGee | |
| 5,519,134 A | 5/1996 | Acevedo et al. | |
| 5,521,302 A | 5/1996 | Cook | |
| 5,539,082 A | 7/1996 | Nielsen et al. | |
| 5,541,307 A | 7/1996 | Cook et al. | |
| 5,552,540 A | 9/1996 | Haralambidis | |
| 5,554,746 A | 9/1996 | Ravikumar et al. | |
| 5,571,902 A | 11/1996 | Ravikumar et al. | |
| 5,578,718 A | 11/1996 | Cook et al. | |
| 5,581,469 A | 12/1996 | Kim | |
| 5,587,361 A | 12/1996 | Cook et al. | |
| 5,587,469 A | 12/1996 | Cook et al. | |
| 5,587,470 A | 12/1996 | Cook et al. | |
| 5,591,722 A | 1/1997 | Montgomery et al. | |
| 5,594,121 A | 1/1997 | Froehler et al. | |
| 5,596,091 A | 1/1997 | Switzer | |
| 5,597,909 A | 1/1997 | Urdea et al. | |
| 5,602,240 A | 2/1997 | De Mesmaeker et al. | |
| 5,608,046 A | 3/1997 | Cook et al. | |
| 5,610,289 A | 3/1997 | Cook et al. | |
| 5,646,265 A | 7/1997 | McGee | |
| 5,663,312 A | 9/1997 | Chaturvedula | |
| 5,670,633 A | 9/1997 | Cook et al. | |
| 5,700,920 A | 12/1997 | Altmann et al. | |
| 5,998,203 A | 12/1999 | Matulic-Adamic et al. | |
| 6,127,533 A | 10/2000 | Cook et al. | |
| 6,166,197 A | 12/2000 | Cook et al. | |
| 6,172,209 B1 | 1/2001 | Manoharan et al. | |
| 6,262,241 B1 | 7/2001 | Cook et al. | |
| 6,271,358 B1 | 8/2001 | Manoharan et al. | |
| 8,058,255 B2 | 11/2011 | Ford et al. | |
| 8,084,600 B2 | 12/2011 | Natt et al. | |
| 8,097,716 B2 | 1/2012 | Weiler et al. | |
| 8,344,128 B2 | 1/2013 | Natt et al. | |
| 8,404,831 B2 | 3/2013 | Natt et al. | |
| 8,404,832 B2 | 3/2013 | Natt et al. | |
| 8,809,293 B2 | 8/2014 | Chin et al. | |
| 2003/0124651 A1 | 7/2003 | Pasupuleti et al. | |
| 2003/0143732 A1 | 7/2003 | Fosnaugh et al. | |
| 2003/0206887 A1 | 11/2003 | Morrissey et al. | |
| 2004/0053875 A1 | 3/2004 | Kreutzer et al. | |
| 2005/0032733 A1 | 2/2005 | McSwiggen et al. | |
| 2008/0145436 A1 | 6/2008 | Ng et al. | |
| 2009/0209626 A1 | 8/2009 | Khvorova et al. | |
| 2011/0178157 A1* | 7/2011 | Jin | A61K 31/713 514/44 A |
| 2012/0142754 A1* | 6/2012 | Niitsu | C12N 15/113 514/44 A |
| 2012/0252027 A1* | 10/2012 | Butora | C12N 15/111 435/6.12 |
| 2014/0303232 A1 | 10/2014 | Baryza et al. | |
| 2017/0247707 A1* | 8/2017 | Giese | C12N 15/1137 |

FOREIGN PATENT DOCUMENTS

| | | |
|---|---|---|
| WO | 1993/007883 | 4/1993 |
| WO | WO 99/32619 | 7/1999 |
| WO | WO 1999/032619 A1 | 7/1999 |
| WO | 2000/022113 | 4/2000 |
| WO | 2000/031105 | 6/2000 |
| WO | WO 00/44895 | 8/2000 |
| WO | WO 2000/044895 A1 | 8/2000 |
| WO | WO 01/29058 A1 | 4/2001 |
| WO | WO 2001/029058 A1 | 4/2001 |
| WO | 2003/020931 | 3/2003 |
| WO | WO 2003/070918 A2 | 8/2003 |
| WO | WO 2003/070918 A3 | 8/2003 |
| WO | WO 2003/100059 A3 | 12/2003 |
| WO | WO 2003/100059 A2 | 12/2003 |
| WO | 2005/065719 | 7/2005 |
| WO | WO 2005/060697 A2 | 7/2005 |
| WO | WO 2005/060697 A3 | 7/2005 |
| WO | 2005/116204 | 12/2005 |
| WO | 2006/017932 | 2/2006 |
| WO | WO 2006/078414 A2 | 7/2006 |
| WO | WO 2007/107162 A2 | 9/2007 |
| WO | WO 2007107162 A3 | 9/2007 |
| WO | WO 2007/128477 A2 | 11/2007 |
| WO | WO 2007/128477 A3 | 11/2007 |
| WO | WO 2008/147824 A2 | 12/2008 |
| WO | WO 2008/147824 A3 | 12/2008 |
| WO | WO 2009/020344 A2 | 2/2009 |
| WO | WO 2009/152500 A1 | 12/2009 |
| WO | WO 2010/083384 A2 | 7/2010 |
| WO | WO 2010/083384 A3 | 7/2010 |
| WO | 2010/135322 | 11/2010 |
| WO | 2011/003780 | 1/2011 |
| WO | WO 2011/076807 A2 | 6/2011 |
| WO | WO 2011/076807 A3 | 6/2011 |
| WO | WO 2014/136086 A1 | 9/2014 |
| WO | WO 2015/050871 A2 | 4/2015 |
| WO | WO 2015/050871 A3 | 4/2015 |
| WO | WO 2015/051044 A2 | 4/2015 |
| WO | WO 2015/051044 A3 | 4/2015 |
| WO | WO 2015/051045 A2 | 4/2015 |
| WO | WO 2015/051045 A3 | 4/2015 |
| WO | WO 2015/051135 A2 | 4/2015 |
| WO | WO 2015/095340 A1 | 6/2015 |
| WO | WO 2015/095346 A1 | 6/2015 |
| WO | WO 2016/010840 A1 | 1/2016 |
| WO | WO 2016/037053 A1 | 3/2016 |

(56) References Cited

FOREIGN PATENT DOCUMENTS

OTHER PUBLICATIONS

Bentwich, I. et al., "Identification of Hundreds of Conserved and Nonconserved Human MicroRNAs," *Nature Genetics*, vol. 37, No. 7 (2005) pp. 766-770.

Bernstein, E. et al., "Role for a Bidentate Ribonuclease in the Initiation Step of RNA Interference," *Nature*, vol. 409, (2001) pp. 363-366.

Brodersen, P. et al., "Widespread Translational Inhibition by Plant miRNAs and siRNAs," *Science*, 320, 1185 (2008) pp. 1185-0090.

Choung, S. et al., "Chemical Modification of siRNAs to Improve Serum Stability without Loss of Efficacy," *Biochemical and Biophysical Research Communications*, 342 (2006) pp. 919-927.

Chu, Chia-Ying, et al., "Potent RNAi by Short RNA Triggers," *RNA*, vol. 14, No. 9 (2008) pp. 1714-1719.

Clerici, A. et al., "Facile Reduction of Aromatic Aldehydes, Ketones, Diketones and Oxo Aldehydes to Alcohols by an Aqueous $TiCl_3/NH_3$ System: Selectivity and Scope," *Eur. J. Chem.*, 19, (2002) pp. 3326-3335.

Czauderna, F. et al., "Structural Variations and Stabilising Modifications of Synthetic siRNAs in Mammalian Cells," *Nucleic Acids Research*, vol. 31, No. 11, (2003), pp. 2705-2716.

Deleavey, G.F. et al., "Chemical Modification of siRNA," *Current Protocols in Nucleic Acid Chemistry*, Supplement 39 (2009) pp. 16.3.1-16.3.22.

Elbashir, S.M. et al., "Duplexes of 21-Nucleotide RNAs Mediate RNA Interference in Cultured Mammalian Cells," *Nature*, vol. 411, (2001) pp. 494-498.

Elbashir, S.M. et al., "Functional Anatomy of SiRNAs for Mediating Efficient RNAi in Drosophila Melanogaster Embryo Lysate," *The EMBO Journal*, vol. 20, No. 23, (2001) pp. 6877-6888.

Elbashir, S.M. et al., "RNA Interference is Mediated by 21-and 22-Nucleotide RNAs," *Genes Dev.*, 15, (2001) pp. 188-200.

Frank, F. et al., "Structural Basis for 5'-Nucleotide Base-Specific Recognition of Guide RNA by Human AGO2," *Nature*, vol. 465 (2010) pp. 818-822.

Friedman, R.C. et al., "Most Mammalian mRNAs Are Conserved Targets of MicroRNAs," *Genome Research*, 19, (2009) pp. 92-105.

Hadwiger, P. et al., "Chemical Modifications to Achieve Increased Stability and Sensitive Detection of siRNA," *RNA Interference Technology*, Edited by Krishnarao Appasani, Cambridge University Press (2005) pp. 194-206.

Harborth, J. et al., "Sequence, Chemical, and Structural Variation of Small Interfering RNAs and Short Hairpin RNAs and the Effect on Mamalian Gene Silencing," *Antisense and Nucleic Acid Drug Develoopment*, 13:83, (2003) pp. 83-105.

He, L. et al., "MicroRNAs: Small RNAs with a Big Role in Gene Regulation," *Nature Reviews/Genetics*, vol. 5, (2004) pp. 522-531.

Hoerter, J. et al., "siRNA-Like Double-Stranded RNAs Are Specifically Protected Against Degradation in Human Cell Extract," *PLoS ONE*, vol. 6, Issue 5, (2011) pp. 1-9.

Hutvágner, G. et al., "A Cellular Function for the RNA-Interference Enzyme Dicer in the Maturation of the let-7 Small Temporal RNA," *Science*, vol. 293, (2001) pp. 834-838.

International Search Report and Written Opinion for International Patent Application No. PCT/US2014/059301 dated May 8, 2015, 11 pp.

Jackson, A.L. et al., "Expression Profiling Reveals Off-Target Gene Regulation by RNAi," *Nature Biotechnology*, vol. 21, No. 6, (2003) pp. 635-637.

Kraynack, B. et al., "Small Interfering RNAs Containing Full 2'-O-Methylribonucleotide-Modified Sense Strands Display Argonaute2/eIF2C2-Dependent Activity," *RNA*, 12, (2006) pp. 163-176.

Kusenda, B. et al., "MicroRNA Biogenesis, Functionality and Cancer Relevance," *Biomed Pap Med Fac Univ Palacky Olomouc Czech Repub.*, 150(2), (2006) pp. 205-215.

Layzer, J.M. et al., "In Vivo Activity of Nuclease-Resistant siRNAs," *RNA*, 10, (2004) pp. 766-771.

Lewis, B.P. et al., "Prediction of Mammalian MicroRNA Targets," *Cell Press*, vol. 115 (2003) pp. 787-798.

Lewis, B.P. et al., "Conserved Seed Pairing, Often Flanked by Adenosines, Indicates that Thousands of Human Genes are MicroRNA Targets," *Cell*, vol. 120, (2005) pp. 15-20.

Lim, L.P. et al., "The microRNAs of Caenorhabditis Elegans," *Genes & Development*, 17, (2003) pp. 991-1008.

Lingel, A. et al., "Structure and Nucleic-Acid Binding of the Drosophila Argonaute 2 PAZ Domain," *Nature*, vol. 426, (2003) pp. 465-469.

Lingel, A. et al., "Nucleic Acid 3'—end Recognition by the Argonaute2 PAZ Domain," *Nature Structural & Molecular Biology*, vol. 11, No. 6, (2004) pp. 576-577.

Lipardi, C. et al., "RNAi as Random Degradative PCR: siRNA Primers Convert mRNA into dsRNAs that Are Degraded to Generate New siRNAs," *Cell Press*, vol. 107 (2001) pp. 297-307.

Lombardo, A. et al., "Gene Editing in Human Stem Cells Using Zinc Finger Nucleases and Integrase-Defective Lentiviral Vector Delivery," *Nature Biotechnology*, vol. 25, No. 11, (2007) pp. 1298-1306.

Liu, J. et al., "RNA Duplexes with Abasic Substitutions are Potent and Allele-Selective Inhibitors of Huntingtin and Ataxin-3 Expression," *Nucleic Acids Research*, vol. 41, No. 18 (2013) pp. 8788-8801.

Ma, J-B. et al., "Structural Basis for Overhang-Specific Small Interfering RNA Recognition by the PAZ Domain," *Nature*, 429: 318-322 (2004) pp. 1-12.

Macrae, I.J. et al., "Structural Basis for Double-Stranded RNA Processing by Dicer," *Science*, 13 (2006) pp. 195-198. Reproduced in RNA: Collection, a booklet from *Science*, at pp. 16-22.

Martin, V.P. "38. Ein neuer Zugang zu 2'-0-Alkylribonucleosiden and Eigenschaften deren Oligonucleotide," *Helvetica Chimica Acta*, vol. 78 (1995) pp. 486-504. (Abstract in English).

Morrissey, D.V. et al., "Potent and Persistent in vivo anti-HBV Activity of Chemically Modified siRNAs," *Nature Biotechnology*, vol. 23, No. 8, (2005) pp. 1002-1007.

Myers, J.W. et al., "Dicer in RNAi: Its Roles in vivo and utility in vitro," *RNA Interference Technology*, Edited by: Krishnarao Appasani, Cambridge University Press, pp. 29-54.

Nykanen, A. et al., "ATP Requirements and Small Interfering RNA Structure in the RNA Interference Pathway," *Cell*, vol. 107, (2001) pp. 309-321.

Parker, J.S. et al., "Structural Insights into mRNA Recognition from a PIWI Domain-siRNA Guide Complex," *Nature*, 434(7033) (2005) pp. 663-666. Reproduced in Europe PMC Founders Group pp. 1-8.

Sato, A. et al., "Polymer Brush-Stabilized Polyplex for a siRNA Carrier with Long Circulatory Half-Life," *Journal of Controlled Release*, 122, (2007) pp. 209-216.

Schwarz, D.S. et al., "Evidence that siRNAs Function as Guides, Not Primers, in the Drosophila and Human RNAi Pathways," *Molecular Cell*, vol. 10, (2002) pp. 537-548.

Senzer, N. et al., "Phase I Trial of "bi-shRNA$^{furin}$/GMCSF DNA/Autologous Tumor Cell" Vaccine (FANG) in Advanced Cancer," *Molecular Therapy*, vol. 20, No. 3., (2012) pp. 679-686.

Schauer, S.E. et al., "DICER-LIKE1: Blind Men and Elephants in Arabidopsis Development, *TRENDS in Plant Science*, vol. 7, No. 11, (2002) pp. 487-491.

Sharp, P.A., "RNA Interference—2001," *Genes & Development*, 15, (2001) pp. 485-490.

Song, Ji-Joon, et al., "The Crystal Structure of the Argonaute2 PAZ Domain Reveals an RNA Binding Motif in RNAi Effector Complexes," *Nature Structural Biology*, vol. 10, No. 12, (2003) pp. 1026-1032.

Song, E. et al., "RNA Interference Targeting Fas Protects Mice from Fulminant Hepatitis," *Nature Medicine*, vol. 9, No. 3. (2003) pp. 347-351.

Sun, X. et al., "Asymmetric RNA Duplexes Mediate RNA Interference in Mammalian Cells," *Nature Biotechnology*, vol. 26, No. 12, (2008) pp. 1379-1382.

(56) References Cited

OTHER PUBLICATIONS

Taniho, K. et al., "Synthesis and Biological Properties of Chemically Modified siRNAs Bearing 1-Deoxy-D-Ribofuranose in Their 3'-Overhand Region," *Bioorganic & Medicinal Chemistry Letters*, 22 (2012) pp. 2518-2521.
Terrazas, M. et al., "RNA Major Groove Modifications Improve siRNA Stability and Biological Activity," *Nucleic Acids Research*, vol. 37, No. 2. (2009) pp. 346-353.
Wang, Z. et al., "RNA Interference and Cancer Therapy," *Pharm. Res.*, 28, (2011) pp. 2983-2995.
Xiang, S. et al., "Short Hairpin RNA-Expressing Bacteria Elicit RNA Interference in Mammals," *Nature Biotechnology*, vol. 24, No. 6, (2006) pp. 697-702.
Yamato, K. et al., "Enhanced Specificity of HPV16 E6E7 siRNA by RNA-DNA Chimera Modification," *Cancer Gene Therapy*, 18, (2011) pp. 587-597.
Yan, K. S. et al., "Structure and Conserved RNA Binding of the PAZ Domain," *Nature*, vol. 426, (2003) pp. 469-474.
Zamore, P.D. et al., "Ribo-gnome: The Big World of Small RNAs," *Science*, 309 (2005) pp. 1519-1524.
Zamore, P.D. et al., "RNAi: Double-Stranded RNA Directs the ATP-Dependent Cleavage of mRNA at 21 to 23 Nucleotide Intervals," *Cell*, vol. 101, (2000) pp. 25-33.
Zendegui, J.G. et al., "In Vivo Stability and Kinetics of Absorption and Disposition of 3' Phosphopropyl Amine Oligonucleotides," *Nucleic Acids Research*, vol. 20, No. 2, (1992) pp. 307-314.
Zhang, H. et al., "Single Processing Center Models for Human Dicer and Bacterial RNase III," *Cell*, vol. 118, (2004) pp. 57-68.
Zhang, R. et al., "Small But Influential: The Role of MicroRNAs on Gene Regulatory Network and 3'UTR Evolution," *J. Genet. Genomics*, 36 (2009) pp. 1-6.
Bartel, "MicroRNAs: Target Recognition and Regulatory Functions," Cell 136, Jan. 23, 2009, pp. 215-233.
Bernstein, et al., "a bidentate ribonuclease in the initiation step of RNA interference," Nature 409, Feb. 2001, pp. 363-366.
Bentwich, et al., "Identification of hundreds of conserved and nonconserved human mcroRNAs," Nat. Genet. 37, Aug. 2005, pp. 766-770.
Brodersen, et al., "Widespread Translational Inhibition by Plant miRNAs and siRNAs," Science 320, May 2008, pp. 1185-1190.
Chu and Rana, "Potent RNAi by short RNA triggers," RNA 14, 2008, pp. 1714-1719.
Choung, et al., "Chemical modification of siRNAs to improve serum stability without loss of efficacy," Biochemical and Biophysical Research Communications 342, 2006, pp. 919-927.
Czauderna, et al., "Structural variations and stabilizing modifications of synthetic siRNAs in mammalian cells," Nucleic Acids Research, vol. 31, No. 11, 2003, pp. 2705-2716.
Deleavey, et al., "Chemical Modification of siRNA," Current Protocols in Nucleic Acid Chemistry, Dec. 22, 2009, pp. , 16.3.1-16.3.22.
Elbashir, et al., "Duplexes of 21-nucleotide RNAs mediate RNA interference in cultured mammalian cells," Nature 411, May 24, 2001, pp. 494-498.
Elbashir, et al., "Functional anatomy of siRNAs for mediating efficient RNAi in *Drosophila melanogaster* embryo lysate," The EMBO Journal, vol. 20, No. 23, 2001, pp. 6877-6888.
Elbashir, et al., "RNA interference is mediated by 21- and 22-nucleotide RNAs," Genes Dev., 2001, 15, pp. 188-200.
Clerici, et al., Facile Reduction of Aromatic Aldehydes, Ketones, Diketones and Oxo Aldehydes to Alchohols by an Aqueous $TiCl_3$/$NH_3$ System: Selectivity and Scope. Eur. J. Org. Chem, 2002, 19, pp. 3326-3335.
Frank, et al., "Structural basis for 5'-nucleotide base-specific recognition of guide RNA by human AGO2," Nature, vol. 465, Jun. 10, 2010, pp. 818-822.
Friedman, et al., "Most mammalian mRNAs are conserved targets of microRNAs," Genome Res., 2009 19: Oct. 27, 2008, pp. 92-105.
"Pre-Synthesis Labeling of Aminomodifier C3 or C7 CPG," Glen Research (Sterling VA).

Jackson, et al., "Expression profiling reveals off-target gene regulation by RNAi," Natural Biotechnology, Jun. 2003, vol. 21, No. 6, pp. 635-638.
Hadwiger, et al., "Chemical modifications to achieve increased stability and sensitive detection of siRNA," RNA Interference Technology, Cambridge University Press, 2005, pp. 194-206.
Harborth, et al., "Sequence, Chemical, and Structural Variation of Small Interfering RNAs and Short Hairpin RNAs and the Effect on Mammalian Gene Silencing," Antisense and Nucleic Acid Drug Development, 13, 2003, pp. 83-105.
He, et al., "MicroRNAs: Small RNAs with a Big Role in Gene Regulation," Nat. Rev. Genet. 5, Jul. 2004, pp. 522-532.
Hoerter, et al., "siRNA-Like Double-Stranded RNAs are Specifically Protected Against Degradation in Human Cell Extract," Plos One, vol. 6, Issue 5, May 27, 2011, pp. 1-9.
Hutvagner, et al., "A Cellular Function for the RNA-Interference Enzyme Dicer in the Maturation of the let-7 Small Temporal RNA," Science, vol. 293, Aug. 3, 2001, pp. 834-838.
Kraynack, et al., "Small interfering RNAs containing ful 2'-O-methylribonucleotide-modified sense strands display Argonaute2/eIF2C2-dependent activity," RNA 12, 2006, pp. 163-176.
Kusenda, et al., "MicroRNA Biogenesis, Functionality and Cancer Relevance," Biomed Pap Med Fac Univ Palacky Olomouc, Czech Repub., 2006, 150(2), pp. 2015-2215.
Layzer, et al., "In vivo activity of nuclease-resistant siRNAs," RNA 10, 2004, pp. 766-771.
Lewis, et al., "Prediction of Mammalian MicroRNA Targets," Cell, vol. 115, Dec. 26, 2003, pp. 787-798.
Lewis, et al., "Conserved Seed Pairing, Often Flanked by Adenosines, Indicates that Thousands of Human Genes are MicroRNA Targets," Cell, vol. 120, Jan. 14, 2005, pp. 15-20.
Lim, et al., "The microRNAs of Caenorhabditis elegans," Genes Dev., 17, 2003, pp. 91-1008.
Lingel, et al., "Structure and nucleic-acid binding of the *Drosophila* Argonaute 2 PAZ domain," Nature 426, 2003, pp. 465-469.
Lingel, et al., "Nucleic acid 3'-end recognition by the Argonaute2 PAZ domain," Nature 426, vol. 11, No. 6, Jun. 2004, pp. 576-577.
Lipardi, et al., "RNAi as Random Degradative PCR: siRNA Primers Convert mRNA into dsRNAs that are Degraded to Generate New siRNAs," Cell, vol. 107, Nov. 2, 2011, pp. 297-307.
Lombardo, et al., "Gene editing in human stem cells using zinc finger nucleases and integrase-defective lentiviral vector delivery," Nature, vol. 25, No. 11, Nov. 2007, pp. 1298-1306.
Ma, et al., "Structural basis for overhang-specific small interfering RNA recognition by the PAZ domain," Nature 429, May 20, 2004, pp. 318-322.
Macrae, et al., "Structural Basis for Double-Stranded RNA Processing by Dicer," Science 311, 2006, pp. 195-198.
Martin et al., "En neuer Zugang zu 2'-O-Alkylribonukleosiden und Eigenschaften deren Oligonucleotide," Helv., Chim. Acta, 78, 1995, pp. 486-504.
Morrissey, et al., "Potent and persistent in vivo anti-HBV activity of chemically modified siRNAs," Nature Biotech 23, 2005, pp. 1002-1007.
Myers, et al., "Dicer in RNAi: Its roles in vivo and utility in vitro," RNA Interference Technology, ed. Appasani, Cambridge University Press, pp. 29-54.
Nykanen, et al., "ATP Requirements and Small Interfering RNA Structure in the RNA Interference Pathway," Cell 107, 2001, pp. 309-321.
Parker, et al., "Structural insights into mRNA recognition from a PIWI domain—siRNA guide complex," Nature 434, 2005, pp. 663-666.
Sato, et al., "Polymer brush-stabilized polyplex for a siRNA carrier with long circulatory half-life," Science Direct, J. Control Rel. 122, 2007, pp. 209-216.
Senzer, et al., "Phase I Trial of "bi-shRNAi$^{furin}$/GMCSF DNA/Autologous Tumor Cell" Vaccine (FANG) in Advanced Cancer," Molecular Therapy, vol. 20, No. 3, Mar. 2012, pp. 679-686.
Schauer, et al., "DICER-LIKE1: blind men and elephants in *Arabidopsis* development," Trends in Plant Science, vol. 7, No. 11, Nov. 2002, pp. 487-491.

(56) References Cited

OTHER PUBLICATIONS

Schwarz, et al., "Evidence that siRNAs Function as Guides, Not Primers, in the *Drosophila* and Human RNAi Pathways," Molecular Cell, vol. 10, Sep. 2002, pp. 537-548.
Sharp, et al., "RNA interference—2001," Genes Dev. 15, pp. 485-490.
Song, et al., "RNA interference targeting Fas protects mice from fulminant hepatitis," Nature Medicine, vol. 9, No. 3, Mar. 2003, pp. 347-351.
Song, et al., "The crystal structure of the Argonaute2 PAZ domain reveals an RNA binding motif in RNAi effector complexes," Nature Structural Biology, vol. 10, No. 12, Dec. 2003, pp. 1026-1032.
Sun, et al., "Asymmetric RNA duplexes mediate RNA interference in mammalian cells," Nature Biotech, vol. 26, No. 12, Dec. 2008, pp. 1379-1382.
Terrazas, et al., "RNA major groove modifications improve siRNA stability and biological activity," Nucleic Acids Research, vol. 37, No. 2, 2009, pp. 346-353.
Wang, et al., "RNA Interference and Cancer Therapy," Pharm Res. 28, 2011, pp. 2983-2995.
Xiang, et al., "Short hairpin RNA-expressing bacteria elicit RNA interference in mammals," Nature Biotechnology, vol. 24, No. 6, Jun. 2006, pp. 697-702.
Yamato, et al., "Enhanced specificity of HPV16 E6E7 siRNA by RNA-DNA chimera modification," Cancer Gene Therapy 18, 2011, pp. 587-597.
Yan, et al., "Structure and conserved RNA binding of the PAZ domain," Nature, vol. 426, Nov. 27, 2003, pp. 468-474.
Zamore and Haley, "Ribo-gnome: The Big World of Small RNAs," Science, vol. 309, Sep. 2, 2005, pp. 1519-1524.
Zamore, et al., "RNAi: Double-Stranded RNA Directs the ATP-Dependent Cleavage of mRNA at 21 to 23 Nucleotides Intervals," Cell, vol. 101, Mar. 31, 2000, pp. 25-33.
Zendegui, et al., "In vivo stability and kinetics of absorption and disposition of 3'phosphopropyl amine oligonucleotides," Nucleic Acids Research, Oxford University Press, vol. 20, No. 2, 1992, pp. 307-314.
Zhang, et al., "Small but influential: the role of microRNAs on gene regulatory network and 3'UTR evolution," J. Genet. Genomics, ScienceDirect, vol. 36, 2009, pp. 1-6.
Zhang, et al., "Single Processing Center Models for Human Dicer and Bacterial RNase III," Cell, vol. 118, Jul. 9, 2004, pp. 57-68.
International Search Report for PCT/US2014/058314.
International Search Report for PCT/US2014/059301.
Dande, Prasad, et al., "Improving RNA Interference in Mammalian Cells by 4'-Thio-Modified Small Interfering RNA (siRNA): Effect on siRNA Activity and Nuclease Stability When Used in Combination with 2'-O-Alkyl Modifications," J. Med. Chem., 2006, 49, pp. 1624-1634.
Al-Anouti, Fatme, et al., "Comparative Analysis of Antisense RNA, Double-Stranded RNA, and Delta Ribozyme-Mediated Gene Regulation in Toxoplasma gondii," Antisense and Nucleic Acid Drug Development, 12, 2002, pp. 275-281.
Bass, Brenda L., "The Short Answer," News and Views, Macmillan Magazines Ltd, 2001, Nature, vol. 411, pp. 428-429.
Beigelman, Leonid, et al., "Chemical Modification of Hammerhead Ribozymes," Catalytic Activity and Nuclease Resistance, the Journal of Biological Chemistry, The American Society for Biochemistry and Molecular Biology, Inc., 1995, vol. 270, No. 43, Issue of Oct. 27, pp. 25702-2708.
Braasch, Dwaine A., et al., "Novel Antisense and Peptide Nucleic Acid Strategies for Controlling Gene Expression," Biochemistry, The American Chemical Society, 2002, vol. 41, No. 14, pp. 4503-4510.
Braasch, Dwain A., et al., "RNA Interference in Mammalian Cells by Chemically-Modified RNA," Biochemistry, 2003, 42, pp. 7967-7975.
Bramsen, Jesper B., et al., "A large-scale chemical modification screen identifies design rules to generate siRNAs with high activity, high stability and low toxicity," Nucleic Acids Research, 2009, vol. 37, No. 9, pp. 2867-2881 and supplementary Figures.
Chiu, Ya-Lin, et al., "Visualizing a Correlation between siRNA Localization, Cellular Uptake, and RNAi in Living Cells," Chemistry & Biology, vol. 11, 2004, pp. 1165-1175.
Chiu, Ya-Lin, et al., "siRNA function in RNAi: A chemical modification analysis," RNA Society, 2003, 9, pp. 1034-1048.
Corey, David R., "Chemical modification: the key to clinical application of RNA interference?," The Journal of Clinical Investigation, vol. 117, No. 12, 2007, pp. 3615-3622.
Crooke, Rosanne M., "Metabolism of Antisense Oligonucleotides in Rat Liver Homogenates," The Journal of Pharmacology and Experimental Therapeutics, 2000, vol. 292, No. 1, pp. 140-149.
Deleavey, Glen F., "Chemical Modification of siRNA," Current Protocols in Nucleic Acid Chemistry, 2009, Supp 39, pp. 16.3.1-16.3.22.
Dorsett, Yair, "siRNAs: Applications in Functional Genomics and Potential as Therapeutics," 2004, vol. 3, pp. 318-329.
Elbashir, Sayda, M., et al., "Duplexes of 21-nucleotide RNAs mediate RNA interference in cultured mammalian cells," Macmillan Magazines Ltd, Nature, vol. 411, 2001, pp. 494-498.
Hadwiger, Philipp, et al., "Chemical modifications to achieve increased stability and sensitive detection of siRNA," Cambridge University Press, pp. 194-206.
Kawasaki, Hiroaki, et al., "World of small RNAs: from ribozymes to siRNA and miRNA," International Society of Differentiation, 2004, 72, pp. 58-64.
Khan, Alim, et al., "Sustained Polymeric Delivery of Gene Silencing Antisense ODNs, siRNA, DNAzymes an dRibozymes: In Vitro and In Vivo Studies," Journal of Drug Targeting, Jul. 2004, vol. 12, 6, pp. 393-404.
Kim, Sun Hwa, et al., "Local and systemic delivery of VEGF siRNA using polyelectrolyte complex micelles for effective treatment of cancer," Journal of Controlled Release, 129, 2008, pp. 107-116.
Kraynack, Bryan A., et al., "Small interfering RNAs containing full 2'-O-methyliribonucleotide-modified sense strands display Argonaute2/eIF2C2-dependent activity," RNA, 2006, 12, pp. 163-176.
Lipardi, Concetta, et al., "RNAi as Random Degradative PCR: siRNA Primers Convert mRNA into dsRNAs that Are Degraded to Generate New siRNAs," Cell, vol. 107, 2001, pp. 297-307.
Miyagishi, Makoto, et al., "Comparison of the Suppressive Effects of Antisense Oligonucleotides and siRNAs Directed Against the Same Targets in Mammalian Cells," Antisense and Nucleic Acid Drug Development, 13, 2003, pp. 1-7.
Parrish, Susan, et al., "Functional anatomy of a dsRNA Trigger: Differential Requirement for the Two Trigger Strands in RNA Interference," Molecular Cell, vol. 6, 2000, pp. 1077-1087.
Prakash, Thazha, P., "Positional Effect of Chemical Modifications on Short Interference RNA Activity in Mammalian Cells," J. Med. Chem., 2005, 48, pp. 4247-4253.
Schwarz, Dianne S., "Evidence that siRNAs Function as Guides, Not Primers, in the *Drosophila* and Human RNAi Pathways," Molecular Cell, vol. 10, 2002, pp. 537-548.
Shah, Samit, et al., "An ESI-MS method for characterization of native and modified oligonucleotides used for RNA interference and other biological applications," Nature Protocol, Division of Pharmaceutical Sciences, vol. 3, No. 3, 2008, pp. 351-356.
Sioud, M., Ribozymes and siRNAs: From Structure to Preclinical Applications, HEP, 2006, 173: pp. 223-242.
Takahashi, Mayumi, et al., "Synthesis and characterization of 2'-modified-4'-thioRNA: a comprehensive comparison of nuclease stability," Nucleic Acids Research, 2009, vol. 37, No. 4, pp. 1353-1362.
Tavernarakis, Nektarios, et al., "Heritable and inducible genetic interference by double-stranded RNA encoded by transgenes," Nature America Inc., 2000, vol. 24, pp. 180-183.
Terrazas, Montserrat, et al., "RNA major groove modifications improve siRNA stability and biological activity," Nucleic Acids Research, 2009, vol. 37, No. 2, pp. 346-353.

(56) References Cited

OTHER PUBLICATIONS

Zhang, Y-L, et al., "RNA Interference inhibits hepatitis B virus of different genotypes in vitro and in vivo," BMC Microbiol. 2010, vol. 10:214, p. 1-10.
Akhtar S., et al., "Nonviral delivery of synthetic siRNAs in vivo," Journal of Clinical Investigation (2007) 117: 3623-3632.
Atherton E., et al., "The Fluorenylmethoxycarbonyl Amino Protecting Group," The Peptides, S. Udenfriend, J. Meienhofer, Eds., Academic Press, Inc. (1987) 9: 1-38.
Berkner KL et al., "Development of adenovirus vectors for the expression of heterologous genes," BioTechniques (1988) 6: 616-629.
Bucchini D et al., "Pancreatic expression of human insulin gene in transgenic mice," Proc. Natl. Acad. Sci. USA (1986) 83: 2511-2515.
Cook PD, "Medicinal Chemistry of Antisense Oligonucleotides-Future Opportunities," Anti-Cancer Drug Design (1991) 6: 585-607.
Chen S-H et al., "Gene therapy for brain tumers: Regression of experimental gliomas by adenovirus-mediated gene transfer in vivo," Proc. Natl. Acad. Sci. USA (1994) 91: 3054-3057.
Cone RD et al., "High-efficiency gene transfer into mammalian cells: Generation of helper-free recombinant retrovirus with broad mammalian host range," Proc. Natl. Acad. Sci. USA (1984) 81: 6349-6353.
Cometta K et al., "Safety tissues related to retroviral-mediated gene transfer in humans," Human Gene Therapy (1991) 2: 5-14.
Crooke et al., "Pharmacokinetic Properties of Several Novel Oligonucleotide Analogs in Mice," J. Pharmacal. Exp. Ther. (1996), 277: 923-927.
Danos O et al., "Safe and efficient generation of recombinant retroviruses with amphotropic and ecotropic host ranges," Proc. Natl. Acad. Sci. USA (1988) 85: 6460-6464.
Delgado C et al., "The Uses and Properties of PEG-Linked Proteins," Critical Reviews in Therapeutic Drug Carrier Systems (1992) 9(3,4): 249-304.
Docherty K et al., "Nutrient regulation of insulin gene expression," FASEB J. (1994) 8: 20-24.
Englisch U et al., "Chemically Modified Oligonucleotides as Probes and Inhibitors," Angewandte Chemie, International Edition (1991) 30(6): 613-629.
Gassmann M et al., "Maintenance of an extrachromosomal plasmid vector in mouse embryonic stem cells," Proc. Natl. Acad. Sci. USA (1995) 92: 1292-1296.
Kroschwitz JL, "Monomers," Encyclopedia of Polymer Science and Engineering, John Wiley & Sons, New York, pp. 715-727.
Greene et al., Protective Groups in Organic Synthesis, Chapter 2, 2d ed., John Wiley & Sons, New York, 1991, and Oligonucleotides and Analogues a Practical Approach, Ekstein, F. Ed., IRL Press, N. Y., 1991.
Hamm ML et al., "Incorporation of 2'-Deoxy-2'-mercaptocytidine into Oligonucleotides via Phosphoramidite Chemistry," J.Org. Chem. (1997) 62: 3415-3420.
Hsu K-HL et al., "Immunogenicity of Recombinant Adenovirus-Respiratory Syncytial Virus Vaccines with Adenovirus Types 4, 5, and 7 Vectors in Dogs and a Chimpanzee," J. Infectious Disease, (1992) 166: 769-775.
Kabanov, et al., "A new class of antivirals; antisense oligonucleotides combined with a hydrophobic substituent effectively inhibit influenza virus reproduction and synthesis of virus-specific proteins in MDCK cells," FEBS Lett. (1990) 259: 327-330.
Letsinger RL et al., "Cholesteryl-conjugated oligonucleotides: Synthesis, properties, and activity as inhibitors of replication of human immunodeficiency virus in cell culture," Proc. Natl. Acad. Sci. USA (1989) 85: 5553-5556.
Li S et al., "Folate-Mediated Targeting of Antisense Oligodeoxynucleotides to Ovarian Cancer Cells," Pharmaceutical Research (1998) 15(10): 1540-4545.
Manoharan M et al., "Chemical Modifications to Improve Uptake and Bioavailability of Antisense Oligonucleotides," Ann. N. Y. Acad. Sci. (1992) 660: 306-309.
Manoharan M et al., "Introduction of a Lipophilic Thioether Tether in the Minor Groove of Nucleic Acids for Antisense Applications," Bioorg. & Med. Chem. Letters (1993) 3: 2765-2770.
Manoharan M et al., "Cholic Acid-Oligonucleotide Conjugates for Antisense Applications," Bioorg. Med. & Chem. Lett. (1994) 4: 1053-1060.
Manoharan M et al., "Oligonucleotide Conjugates: Alteration of the Pharmacokinetic Properties of Antisense Agents," Nucleosides & Nucleotides (1995) 14: 969-973.
Manoharan M et al., "Lipidic Nucleic Acids," Tetrahedron Letters (1995) 36: 3651-3654.
Manoharan M., "Oligonucleotide Conjugates as Potential Antisense Drugs with Improved Uptake, Biodistribution, Targeted Delivery, and Mechanism of Action," Antisense & Nucleic Acid Drug Devel. (2002) 12: 103-128.
Mishra RK et al., "Improved leishmanicidal effect of phosphorothioate antisense oligonucleotides by LDL-mediated delivery," Biohim. et Biophysica Acta (1995) 1264: 229-237.
Nawrot B et al., "Chemical and Structural Diversity of siRNA Molecules," Current Topics in Medicinal Chemistry (2006) 6: 913-925.
Nguyen T et al., "RNAi therapeutics: an update on delivery," Current Opinion in Molecular Therapeutics (2008) 10(2): 158-167.
Oberhauser et al., "Effective incorporation of 2'-O-methyl-oligoribonucleotides Into Liposomes an dEnhanced Cell Association Through Modification with Tiocholesterol," Nucl. Acids Research (1992) 20: 533-538.
Polisuin NN et al., "Synthesis of Oligonucleotides Containing 2'-Azido-and2'-amino-2'deoxyuridine Using Phosphotriester Chemistry," Tetrahedron Letters (1996) 37(19): 3227-3230.
Rosenfeld MA et al., "Adenovirus-mediated transfer of a recombinant alpha 1-antitrypsin gene to the lung epithelium in vivo," Science (1991) 252: 431-434.
Saison-Behmoaras et al., "Short Modified Antisense Oligonucleotides Directed Against Ha-ras Point Mutation Induce Selective Cleavage of the mRNA and Inhibit T24 Cells Proliferation," The EMBO Journal (1991) 10: 1111-1118.
Samukov VV et al., "2-(4-Nitrophenyl)sulfonylethoxycarbonyl (Nsc) Group as a Base-Labile α-Amino Protection for Solid Phase Peptide Synthesis," Tetrahedron Letters (1994) 35(42): 7821-7824.
Shea et al., "Synthesis, Hybridzation Properties and Antiviral Activity of Lipid-oligodeoxynucleotide Conjugates," Nucl. Acids Research (1990) 18: 3777-3783.
Svinarchuk et al., "Inhibition of HIV proliferation in MT-4 cells by antisense oligonucleotide conjugated to lipophilic groups," Biochimie (1993) 75: 49-54.
Thomson JB et al., "Synthesis and Properties of Diuridine Phosphate Analogues Containing Thio and Amino Modifications," J. Org. Chem. (1996) 61: 6273-6281.
Wagner RW, "The state of the art in antisense research," Nature Medicine (1995) 1(11): 1116-1118.
Williams DJ et al., "Thermodynamic Comparison of the Salt Dependence of Natural RNA Hairpins and RNA Hairpins with Non-Nucleotide Spacers," Biochemistry (1996) 35: 14665-14670.
Zamboni, "Liposomal, Nanoparticle, and Conjugated Formulations of Anticancer Agents," Clin. Cancer Res. (2005) 11: 8230-8234.
Ikeda et al, "Ligand-Targeting Delivery of Therapeutic siRNA," Pharmaceutical Research (2006) 23: 1631-1640.
Rosenfeld MA et al., "In vivo transfer of the human cystic fibrosis transmembrane conductance regulator gene to the airway epithelium," Cell (1992) 68(1): 143-155.
Sanghvi, Antisense Research and Applications, (1993) Chapter 15, p. 289-302, Crook ST and Lebleu B ed., CRC Press.

\* cited by examiner

FIG. 1

```
5'-NNNNNNNNNNNNNNNNNNNNNN-X-3'
3'-X-NNNNNNNNNNNNNNNNNNNNNN-5'
```

A12S17 modification scheme

```
5'-UUuAAUUGAAACcAAGACA-X-3' antisense mF7-3
3'-X-AAAuuAAcuuuGGuucuGu-5' sense
```

X = C3, C6, C12, glycol, cyclohex, phenyl, biphenyl, lithochol (lithocholic acid), C7 amino, C3 amino A = 2'-MOE A; u = 2'-OMe
C = 2'-MOE (5-Me)C; c = 2'-Ome

FIG. 5A Guide

| Format | Pos | P1 | P2 | P3 | P4 | P5 | P6 | P7 | P8 | P9 | P10 | P11 | P12 | P13 | P14 | P15 | P16 | P17 | P18 | P19 | OV20 | OV21 |
|---|---|---|---|---|---|---|---|---|---|---|---|---|---|---|---|---|---|---|---|---|---|---|
| A106S42 | 400 | T | A | t | t | C | c | A | A | G | A | C | C | t | A | t | G | | | | ribp | c6 |
| A107S42 | 400 | | A | t | t | C | c | A | A | G | A | C | C | t | A | t | G | | | | ribp | c6 |
| A107*S42 | 400 | | A | t | t | C | c | A | A | G | A | c | C | t | A | t | G | | | | ribp | c6 |
| A107*3'X058_pos4_DNA_S42 | 400 | | A | t | t | C | c | A | A | G | A | c | C | t | A | t | G | | | | ribp | X058 |
| A107*3'X058_pos6_DNA_S42 | 400 | | A | t | t | C | c | A | A | G | A | c | C | t | A | t | G | | | | ribp | X058 |
| A107*3'X058_pos8_DNA_S42 | 400 | | A | t | t | C | c | A | A | G | A | c | C | t | A | t | G | | | | ribp | X058 |
| A106S42 | 402 | T | T | t | A | t | t | C | c | A | A | G | A | C | C | t | A | | | | ribp | c6 |
| A107S42 | 402 | | T | t | A | t | t | C | c | A | A | G | A | C | C | t | A | | | | ribp | c6 |
| A107*S42 | 402 | | T | t | A | t | t | C | c | A | A | G | A | c | C | t | A | | | | ribp | c6 |
| A107*3'X058_pos2_DNA_S42 | 402 | | T | t | A | t | t | C | c | A | A | G | A | c | C | t | A | | | | ribp | X058 |
| A107*3'X058_pos4_DNA_S42 | 402 | | T | t | A | t | t | C | c | A | A | G | A | c | C | t | A | | | | ribp | X058 |
| A107*3'X058_pos2,4_DNA_S42 | 402 | | T | t | A | t | t | C | c | A | A | G | A | c | C | t | A | | | | ribp | X058 |
| 21mer A22S26 | 400 | T | A | T | T | C | c | A | A | G | A | C | C | t | A | T | G | T | T | C | u | u |

FIG. 5B Sense

| S1 | S2 | S3 | S4 | S5 | S6 | S7 | S8 | S9 | S10 | S11 | S12 | S13 | S14 | S15 | S16 | S17 | S18 | S19 | OV20 | OV21 |
|---|---|---|---|---|---|---|---|---|---|---|---|---|---|---|---|---|---|---|---|---|
| | A | A | c | A | t | A | G | G | t | c | t | t | G | G | A | A | | | ribp | c6 |
| | A | A | c | A | t | A | G | G | t | c | t | t | G | G | A | A | | | ribp | c6 |
| | A | A | c | A | t | A | G | G | t | c | t | t | G | G | A | A | | | ribp | c6 |
| | A | A | c | A | t | A | G | G | t | c | t | t | G | G | A | A | | | ribp | c6 |
| | A | A | c | A | t | A | G | G | t | c | t | t | G | G | A | A | | | ribp | c6 |
| | A | A | c | A | t | A | G | G | t | c | t | t | G | G | A | A | | | ribp | c6 |
| | | c | A | t | A | G | G | t | c | t | t | G | G | A | A | t | A | | ribp | c6 |
| | | c | A | t | A | G | G | t | c | t | t | G | G | A | A | t | A | | ribp | c6 |
| | | c | A | t | A | G | G | t | c | t | t | G | G | A | A | t | A | | ribp | c6 |
| | | c | A | t | A | G | G | t | c | t | t | G | G | A | A | t | A | | ribp | c6 |
| | | c | A | t | A | G | G | t | c | t | t | G | G | A | A | t | A | | ribp | c6 |
| | | c | A | t | A | G | G | t | c | t | t | G | G | A | A | t | A | | ribp | c6 |
| G | A | A | c | A | t | A | G | G | t | c | t | t | G | G | A | A | t | A | u | u |

☐ RNA
☐ 2'-OMe-RNA
▓ DNA
▓ 2'-F-RNA
▓ 2'-MOE-RNA

Hepcidin *in vivo* knockdown – 48 hours post dose

*Hamp1* specific Taqman Assay*

X058 and C6 Ago2 Pulldown
Hepcidin 18-mer oligonucleotides

*In vivo* comparison of A160 & A161 format

FIG. 10
| (siRNA 400) | | | 1 | 2 | 3 | 4 | 5 | 6 | 7 | 8 | 9 | 10 | 11 | 12 | 13 | 14 | 15 | 16 | 17 | 18 | | |
|---|---|---|---|---|---|---|---|---|---|---|---|---|---|---|---|---|---|---|---|---|---|---|
| Guide strand | | | | A | u | | C | c | A | A | G | A | c | C | u | A | u | G | | | ribp | X058 |
| Sense strand | C6 | ribp | | | A | A | G | G | u | u | c | u | G | G | A | u | A | c | A | A | | |
| (siRNA 402) | | | 1 | 2 | 3 | 4 | 5 | 6 | 7 | 8 | 9 | 10 | 11 | 12 | 13 | 14 | 15 | 16 | 17 | 18 | | |
|---|---|---|---|---|---|---|---|---|---|---|---|---|---|---|---|---|---|---|---|---|---|---|
| Guide strand | | | | u | u | u | C | c | A | A | G | A | c | C | u | A | | | | ribp | X058 |
| Sense strand | C6 | ribp | | | A | u | A | A | G | G | u | u | c | u | G | G | A | u | A | c | | |
☐ RNA
☐ 2'-OMe-RNA
▨ DNA
▬ 2'-MOE-RNA
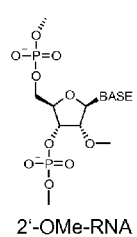
2'-OMe-RNA
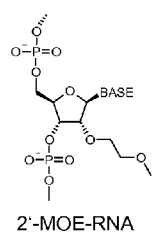
2'-MOE-RNA FIG. 11
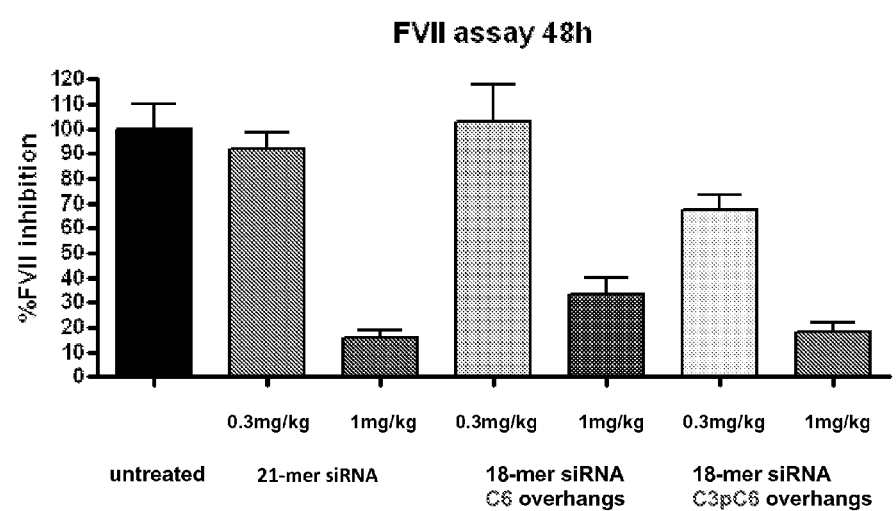
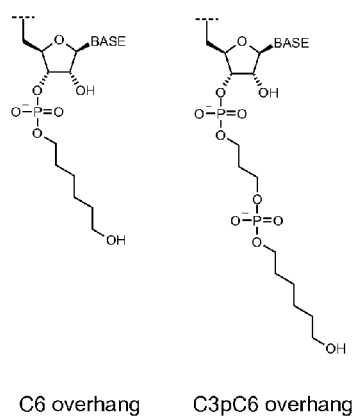
C6 overhang    C3pC6 overhang

FIG. 12

Canonical 21-mer siRNA:

```
                                    19bp stem
                           ┌─────────────────────────┐
guide strand         5'-N NN NNNN NNNNN NNNN-3'
passenger strand     3'-NN N NN     N    NNN  -5'
```

: 2'-OMe
N: 2'-MOE
L: 3' end cap 19-mer or 18-mer format:

```
guide strand         5'-N NN NNNN NNNNN NNL-3'
passenger strand     3'-LNN NN    N    NNN  -5'
                        └─────────────────────┘
                           18 or 19bp stem
```

FIG. 13B.

| Duplex ID | PAZ ligand | NB ref. label or Nickname |
|---|---|---|
| 20 | X109 | hs_ELAVL1_1186_MAN_S42 |
| 21 | X110 | hs_ELAVL1_1186_MAN_S42 |
| 22 | X111 | hs_ELAVL1_1186_MAN_S42 |
| 23 | X112 | hs_ELAVL1_1186_MAN_S42 |
| 24 | X113 | hs_ELAVL1_1186_MAN_S42 |
| 25 | X058 | hs_ELAVL1_1186_MAN_S42 |
| 26 | 21-mer | hs_ELAVL1_1186_A22_S26 |
| 27 | C6 | hs_ELAVL1_1186_A106_S42 |
| 28 | mHamp | mm_HAMP_254_A106*_3'X058_S42 |

PAZ oligos have a DNA modification on the 5' end of AS strand which is different than X058.
This could make a big difference in duration of effect.

| Modification | Modified sequence |
|---|---|
| MAN | U002pUpApApU004pU004pApU004pCpU004pApU004pU004pCpCpGpU005pA005pC027pX109 |
| MAN | UpUpApApU004pU004pApU004pCpU004pApU004pU004pCpCpGpU005pA005pC027pX058 |

FIG. 15
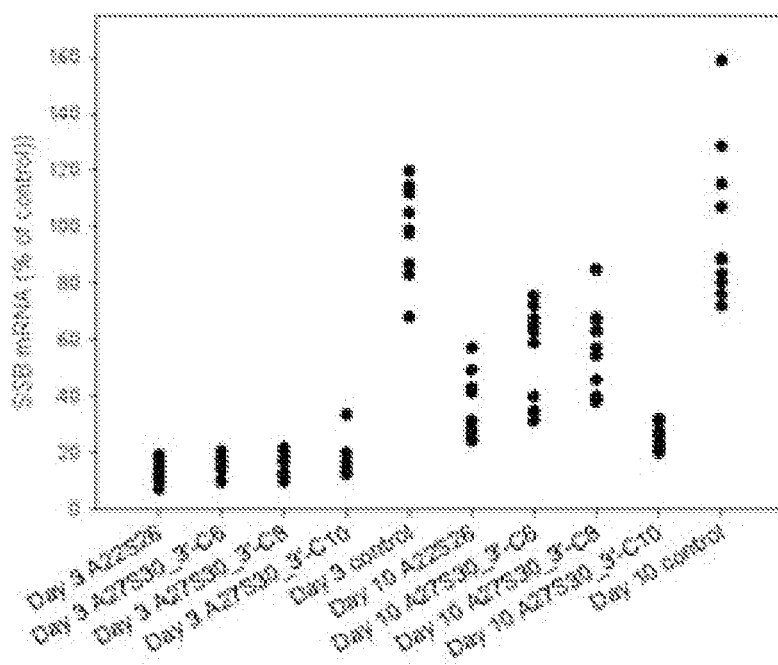
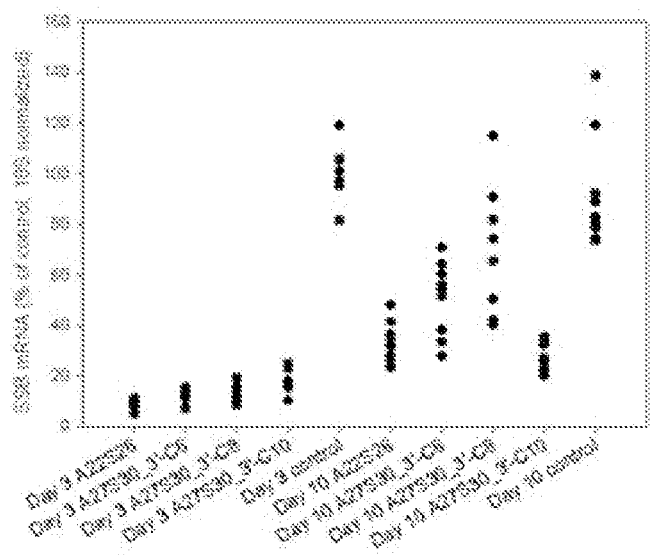

FIG. 16
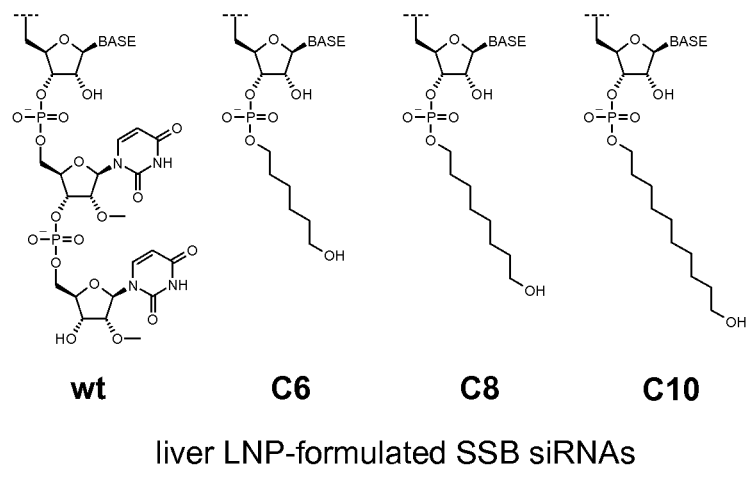
wt  C6  C8  C10
liver LNP-formulated SSB siRNAs
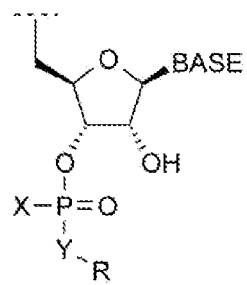
X = O⁻, S⁻, NH$_2$, BH$_3$, CH$_3$, alkyl, aryl, O-alkyl, O-aryl
Y = O, S, NH, CH$_2$
R = alkyl, aryl, alkyl-aryl, aryl-alkyl, ... (PAZ ligand)

FIG. 17
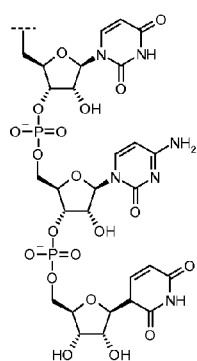
CU overhang
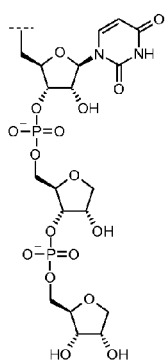
diribitol
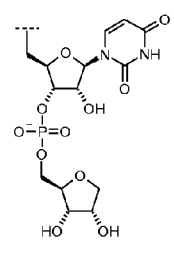
ribitol
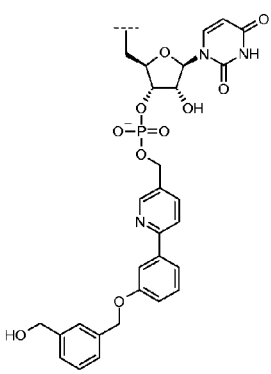
X027
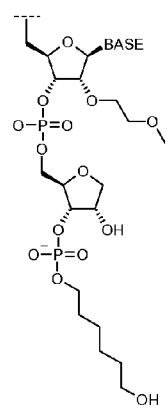
ribitol with C6 cap
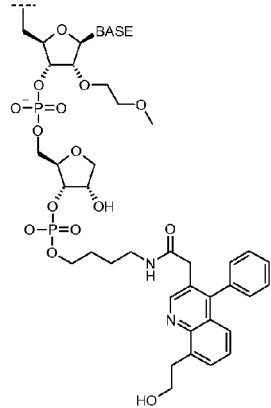
ribitol with X058 cap

FIG. 18
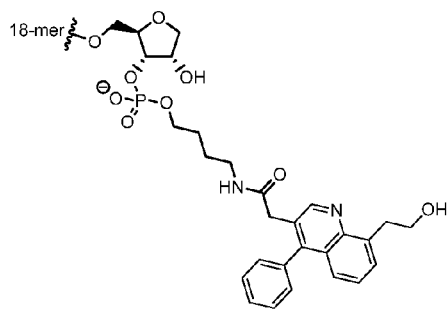
Ribitol X058
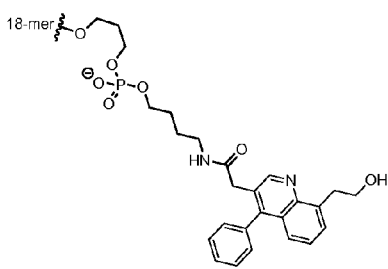
C3 X058
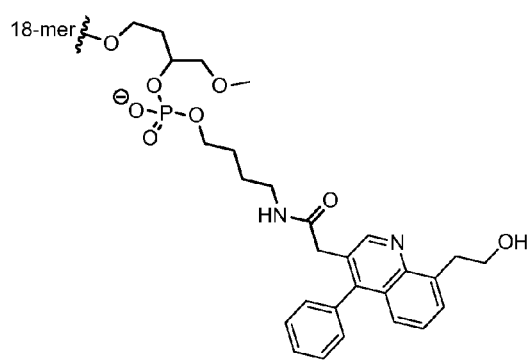
A5300 X058

| Duplex ID | HuR description | IC50 |
|---|---|---|
| 1 | ribitol and X058 (control) | 2.92 pM |
| 2 | ribitol and C6 (control) | 1.48 pM |
| 3 | C3 in place of ribitol and X058 | 11.83 pM |
| 4 | C3 in place of ribitol and C6 | 2.41 pM |
| 5 | C5300 in place of ribitol and X058 | 3.72 pM |
| 6 | C5300 in place of ribitol and C6 | 1.83 pM |

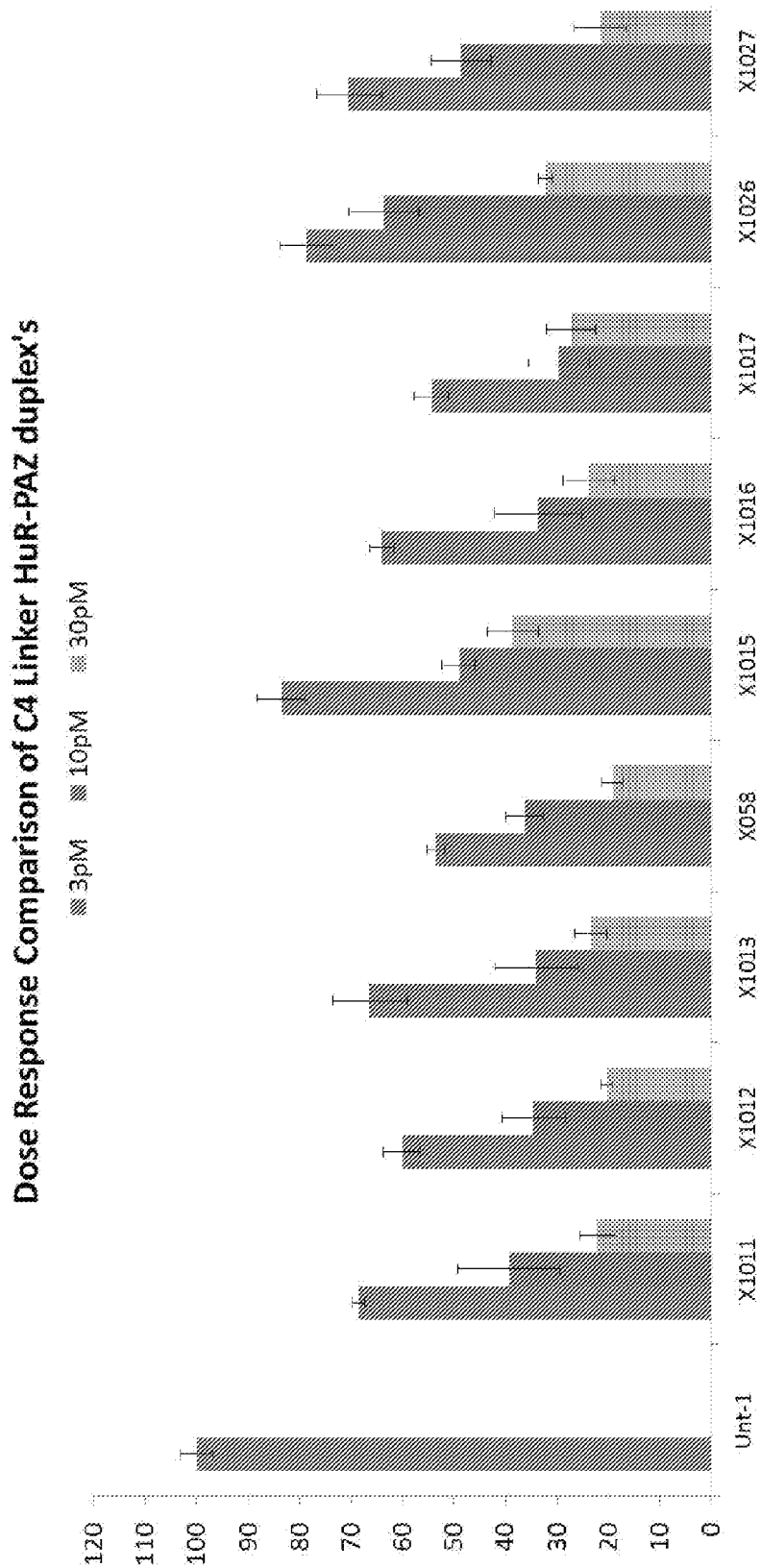

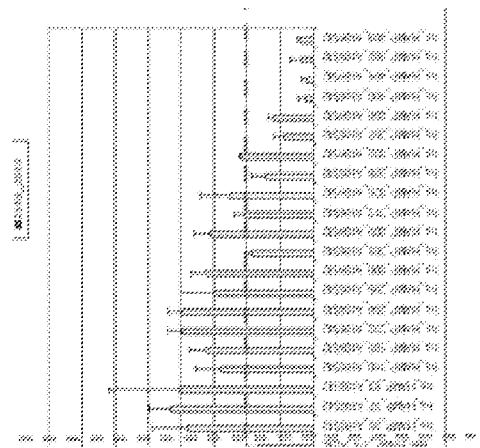
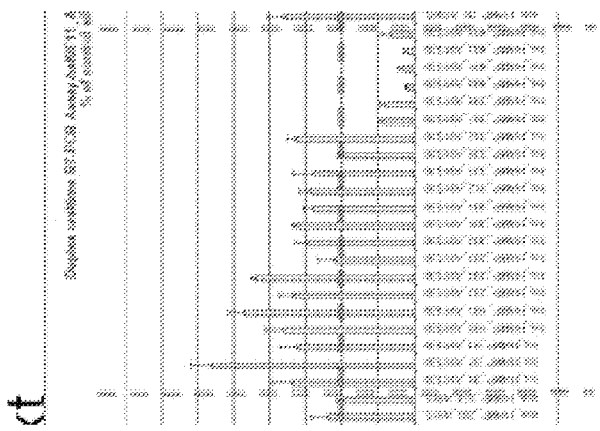
FIG. 27.

US 9,988,627 B2

FORMATS FOR ORGANIC COMPOUNDS FOR USE IN RNA INTERFERENCE

RELATED APPLICATIONS

This application is the U.S. National Phase under 35 U.S.C. § 371 of International Patent Application No. PCT/US2014/059301, filed Oct. 6, 2014, which claims priority to and the benefit of U.S. Provisional Application Ser. No. 61/886,748, filed Oct. 4, 2013 and U.S. Provisional Application Ser. No. 62/025,164, filed Jul. 16, 2014.

SEQUENCE LISTING

The instant application contains a Sequence Listing which has been submitted electronically in ASCII format. Said ASCII copy, created on Mar. 11, 2015, is named PAT055437-WO-PCT02_SL.txt and is 43,447 bytes in size.

FIELD OF THE INVENTION

The disclosure relates to compositions comprising a RNAi agent having a novel format with at least one internal spacer subunit. In some embodiments, these RNAi agents comprise a first and a second 18-mer strand, wherein the first strand is 18 ribonucleotides or 18 total ribonucleotides and spacer subunit(s), and the second strand is 18 total ribonucleotides and spacer subunit(s), wherein: each spacer subunit consists of: (a) a phosphate or modified internucleoside linker and (b) a spacer; a spacer subunit can be at any position in the strand; the two strands form a duplex with at least one blunt end; and the 3' end of one or both strands terminates in a phosphate or modified internucleoside linker and further comprises, in 5' to 3' order: a second spacer; a second phosphate or modified internucleoside linker, and a 3' end cap. In various embodiments, the second strand is 17 ribonucleotides and 1 spacer subunit; 16 ribonucleotides and 2 spacer subunits; or 15 ribonucleotides and 3 spacer subunits; etc. In various embodiments, the spacer subunit is at a position 1 and the duplex forms a blunt-end at the opposite end. In various embodiments, the spacer subunit is at position 18 and the duplex forms a blunt-end at the opposite end. In various embodiments, the spacer subunit is at a non-terminal position (any of 2 to 17) and the duplex is blunt-ended (having two blunt ends). In various embodiments, the first stand is an antisense strand and the second strand is a sense strand. In other embodiments, the first strand is a sense strand and the second strand is an antisense strand. In various embodiments, one or more ribonucleotide (each consisting of a phosphate, a sugar and a base) can be modified or substituted at the phosphate, sugar or base. Various modifications and substitutions are described herein. A spacer subunit comprises (a) a phosphate or modified internucleoside linker and (b) a spacer, but is not a nucleotide or ribonucleotide, as it does not have all of: a phosphate, sugar and base. Various suitable spacers are described herein; a RNAi agent can comprise spacers which are all identical, or a variety of different types of spacers. A 3' end cap is also not a nucleotide or ribonucleotide as it does not have all of: a phosphate, sugar and base; a variety of suitable 3' end caps are described herein. The RNAi agent can also comprise: phosphates but no modified internucleoside linkers; or phosphates and one or more modified internucleoside linker(s) which are all identical or of a variety of different types. Optionally, the first and/or second strand can be modified at the 5' end. Optionally, the sense strand can comprise a 5' end cap which reduces the amount of RNA interference (RNAi) mediated by this strand. Optionally, the RNAi agent is attached to a ligand. RNAi agents having a 18-mer format with at least one internal spacer at any position are shown herein to be efficacious in mediating RNA interference and can be used to devise RNAi agents to a variety of different targets and sequences. In various embodiments, the RNAi agents capable of mediating RNA interference comprise a first and a second 18-mer strand, wherein the first strand is 18 total of: (a) 13-17 ribonucleotides or modified ribonucleotides, (b) at least 1 spacer subunit, and optionally (c) 0-4 of any of DNA, PNA, LNA, TNA, GNA, ANA, FANA, CeNa, HNA or UNA; and the second strand is 18 total of: (a) 13-18 ribonucleotides or modified ribonucleotides, optionally (b) at least 1 spacer subunit, and optionally (c) 0-4 of any of DNA, PNA, LNA, TNA, GNA, ANA, FANA, CeNa, HNA or UNA; wherein: each spacer subunit is (a) a phosphate or modified internucleoside linker and (b) a spacer; a spacer subunit can be at any position in the strand; the two strands form a duplex with at least one blunt end; and the 3' end of one or both strands terminates in a phosphate or modified internucleoside linker and further comprises, in 5' to 3' order: a second spacer; a second phosphate or modified internucleoside linker, and a 3' end cap. The spacer, modified internucleoside linker and 3' end cap can be any of these described herein or known in the art. In some embodiments, the spacer subunit is at an internal position (any of positions 2 to 17 counting 5' to 3') and the two 18-mer strands form a blunt-ended duplex. In various embodiments, the RNAi agents comprise a first and a second strand, wherein each strand is a 30-mer or shorter, the first strand comprises ribonucleotides, and the second strand comprises ribonucleotides and one or more spacer subunit(s), wherein: each spacer subunit consists of: (a) a phosphate or modified internucleoside linker and (b) a spacer; a spacer subunit can be at any position in the strand. In various embodiments, the RNAi agents comprise a first and a second strand, wherein each strand is a 30-mer or shorter, the each comprises ribonucleotides and one or more spacer subunit(s), wherein: each spacer subunit consists of: (a) a phosphate or modified internucleoside linker and (b) a spacer; a spacer subunit can be at any position in the strand. In various embodiments, the disclosure pertains to a composition comprising a RNAi agent comprising a first and a second strand, wherein each strand is a 30-mer or shorter, the first strand is (a) ribonucleotides or modified ribonucleotides and optionally (b) up to 4 DNA nucleotides, and the second strand is (a) ribonucleotides or modified ribonucleotides, (b) one or more spacer subunit(s), and (c) optionally up to 4 DNA nucleotides; wherein: each spacer subunit consists of: (a) a phosphate or modified internucleoside linker and (b) a spacer; and wherein the spacer subunit can be at any position in the strand, wherein the 3' end of at least one strand optionally terminates in a phosphate or modified internucleoside linker and optionally further comprises, in 5' to 3' order: a second spacer; a second phosphate or modified internucleoside linker; and a 3' end cap. The disclosure also relates to processes for making such RNAi agents, and methods and uses of such RNAi agents, e.g., to mediate RNA interference.

BACKGROUND OF THE INVENTION

RNA interference (RNAi) is a post-transcriptional, targeted gene-silencing technique that uses double-stranded RNA (dsRNA) to degrade messenger RNA (mRNA) containing the same sequence as the dsRNA. The process of RNAi occurs naturally in a cell when ribonuclease III (Dicer) cleaves the longer dsRNA into shorter fragments called siRNAs. The smaller RNA segments then mediate the degradation of the target mRNA. Dicer has also been implicated in the excision of small temporal RNAs (stRNAs) from precursor RNA of conserved structure that are implicated in translational control. Hutvagner et al. 2001 Science 293: 834. The RNAi response also features an endonuclease complex, commonly referred to as an RNA-induced silencing complex (RISC), which mediates cleavage of single-stranded mRNA complementary to the antisense strand of the siRNA. Cleavage of the target RNA takes place in the middle of the region complementary to the antisense strand of the siRNA duplex.

siRNAs naturally generated by Dicer typically comprise two 21-nt RNA strands, which have a 19-bp duplex region and two dinucleotide overhangs. See, for example, Elbashir et al. 2001 Nature 411: 494-498; Elbashir et al. 2001 EMBO J. 20: 6877. This is the so-called "canonical" structure of siRNAs.

There exists the continuing need to develop novel artificial structures which have improved activities, e.g., increased RNA interference activity, increased duration of activity, increased resistance to nuclease degradation and/or increased specificity.

BRIEF SUMMARY OF THE INVENTION

The disclosure relates to compositions comprising a RNAi agent having a novel format, designated herein as the 18-mer format with at least one internal spacer, or the 18-mer format with an internal spacer. These RNAi agents comprise a first and a second 18-mer strand, wherein the first strand is 18 ribonucleotides or 18 total ribonucleotides and spacer subunit(s), and the second strand is 18 total ribonucleotides and spacer subunit(s), wherein: each spacer subunit consists of: (a) a phosphate (designated herein as "p" or "PO") or modified internucleoside linker and (b) a spacer; a spacer subunit can be at any position in the strand; the two strands form a duplex with at least one blunt end; and the 3' end of one or both strands terminates in a phosphate or modified internucleoside linker and further comprises, in 5' to 3' order: a second spacer; a second phosphate or modified internucleoside linker, and a 3' end cap. The efficacy of RNAi agents of this format is shown herein. In various embodiments, the spacer subunits are at a non-terminal position (e.g., the spacer subunits are at any of positions 2 to 17 of an 18-mer). In various embodiments, the spacer subunits are at a non-terminal position and the two strands form a blunt-ended duplex. In various embodiments, the RNAi agents capable of mediating RNA interference comprise a first and a second 18-mer strand, wherein the first strand is 18 total of: (a) 13-17 ribonucleotides or modified ribonucleotides, (b) at least 1 spacer subunit, and optionally (c) up to 4 of any of DNA, PNA, LNA, TNA, GNA, ANA, FANA, CeNa, HNA or UNA; and the second strand is 18 total of: (a) 13-18 ribonucleotides or modified ribonucleotides, optionally (b) at least 1 spacer subunit, and optionally (c) 0-4 of any of DNA, PNA, LNA, TNA, GNA, ANA, FANA, CeNa, HNA or UNA; wherein: each spacer subunit is (a) a phosphate or modified internucleoside linker and (b) a spacer; a spacer subunit can be at any position in the strand; the two strands form a duplex with at least one blunt end; and the 3' end of one or both strands terminates in a phosphate or modified internucleoside linker and further comprises, in 5' to 3' order: a second spacer; a second phosphate or modified internucleoside linker, and a 3' end cap. Thus, the first strand can be, as non-limiting examples: (a) 17 ribonucleotides or modified ribonucleotides and 1 spacer subunit; (b) 14 ribonucleotides or modified ribonucleotides and 1 spacer subunit and 3 DNA nucleotides; (c) 16 ribonucleotides or modified ribonucleotides and 2 spacer subunits; (d) 14 ribonucleotides or modified ribonucleotides and 1 spacer subunit and 3 LNA units (mers); (e) 14 ribonucleotides or modified ribonucleotides and 1 spacer subunit and 3 TNA units (mers); etc. The second strand can comprise, as non-limiting examples: (a) 18 ribonucleotides or modified ribonucleotides; (b) 17 ribonucleotides or modified ribonucleotides and 1 spacer subunit; (c) 14 ribonucleotides or modified ribonucleotides and 1 spacer subunit and 3 DNA nucleotides; (d) 16 ribonucleotides or modified ribonucleotides and 2 spacer subunits; (e) 14 ribonucleotides or modified ribonucleotides and 1 spacer subunit and 3 LNA units (mers); (f) 14 ribonucleotides or modified ribonucleotides and 1 spacer subunit and 3 TNA units (mers); etc. The spacer, modified internucleoside linker and 3' end cap can be any of these described herein or known in the art. In some embodiments, the spacer subunit is at an internal position (any of positions 2 to 17 counting 5' to 3') and the two 18-mer strands form a blunt-ended duplex. In various embodiments, the disclosure pertains a novel format described herein as a RNAi agent with an internal spacer. These RNAi agents comprise a first and a second strand, wherein each strand is a 30-mer or shorter, the first strand comprises ribonucleotides, and the second strand comprises ribonucleotides and spacer subunit(s), wherein: each spacer subunit consists of: (a) a phosphate (designated herein as "p" or "PO") or modified internucleoside linker and (b) a spacer; a spacer subunit can be at any position in the strand. In various embodiments, the disclosure pertains to a composition comprising a RNAi agent comprising a first and a second strand, wherein each strand is a 30-mer or shorter, the first strand is (a) ribonucleotides or modified ribonucleotides and optionally (b) up to 4 DNA nucleotides, and the second strand is (a) ribonucleotides or modified ribonucleotides, (b) one or more spacer subunit(s), and (c) optionally up to 4 DNA nucleotides; wherein: each spacer subunit consists of: (a) a phosphate or modified internucleoside linker and (b) a spacer; and wherein the spacer subunit can be at any position in the strand, wherein the 3' end of at least one strand optionally terminates in a phosphate or modified internucleoside linker and optionally further comprises, in 5' to 3' order: a second spacer; a second phosphate or modified internucleoside linker; and a 3' end cap. In various embodiments, the two strands form a duplex with at least one blunt end. In various embodiments, the 3' end of one or both strands terminates in a phosphate or modified internucleoside linker and (a) further comprises a 3' end cap; or (b) further comprises, in 5' to 3' order: a second spacer; a second phosphate or modified internucleoside linker, and a 3' end cap. In some embodiments, the spacer is a ribitol. In various embodiments, the first stand is an antisense strand and the second strand is a sense strand. In other embodiments, the first strand is a sense strand and the second strand is an antisense strand. In various embodiments, one or more ribonucleotide (each consisting of a phosphate, a sugar and a base) can be modified or substituted at the phosphate, sugar or base. Various modifications and substitutions are described herein. A spacer subunit comprises (a) a phosphate or modified internucleoside linker and (b) a spacer, but is not a nucleotide or ribonucleotide, as it does not have all of: a phosphate, sugar and base. Various suitable spacers are described herein; a RNAi agent can comprise spacers which are all identical, or a variety of different types of spacers. A 3' end cap is also not a nucleotide or ribonucleotide as it does not have all of: a phosphate, sugar and base; a variety of suitable 3' end caps are described herein. The RNAi agent can also comprise: phosphates but no modified internucleoside linkers; or phosphates and one or more modified internucleoside linker(s) which are all identical or of a variety of different types. Optionally, the first and/or second strand can be modified at the 5' end. Optionally, the sense strand can comprise a 5' end cap which reduces the amount of RNA interference (RNAi) mediated by this strand. Optionally, the RNAi agent is attached to a ligand. RNAi agents having a 18-mer format with at least one internal spacer at any position are shown herein to be efficacious in mediating RNA interference and can be used to devise RNAi agents to a variety of different targets and sequences. The disclosure also relates to processes for making such RNAi agents, and methods and uses of such RNAi agents, e.g., to mediate RNA interference. A variety of modifications and substitutions are described herein, and their efficacy shown. These include a variety of different types, modifications and substitutions of spacer, modified internucleoside linker and 3' end cap.

In various embodiments, at least one spacer is ribitol or other type of abasic nucleotide, 2'-deoxy-ribitol, diribitol, 2'-methoxyethoxy-ribitol (ribitol with 2'-MOE), C3, C4, C5, C6, or 4-methoxybutane-1,3-diol. In various embodiments, the spacers on the sense and anti-sense strands can be the same or different. An abasic nucleotide such as a ribitol is not a nucleotide or ribonucleotide as a nucleotide or ribonucleotide consists of a phosphate, a sugar and a base, and an abasic nucleotide or ribitol does not have all three of these components.

In various embodiments, the modified internucleoside linker is selected from phosphorothioate, phosphorodithioate, phosphoramidate, boranophosphonoate, an amide linker, and a compound of formula (I):

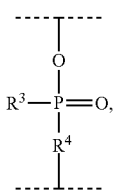

where $R^3$ is selected from $O^-$, $S^-$, $NH_2$, $BH_3$, $CH_3$, $C_{1-6}$ alkyl, $C_{6-10}$ aryl, $C_{1-6}$ alkoxy and $C_{6-10}$ aryl-oxy, wherein $C_{1-6}$ alkyl and $C_{6-10}$ aryl are unsubstituted or optionally independently substituted with 1 to 3 groups independently selected from halo, hydroxyl and $NH_2$; and $R^4$ is selected from O, S, NH, or $CH_2$.

In various embodiments, the 3' end cap is selected from those represented by formula 1a or 1b, disclosed in Tables 1A, 1B, 1C, 1D, 1E, or 1, or otherwise described herein or known in the art. In various embodiments, the 3' end caps on the sense and anti-sense strands can be the same or different.

In one embodiment, the 3' end cap encompasses a compound of formula Ia:

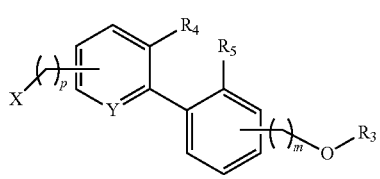

in which:
X is a strand of an RNAi agent, or the 3' end of a molecule comprising a RNAi agent strand which terminates at the 3' end in a phosphate or internucleoside linker and optionally further comprises, in 5' to 3' order: a spacer and a second phosphate or internucleoside linker;

Y is selected from CH and N;

m is selected from 0 and 1;

p is selected from 1, 2 and 3;

$R_3$ is selected from hydrogen, 2-(hydroxy-methyl)-benzyl, 3-(hydroxy-methyl)-benzyl and succinate; or is attached to a solid support; wherein the $(CH_2)_m$—O—$R_3$ moiety is attached to the phenyl ring at position 3 or 4;

$R_4$ is hydrogen;

$R_5$ is hydrogen; or $R_4$ and $R_5$, together with the phenyl rings to which $R_4$ and $R_5$ are attached, form 6H-benzo[c]chromene.

In various embodiments, the 3' end cap encompasses a compound selected from Table 1A.

TABLE 1A

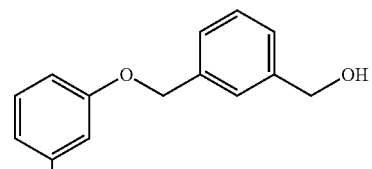

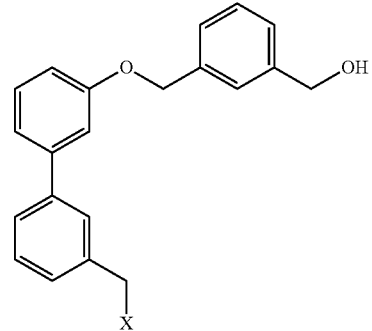

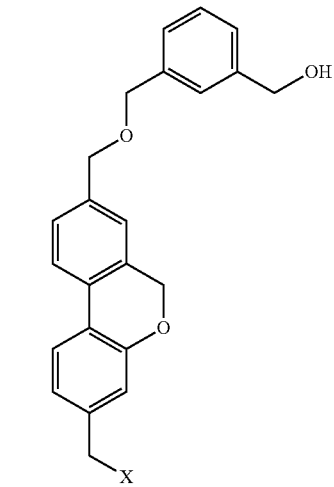

TABLE 1A-continued
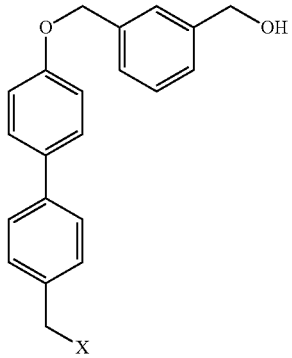
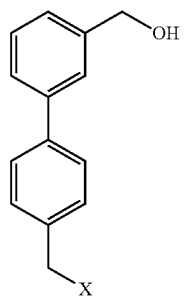
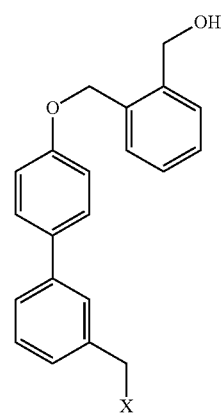
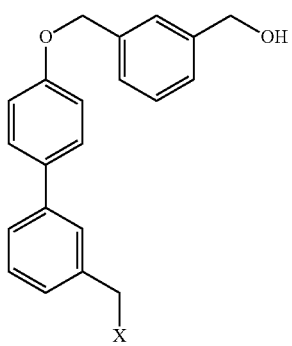
TABLE 1A-continued
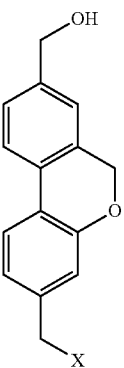
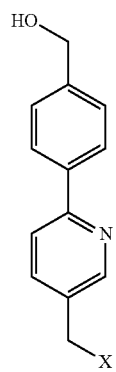
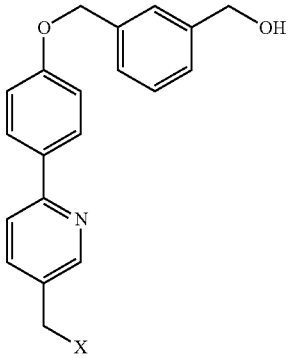
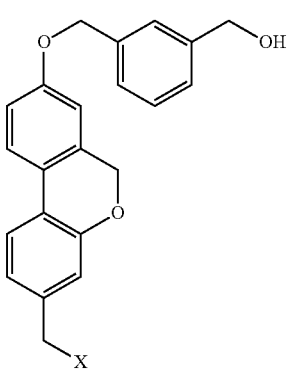

TABLE 1A-continued

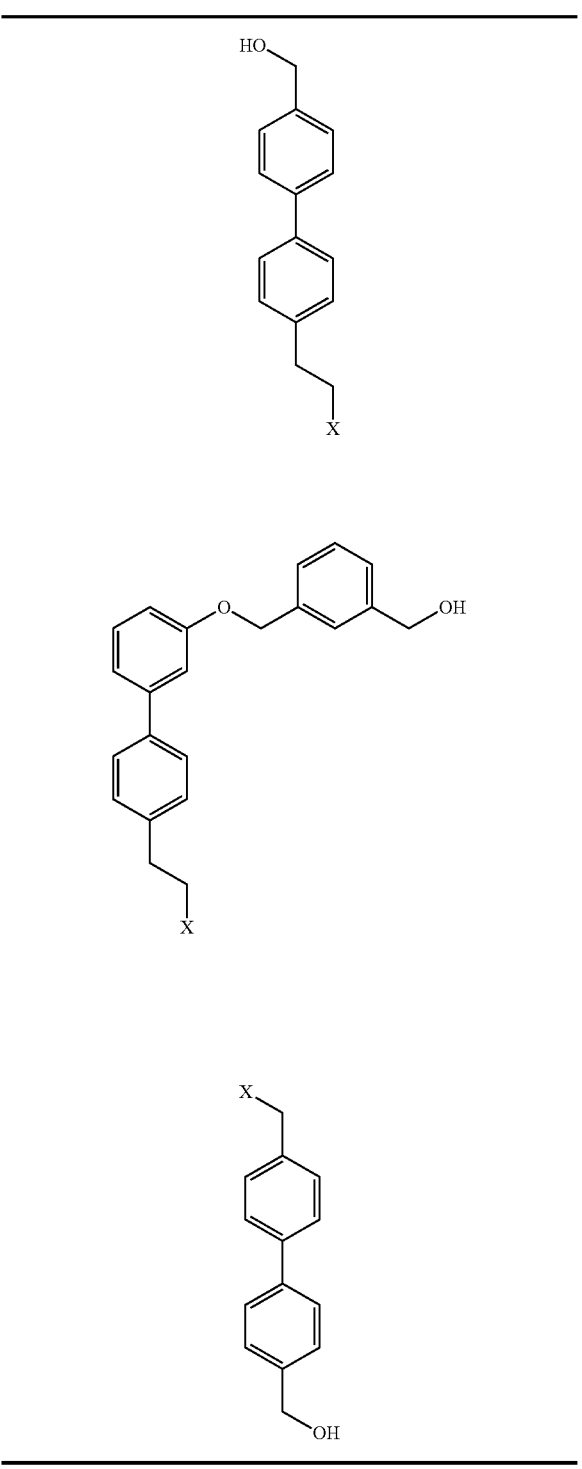

in which:

X is a strand of an RNAi agent, or the 3' end of a molecule comprising a RNAi agent strand which terminates at the 3' end in a phosphate or internucleoside linker and optionally further comprises, in 5' to 3' order: a spacer and a second phosphate or internucleoside linker.

In one embodiment, the 3' end cap encompasses a compound of formula Ib:

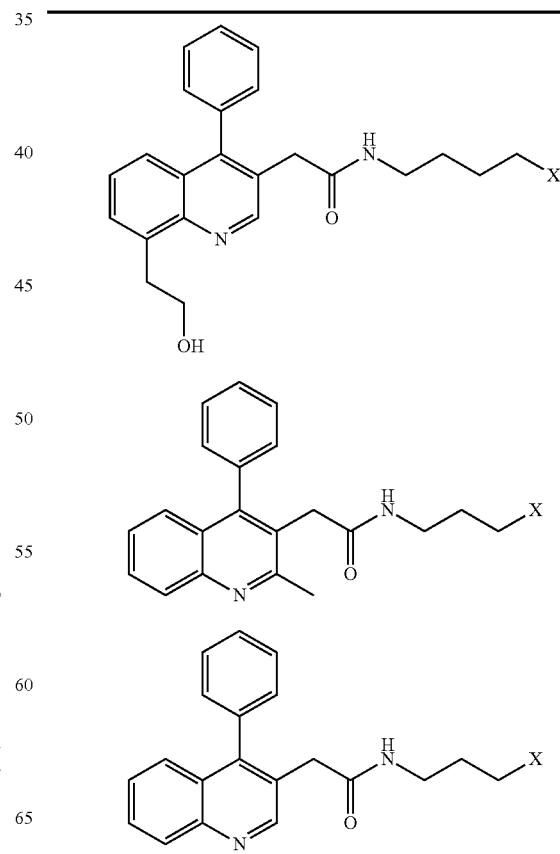

in which:

X is a strand of an RNAi agent, or the 3' end of a molecule comprising a RNAi agent strand which terminates at the 3' end in a phosphate or internucleoside linker and optionally further comprises, in 5' to 3' order: a spacer and a second phosphate or internucleoside linker;

q is selected from 0, 1 and 2;

$R_6$ is selected from phenyl which is unsubstituted or substituted with a group selected from benzoxy and 3,4-dihydroxybutyl;

$R_7$ is selected from hydrogen and hydroxy-ethyl, wherein if $R_7$ is hydroxy-ethyl, the hydroxyl can be optionally functionalized as succinate or attached to a solid support;

$R_8$ is selected from hydrogen and methoxy;

$Y_1$ is selected from CH and N; and $Y_2$ is selected from N and $CR_9$; wherein $R_9$ is selected from hydrogen and methyl.

In various embodiments, the 3' end cap encompasses a compound selected from Table 1B.

TABLE 1B

TABLE 1B-continued
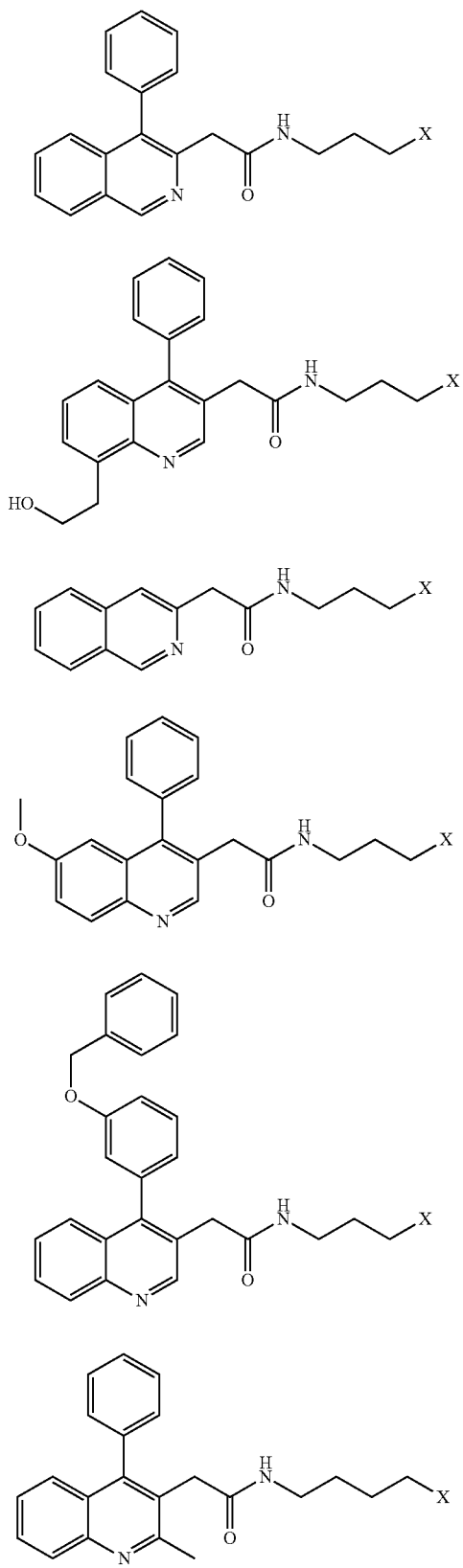
TABLE 1B-continued
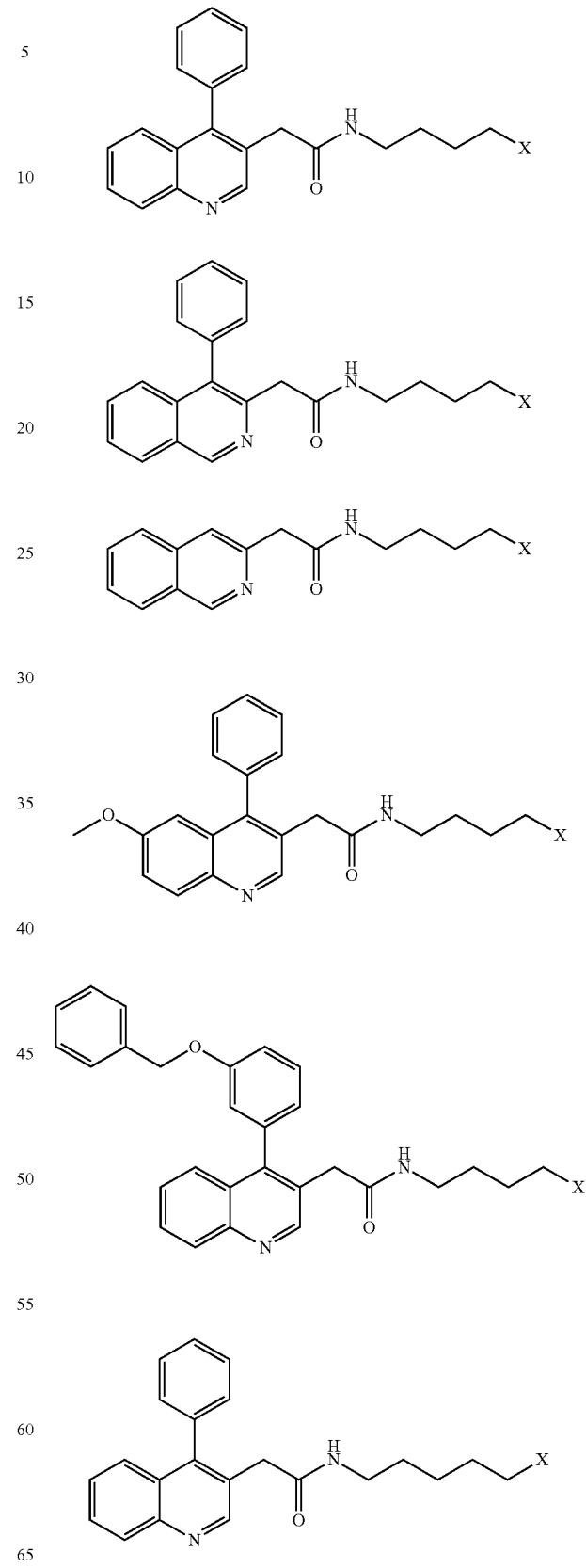

TABLE 1B-continued
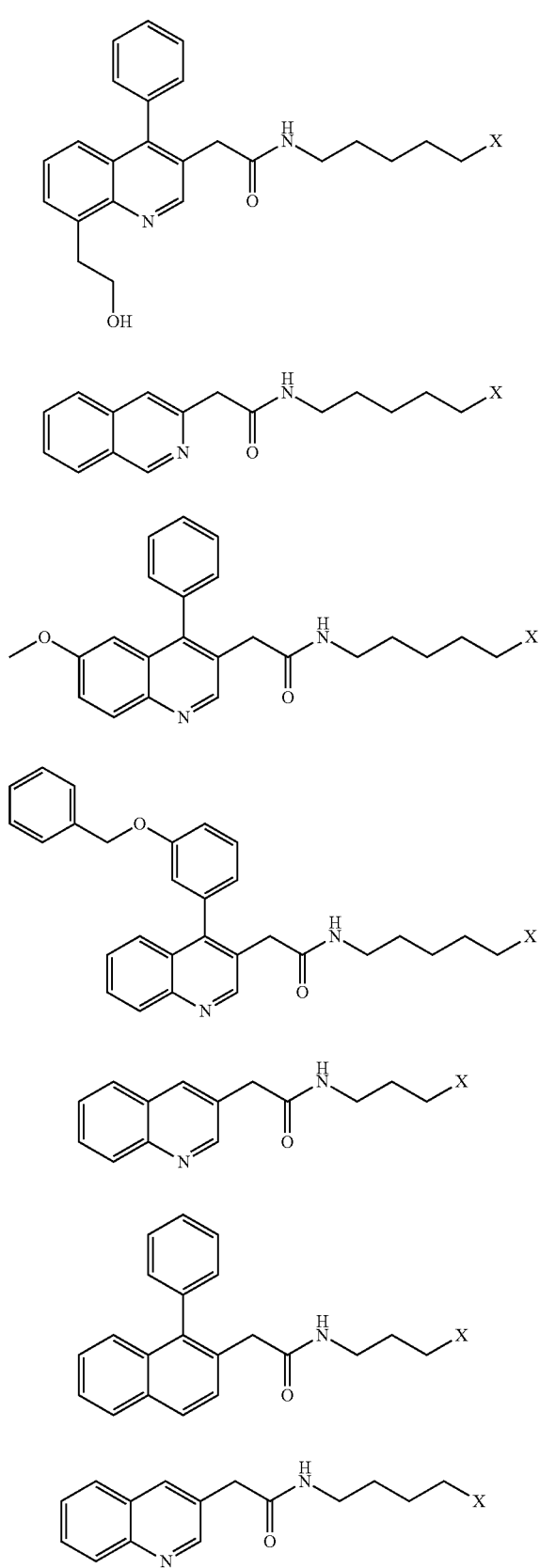
TABLE 1B-continued
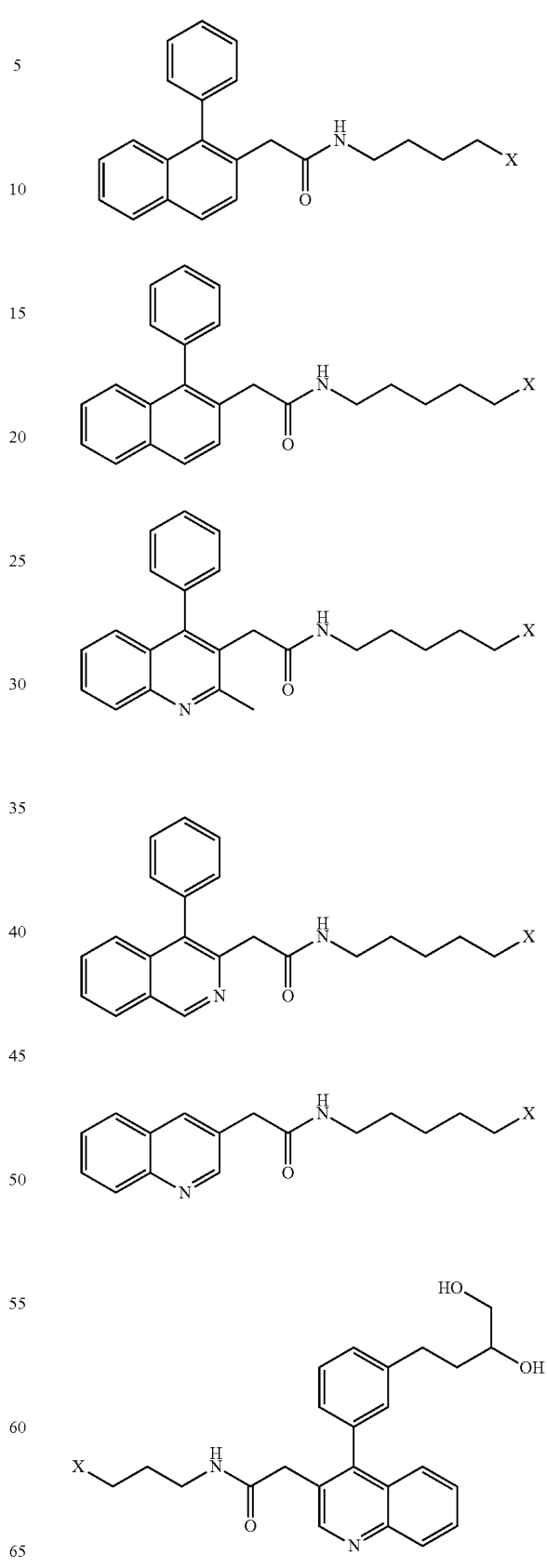

TABLE 1B-continued

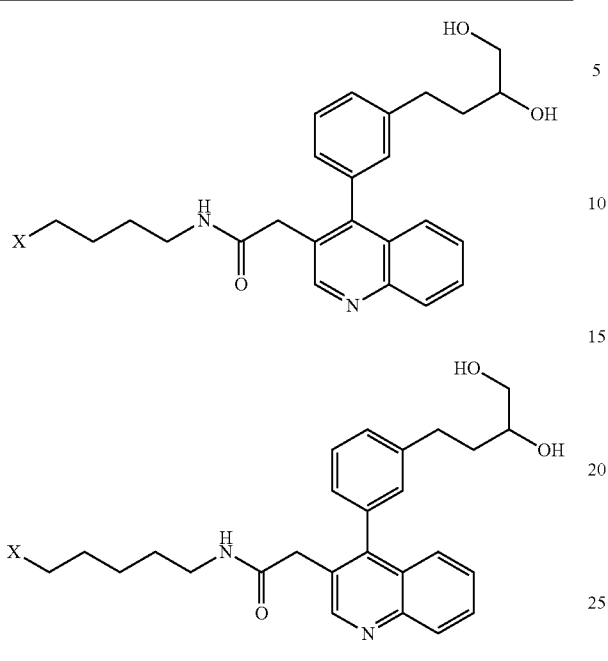

in which:

X is a strand of an RNAi agent, or the 3' end of a molecule comprising a RNAi agent strand which terminates at the 3' end in a phosphate or internucleoside linker and optionally further comprises, in 5' to 3' order: a spacer and a second phosphate or internucleoside linker.

In various embodiments, the 3' end cap encompasses a compound selected from Table 1C.

TABLE 1C

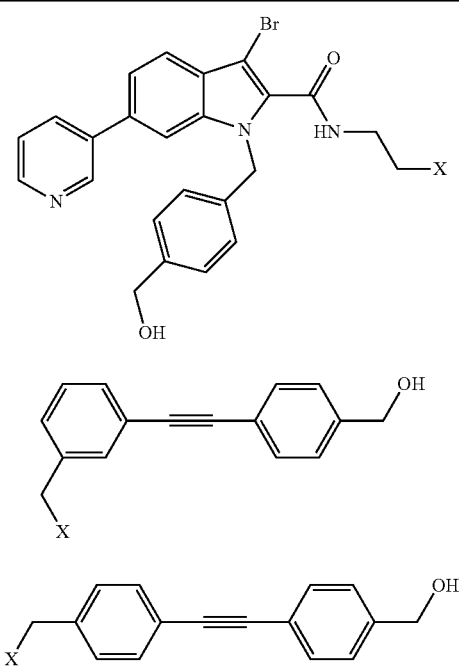

TABLE 1C-continued

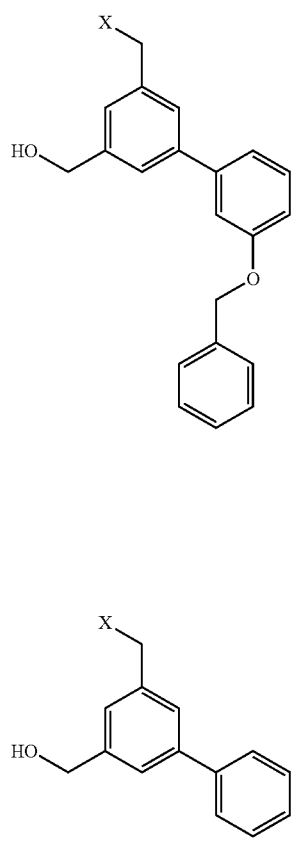

in which

X is a strand of an RNAi agent, or the 3' end of a molecule comprising a RNAi agent strand which terminates at the 3' end in a phosphate or internucleoside linker and optionally further comprises, in 5' to 3' order: a spacer and a second phosphate or internucleoside linker, and q is selected from 1 and 2.

In various embodiments, the 3' end cap encompasses a compound selected from Table 1D.

TABLE 1D

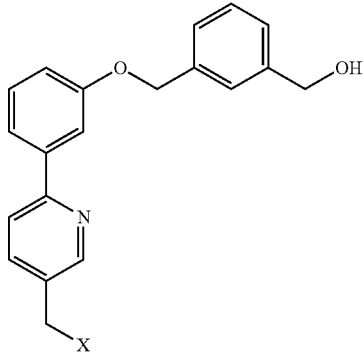

TABLE 1D-continued
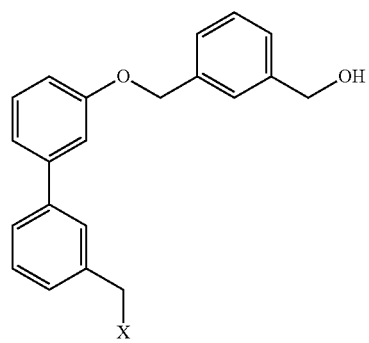
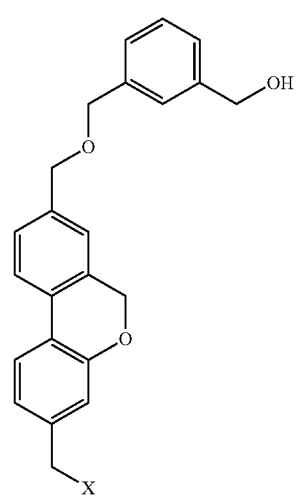
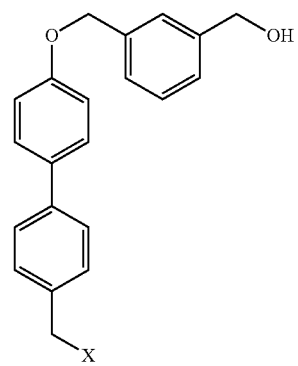
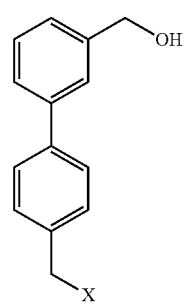
TABLE 1D-continued
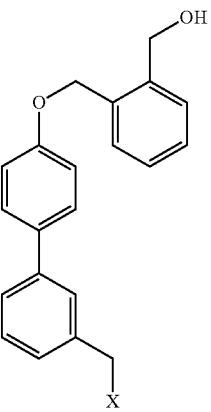
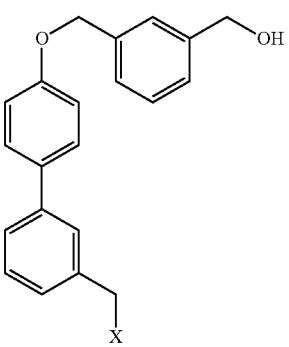
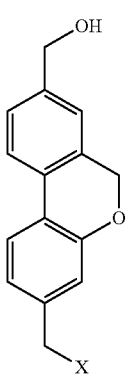
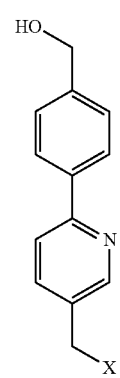

TABLE 1D-continued
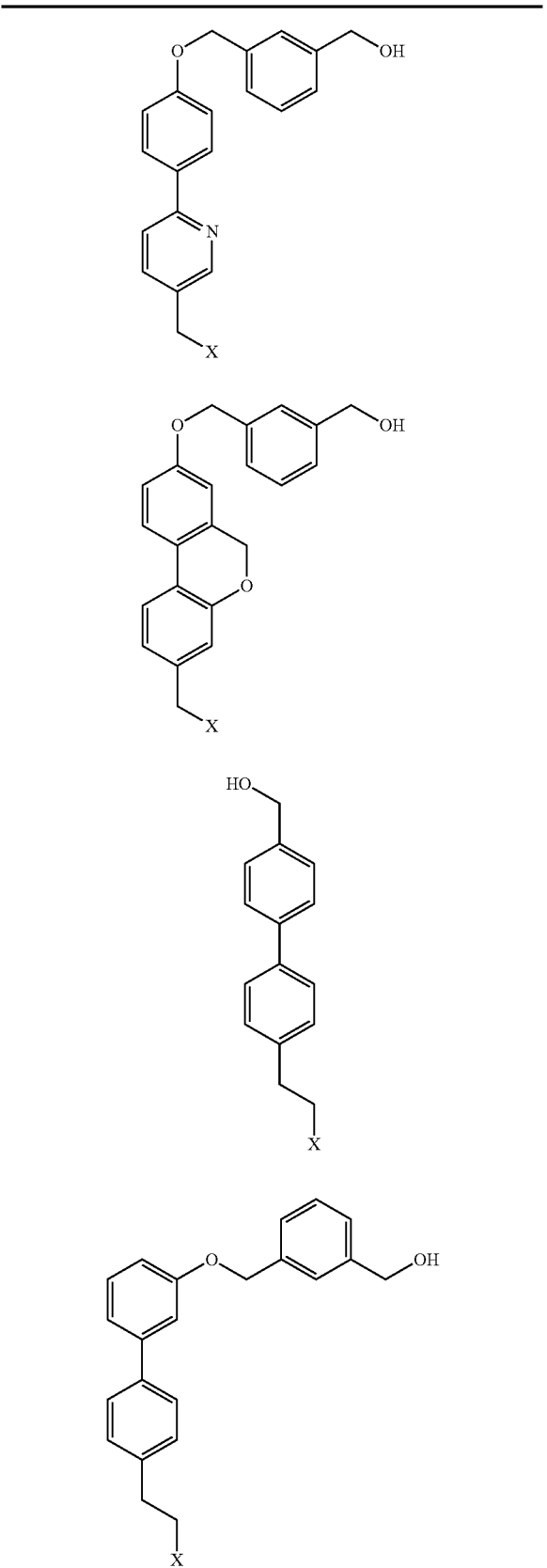
TABLE 1D-continued
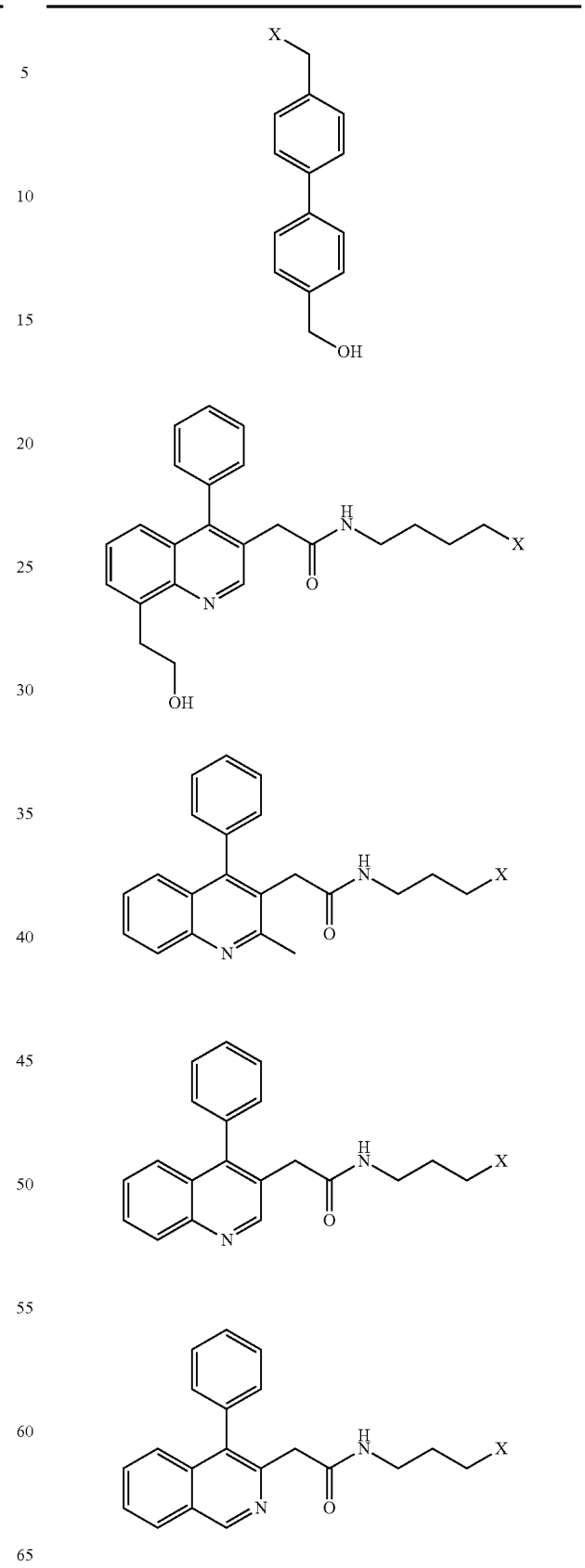

TABLE 1D-continued
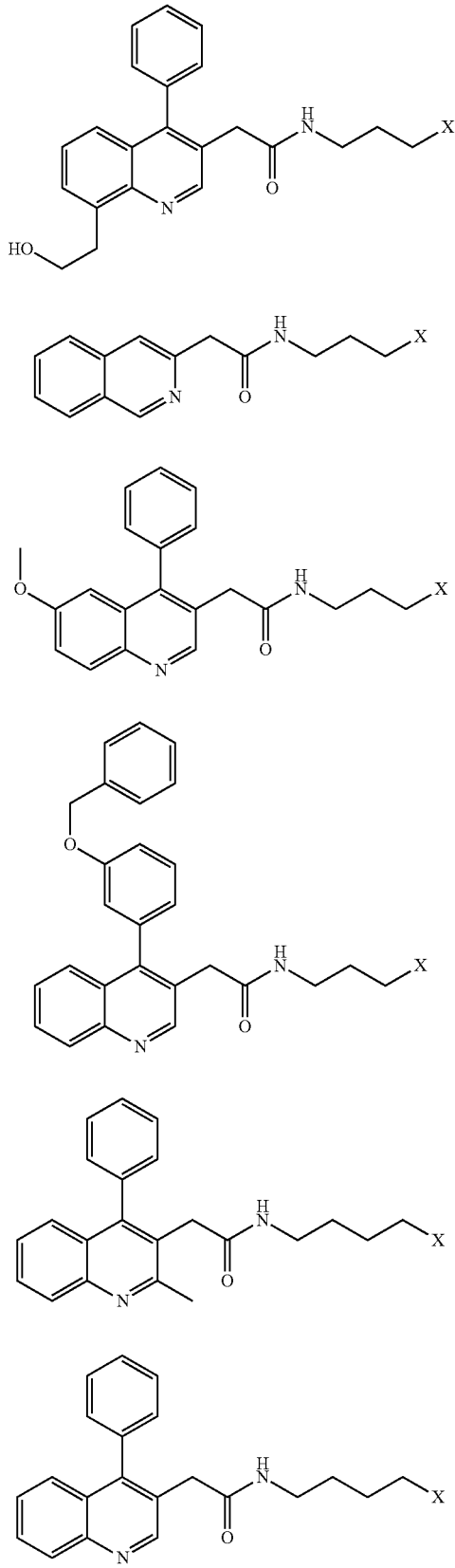
TABLE 1D-continued
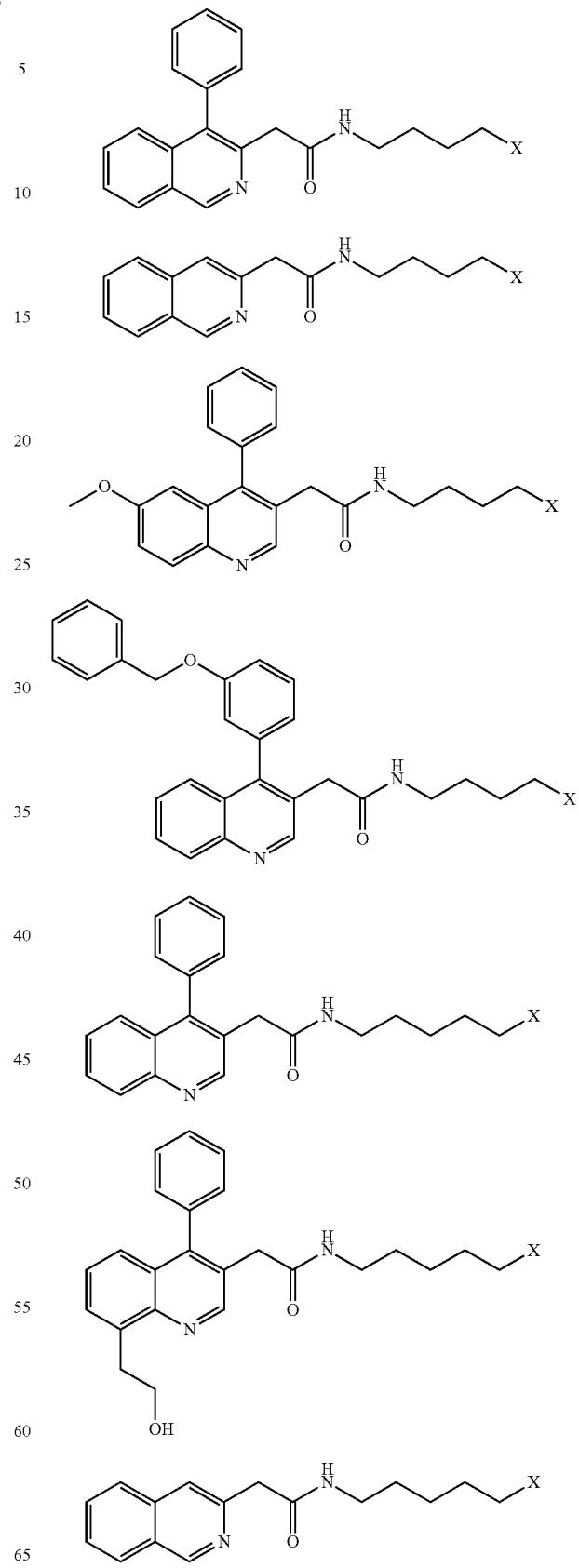

TABLE 1D-continued
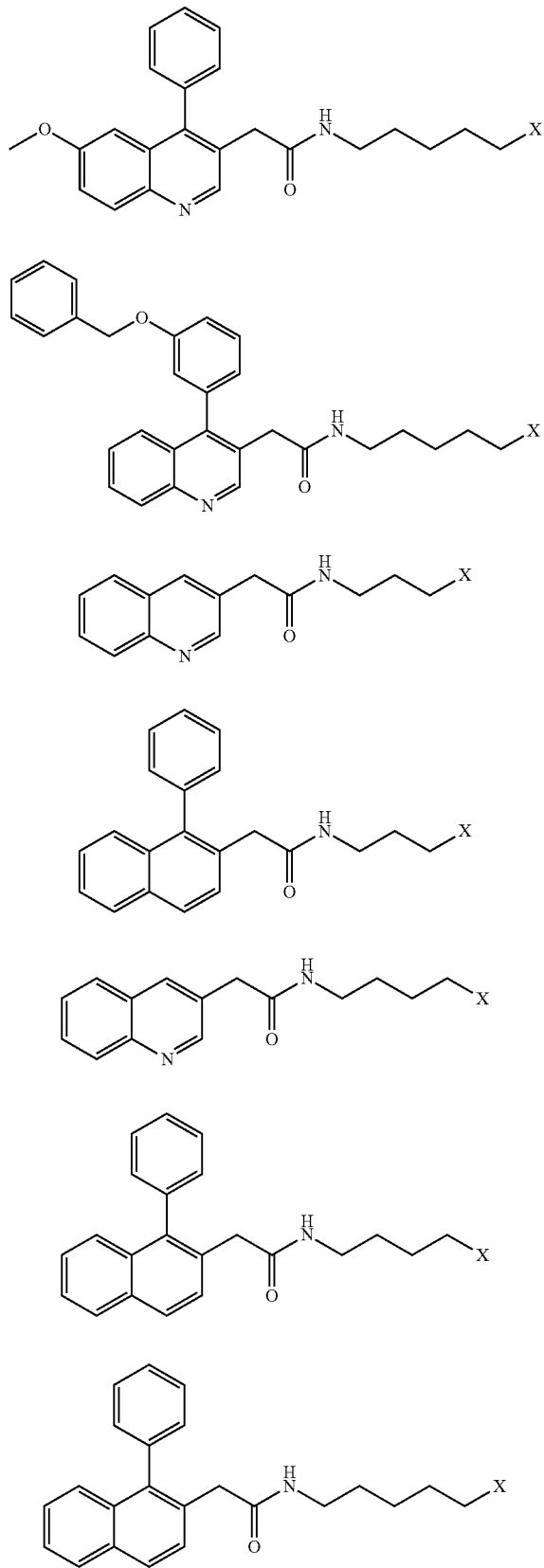
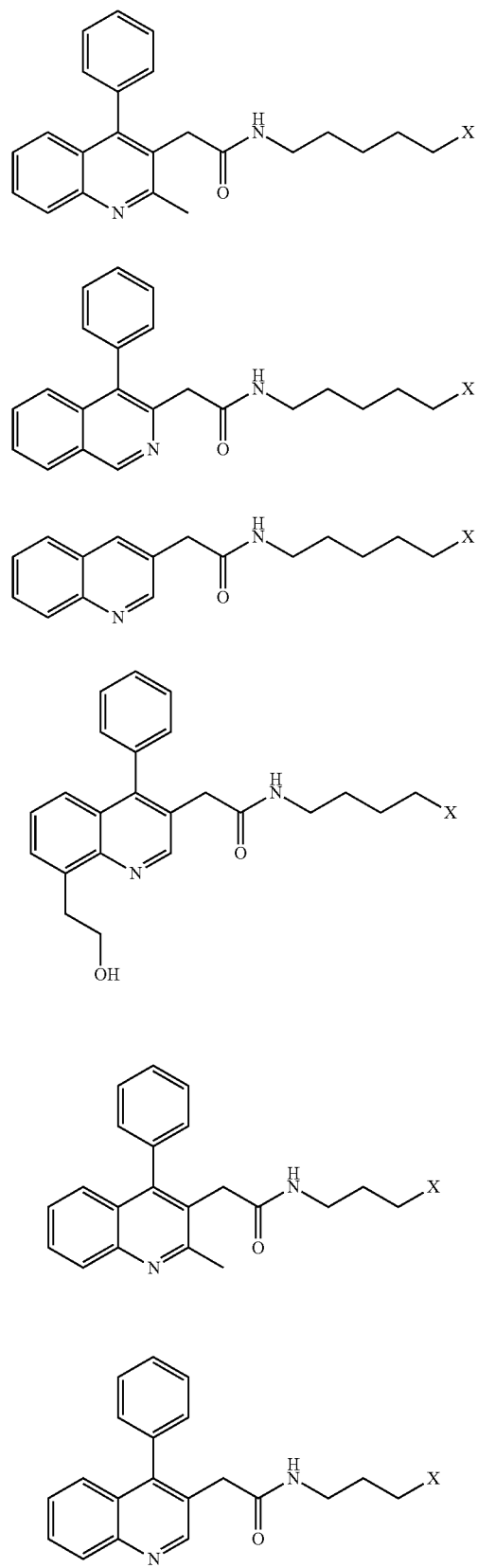

TABLE 1D-continued
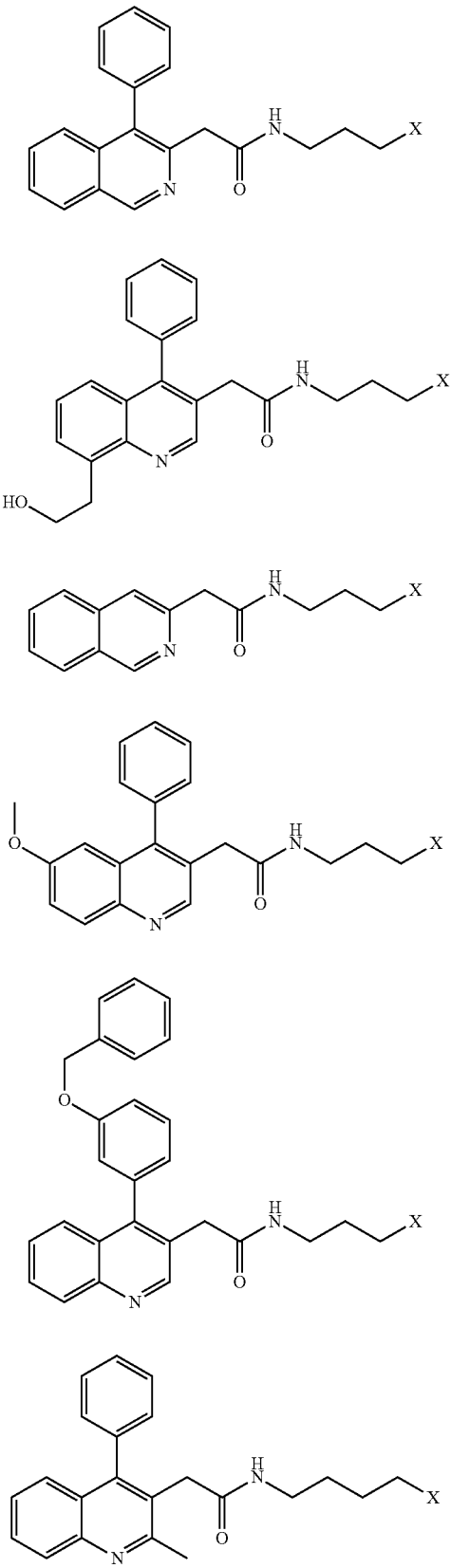
TABLE 1D-continued
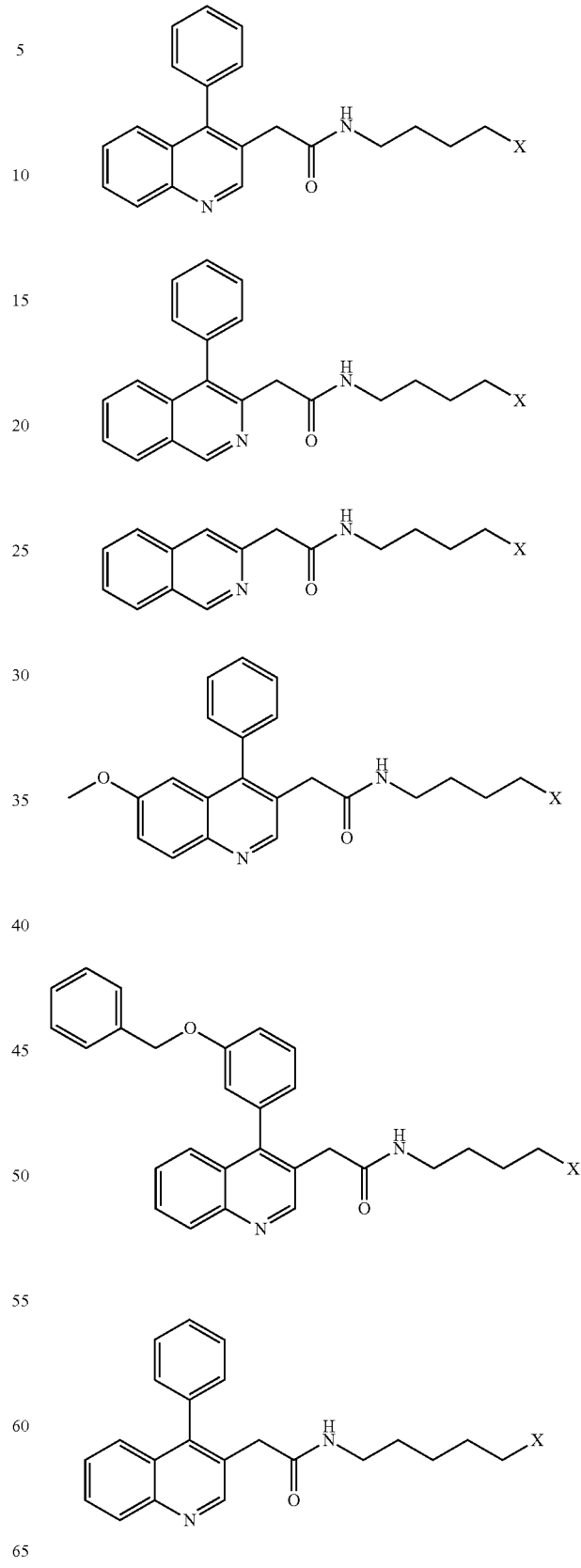

TABLE 1D-continued
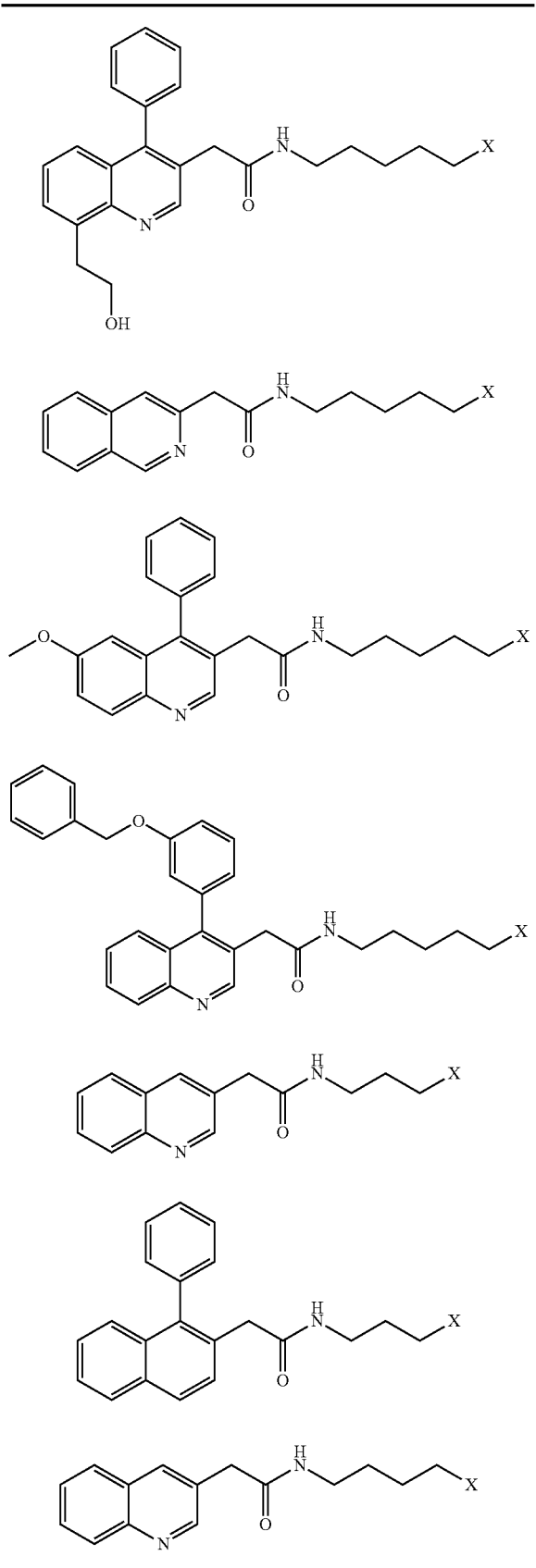
TABLE 1D-continued
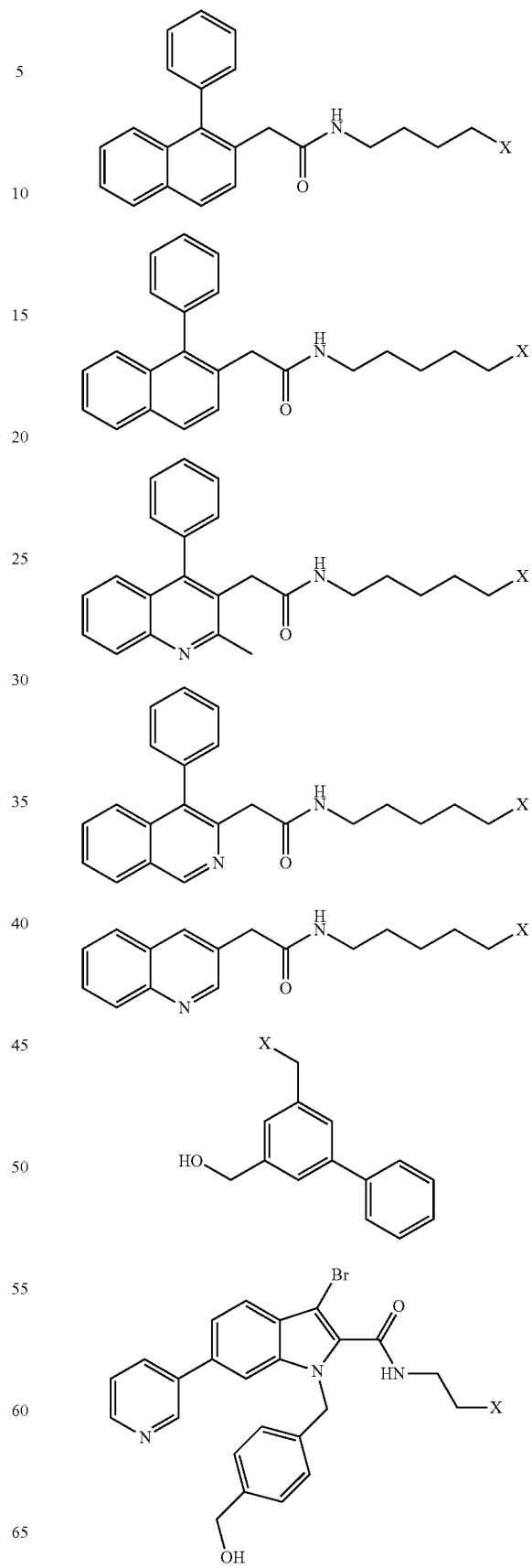

TABLE 1D-continued

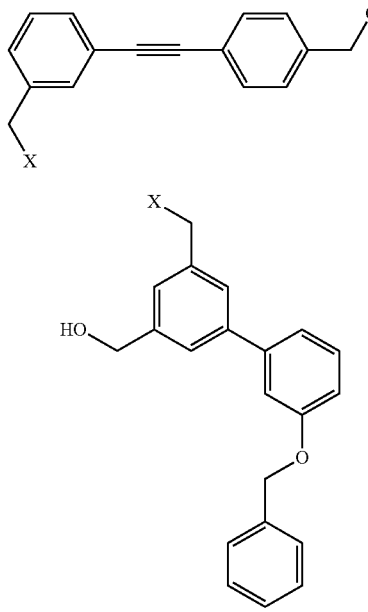

in which

X is a strand of an RNAi agent, or the 3' end of a molecule comprising a RNAi agent strand which terminates at the 3' end in a phosphate or internucleoside linker and optionally further comprises, in 5' to 3' order: a spacer and a second phosphate or internucleoside linker.

In various embodiments, the 3' end cap encompasses a compound selected from Table 1E.

TABLE 1E

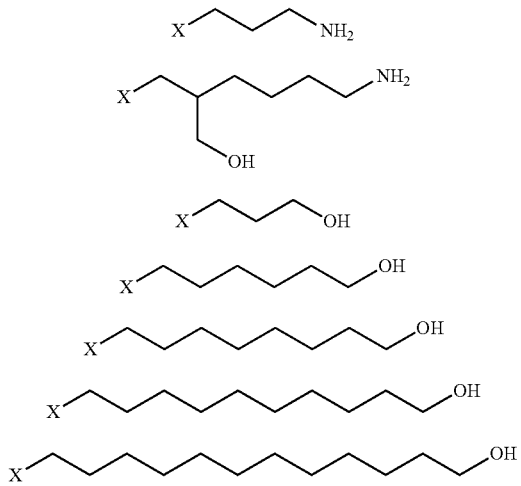

X is a strand of an RNAi agent, or the 3' end of a molecule comprising a RNAi agent strand which terminates at the 3' end in a phosphate or internucleoside linker and optionally further comprises, in 5' to 3' order: a spacer and a second phosphate or internucleoside linker.

In various other embodiments, the 3' end cap is selected from: Triethylene glycol, Cyclohexyl (or Cyclohex), Phenyl, BP (Biphenyl), Adamantane and Lithocholic acid (or Lithochol). These are described in U.S. Pat. Nos. 8,097,716; 8,084,600; 8,344,128; 8,404,831; and 8,404,832.

In some embodiments, the 3' end cap is a ribitol or other type of abasic nucleotide. Thus, in some embodiments, the RNAi agent comprises an 18-mer strand, wherein the 18-mer strand is 18 ribonucleotides or 18 total ribonucleotides and spacer subunits, and wherein the 3' end of the 18-mer strand terminates in a phosphate or modified internucleoside linker and further comprises, in 5' to 3' order: a spacer (e.g., a ribitol or other type of abasic nucleotide, C3, C4, C5, C6, etc.), a phosphate or modified internucleoside linker, and a 3' end cap (e.g., a second ribitol or other type of abasic nucleotide).

Thus, in some embodiments, the RNAi agent comprises an 18-mer strand, wherein the 18-mer strand is 18 ribonucleotides or 18 total ribonucleotides and spacer subunits, and wherein the 3' end of the 18-mer strand terminates in a phosphate or modified internucleoside linker and further comprises, in 5' to 3' order: a ribitol or other type of abasic nucleotide, a phosphate or modified internucleoside linker, and a second ribitol or other type of abasic nucleotide.

In some embodiments, the RNAi agent comprises an 18-mer strand, wherein the 18-mer strand is 18 ribonucleotides or 18 total ribonucleotides and spacer subunits, and wherein the 3' end of the 18-mer strand terminates in a phosphate and further comprises, in 5' to 3' order: a ribitol or other type of abasic nucleotide, a phosphate, and a second ribitol or other type of abasic nucleotide. Such a structure is sometimes designated a "Diribitol" (as diagrammed in FIG. 17. An 18-mer to ELAV1 comprising such a structure is shown to mediate RNAi interference in Table 7 (see "18-mer siRNA with ribprib").

In some embodiments, the RNAi agent comprises an 18-mer strand, wherein the 18-mer strand is 18 ribonucleotides or 18 total ribonucleotides and spacer subunits, and wherein the 3' end of the 18-mer strand terminates in a phosphate or modified internucleoside linker and further comprises, in 5' to 3' order: a spacer, a phosphate or modified internucleoside linker and 3' end cap which is a diribitol. Thus: In some embodiments, the RNAi agent comprises an 18-mer strand, wherein the 18-mer strand is 18 ribonucleotides or 18 total ribonucleotides and spacer subunits, and wherein the 3' end of the 18-mer strand terminates in a phosphate or modified internucleoside linker and further comprises, in 5' to 3' order: a spacer (e.g., a ribitol, C3, C4, C5, C6, etc.), a phosphate or modified internucleoside linker, and a 3' end cap (e.g., a diribitol). In one embodiment, the RNAi agent comprises an 18-mer strand, wherein the 3' end of the 18-mer strand comprises a phosphate and further comprises: a spacer which is ribitol, a second phosphate, and a 3' end cap which is di-ribitol (e.g., a second ribitol, a third phosphate and a third ribitol). This last embodiment is sometimes designated a "tri-ribitol".

In some embodiments, the RNAi agent comprises a 18-mer strand, wherein the 3' end of the 18-mer strand terminates in a phosphate or modified internucleoside linker and further comprises a 3' end cap (but no spacer, or phosphate or modified internucleoside linker). Thus: In some embodiments, the RNAi agent comprises an 18-mer strand, wherein the 18-mer strand is 18 ribonucleotides or 18 total ribonucleotides and spacer subunits, and wherein the 3' end of the 18-mer strand terminates in a phosphate or modified internucleoside linker and further comprises a 3' end cap (e.g., BP, C6, X058 or any other 3' end cap disclosed herein).

In some embodiments, the RNAi agent comprises an 18-mer strand terminating in a 3' phosphate or modified internucleoside linker, and further comprising a spacer (but no phosphate or modified internucleoside linker, or 3' end cap). Thus: In some embodiments, the RNAi agent comprises an 18-mer strand terminating in a 3' phosphate or modified internucleoside linker, and further comprising a spacer (e.g., ribitol). In some embodiments, the RNAi comprises an 18-mer strand terminating in a 3' phosphate or modified internucleoside linker, and further comprising a spacer (e.g., a ribitol). In some embodiments, the RNAi comprises an 18-mer strand terminating in a 3' phosphate or modified internucleoside linker, and further comprising, in 5' to 3' order, a spacer (e.g., a ribitol), a second phosphate or modified internucleoside linker, and a second spacer (e.g., ribitol).

In various embodiments, one or both strands can comprise ribonucleotide subunits, or one or more nucleotide can optionally be modified or substituted. Thus, in various embodiments, the RNAi agent can either contain only naturally-occurring ribonucleotide subunits, or one or more modifications to the sugar, phosphate or base of one or more of nucleotide subunits. In one embodiment, the modifications improve efficacy, stability and/or reduce immunogenicity of the RNAi agent.

One aspect of the present disclosure relates to a RNAi agent comprising at least one non-natural nucleobase. In certain embodiments, the non-natural nucleobase is difluorotolyl, nitroindolyl, nitropyrrolyl, or nitroimidazolyl. In a particular embodiment, the non-natural nucleobase is difluorotolyl. In certain embodiments, only one of the two strands contains a non-natural nucleobase. In certain embodiments, both of the strands contain a non-natural nucleobase.

In one embodiment, the first two base-pairing nucleotides on the 3' end of the sense and/or anti-sense strand are modified. In one embodiment, the first two base-pairing nucleotides on the 3' end of the sense and/or anti-sense strand are 2'-MOE (a 2' MOE clamp).

In one embodiment, the 3' terminal phosphate of the sense and/or anti-sense strands is replaced by a modified internucleoside linker.

In one embodiment, at least one nucleotide of the RNAi agent is modified.

In one embodiment, said at least one modified nucleotide is selected from among 2' alkoxyribonucleotide, 2' alkoxyalkoxy ribonucleotide, or 2'-fluoro ribonucleotide. In another embodiment, said at least one modified nucleotide is selected from 2'-OMe, 2'-MOE and 2'-H. In various aspects, the nucleotide subunit is chemically modified at the 2' position of the sugar. In one aspect, the 2' chemical modification is selected from a halo, a C1-10 alkyl, a C1-10 alkoxy, a halo, and the like. In specific aspects, the 2' chemical modification is a C1-10 alkoxy selected from —OCH$_3$ (i.e., "OMe"), —OCH$_2$CH$_3$ (i.e., "OEt") or —CH$_2$OCH$_2$CH$_3$ (i.e., methoxyethyl or "MOE"); or is a halo selected from F.

In various embodiments, one or more nucleotides is modified or is DNA or is replaced by a peptide nucleic acid (PNA), locked nucleic acid (LNA), morpholino nucleotide, threose nucleic acid (TNA), glycol nucleic acid (GNA), arabinose nucleic acid (ANA), 2'-fluoroarabinose nucleic acid (FANA), cyclohexene nucleic acid (CeNA), anhydrohexitol nucleic acid (HNA), and/or unlocked nucleic acid (UNA); and/or at least one nucleotide comprises a modified internucleoside linker (e.g., wherein at least one phosphate of a nucleotide is replaced by a modified internucleoside linker), wherein the modified internucleoside linker is selected from phosphorothioate, phosphorodithioate, phosphoramidate, boranophosphonoate, an amide linker, and a compound of formula (I) (as described elsewhere herein).

In one embodiment, the first two base-pairing nucleotides on the 3' end of the first and/or second strand are modified.

In one embodiment, the first two base-pairing nucleotides on the 3' end of the first and/or second strand are 2'-MOE.

In various embodiments, one or more nucleotides is modified or is substituted with DNA, a peptide nucleic acid (PNA), locked nucleic acid (LNA), morpholino nucleotide, threose nucleic acid (TNA), glycol nucleic acid (GNA), arabinose nucleic acid (ANA), 2'-fluoroarabinose nucleic acid (FANA), cyclohexene nucleic acid (CeNA), anhydrohexitol nucleic acid (HNA), and/or unlocked nucleic acid (UNA).

In various embodiments, at least one nucleotide comprises a modified internucleoside linker, wherein the modified internucleoside linker is selected from phosphorothioate, phosphorodithioate, phosphoramidate, boranophosphonoate, an amide linker, and a compound of formula (I).

In various embodiments, optionally the 3' terminal phosphate of the sense and/or anti-sense strands is replaced by a modified internucleoside linker.

In various embodiments, the RNAi agent can be modified on one or both 5' end. In various embodiments, the sense strand can comprise a 5' end cap which reduces the amount of the RNA interference mediated by this strand.

In various embodiments, the sense strand comprises a 5' end cap selected: a nucleotide lacking a 5' phosphate or 5'-OH; a nucleotide lacking a 5' phosphate or a 5'-OH and also comprising a 2-OMe or 2'-MOE modification; 5'-deoxy-2'-O-methyl modification; 5'-OME-dT; ddT; and 5'-OTr-dT.

In various embodiments, the RNAi agent is optionally attached to a ligand. The ligand can be selected to improve one or more characteristic, such as, e.g., stability, distribution and/or cellular uptake of the agent, e.g., cholesterol or a derivative thereof.

In various embodiments, the RNAi agent can be isolated or be part of a pharmaceutical composition used for the methods described herein or known in the art.

In various embodiments, the pharmaceutical composition can be a lipid nanoparticle.

In various embodiments, the pharmaceutical composition can be a lipid nanoparticle Optionally, the pharmaceutical compositions can further comprise or be used in conjunction with any known treatment for any target gene-related disease.

The present disclosure further provides methods for reducing the level of target gene mRNA in a cell, particularly in the case of a disease characterized by over-expression or hyper-activity of the target gene product. The present disclosure also encompasses a method of treating a human subject having a pathological state mediated at least in part by target gene expression. Such methods comprise the step of administering to the subject a therapeutic amount of one or more of the RNAi agents of the present disclosure.

In another embodiment, the invention provides an RNAi agent with any one or more of the above properties for use as a medicament.

The methods and compositions of the present disclosure, e.g., the methods and target gene RNAi agent compositions, can be used with any dosage and/or formulation described herein, as well as with any route of administration described herein or known in the art.

In various embodiments, the RNAi agent can be combined with one or more additional RNAi agents in the same formulation. The one or more additional RNAi agents can have the same or different sequences, targets, phosphates or modified internucleoside linkers, spacers, 3' end caps, nucleotide replacements modifications, and/or ligands, etc. In various embodiments, the one or more additional RNAi agents can have a sense and an anti-sense strand wherein each is an 18-mer and together form a blunt-ended duplex. The one or more additional RNAi agent can target the same or different sequence and/or the same or different target gene.

Thus: Multiple RNAi agents can be administered separately or co-administered. The multiple RNAi agents can be administered in the same delivery vehicle, the same type of delivery vehicle, or in different delivery vehicles.

Various additional embodiments are described below.

The details of one or more embodiments of the present disclosure are set forth in the accompanying drawings and the description below.

The details of one or more aspects of the present disclosure are set forth in the accompanying drawings and description below. Elements of the various aspects (e.g., sequences, modifications, substitutions, spacers, modified internucleoside linkers, endcaps, combinations of RNAi agents, delivery vehicles, combination therapy involving a RNAi agent and another agent, etc.) disclosed herein or known in the art which are not mutually exclusive can be combined with each other, provided that the agent or agents are still capable of mediating RNA interference. For example, any RNAi agent sequence disclosed herein can be combined with any set of modifications or endcaps disclosed herein. Similarly, any combination of modifications, 5' end caps, and/or 3' end caps can be used with any RNAi agent sequence disclosed herein. Any RNAi agent disclosed herein (with any combination of modifications or endcaps or without either modifications or endcaps) can be combined with any other RNAi agent or other treatment composition or method disclosed herein.

Other features, objects, and advantages of the present disclosure will be apparent from this description, the drawings, and from the claims.

BRIEF DESCRIPTION OF THE FIGURES

FIG. 1 illustrates the structures and sequence of the RNAi agents comprising a 3' end cap used in Example 1. In this figure, the generic antisense sequence is SEQ ID NO: 1; the generic sense sequence is SEQ ID NO: 2; the antisense mF7 (mouse Factor VII) sequence is SEQ ID NO: 3; and the sense mF7 sequence is SEQ ID NO: 4. The structures of the 3' end caps ("X") are provided herein and/or in U.S. Pat. No. 8,084,600.

FIGS. 5A and 5B detail some of the RNAi agents used in the data shown in FIGS. 5A and 5B and Example 3A. The strands of these RNAi agents comprise a human sequence (hs) 18-mer to Hepcidin (HAMP), wherein the 3' end of the 18-mer terminates in a phosphate and further comprises, in 5' to 3' a spacer (ribitol), a phosphate, and a 3' end cap (C6 or X058). In FIG. 5A, the sequences are represented, from top to bottom, by SEQ ID NOs: 5 to 17. In FIG. 5B, the sequences are represented, from top to bottom, by SEQ ID NOs: 18 to 30.

FIG. 10 shows specific examples of an 18-mer format RNAi agent, comprising two 18-mer strands, the 3' end of each 18-mer strand terminating in a phosphate and further comprising, in 5' to 3' order, a spacer (ribitol or rib), a phosphate (p) and a 3' end cap (X058 or C6). Various substitutions (DNA) and modifications (2'-OMe and 2'-MOE) are also shown. These non-limiting examples are functional siRNAs to human Hepcidin (HAMP). The specific modified siRNA 400 guide strand is SEQ ID NO: 34 and the modified sense strand is SEQ ID NO: 35. The specific modified siRNA 402 guide strand is SEQ ID NO: 36 and the modified sense strand is SEQ ID NO: 150.

FIG. 11 shows the in vitro efficacy of various RNAi agents of different lengths, to Factor VII (FVII). These include a 21-mer format (including two dinucleotide overhangs); a blunt-ended 19-mer format, including 3' end caps (C6) replacing the dinucleotide overhangs); an 18-mer, wherein each strand comprises an 18-mer and a 3' end cap (C6); and an 18-mer format RNAi agent, wherein each strand comprises an 18-mer, further comprising in 5' to 3' order, a spacer (C3), a phosphate (p) and a 3' end cap (C6) (collectively, C3pC6). These RNAi agents do not comprise a ribitol.

FIG. 12 illustrates an example of modification schemes for a canonical 21-mer siRNA, as well as 19-mer and 18-mer formats. The location of 2'-OMe and 2'-MOE modifications is indicated, as is the location of a 3' end cap (L) (which can alternatively comprise a spacer, a second phosphate or modified internucleoside linker and a 3' end cap, not shown). In this figure, the last two nt of the 3' end of each strand are 2'-MOE; this is known as a "2'-MOE clamp" or "MOE clamp". In FIG. 12, the genetic antisense and sense strands are represented by SEQ ID NOs: 45 and 46 (top) and 47 and 48 (bottom).

Figure 13A:
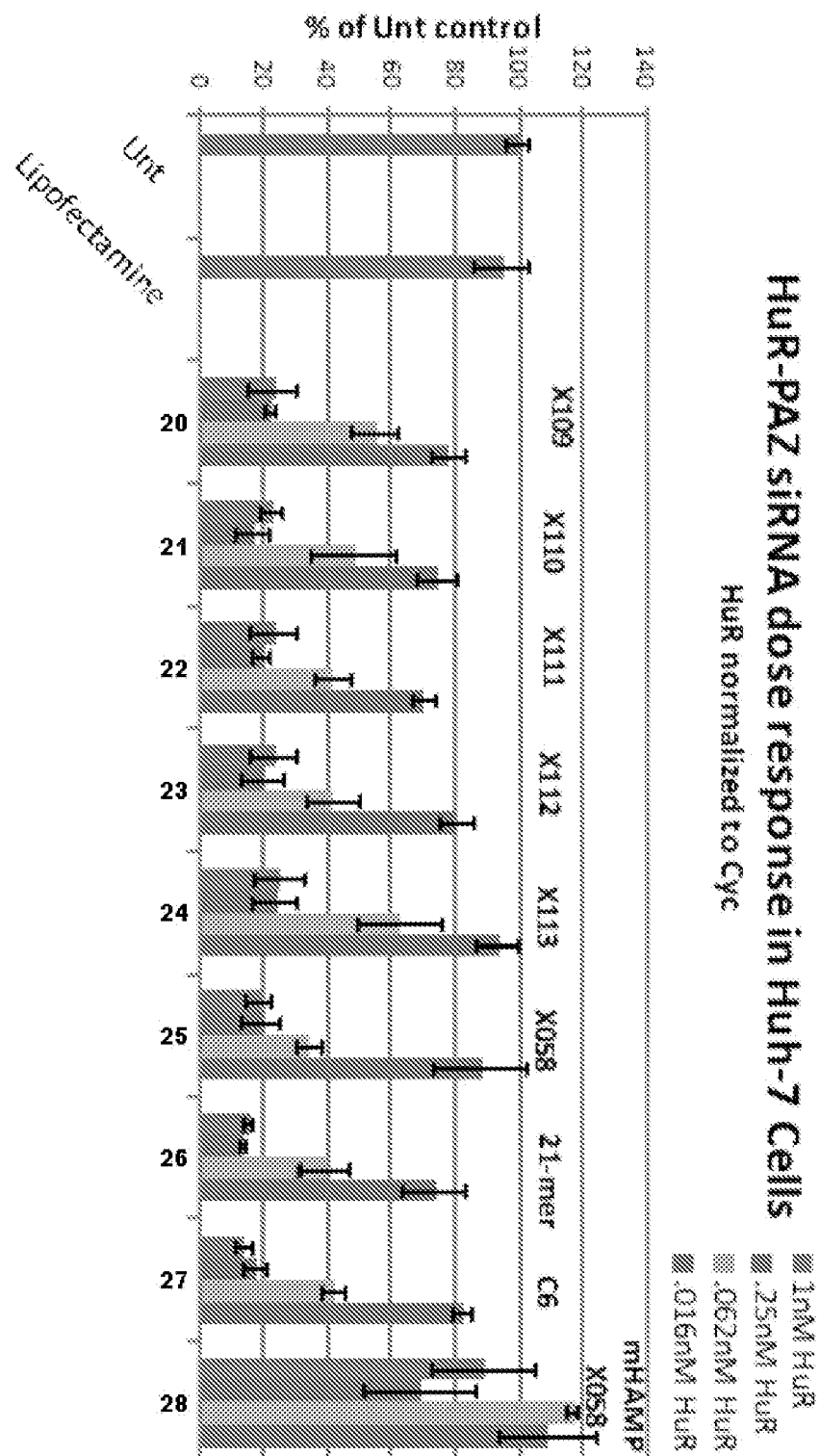

FIG. 13A shows the efficacy of 18-mer RNAi agents to HuR (ELAVL1), with a dose response in Huh-7 cells. 0.016 to 1 nM of RNAi agent is used. The tested RNAi agents comprise a 18-mer strand, wherein the 3' end of the 18-mer strand terminates in a phosphate, further comprising a spacer (ribitol), a phosphate, and a 3' end cap. The various 3' end caps used were: X109, X110, X111, X112, X113, X058, and C6 as a positive control. A corresponding 21-mer is also used. FIG. 13B shows the structure of the molecules used in this experiment and others. The RNAi agents comprising X109, X110, X111, X112, or X113 comprise a DNA modification at the 5' end of the anti-sense strand. The sequences in FIG. 13B are represented by SEQ ID NOs: 96 (first sequence) and 97 (second). The duplexes are numbered 20 to 28. The tested sequence, designated 1186, is listed as human ("hs" or *Homo sapiens*), but is cross-reactive for human, mouse and rat.

Figure 14A:
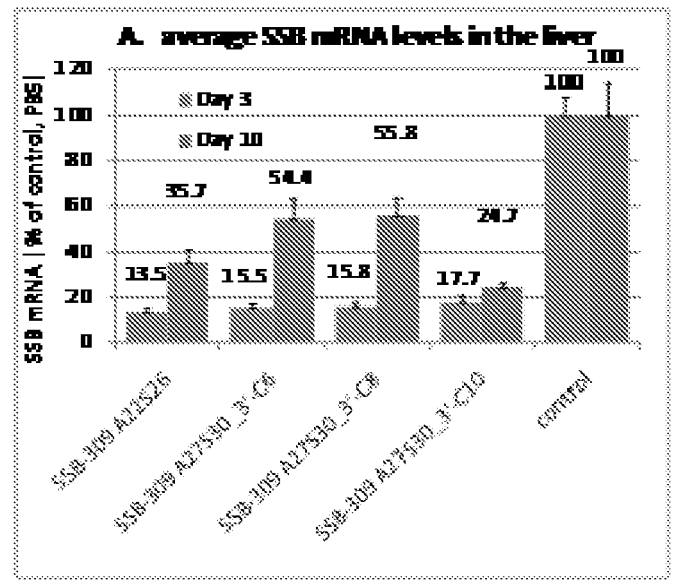
Figure 14B:
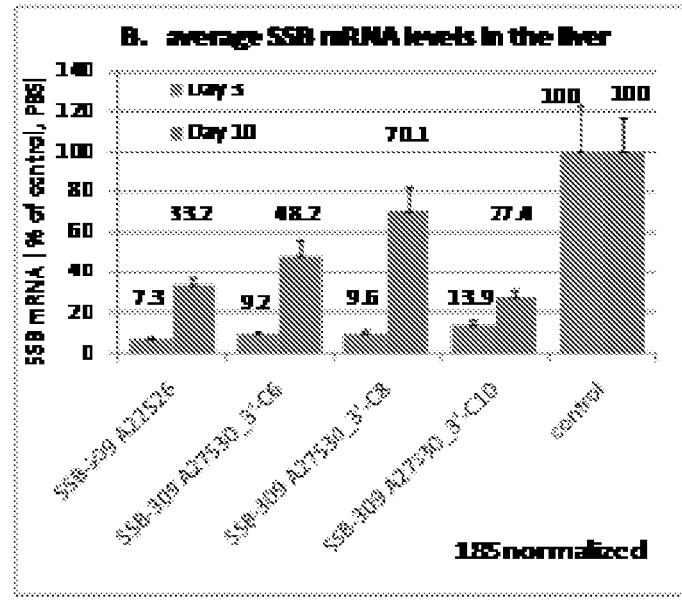

FIGS. 14A and B and 15 show the efficacy of various SSB [Sjogren's syndrome antigen B] RNAi agents comprising a 19-mer with a C6, C8 or C10 3' end cap, as described in Example 5. The compound designated SSB-309 A22S26 is a 21-mer control. These experiments were done in vivo in the mouse. FIG. 15 shows the individual data points used to generate the bar graphs in FIGS. 14A and 14B.

FIG. 16 shows example structures of a 3' terminus of an RNAi agent strand. The strand terminates in a nucleotide (with BASE) and 3' phosphate which is bound to: a dinucleotide (wt or wild-type); or a 3' end cap (C6, C8 or C10). These structures were used in, for example, LNP-formulated SSB siRNAs (such as those used in the experiments illustrated in FIGS. 14A and B and 15), but can be used for any RNAi agent of any sequence or target. Any of the phosphates of either or both strands of the RNAi agent can be replaced by the depicted compound.

FIG. 17 diagrams the terminal structures of, for example, a RNAi agent strand terminating in U. These include: a dinucleotide (e.g., CU overhang), for example, as a dinucleotide overhang of a 21-mer; or 18-mer strand terminating in U (with a phosphate), further comprising a spacer (ribitol), a phosphate, and a 3' end cap (a second ribitol) (collectively, in this case, a diribitol); ribitol; and X027. Also shown are the structures of a 3' terminal nucleotide (a 2'-MOE) bound to, in 5' to 3' order: a spacer (ribitol), a phosphate, and a 3' end cap (C6 or X058).

FIG. 18 illustrates a 18-mer strand, wherein the 3' end of the 18-mer strand terminates in a phosphate or modified internucleoside linker and further comprises: a ribitol, a phosphate and a X058 3' end cap (top); a C3 spacer, a phosphate and a X058 3' end cap (middle); or a A5300 spacer, a phosphate, and a X058 3' end cap (bottom). The Figure depicts the spacers in the context of an 18-mer RNAi agent and a specific 3' end cap, but the spacers can be used with any RNAi agent strand of sequence or target, and with any 3' end cap.

Figure 19:
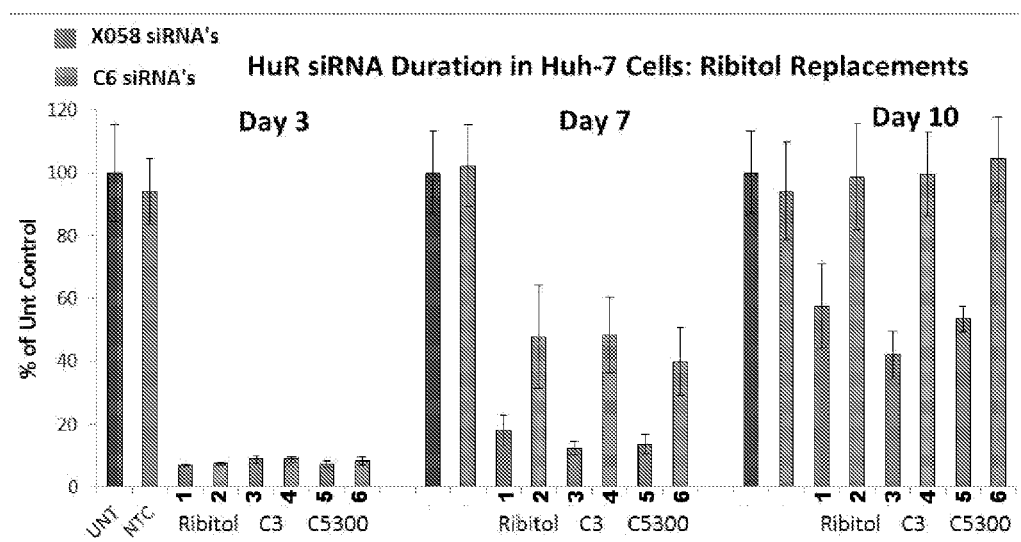

FIG. 19 shows the efficacy and duration of RNAi agent activity of example RNAi agents comprising an 18-mer, wherein the 3' end of the 18-mer terminates in a phosphate and further comprises, in 5' to 3' order: a spacer which is a ribitol (rib), C3 or 4-methoxybutane-1,3-diol (A5300); a phosphate; and a 3' end cap which is X058 or C6. The duplexes are numbered 1 to 6. These are RNAi agents to HuR (ELAVL1). UNT: Untreated (negative control). NTC: Non-target control (negative control using an unrelated RNAi that targets a different target).

Figure 20A:
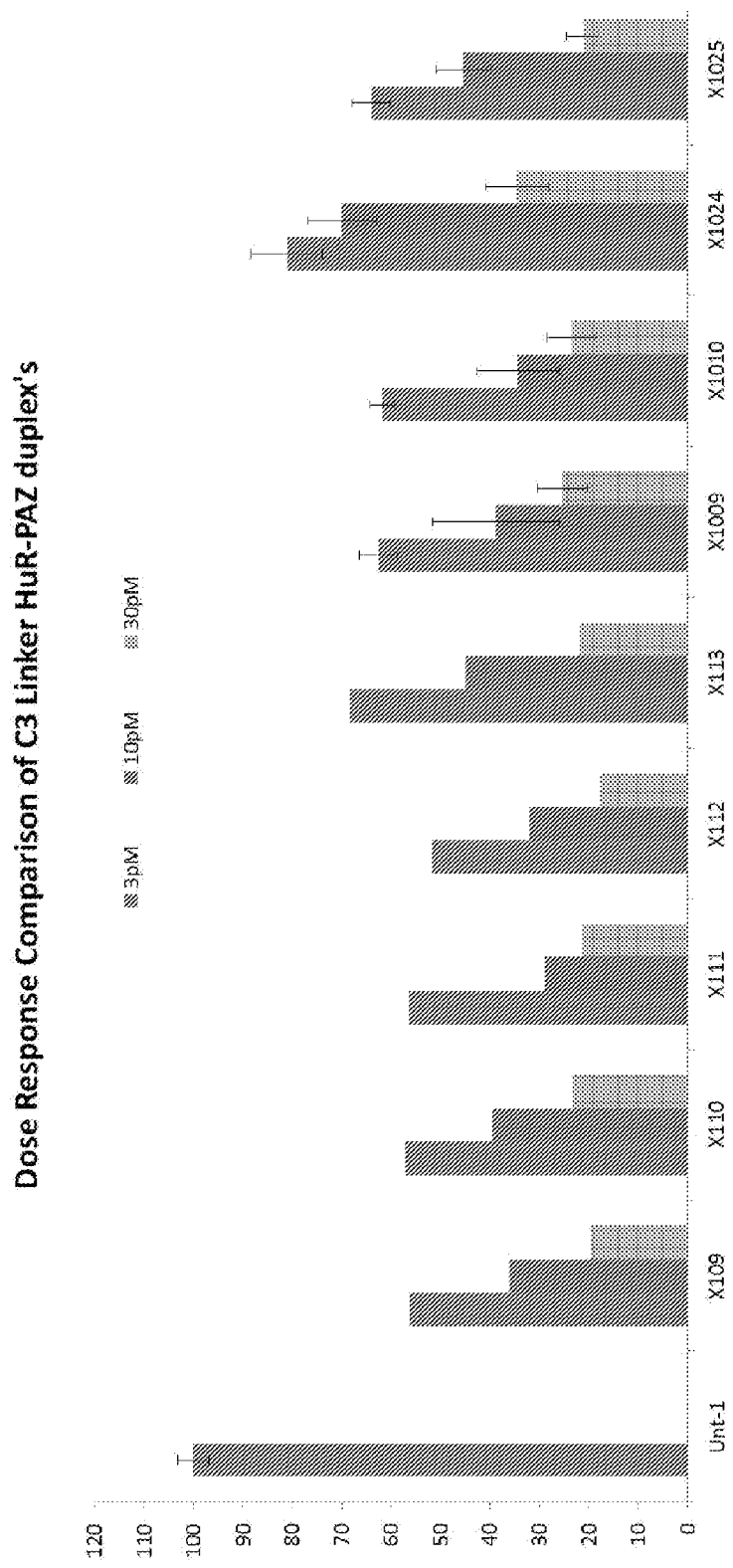
Figure 20C:
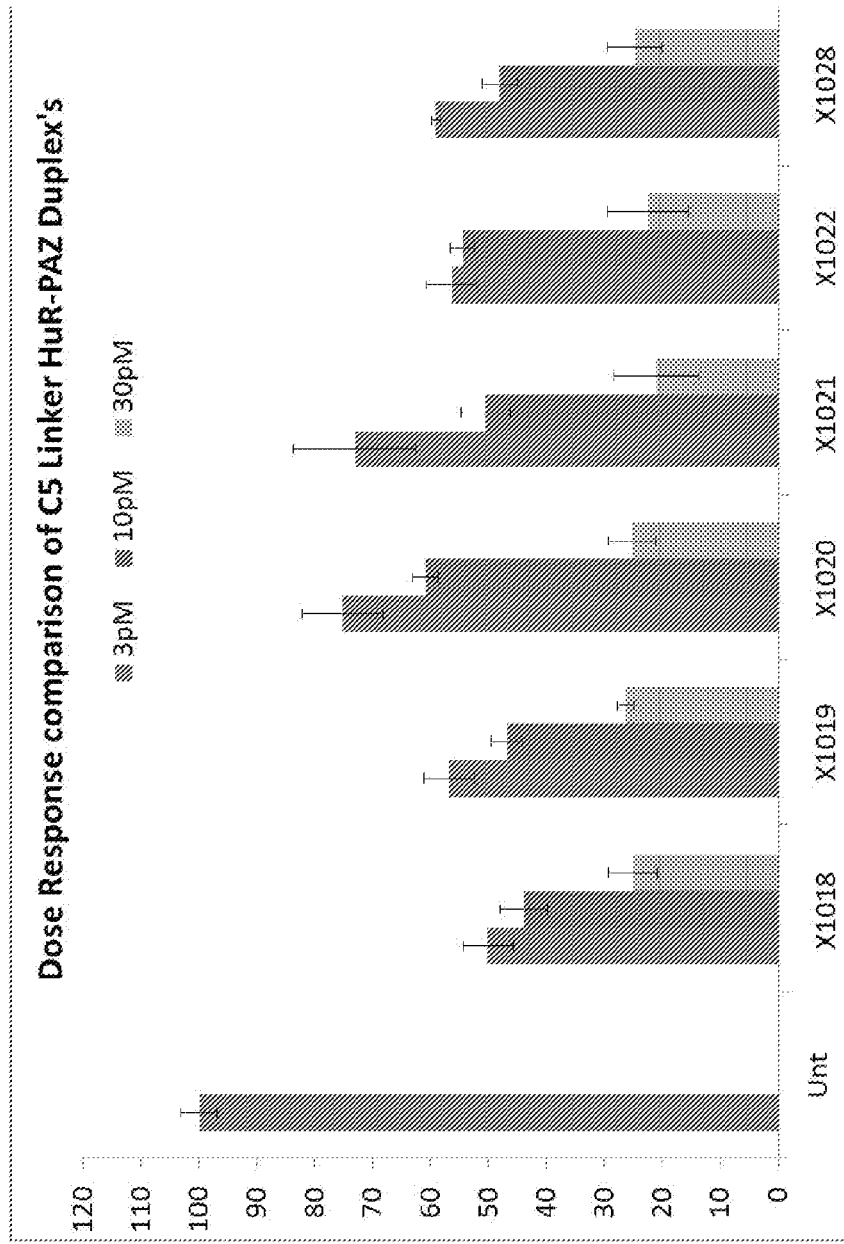

FIGS. 20A-C show the efficacy of HuR RNAi agents comprising a 3' end cap which is: X109, X110, X111, X112, X113, X1009, X1010, X1024 or X1025 (FIG. 20A); X1011, X1012, X1013, X058, X1015, X1016, X1017, X1026, X1027 (FIG. 20B): or X1018; X1019, X1020, X1021, X1022 or X1028 (FIG. 20C). The terms C3 linker, C4 linker and C5 linker indicate portions of the 3' end caps.

Figure 21:
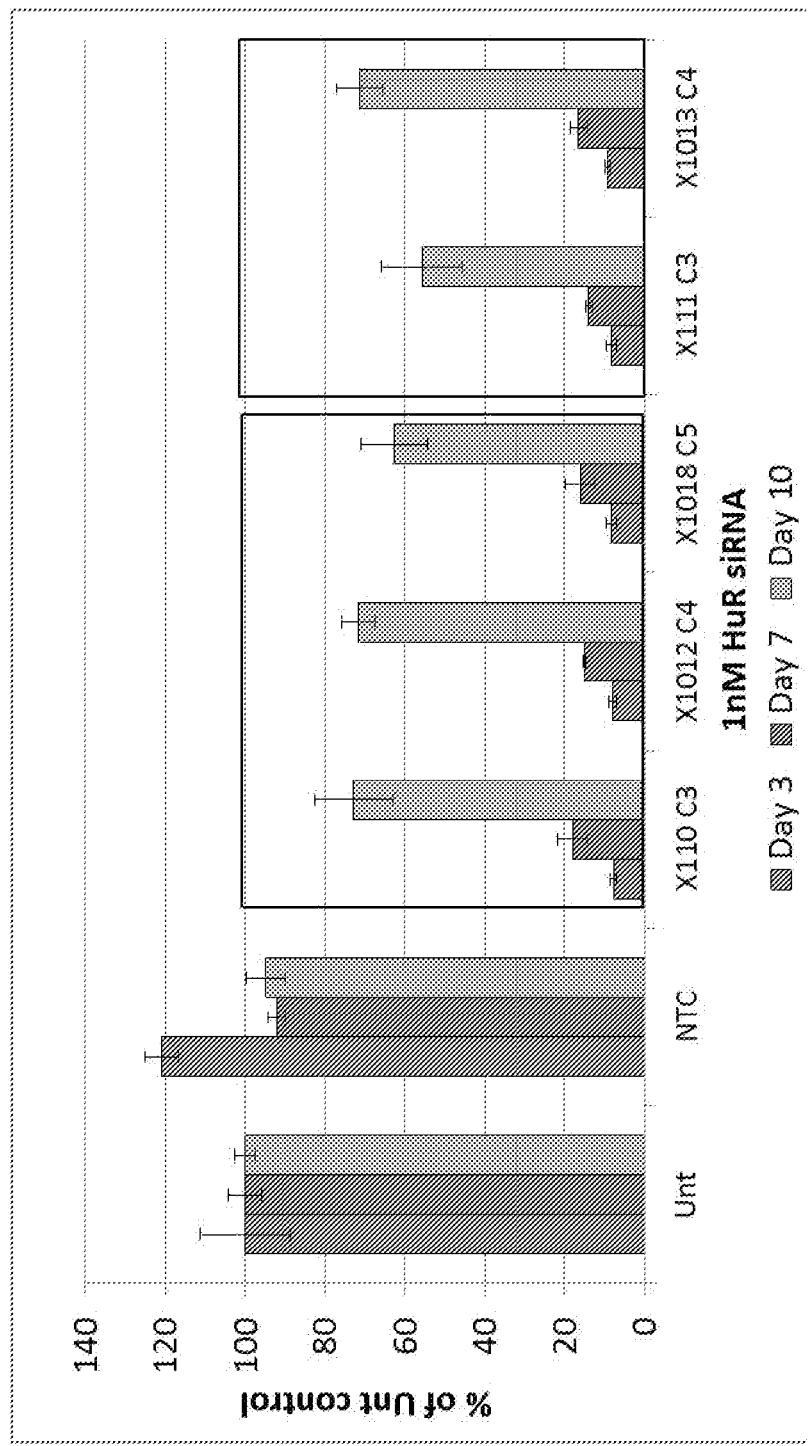
Figure 22:
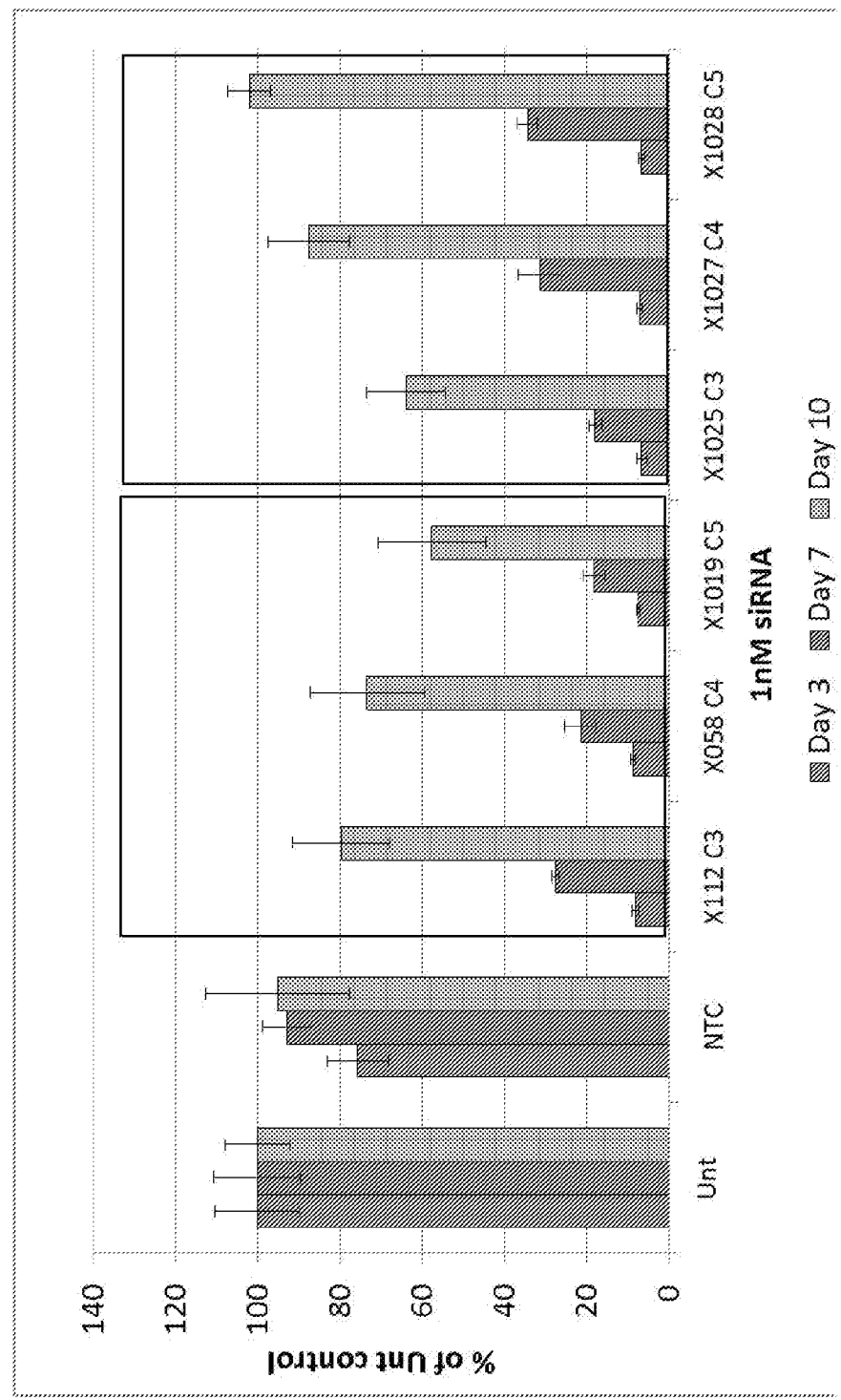

FIGS. 21 and 22 show efficacy and duration of HuR RNAi agents comprising a 3' end cap which is: X110, X1012, X1018, X111, X1013, X112, X058, X1019, X1025, X1027, or X1028. The designations C3, C4 and C5 refer to the length of a linker portion of the 3' end cap.

Figure 23:
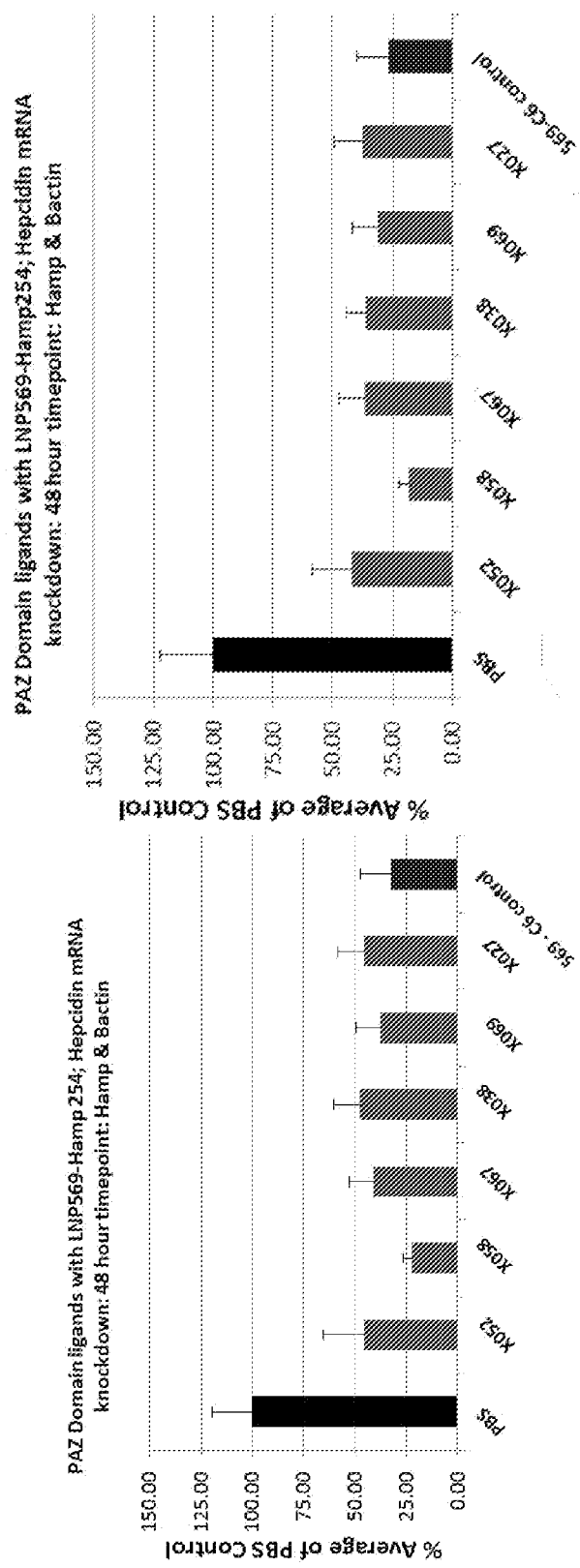

FIG. 23 shows the efficacy of mouse 18-mer Hepcidin RNAi agents, wherein each 18-mer strand terminates in a phosphate and further comprises a ribitol spacer, a phosphate, and a 3' end cap which is X052, X058, X067, X038, X069, X027 or C6 (positive control). PBS: phosphate-buffered saline (negative control). This experiment was performed in vivo in the mouse. These were single 3 mg/kg dose i.v., and Hepcidin mRNA knockdown in liver was measured after 2 and 7 days. All PAZ ligands were equal or more potent than C6 parent at day 2. X058 was the only PAZ ligand still active at day 7; thus, it has an impact on the in vivo duration of effect.

Figure 24:
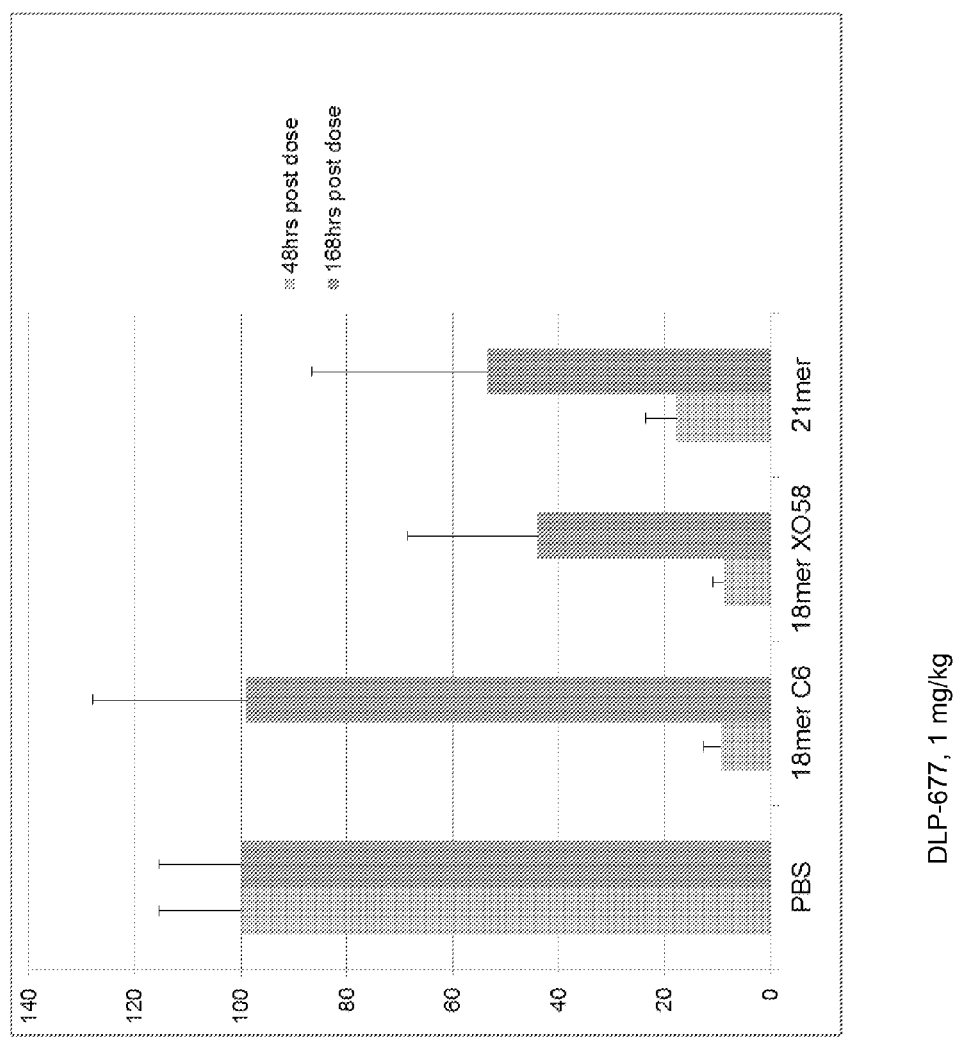

FIG. 24 shows the efficacy after 48 hrs and 168 hrs of 18-mer Hepcidin RNAi agents comprising a ribitol spacer and a C6 3' end cap or X058 3' end cap. These are compared to the 21-mer format. This shows that, at 48 hours, the C6 and X058 formats were more efficacious than the 21-mer format. This experiment was performed in vivo in the mouse.

Figure 25:
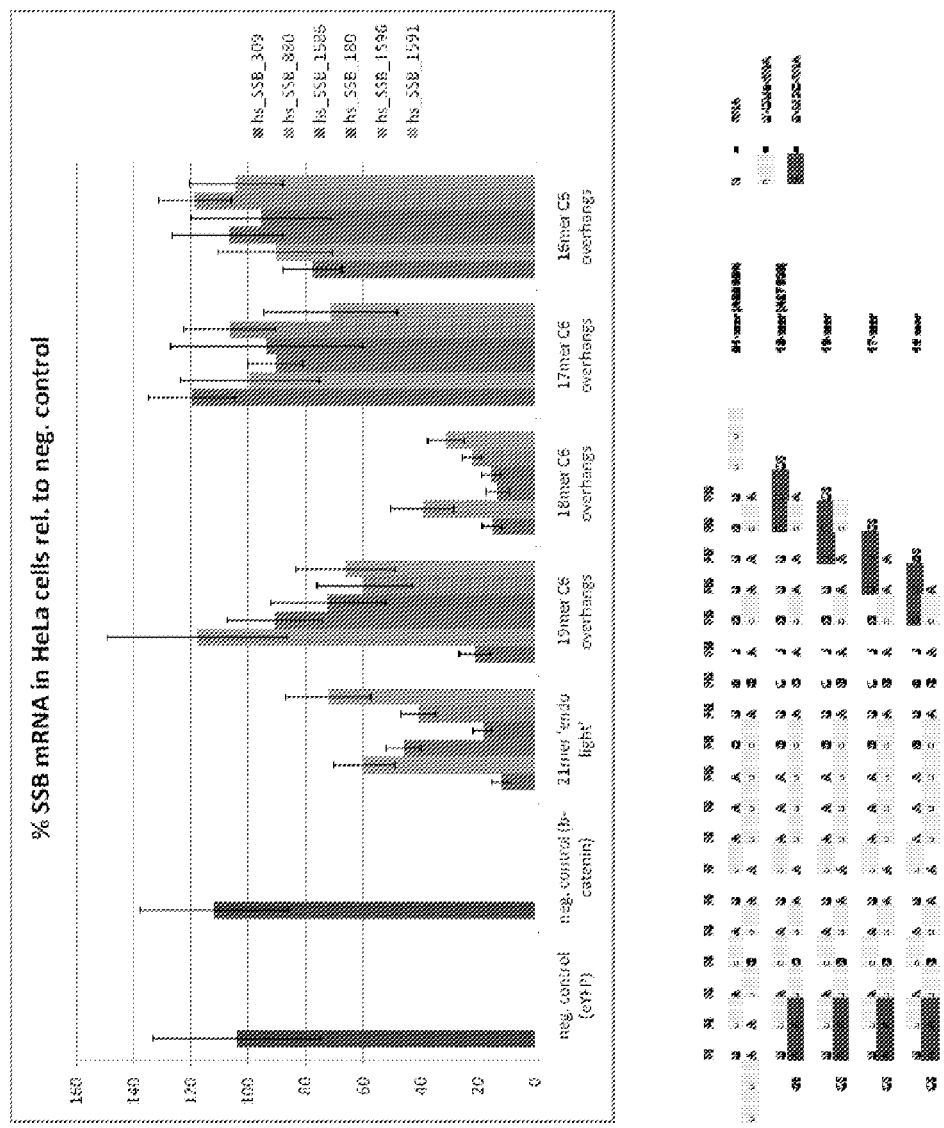

FIG. 25 shows the efficacy of various formats (21-mer, 19-mer, 18-mer, 17-mer, and 16-mer) of several SSB RNAi agents. The numbers (309, 880, 1586, 180, 1596 and 1591) indicate the location within the human (hs) sequence, though these sequences are cross-reactive in human, rat and mouse. The sequences of some of these are provided, from top to bottom, in SEQ ID NOs: 50 to 59.

Figure 26:
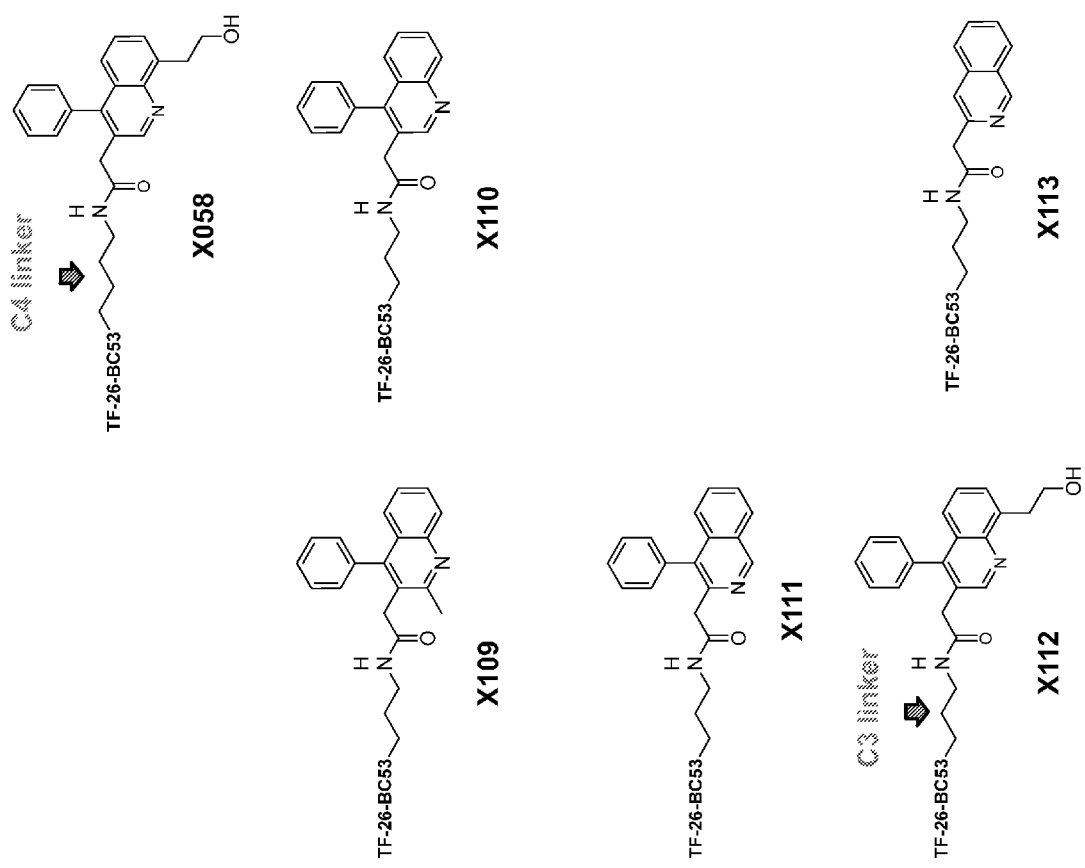

FIG. 26 shows the structure of the X058, X109, X110, X111, X112 and X113 3' end caps. TF-26-BC53 indicates a strand of a RNAi agent, wherein the 3' end of the strand terminates in a phosphate or modified internucleoside linker and optionally further comprises in 5' to 3' order: a spacer and a phosphate or modified internucleoside linker. These 3' end caps can be used with either or both strands of any RNAi agent of any sequence or target.

FIG. 27 shows a comparison of corresponding 19-mer and 18-mer format Hepcidin RNAi agents. RNAi agents include: hs_HAMP (human HAMP) 36, 37, 93, 160, 185, 232, 296, 299, 300, 301, 309, 312, 325, 328, 332, 397, 398, 400, 401, 402, 403 (starting position).

DETAILED DESCRIPTION OF THE INVENTION

The disclosure relates to compositions comprising a RNAi agent having a novel format, designated herein as the 18-mer format with at least one internal spacer, or the 18-mer format with an internal spacer. These RNAi agents comprise a first and a second 18-mer strand, wherein the first strand is 18 ribonucleotides or 18 total ribonucleotides and spacer subunit(s), and the second strand is 18 total ribonucleotides and spacer subunit(s), wherein: each spacer subunit consists of: (a) a phosphate or modified internucleoside linker and (b) a spacer; a spacer subunit can be at any position in the strand; the two strands form a duplex with at least one blunt end; and the 3' end of one or both strands terminates in a phosphate or modified internucleoside linker and further comprises, in 5' to 3' order: a second spacer; a second phosphate or modified internucleoside linker, and a 3' end cap. The efficacy of RNAi agents of this format is shown herein. For example, Table 8 shows that any and each of the nucleotides at positions 1 to 18 in an 18-mer can be substituted with a spacer subunit, and the RNAi agent is still capable of mediating RNA interference. In various embodiments, the RNAi agents capable of mediating RNA interference comprise a first and a second 18-mer strand, wherein the first strand is 18 total of: (a) 13-17 ribonucleotides or modified ribonucleotides, (b) at least 1 spacer subunit, and optionally (c) 0-4 of any of DNA, PNA, LNA, TNA, GNA, ANA, FANA, CeNa, HNA or UNA; and the second strand is 18 total of: (a) 13-18 ribonucleotides or modified ribonucleotides, optionally (b) at least 1 spacer subunit, and optionally (c) 0-4 of any of DNA, PNA, LNA, TNA, GNA, ANA, FANA, CeNa, HNA or UNA; wherein: each spacer subunit is (a) a phosphate or modified internucleoside linker and (b) a spacer; a spacer subunit can be at any position in the strand; the two strands form a duplex with at least one blunt end; and the 3' end of one or both strands terminates in a phosphate or modified internucleoside linker and further comprises, in 5' to 3' order: a second spacer; a second phosphate or modified internucleoside linker, and a 3' end cap. In various embodiments, the terms DNA, PNA, LNA, TNA, GNA, ANA, FANA, CeNa, HNA or UNA indicate a single subunit or mer of these species; thus, "DNA" indicates a single nucleotide (a single subunit of 1 phosphate, 1 sugar and 1 base), "TNA" indicates a single subunit (1 phosphate, 1 sugar and 1 base), etc., rather than a polymer or oligomer of these subunits. Thus, the first strand can be, as non-limiting examples: (a) 17 ribonucleotides or modified ribonucleotides and 1 spacer subunit; (b) 14 ribonucleotides or modified ribonucleotides and 1 spacer subunit and 3 DNA nucleotides; (c) 16 ribonucleotides or modified ribonucleotides and 2 spacer subunits; (d) 14 ribonucleotides or modified ribonucleotides and 1 spacer subunit and 3 LNA subunits (mers); (e) 14 ribonucleotides or modified ribonucleotides and 1 spacer subunit and 3 TNA subunits (mers); etc. The second strand can comprise, as non-limiting examples: (a) 18 ribonucleotides or modified ribonucleotides; (b) 17 ribonucleotides or modified ribonucleotides and 1 spacer subunit; (c) 14 ribonucleotides or modified ribonucleotides and 1 spacer subunit and 3 DNA nucleotides; (d) 16 ribonucleotides or modified ribonucleotides and 2 spacer subunits; (e) 14 ribonucleotides or modified ribonucleotides and 1 spacer subunit and 3 LNA subunits (mers); (f) 14 ribonucleotides or modified ribonucleotides and 1 spacer subunit and 3 TNA subunits (mers); etc. The spacer, modified internucleoside linker and 3' end cap can be any of these described herein or known in the art. In some embodiments, the spacer subunit is at an internal position (any of positions 2 to 17 counting 5' to 3') and the two 18-mer strands form a blunt-ended duplex. In various embodiments, the disclosure pertains a novel format described herein as a RNAi agent with an internal spacer. In various embodiments, the RNAi agents comprise a first and a second strand, wherein each strand is a 30-mer or shorter, the first strand comprises ribonucleotides, and the second strand comprises ribonucleotides and one or more spacer subunit(s), wherein: each spacer subunit consists of: (a) a phosphate or modified internucleoside linker and (b) a spacer; a spacer subunit can be at any position in the strand. In various embodiments, the RNAi agents comprise a first and a second strand, wherein each strand is a 30-mer or shorter, the each comprises ribonucleotides and one or more spacer subunit(s), wherein: each spacer subunit consists of: (a) a phosphate or modified internucleoside linker and (b) a spacer; a spacer subunit can be at any position in the strand. In various embodiments, the two strands form a duplex with at least one blunt end. In various embodiments, the 3' end of one or both strands terminates in a phosphate or modified internucleoside linker and (a) further comprises a 3' end cap; or (b) further comprises, in 5' to 3' order: a second spacer; a second phosphate or modified internucleoside linker, and a 3' end cap. In some embodiments, the spacer is a ribitol. In various embodiments, the first and/or second strands were 18-, 19-, 20-, 21-, 22-, 23-, 24-, 25-, 26-, 27-, 28-, 29- or 30-mers. In various embodiments, the second strand can comprise ribonucleotides and one spacer; ribonucleotides and 2 spacers; ribonucleotides and 3 spacers; etc. In various embodiments, the disclosure pertains to a composition comprising a RNAi agent comprising a first and a second strand, wherein each strand is a 30-mer or shorter, the first strand is (a) ribonucleotides or modified ribonucleotides and optionally (b) up to 4 DNA nucleotides, and the second strand is (a) ribonucleotides or modified ribonucleotides, (b) one or more spacer subunit(s), and (c) optionally up to 4 DNA nucleotides; wherein: each spacer subunit consists of: (a) a phosphate or modified internucleoside linker and (b) a spacer; and wherein the spacer subunit can be at any position in the strand, wherein the 3' end of at least one strand optionally terminates in a phosphate or modified internucleoside linker and optionally further comprises, in 5' to 3' order: a second spacer; a second phosphate or modified internucleoside linker; and a 3' end cap. In various embodiments, the first stand is an antisense strand and the second strand is a sense strand. In other embodiments, the first strand is a sense strand and the second strand is an antisense strand. Generally, in a RNAi agent, the sense strand is more tolerant than the antisense strand to substitutions and modifications, as the sense strand does not mediate RNA interference; as shown herein, even nucleotides in the antisense strand can be substituted with a spacer subunit. In various embodiments, one or more ribonucleotide (each consisting of a phosphate, a sugar and a base) can be modified or substituted at the phosphate, sugar or base. Various modifications and substitutions are described herein. A spacer subunit comprises (a) a phosphate or modified internucleoside linker and (b) a spacer, but is not a nucleotide or ribonucleotide, as it does not have all of: a phosphate, sugar and base. Various suitable spacers are described herein; a RNAi agent can comprise spacers which are all identical, or a variety of different types of spacers. A 3' end cap is also not a nucleotide or ribonucleotide as it does not have all of: a phosphate, sugar and base; a variety of suitable 3' end caps are described herein. The RNAi agent can also comprise: phosphates but no modified internucleoside linkers; or phosphates and one or more modified internucleoside linker(s) which are all identical or of a variety of different types. Optionally, the first and/or second strand can be modified at the 5' end. Optionally, the sense strand can comprise a 5' end cap which reduces the amount of RNA interference (RNAi) mediated by this strand. Optionally, the RNAi agent is attached to a ligand. RNAi agents having a 18-mer format with at least one internal spacer at any position are shown herein to be efficacious in mediating RNA interference and can be used to devise RNAi agents to a variety of different targets and sequences. The disclosure also relates to processes for making such RNAi agents, and methods and uses of such RNAi agents, e.g., to mediate RNA interference. A variety of modifications and substitutions are described herein, and their efficacy shown. These include a variety of different types, modifications and substitutions of spacer, modified internucleoside linker and 3' end cap.

In various embodiments, the disclosure encompasses a RNAi agent comprising a first strand and a second strand, wherein one strand comprises ribonucleotides and the other strand comprises ribonucleotides and spacer subunits, or both strands comprise ribonucleotides and spacer subunits, wherein a spacer subunit is (a) a phosphate or modified internucleoside linker and (b) a spacer, and wherein each strand is no more than a 30-mer, and wherein optionally both strands are 18-mers, wherein optionally the strands form at least one blunt end, wherein the 3'-terminus of at least one strand optionally terminates in a phosphate or modified internucleoside linker and further comprises, in 5' to 3' order: a second spacer, a second phosphate or modified internucleoside liner and a 3' end cap, wherein the spacer is ribitol, 2'-deoxy-ribitol, diribitol, 2'-methoxyethoxy-ribitol (ribitol with 2'-MOE), C3, C4, C5, C5, C6 or 4-methoxybutane-1,3-diol; wherein the modified internucleoside linker is selected from phosphorothioate, phosphorodithioate, phosphoramidate, boranophosphonate, an amide linker, and a compound of formula (I); wherein the 3' end cap is selected from a compound of formula Ia or Ib, a compound from Table 1A, 1B, 1c, 1D, 1E or 1, or any 3' end cap disclosed herein or known in the art; wherein: optionally at least one ribonucleotide is modified or substituted, and/or optionally said at least one modified ribonucleotide is selected from among 2' alkoxyribonucleotide, 2' alkoxyalkoxy ribonucleotide, or 2' fluoro ribonucleotide, and optionally said at least one modified ribonucleotide is selected from 2'-OMe, 2'-MOE and 2'-H; and/or optionally one or more ribonucleotide is modified or is substituted with DNA, a peptide nucleic acid (PNA), locked nucleic acid (LNA), morpholino nucleotide, threose nucleic acid (TNA), glycol nucleic acid (GNA), arabinose nucleic acid (ANA), 2'-fluoroarabinose nucleic acid (FANA), cyclohexene nucleic acid (CeNA), anhydrohexitol nucleic acid (HNA), and/or unlocked nucleic acid (UNA); and/or optionally at least one nucleotide comprises a modified internucleoside linker, wherein the modified internucleoside linker is selected from phosphorothioate, phosphorodithioate, phosphoramidate, boranophosphonate, an amide linker, and a compound of formula (I); and/or optionally the 3' terminal phosphate of the sense and/or anti-sense strands is replaced by a modified internucleoside linker; and/or optionally the first two base-pairing nucleotides on the 3' end of the sense and/or anti-sense strand are modified, and/or optionally the first two base-pairing nucleotides on the 3' end of the sense and/or anti-sense strand are 2'-MOE; and/or optionally the sense or the anti-sense strand comprise an 5' end cap, wherein optionally the sense strand comprises a 5' end cap which reduces the amount of the RNA interference mediated by the this strand, wherein optionally the 5' end cap is selected from: a nucleotide lacking a 5' phosphate or 5'-OH; a nucleotide lacking a 5' phosphate or a 5'-OH and also comprising a 2-OMe or 2'-MOE modification; 5'-deoxy-2'-O-methyl modification; 5'-OME-dT; ddT; and 5'-OTr-dT.

Any of the various elements of various embodiments disclosed herein [e.g., compositions and methods; and selection of spacers and 3' end caps, nucleotide modifications or substitutions, patterns of modifications, and/or 5' end caps and delivery vehicles] which are not mutually exclusive can be combined.

18-Mer Format and 18-Mer Format with Internal Spacer, as Compared to Canonical siRNA Format siRNAs naturally generated in a cell by Dicer typically comprise two 21-nt RNA strands, which form a 19-bp duplex region and two dinucleotide overhangs. This is the so-called "canonical" siRNA structure. See, for example, Elbashir et al. 2001 Nature 411: 494-498; Elbashir et al. 2001 EMBO J. 20: 6877. This is the so-called "canonical" structure or "21-mer" format of siRNAs.

The two dinucleotide overhangs do not contribute to target specificity. Elbashir et al. 2001 Nature 411: 494-498; Elbashir et al. 2001 EMBO J. 20: 6877-6888; and Kraynack et al. 2006 RNA 12:163-176. They do, however, help protect the ends of the siRNA from nuclease degradation and sometimes improve activity.

The terminal dinucleotides of a 21-mer are sometimes replaced by an artificial dinucleotide, such as UU, TT, dTdT, sdT, dTsdT, sdTsdT, or sdTdT.

The terminal dinucleotides can alternatively be deleted (and not replaced), leaving a functional siRNA comprising two 19-nt strands forming a 19-bp duplex. The dinucleotide overhangs can sometimes functionally be replaced by a 3' end cap, leaving a blunt-ended 19-bp duplex with one or two 3' end caps, which can protect the molecule from nucleases. See, for example, U.S. Pat. Nos. 8,097,716, 8,084,600; 8,404,831; 8,404,832, and 8,344,128. The 3' end caps are non-nucleotidic; they are not nucleotides as they do not comprise all components of a nucleotide (phosphate, sugar and base).

Decreasing the length of the siRNA, particularly the antisense strand, below 19 nt can be problematic. siRNA strands naturally produced by Dicer are largely 21-mers (45%). While artificial 19-mers can be functional, they are rarely produced in nature (5%). Lengths less than 19, such as 18-mers, are even rarer (1%). Elbashir et al. 2001 Genes Dev. 15: 188-200. Length reduction below 19 nt, particularly of the anti-sense strand, also generally reduces or completely abolishes RNA interference activity. Less 18-mer siRNA is incorporated into RISC than 21-mer, and the 18-mer also degrades more quickly in cell extracts in vitro. Hoerter et al. May 27 2011 PLOS ONE. Czauderna et al. also concluded that the minimal length of a siRNA strand was about 19 nt. Czauderna et al. 2003 Nucl. Acids Res. 31: 2705-2716. However, a RNAi agent therapeutic comprising a 18-mer would be less expensive to manufacture and would provide a novel format for developing siRNA therapeutics. Hence a need exists to identify the critical parameters that are needed to create an active 18-mer RNAi agent, independent of sequence or target.

A shorter version of a functional siRNA comprises two strands, each an 18-mer, which together form a blunt-ended duplex. The 3' terminus of one or both strands of the 18-mer format further comprises, in 5' to 3' order: a spacer, a second phosphate or modified internucleoside linker, and a 3' end cap. The 18-mer format relates to: An RNAi agent comprising two strands, wherein each strand is an 18-mer, and wherein the two strands together form a blunt-ended duplex, wherein the 3' terminus of one or both strands is bonded to, in 5' to 3' order, a spacer, a second phosphate or modified internucleoside linker, and a 3' end cap. In one aspect the first two base-pairing nucleotides on the 3' end of the sense and/or anti-sense strand are 2'-MOE.

A new novel RNAi agent format, described herein and designated the 18-mer format with at least one internal spacer, or the 18-mer format with an internal spacer, is similar to the 18-mer format, except that any one or more nucleotide can be replaced by a spacer subunit (a phosophate or modified internucleoside linker+a spacer). In various embodiments, the spacer subunit can be at any position (1, 2, 3, 4, 5, 6, 7, 8, 9, 10, 11, 12, 13, 14, 15, 16, 17 or 18), wherein the remaining positions are nucleotides. In various embodiments, the spacer subunit is at a terminal position (position 1 or 18 counting 5' to 3'). In various embodiments, the spacer subunit is at a non-terminal position (positions 2 to 17 counting 5' to 3'), and the two strands form a blunt-ended duplex. In various embodiments, the spacer subunit is at any of positions 5, 6 or 17 counting 5' to 3'. In various embodiments, the spacer subunit is at any of positions 3, 5, 6, 7, 15, 16, or 17 counting 5' to 3. In various embodiments, the spacer subunit is at any of positions 1, 3, 5, 6, 7, 15, 16, 17 or 18 counting 5' to 3. In various embodiments, more than one nucleotide in one or both strands can be substituted with a spacer subunit. In various embodiments wherein the RNAi agent comprises multiple spacers, the spacer can all be the same or of a variety of types of spacer. The 3' end of one or both strands terminates in a phosphate or modified internucleoside linker and further comprises, in 5' to 3' order: a second spacer, a second phosphate or modified internucleoside linker, and a 3' end cap. Generally, the sense strand is more tolerant to modification than the antisense strand, as the sense strand does not mediate RNA interference. We show herein that even in the antisense one or more nucleotides can be replaced with a spacer subunit and RNA interference activity retained. We show that any position, from 1 to 18, can be substituted with spacer subunit and RNA interference activity retained. Another novel RNAi agent format is described herein and designated the internal spacer format. In this format, each strand of the RNAi agent is a 30-mer or shorter, wherein at least one strand comprises nucleotides and at least one spacer subunit. The other strand can comprise only nucleotides, or nucleotides and at least one spacer subunit. Optionally, the 3' end of one or both strands terminates in a phosphate or modified internucleoside linker and (a) further comprises a 3' end cap, or (b) further comprises, in 5' to 3' order: a second spacer, a second phosphate or modified internucleoside linker, and a 3' end cap.

Use of 18-Mer RNAi Agent Format with Internal Spacer for Different Sequences and Targets Various experiments that have shown the 18-mer format and 18-mer format with at least one internal spacer produces molecules that can mediate RNA interference against a variety of different mRNA targets, including Hepcidin, HuR (ELAVL1), PLK1, SSB, FVII (Factor 7 or F7) and other targets, as shown herein below. See, for example, Table 8, which shows that the nucleotide in any position from 1 to 18 can be replaced by a spacer subunit, and RNA interference activity retained. Successful RNAi agents were also constructed for several additional gene targets (not described herein). Successful 18-mer format RNAi agents were also constructed for use against a variety of mammalian targets in a variety of mammalian cells (e.g., mouse and human). Successful RNAi agents were constructed which worked both in vitro and in vivo. Thus, the 18-mer format with at least one internal spacer can be used with a variety of different sequences, targets and mammalian source material.

One of ordinary skill in the art is aware that not every 18-mer sequence will yield a successful RNAi agent, and certainly not in combination with any spacer, phosphate or modified internucleoside linker, and 3' end cap. However, where one skilled in the art does identify that subset of sequences that are successful RNAi agents when formatted as a canonical 21mer siRNA, the format described herein provides the practitioner with a broader set of alternatives when optimizing a RNAi agent for both increased activity and for decreased off-target effect. The disclosed 18mer format can also be used to devise and test various RNAi agents, some of which can have activity approximately equal to that of other formats (e.g., the canonical structure); and some can produce improved qualities (e.g., increased activity, duration or activity, decreased off-target effects, etc.).

The novel 18-mer format with an internal spacer or novel RNAi agent format with an internal spacer disclosed herein, therefore, can be used with a variety of different sequences and gene targets.

Hepcidin 18-mers.

As detailed in Examples 3A and 3B and FIGS. 4 to 10, and 23 and 24, effective RNAi agents of the 18-mer format were constructed targeting human and mouse Hepcidin.

These constructs are detailed in the Examples, Figures and Figure legends. These constructs successfully targeted both mouse and human Hepcidin with 18-mer RNAi agents.

Other 18-mer RNAi agents can be constructed targeting Hepcidin.

HuR (ELAV1) 18-mers.

As detailed in Examples 4 to 6 and FIGS. 13, and 19-22, effective RNAi agents of the 18-mer format were constructed targeting HuR (ELAV1).

In addition, an example of an effective 18-mer RNAi agent to HuR is shown below:

```
AS:  u U a A u U a U c U a U u C c G u A rib C6

S:   C6 rib A a U u A a U a G a U a A g G c A u
``` n (a, c, g, u): 2'Ome-n (a, c, g, u)

The sequence of the AS (anti-sense) strand, shown above 5' to 3', is SEQ ID NO: 39; the sequence of the S (sense) strand, shown above 3' to 5', is SEQ ID NO: 40. This RNAi agent comprises two strands, each comprising, in 5' to 3' order, an 18-mer strand, wherein the 3' end of the 18-mer strand terminates in a phosphate (not shown) and further comprises: a spacer (ribitol, rib), a second phosphate (not shown), and a 3' end cap (C6). Other spacers and 3' end caps can be used, and this and other phosphates can be replaced by a modified internucleoside linker.

Other effective HuR RNAi agents were produced wherein the sequence used was:

U002pUpApApU004pU004pApU004pCpU004pApU004-pU004pCpCpGpU005pA005pC027pXnn nn (SEQ ID NO: 41)

Where:

C027 is ribitol (or other spacer such as C3 or C5300)

002=DNA

004=2'Ome

005=2'MOE

All other positions are RNA

027=ribitol p=phosphate

Xnnn=3' end cap (X058, X109, etc.)

In this and various other sequences disclosed herein, 0004 indicates a nucleotide with a U base with a 2'Ome modification; 0002 indicates a nucleotide with a U base which is DNA; 0005 indicates a nt with a U base with a 2'MOE modification. Similarly, other nucleotides are modified, e.g., 0004 indicates a nucleotide with a U base and a 2'Ome modification.

With this HuR sequence, effective RNAi agents were produced which comprise an 18-mer strand, wherein the 3' end of the 18-mer strand terminates in a phosphate and further comprises, in 5' to 3' order: a spacer (ribitol), a phosphate and a 3' end cap (X058, X109, X110, X111, X112, X113, X1009, X1010, X1011, X1012, X1013, X1015, X1016, X1017, X1018, X1019, X1020, X1021, X1022, X1024, X1025, X1026, X1027, or X1028). These were tested in vitro in cells and all demonstrated at least about 60% to 80% gene knockdown at 30 pM. See, for example, FIG. 13.

Several of these HuR 18-mer constructs were further tested, including those comprising the 18-mer strand, wherein the 3' end of the 18-mer strand terminates in a phosphate and further comprises, in 5' to 3' order: a spacer (ribitol), a phosphate and a 3' end cap (X058, X110, X111, X112, X1012, X1013, X1018, X1019, X1025, X1027, X1028). These were tested in vitro in cells and all demonstrated at least about 80% to 90% gene knockdown at Day 3 at 1 nM.

Additional HuR 18-mer constructs were constructed, which comprised a strand with a 18-mer sequence, wherein the 3' end of the 18-mer strand terminates in a phosphate and further comprises, in 5' to 3' order: (a) a ribitol spacer, a phosphate and X058 3' end cap; (b) a ribitol spacer, a phosphate and C6 3' end cap; (c) a C3 spacer, a phosphate and a X058 3' end cap; (d) a C3 spacer, a phosphate and a C6 3' end cap; (e) a C5300 spacer, a phosphate and a X058 3' end cap; and (f) a C5300 spacer, a phosphate and a C6 3' end cap. Each of these constructs was tested in vitro in cells and all demonstrated about 90% gene knockdown at Day 3 at 1 nM. See FIG. 13B.

Additional 18-mer RNAi agents to HuR were constructed comprising two strands, each an 18-mer, the two strands together forming a blunt-ended duplex, wherein the 3' end of at least one strand terminates in a 3' phosphorothioate (PS) and further comprises, in 5' to 3' order: a spacer (ribitol), a modified internucleoside linker (another phosphorothioate), and a 3' end cap (C6).

Other 18-mer RNAi agents can be constructed targeting HuR.

SSB [Sjogren's Syndrome Antigen B] 18-mers.

Effective 18-mer format RNAi agents were also constructed targeting SSB and PLK1. For example, in some RNAi agents to these targets, the 3' end of one or both 18-mer strand terminates in a phosphate or modified internucleoside linker and further comprises, in 5' to 3' order: a spacer (e.g., C3), a phosphate and a 3' end cap (C6).

For example, the 18-mer format human SSB RNAi agent designated hs_SSB_309_AS_18 mer-C3-C6 was effective at mediating RNA interference in vitro, and is shown below:

```
AS:  UuAcAUuAAAGUCUGU87-C3pC6
     8 = 2' methoxy ethyl T; 7 = 2' methoxy ethyl G S:   cAAcAGAcuuuAAuGu55-C3pC6
     5 = 2' methoxy ethyl A
``` n: 2'Ome-n

The sequence of the AS (anti-sense) strand, shown above 5' to 3', is SEQ ID NO: 42. The sequence of the S (sense) strand, shown above 3' to 5', is SEQ ID NO: 43. 8, 7, 5 and 5 are 2'-MOE nucleosides, as defined as above. Thus, the first and second strand comprise a 18-mer, wherein the 3' end of the first and second strand terminate at the 3' end in a phosphate and further comprise, in 5' to 3' order: a spacer (C3), a phosphate, and a 3' end cap (C6). This structure is collectively known as a C3pC6, and is illustrated, for example, at FIG. 11 (BOTTOM).

A variety of 18-mer format RNAi agents targeting SSB were constructed. These have a variety of target sequences. For example, in various SSB RNAi agents that were constructed, wherein the 3' end of one or both 18-mer strand terminates in a phosphate or modified internucleoside linker and further comprises, in 5' to 3' order: a spacer (C3 or ribitol), a phosphate, and a 3' end cap (C6, BP, a second ribitol, or a diribitol).

Additional 18-mer SSB constructs were prepared in which the 3' end cap is C6, C8 or C10. These also mediated RNA interference (see FIGS. 14A and 14B).

The efficacy of several SSB 18-mer RNAi agents is shown in FIG. 25. These are designated by numbers 309, 880, 1586, 180, 1596 and 1591 in the human (hs) sequence, but are cross-reactive between human, mouse and rat. The 19-mers and 18-mers corresponding to these sequences were tested and the results shown in FIG. 25. For all of these sequences, the 18-mers showed greater RNAi activity than the 19-mer. The formats used were 19-mer blunt-ended with 3' end cap (C6), or 18-mer blunt-ended with 3' end cap (C6). No ribitol or other spacer was used.

Additional 18-mer format SSB RNAi agents were constructed with sequences to human (hs) 309, 880, 1586, 180, 1596 and 1591. These comprise two 18-mer strands which together form a blunt-ended duplex, the 3' end of both strands terminating in a phosphate and further comprising a 3' end cap which is C6. Other constructs of these sequence were constructed comprising: comprise two 18-mer strands which together form a blunt-ended duplex, the 3' end of both strands terminating in a phosphate and further comprising, in 5' to 3' order: a spacer (C3), a second phosphate and a 3' end cap (C6). The structure comprising the spacer, phosphate and 3' end cap, in this case, is also designated C3pC6. All of these molecules were able to mediate RNA interference.

Other 18-mer RNAi agents can be constructed targeting SSB.

Factor VII 18-mers.

A variety of 18-mer format RNAi agents targeting Factor VII (F7) were also constructed. This includes, as a non-limiting example, a RNAi comprising a 18-mer strand terminating in a phosphate or modified internucleoside linker and further comprising, in 5' to 3' order, a spacer (C3), a phosphate, and a 3' end cap (C6).

Two example Factor VII 18-mer RNAi agents are shown in FIG. 11.

One comprises an 18-mer strand, wherein the 3' end of the 18-mer strand terminates in a phosphate and further comprises a 3' end cap which is C6. This construct is designated "C6 overhang" in FIG. 11 and lacks a spacer and second phosphate or internucleoside linker.

Another Factor VII 18-mer RNAi agent diagrammed in FIG. 11 comprises an 18-mer strand, wherein the 3' end of the 18-mer strand terminates in a phosphate and further comprises a spacer which is C3, a second phosphate, and a 3' end cap which is C6. This construct is designated "C3pC6 overhang" in FIG. 11.

The C3 spacer can be replaced by other spacers; the phosphates can be independently substituted or not substituted with modified internucleoside linkers, and the 3' end cap can be substituted with other 3' end caps.

Other 18-mer RNAi agents can be constructed targeting F7.

PLK1 18-mers.

An 18-mer format RNAi agent was also constructed to the target PLK1, comprising an 18-mer strand further comprising at the 3' terminus, in 5' to 3' order, a spacer (C3), a phosphate, and a 3' end cap (C6).

In addition, other 18-mer RNAi agent were constructed targeting PLK1. These include RNAi agents to human sequences starting at nt 1720, 664, 572, 969, 1651, 578 of the PLK1 sequence. Successful 18-mer format RNAi agents were constructed for all these sequences. These all comprise a first strand and a second strand, wherein the first and second strands are 18-mers, and the first and second strand together form a blunt-ended duplex, and wherein the 3' end of the first and second strand terminate in a phosphate and further comprise a 3' end cap, which is C6. These were tested in 786-0 cells in vitro. In all cases except 1720, the 18-mer format PLK1 RNAi agent was more active in mediating RNA interference than the corresponding 19-mer format (also a blunt-ended 19-mer, with C6 3' end cap on both strands).

Thus, successful 18-mer format RNAi agents were constructed for the targets Hepcidin, HuR (ELAVL1), PLK1, SSB and FVII (Factor 7 or F7). Successful 18-mer format RNAi agents were also constructed for several additional gene targets (not described herein). Both mouse and human Hepcidin were successfully targeted. Various RNAi agents of the 18-mer format have been shown to function in vitro and in vivo. The 18-mer format is thus not limited to any particular sequence or target, or mammalian source.

Improved Activity of 18-Mers.

As noted herein, in many cases, the 18-mer format has also shown to have the same or increased activity relative to a corresponding siRNA of a canonical structure. Various siRNAs of a 18-mer format have shown, in different experiments, in vitro and in vivo, to have increased RNA interference activity, increased duration of activity, increased resistance to nuclease degradation, and/or increased specificity.

For example, several test siRNAs were constructed against the target F7, including a 21-mer (of the canonical structure) and a 18-mer, comprising a C3pC6. In this 18-mer, the 3' end of the anti-sense strand terminates in a phosphate or modified internucleoside linker and further comprises, in 5' to 3' order: a spacer which is C3, a phosphate, and a 3' end cap which is C6. Both the 21-mer and 18-mer target the same sequence; both have the same 5' start. The 18-mer, however, showed a lower ED50 (0.44 (±0.022) mg/kg) than the 21-mer (0.61 (±0.017) mg/kg).

In addition, when an 18-mer format Hepcidin RNAi agent (with a X058 3' end cap) was tested in vivo, it was found, after 2 days, to be more potent than a corresponding 21-mer RNAi agents. For hepcidin, several 18-mers more potent than corresponding 21-mers have been developed.

It was also found that a hepcidin 21-mer siRNA was more prone to sense strand incorporation into RISC than the corresponding 18-mer. Thus, in this case, the 21-mer is less specific than the 18-mer format.

18-mer formats of HuR RNAi agents also had improved IC50 compared to a corresponding 23/21-mer and 21-mer. A 23/21-mer HuR RNAi agent was constructed; this construct comprises a 23-mer AS strand terminating in a aa dinucleotide overhang (but no spacer or 3' end cap) and a 21-mer S strand terminating in a X023 3' end cap (without a spacer). The sense strand is 3'-cholesterol-labeled and the construct had an IC50 of approximately 0.9 µM. Replacing the aa dinucleotide overhang with a X058 3' end cap resulted in a double-stranded 21-mer, with AS strand terminating in a X058 3' end cap (without a spacer) and S strand terminating in a X023 3' end cap (without a spacer); this construct had an improved IC50, of approximate 0.7 µM. The corresponding 18-mer format RNAi agents had even further improved IC50. Several corresponding 18-mer format RNAi agents were constructed comprising: an 18-mer AS strand, the 3' end of which terminates in a phosphate and further comprises, in 5' to 3' order: a spacer (ribitol), a phosphate and a X058 3' end cap; and an 18-mer S strand, the 3' end of which terminates in a phosphate and further comprises a spacer (ribitol), a phosphate and a 3' end cap (X023). Several of these constructs demonstrated a further improved IC50 of approximately 0.3 µM.

The improved efficacy of several other 18-mer RNAi agents is shown in FIG. 25. These are designated by numbers 309, 880, 1586, 180, 1596 and 1591 in the human (hs) sequence, but are cross-reactive between human, mouse and rat. The 19-mers and 18-mers corresponding to these sequences were tested and the results shown in FIG. 25. For all of these sequences, the 18-mers showed greater RNAi activity than the 19-mer. The formats used were 19-mer blunt-ended with 3' end cap (C6), or 18-mer blunt-ended with 3' end cap (C6). No ribitol or other spacer was used.

The improved efficacy of 18-mer format RNAi agents compared to 19-mers was also shown with RNAi agents targeting PLK1. These included human sequences starting at nt 1720, 664, 572, 969, 1651, 578 of the PLK1 sequence. Successful 18-mer format RNAi agents were constructed for all these sequences. These all comprise a first strand and a second strand, wherein the first and second strands are 18-mers, and the first and second strand together form a blunt-ended duplex, and wherein the 3' end of the first and second strand terminate in a phosphate and further comprise a 3' end cap, which is C6. These were tested in 786-0 cells. In all cases except 1720, the 18-mer format PLK1 RNAi agent was more active in mediating RNA interference than the corresponding 19-mer format (also a blunt-ended 19-mer, with C6 3' end cap on both strands).

Thus, in several experiments, various 18-mer format RNAi agents have demonstrated improved activity compared to a corresponding 21-mer siRNA.

The present disclosure also encompasses methods of decreasing the expression of a target gene or reducing the level of its gene product, or of treating a disease associated with over-expression of a target gene, in vitro, or in an organism, such as a mammal, such as a human being, wherein the method comprises the step of administering to the human being a physiologically active amount of a composition comprising a RNAi agent of an RNAi agent with an 18-mer with internal spacer format or a RNAi agent with an internal spacer format, as disclosed herein.

Various aspects of the 18-mer format with an internal spacer for RNAi agents are detailed below.

18-mer Format with at Least One Internal Spacer and RNAi Agent with at Least One Internal Spacer The disclosure thus relates to novel formats, which can be used to devise RNAi agents to a variety of different targets and sequences. In some embodiments, the novel format is an 18-mer with at least one internal spacer. This is similar to the 18-mer format, except that at least one nucleotide or ribonucleotide is replaced by a spacer subunit (a phosphate or modified internucleoside linker+a spacer). In various embodiments, the spacer subunit can be at any position (1, 2, 3, 4, 5, 6, 7, 8, 9, 10, 11, 12, 13, 14, 15, 16, 17 or 18), wherein the remaining positions are nucleotides. In various embodiments, more than one nucleotide in one or both strands can be substituted with a spacer subunit. In some embodiments, the spacer is a ribitol and the spacer subunit comprises a phosphate or modified internucleoside linker, and a ribitol. A variety of other spacers and modified internucleoside linkers are described herein. In various embodiments wherein the RNAi agent comprises multiple spacers, the spacers can all be the same or of a variety of types. The 3' end of one or both strands terminates in a phosphate or modified internucleoside linker and further comprises, in 5' to 3' order: a second spacer, a second phosphate or modified internucleoside linker, and a 3' end cap. Generally, the sense strand is more tolerant to modification than the antisense strand, as the sense strand does not mediate RNA interference. We show herein that even in the antisense one or more nucleotides can be replaced with a spacer subunit and RNA interference activity retained. We show that any position, from 1 to 18, can be substituted with spacer subunit and RNA interference activity retained (see Table 8). In various embodiments, the RNAi agents capable of mediating RNA interference comprise a first and a second 18-mer strand, wherein the first strand is 18 total of: (a) 13-17 ribonucleotides or modified ribonucleotides, (b) at least 1 spacer subunit, and optionally (c) 0-4 of any of DNA, PNA, LNA, TNA, GNA, ANA, FANA, CeNa, HNA or UNA; and the second strand is 18 total of: (a) 13-18 ribonucleotides or modified ribonucleotides, optionally (b) at least 1 spacer subunit, and optionally (c) 0-4 of any of DNA, PNA, LNA, TNA, GNA, ANA, FANA, CeNa, HNA or UNA; wherein: each spacer subunit is (a) a phosphate or modified internucleoside linker and (b) a spacer; a spacer subunit can be at any position in the strand; the two strands form a duplex with at least one blunt end; and the 3' end of one or both strands terminates in a phosphate or modified internucleoside linker and further comprises, in 5' to 3' order: a second spacer; a second phosphate or modified internucleoside linker, and a 3' end cap. Thus, the first 18-mer strand can be, as non-limiting examples: (a) 17 ribonucleotides or modified ribonucleotides and 1 spacer subunit; (b) 14 ribonucleotides or modified ribonucleotides and 1 spacer subunit and 3 DNA nucleotides; (c) 16 ribonucleotides or modified ribonucleotides and 2 spacer subunits; (d) 14 ribonucleotides or modified ribonucleotides and 1 spacer subunit and 3 LNA units (mers); (e) 14 ribonucleotides or modified ribonucleotides and 1 spacer subunit and 3 TNA units (mers); etc. The second 18-mer strand can comprise, as non-limiting examples: (a) 18 ribonucleotides or modified ribonucleotides; (b) 17 ribonucleotides or modified ribonucleotides and 1 spacer subunit; (c) 14 ribonucleotides or modified ribonucleotides and 1 spacer subunit and 3 DNA nucleotides; (d) 16 ribonucleotides or modified ribonucleotides and 2 spacer subunits; (e) 14 ribonucleotides or modified ribonucleotides and 1 spacer subunit and 3 LNA units (mers); (f) 14 ribonucleotides or modified ribonucleotides and 1 spacer subunit and 3 TNA units (mers); etc. The spacer, modified internucleoside linker and 3' end cap can be any of these described herein or known in the art. In some embodiments, the spacer subunit is at an internal position (any of positions 2 to 17 counting 5' to 3') and the two 18-mer strands form a blunt-ended duplex. Another novel RNAi agent format is described herein and designated the internal spacer format. In this format, each strand of the RNAi agent is a 30-mer or shorter, wherein at least one strand comprises nucleotides and at least one spacer subunit. The other strand can comprise only nucleotides, or nucleotides and at least one spacer subunit. Optionally, the 3' end of one or both strands terminates in a phosphate or modified internucleoside linker and (a) further comprises a 3' end cap, or (b) further comprises, in 5' to 3' order: a second spacer, a second phosphate or modified internucleoside linker, and a 3' end cap.

The two strands can have the same or different spacers, phosphate or modified internucleoside linker, and/or 3' end caps. In various embodiments, one or more nt can be modified and/or substituted. Various spacers, modified internucleoside linkers and 3' end caps are described below.

Spacers: Ribitol, Diribitol, 2'-Deoxyribitol, 2'-Methoxyethoxy Ribitol, C3, C4, C5, C6, or 4-Methoxybutane-1,3-Diol (5300)

In the present disclosure, in an RNAi agent with an 18-mer with an internal spacer format or a RNAi agent with internal spacer format, any of various spacers can be used in combination with strands of any sequence, with or without substitutions and/or modifications of nt, with phosphates or modified nucleoside spacers, and with any 3' end cap, in any combination without limitation.

A spacer is a chemical moiety intended or used to create or maintain a space (e.g., a proper or functional spacing) between two other chemical moieties; e.g., between two phosphates or modified internucleoside linkers. In various embodiments of an RNAi agent with an 18-mer with internal spacer format or a RNAi agent with an internal spacer format, the spacer is a ribitol, diribitol, 2'-deoxyribitol, or 2'-methoxyethoxy ribitol (ribitol with 2'-MOE) or an equivalent abasic nucleotide known to one skilled in the art, or a lower alkyl or alkoxy group such as a C3, C4, C5 or C6, or 4-methoxybutane-1,3-diol. Various embodiments are described in more detail below.

Ribitol Spacer.

In some embodiments of an RNAi agent with an 18-mer with internal spacer format or a RNAi agent with an internal spacer format, at least one spacer is ribitol.

In one embodiment, the RNAi agent comprises, in 5' to 3' order: an 18-mer strand (comprising a 3' terminal phosphate or a modified internucleoside linker); a spacer which is ribitol; a phosphate or a modified internucleoside linker; and a 3' end cap (e.g., any 3' end cap described herein or otherwise known in the art). In one embodiment, the RNAi agent comprises, in 5' to 3' order: an 18-mer strand comprising a 3' terminal phosphate; a spacer which is ribitol; a phosphate or a modified internucleoside linker; and a 3' end cap. In various embodiments, one 18-mer strand of the RNAi agent comprises ribonucleotides and at least one spacer subunit. For example, the 18-mer strand comprises 17 ribonucleotides and 1 spacer subunit; 16 ribonucleotides and 2 spacer subunits; 15 ribonucleotides and 3 spacer subunits; 14 ribonucleotides and 4 spacer subunits; etc. The other strand comprises ribonucleotides, or ribonucleotides and at least one spacer subunit. In various embodiments, the spacer subunits are at a non-terminal position (e.g., the spacer subunits are at any of positions 2 to 17 of an 18-mer). In various embodiments, the spacer subunits are at a non-terminal position and the two strands form a blunt-ended duplex. In various embodiments, both strands are 18-mers. Optionally, one or more ribonucleotide is modified or substituted with DNA, PNA, LNA, TNA, GNA, ANA, FANA, CeNa, HNA or UNA. In various embodiments, the RNAi agent comprises a strand comprising ribonucleotides and at least one spacer subunit. The other strand comprises ribonucleotides, or ribonucleotides and at least one spacer subunit. Optionally, one or more ribonucleotide is substituted with DNA, PNA, LNA, TNA, GNA, ANA, FANA, CeNa, HNA or UNA, or modified. In various embodiments, one or both strand is a 30-mer or shorter. In various embodiments, the spacer subunits are at a non-terminal position (e.g., not at the first or last position counting 5' to 3').

The structure of a spacer subunit comprising a phosphate andribitol spacer is shown here:

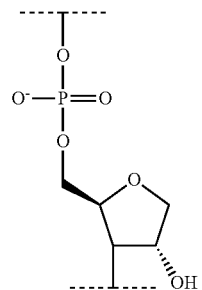

ribitol spacer.

In some documents, the ribitol spacer is designated as N027 (C027, G027, etc.). This terminology indicates that the nucleotide C or G (respectively) normally at this position has been replaced by a spacer.

One embodiment is shown in FIG. 18, wherein the RNAi agent comprises, in 5' to 3' order: an 18-mer strand, wherein the 3' end of the 18-mer strand terminates in a phosphate and further comprises, in 5' to 3' order: a spacer which is ribitol, a phosphate, and a 3' end cap which is X058. This structure can be on any RNAi strand of any sequence or target. In addition, any 3' end cap disclosed herein can be used in place of X058.

A related structure is shown in FIG. 17 ("ribitol with X058"), wherein the last nucleotide of the 18-mer strand is shown (and is a 2'-MOE), and the 3' end of the 18-mer strand terminates in a phosphate and further comprises, in 5' to 3' order: a spacer which is ribitol, a second phosphate, and a 3' end cap which is X058.

Another embodiment is shown in FIG. 17 ("ribitol with C6 cap"), wherein the last nucleotide of the 18-mer strand is shown (and is a 2'-MOE), and the 3' end of the 18-mer strand terminates in a phosphate and further comprises, in 5' to 3' order: a spacer which is ribitol, a phosphate, and a 3' end cap which is C6.

In one embodiment, the RNAi agent comprises, in 5' to 3' order: an 18-mer strand terminating in a 3' phosphate, a ribitol spacer, a phosphate, and a C6 3' end cap. This is diagrammed as ribpC6 (or ribC6) in Table 2.

In one embodiment, the RNAi agent comprises, in 5' to 3' order: an 18-mer strand terminating in a 3' phosphate, a ribitol spacer, a phosphate, and a BP 3' end cap. This is diagrammed as ribpBP (or ribBP) in Table 2.

In one embodiment, the RNAi agent comprises, in 5' to 3' order: an 18-mer strand terminating in a 3' phosphate, a ribitol spacer, a phosphate, and a C10 3' end cap. This is diagrammed as ribpC10 (or ribC10) in Table 2.

In various embodiments, the 3' end cap is triethylene glycol, cyclohexyl, phenyl, BP (biphenyl), lithochol (lithocholic acid), adamantane, C3 amino, C7 amino, C3, C6, C8, C10, C12, X027, X038, X050, X051, X052, X058, X059, X060, X061, X062, X063, X064, X065, X066, X067, X068, X069, X097, X098, X109, X110, X111, X112, X113, X1009, X1010, X1011, X1012, X1013, X1015, X1016, X1017, X1018, X1019, X1020, X1021, X1022, X1024, X1025, X1026, X1027, X1028, X1047, X1048, X1049, X1062, X1063, X1064, or ribitol, or any 3' end cap disclosed herein or known in the art.

In some embodiments, the 3' end cap is a ribitol. Thus, the RNAi agent comprises an 18-mer strand, wherein the 3' end of the 18-mer strand terminates in a phosphate or modified internucleoside linker and further comprises, in 5' to 3' order: a spacer which is ribitol, a second phosphate or modified internucleoside linker, and a 3' end cap which is a second ribitol. In one embodiment, the 3' end of the 18-mer strand terminates in a phosphate and further comprises, in 5' to 3' order: a spacer which is ribitol, a second phosphate, and a 3' end cap which is a second ribitol. Such as structure is illustrated in FIG. 17 (including the 3' terminal nucleotide and phosphate) and designated "diribitol".

The structure comprising an RNAi agent comprising, in 5' to 3' order, an 18-mer strand terminating in a 3' terminal phosphate or a modified internucleoside linker, a ribitol spacer, a phosphate or a modified internucleoside linker, and a 3' end cap (e.g., any 3' end cap disclosed herein) can be used on any RNAi agent of sequence or target, including but not limited to a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, FANA, ANA, HNA, CeNA, and/or UNA.

Diribitol Spacer.

In some embodiments of an RNAi agent with an 18-mer with internal spacer format or a RNAi agent with an internal spacer format, the spacer is Diribitol.

In one embodiment, the RNAi agent comprises, in 5' to 3' order: an 18-mer strand wherein the 3' end of the strand terminates in a phosphate or modified internucleoside linker and further comprises in 5' to 3' order: a spacer (wherein the spacer comprises in 5' to 3' order: a first ribitol; a phosphate or a modified internucleoside linker; a second ribitol; and a phosphate or a modified internucleoside linker); and a 3' end cap. In various embodiments, one 18-mer strand of the RNAi agent comprises ribonucleotides and at least one spacer subunit. For example, the 18-mer strand comprises 17 ribonucleotides and 1 spacer subunit; 16 ribonucleotides and 2 spacer subunits; 15 ribonucleotides and 3 spacer subunits; 14 ribonucleotides and 4 spacer subunits; etc. The other strand comprises ribonucleotides, or ribonucleotides and at least one spacer subunit. In various embodiments, the spacer subunits are at a non-terminal position (e.g., the spacer subunits are at any of positions 2 to 17 of an 18-mer). In various embodiments, both strands are 18-mers. Optionally, one or more ribonucleotide is modified or substituted with DNA, PNA, LNA, TNA, GNA, ANA, FANA, CeNa, HNA or UNA. In various embodiments, the RNAi agent comprises a strand comprising ribonucleotides and at least one spacer subunit. The other strand comprises ribonucleotides, or ribonucleotides and at least one spacer subunit. Optionally, one or more ribonucleotide is substituted with DNA, PNA, LNA, TNA, GNA, ANA, FANA, CeNa, HNA or UNA, or modified. In various embodiments, one or both strand is a 30-mer or shorter. In various embodiments, the spacer subunits are at a non-terminal position (e.g., not at the first or last position counting 5' to 3').

Thus: In one embodiment, the RNAi agent comprises, in 5' to 3' order: an 18-mer strand comprising a 3' terminal phosphate; a first ribitol; a phosphate; a second ribitol; a phosphate or a modified internucleoside linker; and a 3' end cap. In various embodiments, one 18-mer strand of the RNAi agent comprises ribonucleotides and at least one spacer subunit. For example, the 18-mer strand comprises 17 ribonucleotides and 1 spacer subunit; 16 ribonucleotides and 2 spacer subunits; 15 ribonucleotides and 3 spacer subunits;

14 ribonucleotides and 4 spacer subunits; etc. The other strand comprises ribonucleotides, or ribonucleotides and at least one spacer subunit. In various embodiments, the spacer subunits are at a non-terminal position (e.g., the spacer subunits are at any of positions 2 to 17 of an 18-mer). In various embodiments, both strands are 18-mers. Optionally, one or more ribonucleotide is modified or substituted with DNA, PNA, LNA, TNA, GNA, ANA, FANA, CeNa, HNA or UNA. In various embodiments, the RNAi agent comprises a strand comprising ribonucleotides and at least one spacer subunit. The other strand comprises ribonucleotides, or ribonucleotides and at least one spacer subunit. Optionally, one or more ribonucleotide is substituted with DNA, PNA, LNA, TNA, GNA, ANA, FANA, CeNa, HNA or UNA, or modified. In various embodiments, one or both strand is a 30-mer or shorter. In various embodiments, the spacer subunits are at a non-terminal position (e.g., not at the first or last position counting 5' to 3').

This structure of a 3' terminal phosphate, a first ribitol, a phosphate, and a second ribitol is shown here:

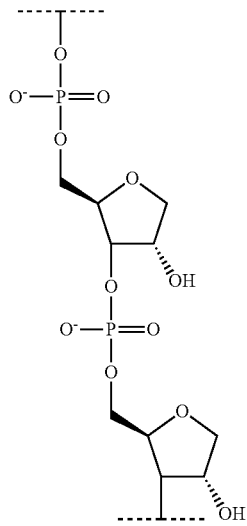

diribitol spacer

In one embodiment, the RNAi agent comprises, in 5' to 3' order: an 18-mer strand comprising a 3' terminal phosphate; a first ribitol spacer; a phosphate; a second ribitol spacer; a phosphate or a modified internucleoside linker; and a 3' end cap.

In one embodiment, the RNAi agent comprises, in 5' to 3' order: an 18-mer strand terminating in a 3' terminal phosphate or a modified internucleoside linker, a first ribitol spacer, a phosphate or a modified internucleoside linker, a second ribitol spacer, a phosphate or a modified internucleoside linker, and a 3' end cap which is a ribitol; this structure is designated a triribitol.

In various embodiments, the 3' end cap is triethylene glycol, cyclohexyl, phenyl, BP (biphenyl), lithochol (lithocholic acid), adamantane, C3 amino, C7 amino, C3, C6, C8, C10, C12, X027, X038, X050, X051, X052, X058, X059, X060, X061, X062, X063, X064, X065, X066, X067, X068, X069, X097, X098, X109, X110, X111, X112, X113, X1009, X1010, X1011, X1012, X1013, X1015, X1016, X1017, X1018, X1019, X1020, X1021, X1022, X1024, X1025, X1026, X1027, X1028, X1047, X1048, X1049, X1062, X1063, or X1064, or any 3' end cap disclosed herein or known in the art or known in the art.

The structure comprising an RNAi agent comprising, in 5' to 3' order, an 18-mer strand terminating in a 3' terminal phosphate or a modified internucleoside linker, a first ribitol spacer, a phosphate or a modified internucleoside linker, a second ribitol spacer, a phosphate or a modified internucleoside linker, and a 3' end cap (e.g., any 3' end cap disclosed herein) can be used on any RNAi agent of sequence or target, including but not limited to a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, FANA, CeNA, and/or UNA.

2'-Methoxyethoxy Ribitol Spacer.

In some embodiments, the spacer is 2'-methoxyethoxy ribitol or other type of abasic nucleotide.

In one embodiment, the RNAi agent comprises a strand, wherein the 3' end of the strand terminates in a phosphate or modified internucleoside linker and further comprises, in 5' to 3' order: a spacer which is 2'-methoxyethoxy ribitol, a second phosphate or modified internucleoside linker, and a 3' end (e.g., any 3' end cap described herein or known in the art). In other words: In one embodiment, the RNAi agent comprises, in 5' to 3' order: a strand comprising a 3' terminal phosphate or a modified internucleoside linker; a spacer which is 2'-methoxyethoxy ribitol; a phosphate or a modified internucleoside linker; and a 3' end cap (e.g., any 3' end cap described herein or known in the art). Thus: In one embodiment, the RNAi agent comprises, in 5' to 3' order: a strand comprising a 3' terminal phosphate; a spacer which is 2'-methoxyethoxy ribitol; a phosphate or a modified internucleoside linker; and a 3' end cap. In various embodiments, one 18-mer strand of the RNAi agent comprises ribonucleotides and at least one spacer subunit. For example, the 18-mer strand comprises 17 ribonucleotides and 1 spacer subunit; 16 ribonucleotides and 2 spacer subunits; 15 ribonucleotides and 3 spacer subunits; 14 ribonucleotides and 4 spacer subunits; etc. The other strand comprises ribonucleotides, or ribonucleotides and at least one spacer subunit. In various embodiments, the spacer subunits are at a non-terminal position (e.g., the spacer subunits are at any of positions 2 to 17 of an 18-mer). In various embodiments, both strands are 18-mers. Optionally, one or more ribonucleotide is modified or substituted with DNA, PNA, LNA, TNA, GNA, ANA, FANA, CeNa, HNA or UNA. In various embodiments, the RNAi agent comprises a strand comprising ribonucleotides and at least one spacer subunit. The other strand comprises ribonucleotides, or ribonucleotides and at least one spacer subunit. Optionally, one or more ribonucleotide is substituted with DNA, PNA, LNA, TNA, GNA, ANA, FANA, CeNa, HNA or UNA, or modified. In various embodiments, one or both strand is a 30-mer or shorter. In various embodiments, the spacer subunits are at a non-terminal position (e.g., not at the first or last position counting 5' to 3').

The structure of the 3' terminal phosphate and 2'-methoxyethoxy ribitol spacer is shown here:

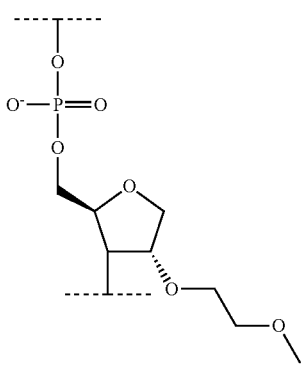

2'-methoxyethoxy ribitol spacer.

In one embodiment, the RNAi agent comprises, in 5' to 3' order: an 18-mer strand, wherein the 3' end of the 18-mer strand terminates in a phosphate and further comprises, in 5' to 3' order: a spacer which is 2'-methoxyethoxy ribitol, a phosphate, and a 3' end cap which is X058. This structure can be on any RNAi strand of any sequence or target. In addition, any 3' end cap disclosed herein can be used in place of X058.

A related structure is 2'-methoxyethoxy ribitol with X058, wherein the last nucleotide of the 18-mer strand is a 2'-MOE), and the 3' end of the 18-mer strand terminates in a phosphate and further comprises, in 5' to 3' order: a spacer which is 2'-methoxyethoxy ribitol, a second phosphate, and a 3' end cap which is X058.

Another embodiment is 2'-methoxyethoxy ribitol with C6 cap, wherein the last nucleotide of the 18-mer strand is a 2'-MOE), and the 3' end of the 18-mer strand terminates in a phosphate and further comprises, in 5' to 3' order: a spacer which is 2'-methoxyethoxy ribitol, a phosphate, and a 3' end cap which is C6.

In one embodiment, the RNAi agent comprises, in 5' to 3' order: an 18-mer strand terminating in a 3' phosphate, a 2'-methoxyethoxy ribitol spacer, a phosphate, and a C6 3' end cap.

In one embodiment, the RNAi agent comprises, in 5' to 3' order: an 18-mer strand terminating in a 3' phosphate, a 2'-methoxyethoxy ribitol spacer, a phosphate, and a BP 3' end cap.

In one embodiment, the RNAi agent comprises, in 5' to 3' order: an 18-mer strand terminating in a 3' phosphate, a 2'-methoxyethoxy ribitol spacer, a phosphate, and a C10 3' end cap.

In another embodiment, the RNAi agent comprises a strand, wherein the 3' end of the strand terminates in a phosphate and further comprises, in 5' to 3' order: a spacer which is 2'-methoxyethoxy ribitol, a phosphate, and a 3' end cap which is X058.

In some embodiments, the 3' end cap is a 2'-methoxyethoxy ribitol. Thus, the RNAi agent comprises an 18-mer strand, wherein the 3' end of the 18-mer strand terminates in a phosphate or modified internucleoside linker and further comprises, in 5' to 3' order: a spacer which is 2'-methoxyethoxy ribitol, a second phosphate or modified internucleoside linker, and a 3' end cap which is a second 2'-methoxyethoxy ribitol. In one embodiment, the 3' end of the 18-mer strand terminates in a phosphate and further comprises, in 5' to 3' order: a spacer which is 2'-methoxyethoxy ribitol, a second phosphate, and a 3' end cap which is a second 2'-methoxyethoxy ribitol.

In various embodiments, the 3' end cap is triethylene glycol, cyclohexyl, phenyl, BP (biphenyl), lithochol (litho-cholic acid), adamantane, C3 amino, C7 amino, C3, C6, C8, C10, C12, X027, X038, X050, X051, X052, X058, X059, X060, X061, X062, X063, X064, X065, X066, X067, X068, X069, X097, X098, X109, X110, X111, X112, X113, X1009, X1010, X1011, X1012, X1013, X1015, X1016, X1017, X1018, X1019, X1020, X1021, X1022, X1024, X1025, X1026, X1027, X1028, X1047, X1048, X1049, X1062, X1063, X1064, or 2'-methoxyethoxy ribitol, or any 3' end cap disclosed herein or known in the art. The structure comprising an RNAi agent comprising, in 5' to 3' order, a strand terminating in a 3' terminal phosphate or a modified internucleoside linker, a 2'-methoxyethoxy ribitol spacer, a phosphate or a modified internucleoside linker, and a 3' end cap (e.g., any 3' end cap disclosed herein including but not limited to those listed in the previous sentence) can be used on any RNAi agent of any length, sequence or target, including but not limited to a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

2'-Deoxyribitol Spacer.

In some embodiments of an RNAi agent with an 18-mer with internal spacer format or a RNAi agent with an internal spacer format, the spacer is 2'-deoxyribitol.

In one embodiment, the RNAi agent comprises, in 5' to 3' order: an 18-mer strand terminating in a 3' phosphate or a modified internucleoside linker, a spacer which is 2'-deoxy-ribitol (2'-deoxyrib), a phosphate or a modified internucleoside linker, and a 3' end cap.

In one embodiment, the RNAi agent comprises, in 5' to 3' order: an 18-mer strand terminating in a 3' phosphate, a spacer which is 2'-deoxyribitol (2'-deoxyrib), a phosphate or a modified internucleoside linker, and a 3' end cap. In various embodiments, one 18-mer strand of the RNAi agent comprises ribonucleotides and at least one spacer subunit. For example, the 18-mer strand comprises 17 ribonucleotides and 1 spacer subunit; 16 ribonucleotides and 2 spacer subunits; 15 ribonucleotides and 3 spacer subunits; 14 ribonucleotides and 4 spacer subunits; etc. The other strand comprises ribonucleotides, or ribonucleotides and at least one spacer subunit. In various embodiments, the spacer subunits are at a non-terminal position (e.g., the spacer subunits are at any of positions 2 to 17 of an 18-mer). In various embodiments, both strands are 18-mers. Optionally, one or more ribonucleotide is modified or substituted with DNA, PNA, LNA, TNA, GNA, ANA, FANA, CeNa, HNA or UNA. In various embodiments, the RNAi agent comprises a strand comprising ribonucleotides and at least one spacer subunit. The other strand comprises ribonucleotides, or ribonucleotides and at least one spacer subunit. Optionally, one or more ribonucleotide is substituted with DNA, PNA, LNA, TNA, GNA, ANA, FANA, CeNa, HNA or UNA, or modified. In various embodiments, one or both strand is a 30-mer or shorter. In various embodiments, the spacer subunits are at a non-terminal position (e.g., not at the first or last position counting 5' to 3'). The structure of a spacer subunit comprising a phosphate and a 2'-deoxyribitol is shown here:

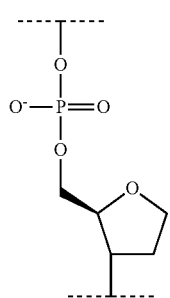

2'-deoxyribitol (2'-deoxyrib).

In one embodiment, the RNAi agent comprises, in 5' to 3' order: an 18-mer strand terminating in a 3' phosphate, a 2'-deoxyribitol spacer, a phosphate, and a C12 3' end cap. This is diagrammed as ribpC10 (or ribC10) in Table 2. This embodiment is designated "2'DeoxyribC12" and illustrated in Table 2.

In various embodiments, the 3' end cap is triethylene glycol, cyclohexyl, phenyl, BP (biphenyl), lithochol (lithocholic acid), adamantane, C3 amino, C7 amino, C3, C6, C8, C10, C12, X027, X038, X050, X051, X052, X058, X059, X060, X061, X062, X063, X064, X065, X066, X067, X068, X069, X097, X098, X109, X110, X111, X112, X113, X1009, X1010, X1011, X1012, X1013, X1015, X1016, X1017, X1018, X1019, X1020, X1021, X1022, X1024, X1025, X1026, X1027, X1028, X1047, X1048, X1049, X1062, X1063, or X1064, or any 3' end cap disclosed herein or known in the art.

The structure comprising an RNAi agent comprising, in 5' to 3' order, an 18-mer strand terminating in a 3' terminal phosphate or a modified internucleoside linker, a 2'-deoxyribitol spacer, a phosphate or a modified internucleoside linker, and a 3' end cap (e.g., any 3' end cap disclosed herein) can be used on any RNAi agent of any sequence or target, including but not limited to a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

C3 Spacer.

In various embodiments of an RNAi agent with an 18-mer with internal spacer format or a RNAi agent with an internal spacer format, the spacer is C3.

In one embodiment, the RNAi agent comprises an 18-mer strand, wherein the 3' end of the 18-mer strand terminates in a 3' phosphate or a modified internucleoside linker, and further comprises a spacer which is C3, a phosphate or a modified internucleoside linker, and a 3' end cap.

In one embodiment, the RNAi agent comprises two 18-mer strands, wherein the 3' end of each 18-mer strand terminates in a 3' phosphate or a modified internucleoside linker, and further comprises a spacer, a second phosphate or a modified internucleoside linker, and a 3' end cap, wherein the spacer in one or both strands is C3. In various embodiments, one 18-mer strand of the RNAi agent comprises ribonucleotides and at least one spacer subunit. For example, the 18-mer strand comprises 17 ribonucleotides and 1 spacer subunit; 16 ribonucleotides and 2 spacer subunits; 15 ribonucleotides and 3 spacer subunits; 14 ribonucleotides and 4 spacer subunits; etc. The other strand comprises ribonucleotides, or ribonucleotides and at least one spacer subunit. In various embodiments, the spacer subunits are at a non-terminal position (e.g., the spacer subunits are at any of positions 2 to 17 of an 18-mer). In various embodiments, both strands are 18-mers. Optionally, one or more ribonucleotide is modified or substituted with DNA, PNA, LNA, TNA, GNA, ANA, FANA, CeNa, HNA or UNA. In various embodiments, the RNAi agent comprises a strand comprising ribonucleotides and at least one spacer subunit. The other strand comprises ribonucleotides, or ribonucleotides and at least one spacer subunit. Optionally, one or more ribonucleotide is substituted with DNA, PNA, LNA, TNA, GNA, ANA, FANA, CeNa, HNA or UNA, or modified. In various embodiments, one or both strand is a 30-mer or shorter. In various embodiments, the spacer subunits are at a non-terminal position (e.g., not at the first or last position counting 5' to 3').

The C3 spacer has the chemical formula —$(CH_2)_3$—. The structure of a spacer subunit comprising a phosphate and a C3 spacer is shown here:

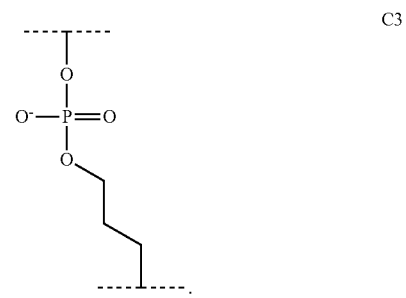

One embodiment is shown in FIG. 18, wherein the RNAi agent comprises, in 5' to 3' order: an 18-mer strand terminating in a 3' phosphate, a C3 spacer, a phosphate, and a 3' end cap which is X058. This structure can be on any RNAi strand of any sequence or target. In addition, any 3' end cap disclosed herein or known in the art can be used in place of X058, and any modified internucleoside linker can be used in place of phosphate.

Another embodiment is shown in FIG. 11, which illustrates a portion of a RNAi agent to Factor VII comprising an 18-mer strand, wherein the 18-mer strand terminates in a phosphate and further comprises in 5' to 3' order: a C3 spacer, a phosphate and a 3' end cap which is C6. This is designated "C3pC6 overhang". This structure can be on any RNAi strand of any sequence or target. In addition, any 3' end cap disclosed herein or known in the art can be used in place of C6, and any modified internucleoside linker can be used in place of phosphate.

The efficacy of a RNAi agent comprising a C3 spacer is shown in FIG. 19. Two different HuR constructs were prepared comprising an 18-mer, wherein the 3' end of the 18-mer terminates in a phosphate and further comprises in 5' to 3' order: a C3 spacer, a phosphate and a 3' end cap (which is C6 or X058). Both of these were able to mediate RNA interference.

In various embodiments, the 3' end cap is triethylene glycol, cyclohexyl, phenyl, BP (biphenyl), lithochol (lithocholic acid), adamantane, C3 amino, C7 amino, C3, C6, C8, C10, C12, X027, X038, X050, X051, X052, X058, X059, X060, X061, X062, X063, X064, X065, X066, X067, X068, X069, X097, X098, X109, X110, X111, X112, X113, X1009, X1010, X1011, X1012, X1013, X1015, X1016, X1017, X1018, X1019, X1020, X1021, X1022, X1024, X1025, X1026, X1027, X1028, X1047, X1048, X1049, X1062, X1063, or X1064, or any 3' end cap disclosed herein or known in the art.

The structure comprising an RNAi agent comprising, in 5' to 3' order, an 18-mer strand terminating in a 3' terminal phosphate or a modified internucleoside linker, a C3 spacer, a phosphate or a modified internucleoside linker, and a 3' end cap (e.g., any 3' end cap disclosed herein) can be used on any RNAi agent of any sequence or target, including but not limited to a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

C4 Spacer, C5 Spacer and C6 Spacer.

In various embodiments of an RNAi agent with an 18-mer with internal spacer format or a RNAi agent with an internal spacer format, the spacer is C4 or C5 or C6.

In one embodiment, the RNAi agent comprises an 18-mer strand, wherein the 3' end of the 18-mer strand terminates in a 3' phosphate or a modified internucleoside linker, and further comprises a spacer which is C4 or C5 or C6, a phosphate or a modified internucleoside linker, and a 3' end cap.

In one embodiment, the RNAi agent comprises two 18-mer strands, wherein the 3' end of each 18-mer strand terminates in a 3' phosphate or a modified internucleoside linker, and further comprises a spacer, a second phosphate or a modified internucleoside linker, and a 3' end cap, wherein the spacer in one or both strands is C4 or C5 or C6. In various embodiments, one 18-mer strand of the RNAi agent comprises ribonucleotides and at least one spacer subunit. For example, the 18-mer strand comprises 17 ribonucleotides and 1 spacer subunit; 16 ribonucleotides and 2 spacer subunits; 15 ribonucleotides and 3 spacer subunits; 14 ribonucleotides and 4 spacer subunits; etc. The other strand comprises ribonucleotides, or ribonucleotides and at least one spacer subunit. In various embodiments, the spacer subunits are at a non-terminal position (e.g., the spacer subunits are at any of positions 2 to 17 of an 18-mer). In various embodiments, both strands are 18-mers. Optionally, one or more ribonucleotide is modified or substituted with DNA, PNA, LNA, TNA, GNA, ANA, FANA, CeNa, HNA or UNA. In various embodiments, the RNAi agent comprises a strand comprising ribonucleotides and at least one spacer subunit. The other strand comprises ribonucleotides, or ribonucleotides and at least one spacer subunit. Optionally, one or more ribonucleotide is substituted with DNA, PNA, LNA, TNA, GNA, ANA, FANA, CeNa, HNA or UNA, or modified. In various embodiments, one or both strand is a 30-mer or shorter. In various embodiments, the spacer subunits are at a non-terminal position (e.g., not at the first or last position counting 5' to 3').

The C3 to C6 spacers can be defined as:
C3=1,3-propane-diol
C4=1,4-butane-diol
C5=1,5-pentane-diol
C6=1,6-hexane-diol In some contexts:
The C4 spacer has the chemical formula —$(CH_2)_4$—.
The C5 spacer has the chemical formula —$(CH_2)_5$—.
The C6 spacer has the chemical formula —$(CH_2)_6$—.

In various embodiments, the 3' end cap is triethylene glycol, cyclohexyl, phenyl, BP (biphenyl), lithochol (lithocholic acid), adamantane, C3 amino, C7 amino, C3, C6, C8, C10, C12, X027, X038, X050, X051, X052, X058, X059, X060, X061, X062, X063, X064, X065, X066, X067, X068, X069, X097, X098, X109, X110, X111, X112, X113, X1009, X1010, X1011, X1012, X1013, X1015, X1016, X1017, X1018, X1019, X1020, X1021, X1022, X1024, X1025, X1026, X1027, X1028, X1047, X1048, X1049, X1062, X1063, or X1064, or any 3' end cap disclosed herein or known in the art.

The structure comprising an RNAi agent comprising, in 5' to 3' order, an 18-mer strand terminating in a 3' terminal phosphate or a modified internucleoside linker, a C4 or C5 or C6 spacer, a phosphate or a modified internucleoside linker, and a 3' end cap (e.g., any 3' end cap disclosed herein) can be used on any RNAi agent of any sequence or target, including but not limited to a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

As a note of clarification, this disclosure notes that the terms "C3" [—$(CH_2)_3$—], "C4" [—$(CH_2)_4$—], and "C5" [—$(CH_2)_5$-] are generally used herein to designate spacers, similar terms (C3, C4, C5 "linkers") are also used to designate a portion of a 3' end cap, as illustrated in FIGS. 20A, 20B and 20C. In these figures, the different linkers are used to differentiate portions various 3' end caps. It is also noted that the term "C3" is used to designate a C3 3' end cap (see, e.g., U.S. Pat. No. 8,097,716), a C3 spacer (FIG. 18), and a C3 linker (FIG. 26). The C6 spacer should also be differentiated from the C6 end cap.

4-methoxybutane-1,3-diol (5300) Spacer.

In various embodiments of an RNAi agent with an 18-mer with internal spacer format or a RNAi agent with an internal spacer format, the spacer is 4-methoxybutane-1,3-diol. 4-methoxybutane-1,3-diol is also designated 5300, A5300, C5300, G5300, and UG5300.

In one embodiment, the RNAi agent comprises, in 5' to 3' order: an 18-mer strand, wherein the 3' end terminates in a 3' phosphate (a 3' terminal phosphate) or a modified internucleoside linker and further comprises: a spacer which is 4-methoxybutane-1,3-diol, a phosphate or a modified internucleoside linker, and a 3' end cap. In various embodiments, one 18-mer strand of the RNAi agent comprises ribonucleotides and at least one spacer subunit. For example, the 18-mer strand comprises 17 ribonucleotides and 1 spacer subunit; 16 ribonucleotides and 2 spacer subunits; 15 ribonucleotides and 3 spacer subunits; 14 ribonucleotides and 4 spacer subunits; etc. The other strand comprises ribonucleotides, or ribonucleotides and at least one spacer subunit. In various embodiments, the spacer subunits are at a non-terminal position (e.g., the spacer subunits are at any of positions 2 to 17 of an 18-mer). In various embodiments, both strands are 18-mers. Optionally, one or more ribonucleotide is modified or substituted with DNA, PNA, LNA, TNA, GNA, ANA, FANA, CeNa, HNA or UNA. In various embodiments, the RNAi agent comprises a strand comprising ribonucleotides and at least one spacer subunit. The other strand comprises ribonucleotides, or ribonucleotides and at least one spacer subunit. Optionally, one or more ribonucleotide is substituted with DNA, PNA, LNA, TNA, GNA, ANA, FANA, CeNa, HNA or UNA, or modified. In various embodiments, one or both strand is a 30-mer or shorter. In various embodiments, the spacer subunits are at a non-terminal position (e.g., not at the first or last position counting 5' to 3').

The structure of a spacer subunit comprising a phosphate and a 4-methoxybutane-1,3-diol spacer is shown here:

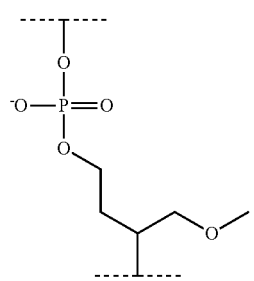

In one embodiment, the RNAi agent comprises, in 5' to 3' order: an 18-mer strand terminating in a 3' phosphate, a spacer which is 4-methoxybutane-1,3-diol, a phosphate or a modified internucleoside linker, and a 3' end cap.

One embodiment is shown in FIG. 18, wherein the RNAi agent comprises, in 5' to 3' order: an 18-mer strand terminating in a 3' phosphate, a 4-methoxybutane-1,3-diol spacer, a phosphate, and a 3' end cap which is X058. This structure can be on any RNAi strand of any sequence or target. In addition, any 3' end cap disclosed herein or known in the art can be used in place of X058, and any modified internucleoside linker can be used in place of phosphate.

The efficacy of a RNAi agent comprising a C5300 spacer is shown in FIG. 19. Two different HuR constructs were prepared comprising an 18-mer, wherein the 3' end of the 18-mer terminates in a phosphate and further comprises a C5300 spacer, a phosphate and a 3' end cap (which is C6 or X058). Both of these were able to mediate RNA interference.

In various embodiments, the 3' end cap is triethylene glycol, cyclohexyl, phenyl, BP (biphenyl), lithochol (lithocholic acid), adamantane, C3 amino, C7 amino, C3, C6, C8, C10, C12, X027, X038, X050, X051, X052, X058, X059, X060, X061, X062, X063, X064, X065, X066, X067, X068, X069, X097, X098, X109, X110, X111, X112, X113, X1009, X1010, X1011, X1012, X1013, X1015, X1016, X1017, X1018, X1019, X1020, X1021, X1022, X1024, X1025, X1026, X1027, X1028, X1047, X1048, X1049, X1062, X1063, or X1064, or any 3' end cap disclosed herein or known in the art.

The structure comprising an RNAi agent comprising, in 5' to 3' order, an 18-mer strand terminating in a 3' terminal phosphate or a modified internucleoside linker, a 4-methoxybutane-1,3-diol spacer, a phosphate or a modified internucleoside linker, and a 3' end cap (e.g., any 3' end cap disclosed herein) can be used on any RNAi agent of any sequence or target, including but not limited to a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

Phosphate or Modified Internucleoside Linker

In various embodiments of the 18-mer RNAi agent, the modified internucleoside linker is: phosphorothioate, phosphorodithioate, phosphoramidate, boranophosphonoate, an amide linker, or a compound of formula (I), as detailed below.

The disclosure relates novel formats, which can be used to devise RNAi agents to a variety of different targets and sequences. In some embodiments, the novel format is an 18-mer with at least one internal spacer. This is similar to the 18-mer format, except that at least one nucleotide or ribonucleotide is replaced by a spacer subunit (a phosophate or modified internucleoside linker+a spacer). In various embodiments, the spacer subunit can be at any position (1, 2, 3, 4, 5, 6, 7, 8, 9, 10, 11, 12, 13, 14, 15, 16, 17 or 18), wherein the remaining positions are nucleotides. In various embodiments, more than one nucleotide in one or both strands can be substituted with a spacer subunit. In some embodiments, the spacer is a ribitol and the spacer subunit comprises a phosphate and a ribitol. A variety of other spacers and modified internucleoside linkers are described herein. In various embodiments wherein the RNAi agent comprises multiple spacers, the spacer can all be the same or of a variety of types of spacer. The 3' end of one or both strands terminates in a phosphate or modified internucleoside linker and further comprises, in 5' to 3' order: a second spacer, a second phosphate or modified internucleoside linker, and a 3' end cap. Generally, the sense strand is more tolerant to modification than the antisense strand, as the sense strand does not mediate RNA interference. We show herein that even in the antisense one or more nucleotides can be replaced with a spacer subunit and RNA interference activity retained. We show that any position, from 1 to 18, can be substituted with spacer subunit and RNA interference activity retained. Another novel RNAi agent format is described herein and designated the internal spacer format. In this format, each strand of the RNAi agent is a 30-mer or shorter, wherein at least one strand comprises nucleotides and at least one spacer subunit. The other strand can comprise only nucleotides, or nucleotides and at least one spacer subunit. Optionally, the 3' end of one or both strands terminates in a phosphate or modified internucleoside linker and (a) further comprises a 3' end cap, or (b) further comprises, in 5' to 3' order: a second spacer, a second phosphate or modified internucleoside linker, and a 3' end cap. Various modified internucleoside linkers are described below. Various modified internucleoside linkers can be used in combinations with strands of any sequence, with or without any or other substitutions and/or modifications of nucleotides, with any spacers, and with any 3' end cap, in any combination without limitation. A spacer subunit, for example, can comprise a phosphate or modified internucleoside linker+a spacer. Various phosphates within the RNAi agent can be replaced by a modified internucleoside linker. A RNAi agent can comprise only phosphates, or phosphates and one or many different types of modified internucleoside linkers.

In some embodiments, the modified internucleoside linker is interposed between the spacer and the 3' end cap (i.e., the 3' end of the strand terminates in a modified internucleoside linker and further comprises a 3' end cap).

In various embodiments, one or more of the phosphates of one or both strands of the RNAi agent are replaced. Thus: In various embodiments, one or more nucleotide of one or both strands has a modified internucleoside linker. In some embodiments, the 3' terminal phosphate is replaced. In some embodiments, one or more nucleotide of one or both strands has a modified internucleoside linker, and/or a modified internucleoside linker is interposed between the spacer and the 3' end cap. In various embodiments, the spacer subunit comprises a modified internucleoside linker and a spacer.

In one embodiment, the present disclosure encompasses a RNAi agent comprising a first and a second strand, wherein the first strand is an 18-mer and the second strand consists of 17 nucleotides and 1 spacer subunit, wherein the spacer subunit comprises (a) a phosphate or modified internucleoside linker and (b) a spacer, wherein the spacer subunit can be at any position in the strand, wherein the strands together form at least one blunt-end, wherein the 3' end of at least one strand terminates in a phosphate or modified internucleoside linker and further comprises, in 5' to 3' order: a second spacer; a second phosphate or modified internucleoside linker; and a 3' end cap, wherein the 3' end cap is selected from the 3' end caps listed in any Table herein or otherwise disclosed herein, and wherein at least one nucleotide has a modified internucleoside linker a modified internucleoside linker (e.g., wherein at least one phosphate of a nucleotide is replaced by a modified internucleoside linker), where the modified internucleoside linker is:

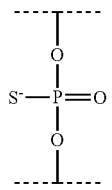

phosphorothioate (PS),

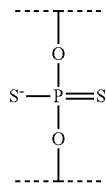

phosphorodithioate, phosphoramidate, boranophosphonoate, an amide linker, or a compound of formula (I):

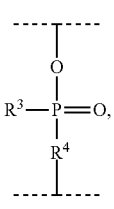

where $R^3$ is selected from $O^-$, $S^-$, $NH_2$, $BH_3$, $CH_3$, $C_{1-6}$ alkyl, $C_{6-10}$ aryl, $C_{1-6}$ alkoxy and $C_{6-10}$ aryl-oxy, wherein $C_{1-6}$ alkyl and $C_{6-10}$ aryl are unsubstituted or optionally independently substituted with 1 to 3 groups independently selected from halo, hydroxyl and $NH_2$; and $R^4$ is selected from O, S, NH, or $CH_2$. In various embodiments, one 18-mer strand of the RNAi agent comprises ribonucleotides and at least one spacer subunit. For example, the 18-mer strand comprises 17 ribonucleotides and 1 spacer subunit; 16 ribonucleotides and 2 spacer subunits; 15 ribonucleotides and 3 spacer subunits; 14 ribonucleotides and 4 spacer subunits; etc. The other strand comprises ribonucleotides, or ribonucleotides and at least one spacer subunit. In various embodiments, the spacer subunits are at a non-terminal position (e.g., the spacer subunits are at any of positions 2 to 17 of an 18-mer). In various embodiments, both strands are 18-mers. Optionally, one or more ribonucleotide is modified or substituted with DNA, PNA, LNA, TNA, GNA, ANA, FANA, CeNa, HNA or UNA. In various embodiments, the RNAi agent comprises a strand comprising ribonucleotides and at least one spacer subunit. The other strand comprises ribonucleotides, or ribonucleotides and at least one spacer subunit. Optionally, one or more ribonucleotide is substituted with DNA, PNA, LNA, TNA, GNA, ANA, FANA, CeNa, HNA or UNA, or modified. In various embodiments, one or both strand is a 30-mer or shorter. In various embodiments, the spacer subunits are at a non-terminal position (e.g., not at the first or last position counting 5' to 3').

In one embodiment, the present disclosure encompasses a RNAi agent comprising a first and a second strand, wherein the first strand is an 18-mer and the second strand consists of 17 nucleotides and 1 spacer subunit, wherein the spacer subunit comprises (a) a phosphate or modified internucleoside linker and (b) a spacer, wherein the spacer subunit can be at any position in the strand, wherein the strands together form at least one blunt-end, wherein the 3' end of at least one strand terminates in a phosphate or modified internucleoside linker and further comprises, in 5' to 3' order: a second spacer; a second phosphate or modified internucleoside linker; and a 3' end cap, wherein the 3' end cap is selected from the 3' end caps listed in any Table herein or otherwise disclosed herein, and wherein at least the 3' terminal nucleotide on one or both strands has a modified internucleoside linker (e.g., wherein the phosphate of the 3' nucleotide on one or both strands is replaced by a modified internucleoside linker), wherein the modified internucleoside linker is phosphorothioate, phosphorodithioate, phosphoramidate, boranophosphonoate, an amide linker, or a compound of formula (I). In various embodiments, the spacer subunit comprises a modified internucleoside linker and a spacer, wherein the modified internucleoside linker is a phosphorothioate, phosphorodithioate, phosphoramidate, boranophosphonoate, an amide linker, or a compound of formula (I).

In various embodiments, the 3' end cap is linked via a terminal phosphate group (i.e., a phosphate group at the 3' end of a RNAi agent strand). Such compounds are shown in, for example, Table 2. Alternatively, in 3' to 5' order, a 3' end cap can be bound to a phosphate or modified internucleoside linker, which is bound to a spacer, which is bound to a phosphate or modified internucleoside linker bound to the 3' carbon at the 3' end of at least one RNAi agent strand.

In one embodiment, compounds of table 2 have a terminal phosphorothioate group bound to the 3' carbon at the 3' end of at least one RNAi agent strand. Thus, in various embodiments, in the 3' end caps listed in Table 2, the phosphate group is replaced by a phosphorothioate. In other words, the composition comprises a RNAi agent comprising a strand, wherein the 3' end of the strand terminates in a phosphorothioate and further comprises a compound of Table 2 (or any other 3' end cap described herein or known in the art). In additional embodiments, the phosphate group of various 3' end caps listed herein as C3, C6, C12, Triethylene glycol, Cyclohexyl, Phenyl, Biphenyl, Adamantane, Lithocholic acid can be replaced by phosphorothioate. In one particular embodiment, the phosphate group in the C3 3' end cap is replaced by phosphorothioate (and designated "PS-C3", as illustrated in Table 2 and described in Example 6 and FIGS. 20 A-E). In one particular embodiment, the phosphate group in the C6 3' end cap is replaced by phosphorothioate (and designated "PS-C6", as illustrated in Table 2). In one particular embodiment, the phosphate group in the C10 3' end cap is replaced by phosphorothioate (and designated "PS-C10", as illustrated in Table 2). In one particular embodiment, the phosphate group in the biphenyl (BP) 3' end cap is replaced by phosphorothioate (and designated "PS-BP", as illustrated in Table 2).

In various embodiments, $R_1$=OH; and $R_2$=a compound of formula (I). This structure is also shown in FIG. 18C.

3' End Caps

The disclosure relates novel formats, which can be used to devise RNAi agents to a variety of different targets and sequences. In some embodiments, the novel format is an 18-mer with at least one internal spacer. This is similar to the 18-mer format, except that at least one nucleotide or ribonucleotide is replaced by a spacer subunit (a phosophate or modified internucleoside linker+a spacer). In various embodiments, the spacer subunit can be at any position (1, 2, 3, 4, 5, 6, 7, 8, 9, 10, 11, 12, 13, 14, 15, 16, 17 or 18), wherein the remaining positions are nucleotides. In various embodiments, more than one nucleotide in one or both strands can be substituted with a spacer subunit. In some embodiments, the spacer is a ribitol and the spacer subunit comprises a phosphate and a ribitol. A variety of other spacers and modified internucleoside linkers are described herein. In various embodiments wherein the RNAi agent comprises multiple spacers, the spacer can all be the same or of a variety of types of spacer. The 3' end of one or both strands terminates in a phosphate or modified internucleoside linker and further comprises, in 5' to 3' order: a second spacer, a second phosphate or modified internucleoside linker, and a 3' end cap. Generally, the sense strand is more tolerant to modification than the antisense strand, as the sense strand does not mediate RNA interference. We show herein that even in the antisense one or more nucleotides can be replaced with a spacer subunit and RNA interference activity retained. We show that any position, from 1 to 18, can be substituted with spacer subunit and RNA interference activity retained. Another novel RNAi agent format is described herein and designated the internal spacer format. In this format, each strand of the RNAi agent is a 30-mer or shorter, wherein at least one strand comprises nucleotides and at least one spacer subunit. The other strand can comprise only nucleotides, or nucleotides and at least one spacer subunit. Optionally, the 3' end of one or both strands terminates in a phosphate or modified internucleoside linker and (a) further comprises a 3' end cap, or (b) further comprises, in 5' to 3' order: a second spacer, a second phosphate or modified internucleoside linker, and a 3' end cap. Various 3' end caps are described below. Various 3' end caps can be used in combinations with strands of any sequence, with or without any or other substitutions and/or modifications of nucleotides, with any spacers, and with any phosphate or modified internucleoside linker, in any combination without limitation.

A 3' end cap is a non-nucleotidic chemical moiety bound to the 3' end of a molecule comprising a RNAi agent, e.g., the 3' terminus (or 3' end) of (a) a molecule comprising a strand, wherein the 3' end of the strand terminates in a phosphate or modified internucleoside linker; or (b) a molecule comprising, in 5' to 3' order: a strand (wherein the 3' end of the strand terminates in a phosphate or modified internucleoside linker), a spacer, and a second phosphate or modified internucleoside linker. The 3' end cap performs at least one of the following functions: allowing RNA interference mediated by the molecule, protecting the molecule from degradation or reducing the amount or rate of degradation of the molecule (e.g., by nucleases), reducing the off-target effects of the sense strand, or increasing the activity, duration or efficacy of RNA interference mediated by the molecule. By describing a 3' end cap as "non-nucleotidic", it is meant that a nucleotide comprises three components: a phosphate, a pentose (e.g., a ribose or deoxyribose) and a nucleobase, and a 3' end cap does not comprise all three of the components.

The structures of various 3' end caps (including those designated "PAZ ligands") are shown below in Table 1, below. It is noted that, although some 3' end caps are designated "PAZ ligands", this disclosure is not bound by any particular theory. It is also noted that some documents refer to a 3' end cap as a "linker", though this terminology is generally not used herein. This terminology is of historic origin, as some 3' end caps were originally fragments left over from synthesis reactions; they linked the 3' end of a nascent RNAi agent strand to a solid substrate or support. Some of these fragments were later found to be effective at reducing the nuclease-driven degradation of RNAi strands while not preventing RNAi activity and thus were later repurposed and renamed "3' end caps". While some documents may refer to a "3' end cap" as a "linker" or a "3' linker" or "3' end linker" or similar term, such terminology is generally not used in this document.

TABLE 1

STRUCTURES OF 3' END CAPS (INCLUDING "PAZ LIGANDS") FOR RNAi AGENTS FOR RNA INTERFERENCE

| Nickname | PAZ ligand |
| --- | --- |
| C3 Amino | X〜〜NH$_2$ |
| C7 Amino | X〜CH(OH)〜〜NH$_2$ |
| C3 | X〜〜OH |
| C6 (sometimes designated X003 or C6-OH) | X〜〜〜OH |
| C8 | X〜〜〜〜OH |
| C10 | X〜〜〜〜〜OH |

TABLE 1-continued
STRUCTURES OF 3' END CAPS (INCLUDING "PAZ LIGANDS") FOR RNAi AGENTS FOR RNA INTERFERENCE
| Nickname | PAZ ligand |
|---|---|
| C12 | 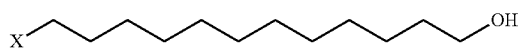 |
| BP | 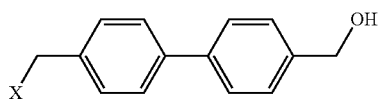 |
| X027 | 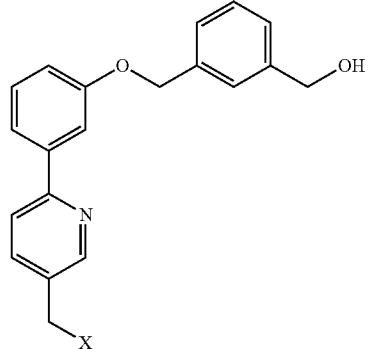 |
| X038 | 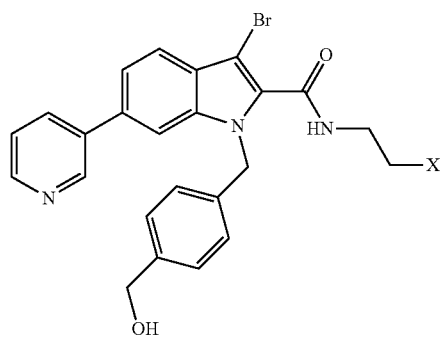 |
| X050 | 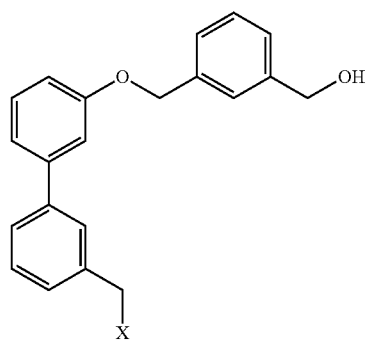 |

TABLE 1-continued
STRUCTURES OF 3' END CAPS (INCLUDING "PAZ LIGANDS") FOR RNAi AGENTS FOR RNA INTERFERENCE
| Nickname | PAZ ligand |
|---|---|
| X051 | 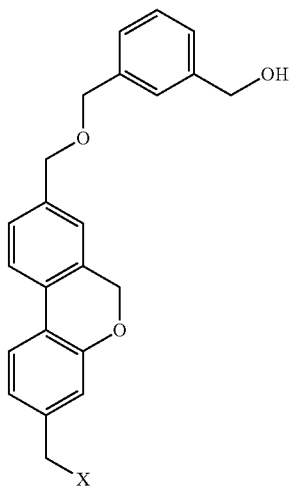 |
| X052 | 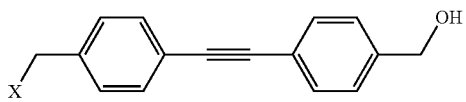 |
| X058 | 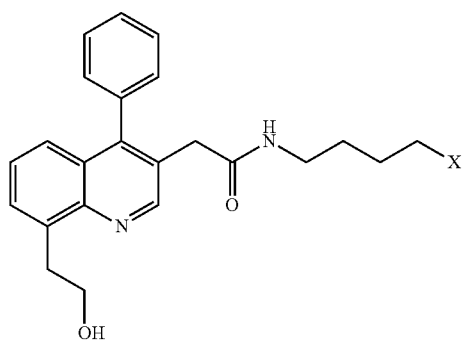 |
| X059 | 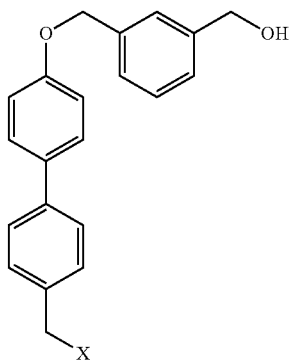 |

TABLE 1-continued
STRUCTURES OF 3' END CAPS (INCLUDING "PAZ LIGANDS") FOR RNAi AGENTS FOR RNA INTERFERENCE
| Nickname | PAZ ligand |
|---|---|
| X060 | 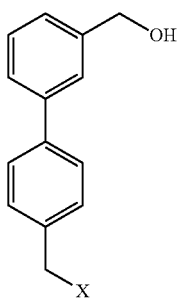 |
| X061 | 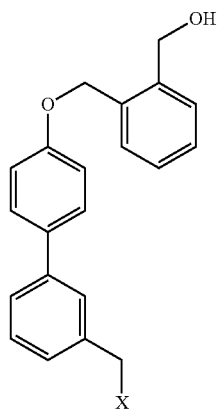 |
| X062 | 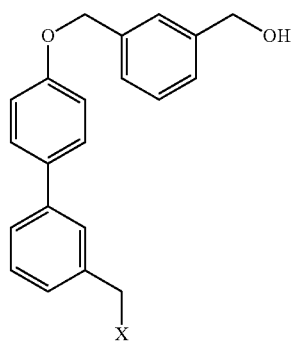 |
| X063 | 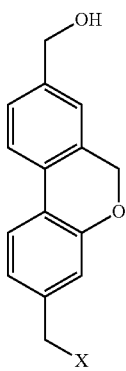 |

TABLE 1-continued
STRUCTURES OF 3' END CAPS (INCLUDING "PAZ LIGANDS") FOR RNAi AGENTS FOR RNA INTERFERENCE
| Nickname | PAZ ligand |
|---|---|
| X064 | 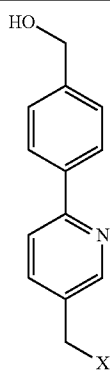 |
| X065 | 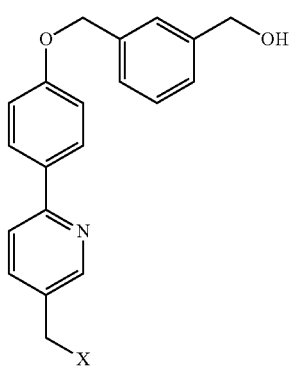 |
| X066 | 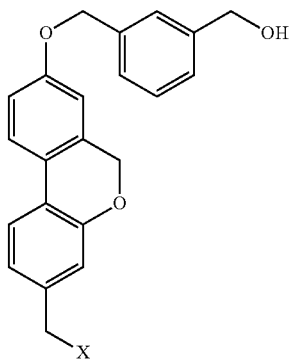 |
| X067 | 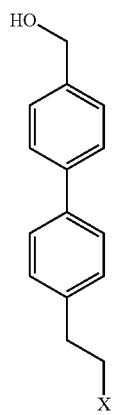 |

TABLE 1-continued
STRUCTURES OF 3' END CAPS (INCLUDING "PAZ LIGANDS") FOR RNAi AGENTS FOR RNA INTERFERENCE
| Nickname | PAZ ligand |
|---|---|
| X068 | 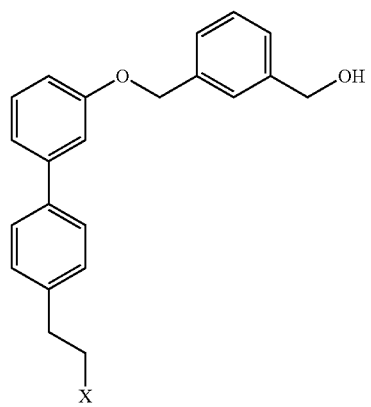 |
| X069 | 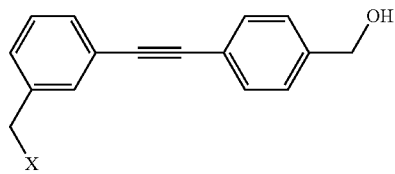 |
| X097 | 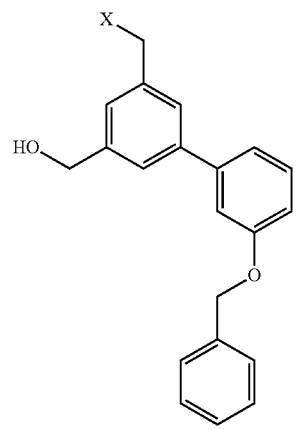 |
| X098 | 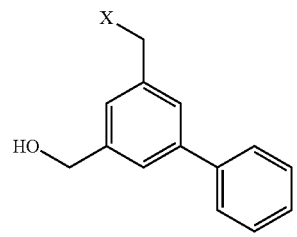 |
| X109 | 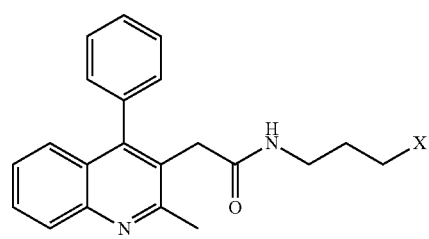 |

TABLE 1-continued

STRUCTURES OF 3' END CAPS (INCLUDING "PAZ LIGANDS") FOR RNAi AGENTS FOR RNA INTERFERENCE

| Nickname | PAZ ligand |
| --- | --- |
| X110 | |
| X111 | |
| X112 | |
| X113 | |
| X1009 | |
| X1010 | |

TABLE 1-continued
STRUCTURES OF 3' END CAPS (INCLUDING "PAZ LIGANDS") FOR RNAi AGENTS FOR RNA INTERFERENCE
| Nickname | PAZ ligand |
|---|---|
| X1011 | 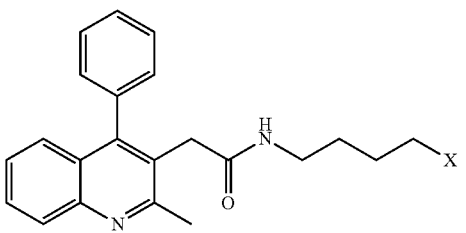 |
| X1012 | 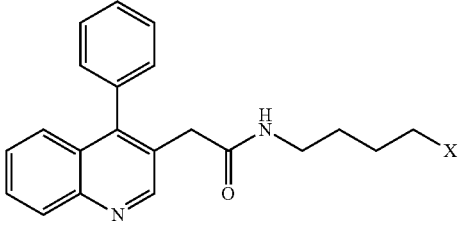 |
| X1013 | 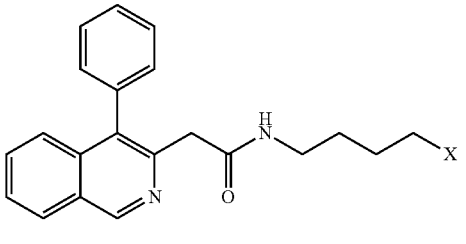 |
| X1015 | 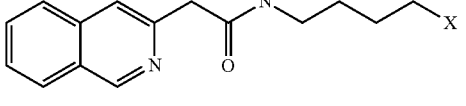 |
| X1016 | 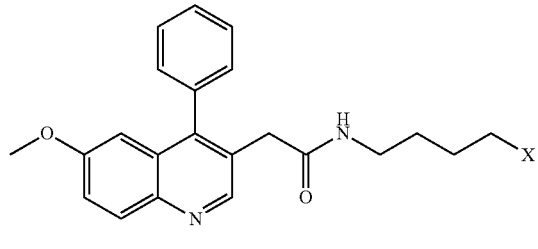 |
| X1017 | 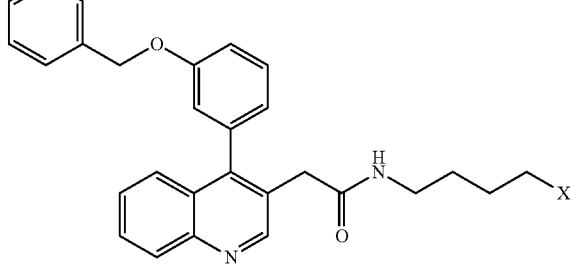 |

TABLE 1-continued
STRUCTURES OF 3' END CAPS (INCLUDING "PAZ LIGANDS") FOR RNAi
AGENTS FOR RNA INTERFERENCE
| Nickname | PAZ ligand |
|---|---|
| X1018 | 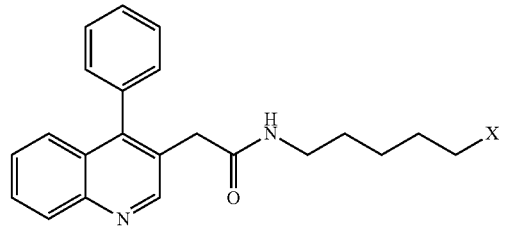 |
| X1019 | 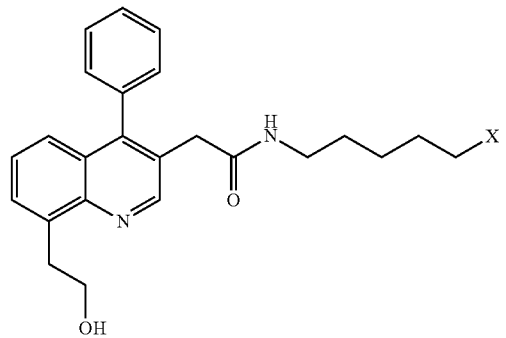 |
| X1020 | 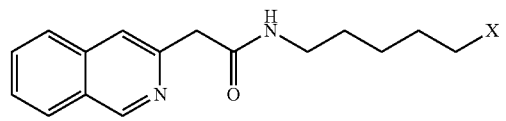 |
| X1021 | 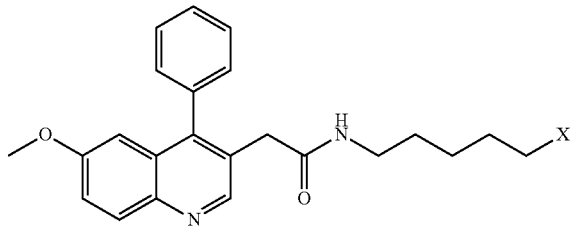 |
| X1022 | 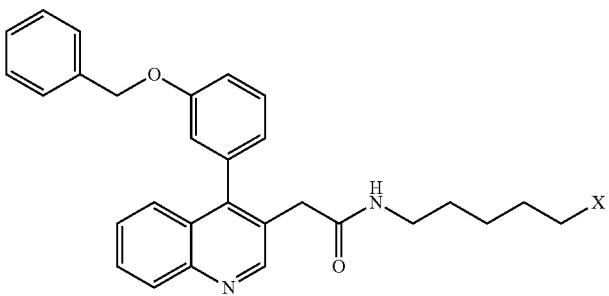 |
| X1024 | 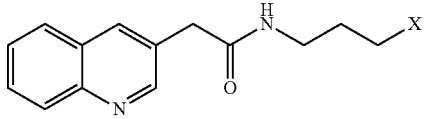 |

US 9,988,627 B2
TABLE 1-continued
STRUCTURES OF 3' END CAPS (INCLUDING "PAZ LIGANDS") FOR RNAi AGENTS FOR RNA INTERFERENCE
| Nickname | PAZ ligand |
|---|---|
| X1025 | 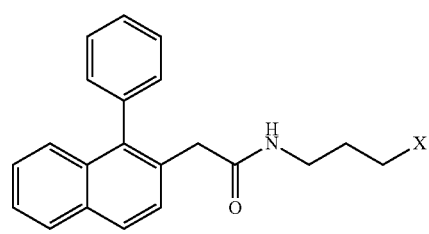 |
| X1026 | 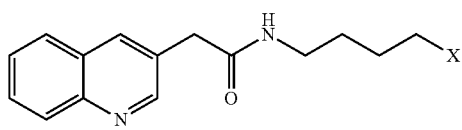 |
| X1027 | 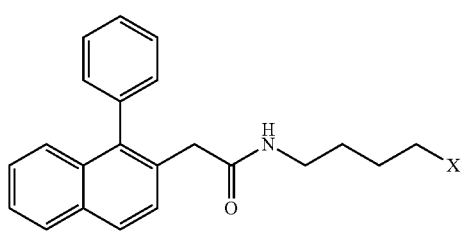 |
| X1028 | 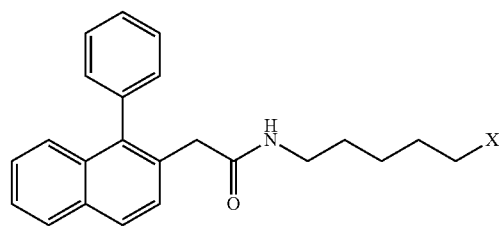 |
| X1047 | 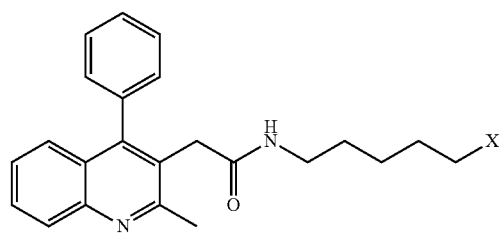 |
| X1048 | 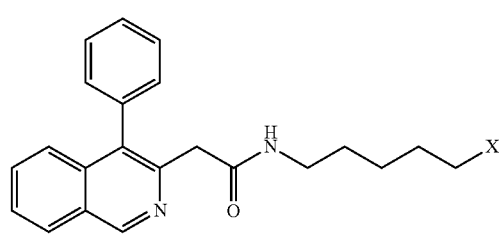 |
| X1049 | 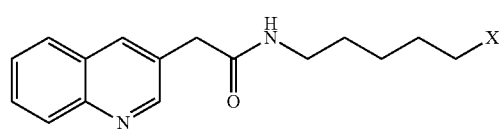 |

TABLE 1-continued

STRUCTURES OF 3' END CAPS (INCLUDING "PAZ LIGANDS") FOR RNAi AGENTS FOR RNA INTERFERENCE

| Nickname | PAZ ligand |
|---|---|
| X1062 | 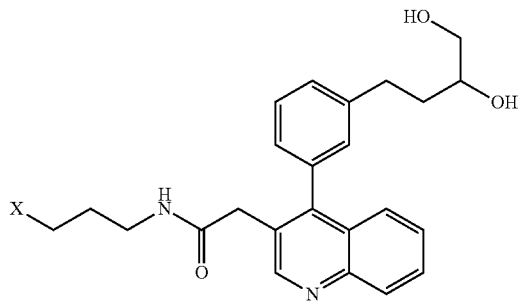 |
| X1063 | 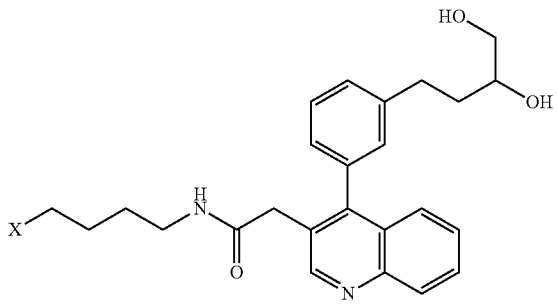 |
| X1064 | 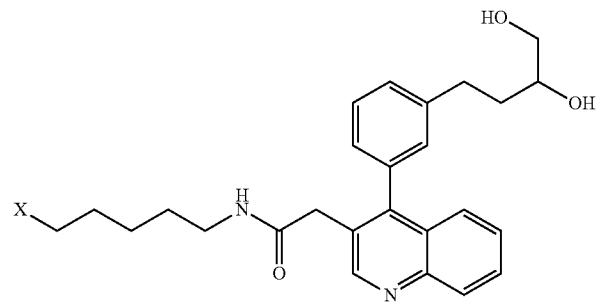 |

The structures of Table 1 can represent, for example, 3' end caps that can be at the 3' end of a molecule comprising, in 5' to 3' order, a strand of a RNAi agent terminating at the 3' end in a phosphate or modified internucleosider linker, a spacer, and a second phosphate or modified internucleoside linker (collectively represented by "X"). In some embodiments, the 3' end cap is on the 3' end of a molecule comprising the antisense strand. In various embodiments, the RNAi agent comprises two strands, e.g., a sense strand and an antisense strand. In various embodiments, at least one of the RNAi strands comprises ribonucleotides and at least one spacer subunit. In various embodiments, one or more ribonucleotides is modified or substituted with DNA, PNA, LNA, TNA, GNA, ANA, FANA, CeNa, HNA or UNA. In various embodiments, one or both strand is a 30-mer or shorter. In various embodiments, the strands are both 18-mers. As non-limiting examples: the 18-mer strand comprises 18 ribonucleotides; the 18-mer strand comprises 17 ribonucleotides and 1 spacer subunit; 16 ribonucleotides and 2 spacer subunits; 15 ribonucleotides and 3 spacer subunits; 14 ribonucleotides and 4 spacer subunits; etc. The other strand comprises ribonucleotides, or ribonucleotides and at least one spacer subunit.

In some embodiments, the 3' end cap is a ribitol. Thus, in some embodiments, the RNAi agent comprises a strand terminating in a phosphate or modified internucleoside linker and further comprising, in 5' to 3' order, a spacer (e.g., a ribitol, C3, C4, C5, C6, etc.), a phosphate or modified internucleoside linker, and a 3' end cap (e.g., a second ribitol). For example, a variety of RNAi agents to SSB, representing several sequences, were constructed wherein at least one strand further comprises at the 3' terminus, in 5' to 3' order, a spacer (ribitol), a phosphate, and a 3' end cap (a second ribitol).

In some embodiments, the 3' end cap is a diribitol. Thus: In some embodiments, the RNAi agent comprises a strand, wherein the 3' end of the 18-mer strand terminates in a phosphate or modified internucleoside linker and further comprises, in 5' to 3' order: a spacer (e.g., a ribitol, C3, C4, C5, C6, etc.), a phosphate or modified internucleoside linker, and a 3' end cap (e.g., a diribitol). For example, a variety of RNAi agents to SSB, representing several sequences, were constructed wherein at least one strand further comprises at the 3' terminus, in 5' to 3' order, a spacer (ribitol), a phosphate, and a 3' end cap (a diribitol). In other words, these SSB RNAi agents comprise a strand, wherein the 3' end of the 18-mer strand terminates in a phosphate and further comprises, in 5' to 3' order: a ribitol, a phosphate, a second ribitol, a second phosphate, and a third ribitol.

RNAi agents of any target or sequence can be constructed and tested which comprise a first and a second strand, wherein the first strand comprises ribonucleotides or ribonucleotides and at least one spacer subunit, and the second strand comprises ribonucleotides and at least one spacer subunit, wherein a spacer subunit is (a) a phosphate or modified internucleoside linker and (b) a spacer, wherein at least one strand is a 30-mer or shorter or both strands are 18-mers, wherein the 3' end of at least one strand terminates in a phosphate or modified internucleoside linker and optionally further comprises, in 5' to 3' order: a second spacer, a second phosphate or modified internucleoside linker, and any 3' end cap disclosed herein or known in the art.

Table 2 illustrates specific 3' end caps, bound to the 3' terminal phosphate or modified internucleoside linker.

In the structures of Tables 1 and 2:

In some embodiments, hydroxyl groups are present and X represents the 3' end of a molecule comprising, in 5' to 3' order, a strand of a RNAi agent, wherein the 3' end of a strand terminates in a phosphate or modified internucleosider linker and further comprises, in 5' to 3' order: a spacer, and a phosphate or modified internucleoside linker. For example, the 3' end of a strand of a RNAi can terminate at a phosphate group, to which is bound (or further comprises), in 5' to 3' order: the spacer, the phosphate or modified internucleoside linker, and the 3' end cap is bound. In various embodiments, the strand is ribonucleotides. In various embodiments, the strand is ribonucleotides and at least one spacer subunit. In various embodiments, one or more ribonucleotides is modified or substituted with DNA, PNA, LNA, TNA, GNA, ANA, FANA, CeNa, HNA or UNA. Non-limiting examples of such a structure are shown in, for example, FIG. 15A (C3), FIG. 18C (C6, C8, and C10); and FIG. 19 (X027, C6 and X058). Table 2 shows the structures of various 3' end caps bound to the phosphate at the 3' end of a strand of an RNAi agent.

In some embodiments, where hydroxyl groups in the 3' end caps are present, the hydroxyl can exist in a protected form. Suitable protecting groups for OH are known in the art. Protected forms of OH include, but are not limited to, ethers, phosphate esters, methyl tetraacetyl glucuronates, peracetyl glycosides and amino acid polypeptide esters.

Table 2, below, presents some structures of various 3' end caps, including some of those shown in Table 1. In several of the structures, the terminal 3' phosphate of a RNAi agent strand is also shown for context, although this phosphate is not part of the 3' end cap.

TABLE 2A

| Structure | Nickname (Alternative nickname) |
|---|---|
| RNAi agents wherein the 3' end of a strand terminates in a phosphate or modified internucleoside linker and further comprises, in 5' to 3' order: a spacer, a second phosphate, and a 3' end cap. The second phosphate and 3' end cap are shown. | |
| 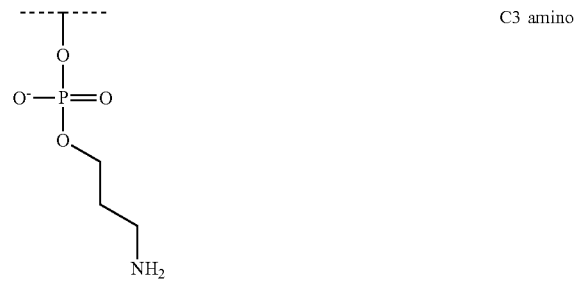 | C3 amino |
| 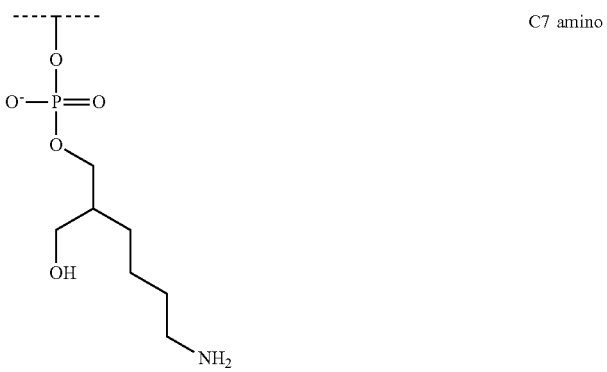 | C7 amino |

TABLE 2A-continued

| Structure | Nickname (Alternative nickname) |
|---|---|
| (phosphate-O-(CH₂)₈-OH) | C8 |
| (phosphate-O-(CH₂)₁₀-OH) | C10 |
| (phosphate-O-CH₂-pyridine-phenyl-O-CH₂-phenyl-CH₂OH) | X027 |
| (phosphate-O-CH₂CH₂-NH-C(O)-indole derivative with Br, N-benzyl-CH₂OH, and pyridyl substituents) | X038 |

TABLE 2A-continued
| Structure | Nickname (Alternative nickname) |
|---|---|
| 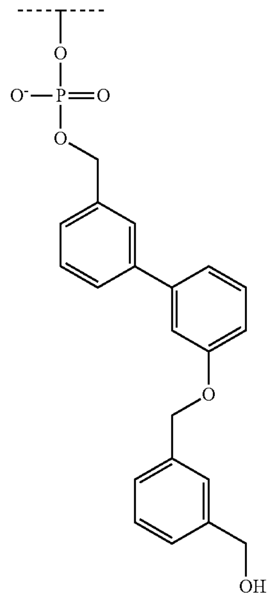 | X050 |
| 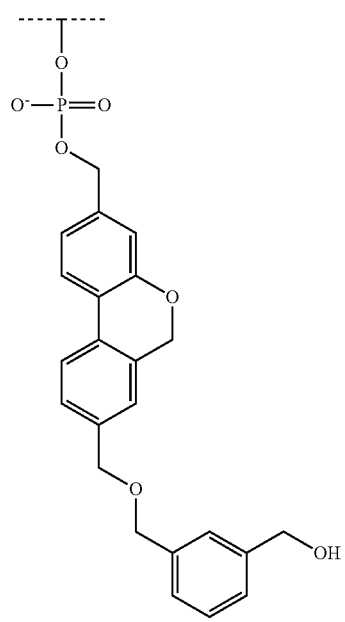 | X051 |

TABLE 2A-continued
| Structure | Nickname (Alternative nickname) |
|---|---|
| 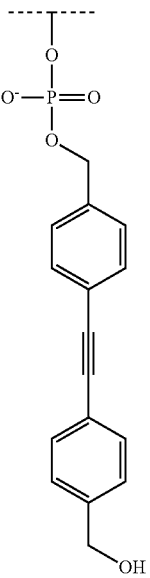 | X052 |
| 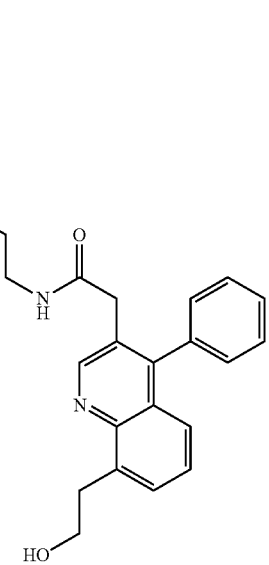 | X058 |

TABLE 2A-continued
| Structure | Nickname (Alternative nickname) |
|---|---|
| 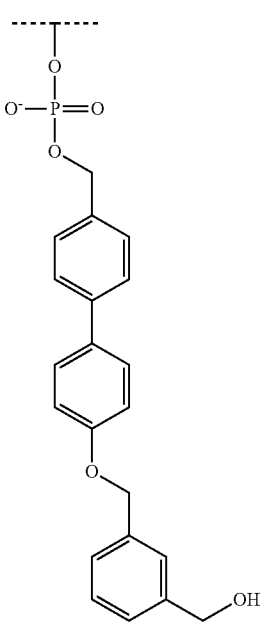 | X059 |
| 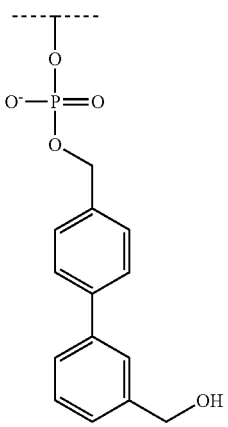 | X060 |
| 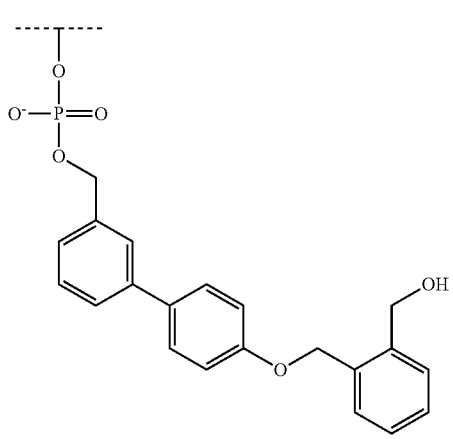 | X061 |

TABLE 2A-continued

| Structure | Nickname (Alternative nickname) |
|---|---|
| 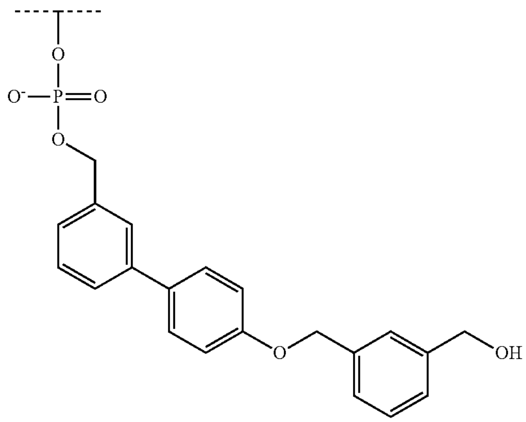 | X062 |
| 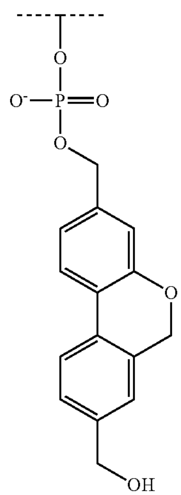 | X063 |
| 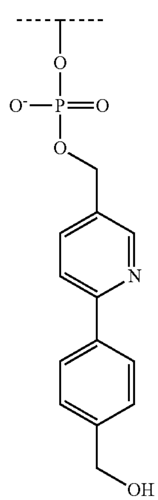 | X064 |

TABLE 2A-continued
| Structure | Nickname (Alternative nickname) |
|---|---|
| 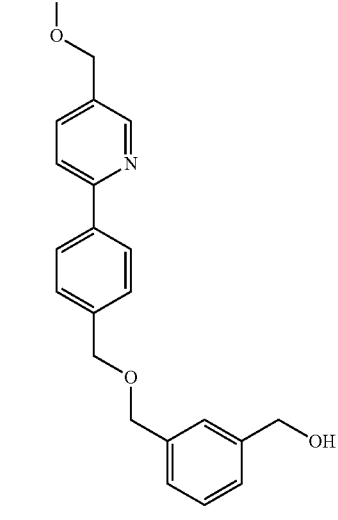 | X065 |
| 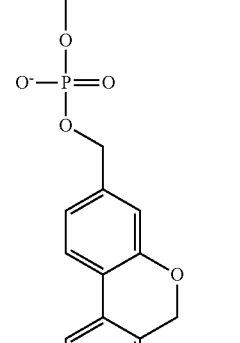 | X066 |

TABLE 2A-continued

| Structure | Nickname (Alternative nickname) |
|---|---|
| 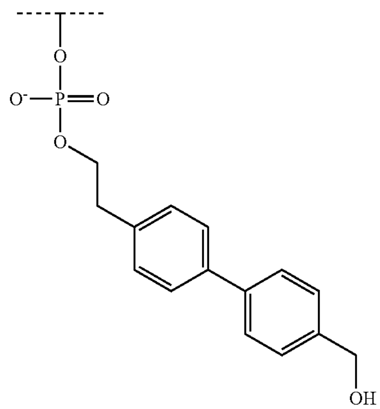 | X067 |
| 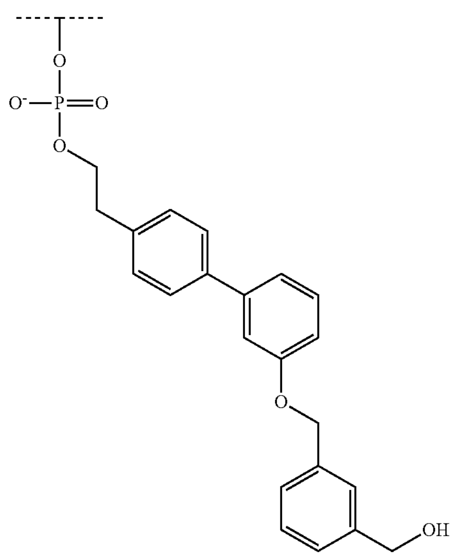 | X068 |
| 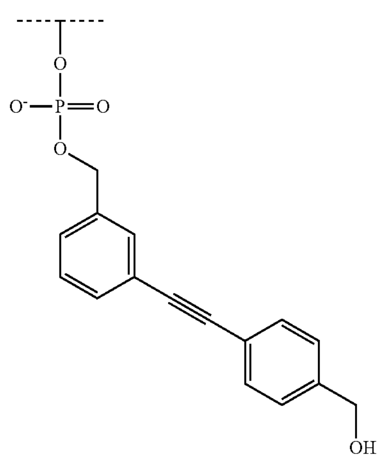 | X069 |

TABLE 2A-continued

| Structure | Nickname (Alternative nickname) |
|---|---|
| 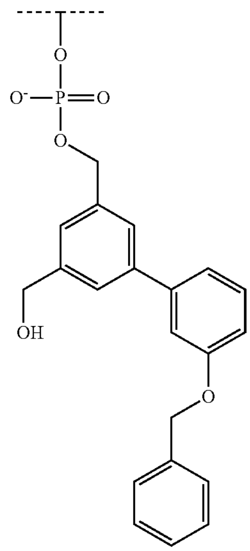 | X097 |
| 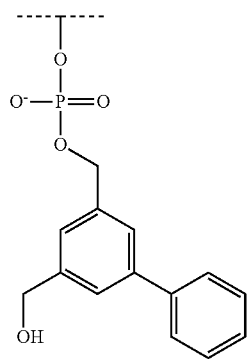 | X098 |
| 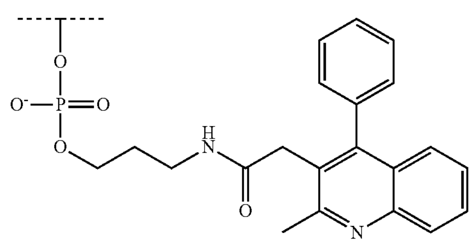 | X109 |
| 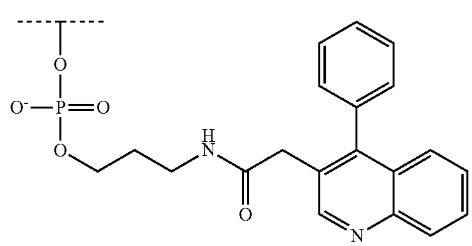 | X110 |

TABLE 2A-continued

| Structure | Nickname (Alternative nickname) |
|---|---|
| 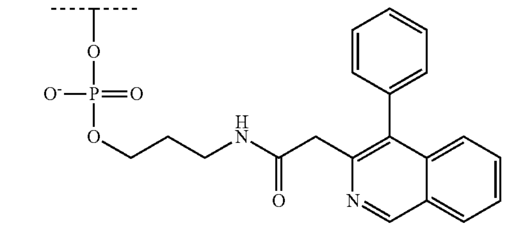 | X111 |
| 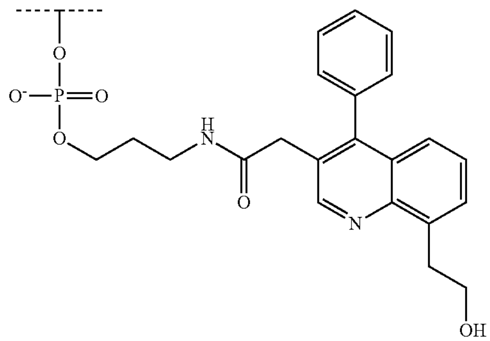 | X112 |
| 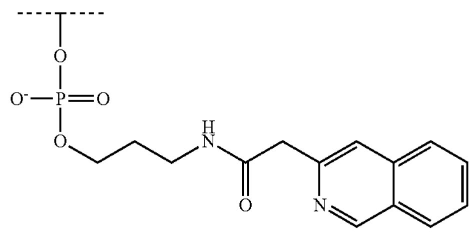 | X113 |
| 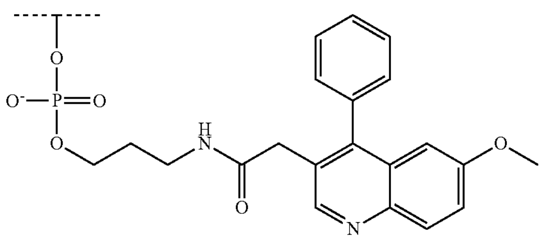 | X1009 |
| 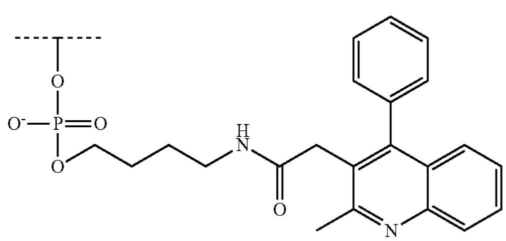 | X1011 |
| 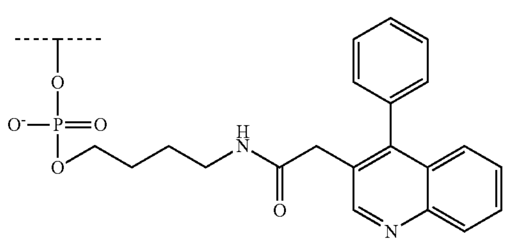 | X1012 |

TABLE 2A-continued

| Structure | Nickname (Alternative nickname) |
|---|---|
| 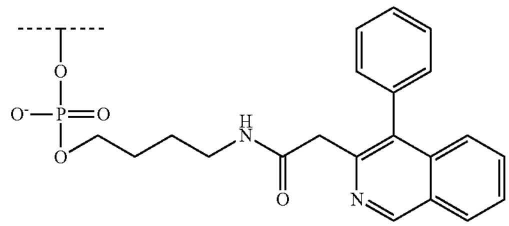 | X1013 |
| 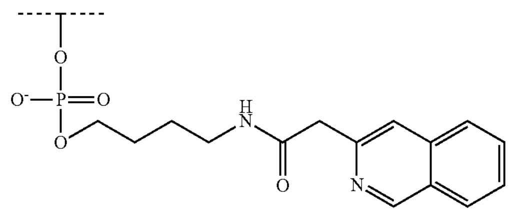 | X1015 |
| 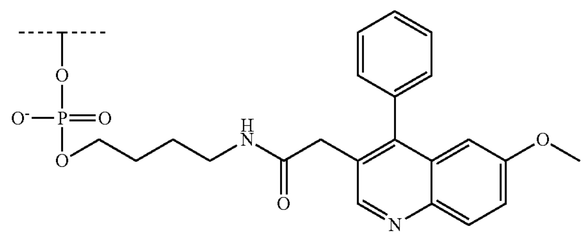 | X1016 |
| 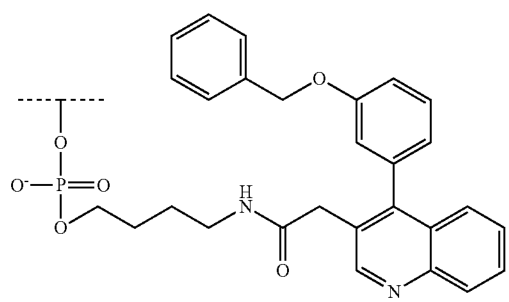 | X1017 |
| 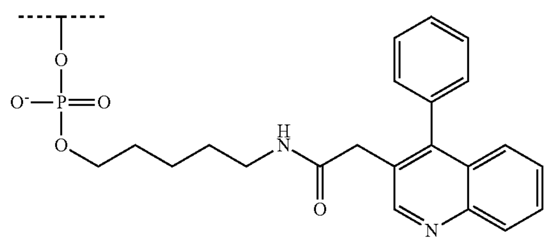 | X1018 |
| 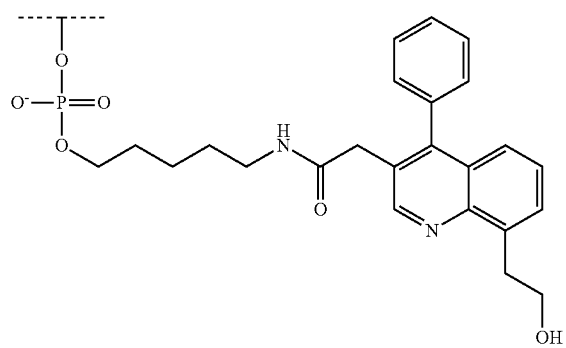 | X1019 |

TABLE 2A-continued
| Structure | Nickname (Alternative nickname) |
|---|---|
| 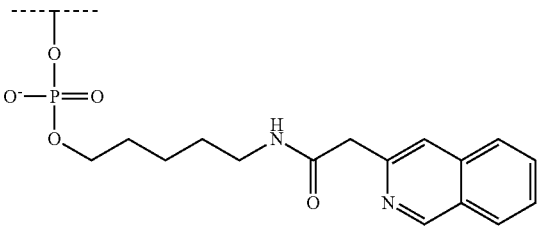 | X1020 |
| 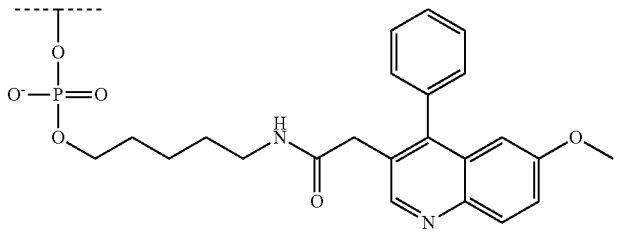 | X1021 |
| 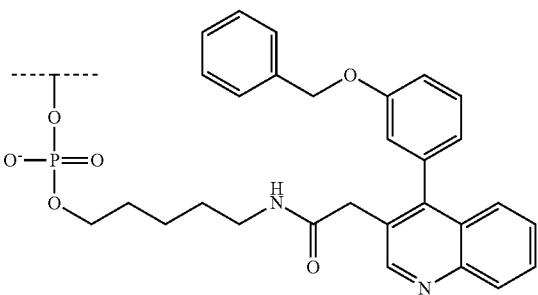 | X1022 |
| 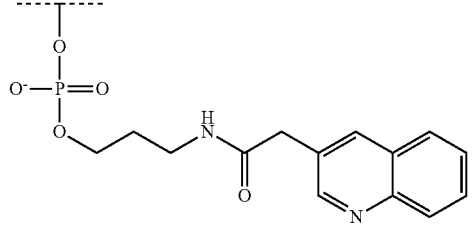 | X1024 |
| 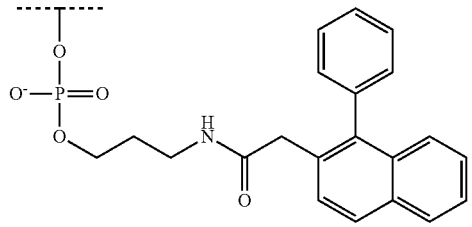 | X1025 |
| 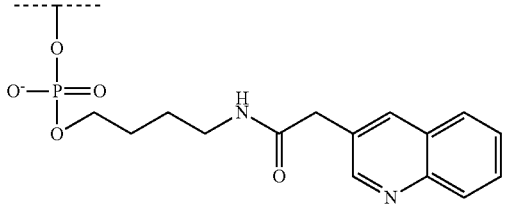 | X1026 |

TABLE 2A-continued

| Structure | Nickname (Alternative nickname) |
|---|---|
| 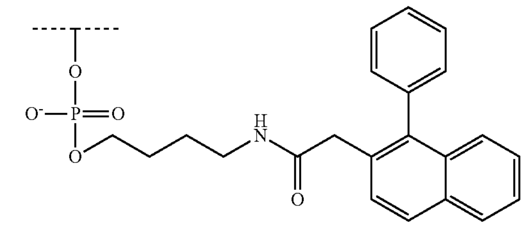 | X1027 |
| 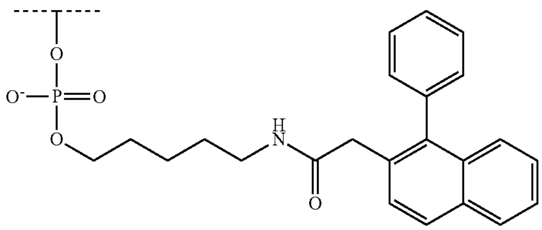 | X1028 |
| 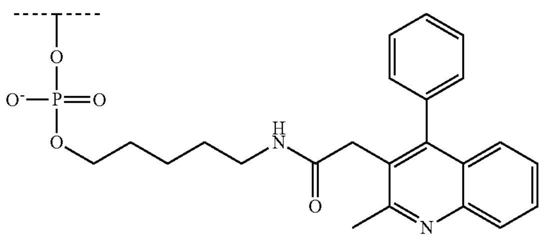 | X1047 |
| 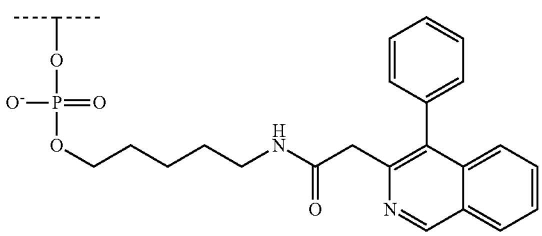 | X1048 |
| 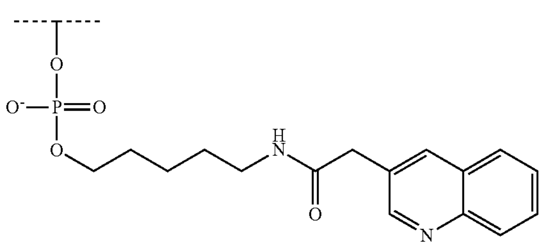 | X1049 |

TABLE 2A-continued

| Structure | Nickname (Alternative nickname) |
|---|---|
| 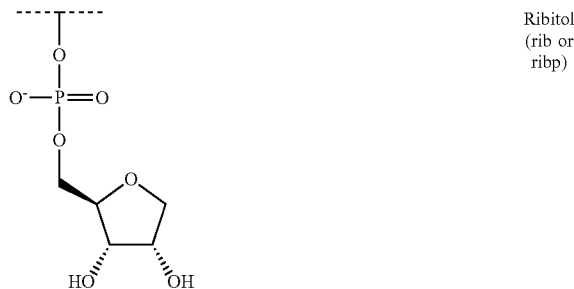 | Ribitol (rib or ribp) |

2.B. RNAi agents comprising a strand, wherein, as shown here, the 3' end of the strand terminates in a phosphate or modified internucleoside linker and further comprises, in 5' to 3' order: a spacer, a second phosphate, and a 3' end cap. The 3' terminal phosphate of the strand, spacer, second phosphate and 3' end cap are shown.

| 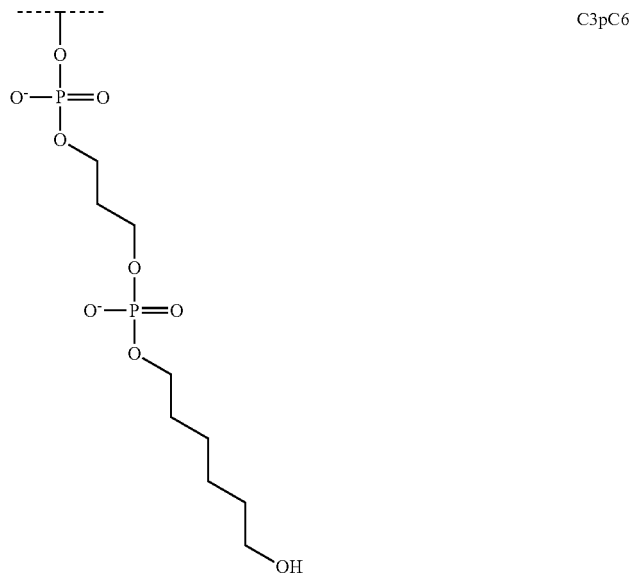 | C3pC6 |
| 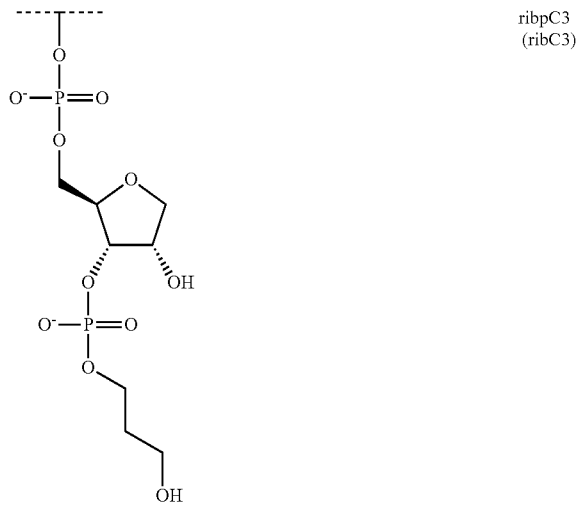 | ribpC3 (ribC3) |

TABLE 2A-continued

| Structure | Nickname (Alternative nickname) |
|---|---|
| 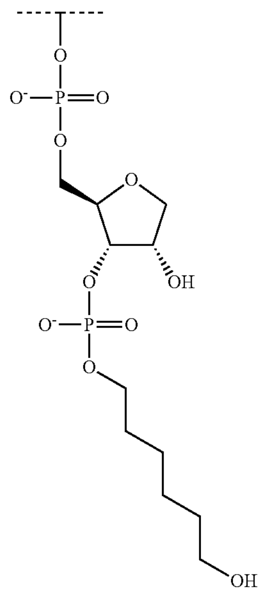 | ribpC6 (ribC6) |
| 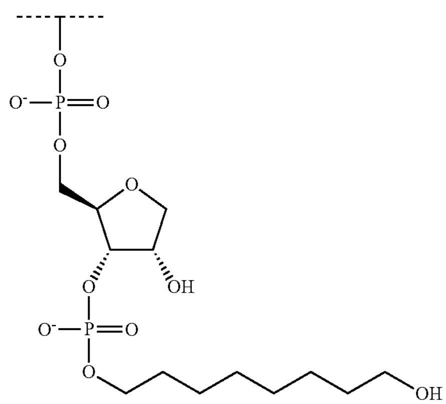 | ribpC8 (ribC8) |
| 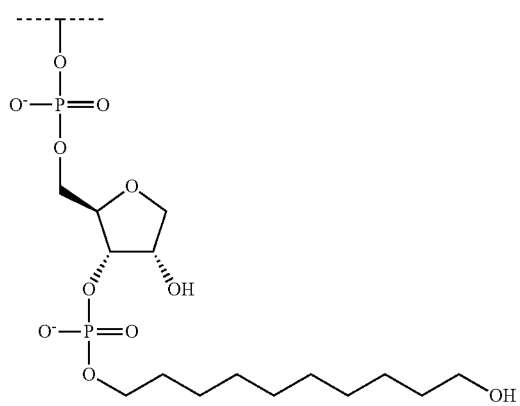 | ribpC10 (ribC10) |

TABLE 2A-continued
| Structure | Nickname (Alternative nickname) |
|---|---|
| 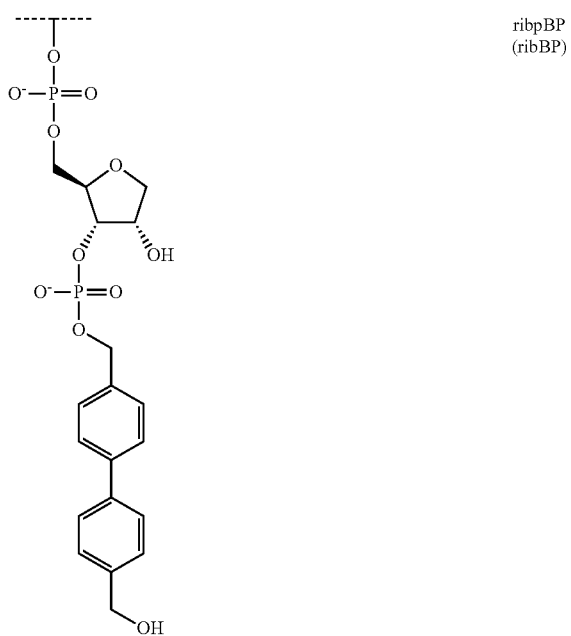 | ribpC12 (ribC12) |
| 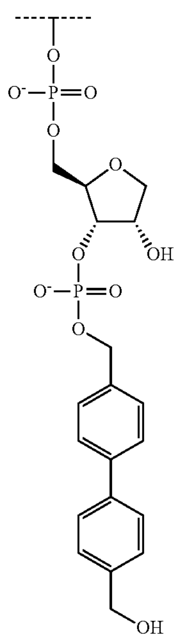 | ribpBP (ribBP) |

TABLE 2A-continued

| Structure | Nickname (Alternative nickname) |
|---|---|
| 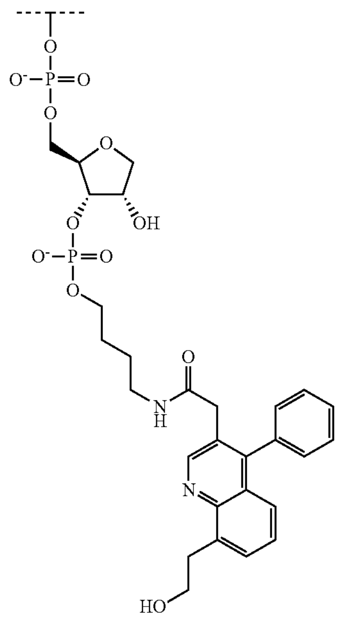 | ribpX058 (ribX058) |
| 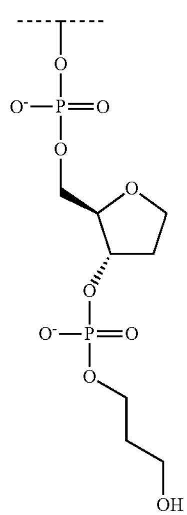 | 2'DeoxyribC3 |

TABLE 2A-continued
| Structure | Nickname (Alternative nickname) |
|---|---|
| 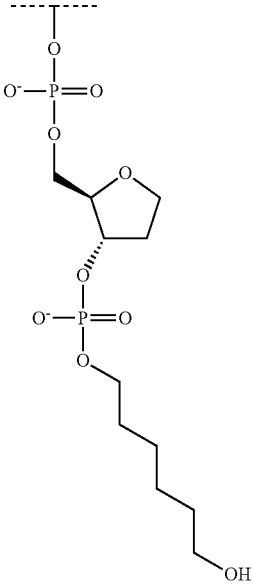 | 2'DeoxyribC6 |
| 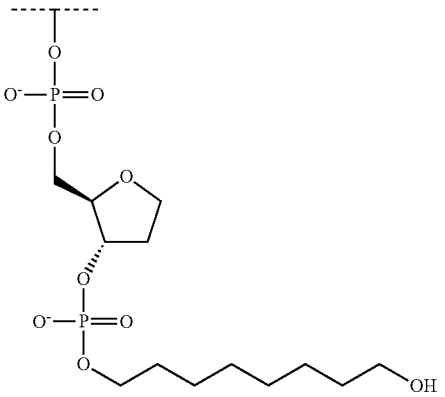 | 2'DeoxyribC8 |
| 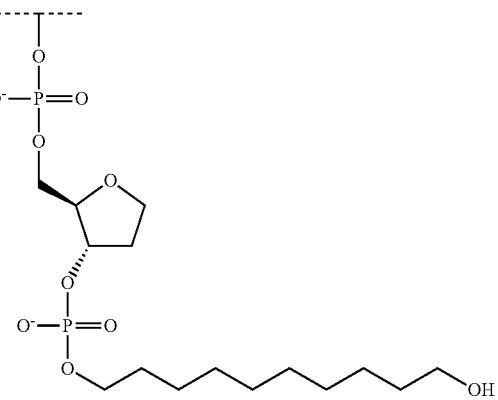 | 2'DeoxyribC10 |

TABLE 2A-continued
| Structure | Nickname (Alternative nickname) |
|---|---|
| 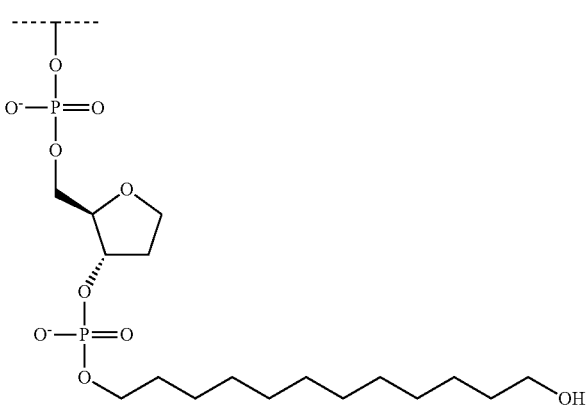 | 2'DeoxyribC12 |
| 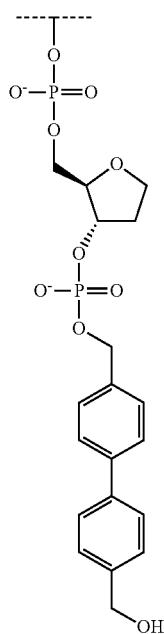 | 2'-DeoxyribBP |

TABLE 2A-continued

| Structure | Nickname (Alternative nickname) |
|---|---|
| 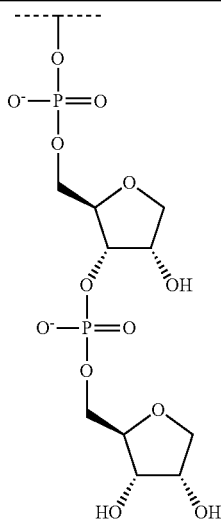 | Diribitol (dirib or diribp) |

Additional structures include, inter alia: ribpX027, ribpX038, ribpX050, ribpX051, ribpX052, ribpX059, ribpX060, ribpX061, ribpX062, ribpX063, ribpX064, ribpX065, ribpX066, ribpX067, ribpX068, ribpX069, ribpX097, ribpX098, ribpX109, ribpX110, ribpX111, ribpX112, ribpX113, ribpX1009, ribpX1011, ribpX1012, ribpX1013, ribpX1015, ribpX1016, ribpX1017, ribpX1018, ribpX1019, ribpX1020, ribpX1021, ribpX1022, ribpX1024, ribpX1025, ribpX1026, ribpX1027, ribpX1028, ribpX1047, ribpX1048, and ribpX1049. These represent a spacer which is ribitol, a phosphate, and a 3' end cap which is X027, X038, X050, etc.

2.C. RNAi agents comprising a strand, wherein, as shown here, the 3' end of the strand terminates in a modified internucleoside linker and further comprises, in 5' to 3' order: a spacer, a modified internucleoside linker, and a 3' end cap.
Example modified internucleoside linkers and 3' end caps are shown.

| Structure | Nickname |
|---|---|
| 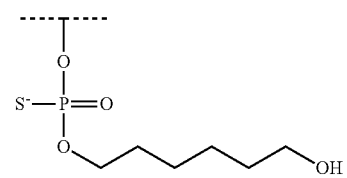 | PS-C6 |
| 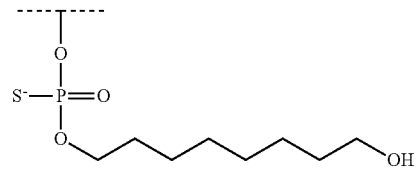 | PS-C8 |
| 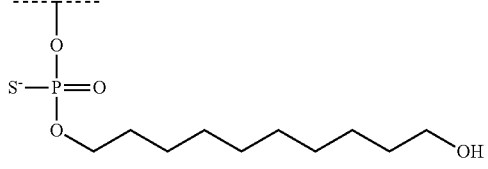 | PS-C10 |
| 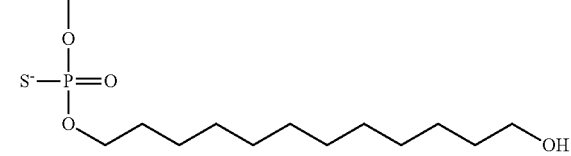 | PS-C12 |

TABLE 2A-continued
| Structure | Nickname (Alternative nickname) |
|---|---|
| 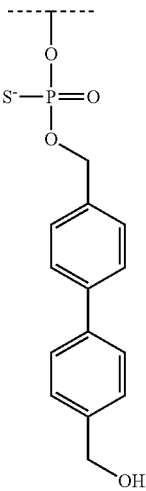 | PS-BP |
| 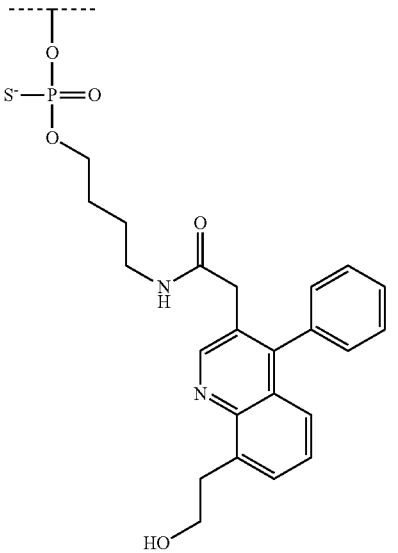 | PS-X058 |
| 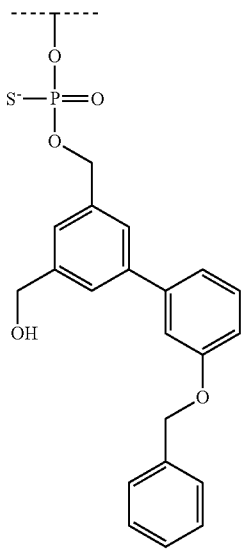 | PS-X097 |

TABLE 2A-continued

| Structure | Nickname (Alternative nickname) |
|---|---|
| 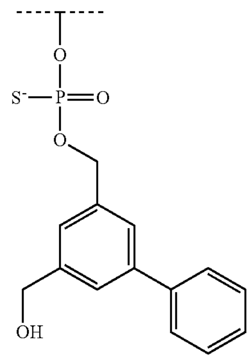 | PS-X098 |
| 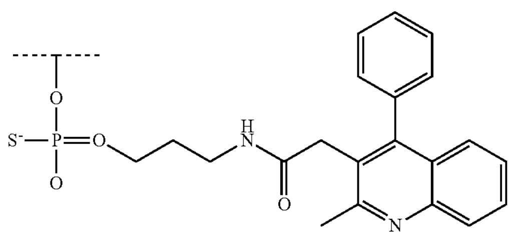 | PS-X109 |
| 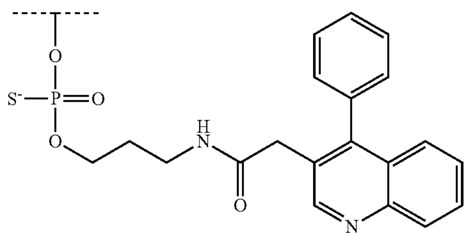 | PS-X110 |
| 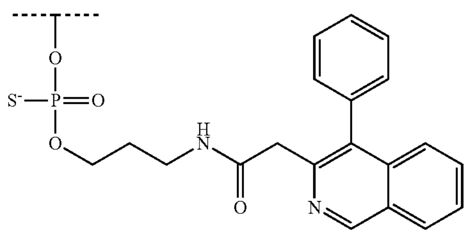 | PS-X111 |

Regarding Table 2 (Including 2.A, 2.B and 2.C):

Synthesis schemes for C7 amino and C3 amino (also designated amino C7 or amino C3, respectively) are not provided, as these molecules are commercially available from and synthesis schemes were previously published by Glen Research (Sterling, Va.).

C7 amino: Catalog Number: 20-2957-xx; Description: 3'-Amino-Modifier C7 CPG 500; 2-Dimethoxytrityloxymethyl-6-fluorenylmethoxycarbonylamino-hexane-1-succinoyl-long chain alkylamino-CPG; Technical Bulletin: Pre-Synthesis Labeling of Aminomodifier C3 or C7 CPG, Glen Research (Sterling, Va.).

C3 amino: Catalog Number: 20-2913-xx; Description: 3'-Spacer C3 CPG; (1-Dimethoxytrityloxy-propanediol-3-succinoyl)-long chain alkylamino-CPG, Glen Research (Sterling, Va.). Glen Research also notes that Glen Research has no definitive data on the propyl CPG to support the assertion that it protects oligos from exonuclease digestion and does not permit polymerase extension. Glen Research's conclusion is based by analogy to the propylamino-modifier CPG [Zendegui et al. Nucleic Acids Research, 1992, 20, 307-314] (Cat. No. 20-2950-41). This modification protects oligos from exonuclease digestion but permits polymerase extension to a small extent since the modifier is eliminated to a level of about 10% from the 3' terminus, leaving the 3'-hydroxyl group available. HPLC experiments have shown that there is no detectable elimination of the propyl group from oligos made from the spacer C3-CPG Example 3' end caps C8 and C10 are also illustrated in FIG. 16C, and ribitol and diribitol in FIG. 17, in the context of a RNAi agent strand.

It is noted that Table 2 lists various 3' end caps that comprise both a spacer (e.g., C3p, ribitol, or 2'-deoxyribitol) and a 3' end cap. Thus, for example, "C3pC6" can be, depending on context, considered as a "3' endcap", or as "a spacer and a phosphate and a 3' end cap" (C3+p+C6). The efficacy of RNAi agents comprising a spacer and a 3' end cap is shown in, for example, 5A, 5B, 10 and 14.

The present disclosure encompasses any RNAi agent comprising a 3' end cap as shown in Tables 1 or 2 or otherwise disclosed herein.

Additional information can be found in U.S. patent applications 61/886,753; 61/930,681; 61/886,748; 61/886,739; and 61/886,760, which are all incorporated by reference in their entirety.

18-Mer RNAi Agents Comprising a 3' End Cap (with No Spacer or Second Phosphate or Modified Internucleoside Linker)

In various embodiments, the RNAi agent comprises a strand, wherein the 3' end of the 18-mer strand terminates in a phosphate or modified internucleoside linker and further comprises a 3' end cap. In some embodiments, the disclosure pertains to a RNAi agent that comprises a first and a second strand, wherein the first and second strands are both 18-mers, the first strand is ribonucleotides or ribonucleotides and at least one space subunit and the second strand is ribonucleotides and at least one spacer subunit, wherein the ribitol spacer can be at any position, and the first and second strand together form a blunt-ended duplex, and wherein the 3' end of the first strand terminates in a phosphate or modified internucleoside linker and further comprises, in 5' to 3' order: a spacer, a phosphate or modified internucleoside linker, and a 3' end cap; and wherein the 3' end of the second strand terminates in a phosphate or modified internucleoside linker and further comprises a 3' end cap. In some embodiments, the disclosure pertains to a RNAi agent that comprises a first and a second strand, wherein the first and second strands are both 18-mers, the first strand is ribonucleotides or ribonucleotides and at least one space subunit and the second strand is ribonucleotides and at least one spacer subunit, wherein the ribitol spacer can be at any position, and the first and second strand together form a blunt-ended duplex, and wherein the 3' end of both the first and second strand terminate in a phosphate or modified internucleoside linker and both further comprise a 3' end cap. In some embodiments, the first strand is the antisense strand and the second strand is the sense strand. In other embodiments, the first strand is the sense strand and the second strand is the antisense strand. Such embodiments lack a spacer or second phosphate or modified internucleoside linker.

In various embodiments, the 3' end cap is triethylene glycol, cyclohexyl, phenyl, BP (biphenyl), lithochol (lithocholic acid), adamantane, C3 amino, C7 amino, C3, C6, C8, C10, C12, X027, X038, X050, X051, X052, X058, X059, X060, X061, X062, X063, X064, X065, X066, X067, X068, X069, X097, X098, X109, X110, X111, X112, X113, X1009, X1010, X1011, X1012, X1013, X1015, X1016, X1017, X1018, X1019, X1020, X1021, X1022, X1024, X1025, X1026, X1027, X1028, X1047, X1048, X1049, X1062, X1063, or X1064, or any 3' end cap disclosed herein or known in the art.

An example is shown in FIG. 17 ("ribitol"), wherein the RNAi agent comprises a strand, wherein the 3' end of the 18-mer strand terminates in a phosphate and further comprises a 3' end cap which is ribitol.

Another example is shown in FIG. 11, wherein an RNAi agent to Factor 7 (FVII) comprises a strand, wherein the 3' end of the 18-mer strand terminates in a phosphate and further comprises a 3' end cap which is C6 (designated "C6 overhang").

Thus:

In various embodiments, the disclosure encompasses:

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is C7 amino.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is C3 amino.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is C3.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is C6.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is C8.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is C10.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is C12.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X027.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X038.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X050.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X051.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X052.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X058.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X059.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X060.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X061.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X062.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X063.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X064.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X065.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X066.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X067.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X068.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X069.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X097.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X098.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X109.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X110.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X111.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X112.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X113.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X1009.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X1010.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X1011.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X1012.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X1013.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X1015.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X1016.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X1017.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X1018.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X1019.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X1020.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X1021.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X1022.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X1024.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X1025.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X1026.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X1027.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X1028.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X1047.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X1048.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is X1049.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, wherein the 3' end of at least one strand terminates in a phosphate or modified internucleoside linker and further comprises a 3' end cap, and wherein the 3' end cap is ribitol.

For each and every of the RNAi agents listed in this section, the RNAi agent can be of any sequence or target, and can be, as a non-limiting example, a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

RNAi Agents Comprising a Spacer, a Second Phosphate or Modified Internucleoside Linker, and a 3' End Cap In various embodiments, the disclosure pertains to an RNAi agent comprising a 18-mer strand, wherein the 3' end of the 18-mer strand terminates in a phosphate or a modified internucleoside linker, and further comprises, in 5' to 3' order: a spacer, a second phosphate or a modified internucleoside linker, and a 3' end cap (e.g., any 3' end cap listed in Tables 1 or 2 or otherwise disclosed herein or known in the art).

In various embodiments, the disclosure encompasses:

An RNAi agent comprising a first and a second strand, wherein the first and/or second strand is an 18-mer strand, and the 3' end of the 18-mer strand terminates in a phosphate or a modified internucleoside linker and further comprises, in 5' to 3' order: a spacer, a second phosphate or a modified internucleoside linker, and a 3' end cap.

An RNAi agent comprising a first and a second strand, wherein the first and/or second strand is an 18-mer strand, and the 3' end of the 18-mer strand terminates in a phosphate or a modified internucleoside linker and further comprises, in 5' to 3' order: a spacer, a second phosphate or a modified internucleoside linker, and a 3' end cap, and wherein the spacer is a ribitol.

An RNAi agent comprising a first and a second strand, wherein the first and/or second strand is an 18-mer strand, and the 3' end of the 18-mer strand terminates in a phosphate or a modified internucleoside linker and further comprises, in 5' to 3' order: a spacer, a second phosphate or a modified internucleoside linker, and a 3' end cap, and wherein the spacer is a 2'-deoxy-ribitol.

An RNAi agent comprising a first and a second strand, wherein the first and/or second strand is an 18-mer strand, and the 3' end of the 18-mer strand terminates in a phosphate or a modified internucleoside linker and further comprises, in 5' to 3' order: a spacer, a second phosphate or a modified internucleoside linker, and a 3' end cap, and wherein the spacer is a diribitol.

An RNAi agent comprising a first and a second strand, wherein the first and/or second strand is an 18-mer strand, and the 3' end of the 18-mer strand terminates in a phosphate or a modified internucleoside linker and further comprises, in 5' to 3' order: a spacer, a second phosphate or a modified internucleoside linker, and a 3' end cap, and wherein the spacer is a 2'-methoxyethoxy-ribitol.

An RNAi agent a first and a second strand, wherein the first and/or second strand is an 18-mer strand, and the 3' end of the 18-mer strand terminates in a phosphate or a modified internucleoside linker and further comprises, in 5' to 3' order: a spacer, a second phosphate or a modified internucleoside linker, and a 3' end cap, and wherein the spacer is a C3.

An RNAi agent comprising a first and a second strand, wherein the first and/or second strand is an 18-mer strand, and the 3' end of the 18-mer strand terminates in a phosphate or a modified internucleoside linker and further comprises, in 5' to 3' order: a spacer, a second phosphate or a modified internucleoside linker, and a 3' end cap, and wherein the spacer is a C4.

An RNAi agent comprising a first and a second strand, wherein the first and/or second strand is an 18-mer strand, and the 3' end of the 18-mer strand terminates in a phosphate or a modified internucleoside linker and further comprises, in 5' to 3' order: a spacer, a second phosphate or a modified internucleoside linker, and a 3' end cap, and wherein the spacer is a C5.

An RNAi agent comprising a first and a second strand, wherein the first and/or second strand is an 18-mer strand, and the 3' end of the 18-mer strand terminates in a phosphate or a modified internucleoside linker and further comprises, in 5' to 3' order: a spacer, a second phosphate or a modified internucleoside linker, and a 3' end cap, and wherein the spacer is a C6.

An RNAi agent comprising a first and a second strand, wherein the first and/or second strand is an 18-mer strand, and the 3' end of the 18-mer strand terminates in a phosphate or a modified internucleoside linker and further comprises, in 5' to 3' order: a spacer, a second phosphate or a modified internucleoside linker, and a 3' end cap, and wherein the spacer is 4-methoxybutane-1,3-diol.

In each and every RNAi agent in this section, the 3' end cap is selected from: triethylene glycol, cyclohexyl, phenyl, BP (biphenyl), lithochol (lithocholic acid), adamantane, C3 amino, C7 amino, C3, C6, C8, C10, C12, X027, X038, X050, X051, X052, X058, X059, X060, X061, X062, X063, X064, X065, X066, X067, X068, X069, X097, X098, X109, X110, X111, X112, X113, X1009, X1010, X1011, X1012, X1013, X1015, X1016, X1017, X1018, X1019, X1020, X1021, X1022, X1024, X1025, X1026, X1027, X1028, X1047, X1048, X1049, X1062, X1063, X1064, or ribitol. In addition, for each and every of the RNAi agents listed in this section, the RNAi agent can be of any sequence or target, and can be, as a non-limiting example, a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

Additional Embodiments Comprising a Spacer, a Phosphate or Modified Internucleoside Linker, and a 3' End Cap This disclosure encompasses, inter alia:

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is C3 and the 3' end cap is C6. This structure is designated C3pC6. Efficacious RNAi agents were constructed to several targets comprising a first strand and a second strand, wherein both strands are 18-mers, and the 3' end of the first and second strand terminates in a phosphate and further comprises, in 5' to 3' order: a C3 spacer, a second phosphate, and a C6 3' end cap [collectively, C3pC6]. Such efficacious RNAi agents include several to SSB (human sequences 309, 880, 1586, 180, 1596 and 1591).

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is C3. This structure is designated ribC3 or ribpC3.

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is C6. This structure is designated ribpC6. The efficacy of a RNAi agent comprising a ribpC6 is shown in FIG. 5A. An efficacious RNAi agent comprising this 3' end cap is shown in FIG. 11.

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is C6. This structure is designated ribC6 or ribpC6.

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is C8. This structure is designated ribC8 or ribpC8.

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is C10. This structure is designated ribC10 or ribpC10.

An RNAi agent comprising a first and a second strand, each strand being an 18-mer and the first and second strand together forming a blunt-ended duplex, wherein the 3' end of first and/or second strand terminates in a phosphate and further comprises, in 5' to 3' order: a spacer, a second phosphate, and a 3' end cap, and wherein the spacer is ribitol and the 3' end cap is C12. This structure is designated ribC12 or ribpC12.

Figure 4A:
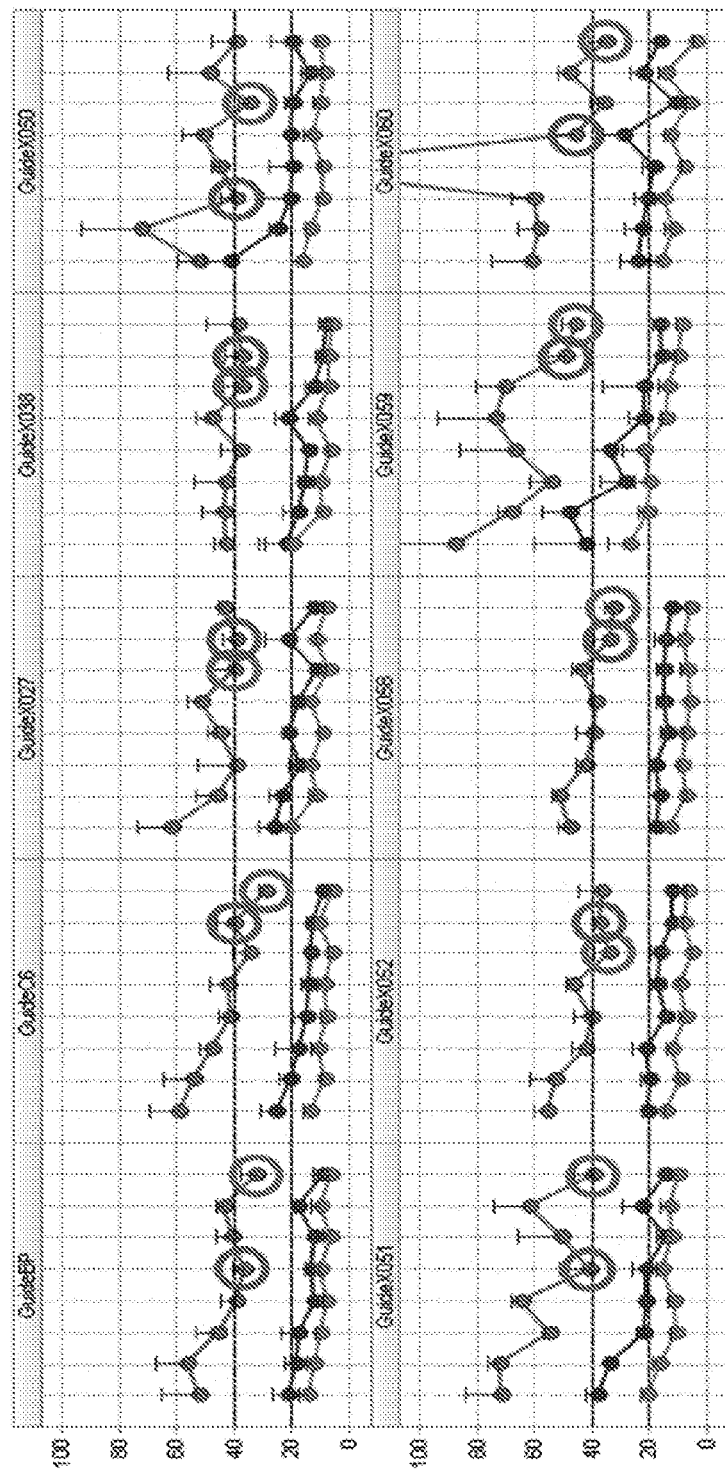
FIGS. 4A and 4B show residual expression level, indicating in vitro RNA interference or KD (knockdown) mediated by various RNAi agents comprising an 18-mer guide strand, wherein the 3' end of the 18-mer strand terminates in a phosphate and further comprises: a spacer (ribitol or Rib) and a 3' end cap; or only a 3' end cap. In various constructs 3' end cap used is: BP (biphenyl), C6, X027, X038, X050, X051, X052, X058, X059, X060, X061, X062, X063, X064, X065, X066, X067, X068, and X069, as described in Example 3A. These RNAi agents are without a 2'-MOE clamp (–) or with a 2'-MOE clamp (MOE); or without a ribitol spacer (–) or with a ribitol spacer (rib). Descriptions for FIG. 5A are provided at the bottom of FIG. 5B, and this data pertains to Example 3A.

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is BP. This structure is designated ribpBP. The efficacy of a RNAi agent comprising this 3' end cap is shown in FIG. 4A.

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is X027. This structure is designated ribX027. The efficacy of a RNAi agent comprising this 3' end cap is shown in FIG. 4A.

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is X038. This structure is designated ribX038. The efficacy of a RNAi agent comprising this 3' end cap is shown in FIG. 4A.

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is X050. This structure is designated ribX050. The efficacy of a RNAi agent comprising this 3' end cap is shown in FIG. 4A.

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is X051. This structure is designated ribX051. The efficacy of a RNAi agent comprising this 3' end cap is shown in FIG. 4A.

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is X052. This structure is designated ribX052. The efficacy of a RNAi agent comprising this 3' end cap is shown in FIG. 4A.

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is X058. This structure is designated ribX058. The efficacy of a RNAi agent comprising this 3' end cap is shown in FIG. 4A. An efficacious RNAi agent comprising this 3' end cap is shown in FIG. 11.

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is X059. This structure is designated ribX059. The efficacy of a RNAi agent comprising this 3' end cap is shown in FIG. 4A.

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is X060. This structure is designated ribX060. The efficacy of a RNAi agent comprising this 3' end cap is shown in FIG. 4A.

Figure 4B:
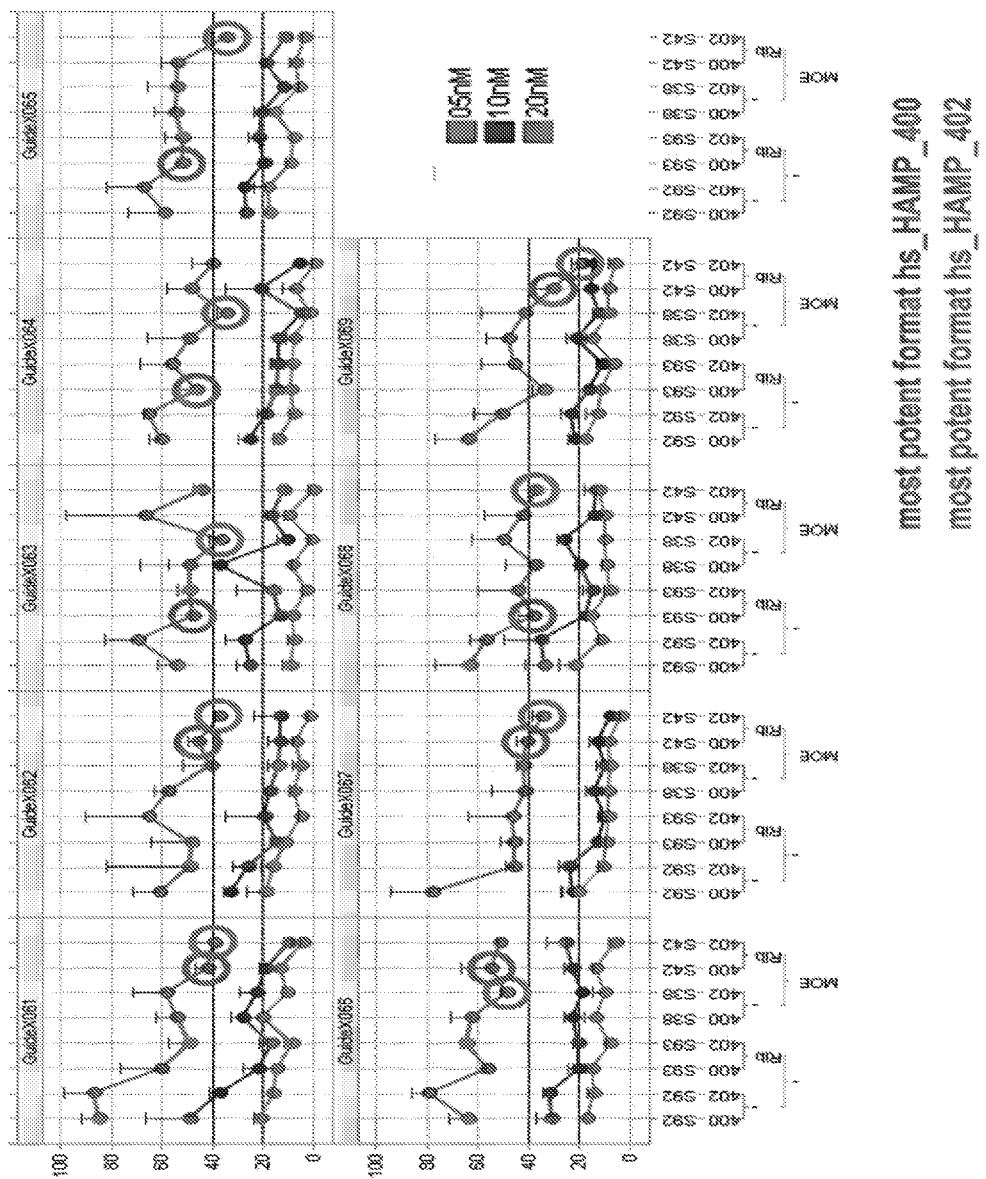

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is X061. This structure is designated ribX061. The efficacy of a RNAi agent comprising this 3' end cap is shown in FIG. 4B.

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is X062. ribX062. The efficacy of a RNAi agent comprising this 3' end cap is shown in FIG. 4B.

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is X063. This structure is designated ribX063. The efficacy of a RNAi agent comprising this 3' end cap is shown in FIG. 4B.

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is X064. ribX064. The efficacy of a RNAi agent comprising this 3' end cap is shown in FIG. 4B.

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is X065. This structure is designated ribX065. The efficacy of a RNAi agent comprising this 3' end cap is shown in FIG. 4B.

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is X066. This structure is designated ribX066. The efficacy of a RNAi agent comprising this 3' end cap is shown in FIG. 4B.

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is X067. This structure is designated ribX067. The efficacy of a RNAi agent comprising this 3' end cap is shown in FIG. 4B.

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is X068. This structure is designated ribX068. The efficacy of a RNAi agent comprising this 3' end cap is shown in FIG. 4B.

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is X069. This structure is designated ribX069. The efficacy of a RNAi agent comprising this 3' end cap is shown in FIG. 4B.

An RNAi agent comprising a first and a second strand, each strand being an 18-mer and the first and second strand together forming a blunt-ended duplex, wherein the 3' end of the first and/or second strand terminates in a phosphate and further comprises, in 5' to 3' order: a spacer, a second phosphate, and a 3' end cap, and wherein the spacer is ribitol and the 3' end cap is selected from any one or more of the 3' end caps disclosed herein, and wherein the first two base-pairing nucleotides on the 3' end of the sense and/or anti-sense strand are 2'-MOE.

For each and every of structure listed in this section, the RNAi agent can be of any sequence or target, and can be, as a non-limiting example, a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

The disclosure also encompasses a RNAi agent comprising a first strand and a second strand, wherein the first and/or second strand terminates in a PS (phosphorothioate), and further comprises a 3' end cap. The disclosure also a RNAi agent comprising a first strand and a second strand, wherein the first and/or second strand terminates in a PS (phosphorothioate), and further comprises, in 5' to 3' order: a spacer, phosphate or a modified internucleoside linker, and a 3' end cap.

Thus, the disclosure encompasses:

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, and wherein the 3' end of the first and/or second strand terminates in a PS and further comprises a 3' end cap, wherein the 3' end cap is C3. This structure is designated PS-C3.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, and wherein the 3' end of the first and/or second strand terminates in a PS and further comprises a 3' end cap, wherein the 3' end cap is C6. This structure is designated PS-C6.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, and wherein the 3' end of the first and/or second strand terminates in a PS and further comprises a 3' end cap, wherein the 3' end cap is C8. This structure is designated PS-C8.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, and wherein the 3' end of the first and/or second strand terminates in a PS and further comprises a 3' end cap, wherein the 3' end cap is C10. This structure is designated PS-C10.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, and wherein the 3' end of the first and/or second strand terminates in a PS and further comprises a 3' end cap, wherein the 3' end cap is C12. This structure is designated PS-C12.

A RNAi agent comprising a first strand and a second strand, wherein the first strand is ribonucleotides or ribonucleotides and at least one space subunit, and the second strand is ribonucleotides and at least one spacer subunit, and together the first and second strand optionally form a blunt-ended duplex, and wherein the 3' end of the first and/or second strand terminates in a PS and further comprises a 3' end cap, wherein the 3' end cap is BP. This structure is designated PS-BP.

Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"Alkyl" is a monovalent saturated hydrocarbon chain having the specified number of carbon atoms. For example, $C_{1-6}$ alkyl refers to an alkyl group having from 1 to 6 carbon atoms. Alkyl groups may be straight or branched. Representative branched alkyl groups have one, two, or three branches. Examples of alkyl groups include, but are not limited to, methyl, ethyl, propyl (n-propyl and isopropyl), butyl (n-butyl, isobutyl, sec-butyl, and t-butyl), pentyl (n-pentyl, isopentyl, and neopentyl), and hexyl.

"Aryl" is a hydrocarbon ring system having an aromatic ring. Aryl groups are monocyclic ring systems or bicyclic ring systems. Monocyclic aryl ring refers to phenyl. Bicyclic aryl rings refer to naphthyl and to rings wherein phenyl is fused to a $C_{5-7}$ cycloalkyl or $C_{5-7}$ cycloalkenyl ring as defined herein.

In some contexts, the term "ribonucleotide" includes a modified ribonucleotide (e.g., a ribonucleotide having a modification at the sugar, phosphate or base).

RNA Interference

As used herein, "RNA interference" (RNAi) is a post-transcriptional, targeted gene-silencing technique that uses a RNAi agent to degrade messenger RNA (mRNA) containing a sequence which is the same as or very similar to the RNAi agent. See: Zamore and Haley, 2005, Science, 309, 1519-1524; Zamore et al., 2000, Cell, 101, 25-33; Elbashir et al., 2001, Nature, 411, 494-498; and Kreutzer et al., PCT Publication WO 00/44895; Fire, PCT Publication WO 99/32619; Mello and Fire, PCT Publication WO 01/29058; and the like. The process of RNAi occurs naturally when long dsRNA is introduced into a cell and cleaved by ribonuclease III (Dicer) into shorter fragments called siRNAs. Naturally produced siRNAs are typically about 21 nucleotides long and comprise about 19 base pair duplexes with two 2-nt overhangs (the "canonical" structure). One strand of the siRNA is incorporated into the RNA-induced silencing complex (RISC). This strand (known as the anti-sense or guide strand) guides RISC to a complementary mRNA. One or more nucleases in the RISC then mediates cleavage of the target mRNA to induce silencing. Cleavage of the target RNA takes place in the middle of the region complementary to the anti-sense strand. See: Nykanen, et al. 2001 Cell 107:309; Sharp et al. 2001 Genes Dev. 15:485; Bernstein, et al. 2001 Nature 409:363; Elbashir, et al. 2001 Genes Dev. 15:188.

As used herein, the term "RNAi agent" is a molecule capable of mediating RNA interference. The term encompasses a variety of structures and formats, including, as a non-limiting example, siRNAs (including but not limited to those of the "canonical" structure or 18-mer format with an internal spacer), in addition to various natural and artificial structures capable of mediating RNA interference. As detailed below, RNAi agents can be longer or shorter than the canonical, and/or blunt-ended, and/or comprise one or more modification, mismatch, gap, and/or nucleotide replacement. The 3' end caps of the present disclosure can be used with any RNAi agent and can allow two functions: (1) allowing RNA interference; and (2) increasing duration of activity and/or biological half-life, which may be accomplished, for example, by increased binding to the PAZ domain of Dicer and/or reducing or preventing degradation of the RNAi agent (e.g., by nucleases such as those in the serum or intestinal fluid).

The RNAi agent(s) of the present disclosure target (e.g., bind to, anneal to, etc.) the target mRNA. The use of the RNAi agent to the target results in a decrease of target activity, level and/or expression, e.g., a "knock-down" or "knock-out" of the target gene or target sequence. Particularly, in one embodiment, in the case of a disease state characterized by over-expression or hyper-activity of target gene, administration of a RNAi agent to target gene knocks down the target gene target enough to restore a normal level of target gene activity.

A suitable RNAi agent can be selected by any process known in the art or conceivable by one of ordinary skill in the art. For example, the selection criteria can include one or more of the following steps: initial analysis of the target gene sequence and design of RNAi agents; this design can take into consideration sequence similarity across species (human, cynomolgus, mouse, etc.) and dissimilarity to other (non-target gene) genes; screening of RNAi agents in vitro (e.g., at 10 nM in cells); determination of EC50 in cells; determination of viability of cells treated with RNAi agents, including insensitive cells which do not require target gene for survival, or sensitive cells, which do require target gene for survival; testing with human PBMC (peripheral blood mononuclear cells), e.g., to test levels of TNF-alpha to estimate immunogenicity, wherein immunostimulatory sequences are less desired; testing in human whole blood assay, wherein fresh human blood is treated with an RNAi agent and cytokine/chemokine levels are determined [e.g., TNF-alpha (tumor necrosis factor-alpha) and/or MCP1 (monocyte chemotactic protein 1)], wherein Immunostimulatory sequences are less desired; determination of gene knockdown in vivo using subcutaneous tumors in test animals; target gene target gene modulation analysis, e.g., using a pharmacodynamic (PD) marker, for example, other factors whose expression is affected by target gene, wherein target gene knockdown leads to a dose-dependent reduction of abundance of those components; and optimization of specific modifications of the RNAi agents.

RNAi agents comprising a 3' end cap described herein are thus useful in RNA interference of target gene.

It is known in the art that naked siRNA (lacking a suitable 3' end cap, such as those disclosed herein) has a short duration of activity in vivo; it is rapidly degraded by nucleases in serum, often with a half-life of minutes. Layzer et al. 2004 RNA 10: 766-771; Choung et al. 2006 Biochem. Biophys. Res. Comm. 342: 919-927; and Sato et al. 2007 J. Control. Rel. 122: 209-216. Many 3' end caps previously described do not both allow RNA interference and either protect the molecules from nucleases or extend time of duration.

RNAi agents comprising 3' end caps disclosed herein mediate these activities.

Non-limiting examples of RNAi agent structures suitable for use with the disclosed 3' end caps are described below.

Structure of a RNAi Agent: Antisense Strand and Sense Strand of Various (Optional) 5' End Caps, (Optional) Modifications; (Optional) Patterns of Modification.

RNAi agents mediate RNA interference and comprise a first strand and a second strand, e.g., a sense strand and an antisense strand (or an antisense and a sense strand), wherein the strands are optionally primarily RNA (optionally wherein one or more nucleotides are replaced and/or modified), (optionally) further comprising one or two overhangs, and (optionally) one or two 5' end caps, wherein the optional modifications can optionally be in various patterns of modification. RNAi agents of the present disclosure comprise a 3' end cap on either the sense and/or anti-sense strand.

Anti-Sense and Sense Strands

The term "antisense strand" (AS), as used herein, refers to the strand of a RNAi agent which includes a region that is fully or substantially complementary to a target sequence. The "antisense strand" is sometimes termed the "guide" strand. As used herein, the term "region of complementarity" refers to the region on the antisense strand that is fully or substantially complementary to a target mRNA sequence. Where the region of complementarity is not fully complementary to the target sequence, the mismatches may be in the internal or terminal regions of the molecule. Generally, the most tolerated mismatches are in the terminal regions, e.g., within 5, 4, 3, or 2 nucleotides of the 5' and/or 3' terminus. The portion of antisense strand most sensitive to mismatches is termed the "seed region".

The term "sense strand" (S), as used herein, refers to the strand of a RNAi agent that includes a region that is substantially complementary to a region of the antisense strand as that term is defined herein. The "sense" strand is sometimes termed the "passenger" or "anti-guide" strand. By their sequences, the antisense strand targets the desired mRNA, while the sense strands targets a different target. Thus, if the antisense strand is incorporated into RISC, the correct target is targeted. Incorporation of the sense strand can lead to off-target effects. These off-target effects can be limited by use of modifications, or use of 5' end caps on the sense strand, as described below. In general, the sense strand is known to those of skill in the art to be more tolerant of modification than the antisense strand. This is logical, as the sense strand is not incorporated into the RISC and does not directly mediate RNA interference. In the present disclosure, the space subunit can be incorporated into (replacing a nucleotide in) the sense or antisense strand.

The sequence of a gene may vary from individual to individual, especially at wobble positions within the coding segment, or in the untranslated region; individuals may also differ from each other in coding sequence, resulting in additional differences in mRNA. The sequence of the sense and antisense strands of the RNAi agent can thus be tailored to correspond to that of an individual patient, if and where needed. RNAi agents can also be modified in sequence to reduce immunogenicity, binding to undesired mRNAs (e.g., "off-target effects") or to increase stability in the blood. These sequence variants are independent of chemical modification of the bases or 5' or 3' or other end-caps of the RNAi agents.

(Optional) 5' End Cap(s)

A "5' cap" can be optionally attached at the 5' end of the sense or antisense strand. The functions of the antisense and strands differ, as do the structural requirements of the 5' ends of these strands. A 5' end cap on the antisense strand should not interfere with RNAi activity mediated by this strand; however, in some embodiments, the 5' end cap on the sense strand can interfere with RNAi activity mediated by the sense strand. Either strand can be loaded into RISC, but only the antisense strand targets the desired target. Loading of the sense strand can lead to off-target effects, e.g., RNA interference of an undesired target. Jackson et al. 2003 Nat. Biotech. 21: 635-637

In the case of the antisense strand: the 5' end cap should not interfere with RNAi activity of this strand, but can provide at least some protection (e.g., from nucleases such as those in serum or intestinal fluid). A 5'-phosphate on the guide strand is generally required for optimal RNAi activity. A 5' dT modification provides antisense strand stability and increases potency. Blocking of phosphorylation leads to decreased activity. In contrast, 1 to 3 ribonucleotides added to the 5' end improved inhibition. Morrissey et al. 2005 Nat. Biotech. 23: 1002-1007. Some of the molecular interactions of the antisense strand 5' end with the Argonaute-2 (Ago2) component of RISC have been elucidated. Parker et al. 2005. Nature 434: 663-666; and Frank et al. 2010 Nature 465: 818-822.

In contrast, in the case of the sense strand: a 5' end cap that inhibits RNA interference can be useful on this strand. As noted above, a 5'-phosphate is generally required for optimal RNAi activity. Removal of the 5'-OH group is the simplest approach to prevent phosphorylation of the sense strand. 2'-O-methyl modification of position 1 further dampens sense strand activity. 2'-MOE modification might be even more effective. FIG. 17E shows various building blocks (I, II, III and IV) for construction of RNAi agents with a 5' end cap. Synthesis of these building blocks is provided in FIGS. 17G, 17H and 17I.

Capping of sense strands with 5'-deoxy-2'-O-methyl modification effectively prevents sense strand activity, as illustrated by HAMP RNAi agents shown in FIG. 17A and data shown in FIG. 17B. Sense strand activity is also lowered by current lead stem chemistry (A107→A107*).

Example 5' end caps thus include: ddT, 5'-OME-dT and 5'-OTr-dT (diagrammed in FIG. 17C).

2',5'-dideoxythymidine at the 5'-end of the guide strand reduces siRNA activity in a dose-dependent manner. 2',5'-dideoxythymidine is equivalent to 5'-O-methyl-deoxythymidine with respect to inactivation potency, but more readily synthesized. To more completely inactivate the sense strand, two simultaneous modifications maybe required, e.g.

removal or blocking of the 5'-OH group combined with a 2'-modification which is not tolerated in position 1 of the guide strand (e.g. 2'-O-MOE or 2'-OMe).

Thus, the RNAi agent can comprise a 5' end cap on the sense strand, wherein the 5' end cap reduces RNAi activity of the sense strand. Such a 5' end cap is not present on the antisense strand. In various embodiments, the 5' end cap can comprise: a nucleotide which lacks a 5' phosphate or 5'-OH; a nucleotide which lacks a 5' phosphate or a 5'-OH and also comprises a 2'-OMe or 2'-MOE modification; 5'-deoxy-2'-O-methyl modification; 5'-OME-dT; ddT; and 5'-OTr-dT.

In addition to 5' end caps, other modifications or sets of modifications can be used to reduce activity of the sense strand. As a non-limiting example, 2'-MOE modifications can be used at multiple positions in the sense strand to create an active RNAi agent, but highly increasing the number of 2'-MOE modifications can inactivate the sense strand. A sense strand wherein half or more of the positions are 2'-MOE is generally inactive. A sense strand wherein all the positions are 2'-MOE is inactive.

In one embodiment, the sense strand can comprise one or more morpholinos to reduce its activity.

The 3' end caps of the present disclosure can be used with any RNAi agent comprising a 5' end cap on the sense strand and/or any modification or set of modifications which reduces activity of the sense strand.

(Optional) Additional Nucleotide Replacements and/or Modifications

The strands of a siRNA can generally comprise RNA molecules as expressed or found in nature (i.e., are naturally occurring), but also non-naturally occurring analogs and derivatives of nucleotides comprising one or more ribonucleotide/ribonucleoside analogs or derivatives as described herein or as known in the art.

In some of the positions, the RNA nucleotides can be replaced by DNA, or a nucleotide of a different backbone, or PNA, LNA, Morpholino, TNA, GNA, ANA, HNA, CeNA, FANA, and/or UNA; and/or modified (including, but not limited to, 2'-MOE, 2'-OMe, 2'-F, and 2'-H). In some embodiments, the replacement or substitution of RNA with DNA, or a nucleotide of a different backbone, or PNA, LNA, Morpholino, TNA, GNA, ANA, HNA, CeNA, FANA can be considered a "modification". In various embodiments, the RNAi agent can comprise one or more LNA which are at 5' end and/or at 3' end (e.g., positions 18 and 19 in a 19-mer or positions 17 and 18 in an 18-mer), and/or in the middle of a strand.

In some embodiments, the nucleotide replacements are in the last two base-pairing nt (counting from 5' to 3'), forming a clamp. A clamp includes without limitation a 2'-MOE clamp [wherein the last two base-pairing nt (counting from 5' to 3') each have a 2'-MOE modification]. Other variants of the clamp are possible, wherein, for example, wherein the last two base-pairing nt (counting from 5' to 3') each are DNA, 2'-OMe, 2'-F or LNA, as shown in FIG. 20 C-E. It is noted that the last two nt (counting from 5' to 3') can also be considered to be the first two base-pairing nucleotides at the 3' end of each strand (counting from 3' to 5'). As shown herein and in U.S. Pat. No. 8,084,600, the clamp can be on the antisense and/or sense strands.

Thus, while the nucleotides in each strand are generally RNA (meaning that most of the nucleotides are RNA), some may be replaced by DNA or nucleotides of an alternative backbone such as peptide nucleic acids (PNA), locked nucleic acid (LNA), Morpholino, threose nucleic acid (TNA), glycol nucleic acid (GNA), arabinose nucleic acid (ANA), 2'-fluoroarabinose nucleic acid (FANA), cyclohexene nucleic acid (CeNA), and/or anhydrohexitol nucleic acid (HNA). In some embodiments, only 1 or 2 or 3 nt in one or both strands are replaced. In some embodiments, only about 1-3 nt in one or both strands are replaced by DNA. Non-limiting examples of this are shown in FIGS. 15B and 17A.

The RNA nucleotides in either strand can thus be replaced and/or modified.

The RNA can be modified in the nucleobase structure or in the ribose-phosphate backbone structure. However, in most embodiments, the molecules comprising ribonucleoside analogs or derivatives retains the ability to form a duplex. As non-limiting examples, an RNA molecule can also include at least one modified ribonucleoside, including but not limited to a 2'-O-methyl modified nucleotide, a nucleoside comprising a 5' phosphorothioate group, a terminal nucleoside linked to a cholesteryl derivative or dodecanoic acid bisdecylamide group, a locked nucleoside, an abasic nucleoside, a 2'-deoxy-2'-fluoro modified nucleoside, a 2'-amino-modified nucleoside, 2'-alkyl-modified nucleoside, morpholino nucleoside, an unlocked ribonucleotide (e.g., an acyclic nucleotide monomer, as described in WO 2008/147824), a phosphoramidate or a non-natural base comprising nucleoside, or any combination thereof. Alternatively, an RNA molecule can comprise at least two modified ribonucleosides, at least 3, at least 4, at least 5, at least 6, at least 7, at least 8, at least 9, at least 10, at least 15, up to the entire length of the dsRNA molecule. The modifications need not be the same for each of such a plurality of modified ribonucleosides in an RNA molecule. In one embodiment, modified RNAs contemplated for use in methods and compositions described herein comprise a 3' end cap as disclosed herein and have the ability to form the required duplex structure and that permit or mediate the specific degradation of a target RNA via a RISC pathway.

Examples of modified nucleotides which can be used to generate the RNAi agent include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

A "modified variant" of a sequence disclosed herein includes any variant comprising the same sequence, but with a modification in the base, sugar, phosphate or backbone (but not a base substitution, e.g., A for G, or C for U). Thus, a modified variant can comprise any modified nucleotide described above (e.g., 5-fluorouracil, 5-bromouracil, 5-chlorouracil, 5-iodouracil, hypoxanthine, xantine, 4-acetylcytosine, 5-(carboxyhydroxylmethyl) uracil, etc.). When a base is replaced by a corresponding modified base (e.g., A for modified A), these modified nucleotides do not constitute a mismatch or base difference. Thus a given sequence with a U at a particular position and a modified variant comprising a 5-fluorouracil, 5-bromouracil, 5-chlorouracil, or 5-iodouracil at the same sequence would differ by 0 nt (or have no mismatches); however, a given sequence with a C at a particular position and a different sequence with a 5-fluorouracil (wherein the two sequences are otherwise identical) would differ by 1 nt (1 mismatch).

In some embodiments, the RNAi agent according to the present invention confers a high in vivo stability by including a 3' end cap and at least one modified nucleotide in at least one of the strands. Thus the RNAi agent according to the present invention preferably contains at least one modified or non-natural ribonucleotide. A lengthy description of many known chemical modifications are set out in published PCT patent application WO 200370918 and will not be repeated here. Suitable modifications for oral delivery are more specifically set out in the Examples and description herein. Suitable modifications include, but are not limited to modifications to the sugar moiety (i.e. the 2' position of the sugar moiety, such as for instance 2'-O-(2-methoxyethyl) or 2'-MOE) (Martin et al., Helv. Chim. Acta, 1995, 78, 486-504) i.e., an alkoxyalkoxy group) or the base moiety (i.e. a non-natural or modified base which maintains ability to pair with another specific base in an alternate nucleotide chain).

Other modifications include so-called 'backbone' modifications including, but not limited to, replacing the phosphoester group (connecting adjacent ribonucleotides with for instance phosphorothioates, chiral phosphorothioates or phosphorodithioates). In various embodiments, one or more phosphate group is replaced with:

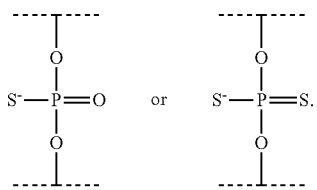

In various additional embodiments, one or more phosphate group is replaced by:

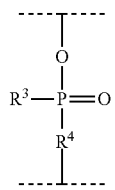

where $R^3$ is selected from $O^-$, $S^-$, $NH_2$, $BH_3$, $CH_3$, $C_{1-6}$ alkyl, $C_{6-10}$ aryl, $C_{1-6}$ alkoxy and $C_{6-10}$ aryl-oxy, wherein $C_{1-6}$ alkyl and $C_{6-10}$ aryl are unsubstituted or optionally independently substituted with 1 to 3 groups independently selected from halo, hydroxyl and $NH_2$; and $R^4$ is selected from O, S, NH, or $CH_2$. Some of these replacement phosphate groups are also shown in FIG. 18C.

In various embodiments, in the modified nucleoside linker, the phosphate of the phosphate group is replaced by arsenic (As), selenium (Se), or antimony (Sb). In one embodiment, the spacer is ribitol and no phosphate groups are replaced. In various embodiments, in the modified nucleoside linker, the phosphate group is replaced by a sulfonamide group or a cyano group or carboxamide. In various embodiments, in the modified nucleoside linker, the phosphate group is replaced by an arsenic, selenium, antimony or sulfonamide group or a cyano group or carboxamide. In various embodiments, in the modified nucleoside linker, the phosphate group is replaced by an arsenic, selenium, antimony or sulfonamide group or a cyano group or carboxamide.

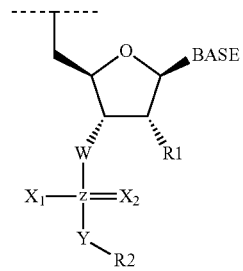

W=O, S, NH, $CH_2$, . . .
$X_1$, $X_2$=$O^-$, $S^-$, $NH_2$, $BH_3^-$, $CH_3$, alkyl, aryl, O-alkyl, O-aryl, . . .
Y=O, S, NH, $CH_2$, . . .
Z=C, Si, P, S, As, Se, Sb, Te, . . .
R1=H, OH, F, $NH_2$, O-alkyl, O-aryl, O-alkyl-aryl, O-aryl-alkyl, NH-alkyl, N-dialkyl, . . .
R2=alkyl, aryl, alkyl-aryl, aryl-alkyl, . . . (PAZ ligand)
BASE=H, adenine, cytosine, guanine, uracil, thymine, . . .

Thus, the nucleotides of either or both strands of a RNAi agent useful with 3' end caps disclosed herein can be replaced and/or modified.

(Optional) Patterns of Modifications

In some cases of modifying the nucleotides of a RNAi agent, the modifications are not random, but are arrayed in patterns. These patterns (or schemes) increase the efficacy (RNAi activity), decrease activity of the sense strand or otherwise decrease off-target effects, reduce degradation or immunogenicity, and/or increase the biological half-life (e.g., time of duration of activity) of the RNAi agent.

In one pattern of modification, multiple positions of the sense strand are 2'-MOE. As a non-limiting example, most or all of the pyrimidines are 2'MOE in the sense strand. Modifying more than half of the positions in a sense strand with 2'-MOE can decrease activity. When all the positions of the sense strand are 2'-MOE often abolishes activity.

Various patterns of modifications are known in the art or are shown in, for example, FIG. 12.

Many modification patterns include a MOE clamp (wherein the last two base-pairing nucleotides counting from 5' to 3' have 2'-MOE modifications). The last two nt counting from 5' to 3' can also be considered to be the first two base-pairing nucleotides at the 3' end of each strand (counting from 3' to 5').

FIG. 15B (top) shows a "wt" ("wild-type") siRNA and a corresponding non-limiting example modification scheme of this siRNA. The example modified siRNA has 2'-OMe and phosphorothioate (s).

FIG. 12 (bottom) shows non-limiting examples of modification schemes for the canonical 21-mer siRNA, and for the 18- or 19-mer formats. In these schemes, "L" indicates the 3' end cap (e.g., a PAZ Ligand). In other cases, "L" indicates, in 5' to 3' order, a spacer, a phosphate or modified internucleoside linker, and a 3' end cap.

In various other modification patterns, the RNAi agent comprises at least one 5'-uridine-adenine-3' (5'-ua-3') dinucleotide, wherein the uridine is a 2'-modified nucleotide; at least one 5'-uridine-guanine-3' (5'-ug-3') dinucleotide, wherein the 5'-uridine is a 2'-modified nucleotide; at least one 5'-cytidine-adenine-3' (5'-ca-3') dinucleotide, wherein the 5'-cytidine is a 2'-modified nucleotide; and/or at least one 5'-uridine-uridine-3' (5'-uu-3') dinucleotide, wherein the 5'-uridine is a 2'-modified nucleotide.

Other patterns of modifications can be used with any RNAi agent comprising a 3' end cap as disclosed herein.

Particularly preferred modification patterns include but are not limited to:

All 3' overhangs as 2'-OMe-U 2'-OMe-U
A85: All U as 2'-OMe-U, except pos. 1, 2 and 14
S26: All U as 2'-OMe-U and all C as 2'-OMe-C
A51: All U as 2'-OMe-U and all C as 2'-OMe-C, except pos. 1, 2 and 14
S26: All U as 2'-OMe-U and all C as 2'-OMe-C
A48: UA as 2'-OMe-U A and all CA as 2'-OMe-C A, first 5'-N is DNA
S26: All U as 2'-OMe-U and all C as 2'-OMe-C The 3' end caps disclosed herein can thus be used with any RNAi agent, wherein at least one nucleotide of at least one strand of the RNAi agent has been replaced and/or modified, and wherein the modification(s) of the nucleotide(s) can be arrayed in a pattern(s) of modification.

In various patterns of modification, the pattern comprises a 2'-MOE clamp [wherein the last two base-pairing nt (counting from 5' to 3') each have a 2'-MOE modification]. Other variants of the clamp are possible, wherein, for example, wherein the last two base-pairing nt (counting from 5' to 3') each are DNA, 2'-OMe, 2'-F or LNA, as shown in FIG. 20 C-E. It is noted that the last two nt (counting from 5' to 3') can also be considered to be the first two base-pairing nucleotides at the 3' end of each strand (counting from 3' to 5'). As shown herein and in U.S. Pat. No. 8,084,600, the clamp can be on the antisense and/or sense strands.

Any embodiments of any RNAi agent described herein can be combined with any other embodiment, provided that the embodiments are not mutually exclusive (e.g., a single RNAi agent cannot simultaneously have both exactly 0 and exactly 2 overhangs).

Thus, the 3' end caps disclosed herein can be used with any RNAi agent as described herein or as known in the art, wherein the strands of the RNAi agent can comprise 0, 1, or 2 overhangs or 0, 1 or 2 blunt ends, one or more nucleotides of one or both stands can be replaced or modified, and the modification(s) can be arrayed in a pattern(s) or scheme(s) of modification, and the antisense and/or sense strand can comprise a 5' end cap, wherein the 5' end cap of the sense strand (if present) reduces RNA interference activity mediated by the sense strand.

The 3' end caps disclosed herein can also be used with any additional RNAi agent format or structure disclosed herein or known in the art.

Additional RNAi Agents

In additional to the structures listed above, additional types of molecules have been devised which are also capable of mediating RNA interference. In these structures, the strands are not necessarily RNA, and the strands can be can be longer or shorter than the canonical, and/or blunt-ended, and/or comprise one or more modification, mismatch, gap, and/or nucleotide replacement.

The term "RNAi agent" is intended to encompass any molecule described herein or known in the art capable of mediating RNA interference, including, without limitation, siRNA (whether of canonical, 18-mer format with an internal spacer, or other structure), or any other molecule capable of mediating RNA interference. The 3' end caps described herein can be used with any RNAi agent.

Thus, the 3' end caps disclosed herein can be used on any RNAi agent (including siRNA) or on any other RNAi agent, including, inter alia, and without limitation:

shRNA (small hairpin RNA or short hairpin RNA), which comprises a sequence of RNA that makes a tight hairpin turn and, like siRNAs, silences targets via RISC. The antisense and sense strand are thus connected by a hairpin. shRNAs can be expressed, for example, via delivery of plasmids or through viral or bacterial vectors. Various varieties of shRNAs are known in the art. See, for example: Xiang et al. 2006. Nature Biotech. 24: 697-702; Macrae et al. 2006 Science 311: 195-8. Lombardo et al. 2007. Nature Biotech. 25: 1298-1306; Wang et al. 2011. Pharm. Res. 28: 2983-2995; Senzer et al. 2011. Mol. Ther. 20: 679-686.

miRNA (microRNA), which is a small RNA molecule (ca. 22 nt) that, like siRNAs, also silences targets via RISC. Naturally-occurring miRNAs are encoded by eukaryotic nuclear DNA; miRNAs are generated by post-transcriptional RNA processing, and function via base-pairing with complementary sequences within mRNA molecules, usually resulting in translational repression or target degradation and gene silencing. The human genome can encode over 1000 miRNAs, which may target about 60% of mammalian genes and are abundant in many human cell types. Various varieties of naturally-occurring and artificial derivatives of miRNAs are known in the art. See, for example: Lewis et al. 2003. Cell 115: 787-798; Lim et al. 2003. Genes Dev. 17: 991-1008; He et al. 2004. Nat. Rev. Genet. 5: 522-31; Bentwich et al. 2005. Nat. Genet. 37: 766-70; Lewis et al. 2005. Cell 120: 15-20; Kusenda et al. 2006. Biomed Pap Med Fac Univ Palacky Olomouc Czech Repub 150: 205-15; Zhang et al. 2006. J. Gen. Gen. 36: 1-6; Brodersen et al. 2008. Science 320: 1185-90; Friedman et al. 2009. Genome Res. 19 (1): 92-105; Bartel 2009. Cell 136 (2): 215-33.

sisiRNA (small internally segmented interfering RNA), wherein the sense strand comprises at least one single-stranded nick. This nick decreases the incorporation of the sense strand into the RISC complex and thus reduces off-target effects. See: WO 2007/107162.

DNA-RNA chimera, wherein the seed portion of each strand is DNA, while the remainder of each strand is RNA. See: Yamato et al. 2011. Cancer Gene Ther. 18: 587-597.

siRNA comprising two mismatches, wherein that the molecule comprises three short double-stranded regions. In one embodiment of this RNAi agent, the guide (antisense) strand is a 22-mer, while the sense strand is a 20-mer (producing only a single 2-nt overhang on the 3' end of the anti-sense strand; and two mismatches produce double-stranded regions of 6, 8 and 4 bp. See: U.S. Pat. App. 2009/0209626 aiRNA (asymmetrical interfering RNA), wherein the sense strand is shorter than 19-nt long, so that the anti-sense strand is preferentially loaded into RISC, and thus off-target effects are reduced. In various embodiments of this RNAi agent, the anti-sense strand is 21-nt long, but the sense strand is only 15 or 16 nt long. See: Sun et al. 2008 Nature Biotech. 26: 1379-1382; and Chu and Rana. 2008 RNA 14: 1714-1719.

Thus, any 3' end cap disclosed herein can be used with any of the various formats of RNAi agents described above or otherwise known in the art, including siRNAs (including but not limited to those of the canonical structure), shRNAs, miRNAs, sisiRNAs, DNA-RNA chimeras, siRNAs comprising two mismatches (or more mismatches), or aiRNAs.

3' End Caps

The 18-mer format with an internal spacer RNAi agent of the present disclosure comprises a 3' end cap. The terms "3' end cap", "3' end cap modification", "end cap", "Cap", "3' end modification" and the like include a chemical moiety attached to the end of a double-stranded nucleotide duplex, but is used herein to exclude a chemical moiety that is a nucleotide or nucleoside. A "3' end cap" is attached at the 3' end of a nucleotide or oligonucleotide (e.g., is a modification at the 3' carbon at the terminus of at least one strand) and protects the molecule from degradation, e.g., from nucleases, such as those in blood serum or intestinal fluid. "3' end caps" include but are not limited to "PAZ ligands," which term includes 3' end caps which interact with the PAZ domain of the enzyme Dicer. 3' end caps are sometimes referred to as "non-nucleotide overhang mimics" or "LMW [Low molecular weight] mimics of dinucleotide overhangs" or the like.

This disclosure notes that some documents refer to a 3' end cap as described herein (e.g., X109 or X110 or X111, etc.) as an "overhang" or a "3' overhang"; however, this document differentiates a 3' end cap from an "overhang" and uses the term "overhang" only to refer to a nucleotidic overhang (e.g., one comprising only nucleotides such as A, C, G, U or T, such as UU or TT). Thus, as defined herein, a "3' end cap" is not an overhang.

As defined herein, a 3' end cap can be used in place of or in addition to an overhang (i.e., a nucleotidic overhang). Earlier work with canonical siRNA structures suggested that the 2-nt overhang was useful for RNA interference activity, while blunt-ended dsRNAs (lacking the overhangs) were generally not effective. See, for example, Elbashir et al. 2001 EMBO J. 23: 6877-6888, especially FIG. 1F. However, dsRNA, even with the overhangs, were subject to enzymatic degradation. As noted elsewhere by the Applicants, "unmodified siRNAs are subject to enzymatic digestion, mainly by nucleases." (WO 2007/128477, page 1). 3' end caps were thus designed to perform several functions, including (1) allowing the molecule to mediate RNA interference activity, and (2) protecting the molecule from degradation.

It is noted, though, that the 3' end caps disclosed herein can be used in addition to as well as in place of 3' overhangs.

Because a 3' end cap can be used instead of an overhang such as UU or TT, the 3' end caps described herein are sometimes referred to as "3'-Dinucleotide surrogates".

A few 3' end caps have been disclosed for use with siRNAs. It is noted that of the 3' end caps which have been described chemically, many of these have been shown not to be functional. A functional 3' end cap can be able to perform these functions: (1) allow the double-stranded RNA to function in RNA interference; and (2) increase the stability of the molecule, e.g., by protecting it from nucleases, such as those found in blood serum or intestinal fluid.

Non-Functional 3' End Caps

Many 3' end caps described in the literature are unable to perform both of these functions. In some cases, the placement of the end caps is important; some end caps may be functional when placed on only one strand, but not functional if placed on both strands and/or on both 5' and 3' ends of both strands.

It is impossible to predict which 3' end caps will perform both functions without experimentation. In fact, while many endcaps were predicted to be suitable for RNA interference (e.g., in US 2003/0143732), many later were discovered not to perform both functions.

Other scientists have empirically found that, despite predictions, some endcaps or overhangs (1) stabilized the siRNA but (2) did NOT allow RNAi activity. For example, the TT (dithymidine) in combination with 2'-OMe modifications at all positions, Czauderna et al. 2003 Nucl. Acids Res. 31:2705-2716, FIG. 4B. Hadwiger et al. also note that complete 2'-O-methylation rendered the siRNA serum nuclease-resistant, although gene silencing activity was almost completely abolished. Hadwiger et al. 2005, pages 194-206, in RNA Interference Technology, ed. K. Appasani, Cambridge University Press, Cambridge, UK.

Other endcaps or overhangs (1) did NOT stabilize the siRNA, though (2) they did allow RNAi activity. For example, the TT at both 3' ends or both 5' ends of a siRNA. Czauderna et al. 2003, FIG. 4B.

Still other endcaps (1) did NOT stabilize the siRNA AND (2) did NOT allow RNAi activity such examples include: the amino-C6 linker or inverted abasic nucleotide. Czauderna et al. 2003, FIG. 4B.

Additional examples of 3' end caps which are non-functional under at least some conditions include:

Inverted (deoxy) abasics, which were neither stabilize siRNA nor allow siRNA activity when present on both 5' and both 3' ends. See: Czauderna et al. 2003 Nucl. Acids Res. 31:2705-2716, FIG. 4B.

Modified base nucleotides such as 5-propynyl-U, which do not both stabilize the siRNA and allow RNAi activity. Deleavey et al. 2009 Curr. Prot. Nucl. Acid Chem. 16.3.1-16.3.22; Terrazas et al. 2009 Nucleic Acids Res. 37: 346-353.

At least some amino-substituted lower alkyls, including aminohexyl phosphate, which was not able to stabilize the siRNA. When present on both 5' ends and both 3' ends, it prevented RNAi activity. See: Czauderna et al. 2003, FIG. 4B.

Fluoroscein (e.g., a fluorescent chromophore), which was found to inhibit RNA interference activity when conjugated to the 3' end of the antisense strand. The sense strand can tolerate, for example, a conjugation of fluoroscein at the 3'-end, but the antisense strand cannot. Harboth et al. 2003 Antisense Nucl. Acid Drug Dev. 13: 83-105. See: Harboth et al. 2003 Antisense Nucl. Acid Drug Dev 13: 83-105.

Cyanine (e.g., Cy5), which is non-functional. See: Song et al. 2003 Nature Med. 9: 347-351. See page 347, second col.

3' phosphate as a 3' end cap, suggested by U.S. Pat. No. 5,998,203 (paragraph [017]), but later shown not to both stabilize the 3' end of a siRNA and allow RNAi activity, Schwarz et al. 2002 Mol. Cell 10: 537-548; and Lipardi et al. 2001 Cell 107: 299-307.

3'-aminopropylphosphoester, which reduced RNA interference activity. See: Schwarz et al. 2002 Mol. Cell 10: 537-548, FIG. 2.

Thus, not all moieties tested as 3' end caps are capable of both allowing RNA interference and protecting the molecule from degradation.

Functional 3' End Caps

In contrast to the non-functional 3' end caps and overhangs described above, functional 3' end caps are described in, for example, U.S. Pat. Nos. 8,097,716; 8,084,600; 8,344,128; 8,404,831; and 8,404,832. These disclose functional 3' end caps comprising a phosphate and nicknamed as C3, C6, C12, Triethylene glycol, Cyclohexyl (or Cyclohex), Phenyl, Biphenyl, Adamantane and Lithocholic acid (or Lithochol).

These functional 3' end caps are diagrammed below, wherein they are shown bonded to a phosphate:

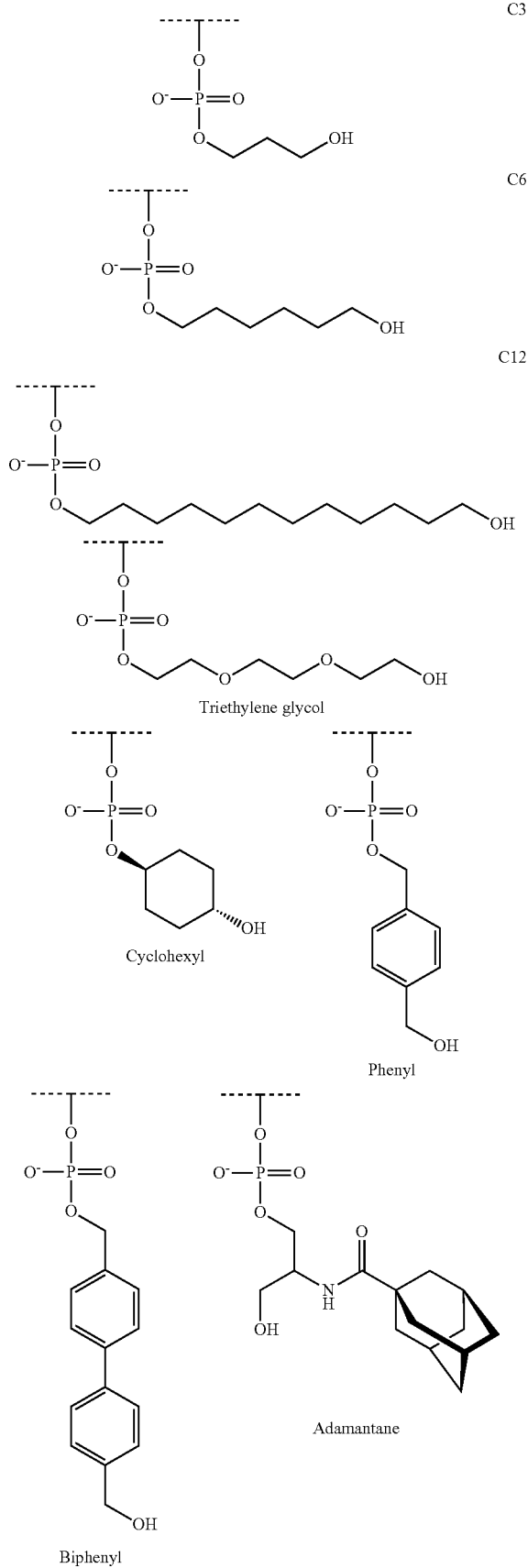

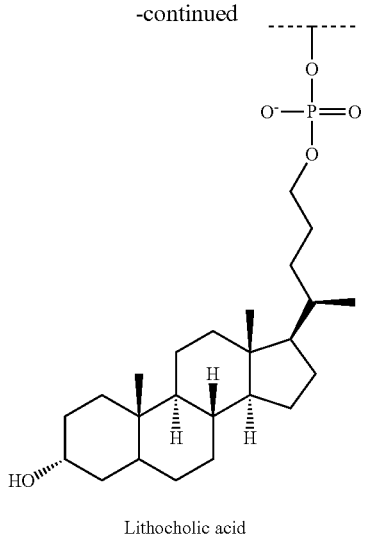

Lithocholic acid

It is noted that the terminology used in the present disclosure differs slightly from that used in U.S. Pat. Nos. 8,097,716; 8,084,600; 8,344,128; 8,404,831; and 8,404,832. In various embodiments, the present disclosure pertains to RNAi agents comprising a first strand and a second strand, wherein, in some embodiments, the 3' end of the first and/or second strand terminates in a phosphate (or modified internucleoside linker) and further comprises a 3' end cap. In the diagrams directly above, the phosphate and the 3' end cap are shown.

The 3' end caps disclosed in U.S. Pat. Nos. 8,097,716; 8,084,600; 8,344,128; 8,404,831; and 8,404,832 were superior to those which were devised before them. For example, unlike other possible endcaps, these were able to both protect the siRNAs from degradation (e.g., from nucleases, such as in blood or intestinal fluid), and also allow RNA interference.

However, in at least some cases, many of the novel 3' end caps of the present disclosure (e.g., those listed in Tables 1 and 2) are even further improved. For example, siRNAs with X058 (as disclosed herein) show a higher duration of activity than a siRNA with C6 (FIG. 22). HuR siRNAs with X058 showed greater efficacy at Day 7 and at Day 10 in Huh-7 cells.

Various novel 3' end caps disclosed herein include those designated as PAZ ligands, as they interact with the PAZ domain of Dicer.

PAZ Ligands

As noted above, when a long dsRNA molecule is introduced into a cell, Dicer chops the dsRNA is shorter segments called siRNAs. A homologue of Dicer is common to all organisms in which dsRNA-mediated gene silencing has been observed. Myers et al. 2005. In RNA Interference Technology, ed. Appasani, Cambridge University Press, Cambridge UK, p. 29-54; Bernstein et al. 2001 Nature 409: 363-366; and Schauer et al. 2002 Trends Plant Sci. 7: 487-491. Dicer is an RNase III enzyme and is composed of six recognizable domains. At or near the N-terminus is an approx. 550 aa DExH-box RNA helicase domain, which is immediately followed by a conserved approx. 100 aa domain called DUF283. Just C-terminal to DUF283 domain is the PAZ (for Piwi/Argonaute/Zwille) domain. The domain recognizes single stranded dinucleotide overhangs. Lingel et al. 2003 Nature 426: 465-469; Song et al. 2003 Nature Struct. Biol. 10: 1026-1032; Yan et al. 2003 Nature 426:

468-474; Lingel et al. 2004 Nature Struct. Mol. Biol. 11: 576-577; Ma et al. 2004 Nature 429: 318-322. Presumably, the PAZ domain in Dicer could also bind RNA to position the catalytic domains for cleavage. Zhang et al. 2004 Cell 118: 57-68. The C-terminus of the Dicer protein is composed of two RNAse III catalytic domains and a putative dsRNA-binding domain.

Table 2 lists various 3' end caps, including many PAZ ligands.

Arrangement and Non-Identical Nature of 3' End Caps

The anti-sense and sense strands are biochemically distinct. As noted above, the antisense strand is preferably loaded into RISC, as this strand targets the desired target. Incorporation of the sense strand can lead to off-target effects.

It is known that some 3' end caps can be more useful on one strand than on the other. For example, as noted above, The sense strand can tolerate, for example, a conjugation of fluorescein at the 3'-end, but the antisense strand cannot. Harboth et al. 2003 Antisense Nucl. Acid Drug Dev. 13: 83-105.

RNAi Agent with an Internal Spacer and a 3' End Cap (but No Spacer or Second Phosphate or Modified Internucleoside Linker)

This document and related documents, including U.S. Patent Applications 61/886,753; 61/930,681; PCT/US14/58703; PCT/US14/58705; and PCT/US14/58314, which are incorporated by reference in their entirety, describe a format of RNAi agent comprising two strands, wherein one or both strands terminates at the 3' end in a phosphate or modified internucleoside linker, and further comprises, in 5' to 3' order: a spacer, a second phosphate or modified internucleoside linker, and a 3' end cap.

However, it is also known in the art that effective RNAi agents can be constructed wherein one or both strands terminates at the 3' end in a phosphate or modified internucleoside linker, and further comprises a 3' end cap (but no additional spacer or second phosphate or modified internucleoside linker). Examples of such molecules are described, for example, in U.S. Pat. Nos. 8,097,716; 8,084,600; 8,344,128; 8,404,831; and 8,404,832.

In addition, this disclosure and related documents, including U.S. Patent Applications 61/886,753; 61/930,681; PCT/US14/58703; PCT/US14/58705; and PCT/US14/58314, also show that effective 18-mer RNAi agent formats can omit up to two of these elements (e.g., omitting the 3' end cap; or omitting the second phosphate or modified internucleoside linker and the 3' end cap; or omitting the spacer and the second phosphate or modified internucleoside linker but retaining the 3' end cap).

Thus:

In various embodiments, the RNAi agent comprises a strand comprising ribonucleotides and at least one spacer subunit, the strand terminating in a phosphate or modified internucleoside linker and further comprising a 3' end cap (but no spacer, or phosphate or modified internucleoside linker). Thus: In some embodiments, the RNAi agent comprises a first and a second 18-mer strand, wherein the first strand is ribonucleotides or ribonucleotides and at least one spacer subunit, and the second strand is ribonucleotides and at least one spacer subunit, and wherein the 3' end of one or both 18-mer strands terminates in a phosphate or modified internucleoside linker and further comprises a 3' end cap (e.g., BP or C6 or any 3' end cap disclosed herein). For example, a variety of RNAi agents to SSB were constructed comprising: an 18-mer strand, wherein the 3' end of the 18-mer strand terminates in a phosphate and further comprises a 3' end cap (e.g., BP or C6).

In Addition:

A RNAi agent to Factor VII comprising an 18-mer strand comprising a 3' end cap (C6) was shown to be effective in mediating RNA interference in vitro.

In some embodiments, the RNAi agent comprises an 18-mer strand, wherein the 18-mer strand is 18 ribonucleotides or 18 total ribonucleotides and spacer subunits, and wherein the 3' end of one or both 18-mer strands terminates in a phosphate or modified internucleoside linker and further comprises a 3' end cap (but no phosphate or modified internucleoside linker, or additional spacer).

Thus: In some embodiments, the RNAi agent comprises an 18-mer strand, wherein the 18-mer strand is 18 ribonucleotides or 18 total ribonucleotides and spacer subunits, and wherein the 3' end of the 18-mer strand terminates in a phosphate and further comprises a ribitol. It is noted in this case, the designation of the ribitol as a spacer (rather than a 3' end cap) is purely arbitrary. Thus, the present disclosure also contemplates: a RNAi agent comprising an 18-mer strand, wherein the 3' end of the 18-mer strand terminates in a phosphate and further comprises a 3' end cap (e.g., a ribitol).

Other modifications known to one skilled in the art are contemplated as being encompassed within the invention. Exemplary modifications include, but are not limited to, the presence of gaps or mismatches between the base pairs in the sense and antisense strands, the presence of nicks or breaks in the internucleoside linkages in the sense strand, and the like.

Pharmaceutical Compositions

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Aqueous suspensions contain the active materials in a mixture with excipients suitable for the manufacture of aqueous suspensions.

Oral administration of the compositions of the invention include all standard techniques for administering substances directly to the stomach or gut, most importantly by patient controlled swallowing of the dosage form, but also by other mechanical and assisted means of such delivery.

Dosage levels of the order of from about 0.1 mg to about 140 mg per kilogram of body weight per day are useful in the treatment of the above-indicated conditions (about 0.5 mg to about 7 g per subject per day). The amount of active ingredient that can be combined with the carrier materials to produce a single dosage form varies depending upon the host treated and the particular mode of administration. Dosage unit forms generally contain between from about 1 mg to about 500 mg of an active ingredient. It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

Therapeutic effect of the therapeutic agents of the invention may be enhanced by combination with other agents. Typically such other agents will include agents known for use in treating similar diseases, such as angiogenic disorders.

The RNAi agents of the invention and formulations thereof can be administered orally, topically, parenterally, by inhalation or spray, or rectally in dosage unit formulations containing conventional non-toxic pharmaceutically acceptable carriers, adjuvants and/or vehicles. The term parenteral as used herein includes percutaneous, subcutaneous, intravascular (e.g., intravenous), intramuscular, intraperitoneal, or intrathecal injection, or infusion techniques and the like. Where two or more different RNAi agents are administered, each may be administered separately or co-administered. Where each is administered separately, the method and/or site of administration may be the same or different, e.g., both RNAi agents may be administered intravenously or subcutaneously, or a first RNAi agent may be administered intravenously with a second Rai agent administered subcutaneously, etc.

In various embodiments, the disclosure encompasses a composition or pharmaceutical composition comprising a RNAi agent as described herein, the composition further comprising a helper lipid, a neutral lipid, and/or a stealth lipid. Additional compositions that can be used for delivery of the various RNAi agents are known in the art, e.g., are provided in U.S. Applications No. 61/774,759; 61/918,175, filed Dec. 19, 2013; 61/918,927; 61/918,182; 61/918941; 62/025224; 62/046487; and International Applications No. PCT/US04/042911; PCT/EP2010/070412; PCT/IB2014/059503.

In one particular specific embodiment, the present disclosure relates to a method of treating a target gene-related disease in an individual, comprising the step of administering to the individual a therapeutically effective amount of a composition comprising a RNAi agent comprising a first strand and a second strand, wherein the first and/or second strand comprise a 3' end cap selected from the 3' end caps listed in Table 2. In one particular specific embodiment, the present disclosure relates to a method of inhibiting the expression of target gene in an individual, comprising the step of administering to the individual a therapeutically effective amount of a composition comprising a RNAi agent of the present disclosure.

In one embodiment of the method, the composition further comprises a pharmaceutically effective formulation.

Various particular specific embodiments of these embodiments are described below.

In one embodiment, the method further comprises the administration of an additional treatment. In one embodiment, the additional treatment is a therapeutically effective amount of a composition.

In one embodiment, the additional treatment is a method (or procedure).

In one embodiment, the additional treatment and the RNAi agent can be administered in any order, or can be administered simultaneously.

In one embodiment, the method further comprises the step of administering an additional treatment for the disease.

In one embodiment, the method further comprises the step of administering an additional treatment or therapy selected from the list of an additional antagonist to a target gene-related disease.

In one embodiment, the composition comprises a second RNAi agent to target gene. In various embodiments, the second RNAi agent is physically separate from the first, or the two are physically connected (e.g., covalently linked or otherwise conjugated).

Other Embodiments

Various particular specific embodiments of this disclosure are described below.

In one embodiment, the disclosure pertains to a composition according to any of the embodiments described herein, for use in a method of treating a target gene-related disease in an individual, the method comprising the step of administering to the individual a therapeutically effective amount of a composition according to any of the claims.

One embodiment of the disclosure is the use of a composition according to any of these embodiments, in the manufacture of a medicament for treatment of an target gene-related disease.

In one embodiment, the disclosure pertains to the composition of any of the above embodiments, for use in the treatment of an target gene-related disease.

Additional Definitions

Unless defined otherwise, the technical and scientific terms used herein have the same meaning as that usually understood by a specialist familiar with the field to which the present disclosure belongs.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein.

Claims to the present disclosure are non-limiting and are provided below.

Although particular embodiments and claims have been disclosed herein in detail, this has been done by way of example for purposes of illustration only, and is not intended to be limiting with respect to the scope of the appended claims, or the scope of subject matter of claims of any corresponding future application. In particular, it is contemplated by the inventors that various substitutions, alterations, and modifications may be made to the present disclosure without departing from the spirit and scope of the present disclosure as defined by the claims. The choice of nucleic acid starting material, clone of interest, or library type is believed to be a matter of routine for a person of ordinary skill in the art with knowledge of the embodiments described herein or known in the art. Other aspects, advantages, and modifications considered to be within the scope of the following claims. Redrafting of claim scope in later-filed corresponding applications may be due to limitations by the patent laws of various countries and should not be interpreted as giving up subject matter of the claims.

Various additional formulations and obvious variants of the described 3' end caps can be devised by those of ordinary skill in the art. Non-limiting example RNAi agents wherein one or both strands comprises a 3' end cap are described in the Examples below, which do not limit the scope of the present disclosure as described in the claims.

EXAMPLES

Example 1. Serum Stability of siRNAs with 3' End Caps

The efficacy of a variety of different 3' end caps (3'-terminal overhangs) was tested.

10 siRNAs were prepared with an identical sequence (mF7-III target gene, 19-mer blunt-ended, A12S17 modification scheme)

10 different non-nucleotidic 3'-terminal caps were used.

These were tested in mouse and human sera at 4 time points

Parent mF7-III in A6S11 format and wt (wild-type) luc (luciferase) siRNAs were used as controls The molecules used are diagrammed in FIG. 1.

Table 5 below provides the sequences for these molecules.

TABLE 5

| siRNA ID | Project | Serum | Format sense | siRNA passenger sequence | Format anti | siRNA guide sequence |
|---|---|---|---|---|---|---|
| 144033 | mFVII 3'-caps | Mouse | S17 | uGu cuu GGu uuc AAu uA5 5 C3 | A12 | UUu AAU UGA AAC cAA GA6 5 C3 |
| 149853 | mFVII 3'-caps | Mouse | S17 | uGu cuu GGu uuc AAu uA5 5 C6 | A12 | UUu AAU UGA AAC cAA GA6 5 C6 |
| 149855 | mFVII 3'-caps | Mouse | S17 | uGu cuu GGu uuc AAu uA5 5 C12 | A12 | UUu AAU UGA AAC cAA GA6 5 C12 |
| 149857 | mFVII 3'-caps | Mouse | S17 | uGu cuu GGu uuc AAu uA5 5 glycol | A12 | UUu AAU UGA AAC cAA GA6 5 glycol |
| 149859 | mFVII 3'-caps | Mouse | S17 | uGu cuu GGu uuc AAu uA5 5 cyclohex | A12 | UUu AAU UGA AAC cAA GA6 5 cyclohex |
| 149861 | mFVII 3'-caps | Mouse | S17 | uGu cuu GGu uuc AAu uA5 5 phenyl | A12 | UUu AAU UGA AAC cAA GA6 5 phenyl |
| 149863 | mFVII 3'-caps | Mouse | S17 | uGu cuu GGu uuc AAu uA5 5 biphenyl | A12 | UUu AAU UGA AAC cAA GA6 5 biphenyl |
| 149865 | mFVII 3'-caps | Mouse | S17 | uGu cuu GGu uuc AAu uA5 5 lithochol | A12 | UUu AAU UGA AAC cAA GA6 5 lithochol |
| 149867 | mFVII 3'-caps | Mouse | S17 | uGu cuu GGu uuc AAu uA5 5 amino C7 | A12 | UUu AAU UGA AAC cAA GA6 5 amino C7 |
| 149869 | mFVII 3'-caps | Mouse | S17 | uGu cuu GGu uuc AAu uA5 5 amino C3 | A12 | UUu AAU UGA AAC cAA GA6 5 amino C3 |
| 8548 | Luc stability ctrl. | Mouse | S0 | TCGAAGTACTCAGCGTAAGTT | A0 | CTTACGCTGAGTACTTCGATT |
| 144049 | mFVII w/o cap | Mouse | S1 | uGu cuu GGu uuc AAu uAA AdTsdT | A1 | UUu AAU UGA AAC cAA GAc AdTsdT |
| 144033 | mFVII 3'-caps | Human | S17 | uGu cuu GGu uuc AAu uA5 5 C3 | A12 | UUu AAU UGA AAC cAA GA6 5 C3 |
| 149853 | mFVII 3'-caps | Human | S17 | uGu cuu GGu uuc AAu uA5 5 C6 | A12 | UUu AAU UGA AAC cAA GA6 5 C6 |
| 149855 | mFVII 3'-caps | Human | S17 | uGu cuu GGu uuc AAu uA5 5 C12 | A12 | UUu AAU UGA AAC cAA GA6 5 C12 |
| 149857 | mFVII 3'-caps | Human | S17 | uGu cuu GGu uuc AAu uA5 5 glycol | A12 | UUu AAU UGA AAC cAA GA6 5 glycol |
| 149859 | mFVII 3'-caps | Human | S17 | uGu cuu GGu uuc AAu uA5 5 cyclohex | A12 | UUu AAU UGA AAC cAA GA6 5 cyclohex |
| 149861 | mFVII 3'-caps | Human | S17 | uGu cuu GGu uuc AAu uA5 5 phenyl | A12 | UUu AAU UGA AAC cAA GA6 5 phenyl |
| 149863 | mFVII 3'-caps | Human | S17 | uGu cuu GGu uuc AAu uA5 5 biphenyl | A12 | UUu AAU UGA AAC cAA GA6 5 biphenyl |
| 149865 | mFVII 3'-caps | Human | S17 | uGu cuu GGu uuc AAu uA5 5 lithochol | A12 | UUu AAU UGA AAC cAA GA6 5 lithochol |

TABLE 5-continued

| siRNA ID | Project | Serum | Format sense | siRNA passenger sequence | Format anti | siRNA guide sequence |
|---|---|---|---|---|---|---|
| 149867 | mFVII 3'-caps | Human | S17 | uGu cuu GGu uuc AAu uA5 5 amino C7 | A12 | UUu AAU UGA AAC cAA GA6 5 amino C7 |
| 149869 | mFVII 3'-caps | Human | S17 | uGu cuu GGu uuc AAu uA5 5 amino C3 | A12 | UUu AAU UGA AAC cAA GA6 5 amino C3 |
| 144049 | mFVII w/o cap anti | Human | NA | NA | A12 | UUu AAU UGA AAC cAA GAc AdTsdT |
| 144053 | mFVII w/o cap sense | Human | S17 | uGu cuu GGu uuc AAu uAA AdTsdT | NA | NA |

The siRNA passenger strand sequences are provided as SEQ ID NOs: 60-72 and 140-149, in order. The siRNA guide strand sequences are provided in SEQ ID NOs: 73-95, in order. The 3' end caps used in this example are diagrammed below, in the context of the RNAi agent strand:

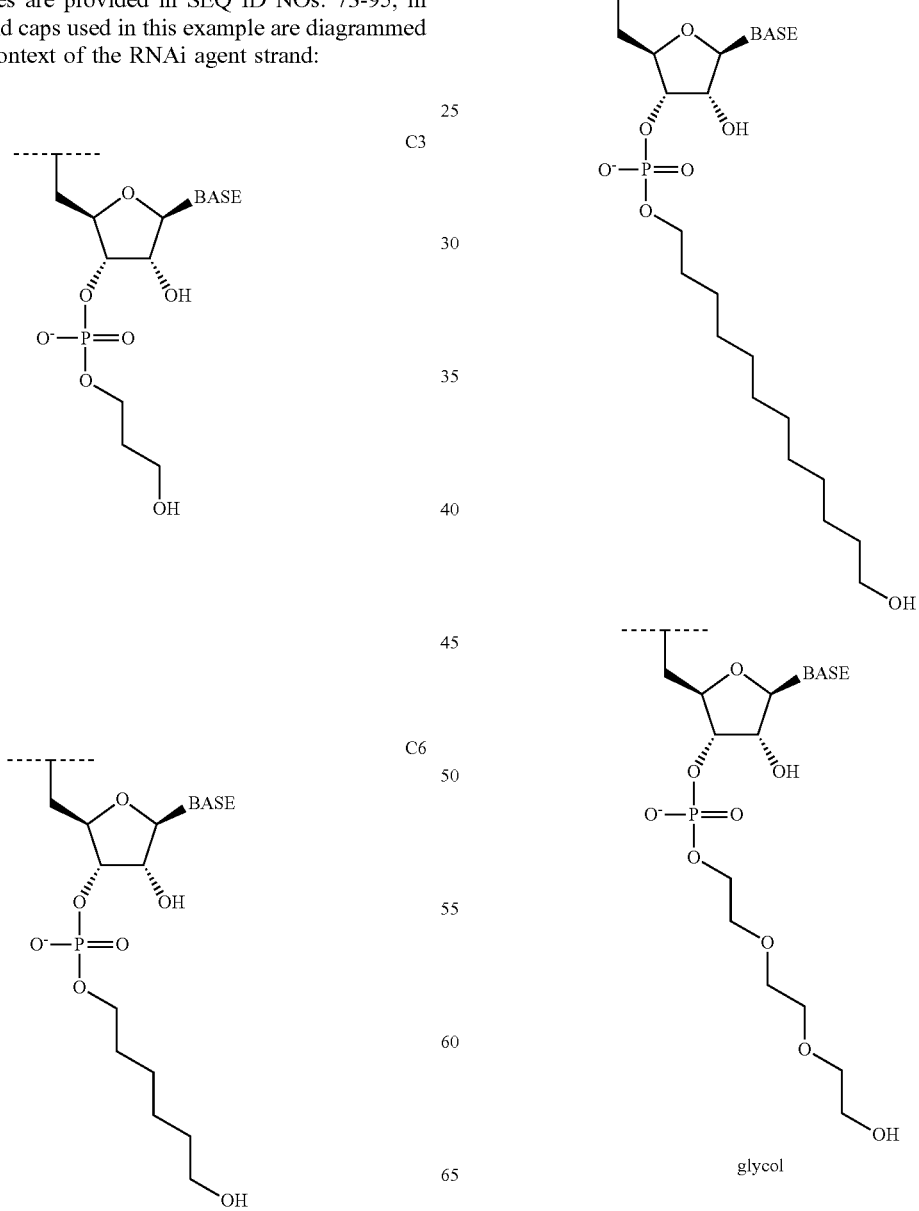

-continued

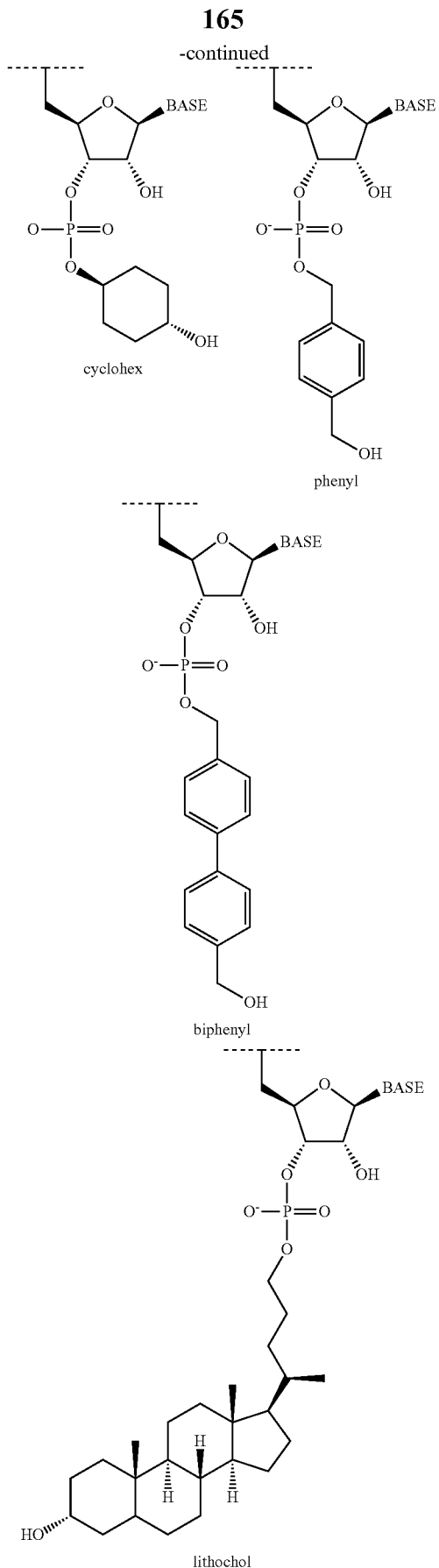

cyclohex phenyl biphenyl lithochol

-continued

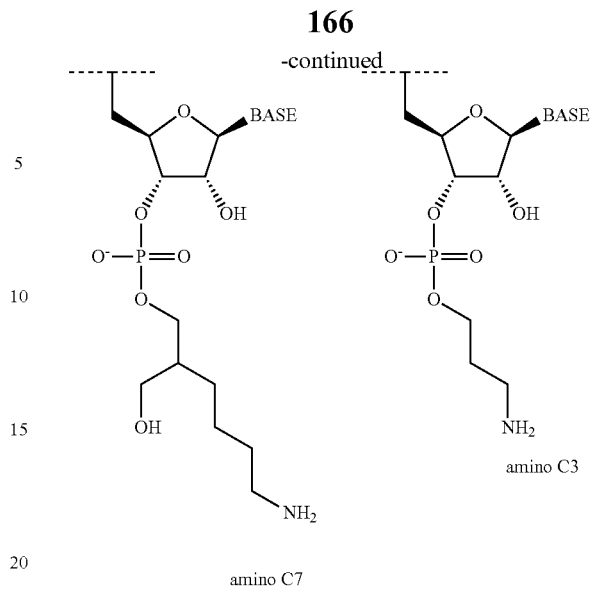

amino C7 amino C3

Materials and Methods:

RNA samples were incubated in 100% mouse serum and human serum at 37° C., withdrawn at 0, 5', 6 h and 24 h time points and snap-frozen. Oligos were separated by precast hydrogels (Elchrom Scientific) and visualized with SYBR gold (Biorad, Chemidoc XRS).

Figure 2:
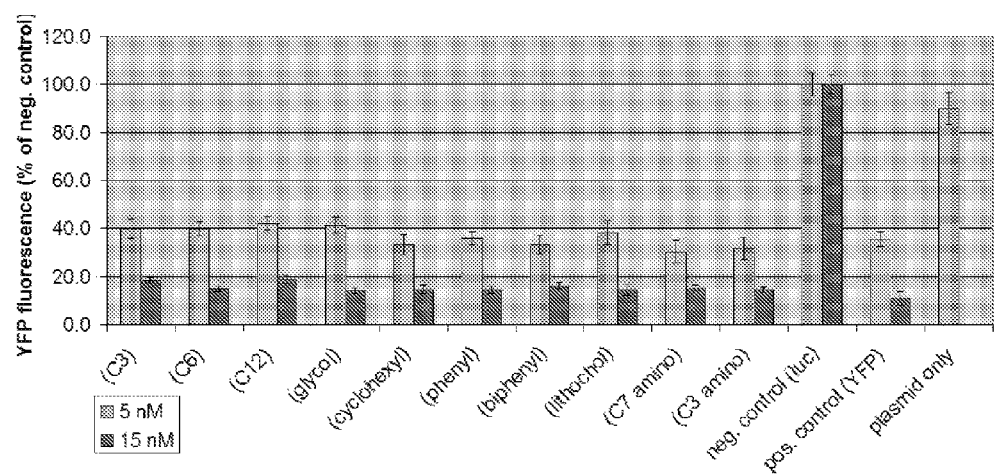
FIG. 2 shows the efficacy of a RNAi agent comprising a 3' end cap [C3, C6, C12, glycol (triethylene glycol), cyclohexyl, phenyl, biphenyl, lithochol, C7 amino or C3 amino] as described in Example 1, in allowing the RNAi agent to mediate RNA interference. The structure of these 3' end caps is described herein and/or in U.S. Pat. No. 8,084,600.

FIG. 2 shows the efficacy of various 3' end caps described in Example 1 in allowing the RNAi agent to mediate RNA interference. All of the 3' end caps—C3, C6, C12, Triethylene glycol, Cyclohexyl, Phenyl, Biphenyl, Adamantane and Lithocholic acid—allow the RNAi agent to perform RNA interference.

Figure 3:
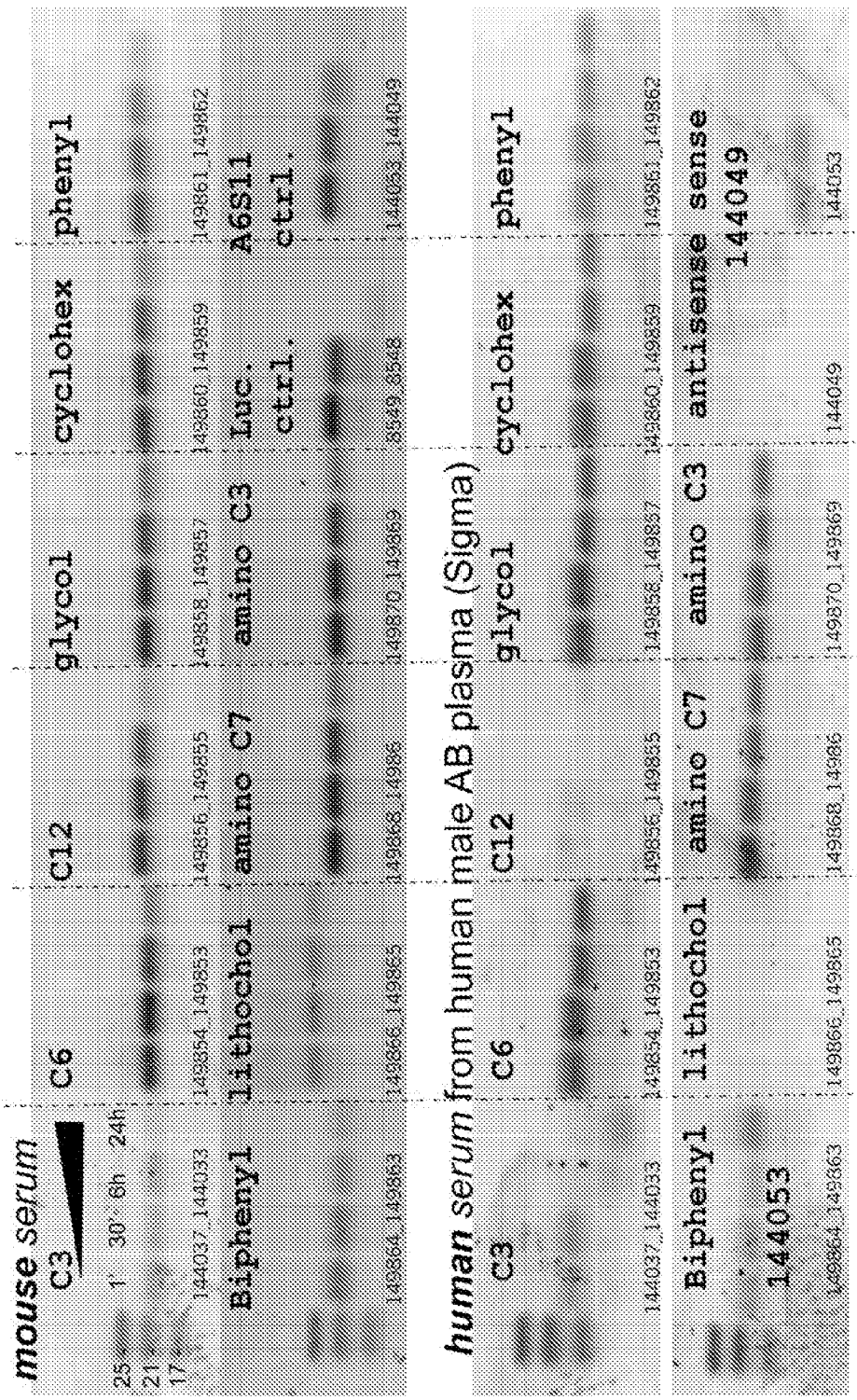
FIG. 3 shows the efficacy of the 3' end caps described in Example 1 in reducing and/or preventing nuclease degradation in serum.

FIG. 3 shows the efficacy of various 3' end caps described in Example 1 in reducing and/or preventing nuclease degradation in serum.

In mouse serum all 3'-capped A12S17 siRNAs display high resistance up to 24 h.

In human serum C3, C12 and lithochol appear to be less stable as compared to the other derivatives. However, in both experiments, C3, biphenyl and litochol display significantly weaker bands as compared to the other derivatives. However, there is a need to clarify whether this is due to lower synthesis/dsRNA quality (as indicated by gel-based QC) or due to a technical gel-based artifact (lithocholic acid may stick to human serum and thus gets protected from SYBR GOLD intercalation).

Single-strand antisense A12 is degraded rapidly in human serum whereas the parent sense S17 strand (with more chemical modifications) resists a bit longer but not as long as the dsRNA. Enzymatic stability correlates with thermal dsRNA stability.

Thus, this Example shows that siRNAs with these various 3' end caps were able to mediate RNA interference against FVII (Factor VII). The 3' end cap modifications designated as C3, C6, C12, glycol, cyclohex, phenyl, biphenyl, lithochol, C7 amino and C3 amino showed increased stability in mouse serum at 1', 30', 6 h and 24 hrs compared to luciferase and dTsdT controls. Those 3'-end modifications designated C3, C6, glycol, cyclohex, phenyl and biphenyl, C7 amino and C3 amino also showed increased stability in human serum compared to controls.

Example 2

The synthesis of various 3' end cap succinate esters and alcohols are presented below.

| | |
|---|---|
| Example 2.A | X027 succinate ester |
| Example 2.B | X038 succinate ester |
| Example 2.C | X052 succinate ester |
| Example 2.D | X058 succinate ester |
| Example 2.E | X067 succinate ester |
| Example 2.F | X069 succinate ester |
| Example 2.G | General procedure for the high density loading of controlled pore glass supports with PAZ ligand succinates |
| Example 2.H | Synthesis of X050, X059, X061, X062, X065, X068 alcohols and succinate esters |
| Example 2.I | X060 and X064 alcohols and succinate esters |
| Example 2.J. | X063 succinate ester |
| Example 2.K | X066 succinate ester |
| Example 2.L | X051 succinate ester |
| Example 2.M | Synthesis of X097 succinate ester |
| Example 2.N | Synthesis of X098 succinate ester |
| Example 2.O | Synthesis of siRNA conjugated with X109 |
| Example 2.P | Synthesis of siRNA conjugated with X110 |
| Example 2.Q | Synthesis of siRNA conjugated with X111 |
| Example 2.R | Synthesis of siRNA conjugated with X112 |
| Example 2.S | Synthesis of siRNA conjugated with X113 |
| Example 2.T | General procedure for the high density loading of controlled pore glass supports with PAZ ligand succinates |

Example 2

The synthesis of various 3' end cap succinate esters and alcohols are presented below.

| | |
|---|---|
| Example 2.A | X027 succinate ester |
| Example 2.B | X038 succinate ester |
| Example 2.C | X052 succinate ester |
| Example 2.D | X058 succinate ester |
| Example 2.E | X067 succinate ester |
| Example 2.F | X069 succinate ester |
| Example 2.G | General procedure for the high density loading of controlled pore glass supports with PAZ ligand succinates |
| Example 2.H | Synthesis of X050, X059, X061, X062, X065, X068 alcohols and succinate esters |
| Example 2.I | X060 and X064 alcohols and succinate esters |
| Example 2.J. | X063 succinate ester |
| Example 2.K | X066 succinate ester |
| Example 2.L | X051 succinate ester |
| Example 2.M | Synthesis of X097 succinate ester |
| Example 2.N | Synthesis of X098 succinate ester |
| Example 2.O | Synthesis of siRNA conjugated with X109 |
| Example 2.P | Synthesis of siRNA conjugated with X110 |
| Example 2.Q | Synthesis of siRNA conjugated with X111 |
| Example 2.R | Synthesis of siRNA conjugated with X112 |
| Example 2.S | Synthesis of siRNA conjugated with X113 |
| Example 2.T | General procedure for the high density loading of controlled pore glass supports with PAZ ligand succinates |

2.A. Synthesis of X027 Succinate Ester

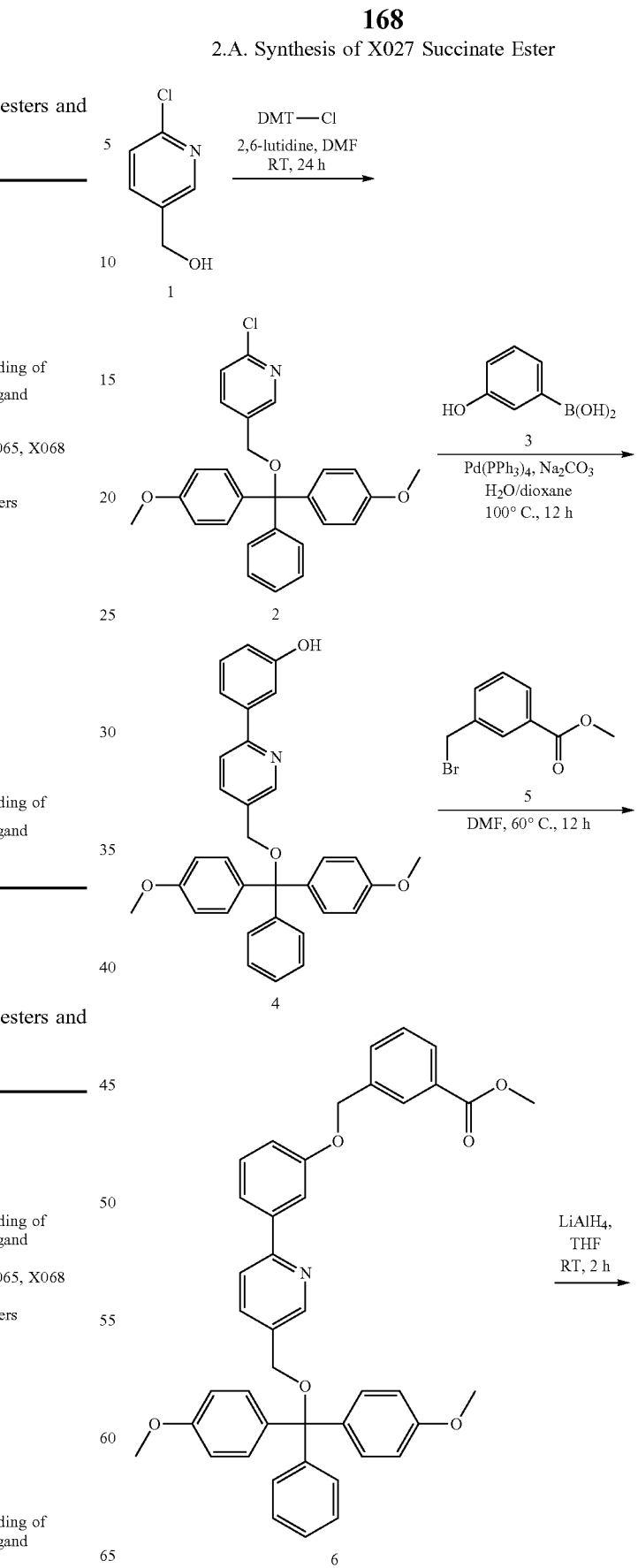

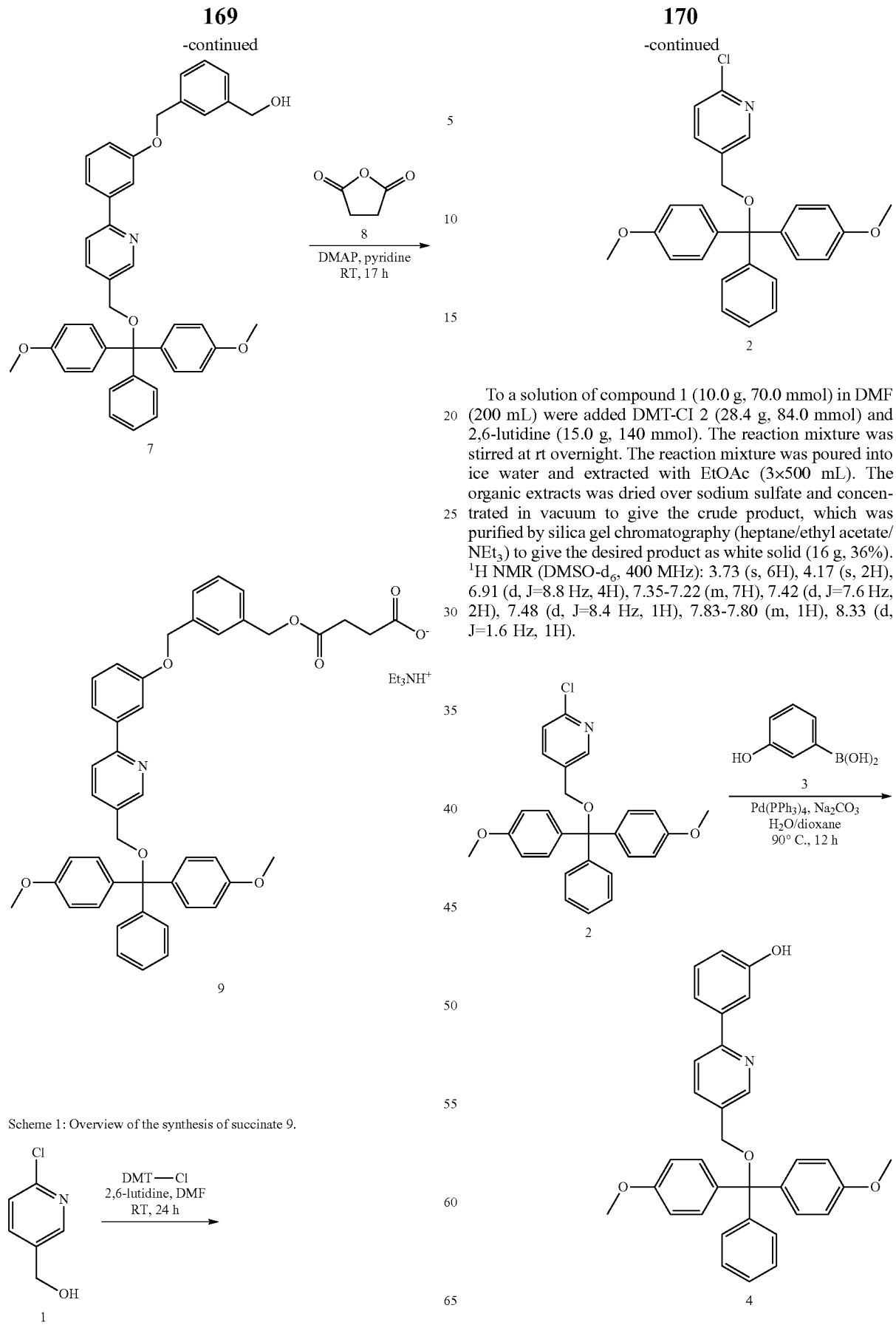

To a solution of compound 1 (10.0 g, 70.0 mmol) in DMF (200 mL) were added DMT-Cl 2 (28.4 g, 84.0 mmol) and 2,6-lutidine (15.0 g, 140 mmol). The reaction mixture was stirred at rt overnight. The reaction mixture was poured into ice water and extracted with EtOAc (3×500 mL). The organic extracts was dried over sodium sulfate and concentrated in vacuum to give the crude product, which was purified by silica gel chromatography (heptane/ethyl acetate/NEt$_3$) to give the desired product as white solid (16 g, 36%). $^1$H NMR (DMSO-d$_6$, 400 MHz): 3.73 (s, 6H), 4.17 (s, 2H), 6.91 (d, J=8.8 Hz, 4H), 7.35-7.22 (m, 7H), 7.42 (d, J=7.6 Hz, 2H), 7.48 (d, J=8.4 Hz, 1H), 7.83-7.80 (m, 1H), 8.33 (d, J=1.6 Hz, 1H).

Scheme 1: Overview of the synthesis of succinate 9.

To a solution of compound 2 (8.0 g, 18 mmol) in dioxane (160 mL)/H$_2$O (40 mL) were added 3-hydroxyphenylboronic acid 4 (3.5 g, 25 mmol), Pd(PPh$_3$)$_4$ (1.1 g, 1.0 mmol), and Na$_2$CO$_3$ (4.0 g, 38 mmol). The reaction mixture was bubbled with nitrogen gas and stirred at 90° C. overnight. Then reaction mixture was poured into water and extracted with EtOAc (3×800 mL). The organic extracts was dried over sodium sulfate, concentrated in vacuum, and purified by silica gel chromatography (heptane/ethyl acetate/NEt$_3$) to give 4 as an impure light yellow oil (6 g).

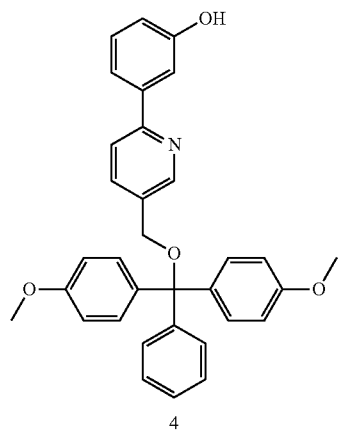

4

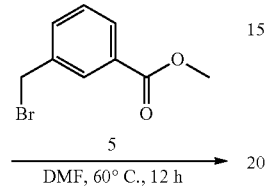

5
DMF, 60° C., 12 h

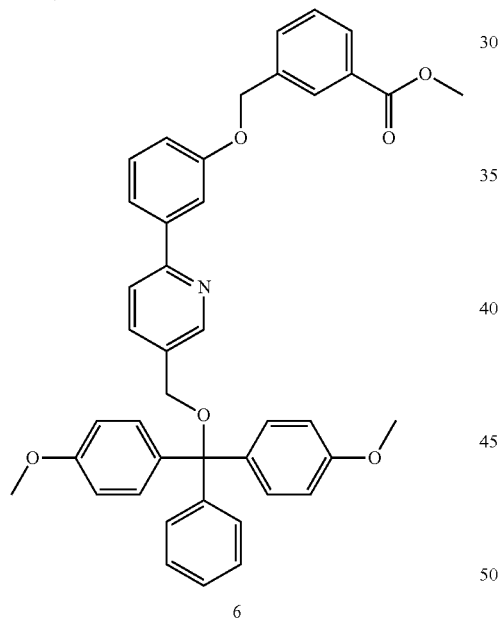

6

To a solution of compound 4 (10 g crude, 20 mmol) in acetone (600 mL) were added compound 5 (4.0 g, 17.6 mmol), K$_2$CO$_3$ (4.0 g, 28 mmol), and KI (316 mg, 1.9 mmol). The reaction mixture was stirred at reflux overnight. After the reaction mixture was cooled, the solvent was concentrated in vacuum. The reside was diluted with water and extracted with EtOAc (3×800 mL). The organic phase was dried over sodium sulfate and concentrated in vacuum to give the crude product, which was purified by silica gel chromatography (heptane/ethyl acetate/NEt$_3$) to give 6 as light yellow oil (9 g, 69%). $^1$H NMR (DMSO-d$_6$, 400 MHz): 3.74 (s, 6H), 3.84 (s, 3H), 4.19 (s, 2H), 6.93 (d, J=8.8 Hz, 4H), 7.11-7.08 (m, 1H), 7.27-7.23 (t, J=7.2 Hz, 1H), 7.46-7.31 (m, 9H), 7.59-7.55 (t, J=7.6 Hz, 1H), 7.68 (d, J=8.0 Hz, 1H), 7.79-7.75 (m, 2H), 7.84-7.80 (m, 1H), 7.97-7.92 (m, 2H), 8.10 (s, 1H), 8.61 (d, J=1.6 Hz, 1H).

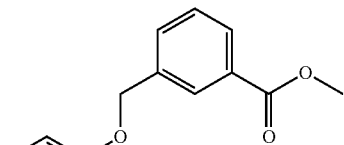
LiAlH$_4$,
THF
RT, 2 h

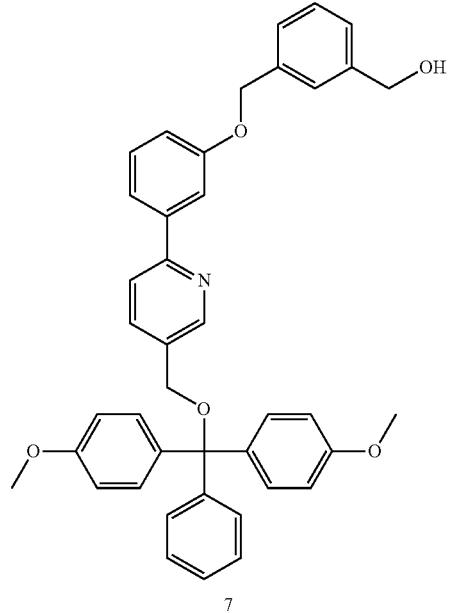

7

Lithium aluminum hydride (30.7 mL of 1.0 M suspension in THF, 30.7 mmol) was added to a solution of compound 6 (8.0 g, 12 mmol) in THF (150 mL) at 0° C. After 2 hours at 0° C., the reaction mixture was quenched with water (200 mL), and then the reaction mixture was extracted with dichloromethane (3×200 mL), The combined organic phase was dried over sodium sulfate, filtered, and concentrated in vacuum to give the desired product 7 as white solid (6.1 g, 80%). ¹H NMR (DMSO-d₆, 400 MHz): 3.74 (s, 6H), 4.19 (s, 2H), 5.54 (d, J=5.6 Hz, 2H), 5.18 (s, 2H), 5.27-5.24 (t, J=6.0 Hz, 1H), 6.93 (d, J=8.8 Hz, 4H), 7.10-7.07 (m, 1H), 7.47-7.23 (m, 14H), 7.67 (d, J=8.0 Hz, 1H), 7.75 (s, 1H), 7.83-7.81 (m, 1H), 7.95 (d, J=8.0 Hz, 1H), 8.61 (d, J=1.2 Hz, 1H).

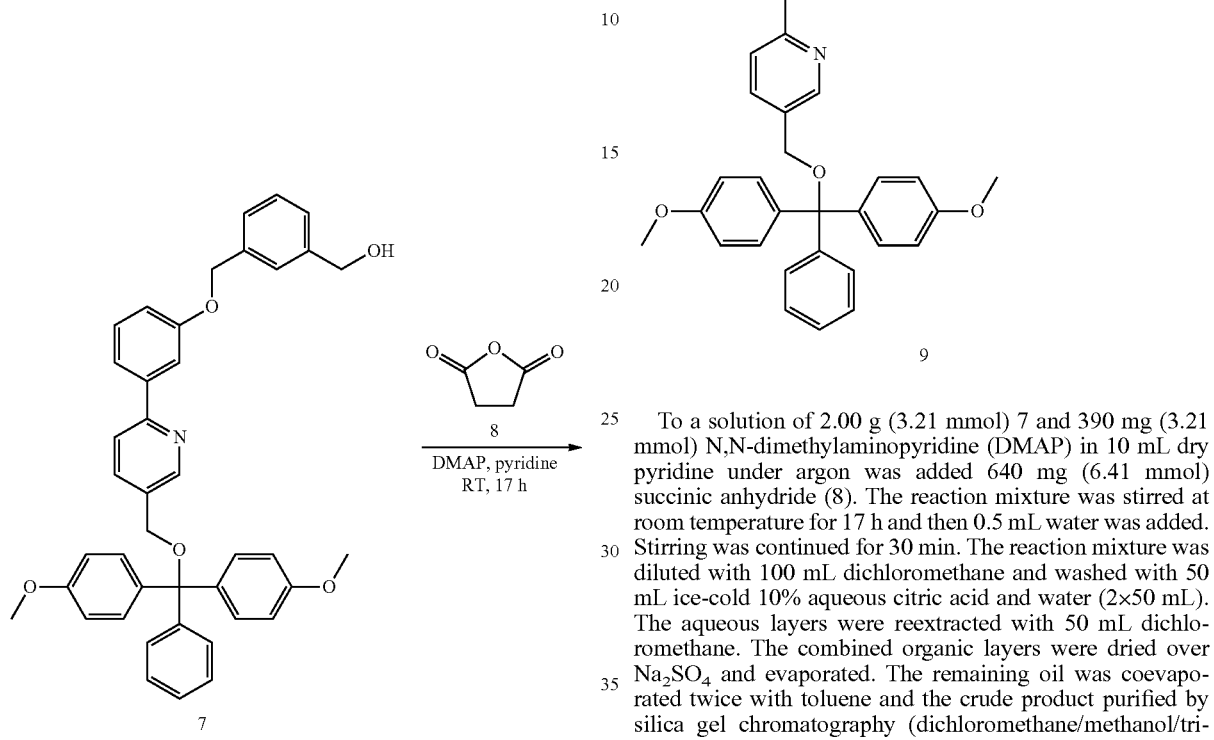

To a solution of 2.00 g (3.21 mmol) 7 and 390 mg (3.21 mmol) N,N-dimethylaminopyridine (DMAP) in 10 mL dry pyridine under argon was added 640 mg (6.41 mmol) succinic anhydride (8). The reaction mixture was stirred at room temperature for 17 h and then 0.5 mL water was added. Stirring was continued for 30 min. The reaction mixture was diluted with 100 mL dichloromethane and washed with 50 mL ice-cold 10% aqueous citric acid and water (2×50 mL). The aqueous layers were reextracted with 50 mL dichloromethane. The combined organic layers were dried over Na₂SO₄ and evaporated. The remaining oil was coevaporated twice with toluene and the crude product purified by silica gel chromatography (dichloromethane/methanol/triethylamine 97:2:1) to give 1.35 g (1.64 mmol, 51%) 9 as an off-white foam. ¹H NMR (400 MHz, CDCl₃): 1.12 (t, J=7.3 Hz, 9H), 2.51-2.55 (m, 2H), 2.59-2.62 (m, 2H), 2.89 (q, J=7.3 Hz, 6H), 3.72 (s, 6H), 4.17 (s, 2H), 5.08 (s, 4H), 5.68 (s br., 1H), 6.76-6.80 (m, 4H), 6.93 (dd, J=8.1, 2.5 Hz, 1H), 7.14-7.18 (m, 1H), 7.21-7.34 (m, 10H), 7.41-7.46 (m, 4H), 7.62 (dd, J=5.1, 2.5 Hz, 2H), 7.71 (dd, J=8.2, 1.9 Hz, 1H), 8.59 (d, J=1.5 Hz, 1H).

2. B Synthesis of X038 Succinate Ester

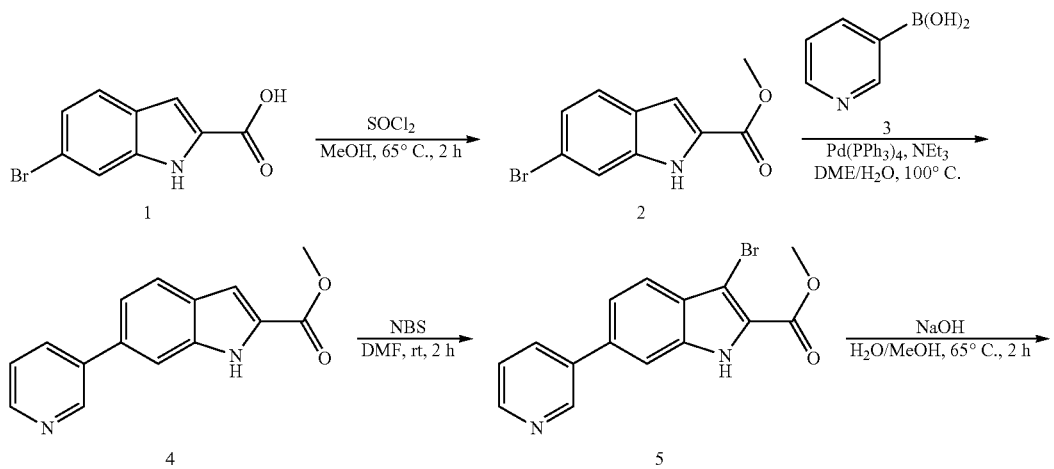

-continued
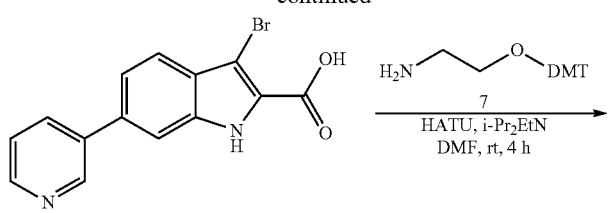
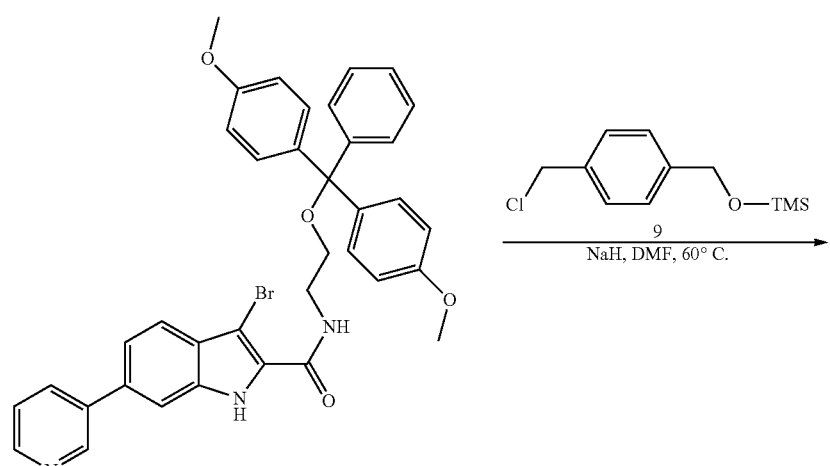
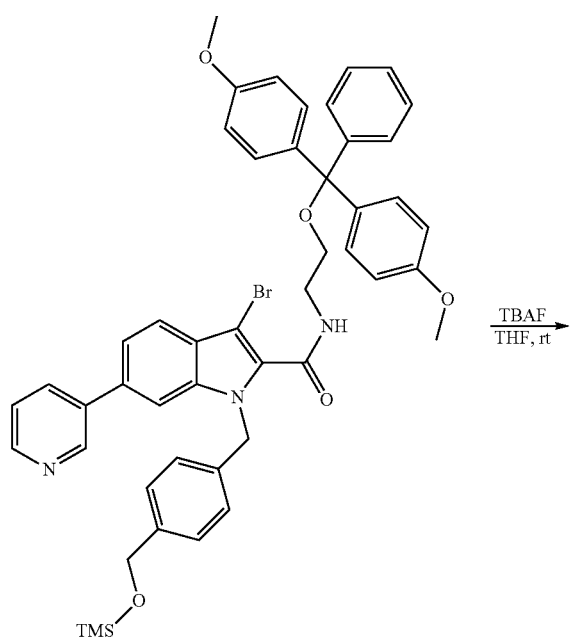

-continued
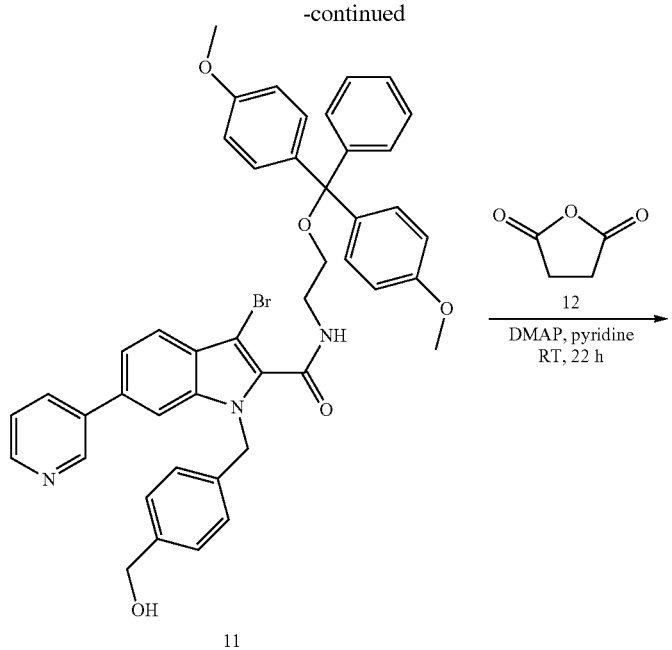
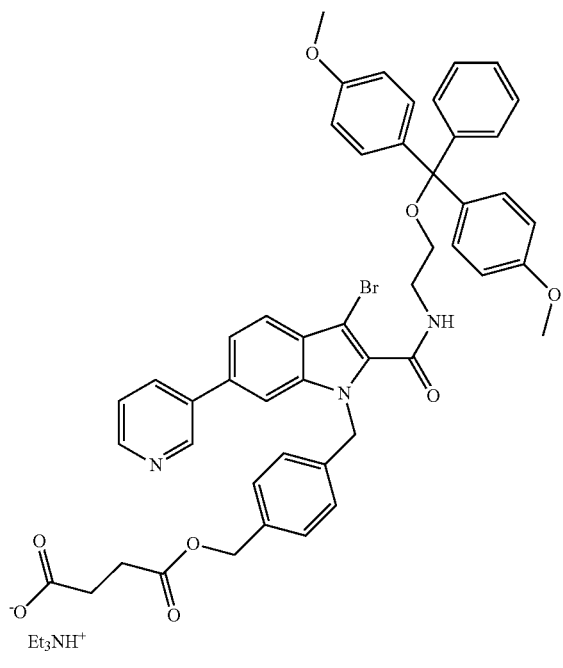
Scheme 1: Overview of the synthesis of succinate 13.
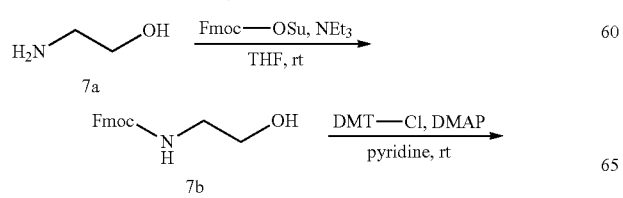
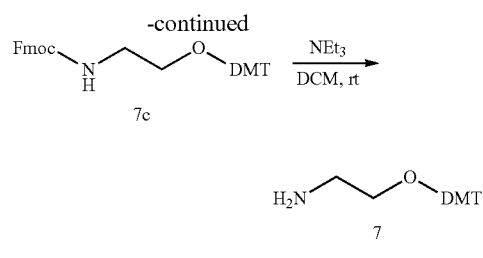

Scheme 2: Overview of the synthesis of 7.

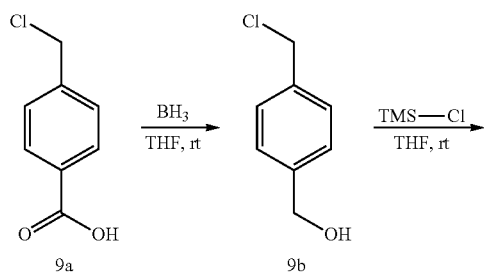

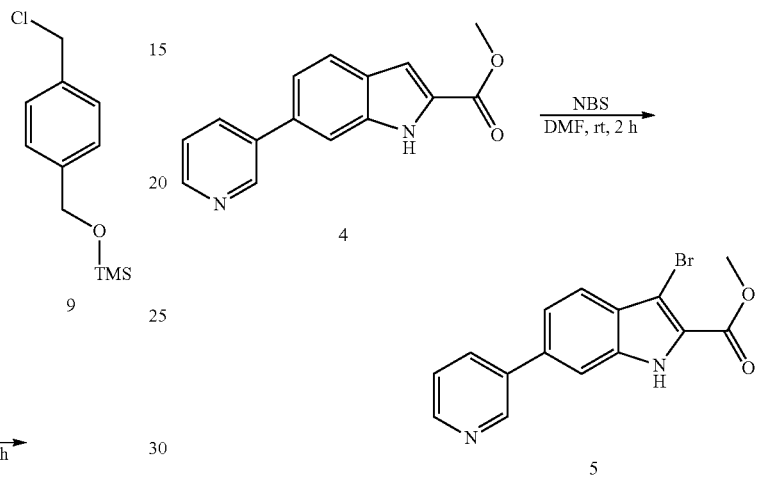

Scheme 3: Overview of the synthesis of 9.

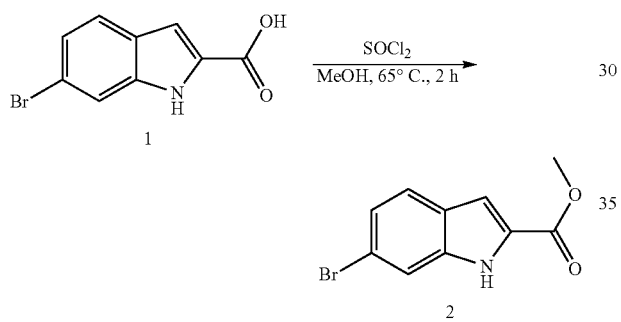

Into a 2000-mL 3-necked round-bottom flask was placed a solution of 6-bromo-1H-indole-2-carboxylic acid 1 (100 g, 417 mmol) in methanol (1000 mL). This was followed by the addition of thionyl chloride (100 g, 840 mmol) dropwise with stirring. The resulting solution was heated to reflux for 2 h. The reaction mixture was cooled to rt and a precipitate was formed. The solids were collected by filtration, washing with methanol, and dried in an oven under reduced pressure, giving 2 (95 g, 90%) as a white solid.

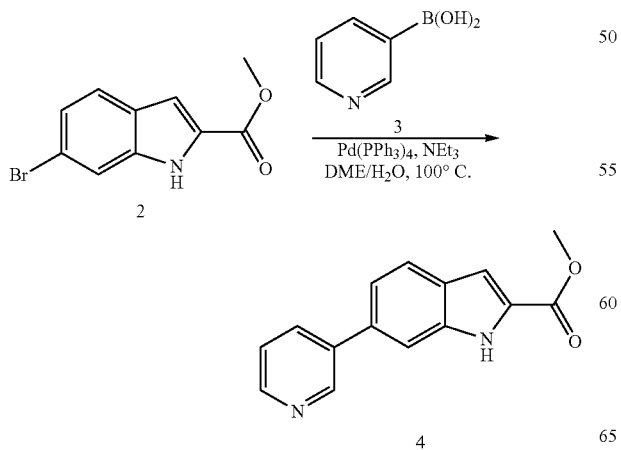

Into a 2000-mL 3-necked round-bottom flask, purged and maintained with an inert atmosphere of nitrogen, was placed a solution of 2 (90 g, 354 mmol) in ethylene glycol dimethyl ether (500 mL), water (500 mL), (pyridin-3-yl)boronic acid 3 (43.6 g, 355 mmol), NEt$_3$ (107 g, 1.06 mol), and Pd(PPh$_3$)$_4$ (9 g, 7.79 mmol). The resulting solution was heated to reflux overnight. The reaction mixture was cooled to room temperature and was quenched by the addition of 800 mL of water, forming a precipitate. The solids were collected by filtration, washing with water, and dried in an oven under reduced pressure, giving 4 (78 g, 87%) as a brown solid.

Into a 2000-mL round-bottom flask was placed a solution of 4 (75 g, 297 mmol) in DMF (500 mL). This was followed by the addition of NBS (53.5 g, 301 mmol), portionwise. The resulting solution was stirred for 2 h at rt. The reaction was then quenched by the addition of 1000 mL of water, forming a precipitate. The solids were collected by filtration, washing with water and dried in an oven under reduced pressure, giving 5 (70 g, 71%) as a brown solid. $^1$H NMR (400 MHz, CDCl$_3$): 3.94 (s, 3H), 7.51-7.58 (m, 2H), 7.67-7.76 (m, 2H), 8.11 (d, J=7.6 Hz, 1H), 8.60 (d, J=4.4 Hz, 1H), 8.91 (s, 1H), 12.48 (s, 1H).

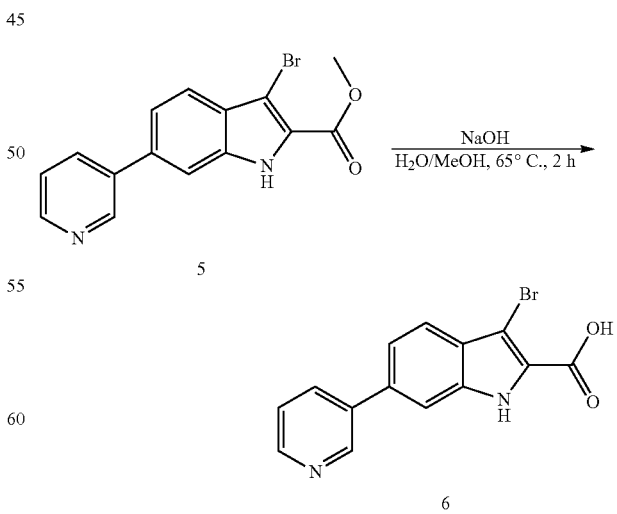

Into a 2000-mL round-bottom flask was placed a solution of 5 (68 g, 205) in methanol (500 mL), water (100 mL), and sodium hydroxide (25 g, 625 mmol). The resulting solution was heated to reflux for 2 hr. The resulting solution was cooled to room temperature and diluted with 500 mL of water. The pH value of the solution was adjusted to 5-6 with 2N HCl (aq), forming a precipitate. The solids were collected by filtration, washing with water, and dried in an oven under reduced pressure, giving 6 (50 g, 77%) as a light yellow solid. $^1$H NMR (400 MHz, CDCl$_3$): 7.50-7.53 (m, 2H), 7.65-7.71 (m, 2H), 8.09 (d, J=7.6 Hz, 1H), 8.59 (d, J=4 Hz, 1H), 8.91 (s, 1H), 12.30 (s, 1H), 13.55 (s, 1H).

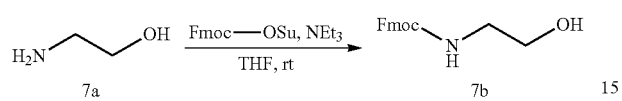

Into a 2000-mL round-bottom flask was placed a solution of 2-aminoethan-1-ol 7a (30 g, 491 mmol) in THF (600 mL), Fmoc-OSu (166 g, 491 mmol), and NEt$_3$ (199 g, 1.97 mol). The resulting solution was stirred overnight at rt. The mixture was concentrated under vacuum and purified by silica gel chromatography (ethyl acetate/petroleum ether), giving 7b (130 g, 93%) as a white solid.

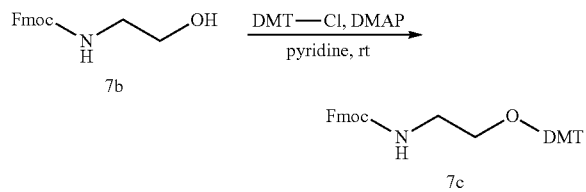

Into a 2000-mL round-bottom flask was placed a solution of 7b (130 g, 459 mmol) in pyridine (500 mL), 1-[chloro (4-methoxyphenyl)benzyl]-4-methoxybenzene (DMT-Cl) (233 g, 688 mmol), and 4-dimethylaminopyridine (2.8 g, 22.9 mmol). The resulting solution was stirred overnight at rt. The reaction was then quenched by the addition of water, and the resulting solution was extracted with ethyl acetate (3×500 mL). The combined organic layers were dried over sodium sulfate and concentrated in vacuum. The residue was purified by silica gel chromatography (ethyl acetate/petroleum ether), giving 7c (210 g, 78%) as a brown solid.

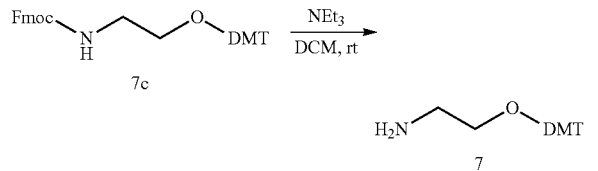

Into a 2000-mL round-bottom flask was placed a solution of 7c (210 g, 359 mmol) in dichloromethane (500 mL) and NEt$_3$ (500 mL). The resulting solution was stirred overnight at rt. The resulting mixture was concentrated under vacuum. The residue was purified by silica gel chromatography (ethyl acetate/petroleum ether), giving 7 (95 g, 73%) a brown solid. $^1$H NMR (400 MHz, CDCl$_3$) 2.42 (br. s, 2H), 3.70-3.82 (m, 2H), 3.80 (s, 6H), 6.79-6.87 (m, 4H), 7.19-7.25 (m, 2H), 7.29 (d, J=9.2 Hz, 2H), 7.33-7.40 (m, 3H), 7.49 (d, J=7.6 Hz, 2H).

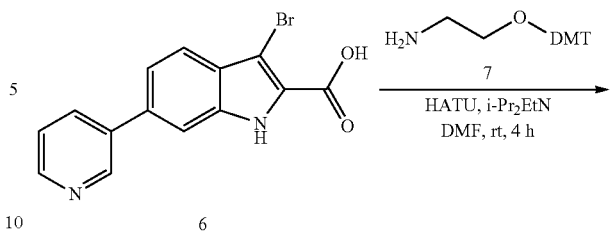

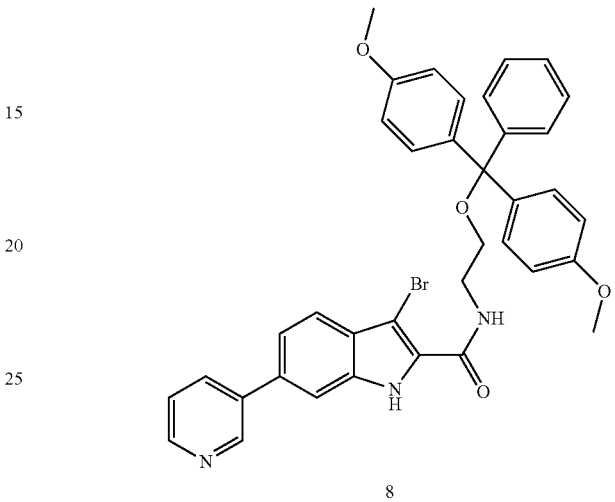

Into a 2000-mL round-bottom flask was placed a solution of 6 (40 g, 126 mmol) in DMF (800 mL), 7 (69 g, 190 mmol), HATU (96 g, 252 mmol), and i-Pr$_2$EtN (65 g, 503 mmol). The resulting solution was stirred for 4 h at rt and then quenched by the addition of 1000 mL of water. The resulting solution was extracted with ethyl acetate (3×800 mL). The combined organic layers were dried over sodium sulfate and concentrated under vacuum. The residue was purified by silica gel chromatography (ethyl acetate/petroleum ether), giving 8 (30 g, 36%) of as a light yellow solid.

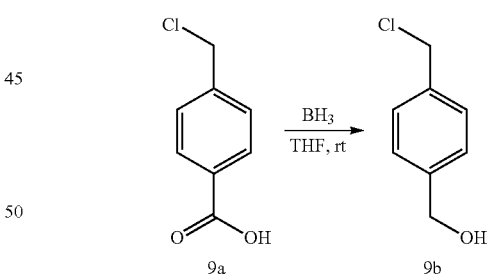

Into a 2000-mL round-bottom flask was placed a solution of 4-(chloromethyl)benzoic acid 9a (50 g, 293 mmol) in THF (200 mL). This was followed by the addition of 1 M BH$_3$/THF (586 mL, 586 mmol) dropwise with stirring at 0° C. over 1 hr. The resulting solution was stirred for 4 h at rt. The reaction was then quenched by the addition of 600 mL of 1 N HCl. The solution was extracted with 500 ml of ethyl acetate. The organic layer was washed with 300 ml of sodium carbonate (aq.), and 300 ml of brine. The organic layer was dried over sodium sulfate and concentrated under vacuum giving 9b (35 g, 76%) as a white solid. $^1$H NMR (400 MHz, CDCl$_3$) 4.50 (d, J=4.8 Hz, 2H), 4.75 (s, 2H), 5.21 (t, J=4.8 Hz, 1H), 7.32 (d, J=7.6 Hz, 2H), 7.39 (d, J=7.6 Hz, 2H).

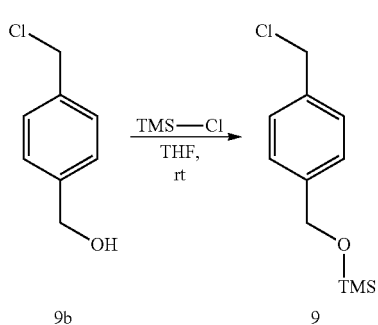

Into a 1000-mL 3-necked round-bottom flask was placed a solution 9b (35 g, 223 mmol) in THF (300 mL) and TEA (68 g, 672 mmol). This was followed by the addition of TMS-Cl (36.4 g, 335 mmol) dropwise with stirring. The resulting solution was stirred overnight at rt. The reaction was then quenched by the addition of 500 mL of water and extracted with 500 ml of ethyl acetate. The organic layer was washed with 500 ml of NaHCO$_3$ (aq.), 500 ml of brine, and dried over sodium sulfate. The residue was concentrated under vacuum giving 9 (35 g, 68%) as colorless oil.

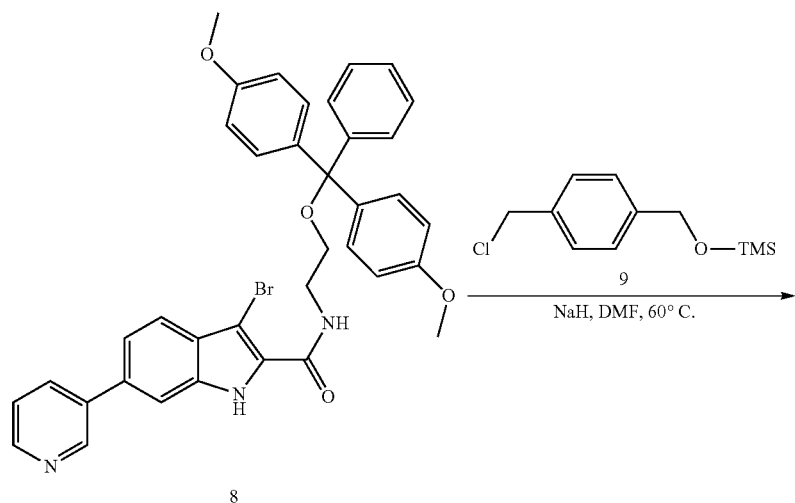

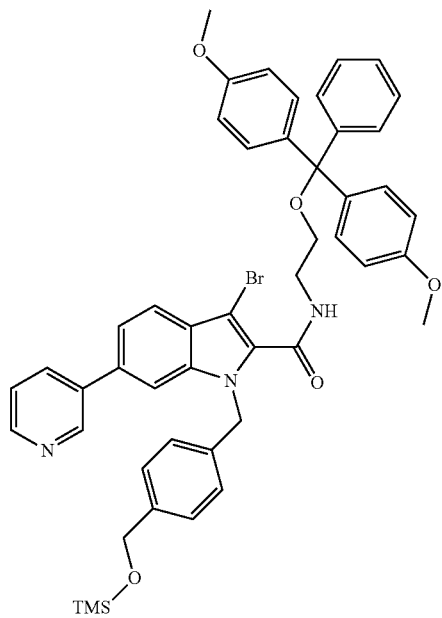

Into a 1000-mL 3-necked round-bottom flask was placed a solution of 8 (30 g, 45.3 mmol) in DMF (300 mL), and sodium hydride (1.1 g, 45.8 mmol). The mixture was stirred at rt for 0.5 h. A solution of 9 (15.5 g, 67.8 mmol) in THF (100 ml) was then added, and the resulting solution was stirred overnight at 60° C. The reaction mixture was cooled to rt and quenched by the addition of 500 mL of water. The resulting solution was extracted with dichloromethane (3×500 mL), and the combined organic layers were concentrated under vacuum. The residue was purified by silica gel chromatography (ethyl acetate/petroleum ether), giving 10 (15 g, 39%) as a white solid.

and extracted with 500 mL of ethyl acetate. The organic layer was washed with water (2×300 mL) and 300 mL of brine, and dried over sodium sulfate. The resulting mixture was concentrated under vacuum and the crude product was re-crystallized from hexane, giving 11 (5.5 g, 40%) as a yellow solid. $^1$H NMR (400 MHz, CDCl$_3$): 3.30 (m, 2H), 3.66-3.65 (m, 2H), 3.78 (s, 6H), 4.51 (s, 2H), 5.68 (s, 2H), 6.84 (d, J=8.8 Hz, 4H), 7.09 (d, J=8 Hz, 2H), 7.19-7.35 (m, 9H), 7.47-7.54 (m, 4H), 7.70 (d, J=9.2 Hz, 2H), 8.10 (d, J=8 Hz, 1H), 8.51 (d, J=4.8 Hz, 1H), 8.79 (s, 1H).

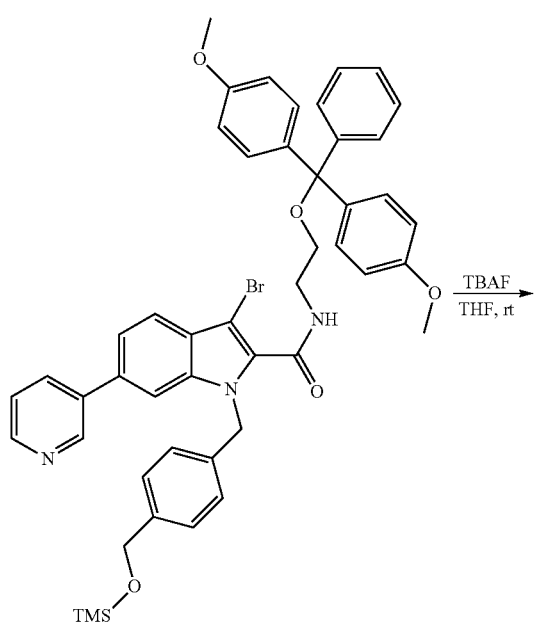
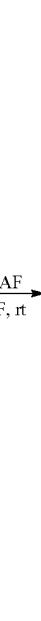
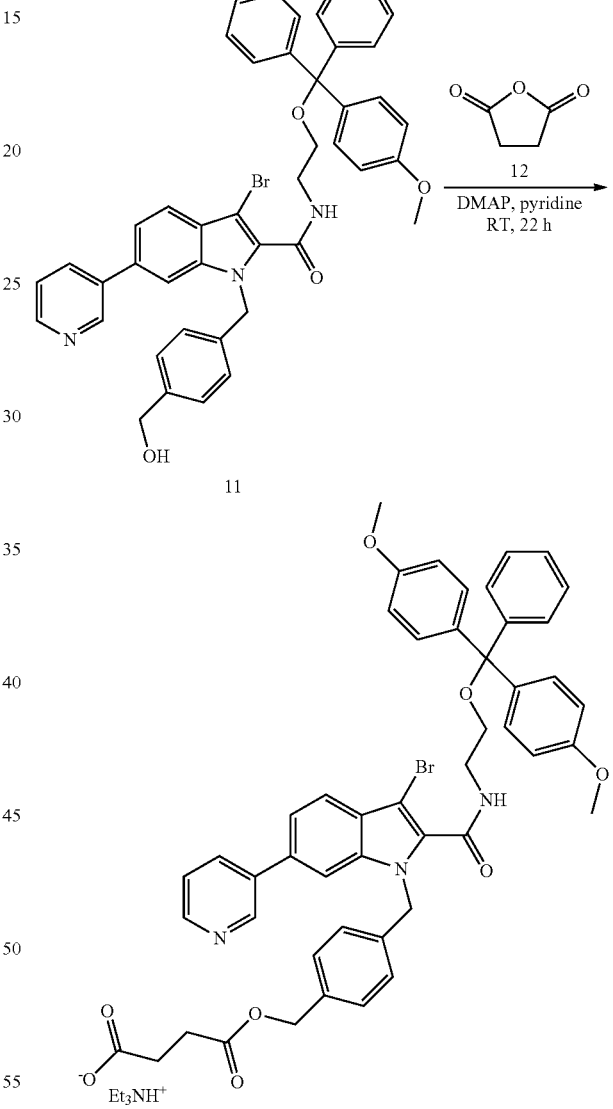

Into a 500-mL round-bottom flask was placed a solution of 10 (15 g, 17.6 mmol) in THF (150 mL) and TBAF (7 g, 26.8 mmol). The resulting solution was stirred for 30 min at rt. The resulting solution was diluted with 300 mL of water To a solution of 1.57 g (2.00 mmol) 11 and 244 mg (2.00 mmol) N,N-dimethylaminopyridine (DMAP) in 8 mL dry pyridine under argon was added 400 mg (4.00 mmol) succinic anhydride (12). The reaction mixture was stirred at room temperature for 22 h and then 0.5 mL water was added. Stirring was continued for 30 min. The reaction mixture was taken up in 100 mL dichloromethane and washed with 50 mL ice-cold 10% aqueous citric acid and water (2×50 mL). The aqueous layers were reextracted with 50 mL dichloromethane. The combined organic layers were dried over Na$_2$SO$_4$ and evaporated. The remaining oil was coevaporated twice with toluene and the crude product purified by silica gel chromatography (dichloromethane/methanol/triethylamine 94:5:1) to give 2.05 g (2.00 mmol, quant.) 13 as an off-white foam. $^1$H NMR (400 MHz, CDCl$_3$): 1.05 (t, J=7.2 Hz, 9H), 2.45 (t, J=6.5 Hz, 2H), 2.54 (t, J=6.5 Hz, 2H), 2.66 (q, J=7.2 Hz, 6H), 3.29 (t, J=4.9 Hz, 2H), 3.60 (q, J=5.1 Hz, 2H), 3.70 (s, 6H), 4.97 (s, 2H), 5.75 (s, 2H), 6.72-6.76 (m, 4H), 7.01 (d, J=8.1 Hz, 2H), 7.12-7.23 (m, 6H), 7.26-7.31 (m, 5H), 7.35-7.41 (m, 4H), 7.63 (d, J=8.3 Hz, 1H), 7.79 (dt, J=8.1, 1.9 Hz, 1H), 8.49 (dd, J=4.8, 1.5 Hz, 1H), 8.73 (d, J=2.0 Hz, 1H).

2.C. Synthesis of X052 Succinate Ester

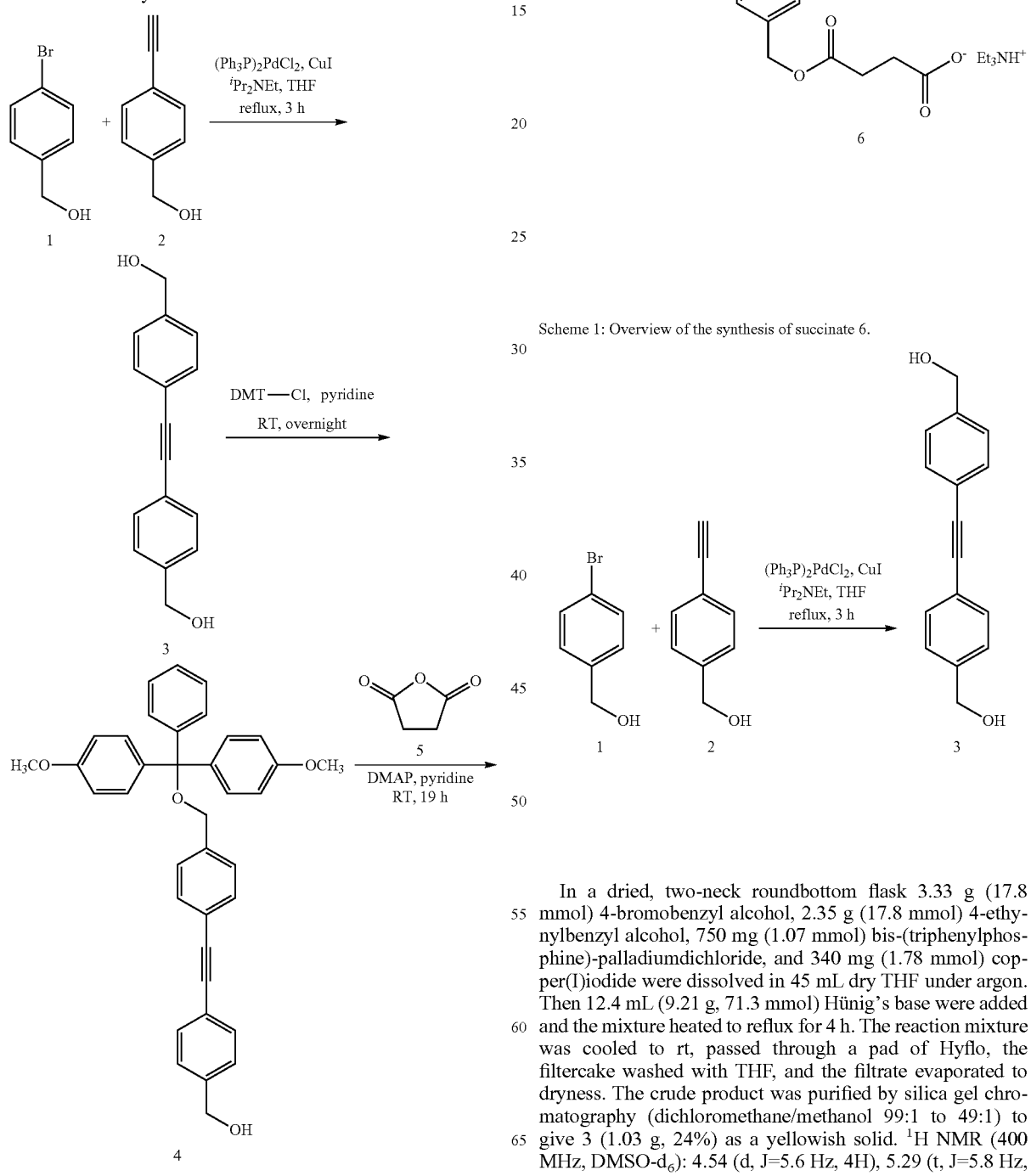

Scheme 1: Overview of the synthesis of succinate 6.

In a dried, two-neck roundbottom flask 3.33 g (17.8 mmol) 4-bromobenzyl alcohol, 2.35 g (17.8 mmol) 4-ethynylbenzyl alcohol, 750 mg (1.07 mmol) bis-(triphenylphosphine)-palladiumdichloride, and 340 mg (1.78 mmol) copper(I)iodide were dissolved in 45 mL dry THF under argon. Then 12.4 mL (9.21 g, 71.3 mmol) Hünig's base were added and the mixture heated to reflux for 4 h. The reaction mixture was cooled to rt, passed through a pad of Hyflo, the filtercake washed with THF, and the filtrate evaporated to dryness. The crude product was purified by silica gel chromatography (dichloromethane/methanol 99:1 to 49:1) to give 3 (1.03 g, 24%) as a yellowish solid. $^1$H NMR (400 MHz, DMSO-d$_6$): 4.54 (d, J=5.6 Hz, 4H), 5.29 (t, J=5.8 Hz, 2H), 7.37 (d, J=8.3 Hz, 4H), 7.51 (d, J=8.1 Hz, 4H).

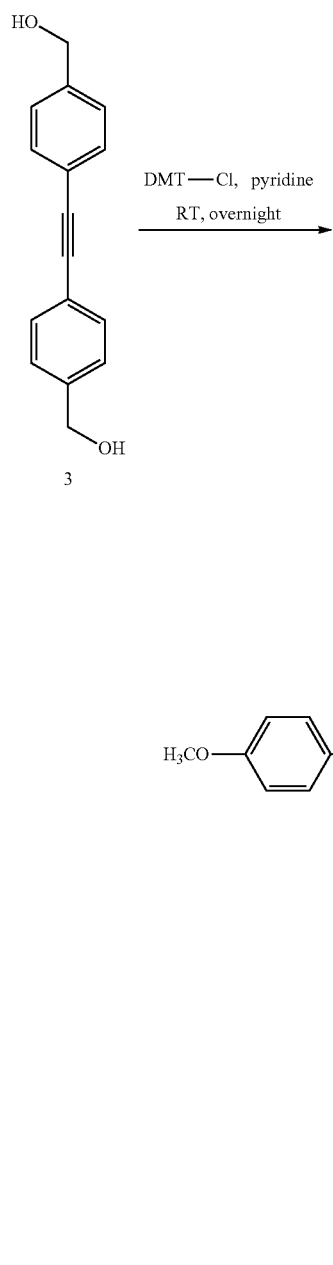

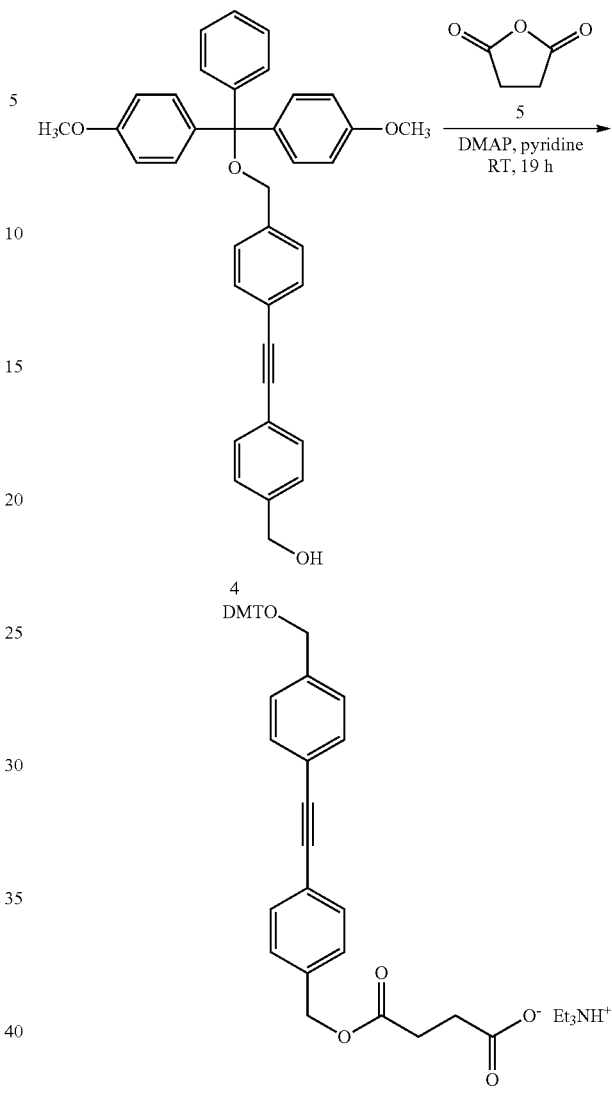

Diol 3 (960 mg, 4.03 mmol) was dissolved in 17 mL pyridine under argon and cooled to 0° C. Then 4,4'-dimethoxytriphenylchloromethane (DMT-Cl, 1.37 mg, 4.03 mmol) was added portionwise over 15 min. The solution was stirred overnight at ambient temperature. The reaction mixture was dissolved in 100 mL dichloromethane and extracted twice with 50 mL sat. aqueous NaHCO₃ each. The aqueous layers where reextracted with 100 mL dichloromethane. The combined organic layers were dried over Na₂SO₄ and evaporated to dryness. The crude product was coevaporated twice with toluene and purified by silica gel chromatography (heptane/ethyl acetate 3:1 to 2:1 with 0.1% Et₃N) to give 4 as a foam in 61% yield (1.32 g, 2.44 mmol). ¹H NMR (400 MHz, CDCl₃): 1.67 (t br., 1H), 3.72 (s, 6H), 4.11 (s, 2H), 4.64 (s br., 2H) 6.76-6.79 (m, 4H), 7.13-7.17 (m, 1H), 7.21-7.34 (m, 10H), 7.41-7.47 (m, 6H).

To a solution of 1.30 g (2.40 mmol) 4 and 290 mg (2.40 mmol) N,N-dimethylaminopyridine (DMAP) in 12 mL dry pyridine under argon was added 480 mg (4.81 mmol) succinic anhydride (5). The reaction mixture was stirred at room temperature for 19 h and then quenched by addition of 1.5 mL water. Stirring was continued for 60 min before the reaction mixture was diluted with 150 mL dichloromethane and washed with 75 mL ice-cold 10% aqueous citric acid and water (2×75 mL). The aqueous layers were reextracted with 150 mL dichloromethane. The combined organic layers were dried over Na₂SO₄ and evaporated. The remaining oil was coevaporated twice with toluene and the crude product purified by silica gel chromatography (dichloromethane/methanol/triethylamine 97:2:1) to give 1.36 g (1.83 mmol, 76%) 6 as an off-white, sticky foam. ¹H NMR (400 MHz, CDCl₃): 1.16 (t, J=7.3 Hz, 9H), 2.50 (t, J=6.5 Hz, 2H), 2.60 (t, J=6.7 Hz, 2H), 2.87 (q, J=7.3 Hz, 6H), 3.72 (s, 6H), 4.11 (s, 2H), 5.05 (s, 2H), 5.65 (s br., 1H), 6.75-6.79 (m, 4H), 7.13-7.16 (m, 1H), 7.21-7.34 (m, 10H), 7.41-7.44 (m, 6H).

2.D. Synthesis of X058 Succinate Ester
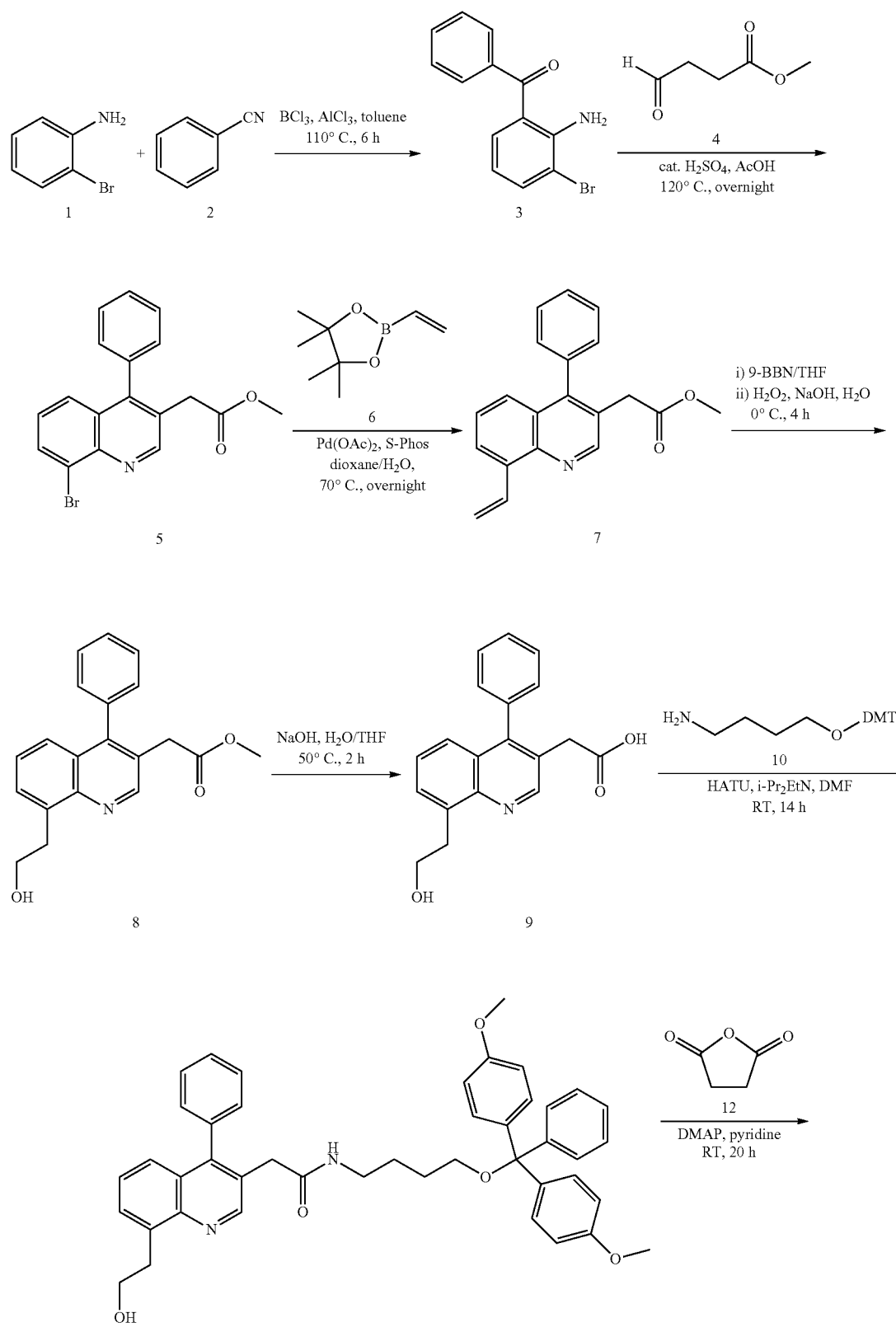

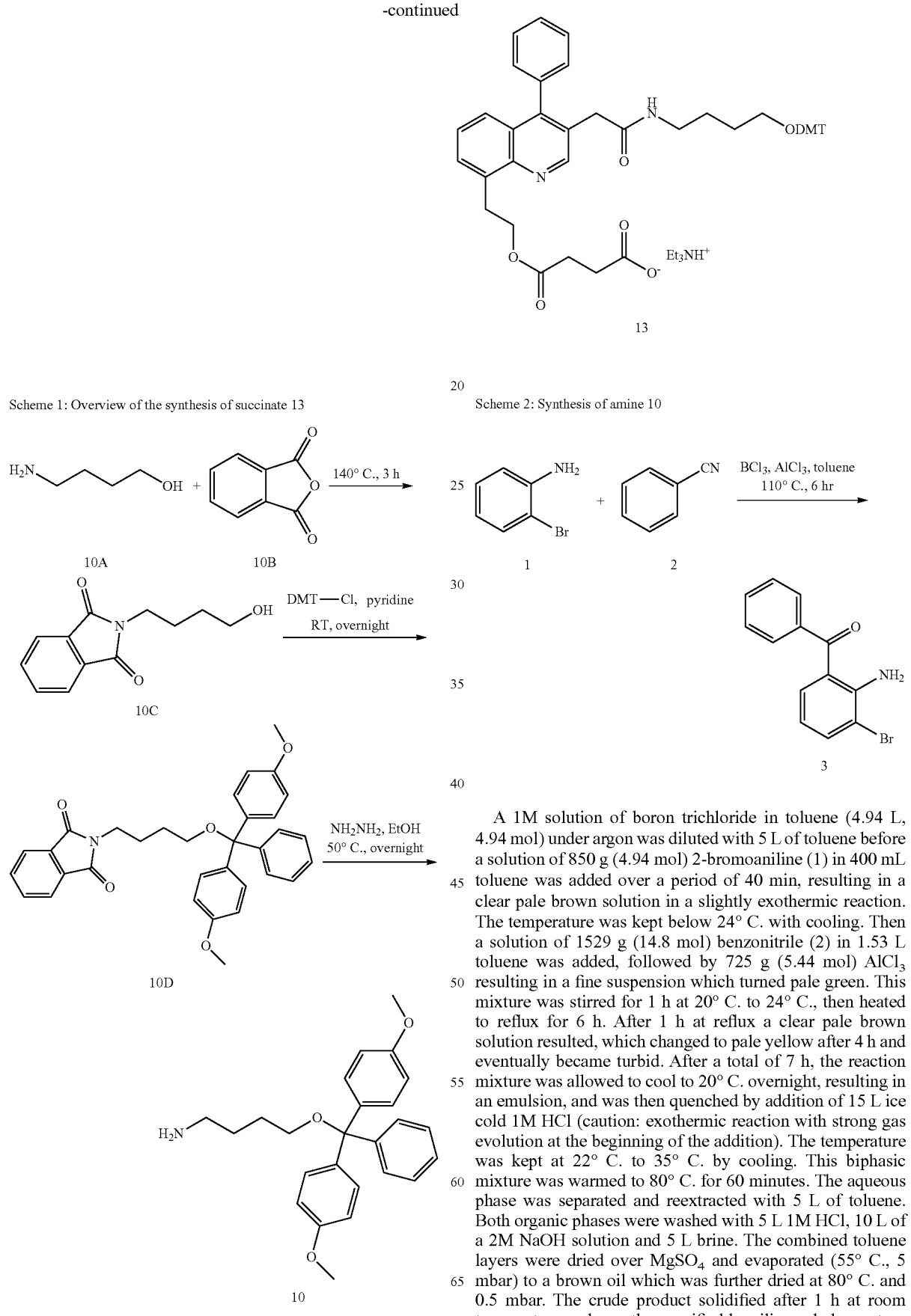

Scheme 1: Overview of the synthesis of succinate 13

Scheme 2: Synthesis of amine 10

A 1M solution of boron trichloride in toluene (4.94 L, 4.94 mol) under argon was diluted with 5 L of toluene before a solution of 850 g (4.94 mol) 2-bromoaniline (1) in 400 mL toluene was added over a period of 40 min, resulting in a clear pale brown solution in a slightly exothermic reaction. The temperature was kept below 24° C. with cooling. Then a solution of 1529 g (14.8 mol) benzonitrile (2) in 1.53 L toluene was added, followed by 725 g (5.44 mol) $AlCl_3$ resulting in a fine suspension which turned pale green. This mixture was stirred for 1 h at 20° C. to 24° C., then heated to reflux for 6 h. After 1 h at reflux a clear pale brown solution resulted, which changed to pale yellow after 4 h and eventually became turbid. After a total of 7 h, the reaction mixture was allowed to cool to 20° C. overnight, resulting in an emulsion, and was then quenched by addition of 15 L ice cold 1M HCl (caution: exothermic reaction with strong gas evolution at the beginning of the addition). The temperature was kept at 22° C. to 35° C. by cooling. This biphasic mixture was warmed to 80° C. for 60 minutes. The aqueous phase was separated and reextracted with 5 L of toluene. Both organic phases were washed with 5 L 1M HCl, 10 L of a 2M NaOH solution and 5 L brine. The combined toluene layers were dried over $MgSO_4$ and evaporated (55° C., 5 mbar) to a brown oil which was further dried at 80° C. and 0.5 mbar. The crude product solidified after 1 h at room temperature and was then purified by silica gel chromatography (heptane/ethyl acetate) yielding 812 g (2.94 mol, 58%) 3. $^1$H NMR (400 MHz, acetonitrile-d$_3$): 6.52-6.68 (m, 3H), 7.42 (dd, J=7.8, 1.3 Hz, 1H), 7.47-7.54 (m, 2H), 7.57-7.64 (m, 3H), 7.66 (dd, J=7.8, 1.3 Hz, 1H).

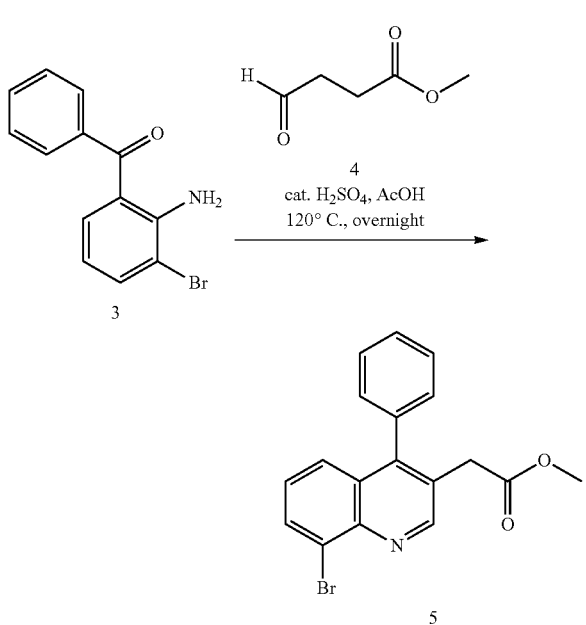

Under argon and with vigorous stirring 120 g (1033 mmol) methyl-4-oxobutanoate (4) was added at once to a solution of benzophenone 3 (233 g, 808 mmol) in 3.5 L glacial acid, resulting in a clear yellow solution. After addition of 2.5 mL (4.60 g, 46.9 mmol) concentrated sulfuric acid the color changed to pale red. The solution was heated to reflux overnight. The yellow solution was then cooled to room temperature and slowly poured in to an ice cold solution of 3 kg ammonium chloride in 10 L of water. The mixture was extracted twice with 5 L of dichloromethane each. The combined organic layers were extracted twice with 6 L saturated, aqueous NaHCO$_3$ solution (caution: gas evolution). The organic layer was dried over MgSO$_4$ and evaporated to dryness to give 338 g of crude product as pale yellow solid. This material was crystallized from 6 L heptane/ethyl acetate 4:1 yielding 136 g (382 mmol, 47%) 5 as colorless crystals. $^1$H NMR (400 MHz, acetonitrile-d$_3$): 3.58 (s, 3H), 3.65 (s, 2H), 7.25-7.31 (m, 2H), 7.32-7.38 (m, 1H), 7.40-7.45 (m, 1H), 7.53-7.61 (m, 3H), 8.07 (dd, J=7.6, 1.5 Hz, 1H), 8.97 (s, 1H).

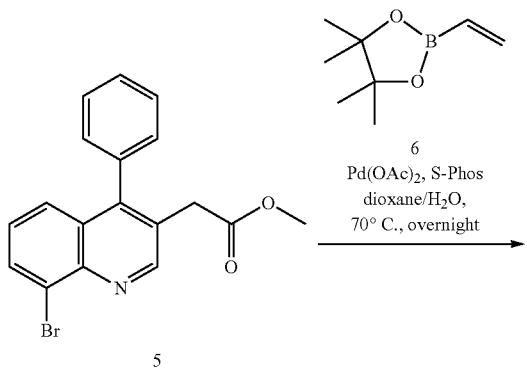

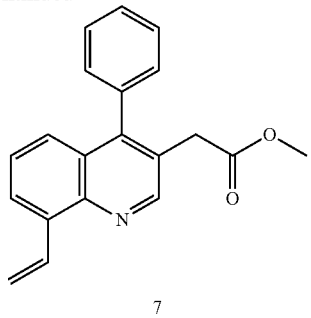

Phenylquinoline 5 (338 g, 949 mmol), vinyl boronate 6 (175 g, 1139 mmol), and potassium carbonate (266 g, 1926 mmol) were dissolved in 4.6 L 1,4-dioxane/water 1:1 under argon. The mixture was stirred for 5 min before adding 31.9 g (78 mmol) S-PHOS and 10.0 g (44.6 mmol) palladium (II)acetate. The mixture was warmed to 70° C. and stirred under argon for 5 h. The yellow mixture was then cooled to room temperature, diluted with 3 L tert.-butylmethylether and extracted twice with 2.5 L water, followed by 2 L brine. The aqueous phases were reextracted with 2 L tert.-butylmethylether. The combined organic layers were dried with MgSO$_4$ and evaporated to dryness resulting in 348 g of a yellow oil. The crude product was purified by silica gel chromatography (heptane/ethyl acetate 4:1) giving 196 g (645 mmol, 68%) 7. $^1$H NMR (400 MHz, acetonitrile-d$_3$): 3.58 (s, 3H), 3.63 (s, 2H), 5.50 (dd, J=11.1, 1.5 Hz, 1H), 6.04 (dd, J=17.9, 1.8 Hz, 1H), 7.24-7.30 (m, 2H), 7.35 (dd, J=8.3, 1.3 Hz, 1H), 7.43-7.50 (m, 1H), 7.51-7.59 (m, 3H), 7.97 (dd, J=7.1, 1.0 Hz, 1H), 8.06 (dd, J=17.9, 11.4 Hz, 1H), 8.91 (s, 1H)

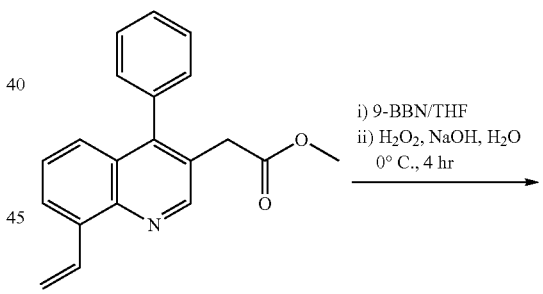

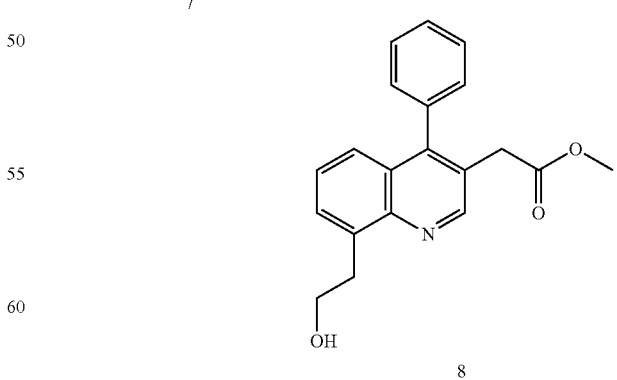

Vinyl-quinoline 7 (194 g, 640 mmol) was dissolved in 3 L THF under argon. The yellow solution was cooled to 15° C. and stirred for 10 min. Then 1.8 L of a 0.5M solution of 9-borabicylo[3.3.1]nonane in THF (900 mmol) was added dropwise during a period of 30 min at 15 to 18° C. Stirring was continued at room temperature overnight. After cooling to −50° C. (dry ice/acetone), 300 mL of a 30% hydrogen peroxide solution in water (2937 mmol) was added dropwise over 5 min (exothermic reaction), followed by the addition of 520 mL of a 3M aqueous NaOH solution (1560 mmol) which resulted in a yellow suspension. The reaction mixture was allowed to warm to 0 to 2° C. and then stirred for 3 h at this temperature. The yellow suspension was diluted with 3 L water and then extracted twice with 3 L ethyl acetate. Both organic layers were washed with 2 L water followed by 2 L brine. The combined organic phases were dried over MgSO$_4$ and evaporated to give a pale brown oil which was purified by silica gel chromatography (2-3% methanol in dichloromethane) yielding 163 g (507 mmol, 79%) 8. $^1$H NMR (400 MHz, DMSO-d$_6$): 3.42 (t, J=6.8 Hz, 2H), 3.53 (s, 3H), 3.65 (s, 2H), 3.76-3.84 (m, 2H), 4.54 (t, J=5.3 Hz, 1H), 7.19 (dd, J=8.6, 1.5 Hz, 1H), 7.21-7.25 (m, 2H), 7.40 (dd, J=8.1, 7.1 Hz, 1H), 7.49-7.59 (m, 3H), 7.62 (d, J=7.1 Hz, 1H), 8.91 (s, 1H).

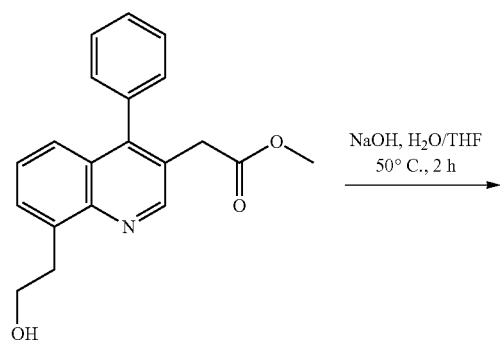

8

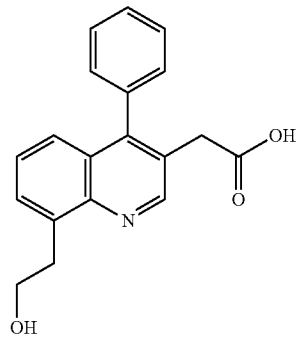

9

Methyl ester 8 (64.5 g, 201 mmol) was dissolved in 600 ml methanol. To this solution was added 450 mL of 0.5M aqueous NaOH (225 mmol). The turbid solution was stirred for 1 h at 50° C. Then the reaction mixture was evaporated to about 600 mL and the residue extracted twice with 800 mL tert.-butylmethylether each. The ether layers were washed with 300 mL water. The combined water phases were evaporated to dryness and the residue coevaporated twice with toluene to give 67 g of a beige solid. This material was dissolved in 1 L water and then 250 mL 1M aqueous citric acid was added carefully. The resulting suspension was stirred for 15 min and then extracted twice with 1 L ethyl acetate each. The organic layers were dried over MgSO4 and evaporated to dryness, yielding 54.1 g (176 mmol, 88%) acid 9 as beige solid. $^1$H NMR (400 MHz, D$_2$O): 3.80 (t, J=6.8 Hz, 2H), 3.82 (s, 2H), 4.32 (t, J=6.8 Hz, 2H), 7.58-7.64 (m, 2H), 7.67-7.73 (m, 1H), 7.73-7.79 (m, 1H), 7.87-7.95 (m, 3H), 7.97 (dd, J=7.1, 1.5 Hz, 1H), 9.14 (s, 1H).

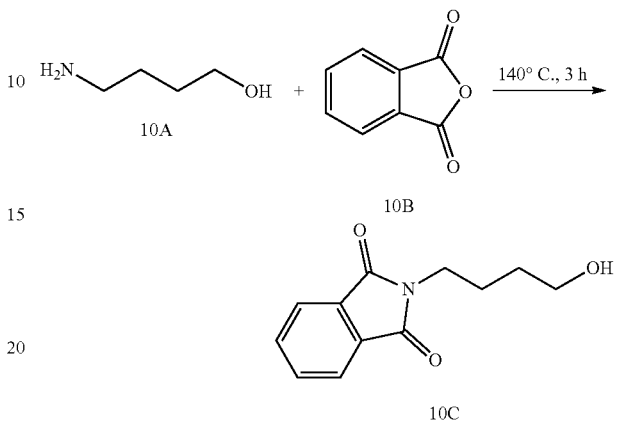

Phthalic anhydride (10B, 140 g, 945 mmol) was mixed with 4-amino-1-butanol (10A) and heated to 140° C. for 3 hours. Over the course of the reaction, the colorless suspension turned into clear, light yellow liquid. The mixture was allowed to cool to 80° C. and poured onto 3 kg of crushed ice. The ice mixture was extracted three times with 2 L of dichloromethane each. The combined organic phases were washed with 2 L saturated aqueous NaHCO$_3$, twice with 2 L water, and then with 2 L brine. The organic layer was dried over MgSO$_4$ and concentrated to give 195 g 10C (889 mmol, 95%) as beige solid This material was used in the next step without further purification. $^1$H NMR (400 MHz, acetonitrile-d$_3$): 1.48-1.58 (m, 2H), 1.67-1.78 (m, 2H), 2.37 (t, J=5.3 Hz, 1H), 3.50-3.57 (m, 2H), 3.66 (t, J=7.3 Hz, 2H), 7.75-7.85 (m, 4H).

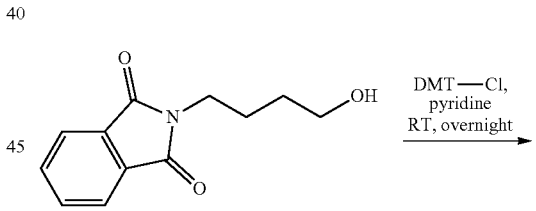

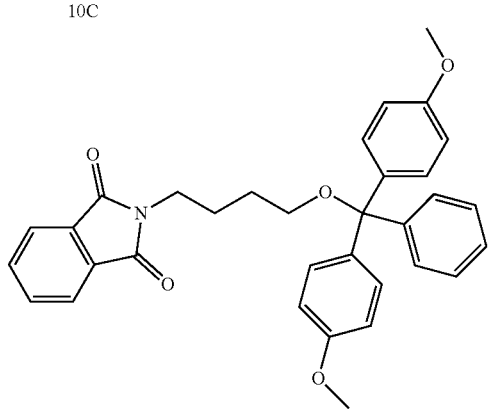

Phthalimide 10C (193 g, 880 mmol) was dissolved in 2.5 L pyridine under argon. Then 4,4'-dimethoxytriphenylchloromethane (DMT-Cl, 328 g, 968 mmol) was added in four portions over 10 min. The temperature of the reaction mixture rose from 23° C. to 26° C. and the yellow solution turned red, then back to yellow again. The solution was stirred overnight at ambient temperature. To quench the reaction 200 mL methanol was added 200 ml and the reaction mixture subsequently evaporated. The residue was dissolved in 5 L ethyl acetate and extracted twice with 5 L 5% aqueous citric acid, once with 5% aqueous NaHCO$_3$ and finally with 5 L brine. The aqueous layers where reextracted with 2 L ethyl acetate. The combined organic layers were dried over MgSO$_4$ and evaporated to dryness. The crude product, 495 g of a brown oil, was purified by silica gel chromatography (heptane/ethyl acetate 4:1 to 3:1). DMT-protected linker 10D was obtained in 81% yield (381 g, 730 mmol). $^1$H NMR (400 MHz, DMSO-d$_6$): 1.48-1.60 (m, 2H), 1.62-1.74 (m, 2H), 3.01 (t, J=6.1 Hz, 2H), 3.56 (t, J=7.1 Hz, 2H), 3.73 (s, 6H), 6.82-6.88 (m, 4H), 7.16-7.25 (m, 5H), 7.25-7.31 (m, 2H), 7.32-7.37 (m, 2H), 7.78-7.87 (m, 4H).

Phthalimide 10D (302 g, 579 mmol) was dissolved in 7 L ethanol at 50° C. and 320 mL (327 g, 3.57 mol) hydrazine hydrate was added. The reaction mixture was heated for 5 h to 50° C. The colorless suspension was cooled to room temperature and diluted with 15 L of water. The resulting emulsion was extracted twice with 6 L tert.-butylmethylether each. The organic phases were washed twice with 4 L 5% aqueous NaHCO$_3$, then with 4 L brine. The combined ether layers were dried over MgSO$_4$ and evaporated to give 226 g (578 mmol) 10 as a pale yellow oil which was used in the next step without additional purification. $^1$H NMR (400 MHz, acetonitrile-d$_3$): 1.42-1.54 (m, 2H), 1.56-1.66 (m, 2H), 2.61 (t, J=7.1 Hz, 2H), 3.06 (t, J=6.6 Hz, 2H), 3.78 (s, 6H), 6.84-6.90 (m, 4H), 7.19-7.26 (m, 1H), 7.28-7.35 (m, 6H), 7.41-7.47 (m, 2H).

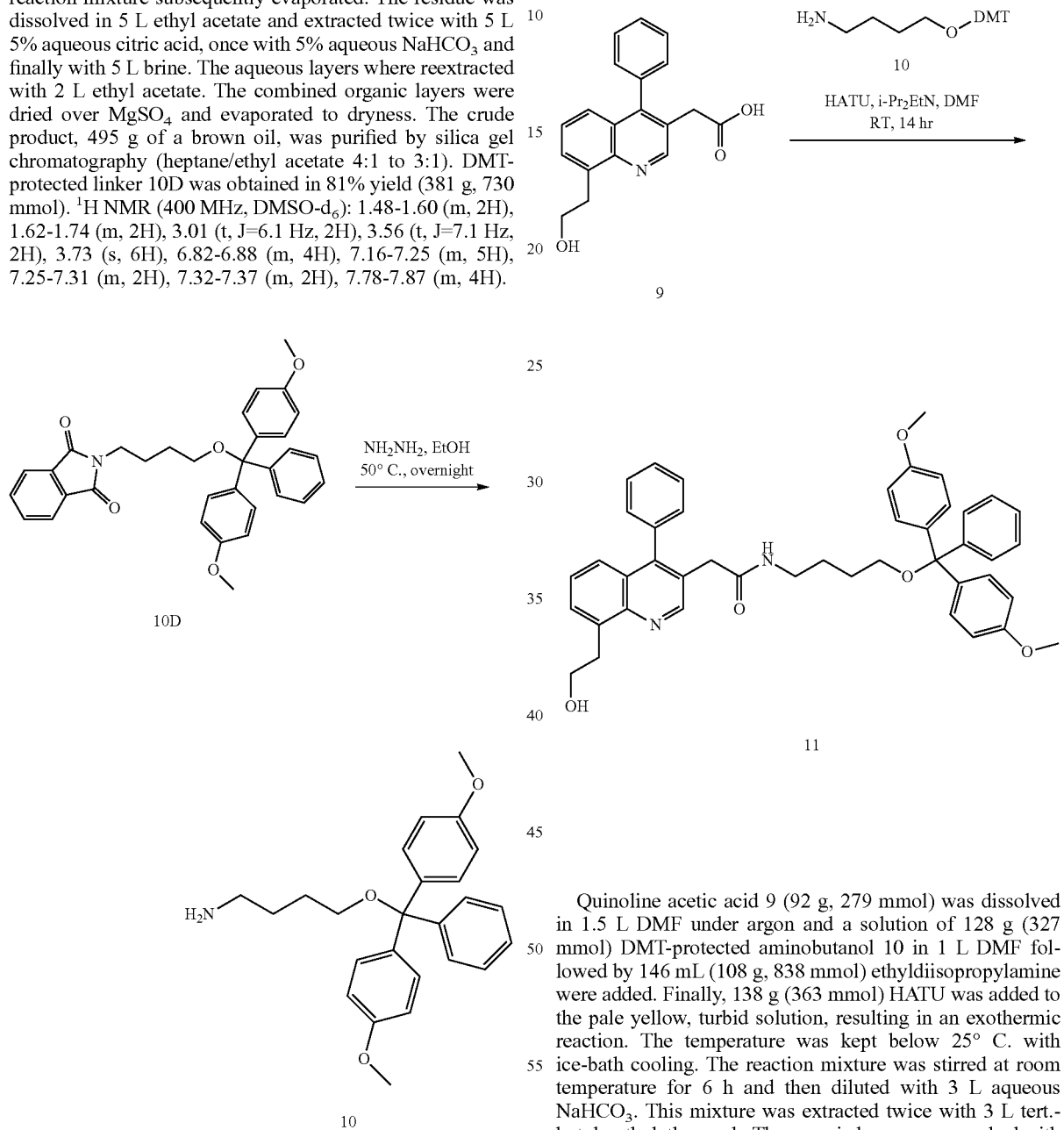

Quinoline acetic acid 9 (92 g, 279 mmol) was dissolved in 1.5 L DMF under argon and a solution of 128 g (327 mmol) DMT-protected aminobutanol 10 in 1 L DMF followed by 146 mL (108 g, 838 mmol) ethyldiisopropylamine were added. Finally, 138 g (363 mmol) HATU was added to the pale yellow, turbid solution, resulting in an exothermic reaction. The temperature was kept below 25° C. with ice-bath cooling. The reaction mixture was stirred at room temperature for 6 h and then diluted with 3 L aqueous NaHCO$_3$. This mixture was extracted twice with 3 L tert.-butylmethylether each. The organic layers were washed with brine, combined, dried, and evaporated. The crude product (180 g pale brown oil) was purified by silica gel chromatography (dichloromethane/methanol/triethylamine 98:2:0.25) to give 134 g (197 mmol, 70%) 11 as colorless foam. $^1$H NMR (400 MHz, DMSO-d$_6$): 1.35-1.57 (m, 4H), 2.97 (t, J=6.3 Hz, 4H), 3.34-3.48 (m, 4H), 3.73 (s, 6H), 3.76-3.83 (m, 2H), 4.54 (t, J=5.3 Hz, 1H), 6.84-6.90 (m, 4H), 7.15-7.32 (m, 10H), 7.34-7.41 (m, 3H), 7.42-7.53 (m, 3H), 7.58 (dd, J=6.8, 1.3 Hz, 1H), 7.62 (t, J=4.8 Hz, 1H), 8.83 (s, 1H).

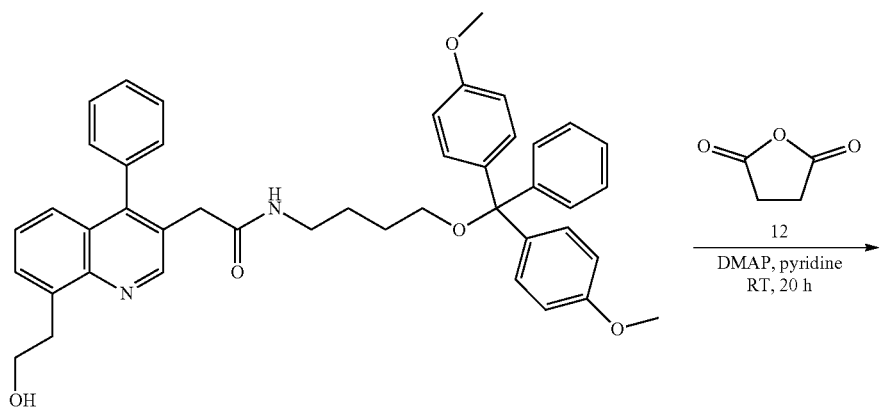

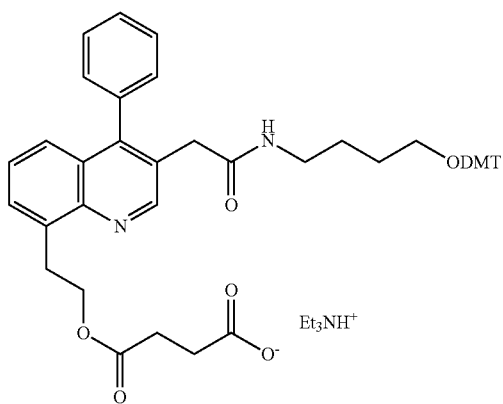

Alcohol 11 (43.8 g, 64.4 mmol) and N,N-dimethylaminopyridine (DMAP, 7.87 g, 64.4 mmol) were dissolved in 600 mL pyridine under argon. Then 12.9 g (128 mmol) succinic anhydride (12) was added and the reaction mixture stirred at room temperature for 20 h. The reaction was quenched by addition of 10 mL water and stirring continued for 30 min. The reaction mixture was diluted with 1200 mL dichloromethane and washed with 600 mL ice-cold 10% aqueous citric acid and twice with 600 mL water. The aqueous layers were reextracted with 600 mL dichloromethane. The combined organic layers were dried over $Na_2SO_4$ and evaporated. The crude product was coevaporated twice with 100 mL toluene and then purified by silica gel chromatography (dichloromethane/methanol/triethylamine 97:2:1 to 94:5:1) to give 57.5 g (quantitative) 13 as an off-white foam. $^1$H NMR (400 MHz, $CDCl_3$): 1.17 (t, J=7.3 Hz, 9H), 1.46-1.60 (m, 4H), 2.52 (t, J=7.2 Hz, 2H), 2.61 (t, J=7.0 Hz, 2H), 2.82 (q, J=7.3 Hz, 6H), 3.06 (t, J=5.8 Hz, 2H), 3.16 (q, J=6.3 Hz, 2H), 3.49 (s, 2H), 3.64 (t, J=6.8 Hz, 2H), 3.80 (s, 6H), 4.53 (t, J=7.5 Hz, 2H), 5.38 (t br., 1H), 6.08 (s br., 1H), 6.80-6.84 (m, 4H), 7.20 (t, J=7.3 Hz, 1H), 7.26-7.38 (m, 10H), 7.41-7.52 (m, 5H), 7.59 (d, J=6.3 Hz, 1H), 8.92 (s, 1H).

2.E. Synthesis of X067 Succinate Ester

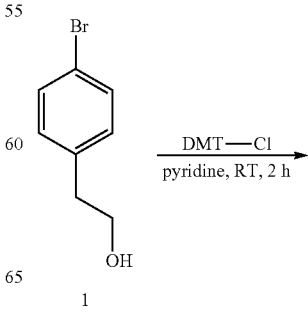

Scheme 1: Overview of the synthesis of 6

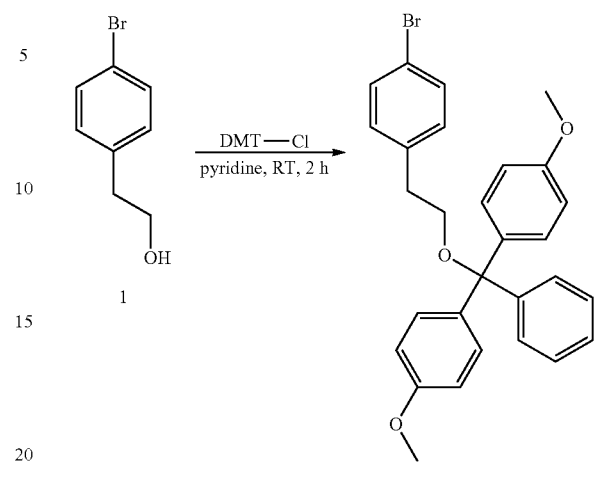

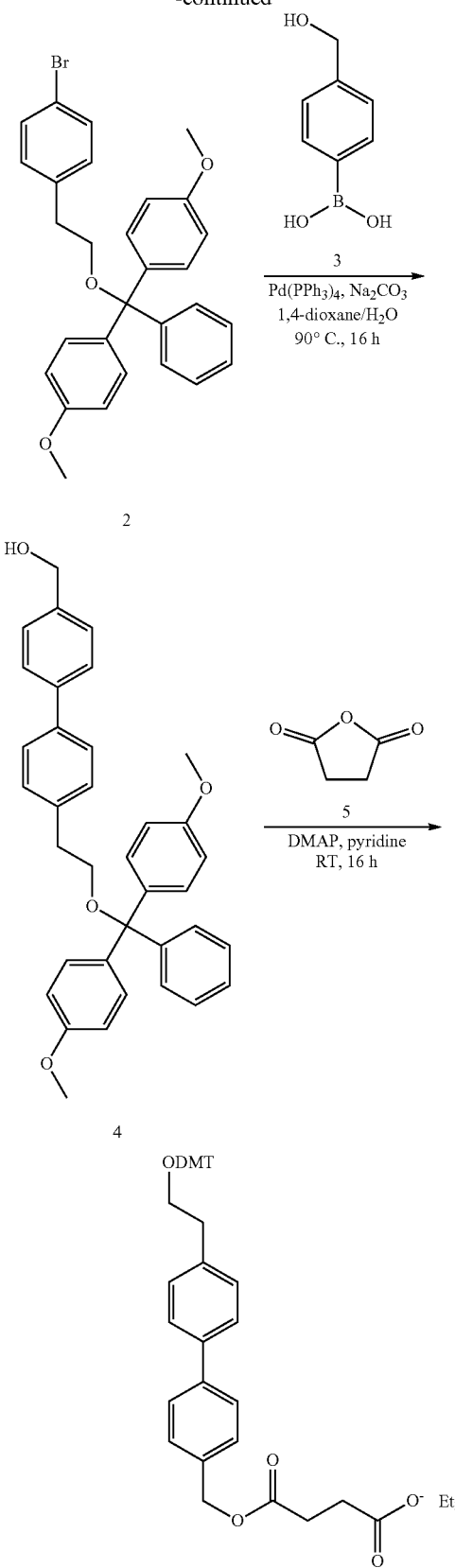

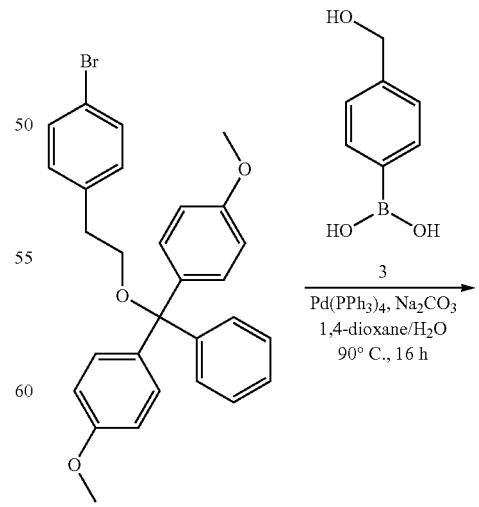

To a 250 mL roundbottom flask was added 2-(4-bromophenyl)ethanol 1 (1.00 g, 4.97 mmol), pyridine (25 mL) and 4,4'-(chloro(phenyl)methylene)bis(methoxybenzene) (DMT-Cl) (1.69 g, 4.97 mmol). The solution was stirred at rt for 2 h. 1 mL of MeOH was added, and the solution was stirred at rt for 10 min. The solution was then concentrated under vacuum, dissolved in 250 mL of EtOAc, and washed with 100 mL sat. aq. NaHCO₃, 100 mL of water, and 100 mL of brine. The organic layer was dried with sodium sulfate, concentrated under vacuum, and purified by silica gel chromatography (heptane/ethyl acetate/NEt₃) to give 2 (2.35 g, 94%) as a foamy solid. $^1$H NMR (400 MHz, DMSO-d₆): 2.80 (t, J=6.6 Hz, 2H), 3.12 (t, J=6.6 Hz, 2H), 3.72 (s, 6H), 6.81-6.87 (m, 4H), 7.12-7.22 (m, 7H), 7.26 (d, J=4.0 Hz, 4H), 7.44-7.50 (m, 2H).

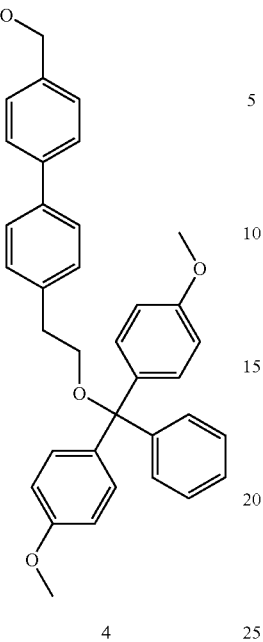

4

To a 40 mL glass vial with rubber septa was added 2 (0.70 g, 1.39 mmol), 4-(hydroxymethyl)phenylboronic acid 3 (0.25 g, 1.67 mmol), Pd(PPh$_3$)$_4$ (80 mg, 0.070 mmol), 2 M (aq) Na$_2$CO$_3$ (2.1 mL, 4.17 mmol), and 1,4-dioxane (7 mL). The contents were briefly placed under vacuum, and then placed under a nitrogen atmosphere. The vial was sealed and heated at 90° C. for 16 h. After cooling to rt, EtOAc was added and the mixture was washed with sat. aq. NaHCO$_3$ and brine. The organic portion was dried with sodium sulfate, concentrated under vacuum, and purified by silica gel chromatography (heptane/ethyl acetate/NEt$_3$) to give 3 (0.64 g, 87%) as a foamy solid. $^1$H NMR (400 MHz, DMSO-d$_6$): 2.86 (t, J=6.6 Hz, 2H), 3.16 (t, J=6.6 Hz, 2H), 3.72 (s, 6H), 4.52 (d, J=6.1 Hz, 2H), 5.19 (t, J=5.8 Hz, 1H), 6.81-6.87 (m, 4H), 7.18 (d, J=9.1 Hz, 4H), 7.20-7.22 (m, 1H), 7.24-7.33 (m, 6H), 7.38 (d, J=8.6 Hz, 2H), 7.57 (d, J=8.1 Hz, 2H), 7.60 (d, J=8.1 Hz, 2H).

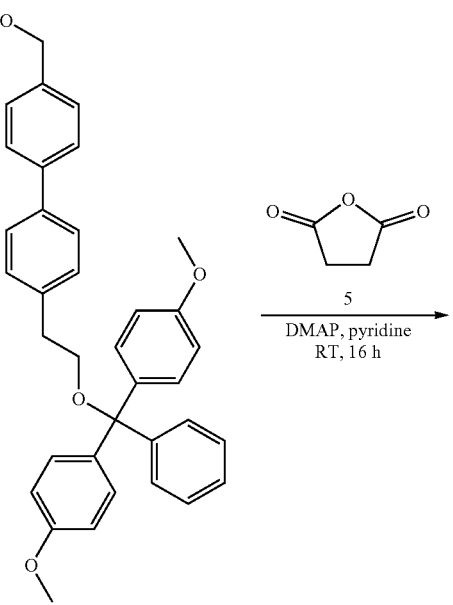

4

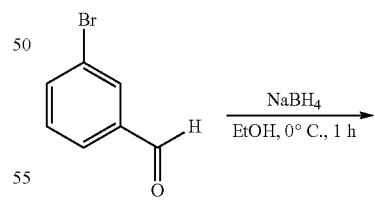

6

To a solution of 3.68 g (6.93 mmol) 4 and 847 mg (6.93 mmol) N,N-dimethylaminopyridine (DMAP) in 35 mL dry pyridine under argon was added 1.39 g (13.9 mmol) succinic anhydride (5). The reaction mixture was stirred at room temperature for 16 h and then 2.5 mL water was added. Stirring was continued for 30 min. The reaction mixture was taken up in 300 mL dichloromethane and washed with 150 mL ice-cold 10% aqueous citric acid and water (2×150 mL). The aqueous layers were reextracted with 150 mL dichloromethane. The combined organic layers were dried over Na$_2$SO$_4$ and evaporated. The remaining oil was coevaporated twice with toluene and the crude product purified by silica gel chromatography (dichloromethane/methanol/triethylamine 97:2:1) to give 4.68 g (6.39 mmol, 92%) 6 as an off-white foam. $^1$H NMR (400 MHz, CDCl$_3$): 1.14 (t, J=7.4 Hz, 9H), 2.51 (t, J=6.8 Hz, 2H), 2.60 (t, J=6.5 Hz, 2H), 2.82-2.90 (m, 8H), 3.24 (t, J=6.8 Hz, 2H), 3.70 (s, 6H), 5.08 (s, 2H), 6.69-6.73 (m, 4H), 7.08-7.21 (m, 9H), 7.28-7.35 (m, 4H), 7.42 (d, J=8.1 Hz, 2H), 7.48 (d, J=8.0 Hz, 2H), 8.04 (s br., 1H).

2. F. Synthesis of X069 Succinate Ester

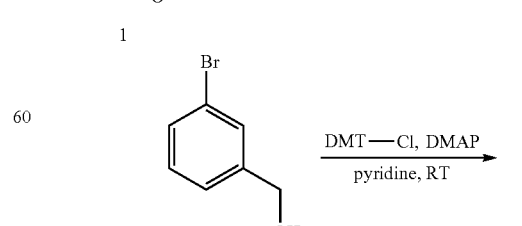

1

2

Scheme 1: Overview of the synthesis of succinate 7

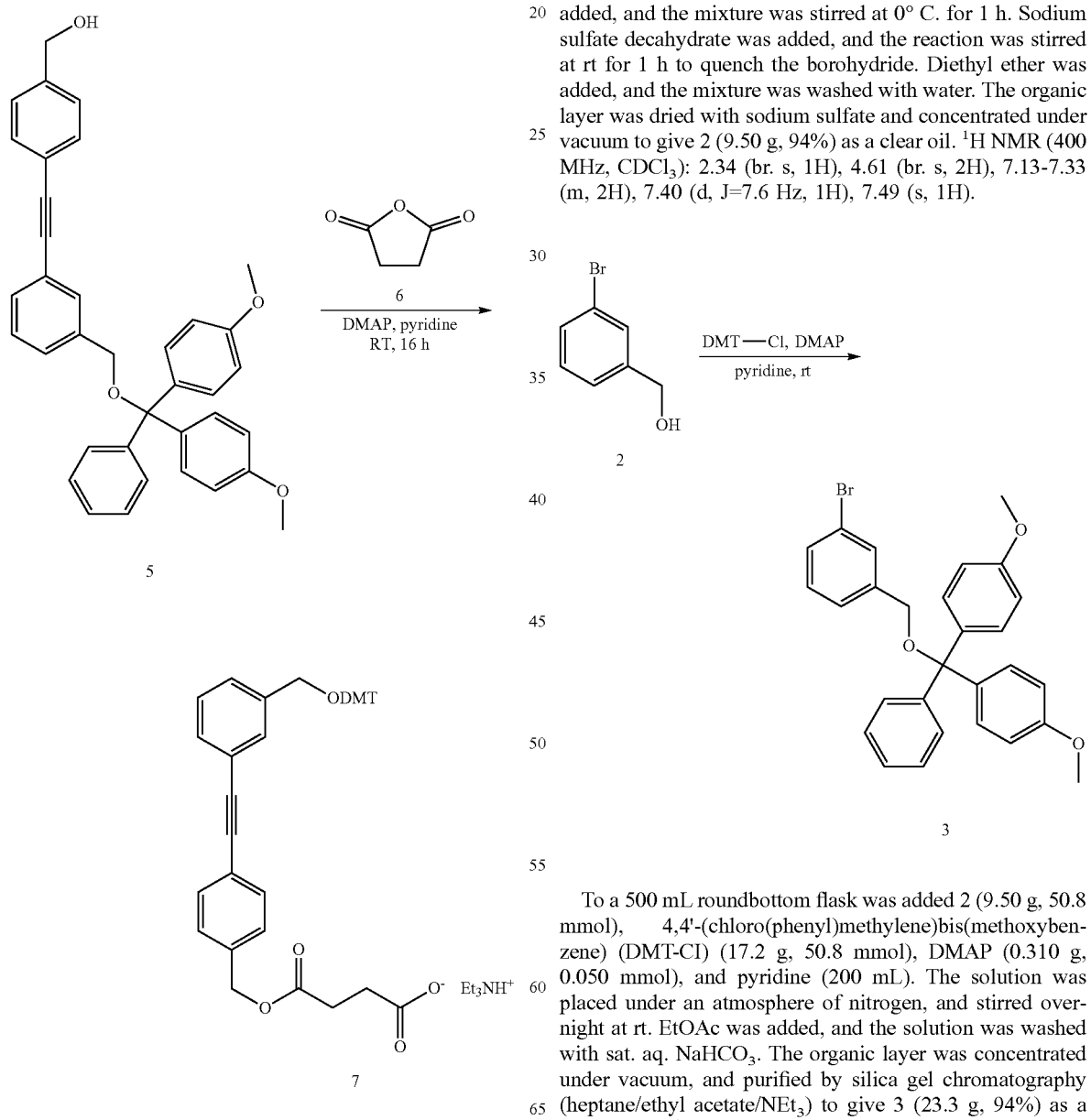

Compound 2 was prepared according to *Eur. J. Org. Chem*, 2002, 19, 3326-3335. In a 250 mL roundbottom was added 3-bromobenzaldehyde 1 (10.0 g, 54.0 mmol) and EtOH (25 mL). The solution was cooled to 0° C. in an ice-water bath, sodium borohydride (1.11 g, 29.5 mmol) was added, and the mixture was stirred at 0° C. for 1 h. Sodium sulfate decahydrate was added, and the reaction was stirred at rt for 1 h to quench the borohydride. Diethyl ether was added, and the mixture was washed with water. The organic layer was dried with sodium sulfate and concentrated under vacuum to give 2 (9.50 g, 94%) as a clear oil. $^1$H NMR (400 MHz, CDCl$_3$): 2.34 (br. s, 1H), 4.61 (br. s, 2H), 7.13-7.33 (m, 2H), 7.40 (d, J=7.6 Hz, 1H), 7.49 (s, 1H).

To a 500 mL roundbottom flask was added 2 (9.50 g, 50.8 mmol), 4,4'-(chloro(phenyl)methylene)bis(methoxybenzene) (DMT-Cl) (17.2 g, 50.8 mmol), DMAP (0.310 g, 0.050 mmol), and pyridine (200 mL). The solution was placed under an atmosphere of nitrogen, and stirred overnight at rt. EtOAc was added, and the solution was washed with sat. aq. NaHCO$_3$. The organic layer was concentrated under vacuum, and purified by silica gel chromatography (heptane/ethyl acetate/NEt$_3$) to give 3 (23.3 g, 94%) as a foamy solid. $^1$H NMR (400 MHz, CDCl$_3$): 3.74 (s, 6H), 4.12 (s, 2H), 6.92 (dd, J=8.0 Hz, 4H), 7.21-7.48 (m, 13H).

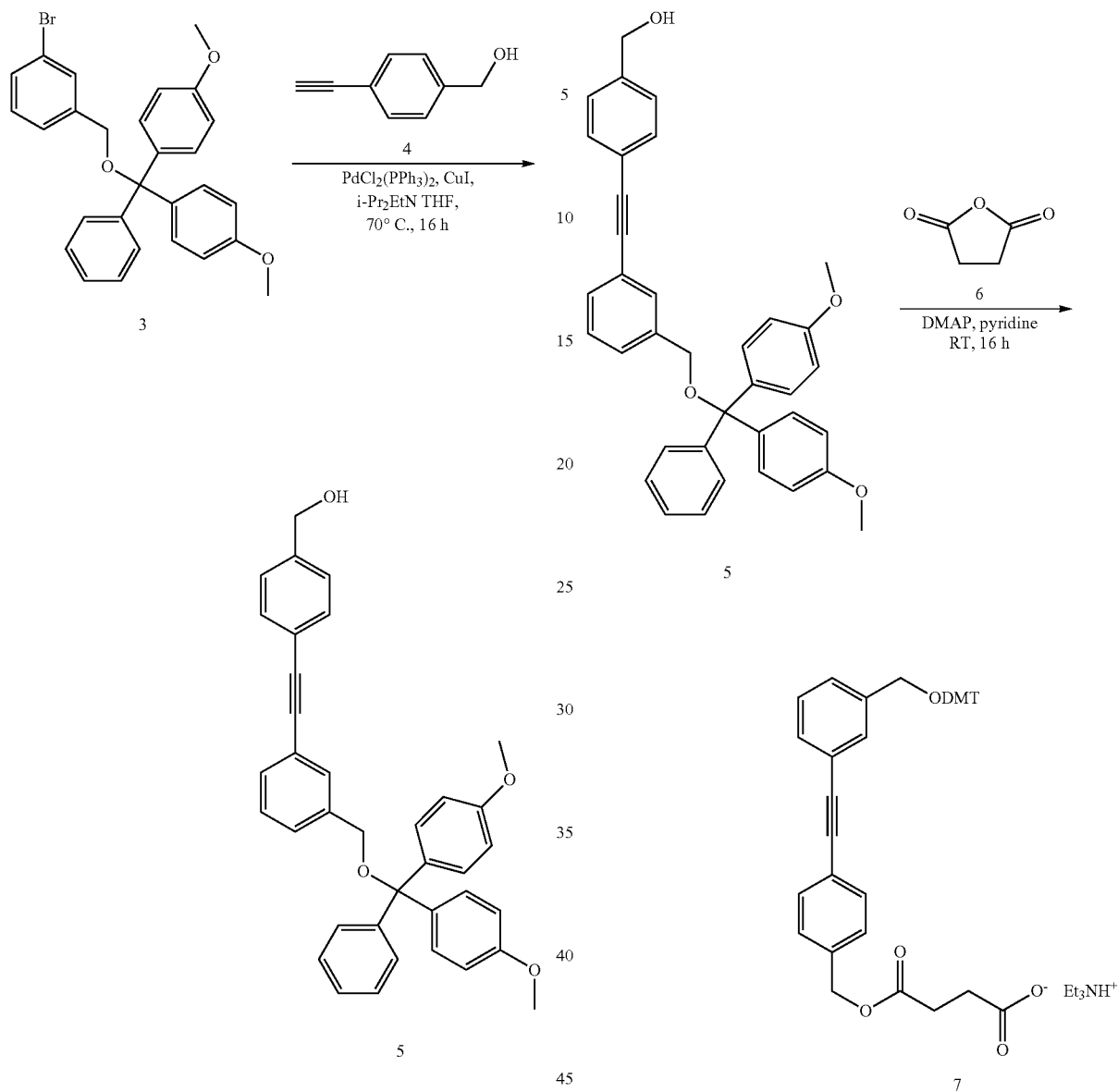

To a 40 mL glass vial with rubber septum was added 3 (1.00 g, 2.04 mmol), 4-ethynylbenzyl alcohol 4 (0.405 g, 3.06 mmol), PdCl$_2$(PPh$_3$)$_2$ (86 mg, 0.123 mmol), CuI (39 mg, 0.204 mmol), iPr$_2$EtN (1.06 g, 8.17 mmol) and THF (7 mL). The contents were briefly placed under vacuum, and then placed under a nitrogen atmosphere. The vial was sealed and heated at 70° C. for 16 h. After cooling to rt, the mixture was filtered through celite, washing with EtOAc, and the filtrated was concentrated under vacuum. The residue was purified by silica gel chromatography (heptane/ethyl acetate/NEt$_3$) to give 5 (0.680 g, 62%) as a foamy solid. $^1$H NMR (400 MHz, CDCl$_3$): 3.74 (s, 6H), 4.12 (s, 2H), 4.53 (d, J=4.0 Hz, 2H), 5.29 (t, J=4.0 Hz, 1H), 6.93 (dd, J=8.0 Hz, 4H), 7.19-7.58 (m, 17H).

To a solution of 4.55 g (8.42 mmol) 5 and 1.03 g (8.42 mmol) N,N-dimethylaminopyridine (DMAP) in 42 mL dry pyridine under argon was added 1.68 g (16.8 mmol) succinic anhydride (6). The reaction mixture was stirred at room temperature for 16 h and then 2.5 mL water was added. Stirring was continued for 30 min. The reaction mixture was taken up in 300 mL dichloromethane and washed with 150 mL ice-cold 10% aqueous citric acid and water (2×150 mL). The aqueous layers were reextracted with 150 mL dichloromethane. The combined organic layers were dried over Na$_2$SO$_4$ and evaporated. The remaining oil was coevaporated twice with toluene and the crude product purified by silica gel chromatography (dichloromethane/methanol/triethylamine 97:2:1) to give 5.81 g (7.83 mmol, 93%) 7 as an off-white, sticky foam. $^1$H NMR (400 MHz, CDCl$_3$): 1.14 (t, J=7.4 Hz, 9H), 2.50 (t, J=6.5 Hz, 2H), 2.60 (t, J=6.6 Hz, 2H), 2.86 (q, J=7.3 Hz, 6H), 3.72 (s, 6H), 4.09 (s, 2H), 5.05 (s, 2H), 5.95 (s br., 1H), 6.75-6.79 (m, 4H), 7.15 (tt, J=7.3, 1.5 Hz, 1H), 7.21-7.36 (m, 11H), 7.42-7.45 (m, 5H).

2.G. General Procedure for the High Density Loading of Controlled Pore Glass Supports with PAZ Ligand Succinates

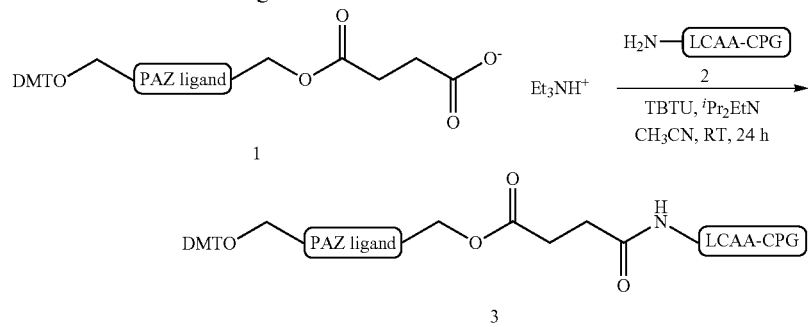

In an Erlenmeyer flask 1.00 mmol PAZ ligand succinate salt 1 was dissolved in 50 mL dry acetonitrile under argon. To this solution 353 mg (1.10 mmol) O-(1H-benzo-1,2,3-triazol-1-yl)-N,N,N'-tetramethyl-uronium tetrafluoroborate (TBTU) was added and the solution shaken for 10 min. Then 10 g long chain alkylamine controlled pore glass (LCAA/CNA-600-CPG, PrimeSynthesis, 2) was added and the reaction mixture gently agitated for 5 min. Finally, 0.685 mL (517 mg, 4.00 mmol) Hünig's base was added and the flask gently shaken for 24 h on an orbital shaker. Loading density was assessed by detritylating an aliquote of the CPG (3-5 mg CPG washed with acetonitrile, dried in vacuo, added to 25 mL 3% dichloroacetic acid in dichloromethane (v/v), absorbance at 504 nm determined). If loading density was in the desired range (60-90 micromol/g), the CPG was filtered off and washed extensively with acetonitrile. Underivatized amino groups were capped by treating the CPG with x mL each of a mixture of acetic anhydride/2,6-lutidine/THF 1:1:8 (v/v/v) and a solution of 1-methylimidazole in THF 16:84 (v/v). The mixture was gently shaken for 15 min at room temperature. Then the CPG was filtered off, washed with acetonitrile and dried under vacuum overnight. Loading density was determined again as above. Loading yields for the succinates in examples 1-6 were in the Range of 64-75 Micromol/g.

2.H. Synthesis of X050, X059, X061, X062, X065, X068 Alcohols and Succinate Esters Prepared in an analogous manner to X027

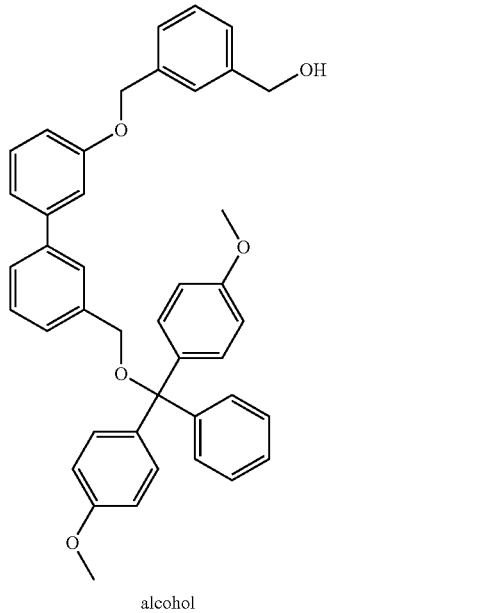

X050 alcohol

-continued

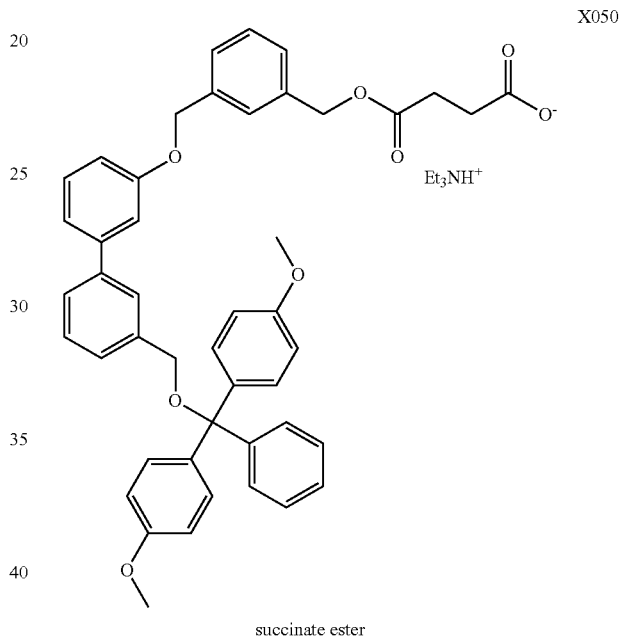

X050 succinate ester

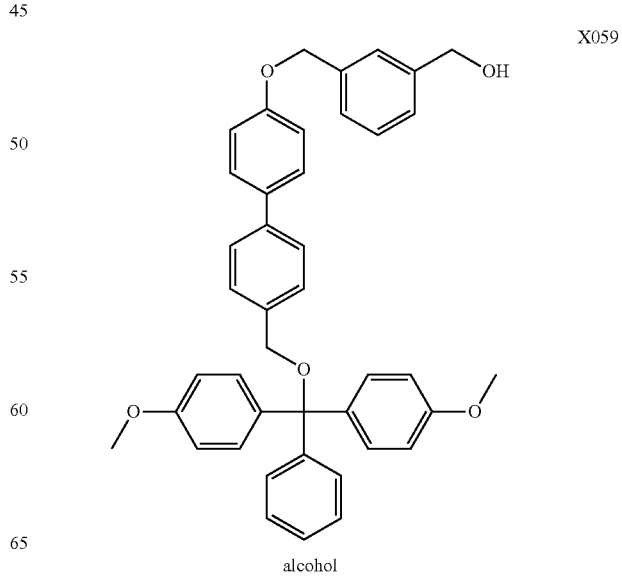

X059 alcohol

X059
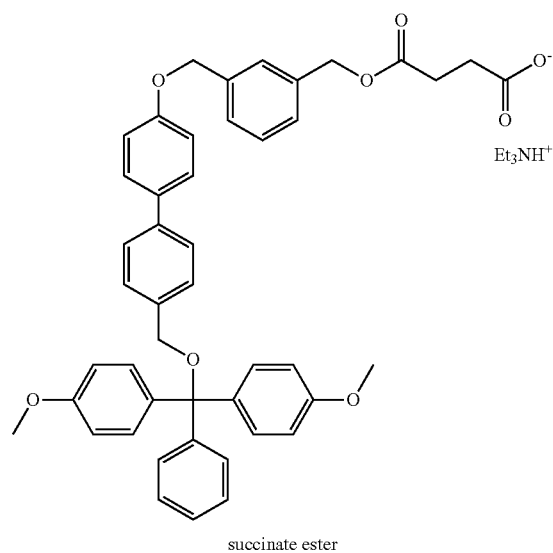
succinate ester
X061
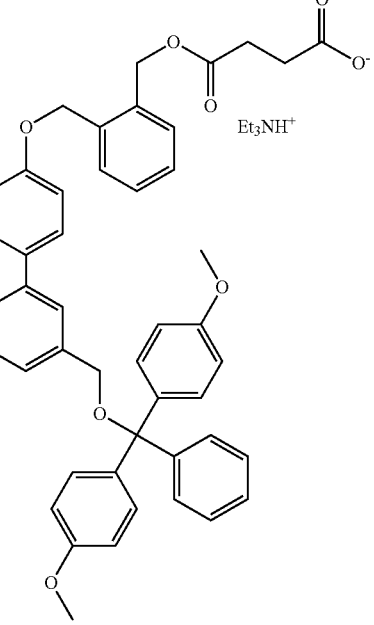
succinate ester
X061
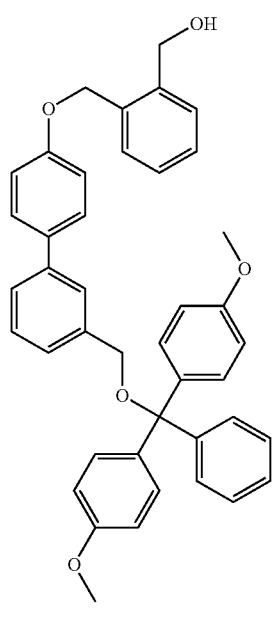
alcohol
X062
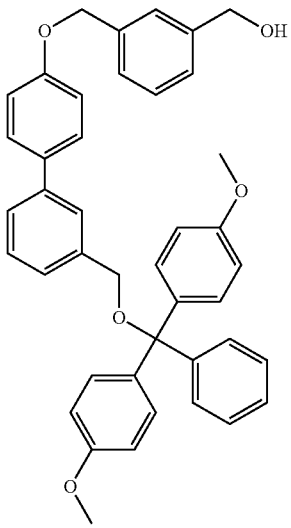
alcohol 215
-continued
X062
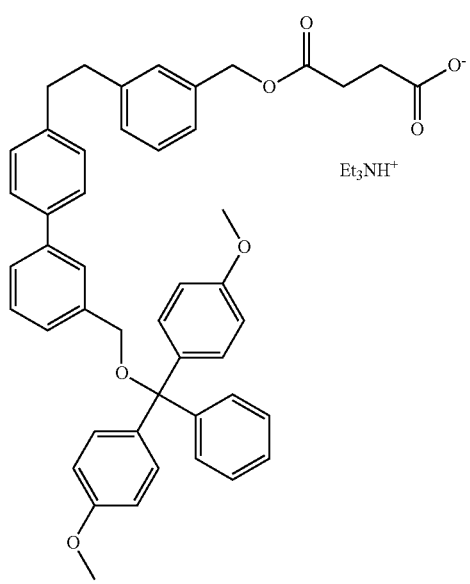
succinate ester
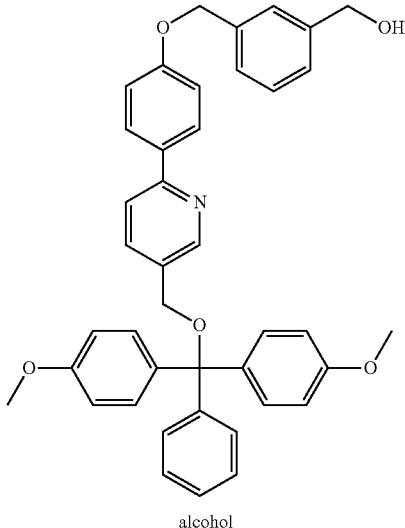
alcohol
216
-continued
X065
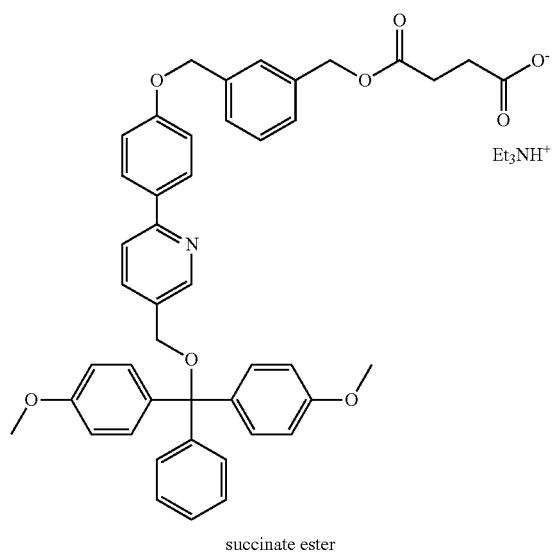
succinate ester
X068
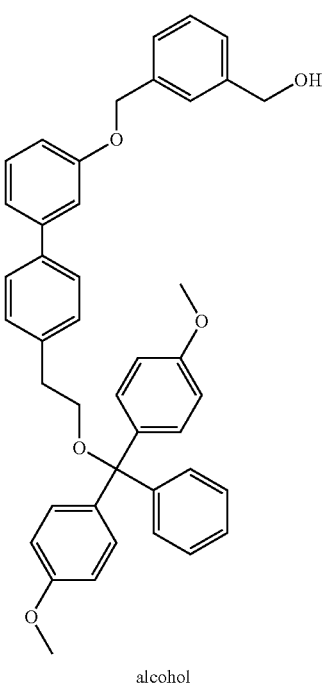
alcohol

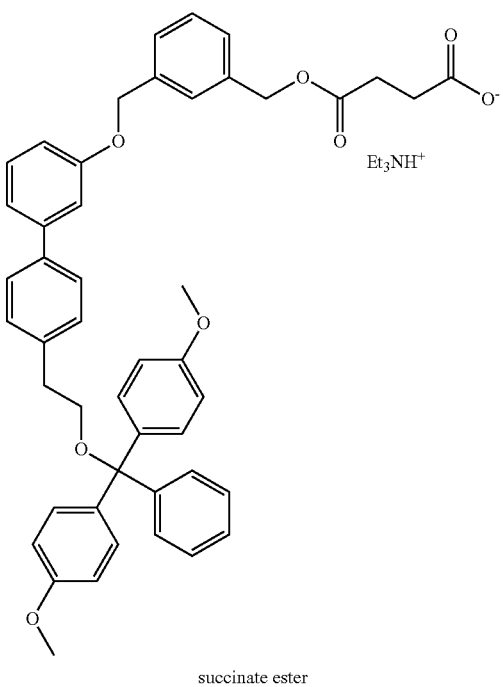

succinate ester

X050 Alcohol:
¹H NMR (400 MHz, DMSO-d₆) δ ppm 3.73 (s, 6H) 4.19 (s, 2H) 4.51 (d, J=5.56 Hz, 2H) 5.17 (s, 2H) 5.21 (t, J=5.81 Hz, 1H) 6.89-6.95 (m, 4H) 7.01 (dd, J=8.08, 2.02 Hz, 1H) 7.19-7.30 (m, 4H) 7.30-7.40 (m, 9H) 7.40-7.49 (m, 5H) 7.53 (s, 1H) 7.57 (d, J=7.58 Hz, 1H). MS (ESI−) m/z: calcd for $C_{42}H_{38}O_5$ 622.3. found 667.9 [MH⁻+formic acid].

X059 Alcohol:
¹H NMR (400 MHz, DMSO-d₆) δ ppm 3.74 (s, 6H) 4.10 (s, 2H) 4.52 (s, 2H) 5.15 (s, 2H) 5.22 (br. s., 1H) 6.90-6.96 (m, 4H) 7.07-7.13 (m, 2H) 7.22-7.30 (m, 2H) 7.30-7.38 (m, 8H) 7.39-7.48 (m, 5H) 7.60 (d, J=8.08 Hz, 4H). MS (ESI−) m/z: calcd for $C_{42}H_{38}O_5$ 622.3. found 621.1 [MH⁻].

X061 Alcohol:
¹H NMR (400 MHz, DMSO-d₆) δ ppm 3.74 (s, 6H) 4.17 (s, 2H) 4.63 (d, J=5.05 Hz, 2H) 5.17-5.22 (m, 3H) 6.93 (d, J=8.59 Hz, 4H) 7.11 (d, J=8.59 Hz, 2H) 7.22-7.37 (m, 10H) 7.40-7.52 (m, 7H) 7.58 (d, J=8.59 Hz, 2H). MS (ESI−) m/z: calcd for $C_{42}H_{38}O_5$ 622.3. found 667.6 [MH⁻+formic acid].

X062 Alcohol:
¹H NMR (400 MHz, DMSO-d₆) δ ppm 3.74 (s, 6H) 4.16 (s, 2H) 4.52 (d, J=6.06 Hz, 2H) 5.14 (s, 2H) 5.19-5.23 (m, 1H) 6.90-6.95 (m, 4H) 7.07-7.12 (m, 2H) 7.21-7.29 (m, 2H) 7.30-7.38 (m, 9H) 7.39-7.48 (m, 5H) 7.49-7.53 (m, 1H) 7.55-7.60 (m, 2H). MS (ESI−) m/z: calcd for $C_{42}H_{38}O_5$ 622.3. found 667.7 [MH⁻+formic acid].

X065 Alcohol:
¹H NMR (400 MHz, DMSO-d₆) δ ppm 3.75 (s, 6H) 4.16 (s, 2H) 4.52 (d, J=6.06 Hz, 2H) 5.17 (s, 2H) 5.21 (t, J=5.81 Hz, 1H) 6.93 (d, J=8.59 Hz, 4H) 7.12 (d, J=9.09 Hz, 2H) 7.22-7.39 (m, 10H) 7.41-7.47 (m, 3H) 7.78 (dd, J=8.34, 2.27 Hz, 1H) 7.85-7.90 (m, 1H) 8.03 (d, J=9.09 Hz, 2H) 8.55 (d, J=1.52 Hz, 1H). MS (ESI+) m/z: calcd for $C_{41}H_{37}NO_5$ 623.3. found 624.7 [MH⁺].

X068 Alcohol:
¹H NMR (400 MHz, DMSO-d₆) δ ppm 2.87 (t, J=6.57 Hz, 2H) 3.16 (t, J=6.57 Hz, 2H) 3.72 (s, 6H) 4.51 (d, J=5.56 Hz, 2H) 5.17 (s, 2H) 5.21 (t, J=5.81 Hz, 1H) 6.85 (d, J=8.59 Hz, 4H) 6.99 (dd, J=8.08, 1.52 Hz, 1H) 7.18 (d, J=9.09 Hz, 4H) 7.20-7.38 (m, 13H) 7.43 (s, 1H) 7.59 (d, J=8.59 Hz, 2H). MS (ESI+) m/z: calcd for $C_{43}H_{40}O_5$ 636.3. found 659.7 [M+Na].

2.I. Synthesis of X060 and X064 Alcohols and Succinate Esters

Prepared in an analogous manner to X067

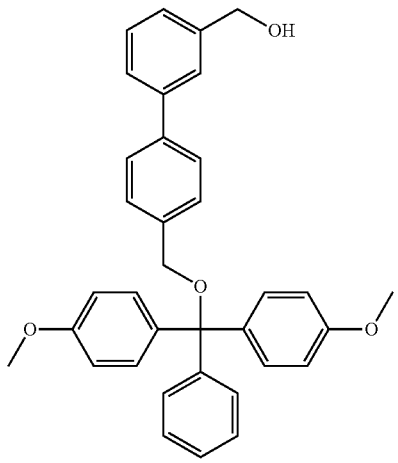

X060 alcohol

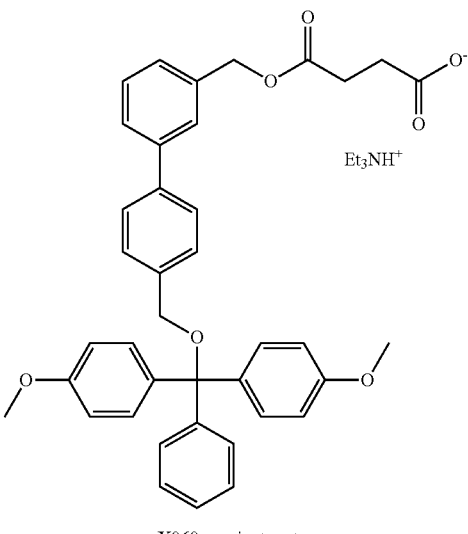

X060 succinate ester

2.J. Synthesis of X063 Succinate Ester

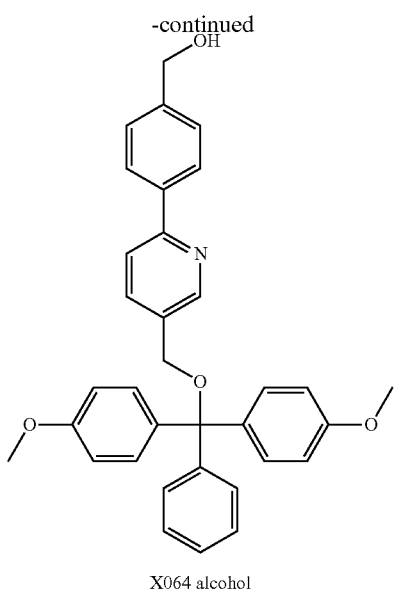

X064 alcohol

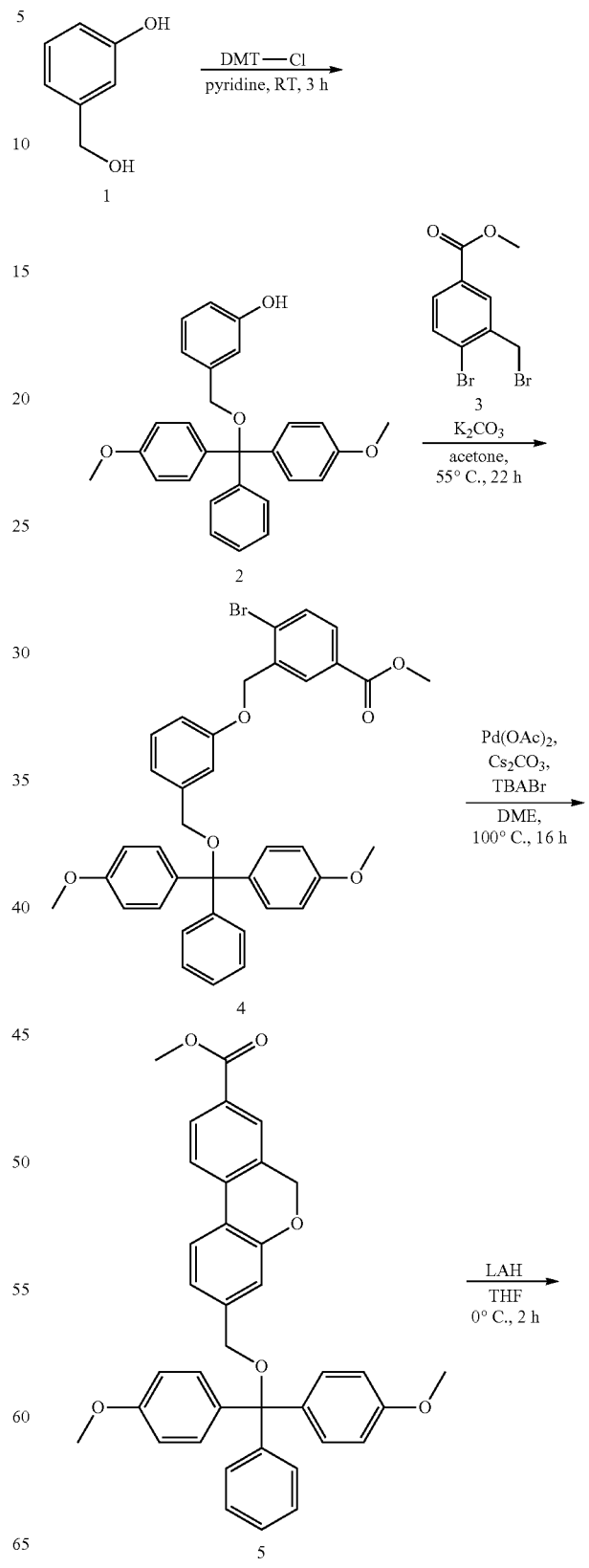

X064 succinate ester

X060 Alcohol:
$^1$H NMR (400 MHz, DMSO-d$_6$) δ ppm $^1$H NMR (400 MHz, DMSO-d$_6$) δ ppm 3.75 (s, 6H) 4.12 (s, 2H) 4.57 (d, J=5.56 Hz, 2H) 5.20-5.26 (m, 1H) 6.90-6.96 (m, 4H) 7.22-7.28 (m, 1H) 7.29-7.38 (m, 7H) 7.39-7.48 (m, 5H) 7.53 (d, J=8.08 Hz, 1H) 7.60 (s, 1H) 7.64 (d, J=8.08 Hz, 2H). MS (ESI+) m/z: calcd for C$_{35}$H$_{32}$O$_4$ 516.2. found 303.4 [DMT$^+$].

X064 Alcohol:
$^1$H NMR (400 MHz, DMSO-d$_6$) δ ppm 3.75 (s, 6H) 4.18 (s, 2H) 4.56 (d, J=5.56 Hz, 2H) 5.24 (t, J=5.81 Hz, 1H) 6.93 (d, J=9.09 Hz, 4H) 7.25 (t, J=7.33 Hz, 1H) 7.32 (d, J=9.09 Hz, 4H) 7.34-7.39 (m, 2H) 7.44 (t, J=8.08 Hz, 4H) 7.82 (dd, J=8.34, 2.27 Hz, 1H) 7.93 (d, J=8.08 Hz, 1H) 8.04 (d, J=8.08 Hz, 2H) 8.59 (d, J=2.02 Hz, 1H). MS (ESI+) m/z: calcd for C$_{34}$H$_{31}$NO$_4$ 517.2. found 518.8 [MH$^+$].

-continued

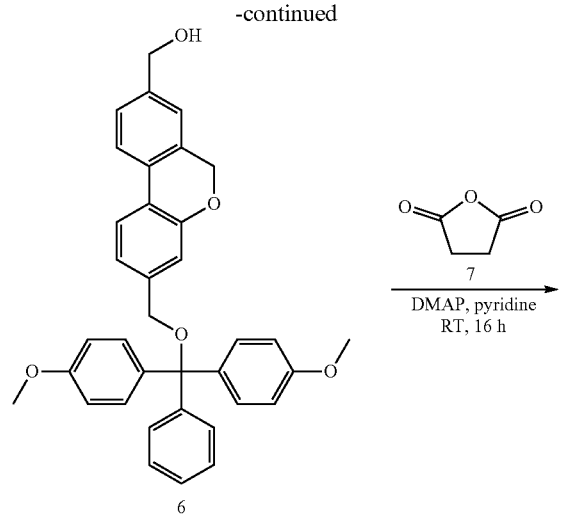

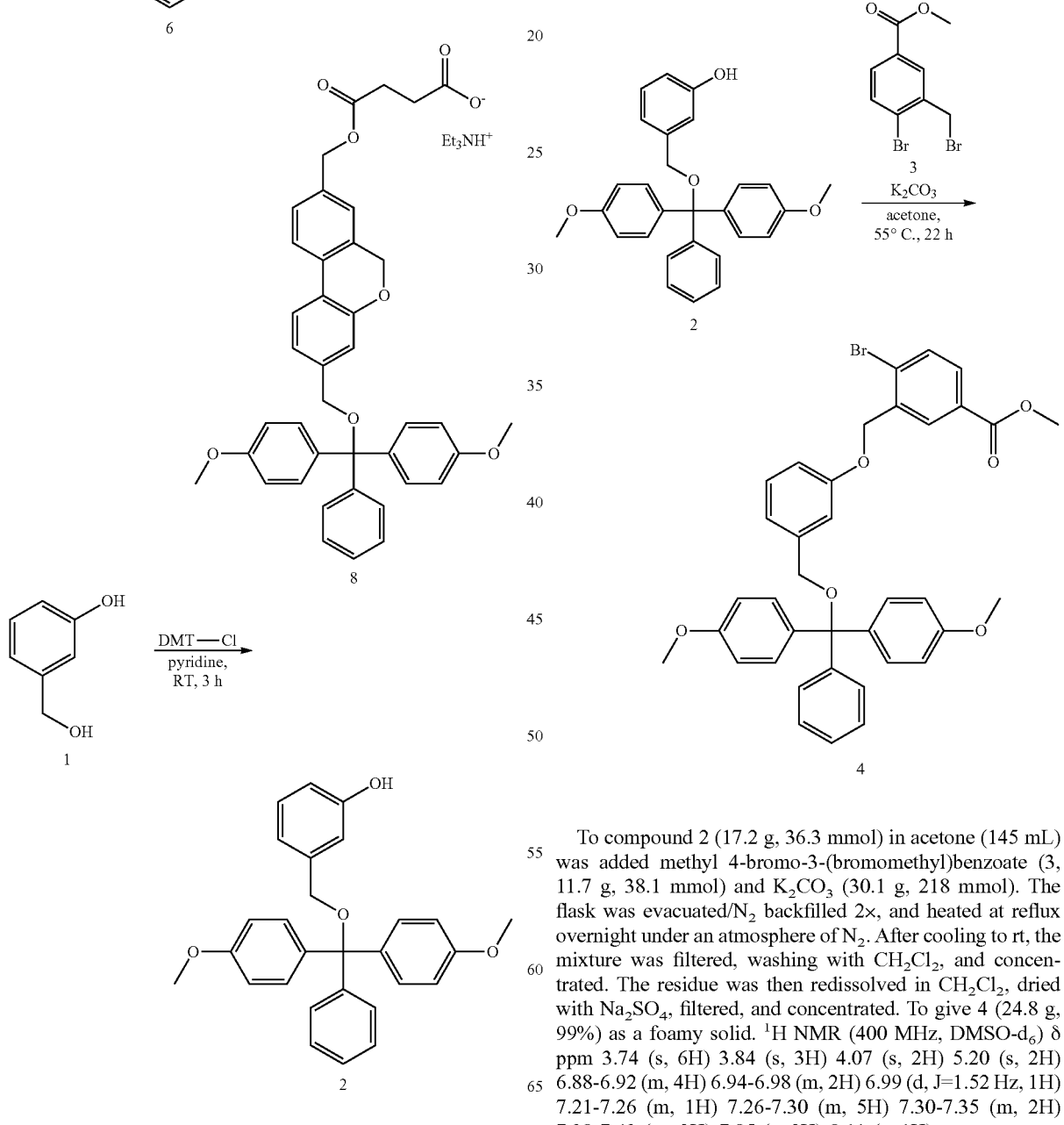

3-(hydroxymethyl)phenol (1, 6.21 g, 50.0 mmol) was dissolved in pyridine (100 mL) and cooled to 0° C. DMT-Cl (16.9 g, 50 mmol) was added and the solution was stirred at rt for 2 h. 500 mL of EtOAc was added, the solution was washed 1× each with 400 mL sat. aq. NaHCO$_3$, water, and brine. The organic portion was dried with Na$_2$SO$_4$, filtered, and concentrated under vacuum. The mixture was re-dissolved in acetone/toluene and concentrated, repeating this process 4-times. The residue was then concentrated under vacuum overnight to give 2 (20.9 g, 98%) as a foamy solid.

$^1$H NMR (400 MHz, DMSO-d$_6$) δ ppm 3.74 (s, 6H) 3.97 (s, 2H) 6.66 (dd, J=8.08, 1.52 Hz, 1H) 6.72 (d, J=7.58 Hz, 1H) 6.83 (d, J=1.52 Hz, 1H) 6.89-6.95 (m, 4H) 7.12 (t, J=7.83 Hz, 1H) 7.17 (d, J=7.58 Hz, 1H) 7.27-7.32 (m, 4H) 7.34 (t, J=7.58 Hz, 2H) 7.40-7.46 (m, 2H) 9.37 (s, 1H).

To compound 2 (17.2 g, 36.3 mmol) in acetone (145 mL) was added methyl 4-bromo-3-(bromomethyl)benzoate (3, 11.7 g, 38.1 mmol) and K$_2$CO$_3$ (30.1 g, 218 mmol). The flask was evacuated/N$_2$ backfilled 2×, and heated at reflux overnight under an atmosphere of N$_2$. After cooling to rt, the mixture was filtered, washing with CH$_2$Cl$_2$, and concentrated. The residue was then redissolved in CH$_2$Cl$_2$, dried with Na$_2$SO$_4$, filtered, and concentrated. To give 4 (24.8 g, 99%) as a foamy solid. $^1$H NMR (400 MHz, DMSO-d$_6$) δ ppm 3.74 (s, 6H) 3.84 (s, 3H) 4.07 (s, 2H) 5.20 (s, 2H) 6.88-6.92 (m, 4H) 6.94-6.98 (m, 2H) 6.99 (d, J=1.52 Hz, 1H) 7.21-7.26 (m, 1H) 7.26-7.30 (m, 5H) 7.30-7.35 (m, 2H) 7.38-7.43 (m, 2H) 7.85 (s, 2H) 8.11 (s, 1H)

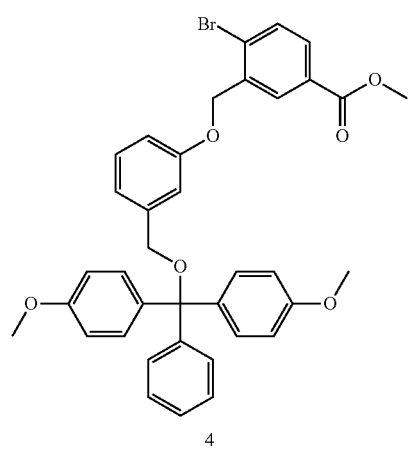

4

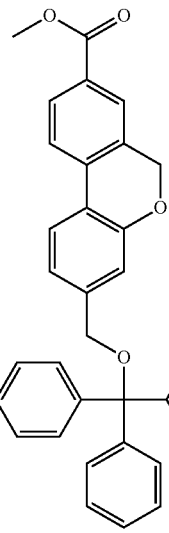

5

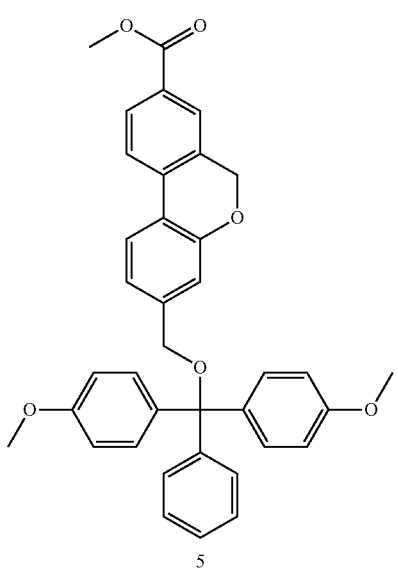

5

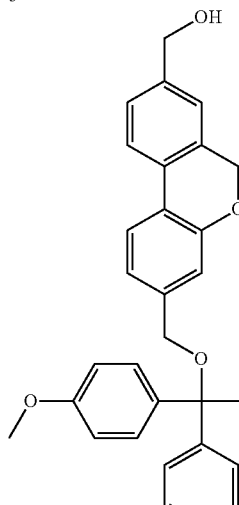

6

To compound 4 (24.8 g, 35.8 mmol) in dimethoxyethane (350 mL) was added Bu$_4$NBr (17.3 g, 53.7 mmol), Cs$_2$CO$_3$ (17.5 g, 53.7 mmol), and Pd(OAc)$_2$ (2.01 g, 8.96 mmol). The flask was degassed with two cycles of vacuum/N$_2$ backfill and heated to reflux overnight, under an atmosphere of N$_2$. After cooling to rt, the mixture was filtered through celite, eluting with THF, and concentrated. The residue was dissolved in 500 mL EtOAc, washed with 400 mL sat. aq. NaHCO$_3$, 2×400 mL water, and 400 mL of brine. The organic fraction was dried with Na$_2$SO$_4$, filtered, and concentrated under vacuum. The residue was purified by silica gel chromatography (CH$_2$Cl$_2$/triethylamine), giving 5 (15.1 g, 68%) as a foamy solid. $^1$H NMR (400 MHz, DMSO-d$_6$) δ ppm 3.74 (s, 6H) 3.87 (s, 3H) 4.11 (s, 2H) 5.23 (s, 2H) 6.89-6.96 (m, 4H) 7.01 (d, J=1.52 Hz, 1H) 7.08 (dd, J=8.08, 1.52 Hz, 1H) 7.22-7.27 (m, 1H) 7.29-7.33 (m, 4H) 7.33-7.38 (m, 2H) 7.41-7.46 (m, 2H) 7.88-7.93 (m, 2H) 7.93-7.99 (m, 2H)

Lithium aluminum hydride (43.4 mL of 1.0 M suspension in THF, 43.4 mmol) was added to a solution of compound 5 (12.0 g, 19.3 mmol) in THF (150 mL) at 0° C. After 2 hours at 0° C., the reaction mixture was quenched by dropwise addition of 20 mL EtOAc, with stirring at 0° C. for 10 min. 1.65 mL H$_2$O, 1.65 mL 20% aq. NaOH, and 4.95 mL H$_2$O were added successively. The mixture was then stirred at rt for 1 h, dried with Na$_2$SO$_4$, filtered through celite, and concentrated under vacuum. The residue was purified by silica gel chromatography (ethyl acetate/heptane/triethylamine), giving 6 (8.47 g, 81%) as a foamy solid. $^1$H NMR (400 MHz, DMSO-d$_6$) δ ppm 3.75 (s, 6H) 4.07 (s, 2H) 4.52 (d, J=5.56 Hz, 2H) 5.13 (s, 2H) 5.21-5.25 (m, 1H) 6.89-6.95 (m, 4H) 6.96 (d, J=1.52 Hz, 1H) 7.03 (dd, J=8.08, 1.52 Hz, 1H) 7.22 (s, 1H) 7.23-7.28 (m, 1H) 7.29-7.33 (m, 4H) 7.33-7.38 (m, 3H) 7.41-7.46 (m, 2H) 7.76 (d, J=7.58 Hz, 1H) 7.81 (d, J=8.08 Hz, 1H). MS (ESI+) m/z: calcd for C$_{36}$H$_{32}$O$_5$ 544.2. found 545.2 [MH$^+$].

2.K. Synthesis of X066 Succinate Ester

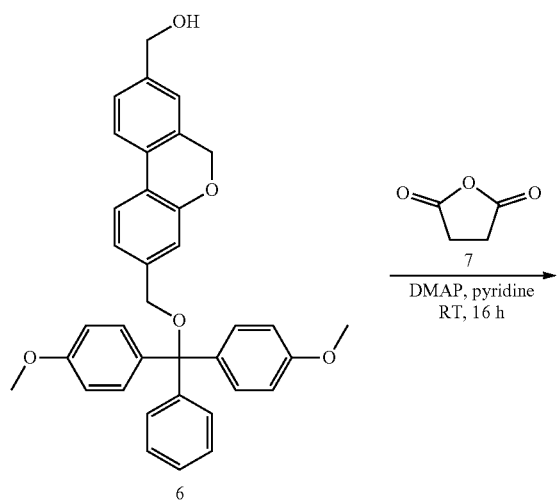

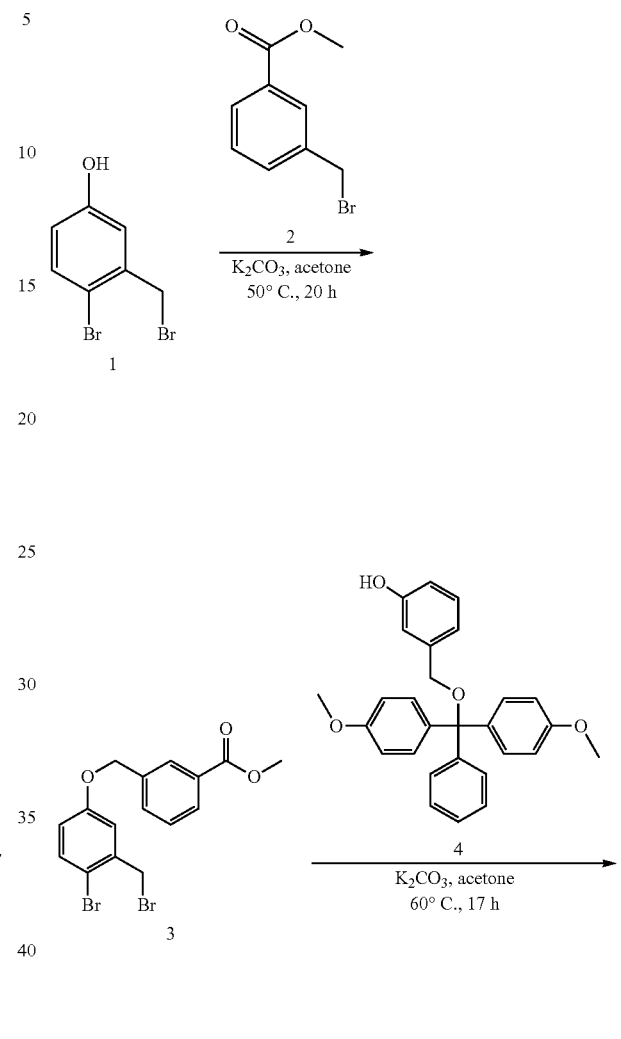

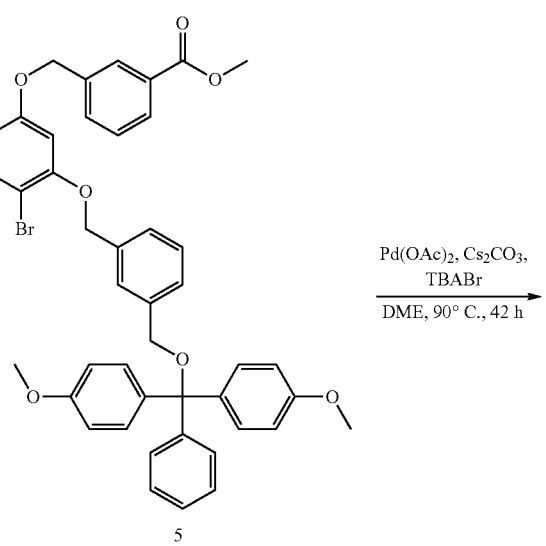

Dimethylaminopyridine (0.124 g, 1.02 mmol) was added to a solution of compound 6 (0.554 g, 1.02 mmol) in pyridine (5 mL) at rt under argon. Succinic anhydride 7 (0.204 g, 2.03 mmol) was added and the solution was stirred at rt for 6 h. 0.5 mL H$_2$O was added, and the solution was stirred for 30 min. 100 mL of CH$_2$Cl$_2$ was added, and the solution was washed 1× with 50 mL cold 10% aq. citric acid and 2× each with 50 mL of water. The aqueous fractions were reextracted with 1×50 mL of CH$_2$Cl$_2$. The combined organic fractions were dried with Na$_2$SO$_4$, filtered, concentrated under vacuum and then diluted/concentrated 2× with toluene. The residue was purified by silica gel chromatography (dichloromethane/methanol/triethylamine) (49:1/1%), giving 8 (0.78 g, 103%) as a foamy solid. $^1$H NMR (400 MHz, CDCl$_3$) δ ppm 1.45 (t, J=7.20 Hz, 2.5H) 2.52-2.60 (m, 2H) 2.65-2.71 (m, 2H) 3.60 (q, J=7.33 Hz, 1.7H) 3.79 (s, 6H) 4.16 (s, 2H) 5.12 (s, 2H) 5.13 (s, 2H) 6.82-6.87 (m, 4H) 7.03 (dd, J=8.08, 1.26 Hz, 1H) 7.08 (s, 1H) 7.17 (s, 1H) 7.19-7.25 (m, 1H) 7.28-7.33 (m, 2H) 7.33-7.37 (m, 1H) 7.38-7.44 (m, 4H) 7.49-7.54 (m, 2H) 7.66 (t, J=7.83 Hz, 2H)

227
-continued

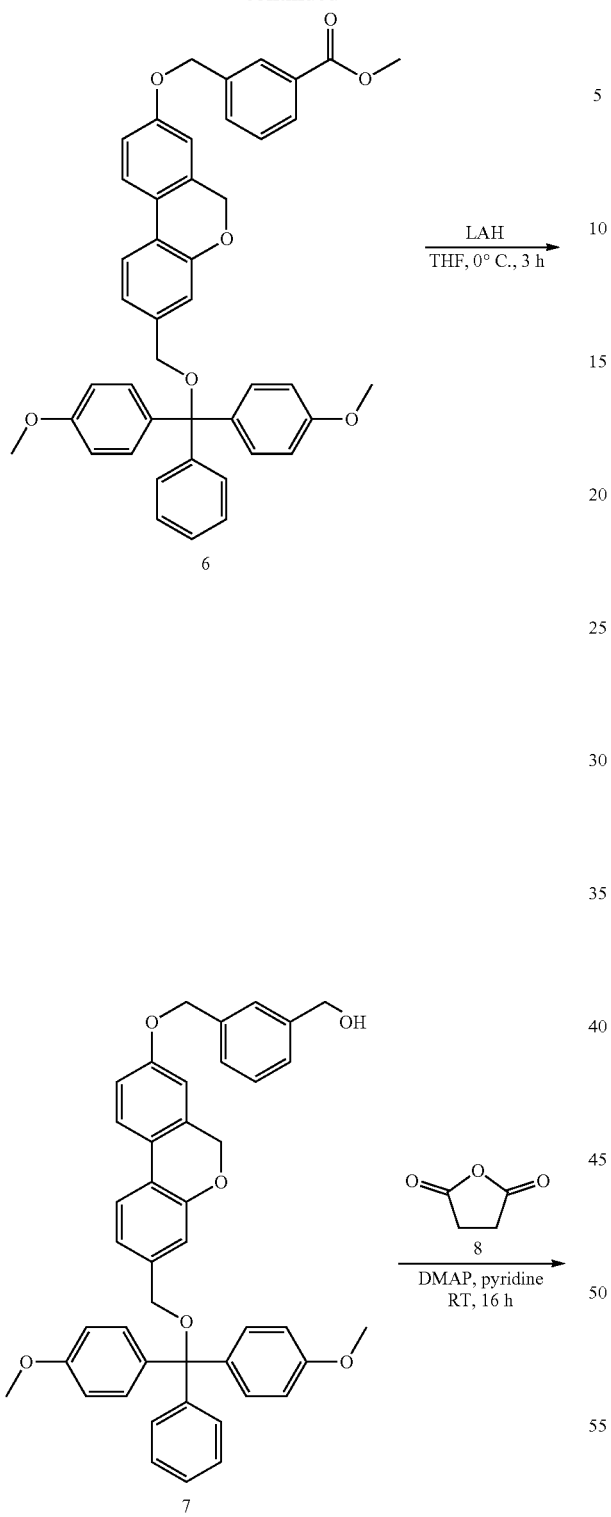

228
-continued

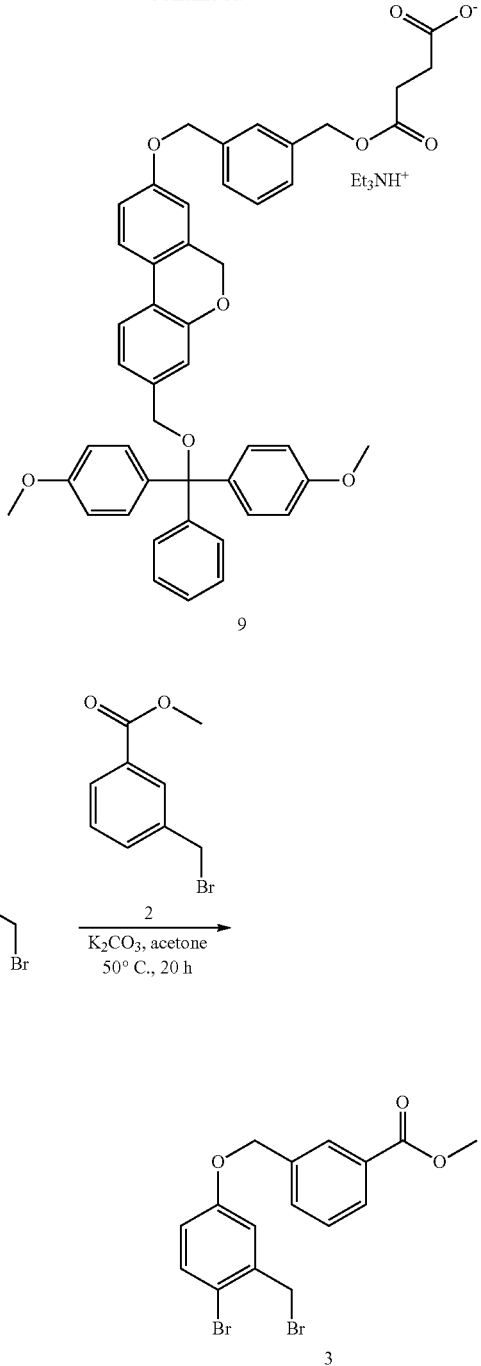

To a 40 mL vial with septa were added 4-bromo-3-(bromomethyl)phenol (1, 0.360 g, 1.25 mmol), methyl 3-(bromomethyl)benzoate (2, 0.856 g, 3.74 mmol), $K_2CO_3$ (0.516 g, 3.74 mmol), and acetone (6 mL). The vial was evacuated/$N_2$ backfilled 2×, and heated at 50° C. for 20 h. after cooling to rt, the mixture was filtered washing with $CH_2Cl_2$, and concentrated under vacuum. The residue was purified by silica gel chromatography (ethyl acetate/heptane), giving 3 (0.391 g, 62%) as a white solid. $^1$H NMR (400 MHz, DMSO-$d_6$) δ ppm 3.88 (s, 3H) 4.67 (s, 2H) 5.21 (s, 2H) 6.98 (dd, J=8.59, 3.03 Hz, 1H) 7.35 (d, J=3.03 Hz, 1H) 7.52-7.58 (m, 2H) 7.72 (d, J=8.08 Hz, 1H) 7.91-7.95 (m, 1H) 8.05 (s, 1H)

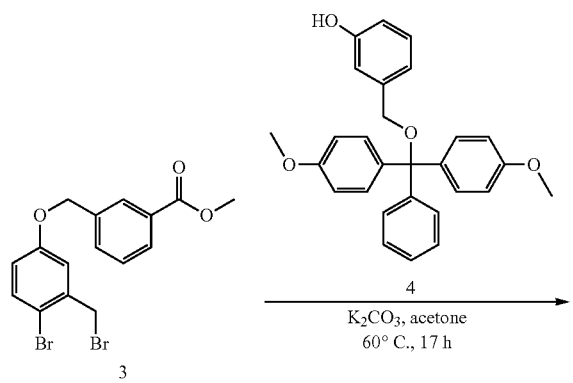

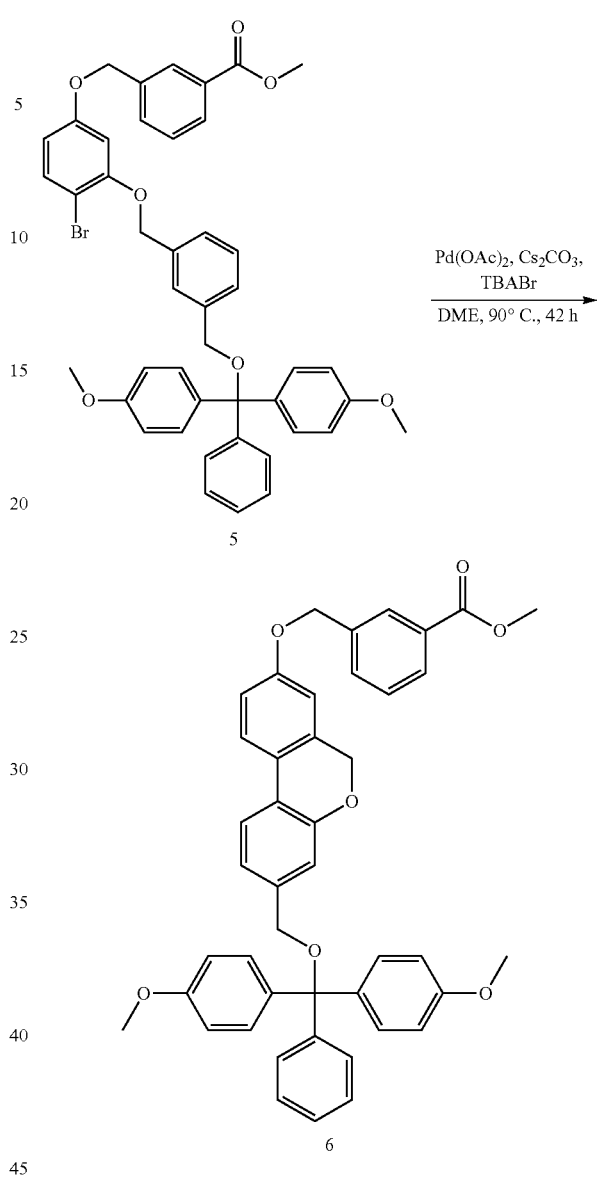

Synthesis of compound 4 is described in the synthesis of X063. To a 40 mL vial with a septa was added compounds 3 (0.390 g, 0.763 mmol), 4 (0.390 g, 0.915 mmol), $K_2CO_3$ (0.316 g, 2.29 mmol) and acetone (4 mL). The vial was sealed and the contents were evacuated/$N_2$ backfilled 2×. The vial was then heated at 60° C. for 17 h. After cooling to rt, the mixture was filtered washing with $CH_2Cl_2$, and concentrated under vacuum. The residue was purified by silica gel chromatography (ethyl acetate/heptane/triethylamine), giving 5 (0.448 g, 77%) as a foamy solid. $^1$H NMR (400 MHz, DMSO-$d_6$) δ ppm 3.74 (s, 6H) 3.85 (s, 3H) 4.10 (s, 2H) 5.08 (s, 2H) 5.20 (s, 2H) 6.87-6.92 (m, 4H) 6.92-7.02 (m, 4H) 7.19-7.26 (m, 3H) 7.26-7.35 (m, 7H) 7.39-7.45 (m, 2H) 7.50 (t, J=7.83 Hz, 1H) 7.56 (d, J=8.59 Hz, 1H) 7.68 (d, J=7.58 Hz, 1H) 7.90 (d, J=7.58 Hz, 2H) 8.02 (s, 1H)

To compound 5 (0.540 g, 0.569 mmol) in a vial with a septa, was added dimethoxyethane (5.7 mL), $Bu_4NBr$ (0.275 g, 0.853 mmol), $Cs_2CO_3$ (0.278 g, 0.853 mmol), and $Pd(OAc)_2$ (0.026 g, 0.11 mmol). The vial was sealed, degassed with two cycles of vacuum/$N_2$ backfill, and heated at 90° C. overnight. ~33% conversion was observed after 17 h by LCMS. An additional 0.100 g of $Pd(OAc)_2$ (0.44 mmol) was added, and the reaction was continued for an additional 24 h. After cooling to rt, the mixture was filtered through celite eluting with EtOAc. The solution was then washed 1× each with aq. sat. $NaHCO_3$, water and brine. The organic portion was dried with $Na_2SO_4$, filtered, and concentrated under vacuum. The residue was purified by silica gel chromatography (ethyl acetate/heptane/triethylamine), giving 6 (0.105 g, 27%) as a foamy solid. $^1$H NMR (400 MHz, DMSO-d6) δ ppm 3.75 (s, 6H) 3.87 (s, 3H) 4.08 (s, 2H) 5.09 (s, 2H) 5.24 (s, 2H) 6.88-6.95 (m, 5H) 6.95-7.00 (m, 2H) 7.05 (dd, J=8.34, 2.78 Hz, 2H) 7.21-7.26 (m, 2H) 7.29-7.36 (m, 6H) 7.39-7.46 (m, 2H) 7.55 (t, J=7.83 Hz, 1H) 7.69-7.77 (m, 3H) 7.92 (d, J=8.08 Hz, 1H) 8.05 (s, 1H)

231

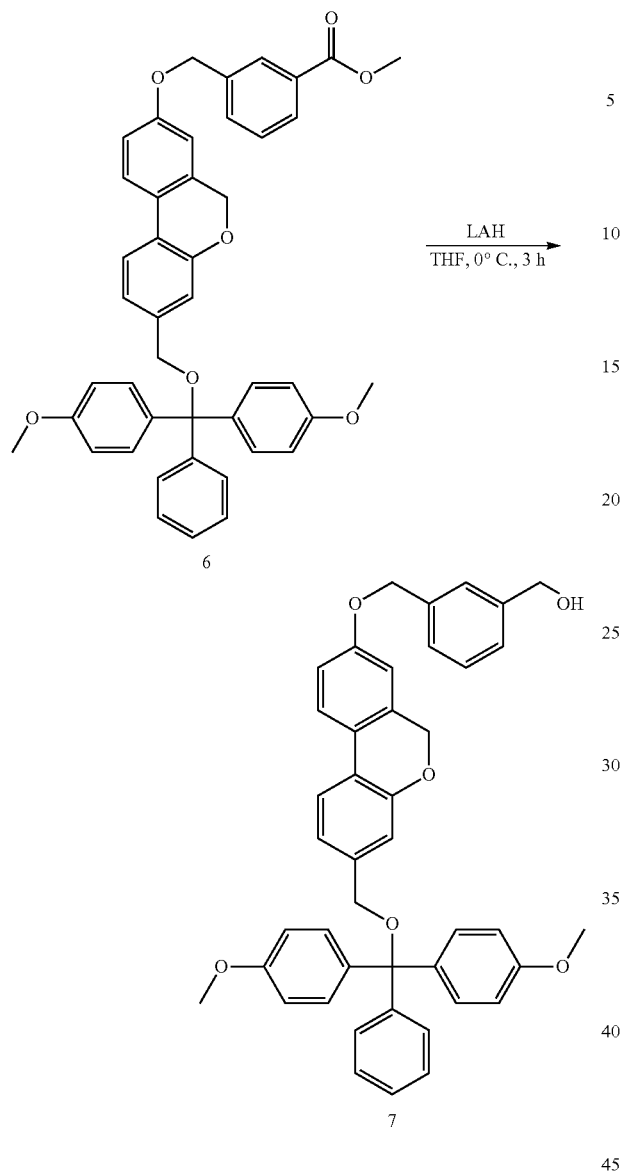

232

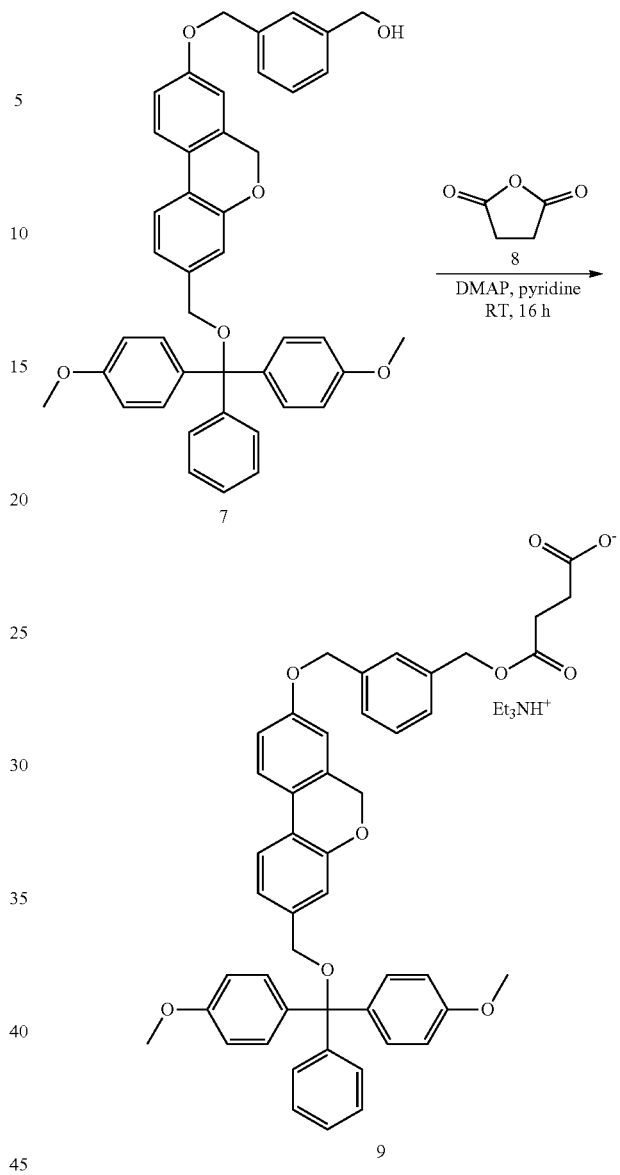

Compound 6 (0.135 g, 0.199 mmol) in THF (2 mL) was cooled to 0° C., under an atmosphere of N$_2$. A 1M suspension of LAH in THF (0.477 mL, 0.477 mmol) was added dropwise, and the solution was stirred at 0° C. for 3 h. 1 mL EtOAc was added dropwise, and the solution was stirred at 0° C. for 20 min. 0.018 mL H$_2$O, 0.018 mL 20% aq. NaOH, and 0.054 mL H$_2$O were added successively, and the mixture was stirred at rt for 1 h. the mixture was dried with Na$_2$SO$_4$, filtered through celite washing with EtOAc, and concentrated under vacuum. The residue was purified by silica gel chromatography (ethyl acetate/heptane/triethylamine), giving 7 (0.110 g, 85%) as a foamy solid. $^1$H NMR (400 MHz, DMSO-d$_6$) δ ppm 3.75 (s, 6H) 4.08 (s, 2H) 4.52 (d, J=5.56 Hz, 2H) 5.04 (t, J=5.81 Hz, 1H) 5.08 (s, 2H) 5.14 (s, 2H) 6.89-6.94 (m, 5H) 6.95 (d, J=2.53 Hz, 1H) 6.98 (dd, J=8.08, 1.52 Hz, 1H) 7.03 (dd, J=8.59, 2.53 Hz, 1H) 7.24 (t, J=7.33 Hz, 1H) 7.26-7.37 (m, 9H) 7.40-7.46 (m, 3H) 7.72 (d, J=8.08 Hz, 2H). MS (ESI+) m/z: calcd for C$_{43}$H$_{38}$O$_6$ 650.3. found 303.4 [DMT$^+$].

Dimethylaminopyridine (0.019 g, 0.157 mmol) was added to a solution of compound 7 (0.102 g, 0.157 mmol) in pyridine (3 mL) at rt under argon. Succinic anhydride 8 (0.031 g, 0.313 mmol) was added, and the solution was stirred at rt for 16 h. 0.5 mL of H$_2$O was added and the solution was stirred for 30 min. 50 mL of CH$_2$Cl$_2$ was added, the solution was washed 1x with 25 mL cold 10% aq. citric acid and 2x each with 25 mL of water. The aqueous fractions were re-extracted with 1x 25 mL of CH$_2$Cl$_2$. The organic fractions were dried with Na$_2$SO$_4$, filtered, concentrated under vacuum, and diluted/concentrated 2x with toluene. The residue was purified by silica gel chromatography (dichloromethane/methanol/triethylamine) (49:1/1%), giving 9 (0.10 g, 76%) as an oil. $^1$H NMR (400 MHz, CDCl$_3$) δ ppm 1.46 (t, J=7.33 Hz, 2.1H) 2.57 (t, J=6.82 Hz, 2H) 2.68 (t, J=6.82 Hz, 2H) 3.61 (q, J=7.16 Hz, 1.4H) 3.80 (s, 6H) 4.15 (s, 2H) 5.09 (s, 2H) 5.09 (s, 2H) 5.15 (s, 2H) 6.78 (d, J=2.53 Hz, 1H) 6.82-6.88 (m, 4H) 6.95-7.04 (m, 2H) 7.06 (s, 1H) 7.18-7.25 (m, 1H) 7.28-7.36 (m, 3H) 7.36-7.46 (m, 7H) 7.50-7.55 (m, 2H) 7.61 (dd, J=8.34, 2.27 Hz, 2H)

2.L. Synthesis of X051 Succinate
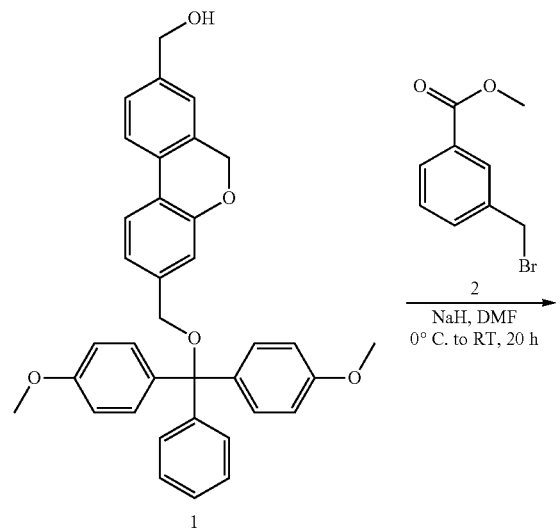
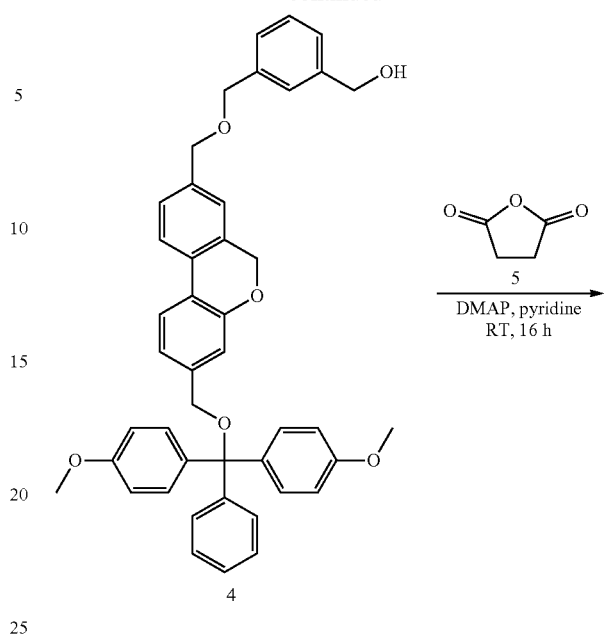
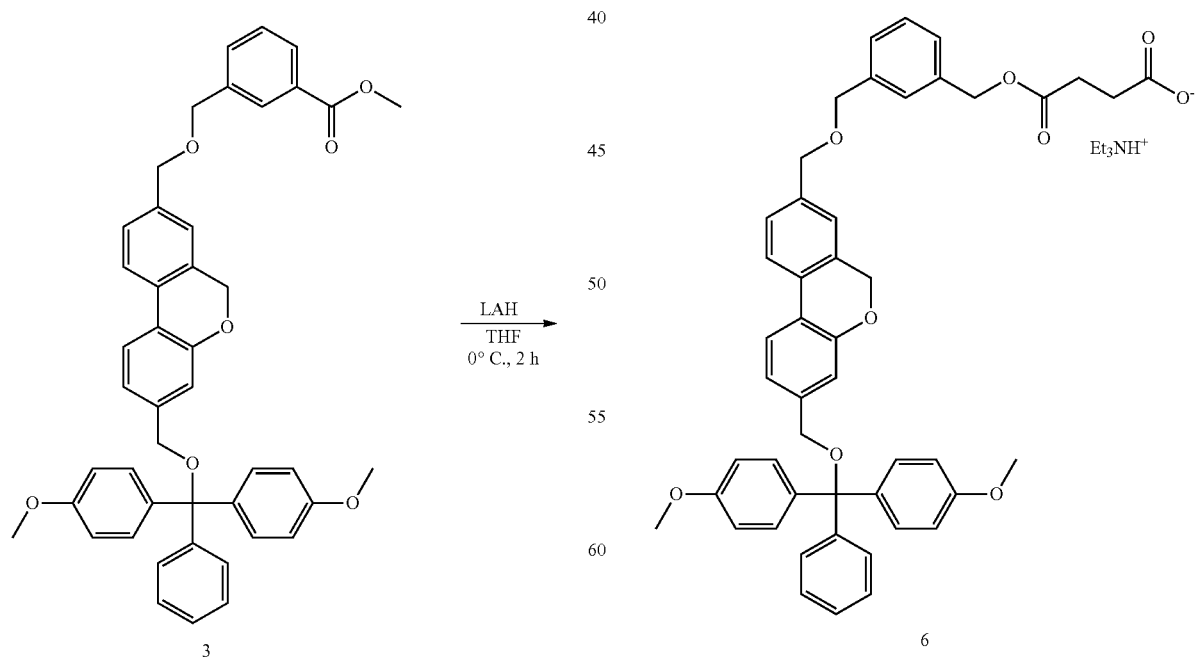

ester

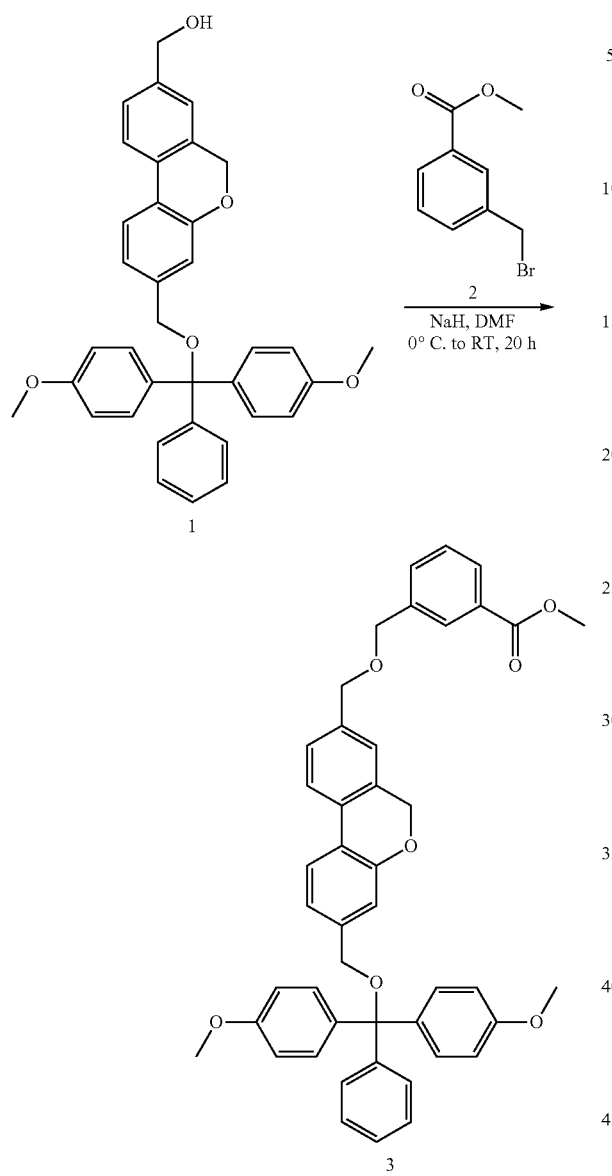

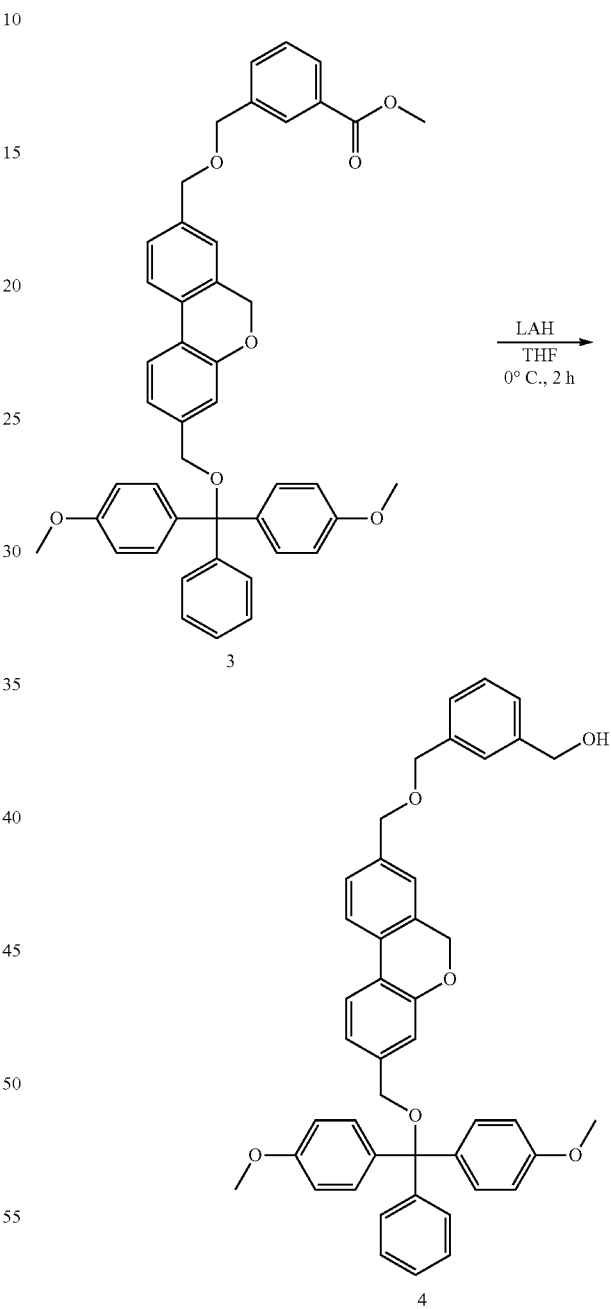

The synthesis of compound 1 is described in the synthesis of X063. Compound 1 (6.70 g, 12.3 mmol) was dissolved in THF (123 mL), evacuated/N$_2$ purged 2×, and cooled to 0° C. A 60% dispersion of NaH in mineral oil was added (0.886 g, 36.9 mmol), and the mixture was stirred at 0° C. for 20 min. Methyl 3-(bromomethyl)benzoate (2, 3.38 g, 14.8 mmol) was then added, and the mixture was stirred at rt for 20 h. The reaction mixture was then diluted with 400 mL of EtOAc and washed 1× with 400 mL sat. aq. NaHCO$_3$. The aqueous layer was back-extracted with 200 mL of EtOAc, and the combined organic layers were washed 1× each with 400 mL water and brine. The organic portion was dried with Na$_2$SO$_4$, filtered, and concentrated under vacuum. The residue was purified by silica gel chromatography (ethyl acetate/heptane/triethylamine), giving 3 (6.55 g, 77%) as a foamy solid. The product contained ~13% of the corresponding ethyl ester that was carried forward to the next step as an equivalent precursor. Methyl ester: $^1$H NMR (400 MHz, DMSO-d$_6$) δ ppm 1.32 (t, J=7.07 Hz, 0.38H) 3.74 (s, 6H) 3.86 (s, 2.52H) 4.08 (s, 2H) 4.32 (q, J=7.07 Hz, 0.25H) 4.58 (s, 2H) 4.64 (s, 2H) 5.14 (s, 2H) 6.93 (d, J=8.59 Hz, 4H) 6.97 (d, J=1.52 Hz, 1H) 7.04 (dd, J=8.08, 1.52 Hz, 1H) 7.25 (t, J=7.33 Hz, 1H) 7.28 (s, 1H) 7.31 (d, J=9.09 Hz, 4H) 7.33-7.41 (m, 3H) 7.44 (d, J=7.58 Hz, 2H) 7.53 (t, J=7.83 Hz, 1H) 7.66 (d, J=8.08 Hz, 1H) 7.80 (d, J=8.08 Hz, 1H) 7.83 (d, J=8.08 Hz, 1H) 7.90 (d, J=7.58 Hz, 1H) 7.97 (s, 1H)

Compound 3 in THF was cooled to 0° C. and placed under an atmosphere of N$_2$. A 1M suspension of LAH in THF (22.5 mL, 22.5 mmol) was added dropwise, and the solution was stirred at 0° C. for 2 h. 1 mL EtOAc was added dropwise, and the solution was stirred at 0° C. for 20 min. Then 0.86 mL H$_2$O, 0.86 mL 20% aq. NaOH, and 2.58 mL H$_2$O were added successively. The mixture was stirred at rt for 1 h, dried with Na$_2$SO$_4$, filtered through celite washing with EtOAc, and concentrated under vacuum. The residue was purified by silica gel chromatography (ethyl acetate/heptane/triethylamine), giving 4 (5.98 g, 96%) as a foamy solid. $^1$H NMR (400 MHz, DMSO-d$_6$) δ ppm 3.74 (s, 6H) 4.08 (s, 2H) 4.50 (d, J=6.06 Hz, 2H) 4.55 (s, 2H) 4.55 (s, 2H) 5.14 (s, 2H) 5.18 (t, J=5.81 Hz, 1H) 6.93 (d, J=8.59 Hz, 4H) 6.97 (d, J=1.01 Hz, 1H) 7.01-7.06 (m, 1H) 7.21-7.28 (m, 4H) 7.28-7.33 (m, 5H) 7.33-7.40 (m, 4H) 7.41-7.46 (m, 2H) 7.80 (d, J=8.08 Hz, 1H) 7.83 (d, J=8.08 Hz, 1H). MS (ESI+) m/z: calcd for C$_{44}$H$_{40}$O$_6$ 664.3. found 665.3 [MH$^+$].

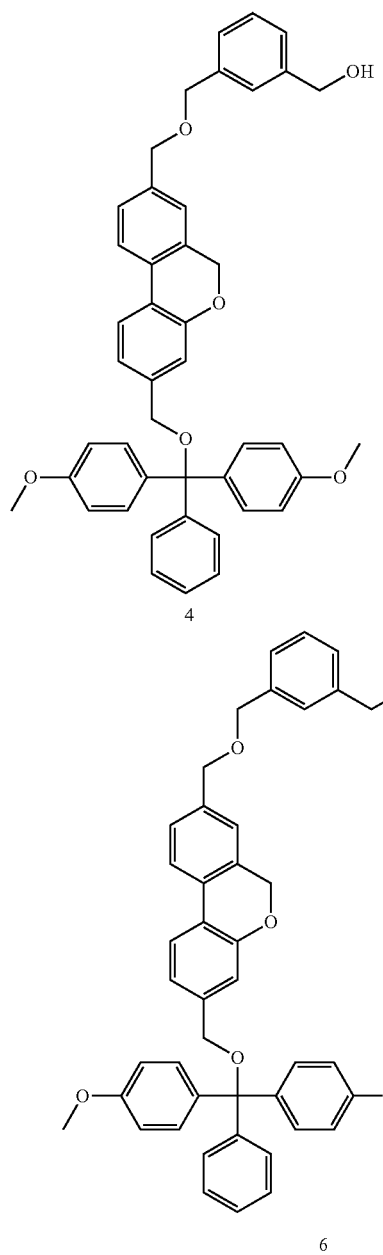

Dimethylaminopyridine (0.37 g, 3.01 mmol) was added to a solution of compound 4 (2.00 g, 3.01 mmol) in pyridine (15 mL) at rt under argon. Succinic anhydride 7 (0.60 g, 6.02 mmol) was added, and the solution was stirred at rt for 17 h. 1 mL of H$_2$O was added and the solution was stirred for 1 h. 100 mL of CH$_2$Cl$_2$ was added, and the solution was washed 1x with 50 mL cold 10% aq. citric acid and 2x each with 50 mL of water. The aqueous fractions were re-extracted with 1x 50 mL of CH$_2$Cl$_2$. The combined organic fractions were dried with Na$_2$SO$_4$, filtered, concentrated under vacuum, and diluted/concentrated 2x with toluene. The residue was purified by silica gel chromatography (dichloromethane/methanol/triethylamine) (39:1/1%), giving 6 (2.48 g, 95%) as an oil. $^1$H NMR (400 MHz, CDCl$_3$) δ ppm 1.17 (t, J=7.33 Hz, 14.2H) 2.56 (t, J=6.69 Hz, 2H) 2.68 (t, J=7.45 Hz, 2H) 2.84 (q, J=7.33 Hz, 9.5H) 3.80 (s, 6H) 4.16 (s, 2H) 4.57 (s, 2H) 4.58 (s, 2H) 5.14 (s, 2H) 5.14 (s, 2H) 6.82-6.88 (m, 4H) 7.01-7.05 (m, 1H) 7.09 (s, 1H) 7.18 (s, 1H) 7.19-7.25 (m, 1H) 7.28-7.34 (m, 5H) 7.34-7.38 (m, 2H) 7.39-7.44 (m, 4H) 7.49-7.55 (m, 2H) 7.68 (dd, J=7.96, 4.42 Hz, 2H)

2.M. Synthesis of X097 Succinate Ester

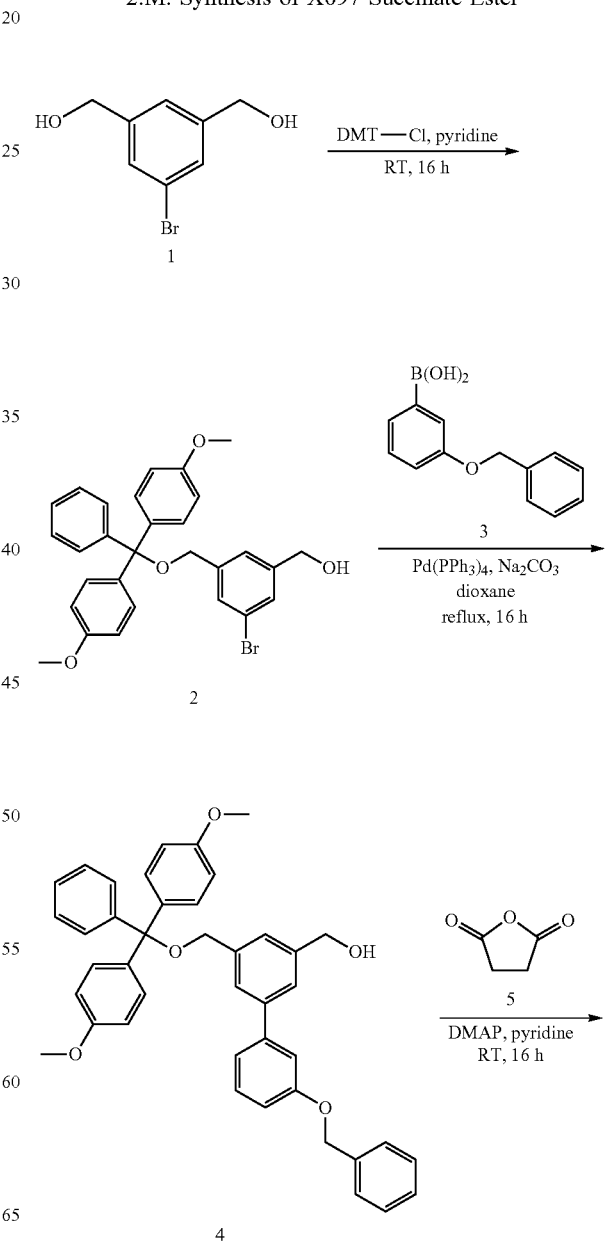

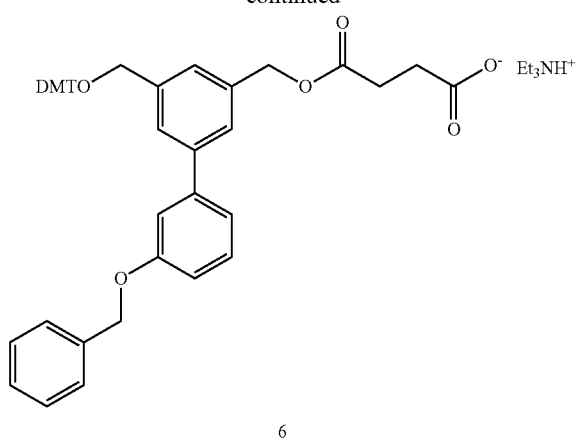

6

Scheme 1: Overview of the synthesis of 6.

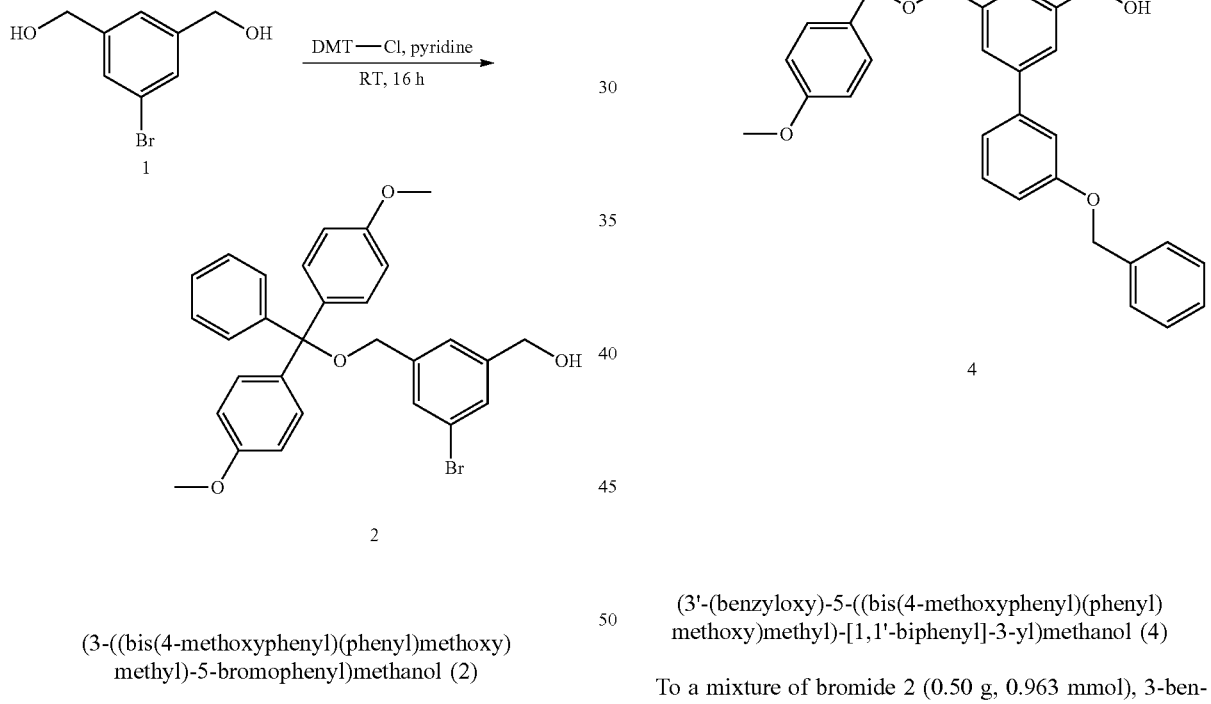

(3-((bis(4-methoxyphenyl)(phenyl)methoxy)methyl)-5-bromophenyl)methanol (2)

A solution of 5-bromo-1,3-dihydroxymethyl benzene 1 (3.00 g, 13.8 mmol), 4,4'-dimethoxytrityl chloride (4.68 g, 13.8 mmol) in pyridine (60 mL) was stirred at room temperature for 16 h. The reaction mixture was partitioned between EtOAc and water. The EtOAc layer was dried over anhydrous $Na_2SO_4$ and evaporated. The crude product was purified by flash chromatography eluting with 1% $Et_3N$ in 5-30% EtOAc/Heptane to provide 2.57 g (36%) of 2. MS (ESI+) m/z: calcd for $C_{29}H_{27}BrO_4$ 518.1. found 303.5 [DMT]+. $^1$H NMR (400 MHz, $CDCl_3$) δ 7.54-7.48 (m, 2H), 7.47-7.37 (m, 6H), 7.36-7.29 (m, 2H), 7.27-7.21 (m, 2H), 6.87 (d, J=8.8 Hz, 4H), 4.67 (d, J=6.0 Hz, 2H), 4.22 (s, 2H), 3.82 (s, 6H), 1.67 (t, J=6.0 Hz, 1H).

(3'-(benzyloxy)-5-((bis(4-methoxyphenyl)(phenyl)methoxy)methyl)-[1,1'-biphenyl]-3-yl)methanol (4)

To a mixture of bromide 2 (0.50 g, 0.963 mmol), 3-benzyloxybenzene boronic acid 3 (0.263 g, 1.155 mmol) and $Pd(PPh_3)_4$ (0.111 g, 0.096 mmol) in 1,4-dioxane (6 mL) under nitrogen atmosphere was added 2M aq. $Na_2CO_3$ (1.44 mL). The mixture was heated at reflux overnight. The reaction is then cooled to room temperature and partitioned between EtOAc and sat. aq. $NaHCO_3$. The organic layer was evaporated and the crude product was purified by flash chromatography eluting with 1% $Et_3N$ in 5-30% EtOAc/Heptane to provide 0.454 g (70%) of 4. MS (ESI+) m/z: calcd for $C_{42}H_{38}O_5$ 622.3. found 303.5 [DMT]+. $^1$H NMR (400 MHz, DMSO) δ 7.52-7.43 (m, 5H), 7.41-7.29 (m, 12H), 7.27-7.16 (m, 3H), 7.01 (m, 1H), 6.95-6.86 (m, 4H), 5.18 (s, 2H), 5.07 (t, J=5.8 Hz, 1H), 4.57 (d, J=5.8 Hz, 2H), 4.18 (s, 2H), 3.74 (s, 6H).

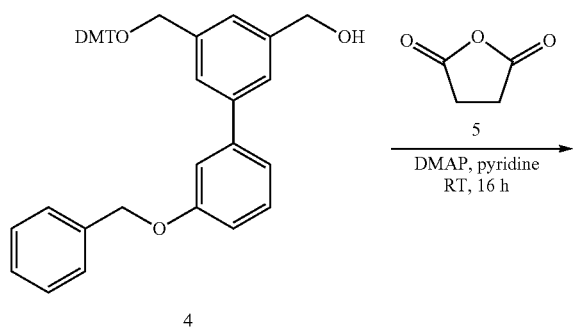

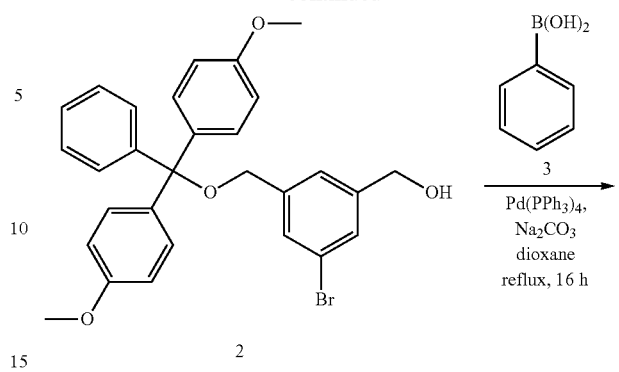

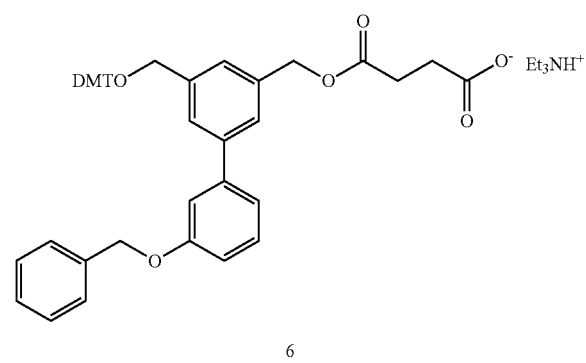

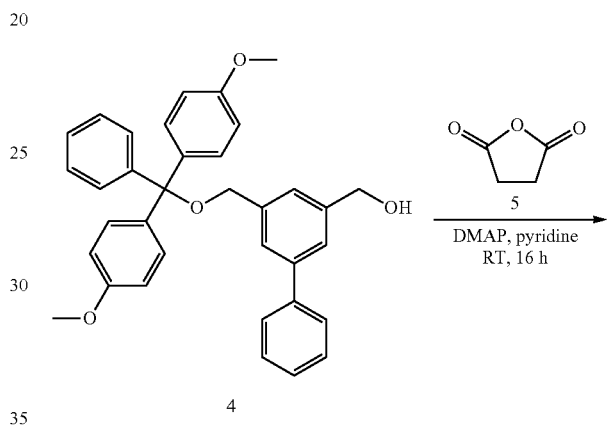

To a solution of 452 mg (0.726 mmol) 4 and 89 mg (0.726 mmol) N,N-dimethylaminopyridine (DMAP) in 5 mL dry pyridine under argon was added 145 mg (1.45 mmol) succinic anhydride (5). The reaction mixture was stirred at room temperature for 18 h and then 0.5 mL water was added. Stirring was continued for 30 min. The reaction mixture was diluted with 100 mL dichloromethane and washed with 50 mL ice-cold 10% aqueous citric acid and water (2×50 mL). The aqueous layers were reextracted with 50 mL dichloromethane. The combined organic layers were dried over $Na_2SO_4$ and evaporated. The remaining oil was coevaporated twice with toluene and the crude product purified by silica gel chromatography (dichloromethane/methanol/triethylamine 94:5:1) to give 510 mg (0.619 mmol, 85%) 6 as a colorless foam. $^1H$ NMR (400 MHz, $CDCl_3$): 1.22 (t, J=7.3 Hz, 9H), 2.57-2.59 (m, 2H), 2.67-2.69 (m, 2H), 2.97 (q, J=7.3 Hz, 6H), 3.79 (s, 6H), 4.24 (s, 2H), 5.14 (s, 2H), 5.18 (s, 2H), 5.72 (s br., 1H), 6.84-6.88 (m, 4H), 6.98 (ddd, J=0.7, 2.2, 8.2 Hz, 1H), 7.19-7.54 (m, 20H).

2.N. Synthesis of X098 Succinate Ester

Scheme 1: Overview of the synthesis of 6.

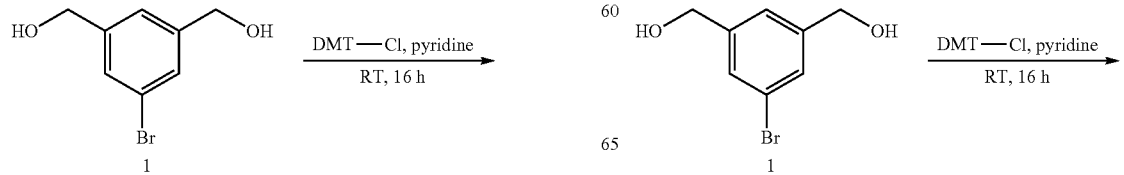

243
-continued

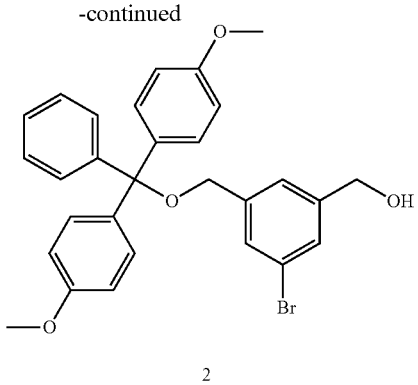

2

(3-((bis(4-methoxyphenyl)(phenyl)methoxy)methyl)-5-bromophenyl)methanol (2)

Same as above

A solution of 5-bromo-1,3-dihydroxymethyl benzene 1 (3.00 g, 13.8 mmol), 4,4'-dimethoxytrityl chloride (4.68 g, 13.8 mmol) in pyridine (60 mL) was stirred at room temperature for 16 h. The reaction mixture was partitioned between EtOAc and water. The EtOAc layer was dried over anhydrous $Na_2SO_4$ and evaporated. The crude product was purified by flash chromatography eluting with 1% $Et_3N$ in 5-30% EtOAc/Heptane to provide 2.57 g (36%) of 2. MS (ESI+) m/z: calcd for $C_{29}H_{27}BrO_4$ 518.1. found 303.5 $[DMT]^+$. $^1H$ NMR (400 MHz, $CDCl_3$) δ 7.54-7.48 (m, 2H), 7.47-7.37 (m, 6H), 7.36-7.29 (m, 2H), 7.27-7.21 (m, 2H), 6.87 (d, J=8.8 Hz, 4H), 4.67 (d, J=6.0 Hz, 2H), 4.22 (s, 2H), 3.82 (s, 6H), 1.67 (t, J=6.0 Hz, 1H).

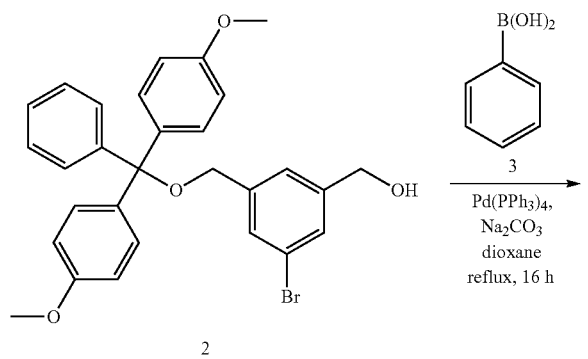

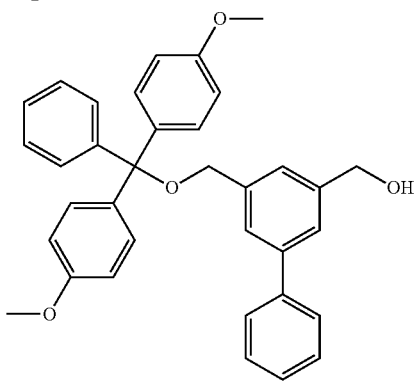

4

244

(5-((bis(4-methoxyphenyl)(phenyl)methoxy)methyl)-[1,1'-biphenyl]-3-yl)methanol (4)

To a mixture of the bromide 2 (0.500 g, 0.960 mmol), benzene boronic acid 3 (0.141 g, 1.16 mmol), and $Pd(PPh_3)_4$ (0.111 g, 0.096 mmol) in 1,4-dioxane (6 mL) under nitrogen atmosphere was added 2M aq. $Na_2CO_3$ (1.44 mL). The mixture was heated at reflux overnight. The reaction was then cooled to room temperature and partitioned between EtOAc and sat. aq. $NaHCO_3$. The organic layer was evaporated and the crude product was purified by flash chromatography eluting with 1% $Et_3N$ in 5-30% EtOAc/Heptane to provide 0.380 g (76%) of 4. MS (ESI+) m/z: calcd for $C_{35}H_{32}O_4$ 516.2. found 303.5 $[DMT]^+$. $^1H$ NMR (400 MHz, DMSO) δ 7.61 (dd, J=8.3, 1.3 Hz, 2H), 7.51-7.42 (m, 5H), 7.39-7.28 (m, 9H), 7.27-7.20 (m, 1H), 6.95-6.86 (m, 4H), 5.08 (t, J=5.8 Hz, 1H), 4.57 (d, J=5.8 Hz, 2H), 4.19 (s, 2H), 3.74 (s, 6H).

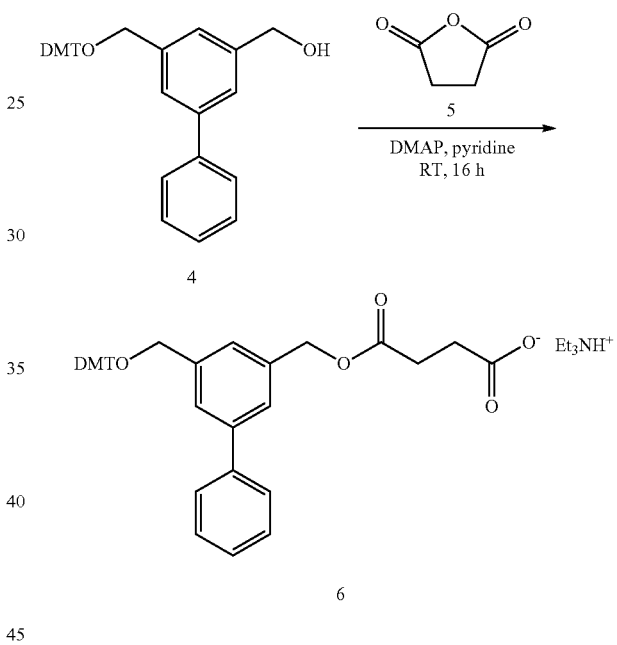

To a solution of 380 mg (0.736 mmol) 4 and 90 mg (0.736 mmol) N,N-dimethylaminopyridine (DMAP) in 5 mL dry pyridine under argon was added 147 mg (1.47 mmol) succinic anhydride (5). The reaction mixture was stirred at room temperature for 18 h and then 0.5 mL water was added. Stirring was continued for 30 min. The reaction mixture was diluted with 100 mL dichloromethane and washed with 50 mL ice-cold 10% aqueous citric acid and water (2×50 mL). The aqueous layers were reextracted with 50 mL dichloromethane. The combined organic layers were dried over $Na_2SO_4$ and evaporated. The remaining oil was coevaporated twice with toluene and the crude product purified by silica gel chromatography (dichloromethane/methanol/triethylamine 94:5:1) to give 460 mg (0.641 mmol, 87%) 6 as an off-white foam. $^1H$ NMR (400 MHz, $CDCl_3$): 1.22 (t, J=7.2 Hz, 9H), 2.59 (t, J=7.1 Hz, 2H), 2.71 (t, J=7.1 Hz, 2H), 2.94 (q, J=7.2 Hz, 6H), 3.81 (s, 6H), 4.26 (s, 2H), 5.20 (s, 2H), 6.04 (s br., 1H), 6.85-6.89 (m, 4H), 7.22-7.55 (m, 15H), 7.62 (d, J=7.9 Hz, 2H).

2.O. Synthesis of siRNA Conjugated with X109 ss-siRNA=antisense single strand sequence used in conjugation=
U002pUpApApU004pU004pApU004pCpU004pAp-U004pU004pCpCpGpU005pA005pC027
(SEQ ID NO: 44)
002=DNA
004=2'Ome
005=2'MOE
C027=ribitol
p=phosphate Thus, in this and various other sequences disclosed herein, 0004 indicates a nucleotide with a U base with a 2'Ome modification; 0002 indicates a nucleotide with a U base which is DNA; U005 indicates a base with a U base with a 2'MOE modification. Similarly, other nucleotides are modified, e.g., C004 indicates a nucleotide with a C base and a 2'Ome modification.

X006=O—(CH$_2$)—NH$_2$

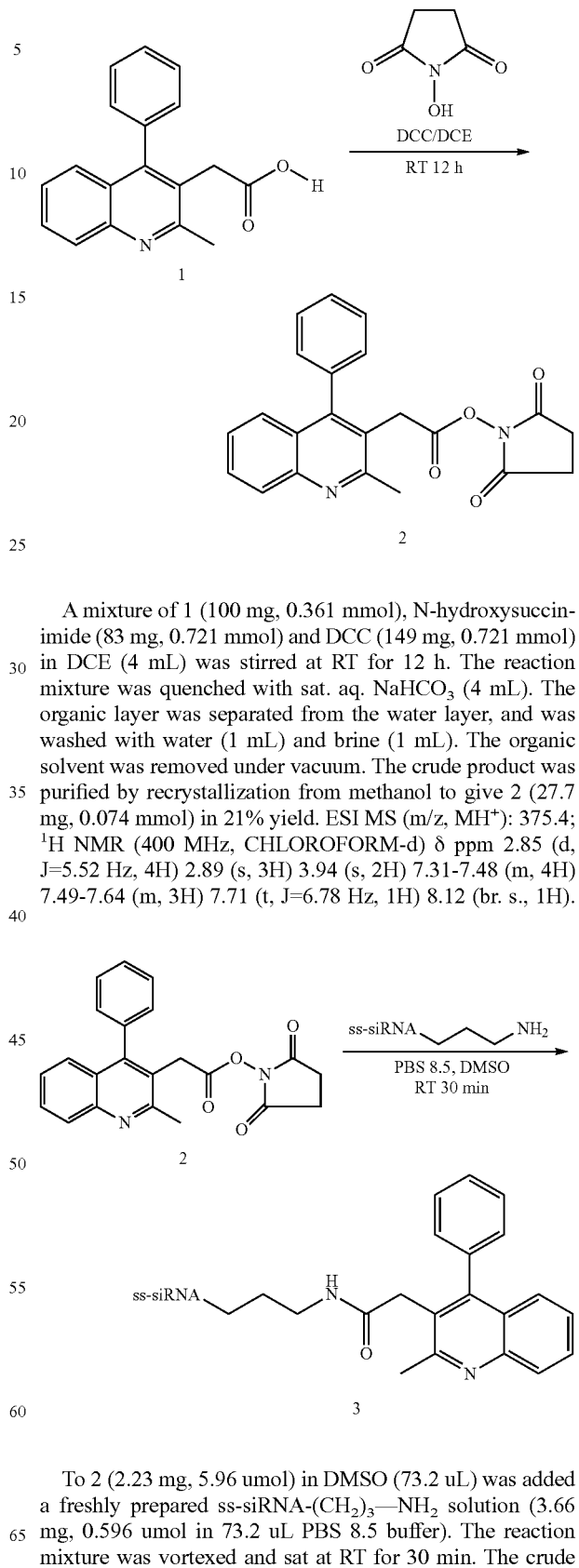

Scheme 1: Overview of the synthesis of 3.

A mixture of 1 (100 mg, 0.361 mmol), N-hydroxysuccinimide (83 mg, 0.721 mmol) and DCC (149 mg, 0.721 mmol) in DCE (4 mL) was stirred at RT for 12 h. The reaction mixture was quenched with sat. aq. NaHCO$_3$ (4 mL). The organic layer was separated from the water layer, and was washed with water (1 mL) and brine (1 mL). The organic solvent was removed under vacuum. The crude product was purified by recrystallization from methanol to give 2 (27.7 mg, 0.074 mmol) in 21% yield. ESI MS (m/z, MH$^+$): 375.4; $^1$H NMR (400 MHz, CHLOROFORM-d) δ ppm 2.85 (d, J=5.52 Hz, 4H) 2.89 (s, 3H) 3.94 (s, 2H) 7.31-7.48 (m, 4H) 7.49-7.64 (m, 3H) 7.71 (t, J=6.78 Hz, 1H) 8.12 (br. s., 1H).

To 2 (2.23 mg, 5.96 umol) in DMSO (73.2 uL) was added a freshly prepared ss-siRNA-(CH$_2$)$_3$—NH$_2$ solution (3.66 mg, 0.596 umol in 73.2 uL PBS 8.5 buffer). The reaction mixture was vortexed and sat at RT for 30 min. The crude product was purified by HPLC with 5-60% 100 mM triethylammonium acetate in acetonitrile/water to afford 3 (1.09 mg, 0.164 umol) in 27.5% yield. TOF MS (ES⁻): 6403.

2.P. Synthesis of siRNA Conjugated with X110

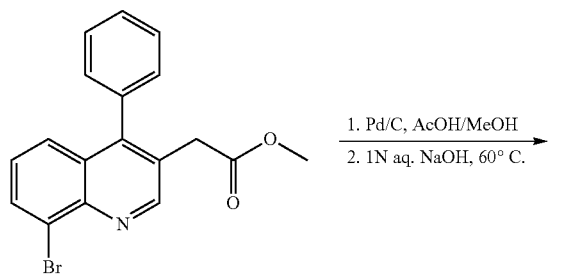
1

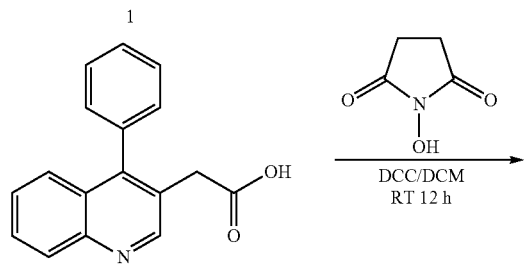
2

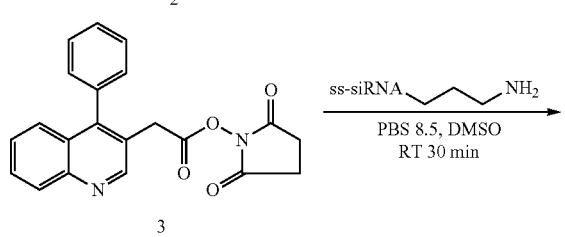
3

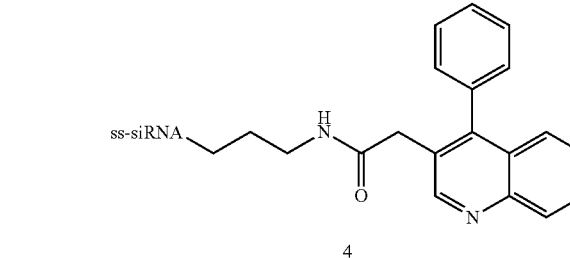
4

Scheme 2: Overview of the synthesis of 4.

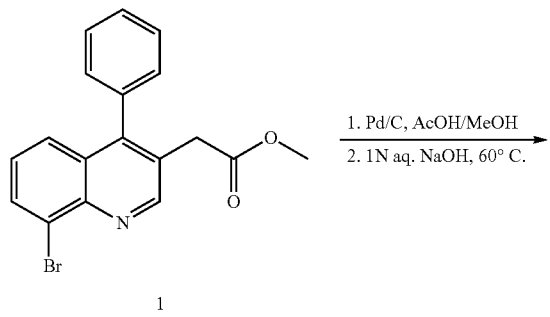
1

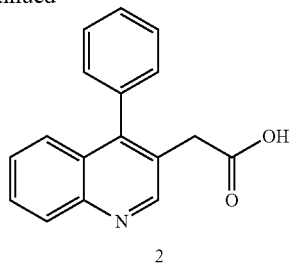
2

A mixture of 1 (500 mg, 1.40 mmol), Pd (30% on carbon, 24.9 mg, 0.070 mmol), and acetic acid (80 ul, 1.40 mmol) in methanol (15 mL) was stirred at RT under H$_2$ (1 atm) for 12 h. The reaction mixture was filtered to remove Pd/C. To the solution was added aq. 1M NaOH (3 mL), and the resulting mixture was heated at 60° C. for 12 h. The mixture was cooled to RT and neutralized with aq. 1M HCl to give form a precipitate. The precipitate was collected by vacuum filtration and dried in the oven to give 2 (166 mg, 0.63 mmol) with 45% yield. ESI MS (m/z, MH⁺): 264.4. ¹H NMR (400 MHz, DMSO-d$_6$) δ ppm 3.58 (s, 2H) 7.18-7.39 (m, 3H) 7.44-7.65 (m, 4H) 7.75 (ddd, J=8.28, 6.78, 1.51 Hz, 1H) 8.01-8.20 (m, 1H) 8.91 (s, 1H) 12.47 (s, 1H).

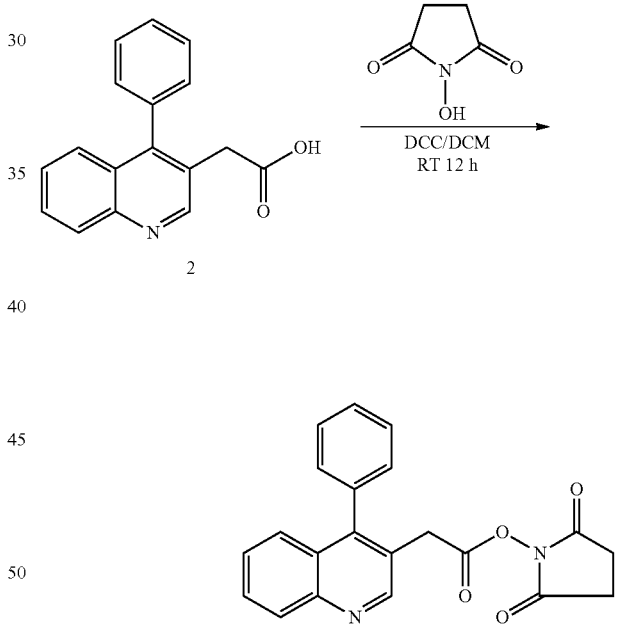

A mixture of 2 (87.6 mg, 0.333 mmol), N-hydroxysuccinimide (77.0 mg, 0.665 mmol) and DCC (137 mg, 0.665 mmol) in DCM (4 mL) was stirred at RT for 12 h. The reaction mixture was quenched with sat. aq. NaHCO$_3$ (4 mL). The organic layer was separated from the water layer, and was washed with water (1 mL) and brine (1 mL). The organic solvent was removed under vacuum. The crude product was purified by recrystallization from methanol to give 3 (27.7 mg, 0.074 mmol) in 49% yield. ESI MS (m/z, MH⁺): 361.2. ¹H NMR (400 MHz, DMSO-d$_6$) δ ppm 2.79 (br. s., 4H) 4.05 (s, 2H) 7.29-7.37 (m, 2H) 7.40 (s, 1H) 7.50-7.64 (m, 4H) 7.80 (s, 1H) 8.10 (s, 1H) 9.02 (s, 1H).

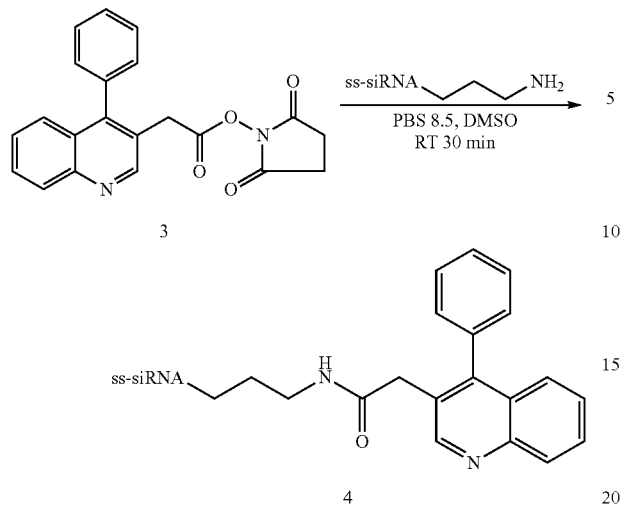

To 3 (1.76 mg, 4.88 umol) in DMSO (240 uL) was added a freshly ss-siRNA-(CH$_2$)$_3$—NH$_2$ solution (2 mg, 0.325 umol in 40 uL PBS 8.5 buffer). The reaction mixture was vortexed and sat at RT for 30 min. The crude product was purified by HPLC with 5-60% 100 mM triethylammonium acetate in acetonitrile/water to afford 4 (0.526 mg, 0.082 umol) in 25% yield. TOF MS (ES⁻): 6388.

2. Q. Synthesis of siRNA Conjugated with X111

1 is commercial, but synthesis is not known in the literature

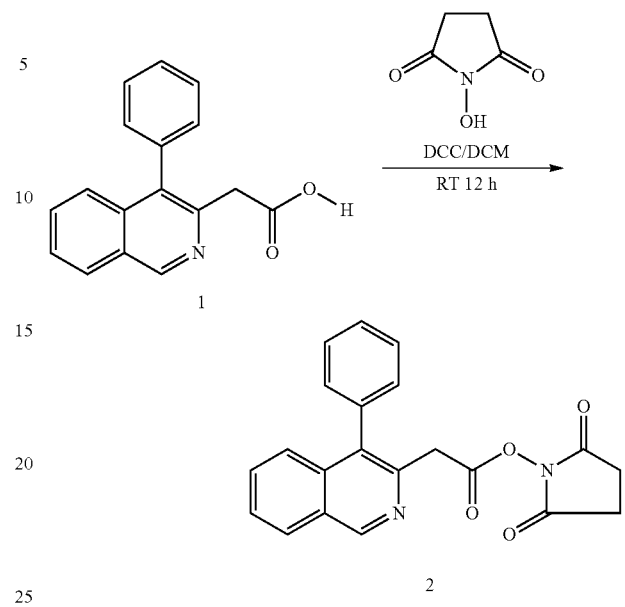

Scheme 3: Overview of the synthesis of 3.

A mixture of 1 (81 mg, 0.308 mmol), N-hydroxysuccinimide (70.8 mg, 0.615 mmol) and DCC (127 mg, 0.615 mmol) in DCM (4 mL) was stirred at RT for 12 h. The reaction mixture was quenched with sat. aq. NaHCO$_3$ (4 mL). The organic layer was separated from the water layer, and was washed with water (1 mL) and brine (1 mL). The organic solvent was removed under vacuum. The crude product was purified by recrystallization from methanol to give 2 (43.7 mg, 0.121 mmol) in 39% yield. ESI MS (m/z, MH⁺): 361.4. ¹H NMR (400 MHz, METHANOL-d$_4$) δ ppm 2.82 (s, 4H) 4.07 (s, 2H) 7.36-7.42 (m, 2H) 7.46-7.51 (m, 1H) 7.55-7.64 (m, 3H) 7.70-7.77 (m, 2H) 8.20 (dt, J=4.52, 2.26 Hz, 1H) 9.29 (s, 1H).

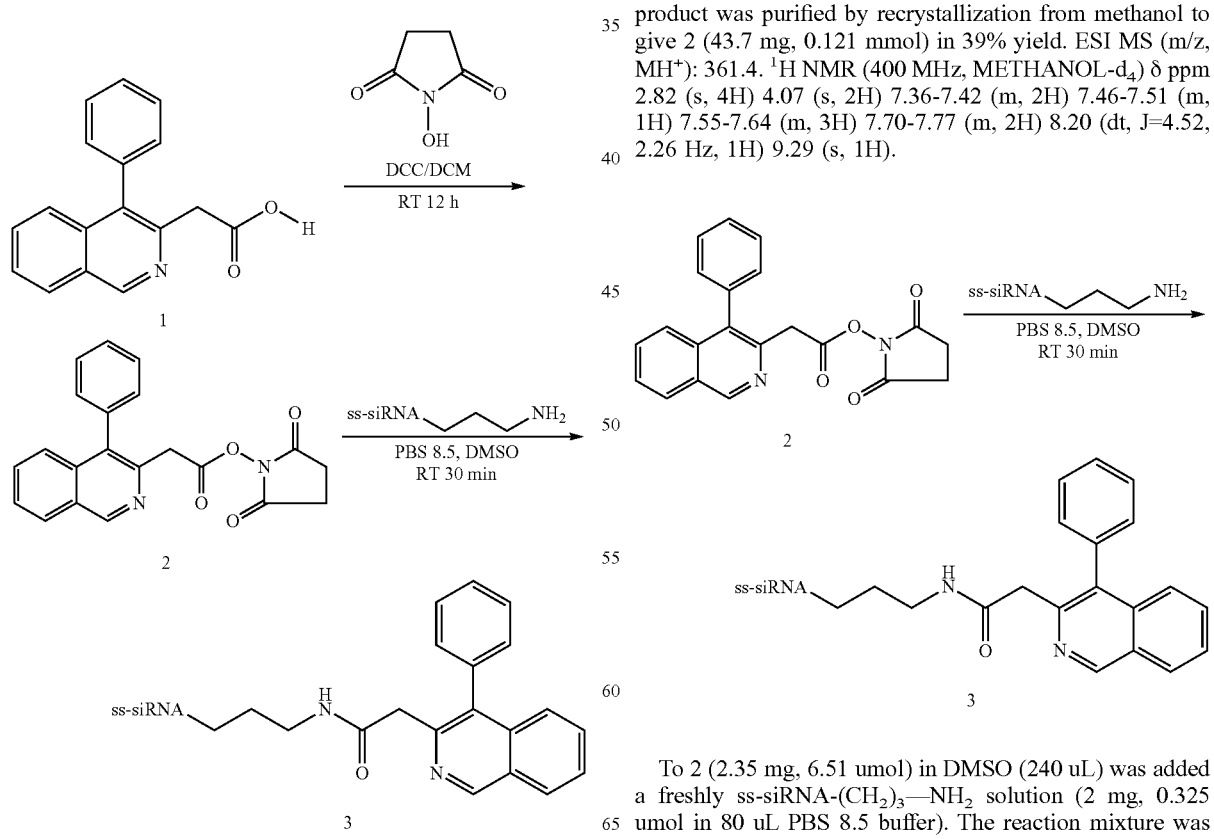

To 2 (2.35 mg, 6.51 umol) in DMSO (240 uL) was added a freshly ss-siRNA-(CH$_2$)$_3$—NH$_2$ solution (2 mg, 0.325 umol in 80 uL PBS 8.5 buffer). The reaction mixture was vortexed and sat at RT for 30 min. The crude product was purified by HPLC with 5-60% 100 mM triethylammonium acetate in acetonitrile/water to afford 3 (0.68 mg, 0.082 umol) in 33% yield. TOF MS (ES⁻): 6390.

2.R. Synthesis of siRNA Conjugated with X112

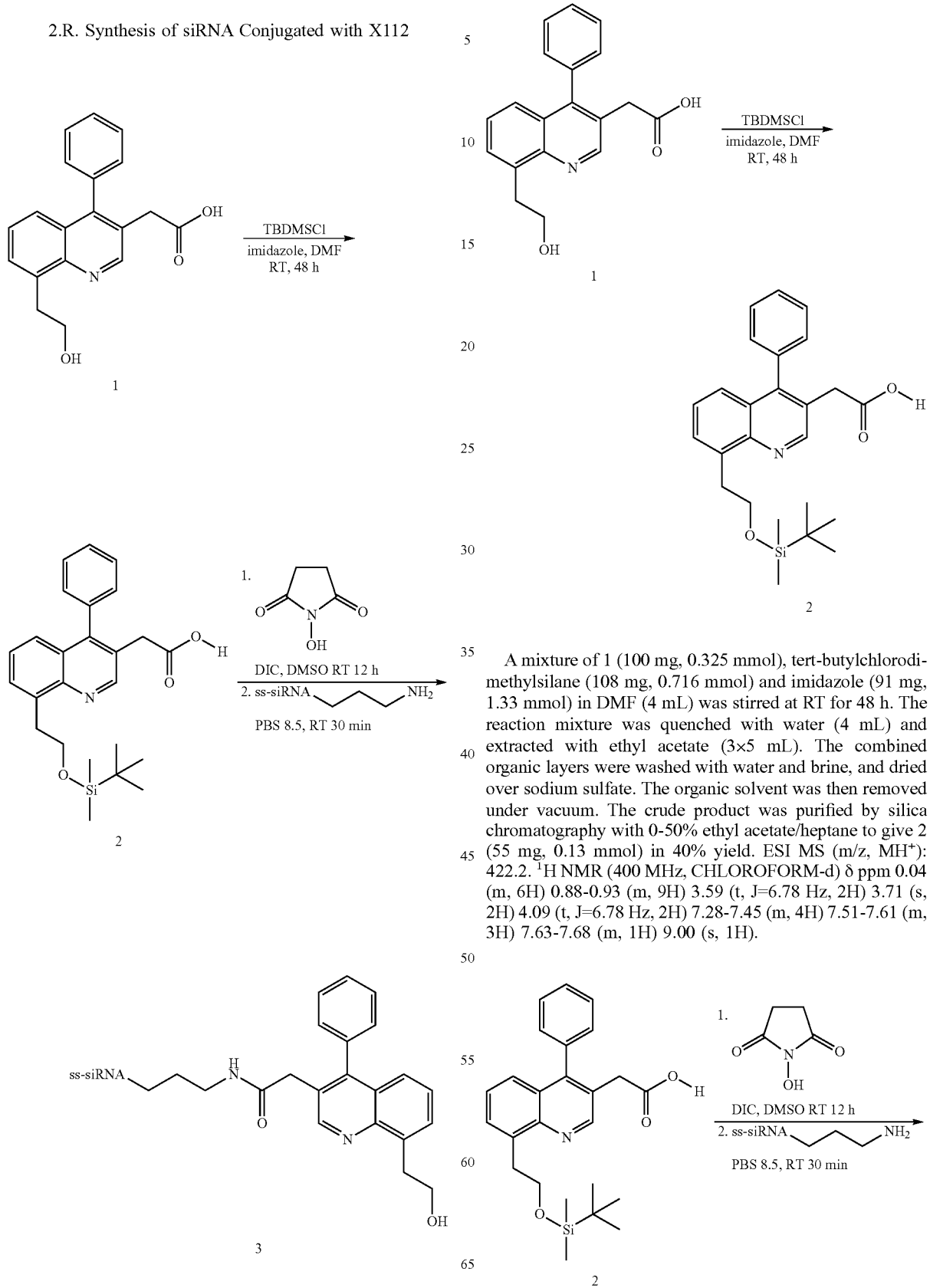

Scheme 4: Overview of the synthesis of 3.

A mixture of 1 (100 mg, 0.325 mmol), tert-butylchlorodimethylsilane (108 mg, 0.716 mmol) and imidazole (91 mg, 1.33 mmol) in DMF (4 mL) was stirred at RT for 48 h. The reaction mixture was quenched with water (4 mL) and extracted with ethyl acetate (3×5 mL). The combined organic layers were washed with water and brine, and dried over sodium sulfate. The organic solvent was then removed under vacuum. The crude product was purified by silica chromatography with 0-50% ethyl acetate/heptane to give 2 (55 mg, 0.13 mmol) in 40% yield. ESI MS (m/z, MH⁺): 422.2. ¹H NMR (400 MHz, CHLOROFORM-d) δ ppm 0.04 (m, 6H) 0.88-0.93 (m, 9H) 3.59 (t, J=6.78 Hz, 2H) 3.71 (s, 2H) 4.09 (t, J=6.78 Hz, 2H) 7.28-7.45 (m, 4H) 7.51-7.61 (m, 3H) 7.63-7.68 (m, 1H) 9.00 (s, 1H).

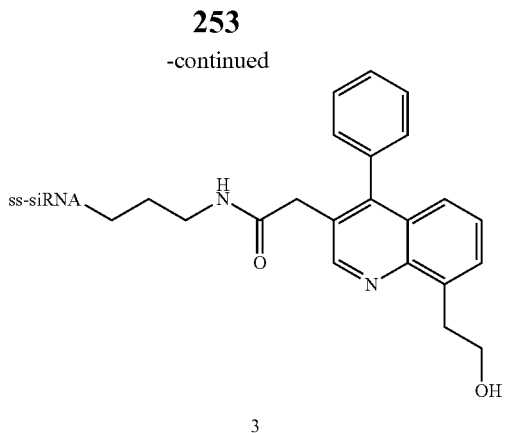

3

A mixture of N-hydroxysuccinimide (2.73 mg, 0.024 mmol), 2 (5.0 mg, 0.012 mmol), and DIC (2 mg, 0.325 umol) in DMSO (200 uL) was stirred at RT for 12 h. 10 uL reaction mixture was diluted with 190 uL DMSO. To the resulting solution was added a freshly ss-siRNA-(CH$_2$)$_3$—NH$_2$ solution (2.19 mg, 0.356 umol in 80 ul PBS 8.5 buffer). The reaction mixture was vortexed and sat at RT for 2 h. The crude product was purified by HPLC with 10-40% 100 mM triethylammonium acetate in acetonitrile/water to afford 3 (0.79 mg, 0.123 umol) in 35% yield. TOF MS (ES$^-$): 6435.

2.S. Synthesis of siRNA Conjugated with X113

1 is commercial and synthesis is known in the literature. Zhang, Yon et al. From PCT Int. Appl., 2010083384, 22 Jul. 2010.

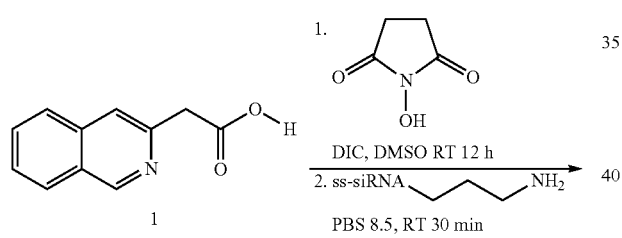

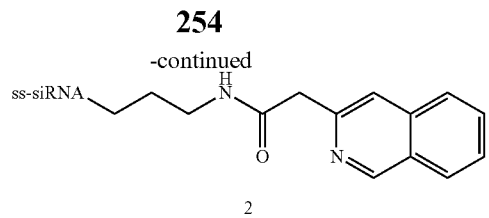

Scheme 5: Overview of the synthesis of 2.

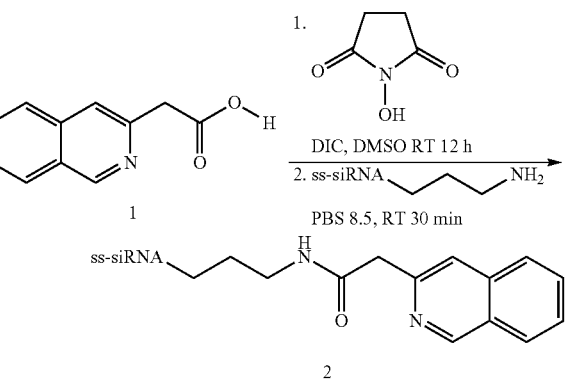

A mixture of N-hydroxysuccinimide (6.18 mg, 0.054 mmol), 1 (5.0 mg, 0.027 mmol), and DIC (6.77 mg, 0.054 mmol) in DMSO (200 uL) was stirred at RT for 12 h. 10 uL of reaction mixture was diluted with 190 uL DMSO. To the resulting solution was added a freshly ss-siRNA-(CH$_2$)$_3$—NH$_2$ solution (2.46 mg, 0.401 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 2 (0.24 mg, 0.038 umol) in 10% yield. TOF MS (ES$^-$): 6315.

2. S. 1. General Procedure for the High Density Loading of Controlled Pore Glass Supports with PAZ Ligand Succinates

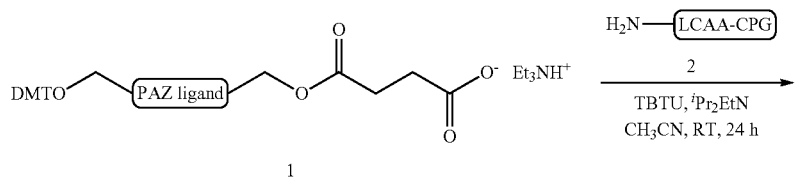

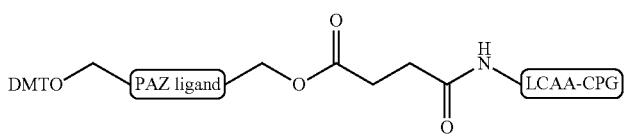

In an Erlenmeyer flask 1.00 mmol PAZ ligand succinate salt 1 was dissolved in 50 mL dry acetonitrile under argon. To this solution 353 mg (1.10 mmol) O-(1H-benzo-1,2,3-triazol-1-yl)-N,N,N',N'-tetramethyl-uronium tetrafluoroborate (TBTU) was added and the solution shaken for 10 min. Then 10 g long chain alkylamine controlled pore glass (LCAA/CNA-600-CPG, PrimeSynthesis, 2) was added and the reaction mixture gently agitated for 5 min. Finally, 0.685 mL (517 mg, 4.00 mmol) Hünig's base was added and the flask gently shaken for 24 h on an orbital shaker. Loading density was assessed by detritylating an aliquote of the CPG (3-5 mg CPG washed with acetonitrile, dried in vacuo, added to 25 mL 3% dichloroacetic acid in dichloromethane (v/v), absorbance at 504 nm determined). If loading density was in the desired range (60-90 micromol/g), the CPG was filtered off and washed extensively with acetonitrile. Underivatized amino groups were capped by treating the CPG with x mL each of a mixture of acetic anhydride/2,6-lutidine/THF 1:1:8 (v/v/v) and a solution of 1-methylimidazole in THF 16:84 (v/v). The mixture was gently shaken for 15 min at room temperature. Then the CPG was filtered off, washed with acetonitrile and dried under vacuum overnight. Loading density was determined again as above. Loading yields for the succinates in examples 1-6 were in the range of 64-75 micromol/g.

2. T. Synthesis of siRNA Conjugated with X1011

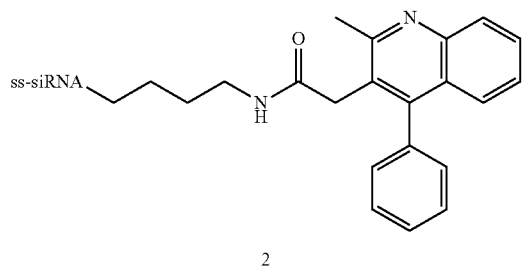

A mixture of N-hydroxysuccinimide (2.489 mg, 0.022 mmol), 1 (3.0 mg, 0.011 mmol), and DIC (2.73 mg, 0.022 mmol) in DMSO (200 uL) was stirred at RT for 12 h. 10 uL of reaction mixture was diluted with 190 uL DMSO. To the resulting solution was added a freshly ss-siRNA-$(CH_2)_4$—$NH_2$ solution (2.00 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 2. TOF MS (ES$^-$): 6418.

2. U. Synthesis of siRNA Conjugated with X1012 and X1018

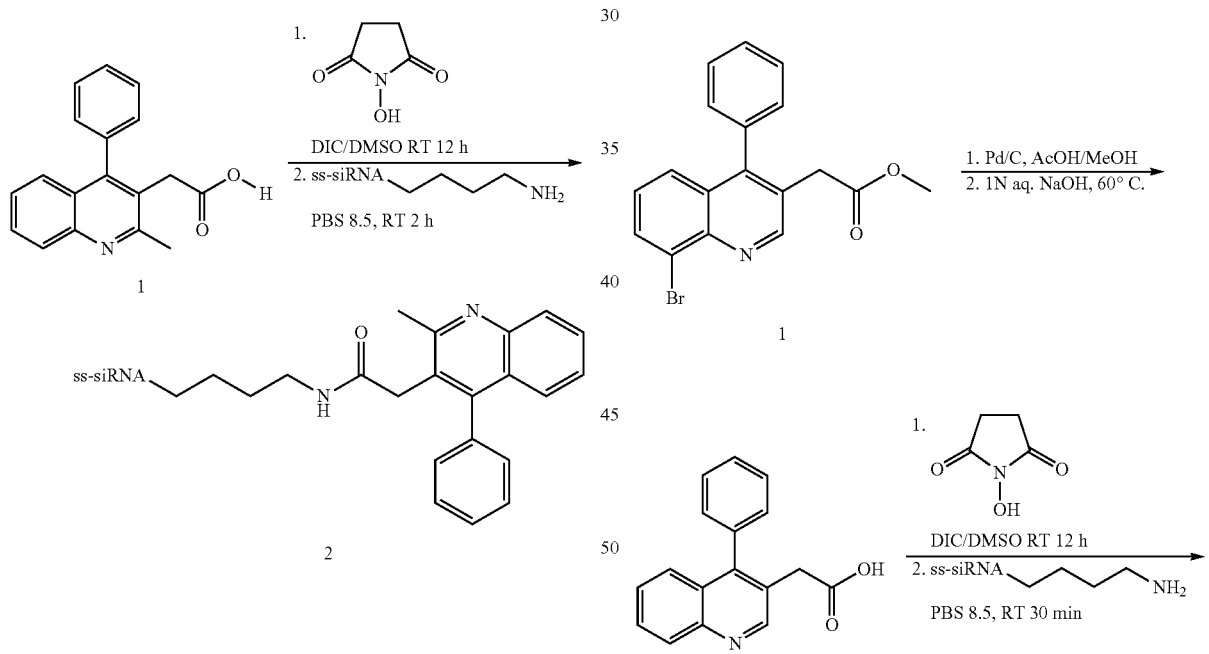

Scheme 1: Overview of the synthesis of 2.

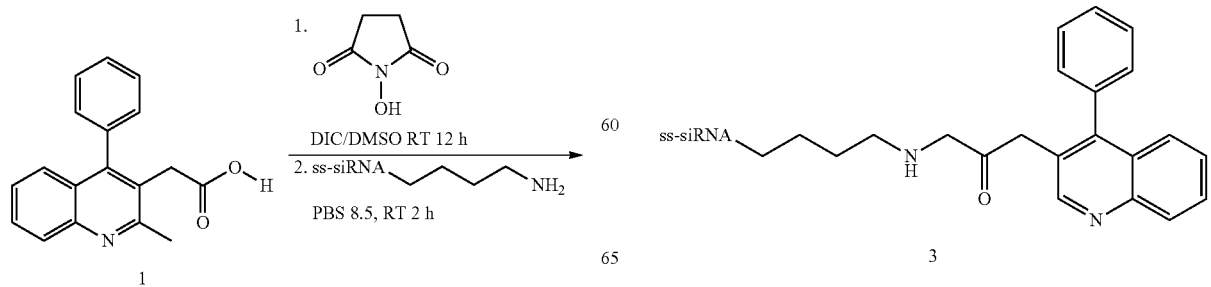

Scheme 2: Overview of the synthesis of 3.

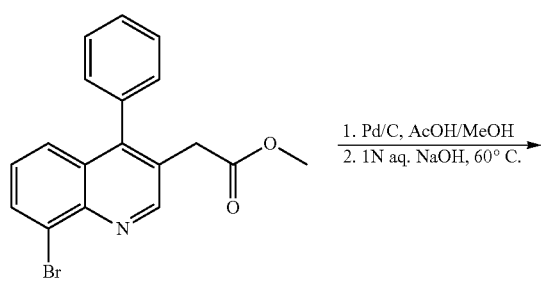

A mixture of 1 (500 mg, 1.40 mmol), Pd (30% on carbon, 24.9 mg, 0.070 mmol), and acetic acid (80 ul, 1.40 mmol) in methanol (15 mL) was stirred at RT under $H_2$ (1 atm) for 12 h. The reaction mixture was filtered to remove Pd/C. To the solution was added aq. 1M NaOH (3 mL), and the resulting mixture was heated at 60° C. for 12 h. The mixture was cooled to RT and neutralized with aq. 1M HCl to give form a precipitate. The precipitate was collected by vacuum filtration and dried in the oven to give 2 (166 mg, 0.63 mmol) with 45% yield. ESI MS (m/z, MH$^+$): 264.4. $^1$H NMR (400 MHz, DMSO-d$_6$) δ ppm 3.58 (s, 2H) 7.18-7.39 (m, 3H) 7.44-7.65 (m, 4H) 7.75 (ddd, J=8.28, 6.78, 1.51 Hz, 1H) 8.01-8.20 (m, 1H) 8.91 (s, 1H) 12.47 (s, 1H).

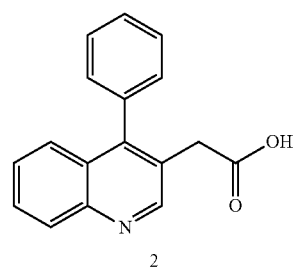

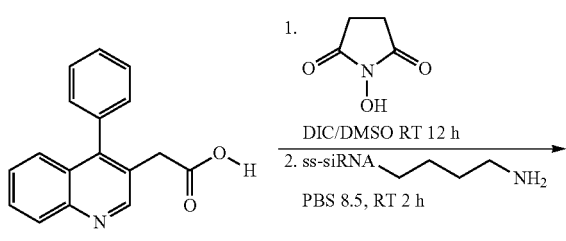

A mixture of N-hydroxysuccinimide (2.489 mg, 0.022 mmol), 2 (2.85 mg, 0.011 mmol), and DIC (2.73 mg, 0.022 mmol) in DMSO (200 uL) was stirred at RT for 12 h. 10 uL of reaction mixture was diluted with 190 uL DMSO. To the resulting solution was added a freshly ss-siRNA-(CH$_2$)$_4$—NH$_2$ solution (2.00 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 3. ESI MS (ES$^+$): 6405.

2. U. Synthesis of siRNA Conjugated with X1018

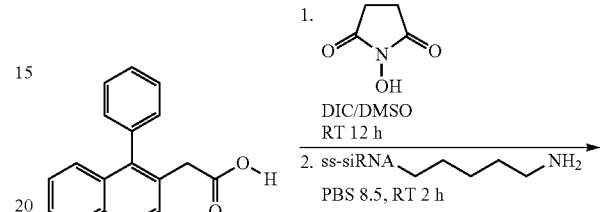

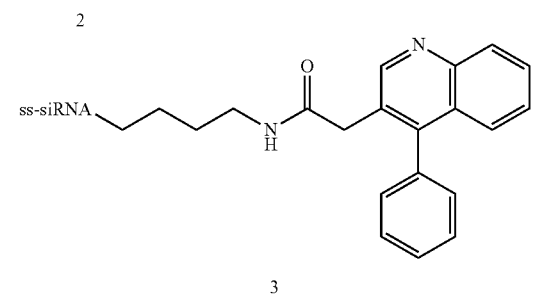

Scheme 3: Overview of the Synthesis of 4

A mixture of N-hydroxysuccinimide (2.483 mg, 0.022 mmol), 2 (2.84 mg, 0.011 mmol), and DIC (2.72 mg, 0.022 mmol) in DMSO (200 uL) was stirred at RT for 12 h. 10 uL of reaction mixture was diluted with 190 uL DMSO. To the resulting solution was added a freshly ss-siRNA-(CH$_2$)$_5$—NH$_2$ solution (2.00 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 4.

2. V. Synthesis of siRNA Conjugated with X1013

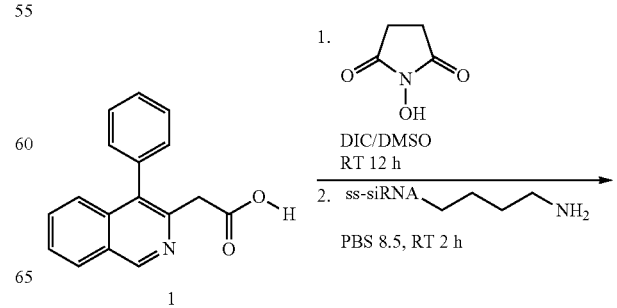

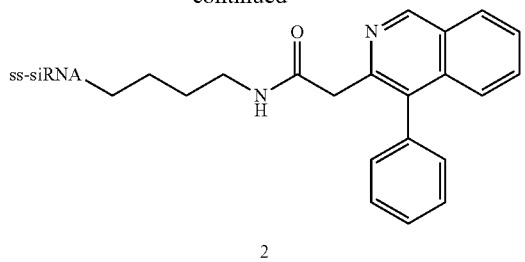

Scheme 4: Overview of the synthesis of 2.

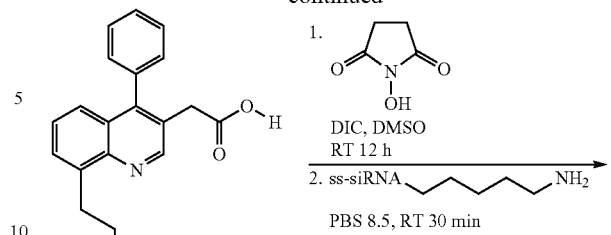

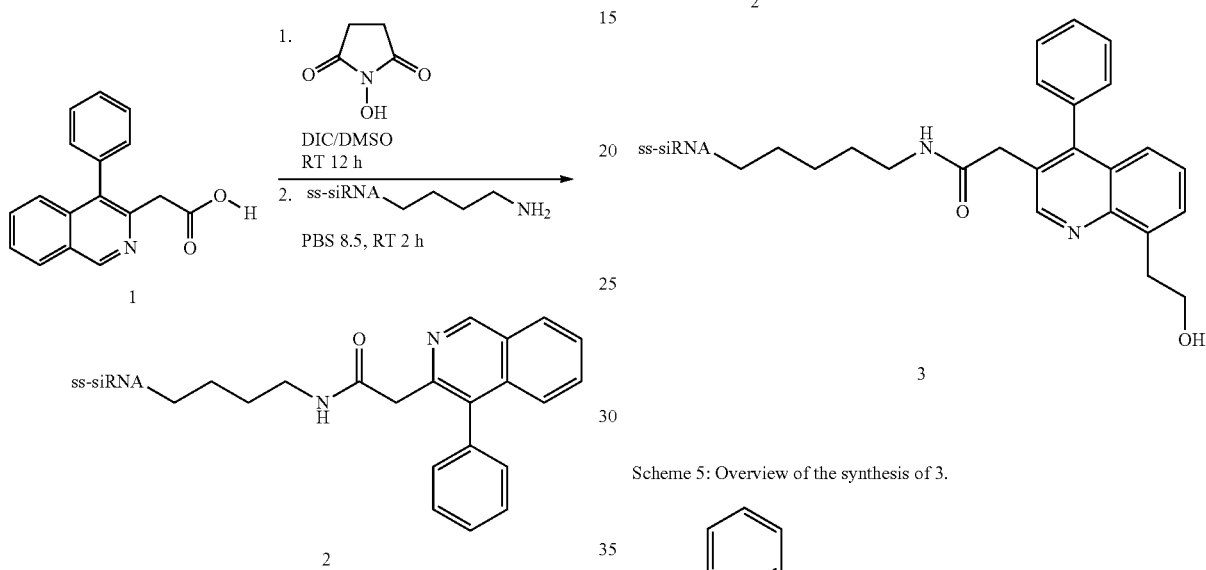

Scheme 5: Overview of the synthesis of 3.

A mixture of N-hydroxysuccinimide (2.489 mg, 0.022 mmol), 2 (2.85 mg, 0.011 mmol), and DIC (2.73 mg, 0.022 mmol) in DMSO (200 uL) was stirred at RT for 12 h. 10 uL of reaction mixture was diluted with 190 uL DMSO. To the resulting solution was added a freshly ss-siRNA-(CH$_2$)$_4$—NH$_2$ solution (2.00 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 2. TOF MS (ES$^-$): 6404.

2.W. Synthesis of siRNA Conjugated with X1019

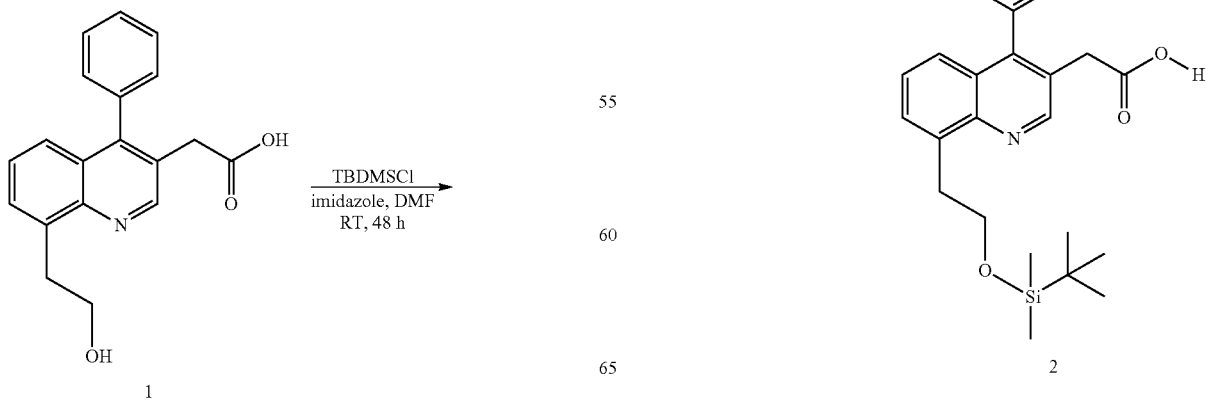

A mixture of 1 (100 mg, 0.325 mmol), tert-butylchlorodimethylsilane (108 mg, 0.716 mmol) and imidazole (91 mg, 1.33 mmol) in DMF (4 mL) was stirred at RT for 48 h. The reaction mixture was quenched with water (4 mL) and extracted with ethyl acetate (3×5 mL). The combined organic layers were washed with water and brine, and dried over sodium sulfate. The organic solvent was then removed under vacuum. The crude product was purified by silica chromatography with 0-50% ethyl acetate/heptane to give 2 (55 mg, 0.13 mmol) in 40% yield. ESI MS (m/z, MH$^+$): 422.2. $^1$H NMR (400 MHz, CHLOROFORM-d) δ ppm 0.04 (m, 6H) 0.88-0.93 (m, 9H) 3.59 (t, J=6.78 Hz, 2H) 3.71 (s, 2H) 4.09 (t, J=6.78 Hz, 2H) 7.28-7.45 (m, 4H) 7.51-7.61 (m, 3H) 7.63-7.68 (m, 1H) 9.00 (s, 1H).

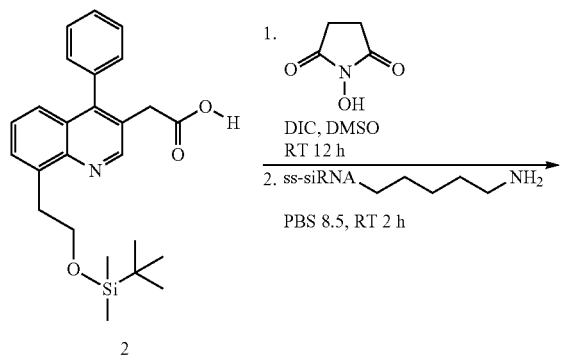

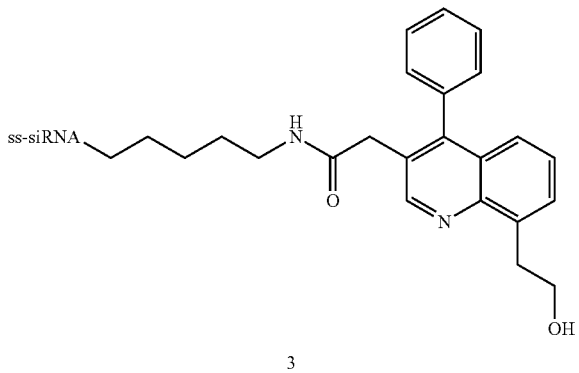

A mixture of N-hydroxysuccinimide (2.48 mg, 0.022 mmol), 2 (4.55 mg, 0.011 mmol), and DIC (2.72 mg, 0.022 mmol) in DMSO (200 uL) was stirred at RT for 12 h. 10 uL reaction mixture was diluted with 190 uL DMSO. To the resulting solution was added a freshly ss-siRNA-(CH$_2$)$_3$—NH$_2$ solution (2 mg, 0.324 umol in 80 ul PBS 8.5 buffer). The reaction mixture was vortexed and sat at RT for 2 h. The crude product was purified by HPLC with 10-40% 100 mM triethylammonium acetate in acetonitrile/water to afford 3. TOF MS (ES$^-$): 6462.

2. X. Synthesis of siRNA Conjugated with X1015

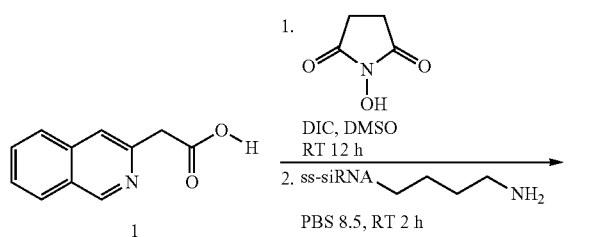

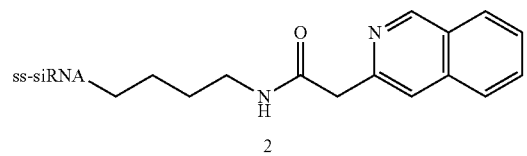

Scheme 6: Overview of the synthesis of 2.

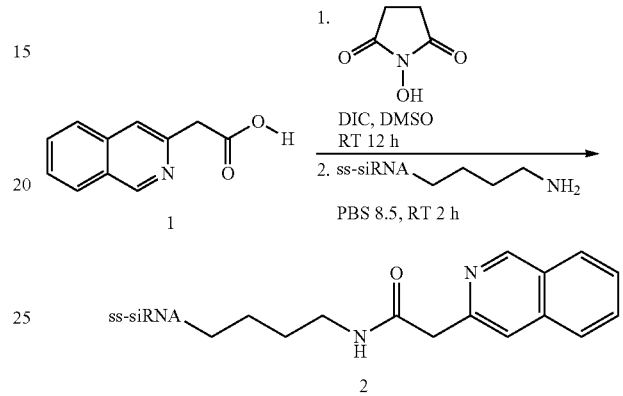

A mixture of N-hydroxysuccinimide (2.49 mg, 0.022 mmol), 1 (2.02 mg, 0.011 mmol), and DIC (2.73 mg, 0.022 mmol) in DMSO (200 uL) was stirred at RT for 12 h. 10 uL of reaction mixture was diluted with 190 uL DMSO. To the resulting solution was added a freshly ss-siRNA-(CH$_2$)$_4$—NH$_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 2. TOF MS (ES$^-$): 6327.

2.Y. Synthesis of siRNA Conjugated with X1020

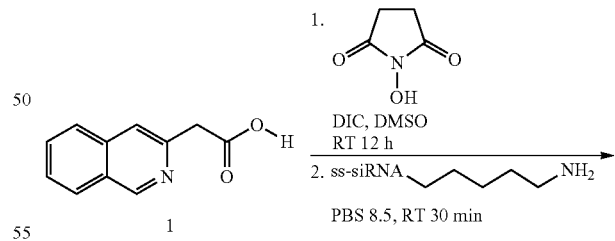

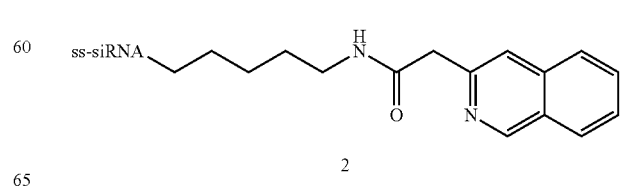

Scheme 7: Overview of the synthesis of 2.

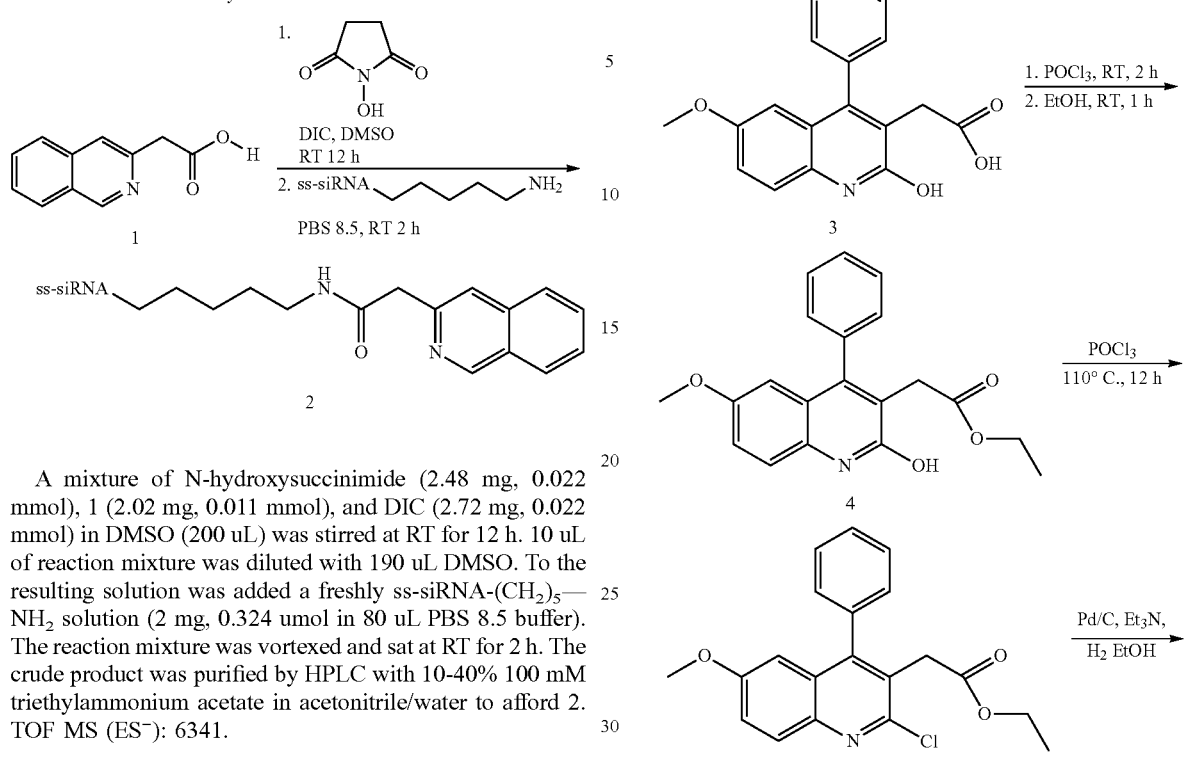

A mixture of N-hydroxysuccinimide (2.48 mg, 0.022 mmol), 1 (2.02 mg, 0.011 mmol), and DIC (2.72 mg, 0.022 mmol) in DMSO (200 uL) was stirred at RT for 12 h. 10 uL of reaction mixture was diluted with 190 uL DMSO. To the resulting solution was added a freshly ss-siRNA-$(CH_2)_5$—$NH_2$ solution (2 mg, 0.324 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 2. TOF MS (ES$^-$): 6341.

2. Z. Synthesis of siRNA Conjugated with X1009

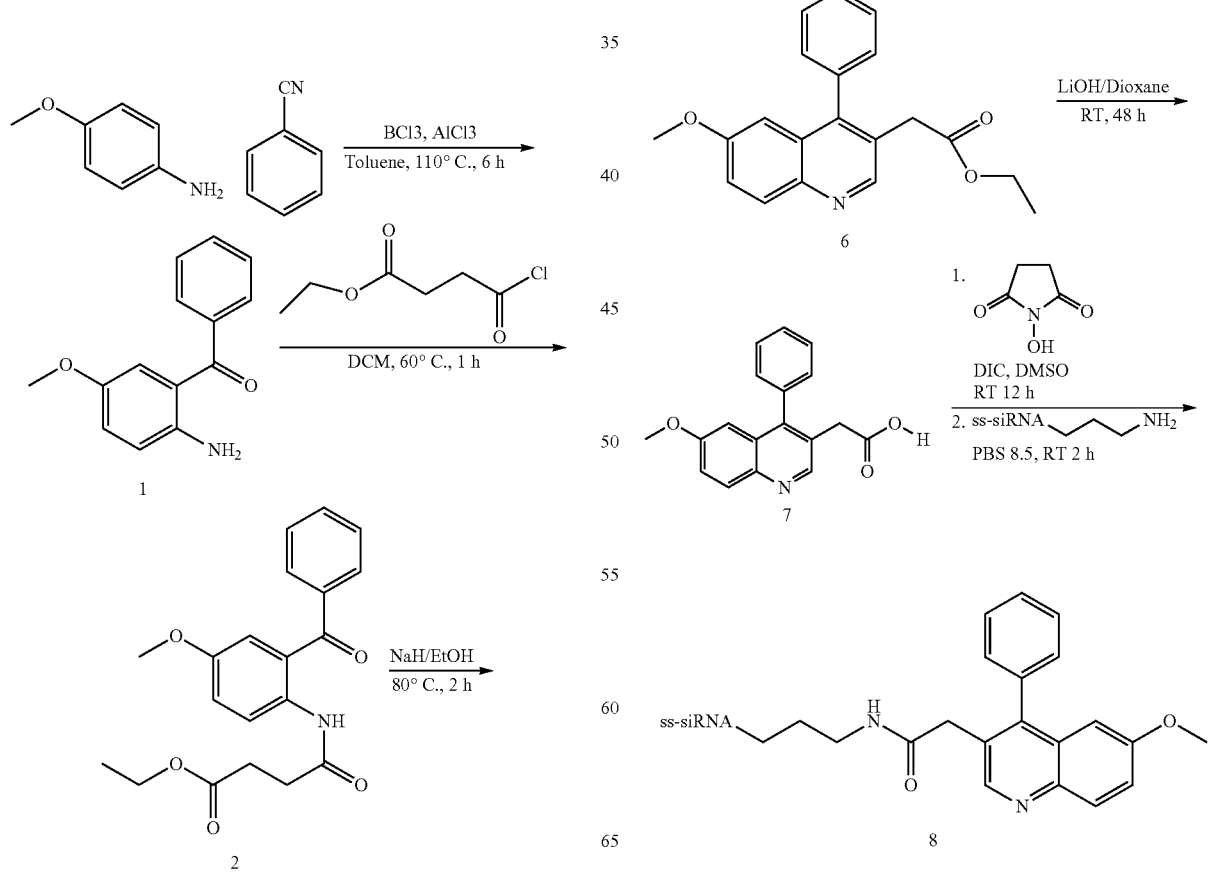

Scheme 7: Overview of the synthesis of 8.

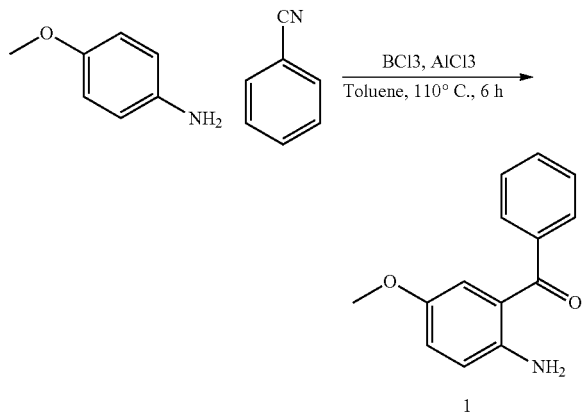

To AlCl$_3$ (1.19 g, 8.93 mmol, 40 ml Toluene solution) under N$_2$ was added 4-methoxyaniline (1 g, 8.12 mmol, 10 ml Toluene solution) dropwise. BCl$_3$ (8.12 ml, 8.12 mmol, 1 M solution in CH$_2$Cl$_2$) and Benzonitrile (2.51 g, 24.36 mmol) were added to the above mixture subsequently. The resulting mixture was stirred at RT for 1 h, then heated at 110° C. for 6 hrs. The reaction mixture was cooled to RT, to which aq. HCl (1 M, 13 ml) was added. The solution was then heated at 80° C. for 1 h. The solution was cooled to RT, and the organic layer and water layer were separated. The water layer was extracted with ethyl acetate (3×50 mL). The combined organic layers were washed with water and brine, and dried over sodium sulfate. The organic solvent was then removed under vacuum. The crude product was purified by silica chromatography with 0-40% ethyl acetate/heptane to give 1 (273 mg, 1.2 mmol) in 15% yield. ESI MS (m/z, MH$^+$): 227.3. $^1$H NMR (400 MHz, CHLOROFORM-d) δ ppm 3.66 (s, 3H) 6.80 (d, J=8.84 Hz, 1H) 6.93-7.05 (m, 2H) 7.40-7.49 (m, 2H) 7.49-7.58 (m, 1H) 7.63-7.72 (m, 2H).

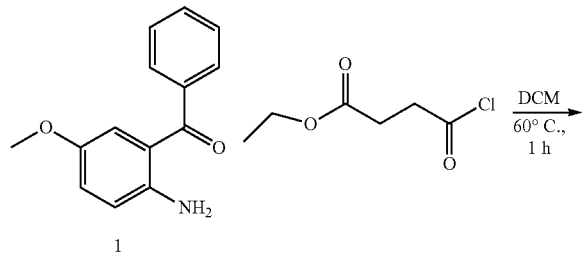

A mixture of 1 (269 mg, 1.18 mmol) and ethyl 4-chloro-4-oxobutanoate (214 mg, 1.3 mmol) in DCM (10 ml) was heated at 60° C. for 1 h. The reaction mixture was cooled and quenched with aq. 1 M NaOH (5 ml). Organic layer and water layer were separated. The water layer was extracted with dichloromethane (3×5 ml). The combined organic layers were washed with water and brine, and dried over sodium sulfate. The organic solvent was then removed under vacuum. The crude product was purified by silica chromatography with 0-60% ethyl acetate/heptane to give 2 (305 mg, 0.86 mmol) in 73% yield. ESI MS (m/z, MH$^+$): 355.5. $^1$H NMR (400 MHz, CHLOROFORM-d) δ ppm 1.26 (t, J=7.28 Hz, 3H) 2.74 (s, 4H) 3.77 (s, 3H) 4.16 (q, J=7.03 Hz, 2H) 7.06 (d, J=3.01 Hz, 1H) 7.14 (dd, J=9.03, 3.01 Hz, 1H) 7.48-7.55 (m, 2H) 7.60-7.66 (m, 1H) 7.73-7.79 (m, 2H) 8.50 (d, J=9.03 Hz, 1H) 10.45 (br. s., 1H).

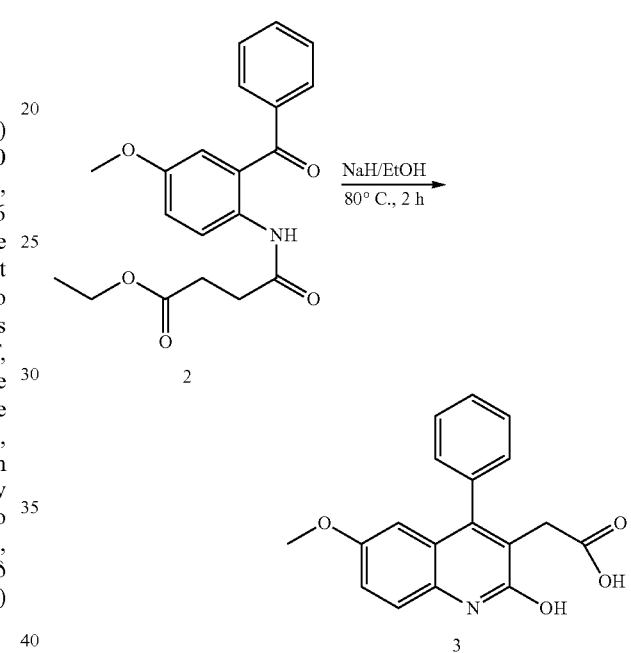

A mixture of 2 (305 mg, 0.86 mmol) and sodium hydride (343 mg, 8.58 mmol) in ethanol (10 ml) was heated at 80° C. for 2 h. The reaction mixture was cooled to RT and quenched with water (5 ml) then neutralized with aq. 1 M HCl (2 ml). The resulting solution was extracted with ethyl acetate (3×10 mL). The combined organic layers were washed with water and brine, and dried over sodium sulfate. The organic solvent was then removed under vacuum to give 3 (250 mg, 0.81 mmol) in 94% yield. ESI MS (m/z, MH$^+$): 309.3. $^1$H NMR (400 MHz, METHANOL-d$_4$) δ ppm 3.38 (s, 2H) 3.63 (s, 3H) 6.51 (d, J=2.51 Hz, 1H) 7.20 (dd, J=9.03, 3.01 Hz, 1H) 7.28-7.47 (m, 3H) 7.52-7.63 (m, 3H).

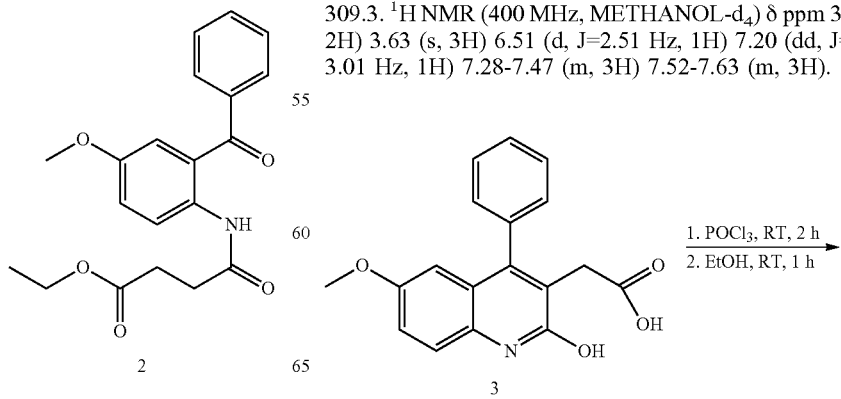

-continued

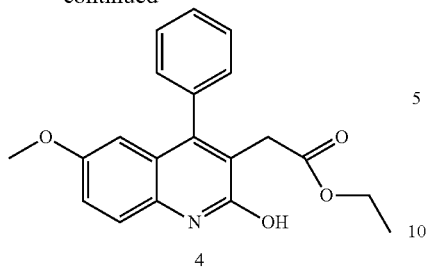
4

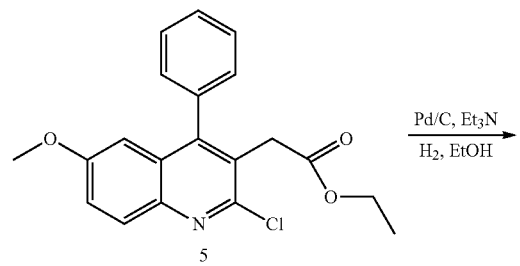
5

A solution of 3 (250 mg, 0.81 mmol) in POCl$_3$ (10 ml) was stirred at RT for 2 h. POCl$_3$ was removed under vacuum, the resulting residue was quenched with ethanol (20 ml). The solution was stirred at RT for 1 h, then ethanol was removed under vacuum. To the residue was added dichloromethane (30 ml) and aq. 1 M NaOH (20 ml). Organic layer and water layer were separated. The water layer was extracted with dichloromethane (2×20 ml). The combined organic layers were washed with water, brine and dried over sodium sulfate. The organic solvent was removed under vacuum to give 4 (270 mg, 0.8 mmol) in 99% yield. ESI MS (m/z, MH$^+$): 338.2. $^1$H NMR (400 MHz, CHLOROFORM-d) δ ppm 1.23-1.27 (m, 3H) 3.48 (s, 2H) 3.66 (s, 3H) 4.04-4.22 (m, 2H) 6.55 (d, J=2.51 Hz, 1H) 7.09-7.15 (m, 1H) 7.24 (d, J=9.03 Hz, 1H) 7.29-7.34 (m, 2H) 7.44-7.64 (m, 3H) 10.49 (br. s., 1H).

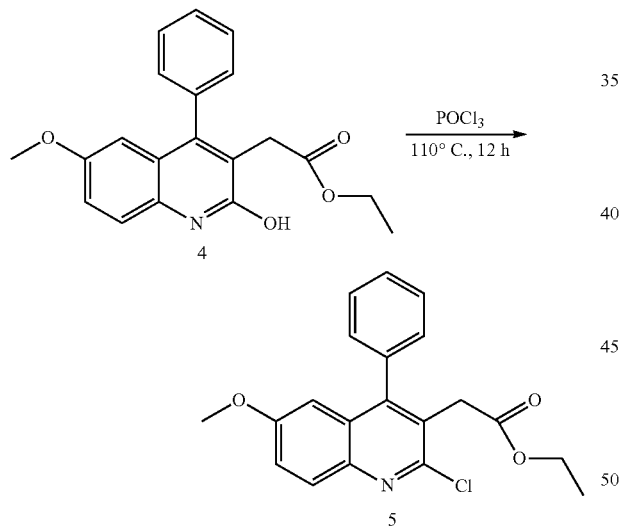

A solution of 4 (270 mg, 0.8 mmol) in POCl$_3$ (10 ml) was heated at 110° C. for 12 h. POCl$_3$ was removed under vacuum. To the residue was added dichloromethane (20 ml) and aq. 1 M NaOH (20 ml). The organic layer and water layer were separated. The water layer was extracted with dichloromethane (2×20 ml). The combined organic layers were washed with water, brine and dried over sodium sulfate. The organic solvent was removed under vacuum to give 5 (265 mg, 0.75 mmol) in 92% yield. ESI MS (m/z, MH$^+$): 356.1. $^1$H NMR (400 MHz, CHLOROFORM-d) δ ppm 1.22-1.27 (m, 3H) 3.70 (s, 5H) 4.17 (q, J=7.03 Hz, 2H) 6.62 (d, J=3.01 Hz, 1H) 7.20-7.34 (m, 2H) 7.38 (dd, J=9.03, 2.51 Hz, 1H) 7.46-7.63 (m, 3H) 8.01 (d, J=9.03 Hz, 1H).

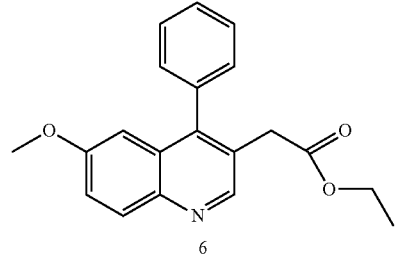

A mixture of 5 (265 mg, 0.745 mmol), triethylamine (1.28 g, 12.66 mmol), and Pd/C (10%, 79 mg, 0.745 mmol) in ethanol (20 ml) was stirred under H$_2$ (1 atm) at RT for 12 h. The reaction mixture was filtered to remove Pd/C. The organic solvent was removed under vacuum to give 6 (182 mg, 0.57 mmol) in 76% yield. ESI MS (m/z, MH$^+$): 322.1. $^1$H NMR (400 MHz, CHLOROFORM-d) δ ppm 1.12 (t, J=7.15 Hz, 3H) 3.51 (s, 2H) 3.62 (s, 3H) 4.01 (q, J=7.19 Hz, 2H) 6.61 (d, J=2.76 Hz, 1H) 7.18-7.31 (m, 3H) 7.39-7.50 (m, 3H) 7.97 (d, J=9.29 Hz, 1H) 8.68 (s, 1H).

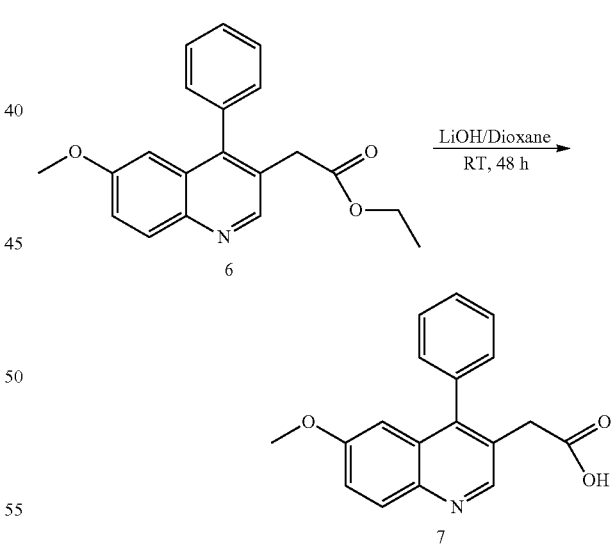

A mixture of 6 (50 mg, 0.16 mmol), aq. 1 M LiOH (0.17 ml, 0.17 mmol) in Dioxane (1 ml) was stirred at RT for 48 hrs. A precipitation from the reaction mixture was filtered and dried to give 7 (32 mg, 0.107 mmol) in 69% yield as lithium salt. ESI MS (m/z, MH$^+$): 294.2. $^1$H NMR (400 MHz, METHANOL-d$_4$) δ ppm 3.48 (s, 2H) 3.63-3.73 (m, 3H) 6.75 (d, J=2.51 Hz, 1H) 7.28-7.43 (m, 3H) 7.48-7.64 (m, 3H) 7.94 (d, J=9.03 Hz, 1H) 8.73 (s, 1H).

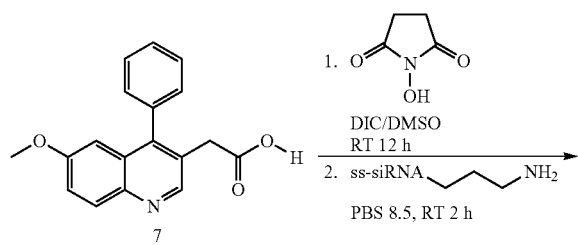

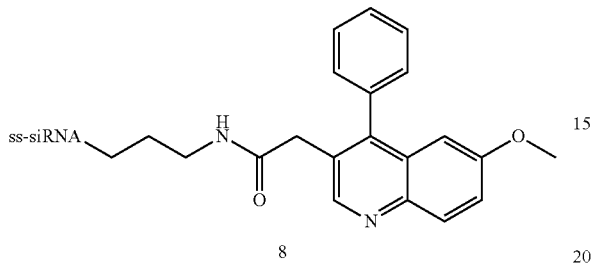

A mixture of N-hydroxysuccinimide (2.49 mg, 0.022 mmol), 7 (3.18 mg, 0.011 mmol), and DIC (2.74 mg, 0.022 mmol) in DMSO (200 uL) was stirred at RT for 12 h. 10 uL of reaction mixture was diluted with 190 uL DMSO. To the resulting solution was added a freshly ss-siRNA-(CH$_2$)$_3$—NH$_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 8. TOF MS (ES$^-$): 6422.

2. AA. Synthesis of siRNA Conjugated with X1016

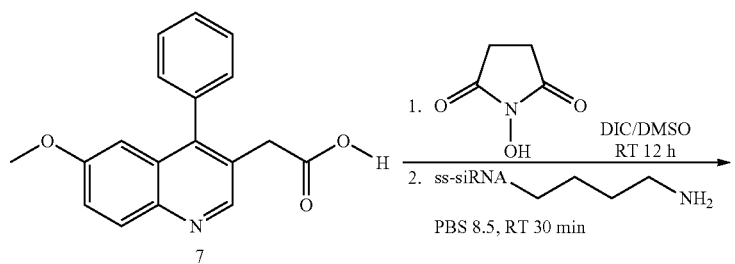

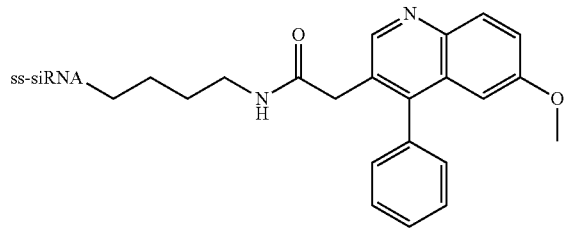

Scheme 8: Overview of the synthesis of 9.

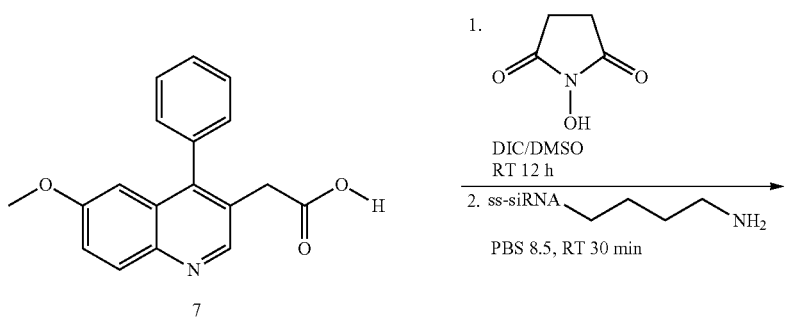

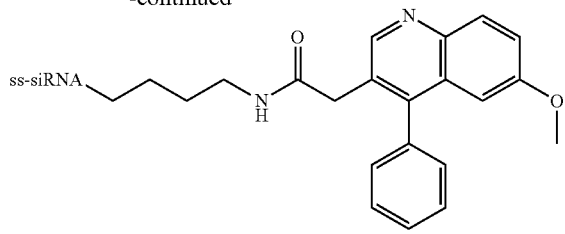

9

A mixture of N-hydroxysuccinimide (2.49 mg, 0.022 mmol), 7 (3.18 mg, 0.011 mmol), and DIC (2.74 mg, 0.022 mmol) in DMSO (200 uL) was stirred at RT for 12 h. 10 uL of reaction mixture was diluted with 190 uL DMSO. To the resulting solution was added a freshly ss-siRNA-$(CH_2)_4$—$NH_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 9. TOF MS (ES$^-$): 6434.

2. BB. Synthesis of siRNA Conjugated with X1021

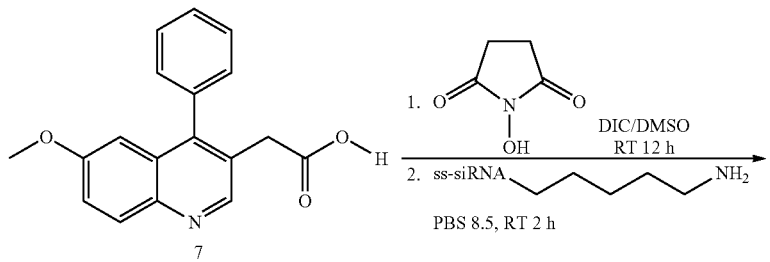

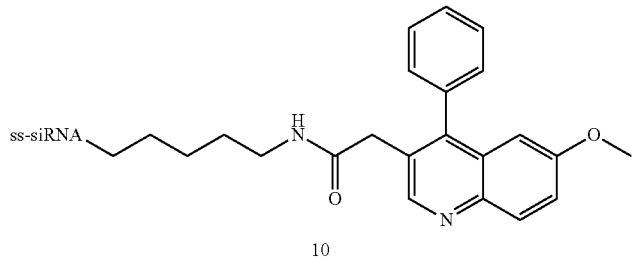

10

Scheme 9: Overview of the synthesis of 10.

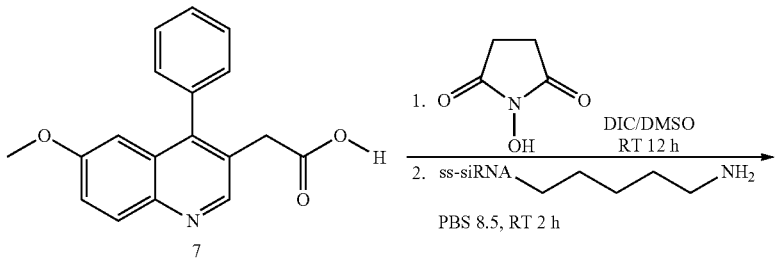

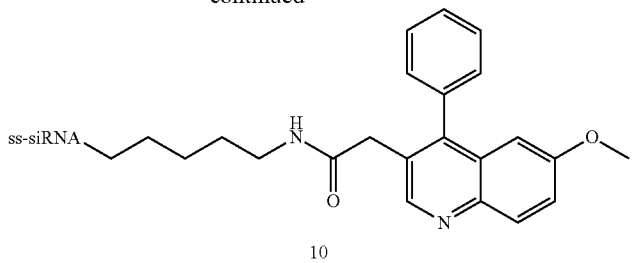

10

A mixture of N-hydroxysuccinimide (2.48 mg, 0.022 mmol), 7 (3.16 mg, 0.011 mmol), and DIC (2.72 mg, 0.022 mmol) in DMSO (200 uL) was stirred at RT for 12 h. 10 uL of reaction mixture was diluted with 190 uL DMSO. To the resulting solution was added a freshly ss-siRNA-$(CH_2)_5$—$NH_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 10. TOF MS (ES$^-$): 6448.

2. CC. Synthesis of siRNA Conjugated with X1010

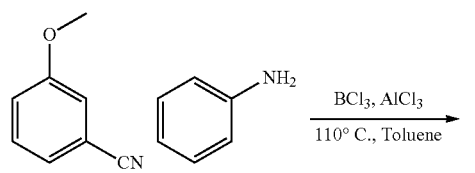

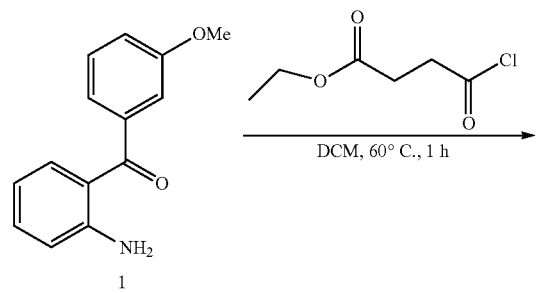

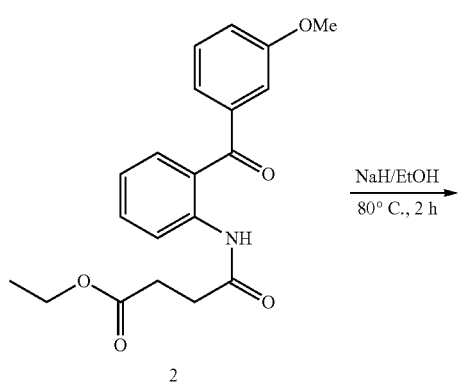

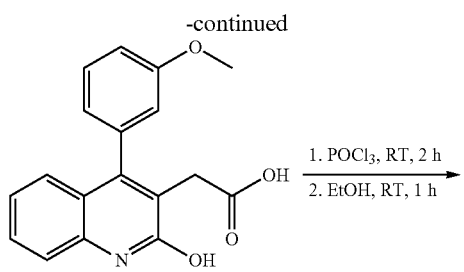

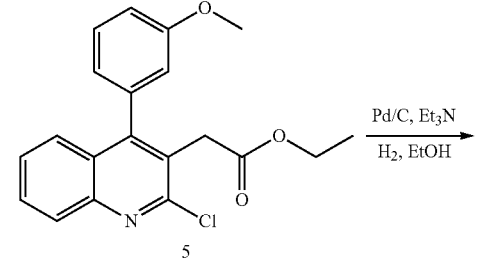

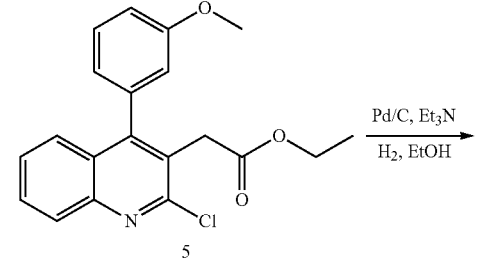

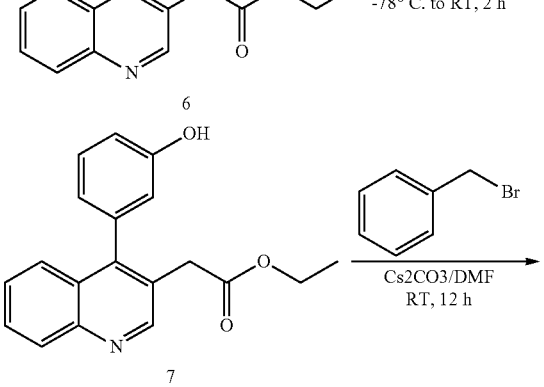

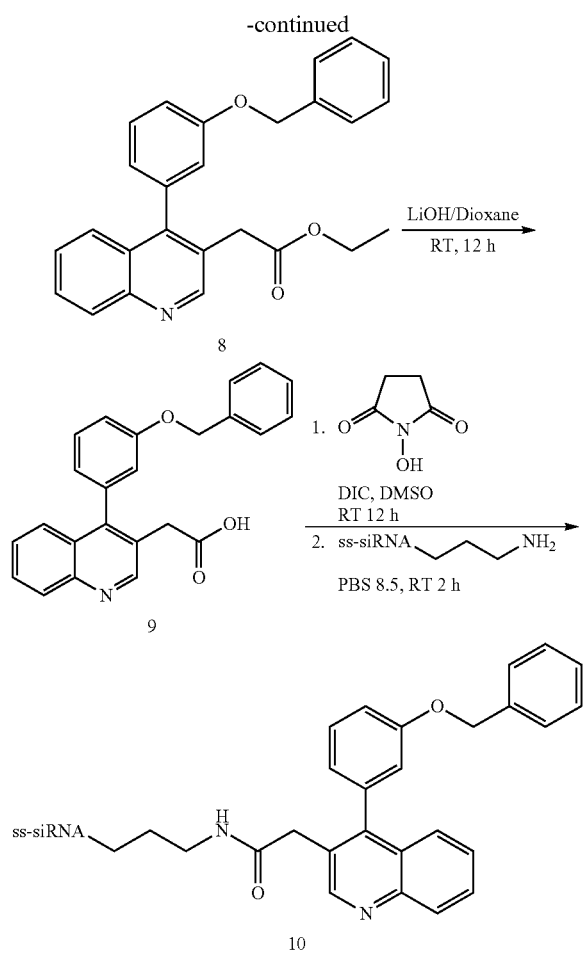

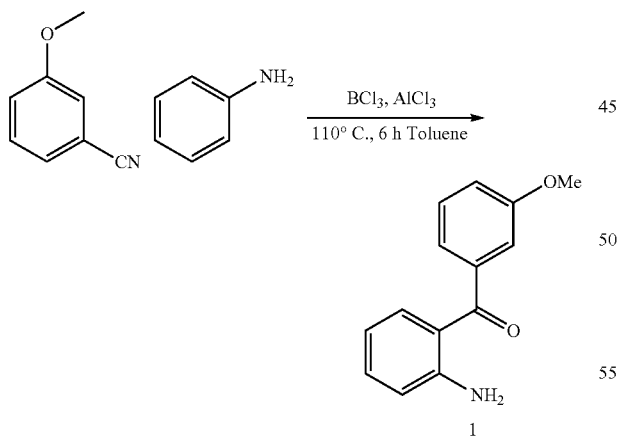

Scheme 10: Overview of the synthesis of 10.

To BCl$_3$ (10.74 ml, 10.74 mmol, 1 M solution in CH$_2$Cl$_2$) under N$_2$ was added aniline (1 g, 10.74 mmol, 10 ml Toluene solution) dropwise. 3-methoxybenzonitrile (4.29 g, 32.2 mmol) and AlCl$_3$ (1.575 g, 11.81 mmol, 40 ml Toluene solution) were added to the above mixture subsequently. The resulting mixture was stirred at RT for 1 h, then heated at 110° C. for 6 hrs. The reaction mixture was cooled to RT, to which aq. HCl (1 M, 13 ml) was added. The solution was then heated at 80° C. for 1 h. The solution was cooled to RT, and the organic layer and water layer were separated. The water layer was extracted with ethyl acetate (3×50 mL). The combined organic layers were washed with water and brine, and dried over sodium sulfate. The organic solvent was then removed under vacuum. The crude product was purified by silica chromatography with 0-40% ethyl acetate/heptane to give 1 (875 mg, 3.85 mmol) in 36% yield. ESI MS (m/z, MH$^+$): 227.9. $^1$H NMR (400 MHz, CHLOROFORM-d) δ ppm 3.74 (s, 3H) 6.00 (br. s., 2H) 6.44-6.56 (m, 1H) 6.63 (dd, J=8.53, 1.00 Hz, 1H) 6.93-7.00 (m, 1H) 7.04-7.11 (m, 2H) 7.14-7.31 (m, 2H) 7.37 (dd, J=8.03, 1.51 Hz, 1H).

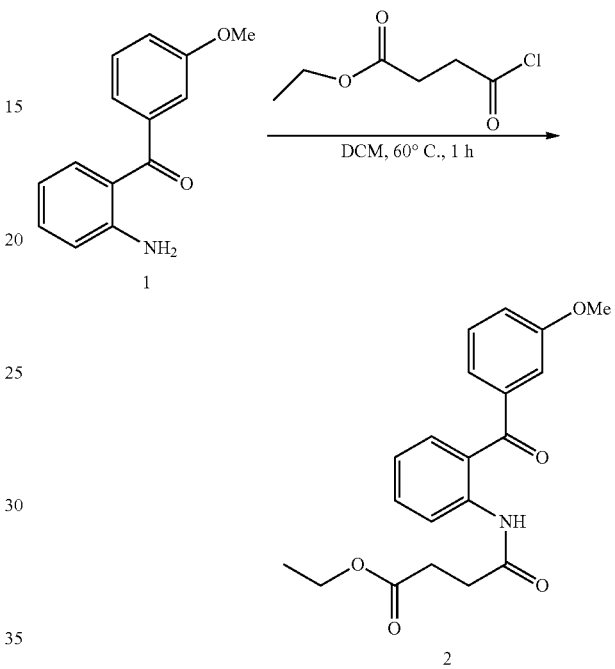

A mixture of 1 (570 mg, 2.51 mmol) and ethyl 4-chloro-4-oxobutanoate (454 mg, 2.76 mmol) in DCM (20 ml) was heated at 60° C. for 1 h. The reaction mixture was cooled and quenched with aq. 1 M NaOH (5 ml). The organic layer and water layer were separated. The water layer was extracted with dichloromethane (3×15 ml). The combined organic layers were washed with water and brine, and dried over sodium sulfate. The organic solvent was then removed under vacuum to give 2 (824 mg, 2.32 mmol) in 92% yield. ESI MS (m/z, MH$^+$): 355.4. $^1$H NMR (400 MHz, CHLOROFORM-d) δ ppm 1.25-1.48 (m, 3H) 2.73-3.01 (m, 4H) 3.88 (s, 3H) 4.18 (q, J=7.07 Hz, 2H) 7.05-7.20 (m, 2H) 7.22-7.30 (m, 2H) 7.37-7.45 (m, 1H) 7.53-7.64 (m, 2H) 8.64 (d, J=8.59 Hz, 1H) 10.90 (br. s., 1H).

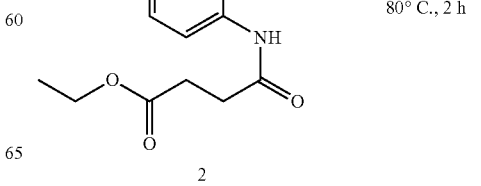

-continued

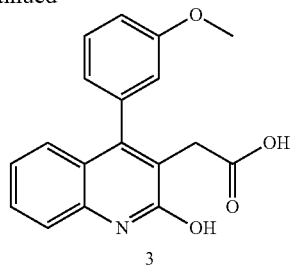
3

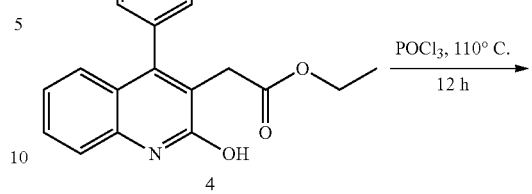
4

A mixture of 2 (824 mg, 2.32 mmol) and sodium hydride (927 mg, 23.19 mmol) in ethanol (20 ml) was heated at 80° C. for 2 h. The reaction mixture was cooled to RT and quenched with water (5 ml) then neutralized with aq. 1 M HCl (2 ml). The resulting solution was extracted with ethyl acetate (3×10 mL). The combined organic layers were washed with water and brine, and dried over sodium sulfate. The organic solvent was then removed under vacuum to give 3 (583 mg, 0.81 mmol) in 81% yield. ESI MS (m/z, MH$^+$): 310.1. $^1$H NMR (400 MHz, CHLOROFORM-d) δ ppm 3.49-3.64 (m, 2H) 3.83-3.89 (m, 3H) 6.83-6.96 (m, 2H) 7.00-7.28 (m, 4H) 7.37-7.56 (m, 4H) 12.02-12.32 (m, 2H).

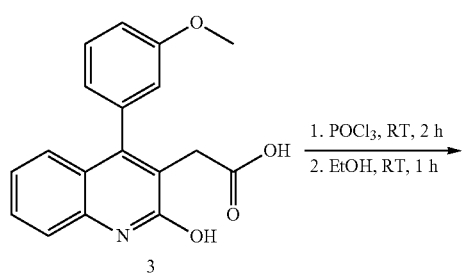
3

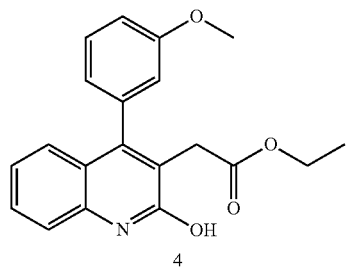
4

A solution of 3 (583 mg, 1.89 mmol) in POCl$_3$ (10 ml) was stirred at RT for 2 h. POCl$_3$ was removed under vacuum, the resulting residue was quenched with ethanol (20 ml). The solution was stirred at RT for 1 h, then ethanol was removed under vacuum. To the residue was added dichloromethane (30 ml) and aq. 1 M NaOH (20 ml). Organic layer and water layer were separated. The water layer was extracted with dichloromethane (2×20 ml). The combined organic layers were washed with water, brine and dried over sodium sulfate. The organic solvent was removed under vacuum to give 4 (760 mg, 2.25 mmol) in 120% yield. ESI MS (m/z, MH$^+$): 338.1. $^1$H NMR (400 MHz, CHLOROFORM-d) δ ppm 1.26 (t, J=7.07 Hz, 3H) 3.44-3.64 (m, 2H) 3.85 (s, 3H) 4.17 (q, J=7.16 Hz, 2H) 6.85-6.93 (m, 2H) 7.03 (ddd, J=8.46, 2.65, 1.01 Hz, 1H) 7.11 (ddd, J=8.21, 6.95, 1.01 Hz, 1H) 7.17 (dd, J=8.21, 1.39 Hz, 1H) 7.32-7.39 (m, 1H) 7.40-7.52 (m, 2H) 11.43 (br. s., 1H)

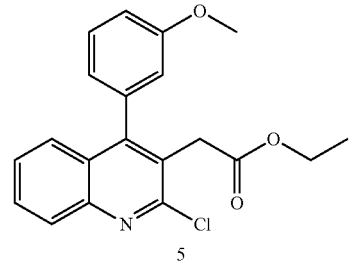
5

A solution of 4 (760 mg, 2.25 mmol) in POCl$_3$ (10 ml) was heated at 110° C. for 12 h. POCl$_3$ was removed under vacuum. To the residue was added dichloromethane (20 ml) and aq. 1 M NaOH (20 ml). The organic layer and water layer were separated. The water layer was extracted with dichloromethane (2×20 ml). The combined organic layers were washed with water, brine and dried over sodium sulfate. The organic solvent was removed under vacuum to give 5 (650 mg, 1.83 mmol) in 97% yield. ESI MS (m/z, MH$^+$): 355.4. $^1$H NMR (400 MHz, CHLOROFORM-d) δ ppm 1.25 (t, J=7.28 Hz, 3H) 3.75 (d, J=1.00 Hz, 2H) 3.85 (s, 3H) 4.18 (q, J=7.03 Hz, 2H) 6.78-6.92 (m, 2H) 6.97-7.13 (m, 1H) 7.39-7.60 (m, 3H) 7.76 (d, J=2.01 Hz, 1H) 8.15 (d, J=8.53 Hz, 1H).

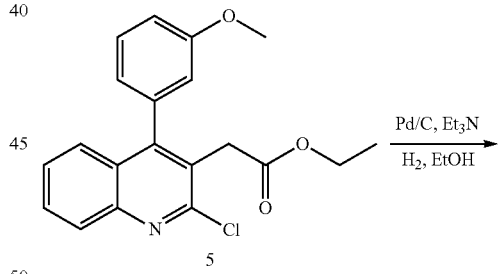
5

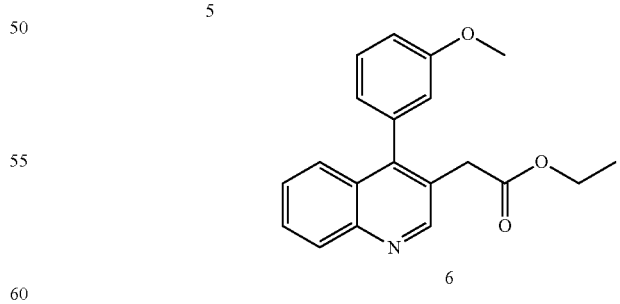
6

A mixture of 5 (650 mg, 1.83 mmol), triethylamine (3.14 g, 31.1 mmol), and Pd/C (10%, 194 mg, 1.827 mmol) in ethanol (20 ml) was stirred under H$_2$ (1 atm) at RT for 12 h. The reaction mixture was filtered to remove Pd/C. The organic solvent was removed under vacuum to give 6 (460 mg, 1.43 mmol) in 78% yield. ESI MS (m/z, MH$^+$): 321.5.

¹H NMR (400 MHz, CHLOROFORM-d) δ ppm 1.20-1.26 (m, 3H) 1.44 (t, J=7.53 Hz, 9H) 3.12 (qd, J=7.28, 4.77 Hz, 6H) 3.65 (s, 2H) 3.79-3.93 (m, 3H) 4.12 (q, J=7.19 Hz, 2H) 6.82-6.92 (m, 2H) 7.06 (ddd, J=8.53, 2.51, 1.00 Hz, 1H) 7.39-7.58 (m, 3H) 7.72 (ddd, J=8.41, 6.65, 1.51 Hz, 1H) 8.19 (d, J=8.53 Hz, 1H) 8.93 (s, 1H) 12.20 (br. s., 3H).

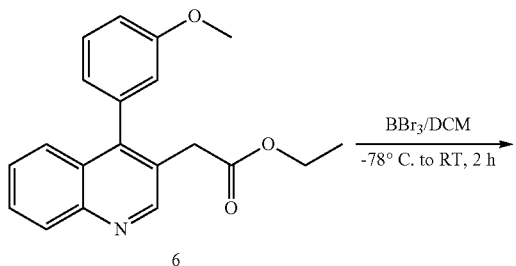

To a solution of 6 (400 mg, 1.245 mmol) in DCM (15 ml) was added BBr₃ (1 M in DCM, 3.73 ml, 3.73 mmol) at −78° C. The reaction mixture was warmed to RT in 2 h. The mixture was cooled down to −78° C., and quenched with ethanol. The organic solvent was removed under vacuum.

To the resulting residue was added ethyl acetate (15 ml) and water (15 ml). The organic and water layer were separated. The water layer was extracted with ethyl acetate (3×15 ml). The combined organic layers were washed with water, brine and dried over sodium sulfate. The organic solvent was removed under vacuum. The crude was purified by recrystallization from dichloromethane to give 7 (282 mg, 0.92 mmol) in 74% yield. ESI MS (m/z, MH⁺): 308.2. ¹H NMR (400 MHz, DMSO-d₆) δ ppm 1.11 (t, J=7.03 Hz, 3H) 3.68 (s, 2H) 3.91-4.11 (m, 2H) 6.50-6.70 (m, 2H) 6.81-6.97 (m, 1H) 7.30-7.48 (m, 2H) 7.51-7.63 (m, 1H) 7.78 (ddd, J=8.53, 7.03, 1.51 Hz, 1H) 8.08 (d, J=8.03 Hz, 1H) 8.93 (s, 1H) 9.75 (br. s., 1H).

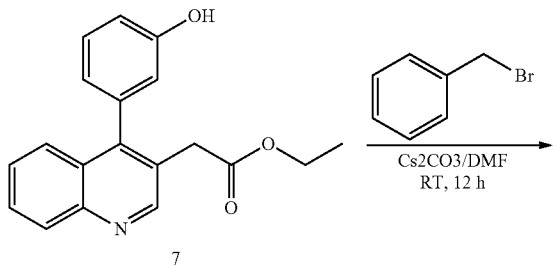

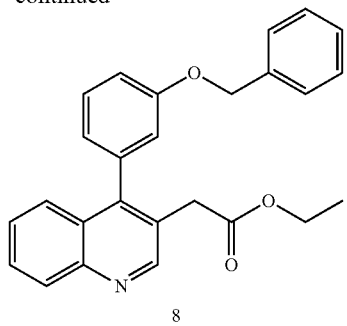

A mixture of 7 (20 mg, 0.065 mmol), benzyl bromide (16.69 mg, 0.098 mmol) and cesium carbonate (42.4 mg, 0.13 mmol) in DMF (500 ul) was stirred at RT for 12 hrs. The reaction mixture was filtered to remove insoluble material. The crude product was purified by HPLC with 5% NH₄OH in 5-95% acetonitrile/water to give 8 (6.9 mg, 0.017 mmol) in 26.7% yield. ESI MS (m/z, MH⁺): 398.3. ¹H NMR (400 MHz, CHLOROFORM-d) δ ppm 1.22 (t, J=7.03 Hz, 3H) 3.64 (s, 2H) 4.12 (q, J=7.03 Hz, 2H) 5.11 (s, 2H) 6.76-7.02 (m, 2H) 7.13 (ddd, J=8.53, 2.51, 1.00 Hz, 1H) 7.31-7.56 (m, 8H) 7.71 (ddd, J=8.28, 6.78, 2.01 Hz, 1H) 8.17 (d, J=8.53 Hz, 1H) 8.92 (s, 1H).

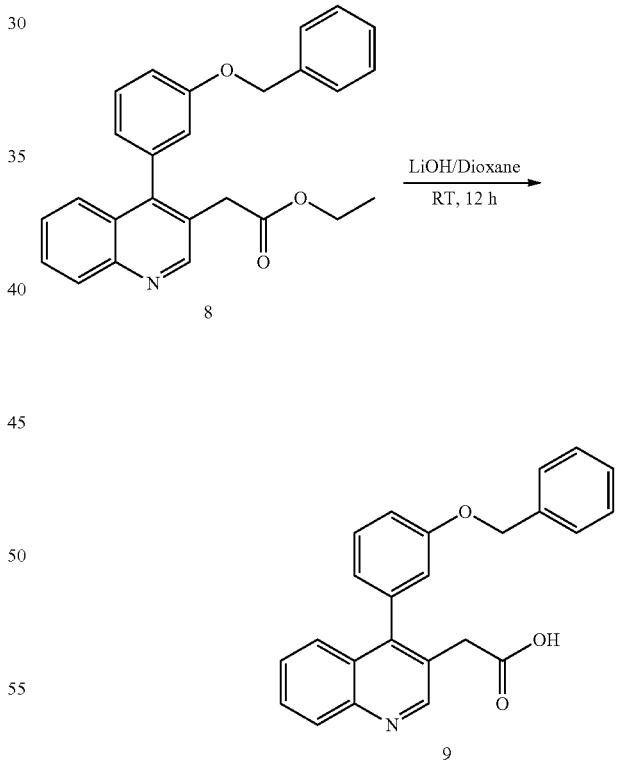

A mixture of 8 (6.9 mg, 0.017 mmol), aq. 1 M LiOH (0.019 ml, 0.019 mmol) in Dioxane (0.5 ml) was stirred at RT for 12 hrs. The organic solvent was removed under vacuum to give 9 (6 mg, 0.016 mmol) in 92% yield as lithium salt. ESI MS (m/z, MH⁺): 370.2. ¹H NMR (400 MHz, METHANOL-d₄) δ ppm 3.42-3.60 (m, 2H) 5.07-5.19 (m, 2H) 6.94 (dt, J=7.53, 1.25 Hz, 1H) 7.06 (dd, J=2.51, 1.51 Hz, 1H) 7.14 (ddd, J=8.53, 2.51, 1.00 Hz, 1H) 7.25-7.42 (m, 3H) 7.42-7.53 (m, 2H) 7.70 (ddd, J=8.41, 4.64, 3.51 Hz, 2H) 8.04 (d, J=8.03 Hz, 1H) 8.56 (s, 2H) 8.88 (s, 1H).

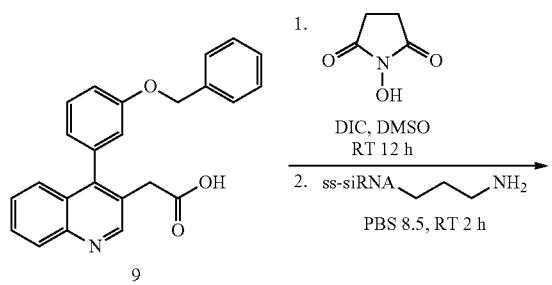

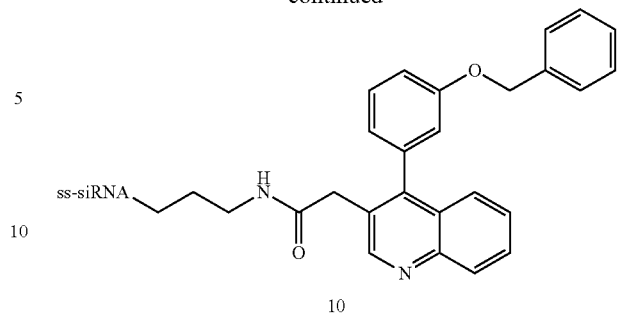

A mixture of N-hydroxysuccinimide (2.49 mg, 0.022 mmol), 9 (4.08 mg, 0.011 mmol), and DIC (2.74 mg, 0.022 mmol) in DMSO (200 uL) was stirred at RT for 12 h. 10 uL of reaction mixture was diluted with 190 uL DMSO. To the resulting solution was added a freshly ss-siRNA-(CH$_2$)$_3$—NH$_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 10. TOF MS (ES$^-$): 6495.

2. DD. Synthesis of siRNA Conjugated with X1017

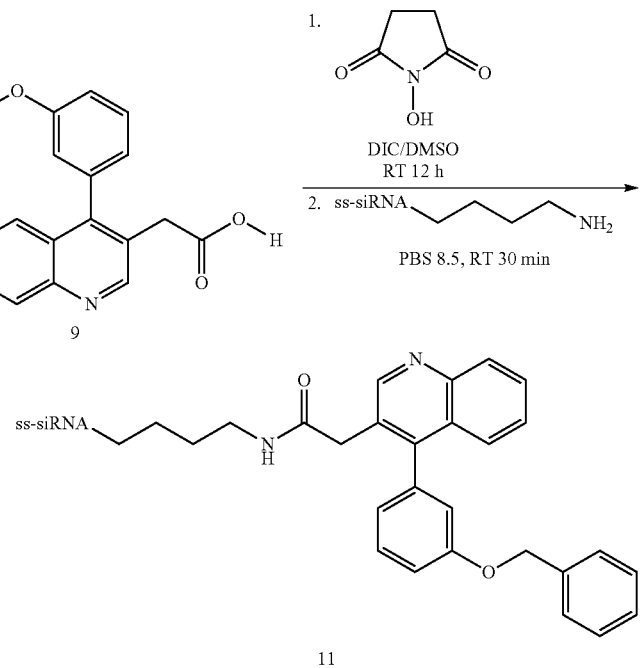

Scheme 11: Overview of the synthesis of 11.

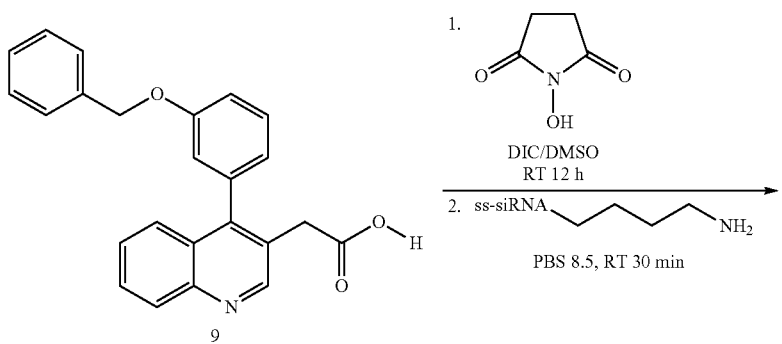

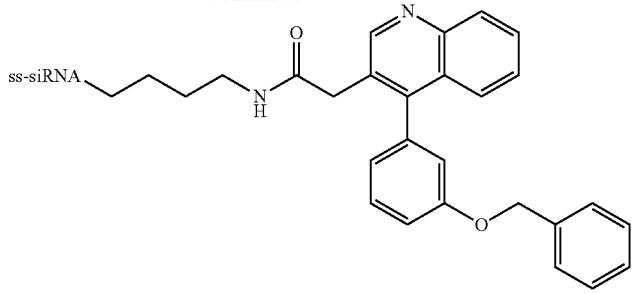

11

A mixture of N-hydroxysuccinimide (2.49 mg, 0.022 mmol), 9 (4.07 mg, 0.011 mmol), and DIC (2.73 mg, 0.022 mmol) in DMSO (200 uL) was stirred at RT for 12 h. 10 uL of reaction mixture was diluted with 190 uL DMSO. To the resulting solution was added a freshly ss-siRNA-$(CH_2)_4$—$NH_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 11. TOF MS (ES$^-$): 6510.

2. EE. Synthesis of siRNA Conjugated with X1022

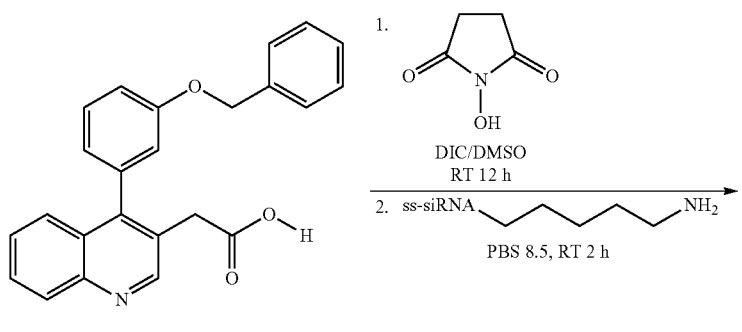

9

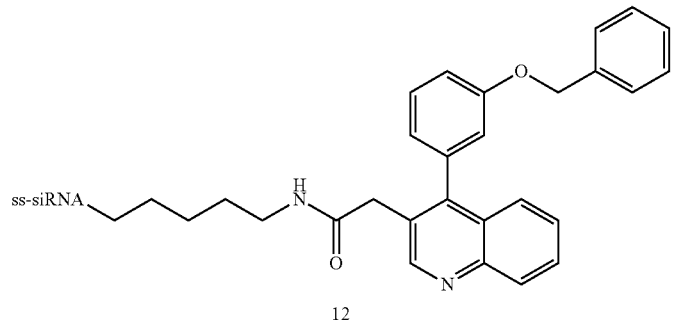

12

Scheme 12: Overview of the synthesis of 12.

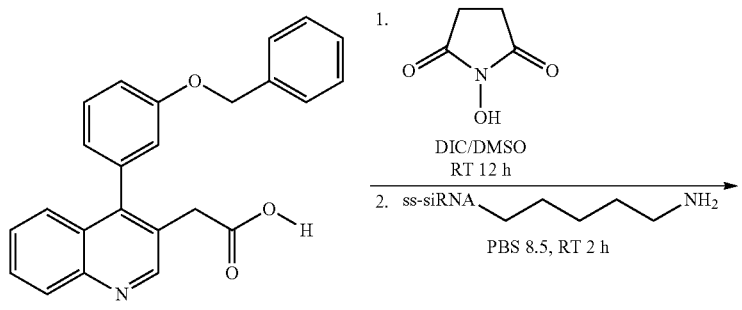

9

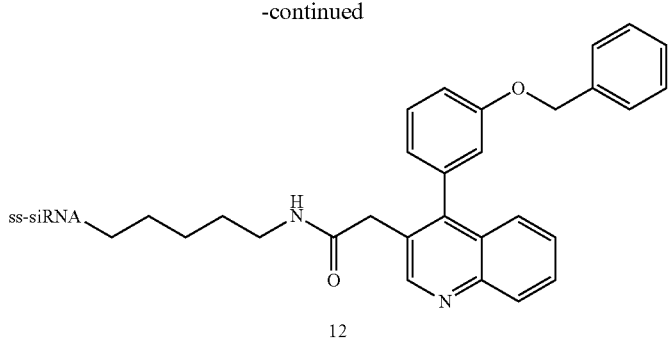

12

A mixture of N-hydroxysuccinimide (2.48 mg, 0.022 mmol), 9 (4.06 mg, 0.011 mmol), and DIC (2.72 mg, 0.022 mmol) in DMSO (200 uL) was stirred at RT for 12 h. 10 uL of reaction mixture was diluted with 190 uL DMSO. To the resulting solution was added a freshly ss-siRNA-$(CH_2)_5$—$NH_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 12. TOF MS (ES⁻): 6524.

A mixture of N-hydroxysuccinimide (2.5 mg, 0.0522 mmol), 1 (2.5 mg, 0.013 mmol), and DIC (2.74 mg, 0.022 mmol) in DMSO (200 uL) was stirred at RT for 12 h. 10 uL of reaction mixture was diluted with 190 uL DMSO. To the resulting solution was added a freshly ss-siRNA-$(CH_2)_3$—$NH_2$ solution (2.0 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 2. TOF MS (ES⁻): 6315.

2. FF. Synthesis of siRNA Conjugated with X1024

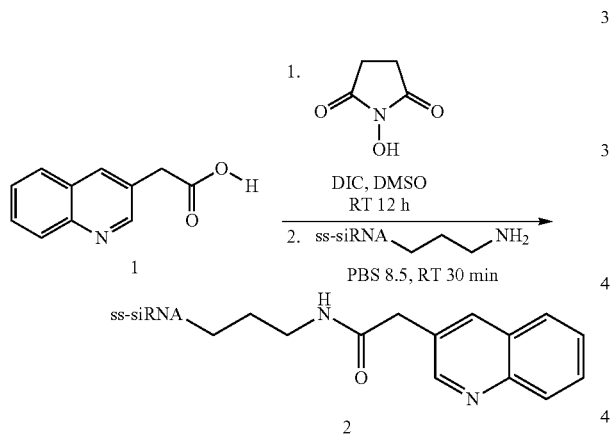

Scheme 13: Overview of the synthesis of 2.

2. GG. Synthesis of siRNA Conjugated with X1026

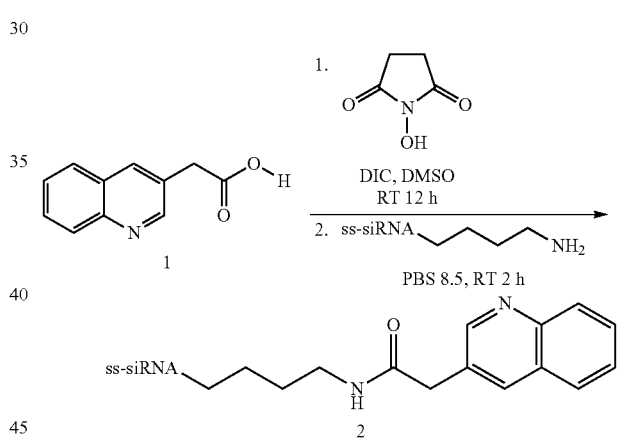

Scheme 14: Overview of the synthesis of 2.

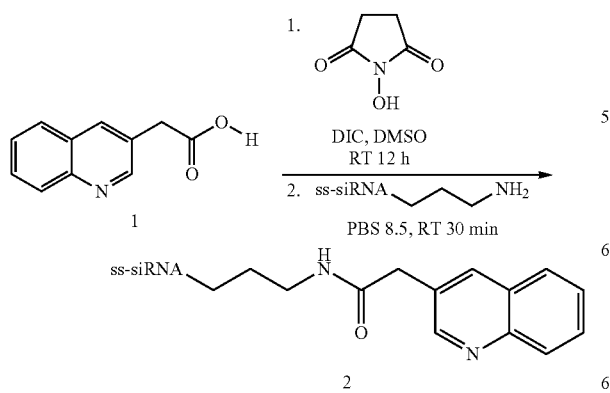

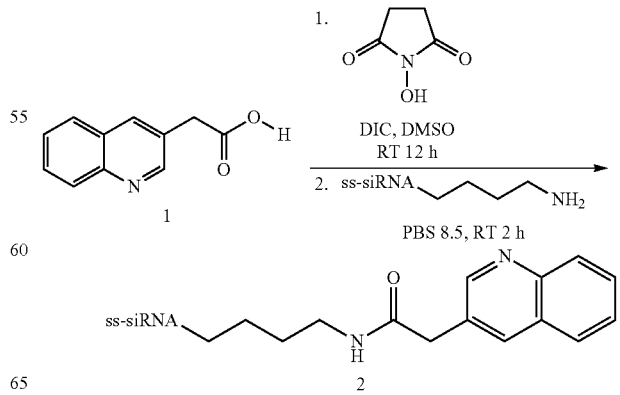

A mixture of N-hydroxysuccinimide (2.49 mg, 0.022 mmol), 1 (2.02 mg, 0.011 mmol), and DIC (2.73 mg, 0.022 mmol) in DMSO (200 uL) was stirred at RT for 12 h. 10 uL of reaction mixture was diluted with 190 uL DMSO. To the resulting solution was added a freshly ss-siRNA-$(CH_2)_4$—$NH_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 2. TOF MS (ES⁻): 6327.

2. HH. Synthesis of siRNA Conjugated with X1025

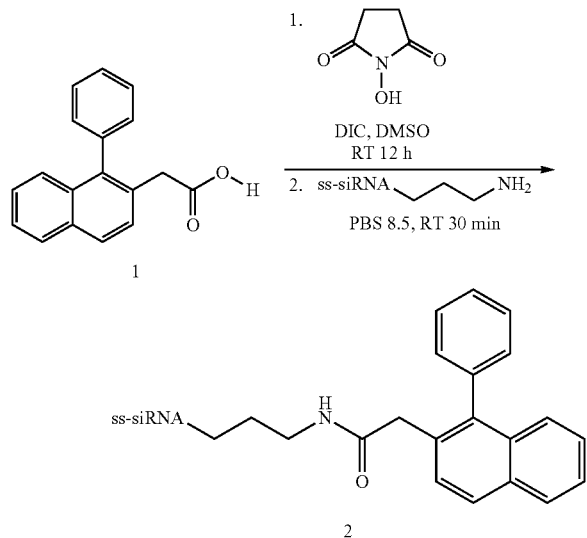

Scheme 15: Overview of the synthesis of 2.

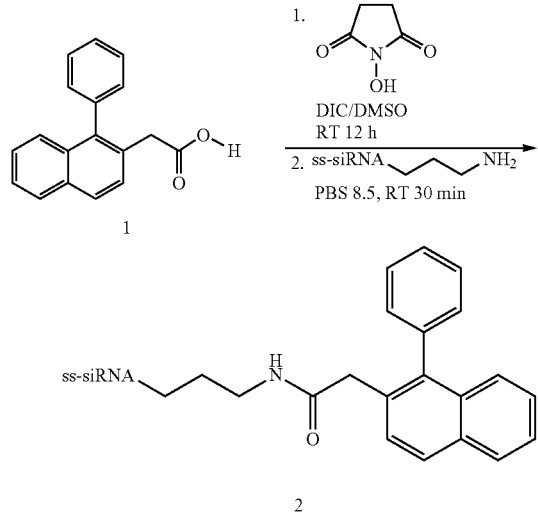

A mixture of N-hydroxysuccinimide (2.49 mg, 0.022 mmol), 1 (2.84 mg, 0.01 mmol), and DIC (2.74 mg, 0.022 mmol) in DMSO (200 uL) was stirred at RT for 12 h. 10 uL of reaction mixture was diluted with 190 uL DMSO. To the resulting solution was added a freshly ss-siRNA-$(CH_2)_3$—$NH_2$ solution (2.0 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 2. TOF MS (ES⁻): 6390.

2. II. Synthesis of siRNA Conjugated with X1027

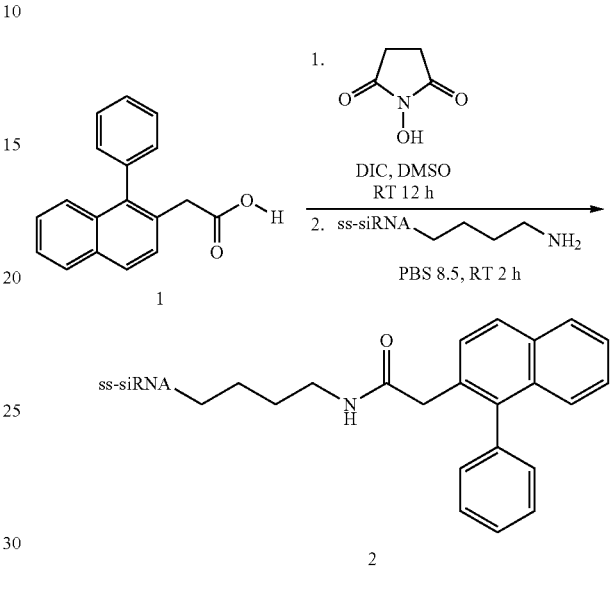

Scheme 16: Overview of the synthesis of 2.

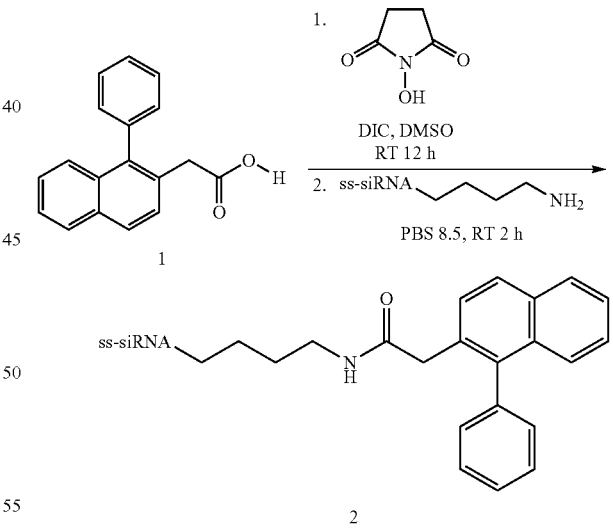

A mixture of N-hydroxysuccinimide (2.49 mg, 0.022 mmol), 1 (2.84 mg, 0.011 mmol), and DIC (2.73 mg, 0.022 mmol) in DMSO (200 uL) was stirred at RT for 12 h. 10 uL of reaction mixture was diluted with 190 uL DMSO. To the resulting solution was added a freshly ss-siRNA-$(CH_2)_4$—$NH_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 2. TOF MS (ES⁻): 6404.

2.JJ. Synthesis of siRNA Conjugated with X1028

Scheme 17: Overview of the synthesis of 2.

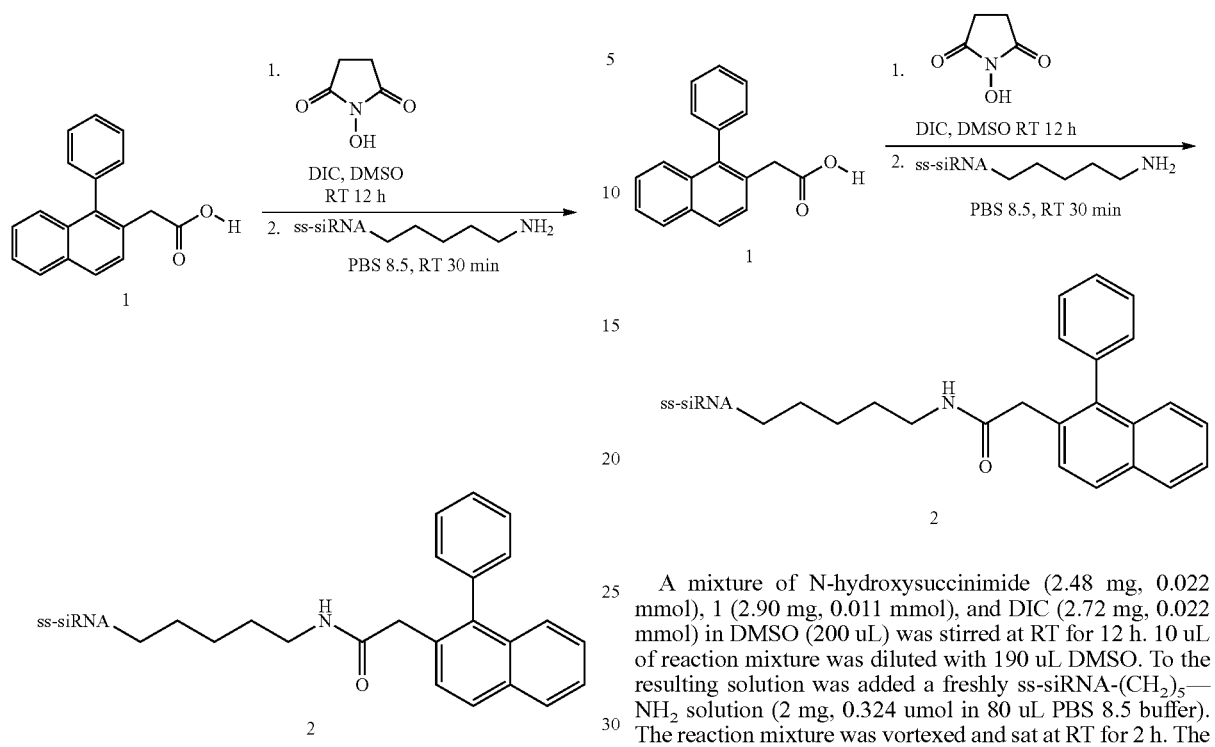

A mixture of N-hydroxysuccinimide (2.48 mg, 0.022 mmol), 1 (2.90 mg, 0.011 mmol), and DIC (2.72 mg, 0.022 mmol) in DMSO (200 uL) was stirred at RT for 12 h. 10 uL of reaction mixture was diluted with 190 uL DMSO. To the resulting solution was added a freshly ss-siRNA-$(CH_2)_5$—$NH_2$ solution (2 mg, 0.324 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 2. TOF MS (ES$^-$): 6417.

2.KK. Synthesis of siRNA Conjugated with X1062

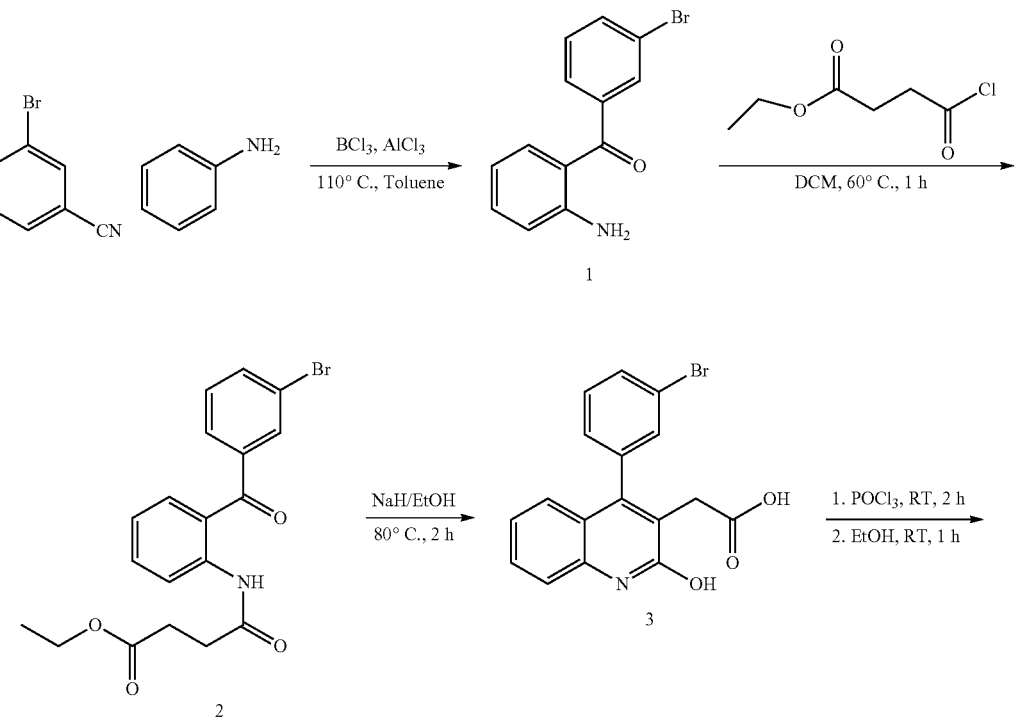

-continued
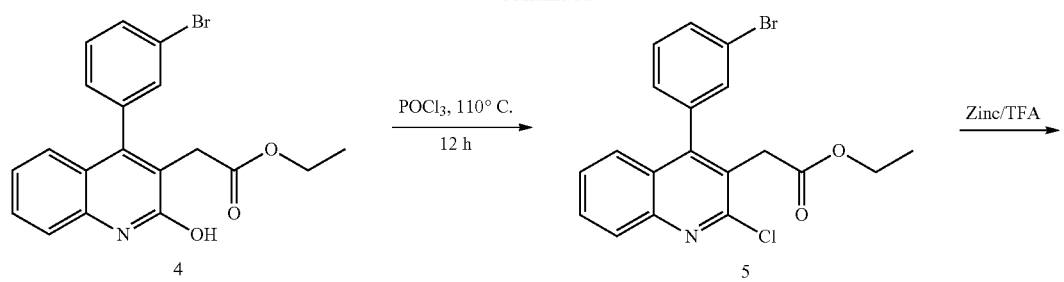
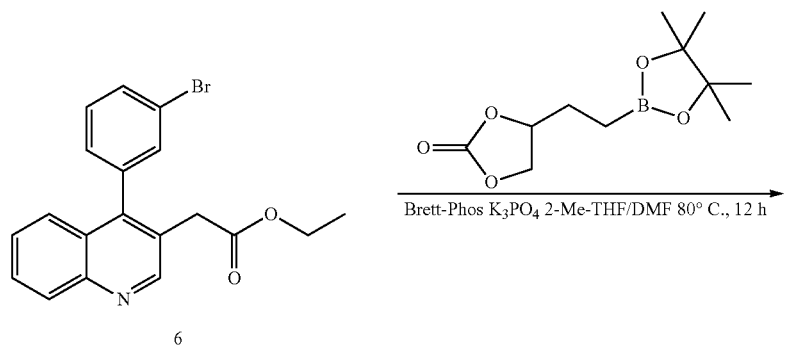
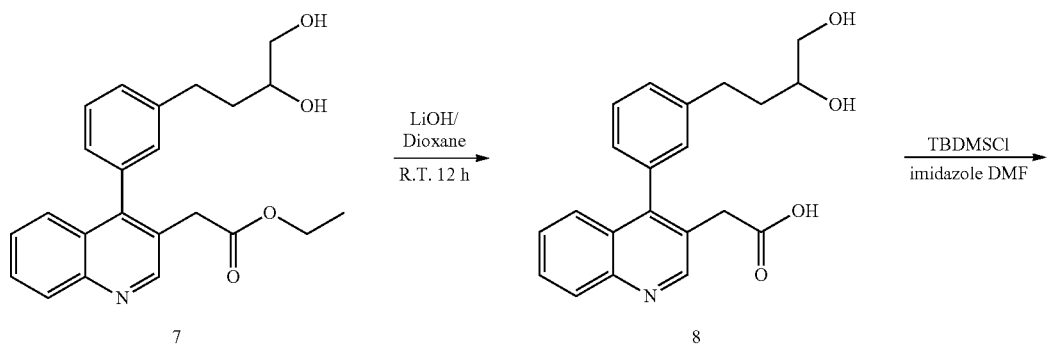
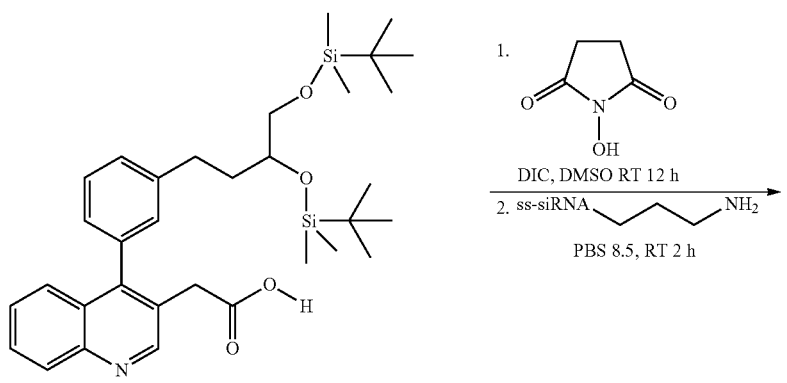

-continued

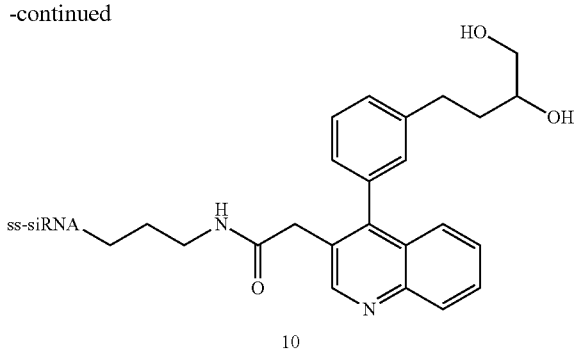

Scheme 1: Overview of the synthesis of 10.

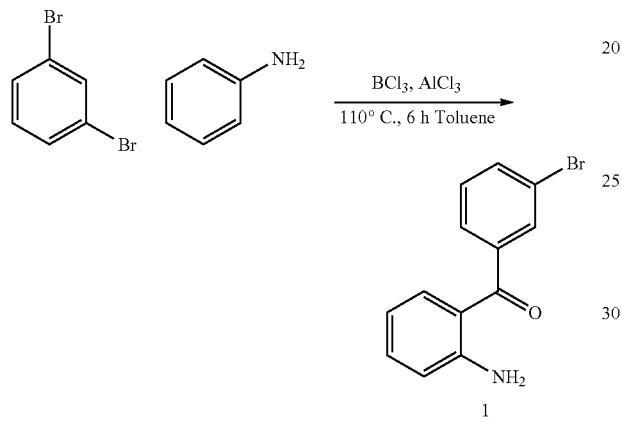

To AlCl₃ (7.88 g, 59.1 mmol) in Toluene (200 ml) was added aniline (5 g, 53.7 mmol, 4.59 ml, in 50 ml Toluene) dropwise under N₂. 3-bromobenzonitrile (29.3 g, 161 mmol) was added to the above mixture subsequently. The resulting mixture was stirred at RT for 1 h, then heated at 110° C. for 6 hrs. The reaction mixture was cooled to RT, to which aq. HCl (1 M, 3 ml) was added. The solution was then heated at 80° C. for 1 h. The solution was cooled to RT, and the organic layer and water layer were separated. The water layer was extracted with ethyl acetate (3×100 mL). The combined organic layers were washed with water and brine, and dried over sodium sulfate. The organic solvent was then removed under vacuum. The crude product was purified by silica chromatography with 0-40% ethyl acetate/heptane to give 1 (4.31 g, 15.6 mmol) in 29% yield. ESI MS (m/z, MH⁺): 278.1 ¹H NMR (400 MHz, CHLOROFORM-d) δ ppm 6.16 (br. s., 2H) 6.64 (t, J=7.53 Hz, 1H) 6.76 (d, J=8.53 Hz, 1H) 7.29-7.49 (m, 3H) 7.56 (d, J=7.53 Hz, 1H) 7.67 (d, J=8.03 Hz, 1H) 7.74-7.84 (m, 1H)

-continued

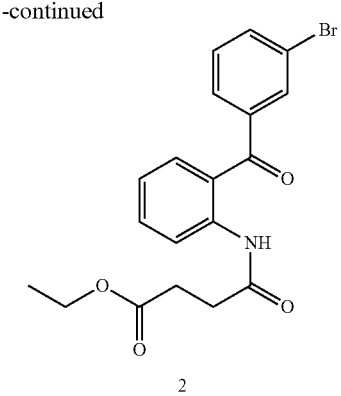

A mixture of 1 (1.02 g, 3.69 mmol) and ethyl 4-chloro-4-oxobutanoate (0.669 g, 4.06 mmol) in DCM (60 ml) was heated at 60° C. for 1 h. The reaction mixture was cooled and quenched with aq. 1 M NaOH (15 ml). The organic layer and water layer were separated. The water layer was extracted with dichloromethane (3×50 ml). The combined organic layers were washed with water and brine, and dried over sodium sulfate. The organic solvent was then removed under vacuum to give 2 (1.44 g, 3.56 mmol) in 96% yield. ESI MS (m/z, MH⁺): 406.2. ¹H NMR (400 MHz, Chloroform-d) δ 10.88 (s, 1H), 8.65 (d, J=8.4 Hz, 1H), 7.86 (d, J=1.8 Hz, 1H), 7.74 (d, J=8.0 Hz, 1H), 7.65-7.51 (m, 3H), 7.39 (t, J=7.8 Hz, 1H), 7.12 (t, J=7.7 Hz, 1H), 4.17 (q, J=7.1 Hz, 2H), 2.77 (dt, J=10.3, 5.2 Hz, 4H), 1.27 (t, J=7.1 Hz, 4H).

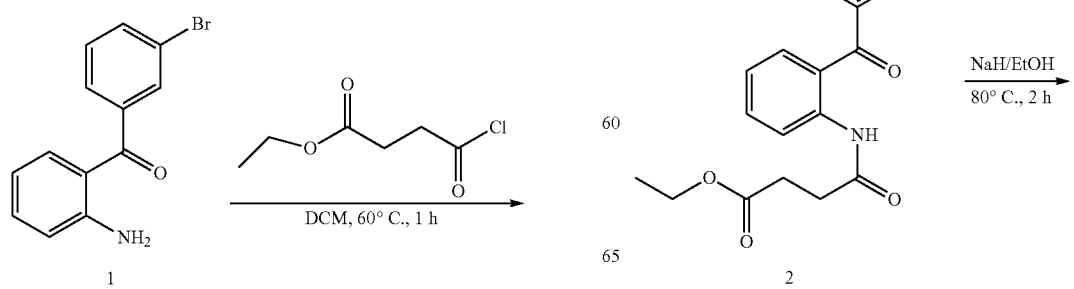

-continued

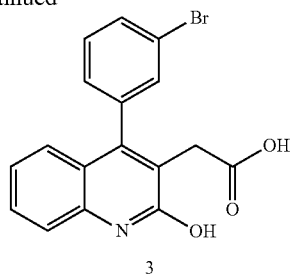

3

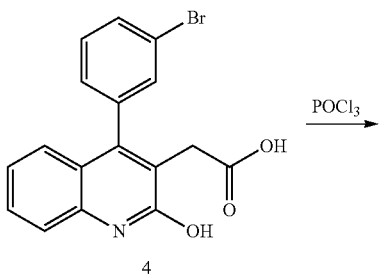

4

A mixture of 2 (1.44 g, 3.56 mmol) and sodium hydride (1.425 g, 35.6 mmol) in ethanol (20 ml) was heated at 80° C. for 2 h. The reaction mixture was cooled to RT and quenched with water (5 ml) then neutralized with aq. 1 M HCl (2 ml). The resulting solution was extracted with ethyl acetate (3×50 mL). The combined organic layers were washed with water and brine, and dried over sodium sulfate. The organic solvent was then removed under vacuum to give 3 (1.2 g, 3.63 mmol) in 94% yield. ESI MS (m/z, MH$^+$): 360.2. $^1$H NMR (400 MHz, Chloroform-d) δ 11.71-11.63 (m, 1H), 11.55-11.42 (m, 3H), 11.37 (d, J=8.3 Hz, 1H), 11.30-11.22 (m, 1H), 11.12 (td, J=7.6, 7.0, 1.2 Hz, 1H), 11.00 (dd, J=8.2, 1.4 Hz, 1H), 7.33 (d, J=3.5 Hz, 2H), 4.87-4.82 (m, 2H).

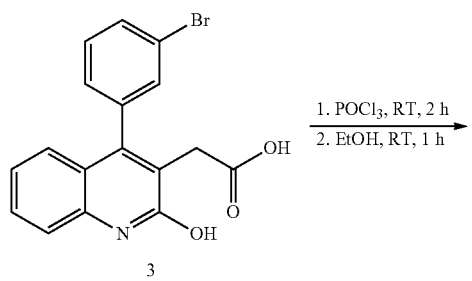

3

1. POCl$_3$, RT, 2 h
2. EtOH, RT, 1 h

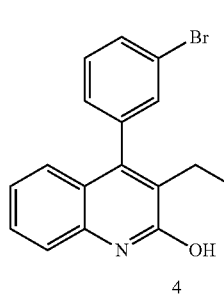

4

A solution of 3 (1.2 g, 1.89 mmol) in POCl$_3$ (15 ml) was stirred at RT for 2 h. POCl$_3$ was removed under vacuum, the resulting residue was quenched with ethanol (50 ml). The solution was stirred at RT for 2 h, then ethanol was removed under vacuum. To the residue was added dichloromethane (50 ml) and aq. 1 M NaOH (20 ml). Organic layer and water layer were separated. The water layer was extracted with dichloromethane (2×50 ml). The combined organic layers were washed with water, brine and dried over sodium sulfate. The organic solvent was removed under vacuum to give 4 (1.76 mg, 4.56 mmol) in 136% yield. ESI MS (m/z, MH$^+$): 388.2. $^1$H NMR (400 MHz, Chloroform-d) δ 7.65 (dt, J=8.2, 1.4 Hz, 1H), 7.54-7.46 (m, 2H), 7.45-7.37 (m, 2H), 7.27 (dt, J=7.8, 1.5 Hz, 1H), 7.17-7.04 (m, 2H), 4.18-4.16 (m, 2H), 3.50 (d, J=1.5 Hz, 2H), 1.27 (h, J=3.7 Hz, 3H).

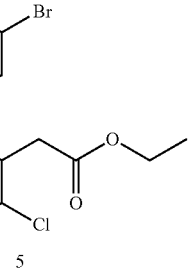

POCl$_3$ →

5

A solution of 4 (1.76 g, 4.56 mmol) in POCl$_3$ (10 ml) was heated at 110° C. for 12 h. POCl$_3$ was removed under vacuum. To the residue was added dichloromethane (50 ml) and aq. 1 M NaOH (20 ml). The organic layer and water layer were separated. The water layer was extracted with dichloromethane (2×50 ml). The combined organic layers were washed with water, brine and dried over sodium sulfate. The organic solvent was removed under vacuum to give 5 (440 mg, 1.09 mmol) in 32.5% yield. ESI MS (m/z, MH$^+$): 406.0. $^1$H NMR (400 MHz, Chloroform-d) δ 8.14-8.05 (m, 1H), 7.76 (ddd, J=8.4, 6.9, 1.4 Hz, 1H), 7.69 (ddd, J=8.0, 1.9, 1.0 Hz, 1H), 7.53-7.41 (m, 3H), 7.36 (dd, J=8.3, 1.3 Hz, 1H), 7.26 (dt, J=7.7, 1.3 Hz, 1H), 4.19 (q, J=7.1 Hz, 2H), 3.72 (s, 2H), 1.27 (t, J=7.1 Hz, 3H).

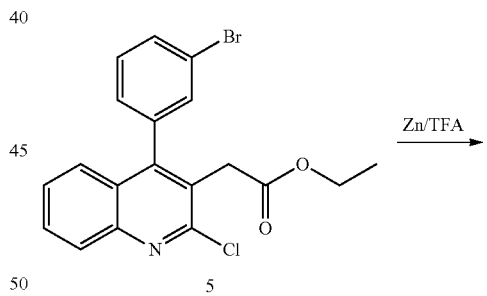

5

Zn/TFA →

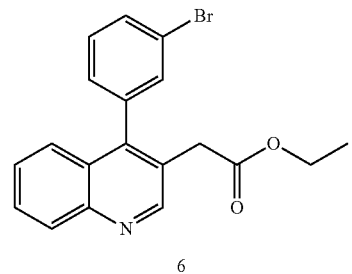

6

A mixture of 5 (50 mg, 0.124 mmol), Zinc power (40.4 mg, 0.618 mmol) in TFA (1 ml) was heated at 40° C. for 12 h. The reaction mixture was quenched with NaOH (1M, 1 ml). The organic layer was extracted with dichloromethane (2×10 ml). The combined organic layers were washed with water, brine and dried over sodium sulfate. The organic solvent was removed under vacuum. The crude product was purified by silica flash chromatograph with elute 0-50% EtOAc/Heptane to give 6 (39 mg, 0.105 mmol) in 85% yield. ESI MS (m/z, MH$^+$): 372.1. $^1$H NMR (400 MHz, CHLOROFORM-d) ppm 1.24 (t, J=7.15 Hz, 3H) 3.63 (s, 2H) 4.02-4.27 (m, 2H) 7.12-7.33 (m, 1H) 7.37-7.61 (m, 4H) 7.61-7.71 (m, 1H) 7.75 (t, J=1.51 Hz, 1H) 8.21 (d, J=8.53 Hz, 1H) 8.94 (s, 1H).

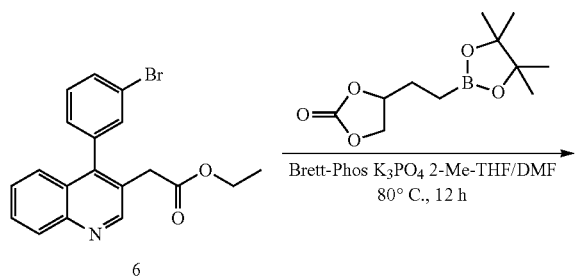

A mixture of 4-(2-(4,4,5,5-tetramethyl-1,3,2-dioxaborolan-2-yl)ethyl)-1,3-dioxolan-2-one) (255 mg, 1.05 mmol), 6 (39 mg, 0.105 mmol), (Brettphos)paddadium(II) phenethylamine chloride (4.21 mg, 5.27 umol) and 1M aqueous K$_3$PO$_4$ (421 uL, 0.421 mmol) in 2-Me THF (500 uL) and DMF (500 uL) was heated at 80° C. for 12 h. The reaction mixture was filtered to remove insoluble material. The organic solvent was removed under vacuum. The crude was purified by HPLC with 5% TFA in 5-95% acetonitrile/water to give 7 (15 mg, 0.04 mmol) in 37.5% yield. ESI MS (m/z, MH$^+$): 380.4. $^1$H NMR (400 MHz, CHLOROFORM-d) ppm 1.22 (td, J=7.15, 2.26 Hz, 3H) 1.73-1.92 (m, 2H) 2.72-2.98 (m, 2H) 3.49 (dd, J=11.04, 7.53 Hz, 1H) 3.56-3.84 (m, 4H) 4.04-4.20 (m, 2H) 7.15 (d, J=7.53 Hz, 1H) 7.13 (d, J=8.78 Hz, 1H) 7.37 (d, J=7.53 Hz, 1H) 7.43-7.56 (m, 3H) 7.74 (br. s., 1H) 8.22 (br. s., 1H) 8.94 (br. s., 1H).

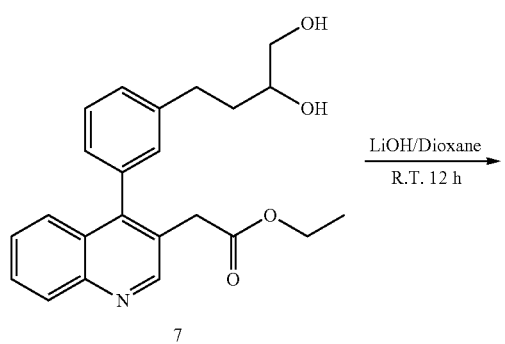

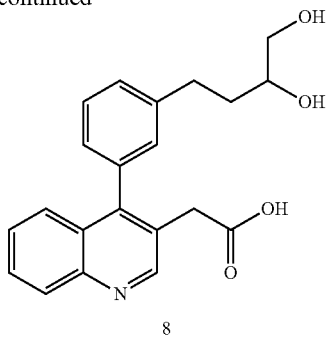

A mixture of 7 (15 mg, 0.04 mmol) and aq. 1 M LiOH (87 uL ml, 0.087 mmol) in dioxane (200 ul) was stirred at RT for 12 hrs. The organic solvent was removed under vacuum to give 8 (14.17 mg, 0.04 mmol) in 100% yield as lithium salt. ESI MS (m/z, MH$^+$): 352.4. $^1$H NMR (400 MHz, METHANOL-d$_4$) δ ppm 1.62-1.80 (m, 1H) 1.80-1.98 (m, 1H) 2.78 (ddd, J=13.33, 6.76, 3.16 Hz, 1H) 2.84-2.99 (m, 1H) 3.46-3.55 (m, 3H) 3.55-3.68 (m, 3H) 6.98-7.25 (m, 2H) 7.31-7.59 (m, 4H) 7.74 (ddd, J=8.40, 6.38, 1.89 Hz, 1H) 8.06 (d, J=8.34 Hz, 1H) 8.86 (s, 1H).

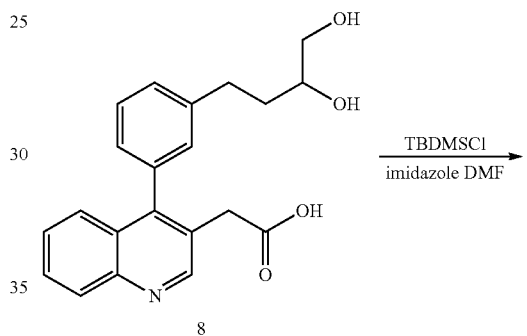

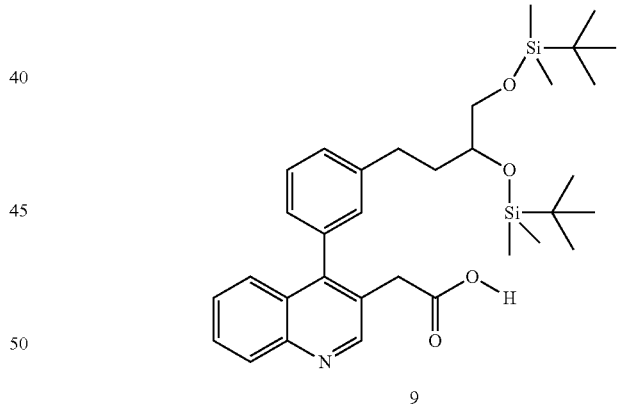

A mixture of 8 (14 mg, 0.039 mmol), TBDMSCl and imidazole (43.6 mg, 0.641 mmol) in DMF (4 ml) was stirred at RT for 24 hrs. The reaction mixture was quenched with water (1 ml). The organic layer was extracted with ethylestate (3×5 ml). The combined organic layers were washed with water, brine and dried over sodium sulfate. The organic solvent was removed under vacuum. The crude product was purified by silica flash chromatograph with elute 0-50% EtOAc/Heptane to give 9 (15.9 mg, 0.025 mmol) in 63.2% yield. ESI MS (m/z, MH$^+$): 580.6. $^1$H NMR (400 MHz, METHANOL-d$_4$) δ ppm-0.12-0.13 (m, 8H) 0.69-0.98 (m, 12H) 1.17-1.36 (m, 5H) 2.60-2.90 (m, 2H) 3.38-3.62 (m, 6H) 3.73 (d, J=4.55 Hz, 1H) 7.02-7.15 (m, 2H) 7.24-7.38 (m, 1H) 7.39-7.47 (m, 3H) 7.64-7.74 (m, 1H) 7.98-8.06 (m, 1H) 8.68-8.89 (m, 1H).

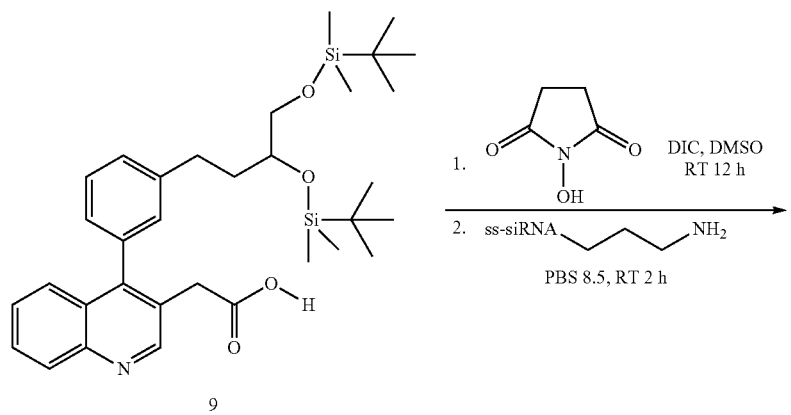

9

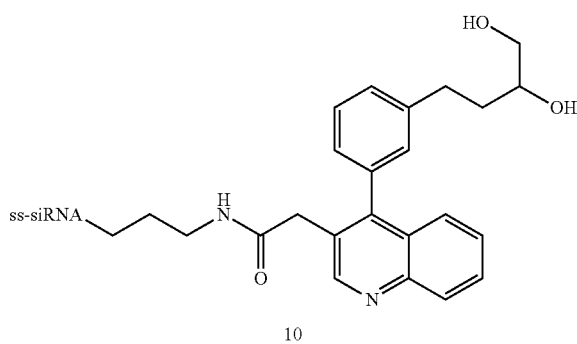

10

A mixture of N-hydroxysuccinimide (2.49 mg, 0.022 mmol), 9 (6.26 mg, 0.011 mmol), and DIC (2.74 mg, 0.022 mmol) in DMSO (200 uL) was stirred at RT for 12 hrs. 10 uL of reaction mixture was diluted with 190 uL DMSO. To the resulting solution was added a freshly ss-siRNA-$(CH_2)_3$—$NH_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 10. TOF MS (ES$^-$): 6478.

2.LL. Synthesis of siRNA Conjugated with X1063

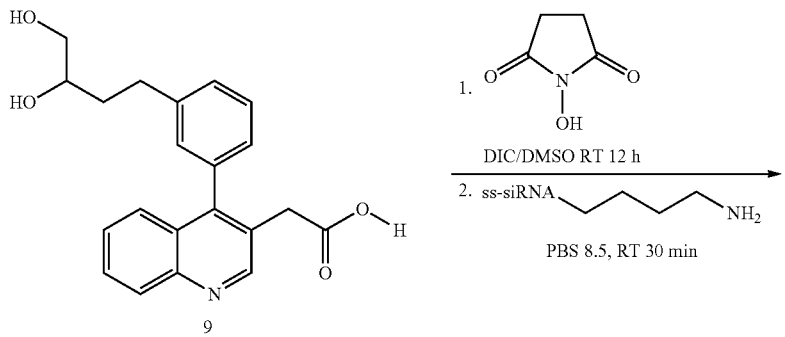

9

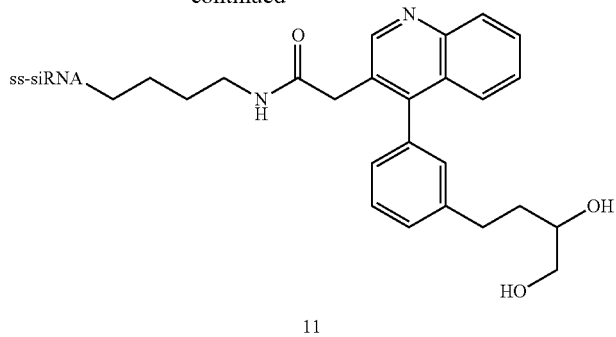

11

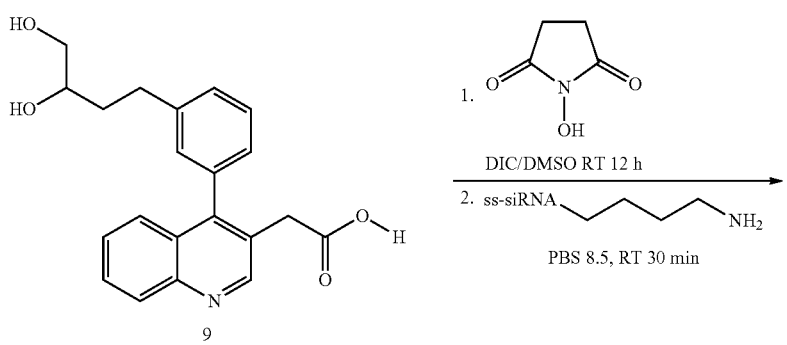

Scheme 2: Overview of the synthesis of 11.

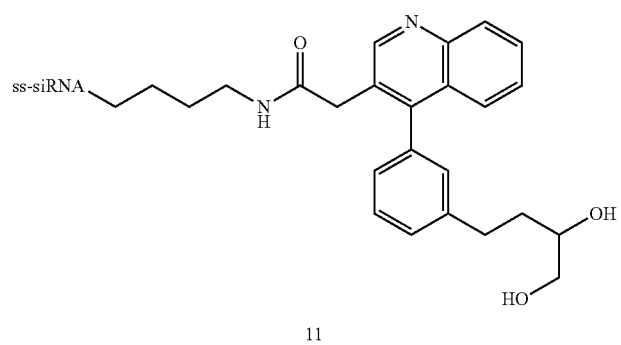

11

A mixture of N-hydroxysuccinimide (2.49 mg, 0.022 mmol), 9 (6.26 mg, 0.011 mmol), and DIC (2.73 mg, 0.022 mmol) in DMSO (200 uL) was stirred at RT for 12 h. 10 uL of reaction mixture was diluted with 190 uL DMSO. To the resulting solution was added a freshly ss-siRNA-(CH$_2$)$_4$—NH$_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 11. TOF MS (ES$^-$): 6492.

2.MM. Synthesis of siRNA Conjugated with X1064

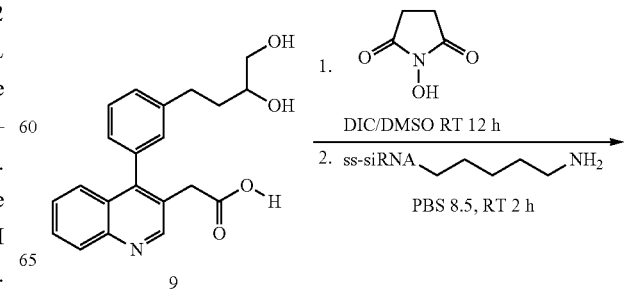

-continued

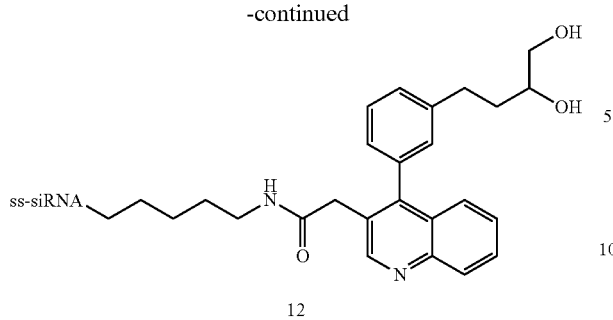

Scheme 3: Overview of the synthesis of 12.

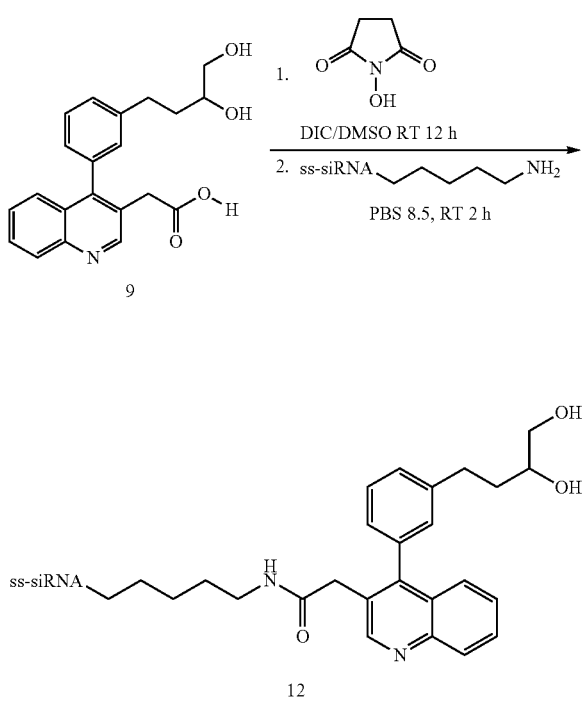

A mixture of N-hydroxysuccinimide (2.48 mg, 0.022 mmol), 9 (6.26 mg, 0.011 mmol), and DIC (2.72 mg, 0.022 mmol) in DMSO (200 uL) was stirred at RT for 12 h. 10 uL of reaction mixture was diluted with 190 uL DMSO. To the resulting solution was added a freshly ss-siRNA-$(CH_2)_5$—$NH_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 12. TOF MS ($ES^-$): 6506.

Example 3. 18-Mer RNAi Agents Comprising a Spacer, a Phosphate or Modified Internucleoside Linker and a 3' End Cap (e.g., PAZ Ligand)

RNA interference activity of 18-mer duplexes comprising a spacer, a phosphate or modified internucleoside linker, and any of various 3' end caps is analyzed. In vitro and in vivo potency is studied, as shown in Example 3A (in vitro data) and 3B (in vivo data).

Example 3A. In Vitro Potency of 18-Mer RNAi Agents Comprising a Spacer, a Phosphate or Modified Internucleoside Linker, and a 3' End Cap (PAZ Ligand)

Potency of 18-mer HAMP (Hepcidin) siRNA-PAZ Ligand Conjugates is studied.

A variety of constructs were made using the same two sequences. Some of these have or do not have a modification at the last two nt at the 3' end (2'-MOE, or MOE). Some of these have or do not have a ribitol spacer (Rib). A variety of 3' end caps is also used.

Hepcidin mRNA down regulation in HuH-7 cells is studied at 3 doses.

Two test sequences used are hs_HAMP_400 and 402. "hs" indicates "*Homo sapiens*". 400 is a sequence beginning at position 400 and 402 is an overlapping sequence beginning at position Parent stem format: A106S42 (2'-OMe chemistry, as shown in FIGS. 5A and 5B). Various other hs_HAMP 400 and 402 are depicted in FIG. 5A (Guide or antisense strand) and 5B (corresponding Sense strand).

Results are shown in FIGS. 4A and 4B and 7 and in Table 5, below.

FIGS. 4A and 4B show the in vitro RNA interference or KD (knockdown) mediated by various RNAi agents comprising a 3' end cap: BP (biphenyl), C6, X027, X038, X050, X051, X052, X058, X059, X060, X061, X062, X063, X064, X065, X066, X067, X068, and X069 on the guide (antisense) strand. The circled data points in FIGS. 4A and 4B represent the most potent format for hs_HAMP_400 and the most potent format for the hs_HAMP_402.

Additional data is provided in Table 5, below. This Table indicates the Nickname ("Oligo Identifier") for the 3' end cap, and the DMT, Succinate and Carboxylate variants thereof; the Carboxylate Kd; the KD (knockdown) mediated by a Hepcidin RNAi agent comprising the 3' end cap (format: S402+ribitol+MOE clamp) at 5 nM in vitro; and the approximate (approx.) IC50

TABLE 6

| Oligo Identifier (Nickname) | Hepcidin KD at 5 nM in vitro (%) | Hepcidin (approx.) IC50 |
|---|---|---|
| BP (biphenyl) | 68 | 2.3 |
| X027 | 57 | 3.3 |
| X038 | 62 | 2.6 |
| X050 | 61 | 4.0 |
| X051 | 61 | 3.4 |
| X052 | 64 | 3.0 |
| X058 | 68 | 2.7 |
| X059 | 55 | 4.1 |
| X060 | 65 | 3.5 |
| X061 | 61 | 3.0 |
| X062 | 63 | 3.5 |
| X063 | 56 | 3.7 |
| X064 | 60 | 3.1 |
| X065 | 66 | 3.0 |
| X066 | 49 | 4.9 |
| X067 | 66 | 2.5 |
| X068 | 63 | 3.0 |
| X069 | 81 | 1.5 |
| C6 | 66 | 2.6 |

Figure 6:
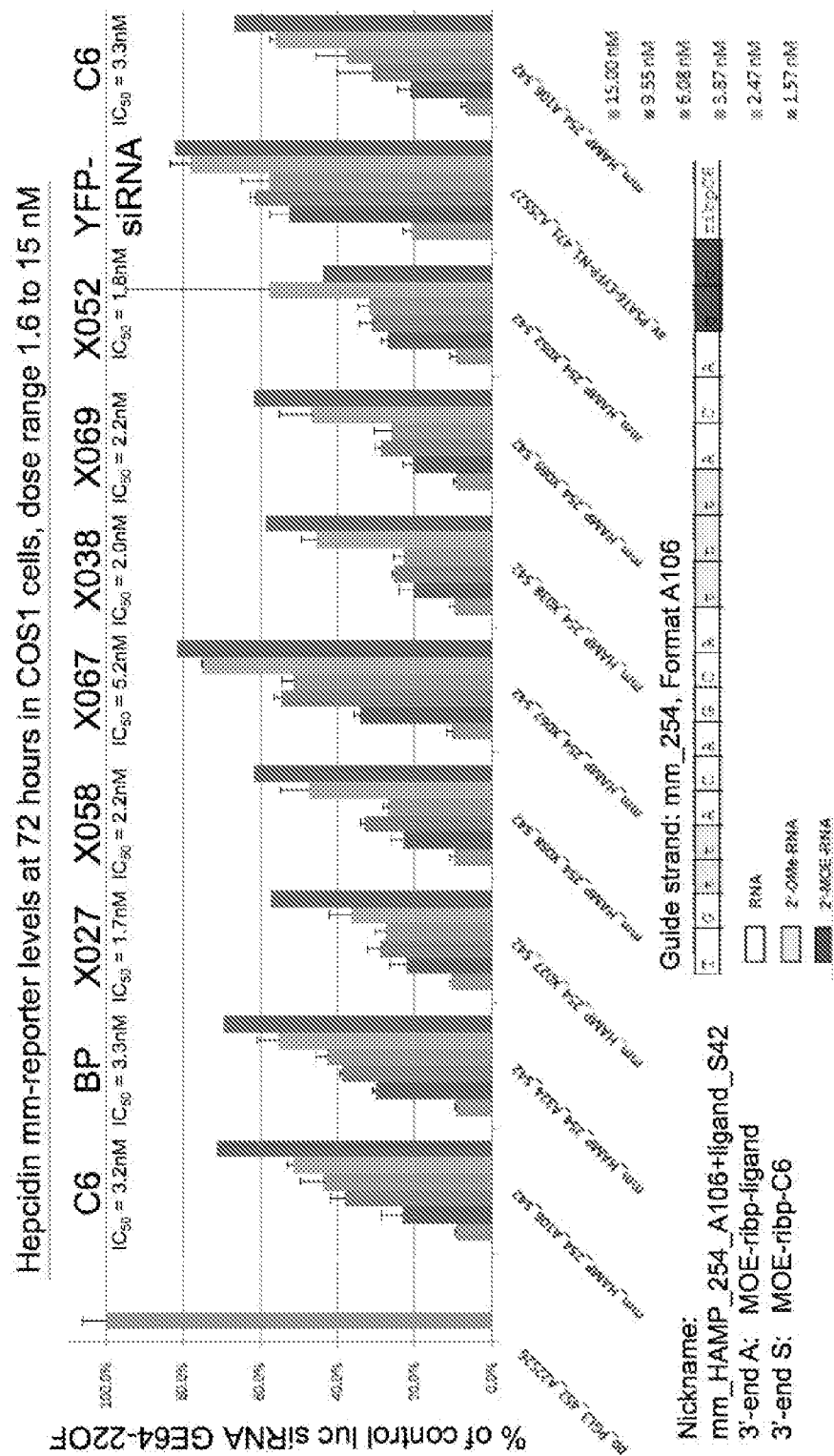
FIG. 6 illustrates mouse hepcidin mm reporter levels at 72 hours in COS1 cells, with a dose range of 1.57 to 15 nM. The guide strand of mouse Hepcidin sequence 254 is SEQ ID NO: 49. The RNAi agents used comprised an 18-mer guide strand, wherein the 3' end of the 18-mer strand terminates in a phosphate and further comprises, in 5' to 3' order: a spacer (ribitol), a phosphate and a 3' end cap. The various 3' end caps used include: X027, X058, X067, X038, X069, and X052. The format of the strands is indicated, as described in Example 3A.

FIG. 6 shows the residual gene activity (wherein residual gene activity=100%—KD) of mouse Hepcidin mm-reporter levels at 72 hours in COS1 cells after various doses of 18-mer RNAi agents comprising a spacer, a phosphate or modified internucleoside linker, and 3' end cap, at a range from 1.57 nM to 15 nM. The format of the strands is indicated. The 3' end of the sense strand terminates in a 2' MOE-clamp—ribp (ribitol spacer)—C6. The 3' end of the antisense strand terminates in a 2' MOE-clamp—ribp (ribitol spacer)—ligand, wherein the ligands used were 3' end caps (X027, X058, X067, etc.).

These data thus show the efficacy of various RNAi agents having the 18-mer format wherein the 3' end cap is BP (biphenyl), C6, X027, X038, X050, X051, X052, X058, X059, X060, X061, X062, X063, X064, X065, X066, X067, X068, or X069.

Example 3B. In Vivo Potency of 18-Mer RNAi Agents Comprising a 3' End Cap (PAZ Ligand)

Example 3A showed the in vitro potency of various 18-mer RNAi agents comprising a 3' end cap. Example 3B shows the in vivo potency of various 18-mer RNAi agents comprising a 3' end cap.

These in vivo experiments used these parameters:
Mice (n=5/group) injected via IV bolus (tail vein): LNP569
PBS
LNP569—Hamp254—X052 (SL52-49CE)—3 mg/kg
LNP569—Hamp254—X058 (IL54-43-XE)—3 mg/kg
LNP569—Hamp254—X067 (YL55-48RE)—3 mg/kg
LNP569—Hamp254—X038 (CL51-55IE)—3 mg/kg
LNP569—Hamp254—X069 (GA35-24OF)—3 mg/kg
LNP569—Hamp254—X027 (ML59-39NE)—3 mg/kg
LNP569—Hamp254—C6 control—3 mg/kg
LNP569 is a lipid nanoparticle preparation of the RNAi agent.
Two timepoints—48 and 168 hrs post-injection (both 3 mg/kg).
Assess hepcidin knockdown in liver (mRNA-qPCR)
Key questions are asked:
Are PAZ domain ligands active in vivo? (This is tested at the 48 hour timepoint.)
Do PAZ domain ligands provide benefit for duration of knockdown? (This is tested at the 168 hour timepoint.)

Figure 7A:
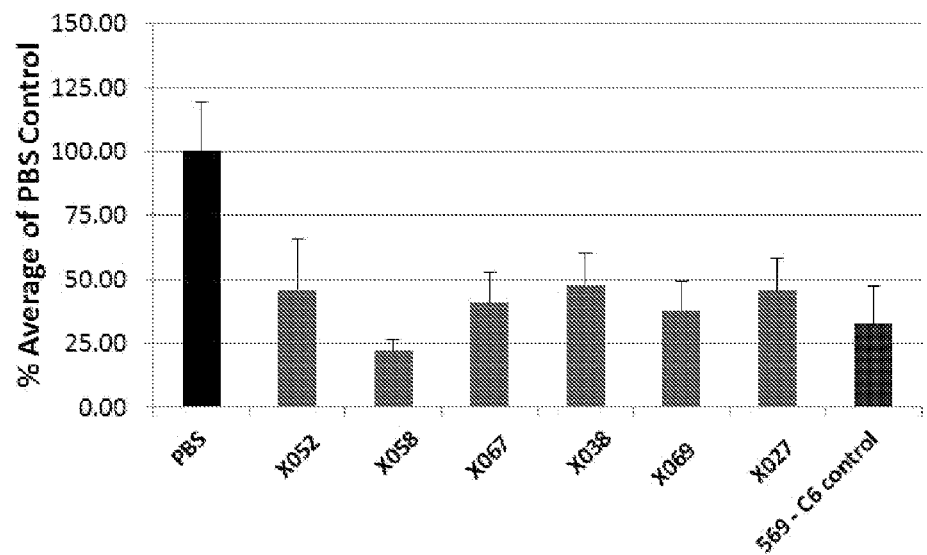
FIGS. 7A and 7B show that in both the ABI Hamp1 Taqman assay (FIG. 8A) and the Hamp1 specific Taqman Assay (FIG. 8B) all of the RNAi agents with different 3' end caps were able to mediate Hepcidin knockdown in vivo at 48 hours post-dose, with a 1×3 mg/kg dose. 3' end caps used were: X052, X058, X067, X038, X069, and X027, with C6 as a control, as described in Example 3B. These are RNAi agents to mouse Hepcidin tested in vivo.
Figure 7B:
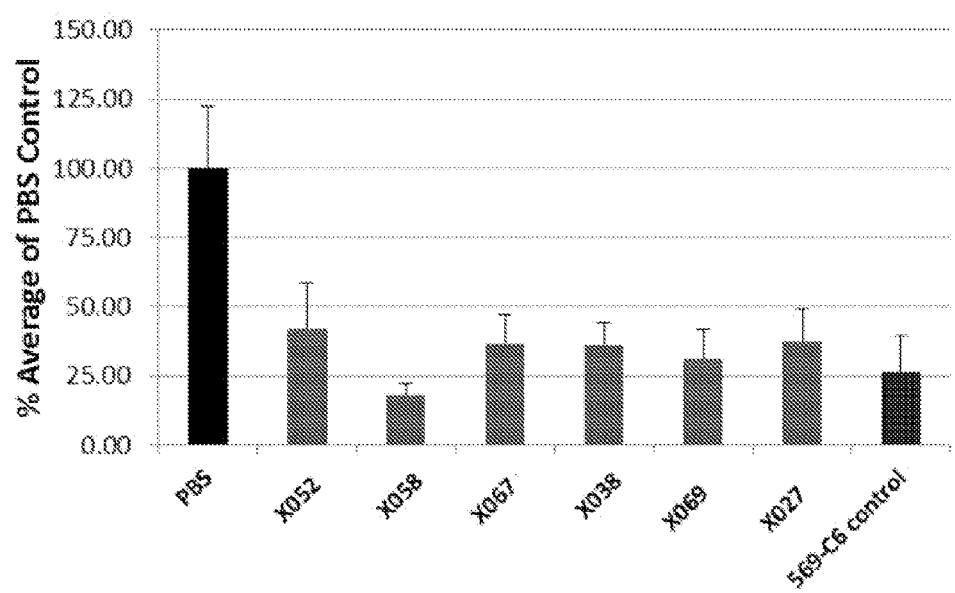

The results are shown in FIGS. 7A and 7B.
FIGS. 7A and 7B show that in both the ABI Hamp1 Taqman assay (FIG. 7A) and the Hamp1 specific Taqman Assay (FIG. 7B) all of the RNAi agents were able to mediate Hepcidin knockdown in vivo at 48 hours post-dose, with a 1×3 mg/kg dose. 3' end caps used were: X052, X058, X067, X038, X069, and X027, with C6 as a control.

The finding that 18-mer RNAi agents with 3' end caps of X052, X058, X067, X038, X069, X027, or C6 are still able to mediate RNA interference at 48 hours indicates that the 3' end caps protect the RNAi agents against degradation or digestion (e.g., by nucleases in the serum).

Figure 8A:
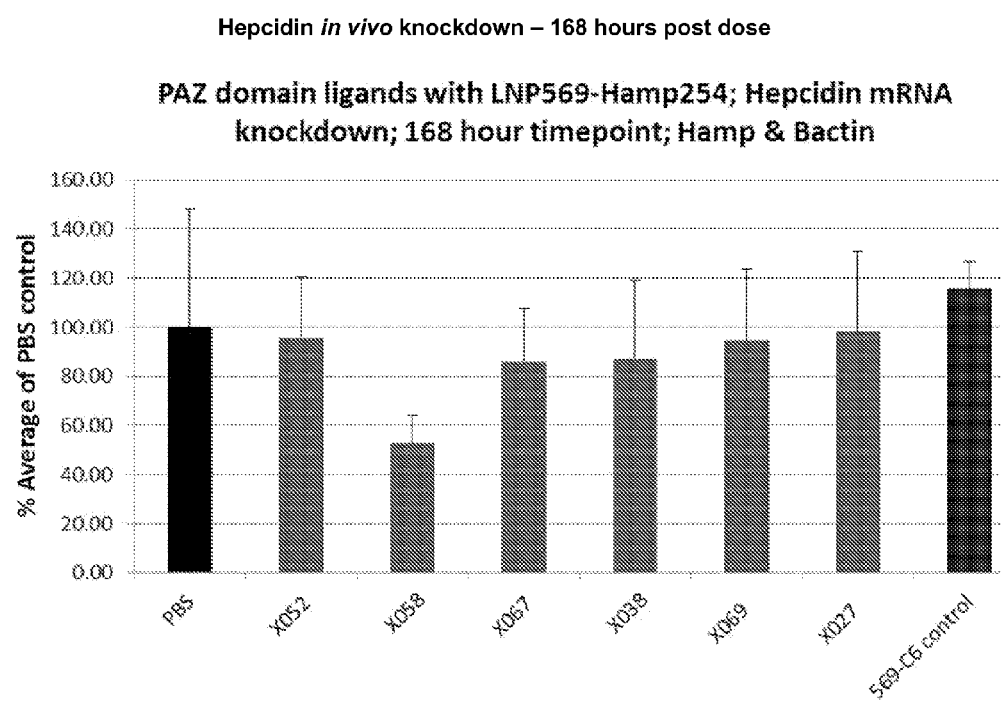
FIG. 8A shows that in the Hamp1 specific Taqman assay, the mouse hepcidin 18-mer Hamp 254 duplex comprising the X058 3' end cap was still able to mediate RNA interference (measured by Hepcidin knockdown) at 168 hours (7 days) post-dose in vivo, with a 1×3 mg/kg dose, as described in Example 3B.
Figure 8B:
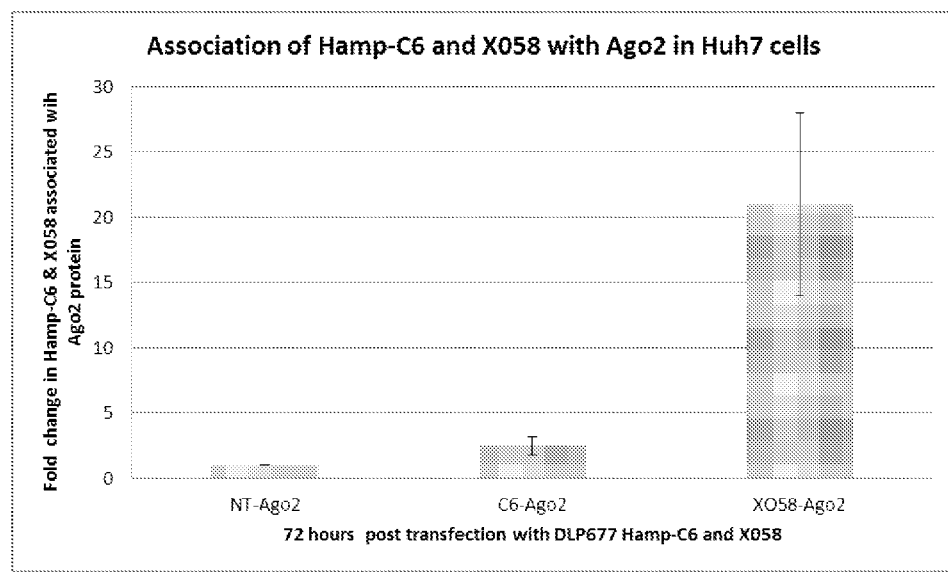
FIG. 8B shows the increased association of the duplex comprising the X058 3' end cap with Ago2, compared to the association of the duplex comprising the C6 3' end cap. These are RNAi agents to mouse Hepcidin tested in vivo.
Figure 9:
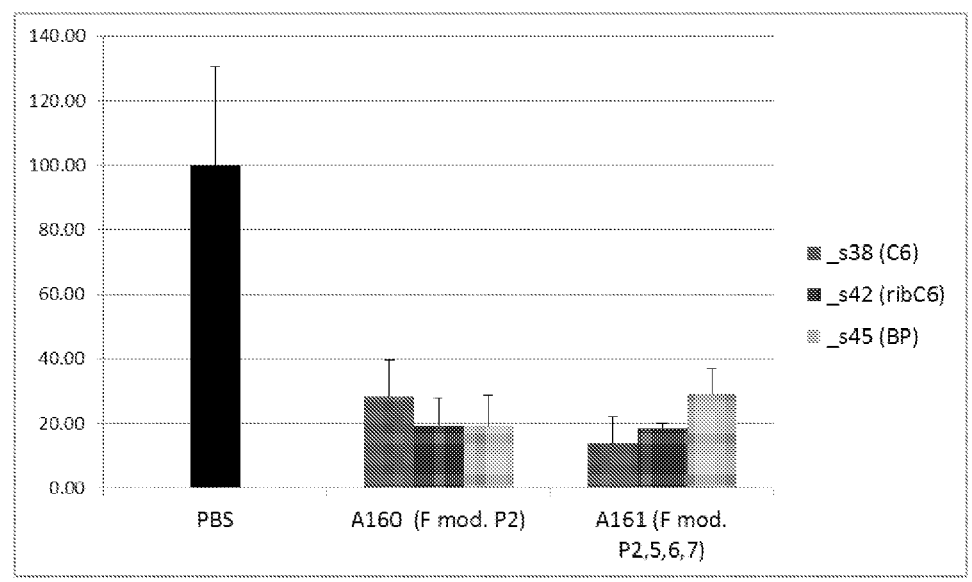
FIG. 9 shows the in vivo comparison of RNAi agents of A160 & A161 formats and various 3' end caps (C6 or BP) or a ribitol spacer and a 3' end cap (ribC6), as described in Example 3B. These are human Hepcidin RNAi agents.

FIG. 8A shows that in the Hamp1 specific Taqman assay, the 18-mer duplex comprising the X058 3' end cap was still able to mediate RNA interference (measured by Hepcidin knockdown) at 168 hours post-dose in vivo. Thus, >50% knockdown was observed in mice after 7 days with a single dose.

These data thus show the efficacy of RNAi agents having the 18-mer format, wherein the 3' end cap is X052, X058, X067, X038, X069, X027, or C6.

Example 3C. Interaction of X058 with Ago2

Without being bound by any particular theory, this disclosure notes that the increased potency and duration of knockdown mediated by 18-mer RNAi agents with a X058 3' end cap in Example 3B may be due to the increased association of X058 with Ago2. FIG. 9B shows the X058 and C6 Ago2 Pulldown experiment using Hepcidin 18-mer oligonucleotides.

Briefly, antibodies to Ago2 were used to pull down Ago2 from cells 72 after dosage with RNAi agents comprising either a X058 or C6 3' end cap, or a non-targeting (NT) control RNAi agent. Analysis was then performed to determine levels of RNAi agents, as shown. FIG. 9B shows that, after 72 hrs, much more RNAi agent with X058 was associated with Ago2 than the RNAi agent with C6.

Thus, these data show that:
HAMP 18-mer (254) siRNAs with X038, X052, X058, X067, or X069 PAZ ligands on guide strand are active in vivo.
X058 shows convincing increased potency and duration of knockdown.

These data thus show the efficacy of RNAi agents having the 18-mer format, wherein the 3' end cap is X038, X052, X058, X067, or X069.

Example 3C. Additional In Vivo Testing

An additional in vivo testing was done with different chemical formats: (A160_S38,S42,S45 & A161_S38,S42, S45).
In the antisense strand:
A160_→F in position 2 and ribC6 overhang
A161_→F in position 2, 5, 6, 7 and ribC6 overhang
In the sense strand:
_S38→C6 overhang
_S42→ribC6 overhang
_S45→BP overhang
Parameters used in this experiment were:
Mice (n=5/group) injected via IV bolus (tail vein): LNP569
PBS
LNP569—Hamp254 A160_S38—3 mg/kg
LNP569—Hamp254 A160_S42—3 mg/kg
LNP569—Hamp254 A160_S45—3 mg/kg
LNP569—Hamp254 A161_S38—3 mg/kg
LNP569—Hamp254 A161_S42—3 mg/kg
LNP569—Hamp254 A161_S45—3 mg/kg
48 hour timepoint.
Assess Hepcidin Knockdown in Liver (mRNA-qPCR)
The results are shown in FIG. 10. FIG. 10 shows the In vivo comparison of A160 & A161 format [various passenger (sense) strand overhangs]. This experiment was done 48 hours post-dose, with a 1×3 mg/kg dose.

Example 4. Additional Studies Showing Efficacy of 18-Mers Comprising a Spacer, a Second Phosphate or Modified Internucleoside Linker, and a 3' End Cap Additional studies are performed using 18-mer RNAi agents comprising a 3' end cap.

FIG. 13A shows the efficacy of 18-mer RNAi agents wherein the 3' end cap is X109, X110, X111, X112, X113, X058 or C6. HuR is the target. Doses used are: 1 nM, 0.25 nM, 0.62 nM, and 0.16 nM. RNAi agents comprising any of the 3' end caps were able to mediate RNA interference, particularly at the highest doses used.

In particular, HuR-PAZ ligands X110, X111 and X112 appear to be similar in potency as X058.

These data thus show the efficacy of RNAi agents having an 18-mer format wherein the 3' end cap is X109, X110, X111, X112, X113, X058 or C6.

Table 6, below, provides additional data showing the efficacy of 18-mer format RNAi agents with various 3' end caps: X059, X050, X061, X051, X027, X062, X060, C6 (X003), X068, X065, X069, X097, X066, X098, X052, X063, BP (X014), X038, X067, X058, X064, and ribprib (X025).

X1026, X1027 (FIG. 23B): or X1018; X1019, X1020, X1021, X1022 or X1028 (FIG. 23C).

A HuR 18-mer RNAi agent is used.

In these experiments, Huh-7 cells are transfected using RNAiMax in a 96-well plate format. RNA is isolated 48 hours post-transfection. HuR mRNA is normalized to PPIA endogenous control. RNAi agent concentrations of 3, 10 and 30 pM are chosen based on IC50 data of the PAZ ligands (3'

TABLE 7

Efficacy of RNAi agents with a 3' end cap to ELAVL1/HuR in Huh-7 cells in vitro

| Nickname siTrack | siRNA | AV 5.04 % residual | 9.95 mRNA (qRT-PCR) | 19.85 | SD 5.04 | 9.95 | 19.85 | (dosing nM) |
|---|---|---|---|---|---|---|---|---|
| untreated - HB | untreated | 100.54 | | | 10.76 | | | |
| av_PSAT6-EYFP-N1_471_A25S27 | eYFP neg. control 1 | 110.06 | 104.72 | 101.98 | 6.52 | 13.38 | 11.84 | |
| av_PNAS-280_1_A25S27 | eYFP neg. control 2 | 102.15 | 96.16 | 98.87 | 15.02 | 6.60 | 9.41 | |
| hs_ELAVL1_1186_MAN_S42 | 18-mer siRNA with X059 | 45.17 | 20.58 | 10.24 | 2.84 | 0.63 | 0.79 | |
| hs_ELAVL1_1186_MAN_S42 | 18-mer siRNA with X050 | 26.69 | 11.48 | 6.92 | 0.99 | 2.40 | 1.41 | |
| hs_ELAVL1_1186_MAN_S42 | 18-mer siRNA with X061 | 26.11 | 11.49 | 6.25 | 5.81 | 0.99 | 0.74 | |
| hs_ELAVL1_1186_MAN_S42 | 18-mer siRNA with X051 | 25.35 | 10.80 | 6.88 | 3.28 | 0.61 | 0.86 | |
| hs_ELAVL1_1186_MAN_S42 | 18-mer siRNA with X027 | 24.54 | 11.67 | 6.17 | 2.90 | 1.38 | 1.03 | |
| hs_ELAVL1_1186_MAN_S42 | 18-mer siRNA with X062 | 24.35 | 11.68 | 5.66 | 2.88 | 1.46 | 1.17 | |
| hs_ELAVL1_1186_MAN_S42 | 18-mer siRNA with X060 | 23.86 | 9.27 | 5.62 | 1.10 | 0.86 | 0.76 | |
| hs_ELAVL1_1186_A106_S42 | 18-mer siRNA with C6 (X003) | 22.42 | 9.77 | 5.65 | 1.90 | 1.60 | 1.31 | |
| hs_ELAVL1_1186_MAN_S42 | 18-mer siRNA with X068 | 22.40 | 10.77 | 5.89 | 2.25 | 1.92 | 1.31 | |
| hs_ELAVL1_1186_MAN_S42 | 18-mer siRNA with X065 | 22.24 | 10.50 | 5.20 | 3.44 | 1.26 | 0.96 | |
| hs_ELAVL1_1186_MAN_S42 | 18-mer siRNA with X069 | 21.93 | 9.57 | 6.13 | 6.25 | 1.11 | 1.57 | |
| hs_ELAVL1_1186_MAN_S42 | 18-mer siRNA with X097 | 21.26 | 9.83 | 6.29 | 3.45 | 1.98 | 1.27 | |
| hs_ELAVL1_1186_MAN_S42 | 18-mer siRNA with X066 | 21.12 | 10.25 | 5.77 | 2.04 | 1.14 | 0.43 | |
| hs_ELAVL1_1186_MAN_S42 | 18-mer siRNA with X098 | 21.06 | 9.94 | 6.15 | 4.39 | 2.16 | 1.29 | |
| hs_ELAVL1_1186_MAN_S42 | 18-mer siRNA with X052 | 21.02 | 8.32 | 6.75 | 1.41 | 1.29 | 0.93 | |
| hs_ELAVL1_1186_MAN_S42 | 18-mer siRNA with X063 | 20.53 | 10.91 | 5.61 | 3.01 | 0.86 | 0.18 | |
| hs_ELAVL1_1186_A324_S42 | 18-mer siRNA with BP (X014) | 20.38 | 9.37 | 6.19 | 2.56 | 1.37 | 0.67 | |
| hs_ELAVL1_1186_A27_S30 | 19-mer pos. control | 19.90 | 8.03 | 5.40 | 1.40 | 0.98 | 0.37 | |
| hs_ELAVL1_1186_MAN_S42 | 18-mer siRNA with X038 | 19.80 | 10.60 | 5.26 | 2.52 | 0.75 | 0.75 | |
| hs_ELAVL1_1186_MAN_S42 | 18-mer siRNA with X067 | 19.07 | 11.38 | 5.82 | 2.02 | 3.00 | 0.94 | |
| hs_ELAVL1_1186_MAN_S42 | 18-mer siRNA with X058 | 18.40 | 10.36 | 6.23 | 2.70 | 2.78 | 0.42 | |
| hs_ELAVL1_1186_MAN_S42 | 18-mer siRNA with X064 | 18.33 | 9.84 | 6.49 | 3.03 | 0.45 | 1.67 | |
| hs_ELAVL1_1186_MAN_S42 | 18-mer siRNA with ribprib (X025) | 17.10 | 9.78 | 5.75 | 3.69 | 1.38 | 0.75 | |
| hs_ELAVL1_1186_A22_S26 | 21-mer pos. control | 16.68 | 8.61 | 5.15 | 2.39 | 1.17 | 0.86 | |

This table provides: the nickname of the RNAi agent (column 1); the length and the 3' end cap used and identification of controls (column 2); % residual mRNA level, as determined by qRT-PCR, at doses of 5.04, 9.95, and 19.85 nM (columns 3-5); standard deviation (SD) (columns 6-8). HuR is normalized to Cyc. The knockdown (RNA interference activity) can be readily calculated by subtracting the % residual mRNA from 100%. Thus, the final line shows that the 21-mer pos. (positive) control exhibits 16.68% residual mRNA, indicating 83.32% knockdown.
These data thus show the efficacy of various RNAi agents having the 18-mer format wherein the 3' end cap is: BP (X014), C6 (X003), rib (X025), X027, X038, X050, X051, X052, X058, X059, X060, X061, X062, X063, X064, X065, X066, X067, X068, X069, X097, or X098. It is noted that the construct designed "18-mer siRNA with ribprib" comprises a first strand and a second strand, wherein the 3' end of one strand terminates in a phosphate and further comprises in 5' to 3' order: a spacer (ribitol), a second phosphate and a 3' end cap (a second ribitol).

Example 5. 18-Mer RNAi Agents Comprising a Spacer, a Second Phosphate or Modified Internucleoside Linker, and a 3' End Cap This Example shows efficacy of 18-mer RNAi agents comprising a spacer, a second phosphate or modified internucleoside linker and a 3' end cap which is: X109, X110, X111, X112, X113, X1009, X1010, X1024 or X1025 (FIG. 23A); X1011, X1012, X1013, X058, X1015, X1016, X1017, X1026, X1027 (FIG. 23B): or X1018; X1019, X1020, X1021, X1022 or X1028 (FIG. 23C).

It is noted that in this example, C3, C4 and C5 "linkers" refer to a portion of the 3' end cap between the R1 and the head group. This terminology should be differentiated from the C3, C4, and C5 "spacers".

The efficacy of such RNAi agents is shown in FIGS. 23A, 23B and 23C.

These data thus show the efficacy of RNAi agents having an 18-mer format, wherein the 3' end cap is X109, X110, X111, X112, X113, X1009, X1010, X1024 or X1025 (FIG. 23A); X1011, X1012, X1013, X058, X1015, X1016, X1017, end caps) previously analyzed. For the X109 to X113 data, an average of two previous data sets is provided.

In general, length of the linker within the 3' end cap does not significantly affect potency of any of the 3' end caps.

In separate but related experiments, IC50 data was determined for several 3' end caps using HuR RNAi agents in Huh-7 cells. Data points for two separate studies are shown below:

| 3' end cap | pM IC50 study#1 | pM IC50 study#2 |
|---|---|---|
| X058 | 5.85 | 12.78 |
| X109 | 3.47 | 3.85 |
| X110 | 1.50 | 6.42 |
| X111 | 1.21 | 3.63 |
| X112 | 0.72 | 2.38 |
| X113 | 2.71 | 4.55 |

These data thus show the efficacy of RNAi agents having an 18-mer format, wherein the 3' end cap is X058, X109, X110, X111, X112, or X113.

Example 6. Additional 18-mer RNAi Agents Comprising a Spacer, a Second Phosphate or Modified Internucleosider Linker, and a C3, C4, or C5 Linker in the 3' End Cap This example shows the efficacy of various 18-mer RNAi agents comprising a 3' end cap which is:
X110, X1012, X1018, X111, X1013, X112, X058, X1019, X1025, X1027, or X1028.

This various 3' end caps (illustrated in Table 1) vary in the length of the linker (C3, C4 or C5) between $R_2$ and the head group.

The target gene is HuR. Huh-7 cells are transfected using RNAiMax transfection reagent. 24 well plates are seeded with 40,000 cells per well. "Reverse transfection" with 1 nM RNAi agent/well is done, followed by incubation for approximately 18 hours. Duplicate plates are set up using one for RNA extraction and the other for duration. Transfection media is replaced with fresh growth media (no RNAi agent) and cells are incubated for an additional 2 days before RNA isolation or split for duration experiments.

Cells are split on days 3 and 7 post-transfection. RNA is isolated at days 3, 7 and 10 post-transfection for HuR mRNA analysis.

Results are shown in FIGS. 21 and 22. The control (NTC) is a mFVII 21-mer RNAi agent.

In FIG. 21, ligand LME844 (X110, X1012 and X1018), the linker length does not appear to alter the duration of activity. For ligand PKF027-895 (X111 and X1013), the shorter linker (C3) and the C4 linker are not significantly different.

In FIG. 22, for ligand LP1230 (X1025, X1027 and X1028), the duration of the C3 linker is better than the longer linkers. There is evidence of this as early as Day 7 post-transfection.

For ligand LKS871 (X112, X058 and X1019), the longer linker appears to have slightly better activity at the later time point and the "trend" is there at Day 7, as well, although the error bars overlaps and it is probably not significant. The X058 activity at Day 10 is about 15% less than demonstrated in a previous duration study, but there will be study to study variability for these types of analyses.

These data thus show the efficacy of RNAi agents comprising a first and a second strand, wherein the 3' end of the first and/or second strand terminate in a phosphate and further comprise, in 5' to 3' order: a spacer (e.g., ribitol), a second phosphate, and a 3' end cap (e.g., X110, X1012, X1018, X111, X1013, X112, X058, X1019, X1025, X1027, or X1028).

Example 7. Efficacy of Additional 3' End Caps

The 3' end caps X1062, X1063 and X1064 were each found to be efficacious when used on RNAi agents. For example, these were effective on HuR siRNAs, wherein the HuR siRNAs were 18-mers as described herein, wherein the 3' end of each strand terminates in a phosphate and further comprises, in 5' to 3' direction, a spacer which is ribitol, a second phosphate, and a 3' end cap which is X1062, X1063 or X1064. Huh7 cells were transfected with siRNAs using RNAi Max transfection reagent; 24-well plates were seeded with 40,000 cells per well; reverse transfection was performed with 1 nM siRNA per well, and cells were incubated for about 18 hours. Transfection medium was replaced (without siRNA), and cells were incubated for an additional 2 days before RNA isolation or split for seeding. Cells were split on days 3 and 7 post transfection for duration time points. RNA was isolated at days 3, 7 and 10 post-transfection for HuR mRNA analysis. HuR siRNAs with 3' end caps which were X1062 demonstrated efficacy (knockdown) of 89.0, 77.9 and 32.7% after 3, 7 or 10 days. HuR siRNAs with 3' end caps which were X1063 and X1064 showed 89.6, 81.5, and 43.7%; and 67.0, 30.9 and 0.0%, respectively, after 3, 7 and 10 days.

Example 8. Efficacy of Additional 18-Mer with at Least One Internal Spacer Format RNAi Agents This example shows the efficacy of a variety of RNAi agents comprising a first strand and a second strand, wherein the first strand is ribonucleotides, and the second strand is ribonucleotides and at least one spacer subunit.

In the various RNAi agents described in this example, a nucleotide at any of positions 1 to 18 was individually replaced by a spacer subunit, and RNA interference activity was retained. The 3' end of each strand terminates in a phosphate or modified internucleoside linker and further comprises, in 5' to 3' order, a second spacer, a second phosphate or modified internucleotide linker, and a 3' end cap.

Table 8. Properties of Various Modified Variants of Human RNAi Agents Derived from Sequence.

The following are used in Table 8 to represent different chemistries and components of the sequences: N=RNA, p=phosphate, N004=2'OMe RNA, N005=2' O MOE RNA, N007=2'F RNA, X027=ribitol spacer, X003=1,6-hexanediol (C6 3' end cap), X058=3' end cap. In these sequences, for example, C027 indicates that the nucleotide C is absent and has been replaced by a spacer, wherein the spacer is ribitol. Similarly, U027, A027, G027 indicate that the nucleotides U, A or G, respectively, are absent and have been replaced by a spacer, which is ribitol. The target used in human APOC3. The numbers in columns 2 represent residual mRNA levels; thus, 5.8 in column 2, row 2, indicates residual mRNA level of 5.8% or 94.2% gene knockdown. SD, standard deviation.

These molecules thus demonstrate that, in a RNAi agent, each of the nucleotides at positions 1 to 18 can individually be replaced by a spacer unit and the molecule is still capable of mediating RNA interference activity.

TABLE 8

| # | % Res mRNA_Huh7_15 nM | SD_% Res mRNA Huh7_15 nM | Sense Modified Sequence String | SEQ ID NO: | Antisense Modified Sequence String | SEQ ID NO: |
|---|---|---|---|---|---|---|
| 1 | 5.8 | 2.8 | G004pA004pC004pA007pG004pU007pA004pU007pU004pC007pU004pC007pA004pG007pU004pG007pC006pU005pU027pX003 | 98 | A007pG007pC004pA007pC004pU007pG004pA007pG004pA007pA004pU007pA004pC007pU004pG007pU005pC027pC027pX058 | 119 |

TABLE 8-continued

| # | % Res mRNA_Huh7_15 nM | SD_% Res mRNA Huh7_15 nM | Sense Modified Sequence String | SEQ ID NO: | Antisense Modified Sequence String | SEQ ID NO: |
|---|---|---|---|---|---|---|
| 2 | 3.4 | 1.1 | G004pA004pC004pA007pG004pU007pA004pU007pU004pC007pU004pC007pA004pG007pU004pG007pC006pU005pU027pX003 | 99 | A007pG007pC004pA007pC004pU007pG004pA007pG004pA007pA004pU007pA004pC007pU004pG007pU027pC006pC027pX058 | 120 |
| 3 | 11.3 | 2.1 | G004pA004pC004pA007pG004pU007pA004pU007pU004pC007pU004pC007pA004pG007pU004pG007pC006pU005pU027pX003 | 100 | A007pG007pC004pA007pC004pU007pG004pA007pG004pA007pA004pU007pA004pC007pU004pG027pU005pC006pC027pX058 | 121 |
| 4 | 9.5 | 1.5 | G004pA004pC004pA007pG004pU007pA004pU007pU004pC007pU004pC007pA004pG007pU004pG007pC006pU005pU027pX003 | 101 | A007pG007pC004pA007pC004pU007pG004pA007pG004pA007pA004pU007pA004pC007pU027pG007pU005pC006pC027pX058 | 122 |
| 5 | 25.6 | 6.4 | G004pA004pC004pA007pG004pU007pA004pU007pU004pC007pU004pC007pA004pG007pU004pG007pC006pU005pU027pX003 | 102 | A007pG007pC004pA007pC004pU007pG004pA007pG004pA007pA004pU007pA004pC027pU004pG007pU005pC006pC027pX058 | 123 |
| 6 | 33.1 | 8.1 | G004pA004pC004pA007pG004pU007pA004pU007pU004pC007pU004pC007pA004pG007pU004pG007pC006pU005pU027pX003 | 103 | A007pG007pC004pA007pC004pU007pG004pA007pG004pA007pA004pU007pA027pC007pU004pG007pU005pC006pC027pX058 | 124 |
| 7 | 22 | 9.1 | G004pA004pC004pA007pG004pU007pA004pU007pU004pC007pU004pC007pA004pG007pU004pG007pC006pU005pU027pX003 | 104 | A007pG007pC004pA007pC004pU007pG004pA007pG004pA007pA004pU027pA004pC007pU004pG007pU005pC006pC027pX058 | 125 |
| 8 | 23.8 | 4.6 | G004pA004pC004pA007pG004pU007pA004pU007pU004pC007pU004pC007pA004pG007pU004pG007pC006pU005pU027pX003 | 105 | A007pG007pC004pA007pC004pU007pG004pA007pG004pA007pA027pU007pA004pC007pU004pG007pU005pC006pC027pX058 | 126 |
| 9 | 56.7 | 10.7 | G004pA004pC004pA007pG004pU007pA004pU007pU004pC007pU004pC007pA004pG007pU004pG007pC006pU005pU027pX003 | 106 | A007pG007pC004pA007pC004pU007pG004pA007pG004pA027pA004pU007pA004pC007pU004pG007pU005pC006pC027pX058 | 127 |
| 10 | 55 | 10.8 | G004pA004pC004pA007pG004pU007pA004pU007pU004pC007pU004pC007pA004pG007pU004pG007pC006pU005pU027pX003 | 107 | A007pG007pC004pA007pC004pU007pG004pA007pG027pA004pA007pA004pU007pA004pC007pU004pG007pU005pC006pC027pX058 | 128 |
| 11 | 22.3 | 4.2 | G004pA004pC004pA007pG004pU007pA004pU007pU004pC007pU004pC007pA004pG007pU004pG007pC006pU005pU027pX003 | 108 | A007pG007pC004pA007pC004pU007pG004pA027pG004pA007pA004pU007pA004pC007pU004pG007pU005pC006pC027pX058 | 129 |
| 12 | 10.5 | 1.5 | G004pA004pC004pA007pG004pU007pA004pU007pU004pC007pU004pC007pA004pG007pU004pG007pC006pU005pU027pX003 | 109 | A007pG007pC004pA007pC004pU007pG027pA007pG004pA007pA004pU007pA004pC007pU004pG007pU005pC006pC027pX058 | 130 |
| 13 | 4.4 | 0.7 | G004pA004pC004pA007pG004pU007pA004pU007pU004pC007pU004pC007pA004pG007pU004pG007pC006pU005pU027pX003 | 110 | A007pG007pC004pA007pC004pU027pG004pA007pG004pA007pA004pU007pA004pC007pU002pG007pU005pC006pC027pX058 | 131 |
| 14 | 3.2 | 0.4 | G004pA004pC004pA007pG004pU007pA004pU007pU004pC007pU004pC007pA004pG007pU004pG007pC006pU005pU027pX003 | 111 | A007pG007pC004pA007pC027pU007pG004pA007pG004pA007pA004pU007pA004pC007pU004pG007pU005pC006pC027pX058 | 132 |
| 15 | 18.3 | 6 | G004pA004pC004pA007pG004pU007pA004pU007pU004pC007pU004pC007pA004pG007pU004pG007pC006pU005pU027pX003 | 112 | A007pG007pC004pA027pC004pU007pG004pA007pG004pA007pA004pU007pA004pC007pU004pG007pU005pC006pC027pX058 | 133 |
| 16 | 6.8 | 0.5 | G004pA004pC004pA007pG004pU007pA004pU007pU004pC007pU004pC007pA004pG007pU004pG007pC006pU005pU027pX003 | 113 | A007pG007pC027pA007pC004pU007pG004pA007pG004pA007pA004pU007pA004pC007pU004pG007pU005pC006pC027pX058 | 134 |
| 17 | 57.4 | 5.3 | G004pA004pC004pA007pG004pU007pA004pU007pU004pC007pU004pC007pA004pG007pU004pG007pC006pU005pU027pX003 | 114 | A007pG027pC004pA007pC004pU007pG004pA007pG004pA007pA004pU007pA004pC007pU004pG007pU005pC006pC027pX058 | 135 |
| 18 | 7.6 | 2 | G004pA004pC004pA007pG004pU007pA004pU007pU004pC007pU004pC007pA004pG007pU004pG007pC006pU005pU027pX003 | 115 | A027pG007pC004pA007pC004pU007pG004pA007pG004pA007pA004pU007pA004pC007pU004pG007pU005pC006pC027pX058 | 136 |
| 19 | 6.3 | 1.4 | G004pA004pC004pA007pG004pU007pA004pU007pU004pC007pU004pC007pA004pG007pU004pG007pC006pU005pU027pX003 | 116 | A007pG007pC004pA007pC004pU007pG004pA007pG004pA007pA004pU007pA004pC007pU004pG007pU005pC006pC027pX058 | 137 |
| 20 | 9.7 | 1.9 | GpApC004pApGpU004pApU004pU004pC004pU004pC004pApGpU004pGpC006pU005pU027pX003 | 117 | A002pGpCpApU004pGpApGpApApU004pApCpU004pGpU005pC006pC027pX058 | 138 |

TABLE 8-continued

| # | % Res mRNA_Huh7_15 nM | SD_% Res mRNA Huh7_15 nM | Sense Modified Sequence String | SEQ ID NO: | Antisense Modified Sequence String | SEQ ID NO: |
|---|---|---|---|---|---|---|
| 21 | 6.5 | 1.4 | GpGpApC004pApGpU004pApU004 pU004pC004pU004pC004pApGpU0 04pGpC004pU004pU002pU002 | 118 | ApGpCpApCpU004pGpApGpApApU00 4pApCpU004pGpU004pCpCpU002pU 002 | 139 |

EMBODIMENTS

1. A composition comprising a RNAi agent comprising a first and a second strand, wherein the first strand is an 18-mer and the second strand consists of 17 nucleotides and 1 spacer subunit, wherein the spacer subunit comprises (a) a phosphate or modified internucleoside linker and (b) a spacer, wherein the spacer subunit can be at any position in the strand, wherein the strands together form at least one blunt-end, wherein the 3' end of at least one strand terminates in a phosphate or modified internucleoside linker and further comprises, in 5' to 3' order: a second spacer; a second phosphate or modified internucleoside linker; and a 3' end cap.

2. The composition of embodiment 1 wherein the 3' end of both the sense and anti-sense strand terminate in a phosphate or modified internucleoside linker and further comprise, in 5' to 3' order: a second spacer; a second phosphate or modified internucleoside linker; and a 3' end cap.

3. The composition of any of embodiments 1 to 2 wherein the two strands comprise the same or different spacers, phosphate or modified internucleoside linker, and/or 3' end caps.

4. The composition of any of embodiments 1 to 3 wherein the strands are ribonucleotides, or, optionally, one or more nucleotide are modified or substituted.

5. The composition of any of embodiments 1 to 4 wherein at least one nucleotide comprises a modified internucleoside linker.

6. The composition of any of embodiments 1 to 5 wherein the RNAi agent is attached to a ligand.

7. The composition of any of embodiments 1 to 6 wherein the spacer is ribitol, 2'-deoxy-ribitol, diribitol, 2'-methoxy-ethoxy-ribitol, C3, C4, C5, C6, or 4-methoxybutane-1,3-diol.

8. The composition of any of embodiments 1 to 7 wherein the spacer on the sense and anti-sense strands are the same or different.

9. The composition of any of embodiments 1 to 8 wherein the modified internucleoside linker is selected from phosphorothioate, phosphorodithioate, phosphoramidate, boranophosphonoate, an amide linker, and a compound of formula (I):

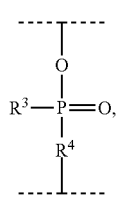

(I)

where $R^3$ is selected from $O^-$, $S^-$, $NH_2$, $BH_3$, $CH_3$, $C_{1-6}$ alkyl, $C_{6-10}$ aryl, O-alkyl and O-aryl; and $R^4$ is selected from O, S, NH and $CH_2$; wherein said $C_{1-6}$ alkyl or $C_{6-10}$ aryl of $R^3$ are unsubstituted or substituted by one to three substituents each independently selected from halo, hydroxyl and $NH_2$.

10. The composition of any of embodiments 1 to 9, wherein the 3' end cap is:

(a) A compound of formula Ia:

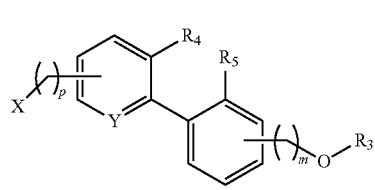

Ia in which:

X is the 3' end of a molecule comprising the sense or antisense strand, wherein the 3' end of the strand terminates in a phosphate or modified internucleoside linker and optionally further comprises in 5' to 3' order: a spacer, and a second phosphate or modified internucleoside linker;

Y is selected from CH and N;

m is selected from 0 and 1;

p is selected from 1, 2 and 3;

$R_3$ is selected from hydrogen, 2-(hydroxy-methyl)-benzyl, 3-(hydroxy-methyl)-benzyl and succinate, or is attached to a solid support; wherein the $(CH_2)_m$—O—$R_3$ moiety is attached to the phenyl ring at position 3 or 4;

$R_4$ is hydrogen;

$R_5$ is hydrogen; or $R_4$ and $R_5$, together with the phenyl rings to which $R_4$ and $R_5$ are attached, form 6H-benzo[c]chromene;

or (b) A compound of formula Ib:

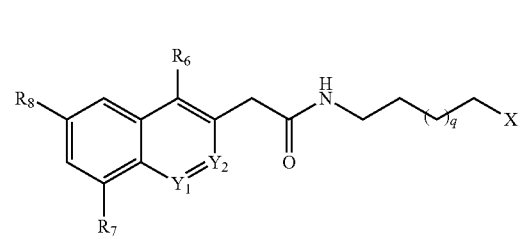

Ib in which:

X is the 3' end of a molecule comprising the sense or antisense strand, wherein the 3' end of the strand terminates in a phosphate or modified internucleoside linker and further comprises in 5' to 3' order: a spacer, and a second phosphate or modified internucleoside linker;

q is selected from 0, 1 and 2;

R₆ is selected from phenyl which is unsubstituted or substituted with a group selected from benzoxy and 3,4-dihydroxybutyl;

R₇ is selected from hydrogen and hydroxy-ethyl, wherein if R₇ is hydroxy-ethyl, the hydroxyl can be optionally functionalized as succinate or attached to a solid support;

R₈ is selected from hydrogen and methoxy;

Y₁ is selected from CH and N; and

Y₂ is selected from N and CR₉; wherein R₉ is selected from hydrogen and methyl.

11. The composition of any of embodiments 1 to 9, wherein the 3' end cap is selected from any of:

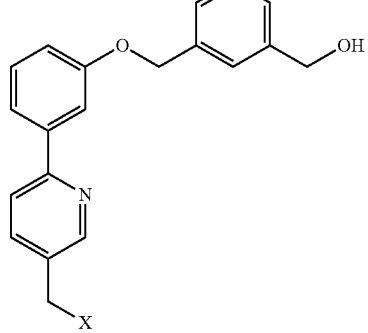

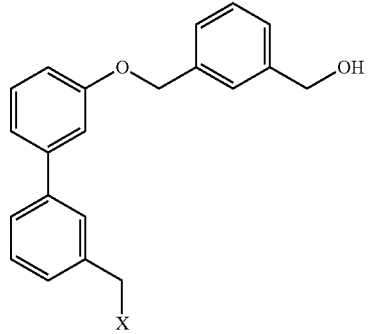

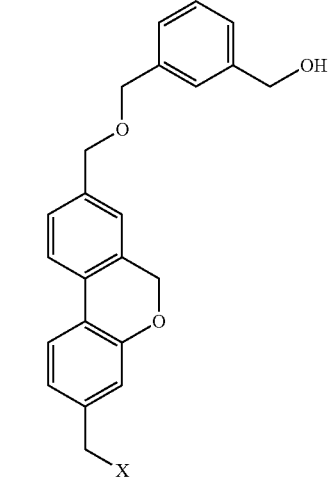

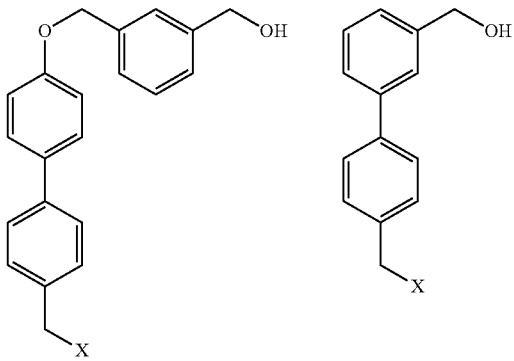

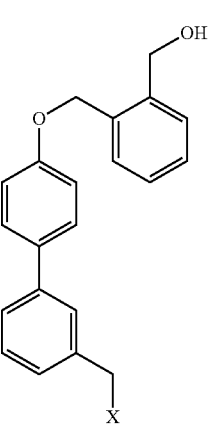
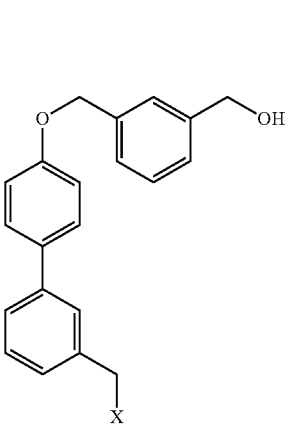

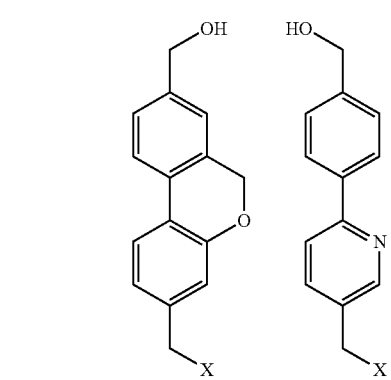

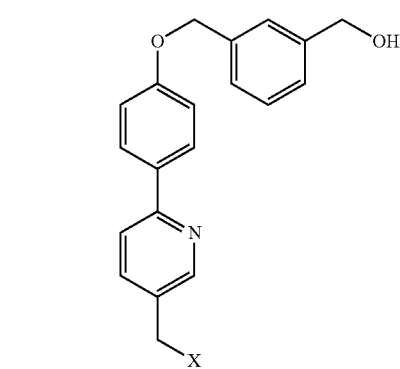

317
-continued
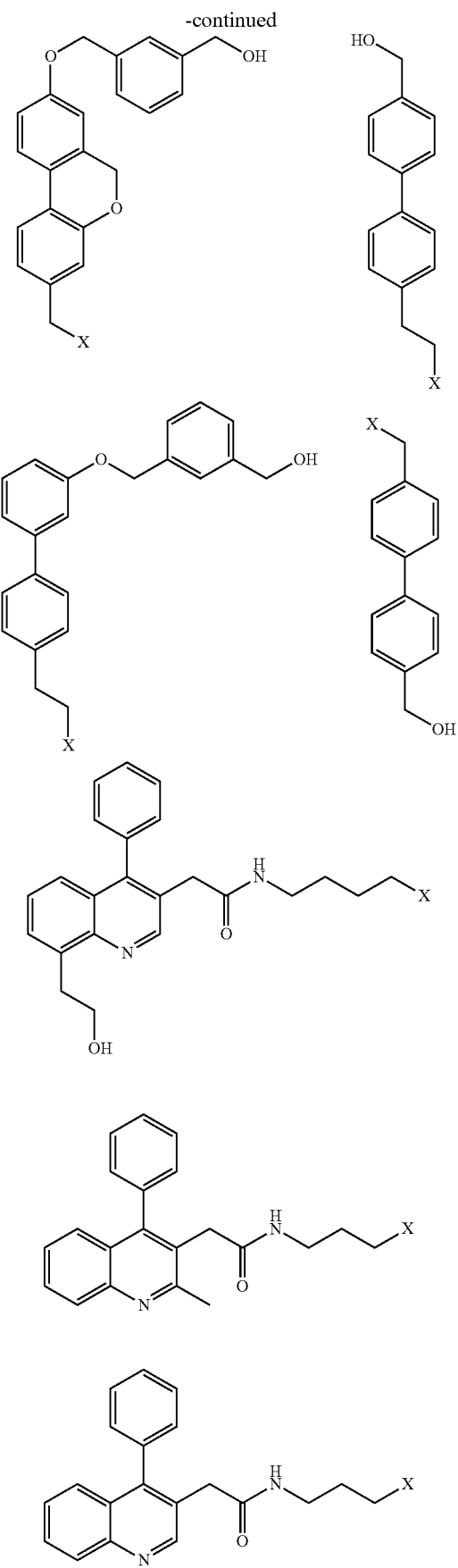
318
-continued
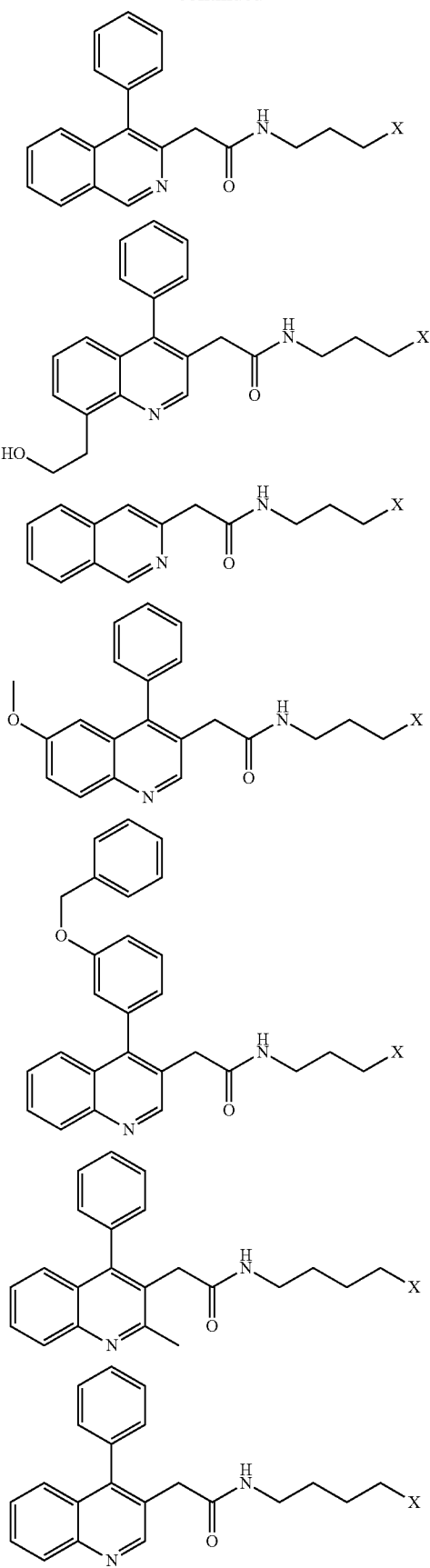

319
-continued
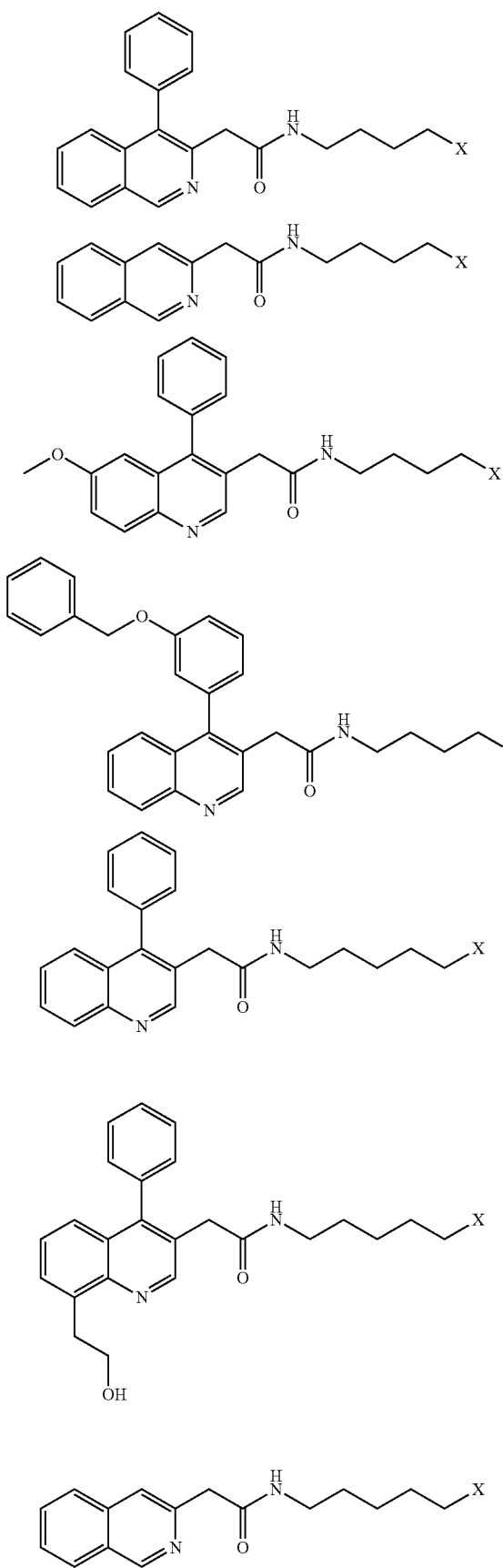
320
-continued
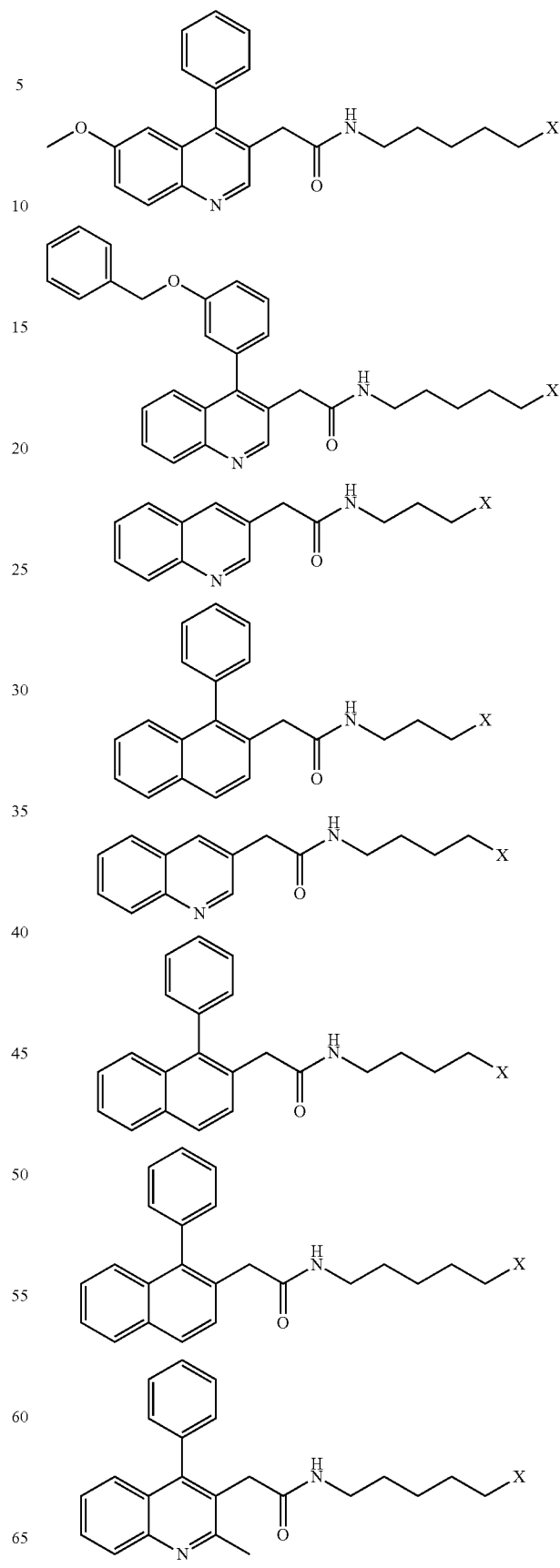

321
-continued

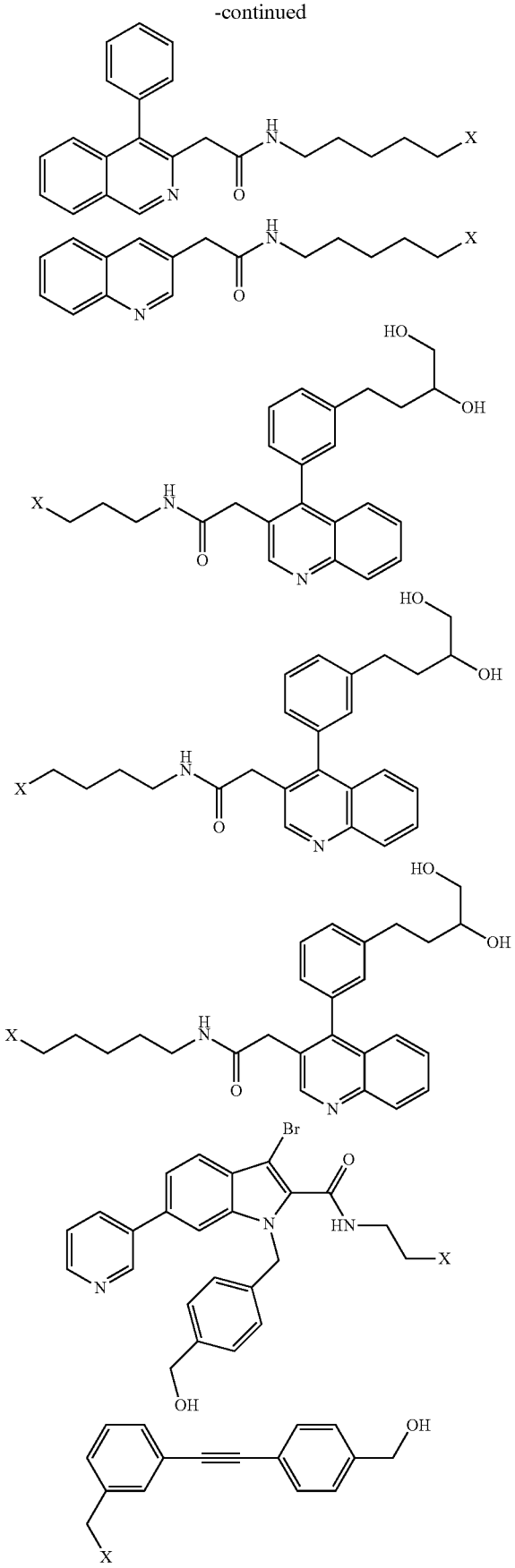

322
-continued

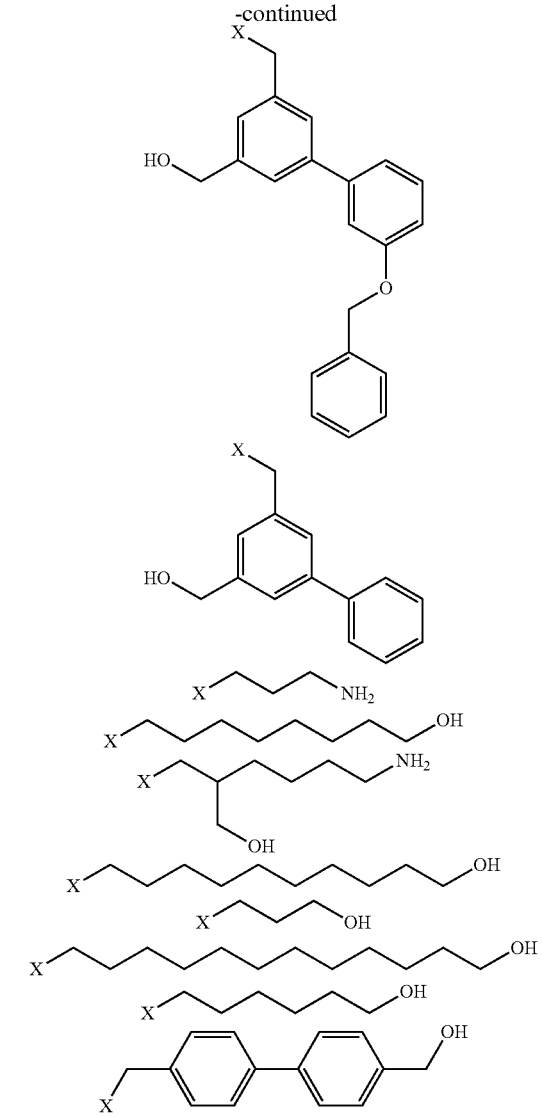

In which:
X is the 3' end of a molecule comprising the first or second strand, wherein the 3' end of the strand terminates in a phosphate or modified internucleoside linker and further comprises in 5' to 3' order: a spacer, and a second phosphate or modified internucleoside linker, and
q is selected from 1 and 2; or
Wherein the 3' end cap is selected from any of: triethylene glycol, cyclohexyl, phenyl, lithochol (lithocholic acid), or adamantane.

12. The composition of any of embodiments 1 to 8 wherein the 3' end cap is selected from those represented by formula 1a or 1b, disclosed in any Table herein, or otherwise described herein.

13. The composition of any of embodiments 1 to 12 wherein the 3' end cap on the sense and anti-sense strands are the same or different.

14. The composition of any of embodiments 1 to 13 wherein one or more nucleotide are modified or substituted.

15. The composition of any of embodiments 1 to 14 wherein the RNAi agent contains one or more modifications to the sugar, phosphate or base of one or more of the nucleotide subunits.

16. The composition of any of embodiments 1 to 15 wherein the RNAi agent comprises at least one non-natural nucleobase.

17. The composition of any of embodiments 1 to 16 wherein the non-natural nucleobase is difluorotolyl, nitroindolyl, nitropyrrolyl, or nitroimidazolyl.

18. The composition of any of embodiments 1 to 17 wherein the non-natural nucleobase is difluorotolyl.

19. The composition of any of embodiments 1 to 18 wherein the first two base-pairing nucleotides on the 3' end of the sense and/or anti-sense strand are modified.

20. The composition of any of embodiments 1 to 19 wherein the first two base-pairing nucleotides on the 3' end of the sense and/or anti-sense strand are 2'-MOE.

21. The composition of any of embodiments 1 to 20 wherein the 3' end of the sense and/or anti-sense strands terminates in a modified internucleoside linker.

22. The composition of any of embodiments 1 to 21 wherein one or more nucleotides is modified or is substituted with DNA, peptide nucleic acid (PNA), locked nucleic acid (LNA), morpholino nucleotide, threose nucleic acid (TNA), glycol nucleic acid (GNA), and/or unlocked nucleic acid (UNA).

23. The composition of any of embodiments 1 to 22 wherein the RNAi agent is modified on one or both 5' end.

24. The composition of any of embodiments 1 to 23 wherein the sense strand comprise a 5' end cap which reduces the RNA interference mediated by this strand.

25. The composition of any of embodiments 1 to 24 wherein the RNAi agent is optionally attached to a ligand.

26. The composition of any of embodiments 1 to 25 wherein the RNAi agent is optionally attached to a ligand, wherein the ligand improves stability, distribution and/or cellular uptake of the agent.

27. The composition of any of embodiments 1 to 26 wherein the composition is comprised in a pharmaceutical composition.

28. The composition of any of embodiments 1 to 27 wherein the composition is comprised in a pharmaceutical composition which is a lipid nanoparticle.

29. The composition of any of embodiments 1 to 28 wherein the composition is comprised in a pharmaceutical composition which is a lipid nanoparticle comprising a helper lipid, a neutral lipid, and/or a stealth lipid.

30. The composition of any of embodiments 1 to 29 wherein the composition is comprised in a pharmaceutical composition used in conjunction with any known treatment.

31. The composition of any of embodiments 1 to 30 for use as a medicament.

32. A method for reducing the level and/or activity of a target gene in a cell, comprising the step of introducing into the cell a composition of any of embodiment 1 to 31, wherein the RNAi agent targets the target gene.

A method of treating a human subject having a pathological state mediated at least in part by target gene expression, the method comprising the step of administering to the subject a therapeutically effective amount of a composition of any of embodiment 1 to 31, wherein the RNAi agent targets the target gene.

Unless defined otherwise, the technical and scientific terms used herein have the same meaning as that usually understood by a specialist familiar with the field to which the disclosure belongs.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein. Unless indicated otherwise, each of the references cited herein is incorporated in its entirety by reference.

Claims are non-limiting and are provided below.

Although particular embodiments and claims have been disclosed herein in detail, this has been done by way of example for purposes of illustration only, or is not intended to be limiting with respect to the scope of the appended claims, or the scope of subject matter of claims of any corresponding future application. In particular, it is contemplated by the inventors that various substitutions, alterations, and modifications may be made to the disclosure without departing from the spirit and scope of the disclosure as defined by the claims. The choice of nucleic acid starting material, clone of interest, or library type is believed to be a matter of routine for a person of ordinary skill in the art with knowledge of the embodiments described herein. Other embodiments, advantages, and modifications considered to be within the scope of the following claims. Those skilled in the art will recognize or be able to ascertain, using no more than routine experimentation, many equivalents of the specific embodiments of the disclosure described herein. Such equivalents are intended to be encompassed by the following claims. Redrafting of claim scope in later filed corresponding applications may be due to limitations by the patent laws of various countries and should not be interpreted as giving up subject matter of the claims.

The invention claimed is:

1. An RNAi agent comprising a first and a second 18-mer strand, wherein
the first 18-mer strand is 18 total of:
(a) 13-17 ribonucleotides and/or modified ribonucleotides,
(b) at least one internal spacer subunit comprising ribitol, and optionally
(c) 0-4 of any of DNA, PNA, LNA, TNA, GNA, ANA, FANA, CeNa, HNA or UNA; and
the second 18-mer strand is 18 total of:
(a) 13-18 ribonucleotides and/or modified ribonucleotides, optionally
(b) at least one spacer subunit, and optionally
(c) 0-4 of any of DNA, PNA, LNA, TNA, GNA, ANA, FANA, CeNa, HNA or UNA;
wherein each spacer subunit is
(a) a phosphate or modified internucleoside linker and
(b) a spacer,
wherein the first and second 18-mer strands together form at least one blunt-end, and
wherein the 3' end of at least one of the first or second 18-mer strands terminates in a phosphate or modified internucleoside linker which is optionally further substituted by,
(a) a first 3' end cap; or
(b) in 5' to 3' order: a second spacer; a second phosphate or modified internucleoside linker; and a second 3' end cap.

2. The RNAi agent of claim 1 wherein the 3' end of at least one of the first and second 18-mer strands terminates in the phosphate or modified internucleoside linker which is further substituted by, in 5' to 3' order: the second spacer; the second phosphate or modified internucleoside linker; and the second 3' end cap.

3. The RNAi agent of claim 1 wherein: the first 18-mer strand is 17 ribonucleotides and/or modified ribonucleotides and 1 internal spacer subunit; and the second 18-mer strand is 18 ribonucleotides and/or modified ribonucleotides.

4. The RNAi agent of claim 1 wherein the at least one spacer subunit of the second 18-mer strand is at any of positions 2 to 17, and the first and second 18-mer strands form a blunt-ended duplex.

5. The RNAi agent of claim 1 wherein at least one nucleotide comprises a modified internucleoside linker.

6. The RNAi agent of claim 1 wherein the RNAi agent is attached to a ligand.

7. The RNAi agent of claim 1 wherein the first 18-mer strand is 17 ribonucleotides and/or modified ribonucleotides and 1 internal spacer subunit; and the second 18-mer strand is 18 ribonucleotides and/or modified ribonucleotides, and wherein the internal spacer subunit comprises a ribitol.

8. The RNAi agent of claim 1 wherein the modified internucleoside linker of the spacer subunit of the second 18-mer strand, and/or at the 3' end of the at least one of the first or second 18-mer strands, and/or the second modified internucleoside linker is selected from phosphorothioate, phosphorodithioate, phosphoramidate, boranophosphonoate, an amide linker, and a compound of formula (I):

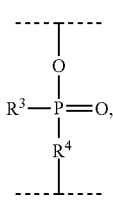

(I)

where $R^3$ is selected from $O^-$, $S^-$, $NH_2$, $BH_3$, $CH_3$, $C_{1-6}$ alkyl, $C_{6-10}$aryl, O-alkyl and O-aryl; and $R^4$ is selected from O, S, NH and $CH_2$; wherein said $C_{1-6}$alkyl or $C_{6-10}$aryl of $R^3$ are unsubstituted or substituted by one to three substituents each independently selected from halo, hydroxyl and $NH_2$.

9. The RNAi agent of claim 1, wherein the first and/or second 3' end cap is: A compound formula Ia:

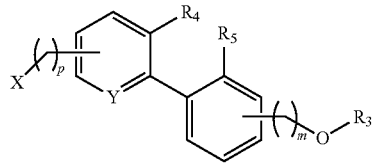

Ia in which:
X is the attachment to the phosphate or modified internucleoside linker at the 3' end of the at least one of the first or second 18-mer strands, or
the attachment to the second phosphate or modified internucleoside linker of the at least one of the first or second 18-mer strand;
Y is selected from CH and N;
m is selected from 0 and 1;
p is selected from 1, 2 and 3;
$R_3$ is selected from hydrogen, 2-(hydroxy-methyl)-benzyl, 3-(hydroxy-methyl)-benzyl and succinate, or is attached to a solid support; wherein the $(CH_2)_m$—O—$R_3$ moiety is attached to the phenyl ring at position 3 or 4;
$R_4$ is hydrogen;
$R_5$ is hydrogen; or
$R_4$ and $R_5$, together with the phenyl rings to which $R_4$ and $R_5$ are attached, form 6H-benzo[c]chromene;
or
A formula Ib:

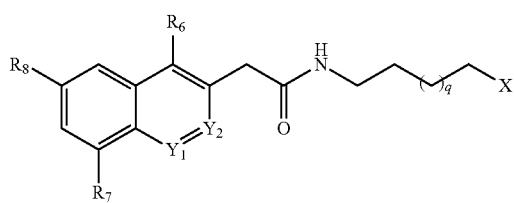

Ib in which:
X is the attachment to the phosphate or modified internucleoside linker at the 3' end of the at least one of the first or second 18-mer strands, or
the attachment to the second phosphate or modified internucleoside linker of the at least one of the first or second 18-mer strands;

q is selected from 0, 1 and 2;
$R_6$ is selected from phenyl which is unsubstituted or substituted with benzoxy;
$R_7$ is selected from hydrogen and hydroxy-ethyl, wherein if $R_7$ is hydroxy-ethyl, the hydroxyl can be optionally functionalized as succinate or attached to a solid support;
$R_8$ is selected from hydrogen and methoxy;
$Y_1$ is selected from CH and N; and
$Y_2$ is selected from N and $CR_9$; wherein $R_9$ is selected from hydrogen and methyl.

10. The RNAi agent of claim 9, wherein the first and/or second 3' end cap is selected from any of:

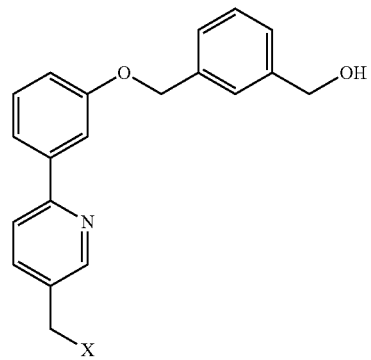

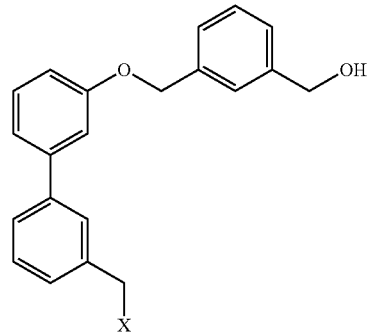

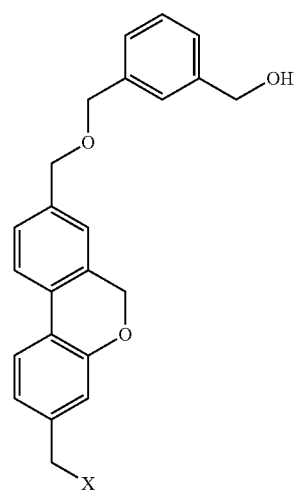

385
-continued
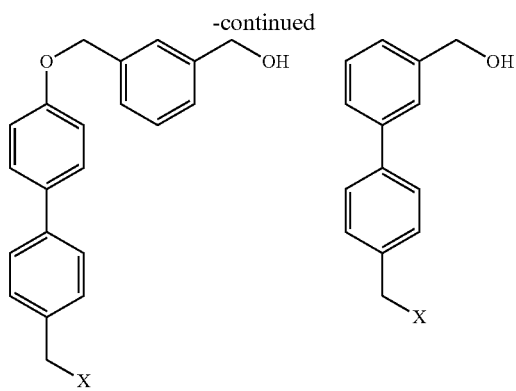
386
-continued
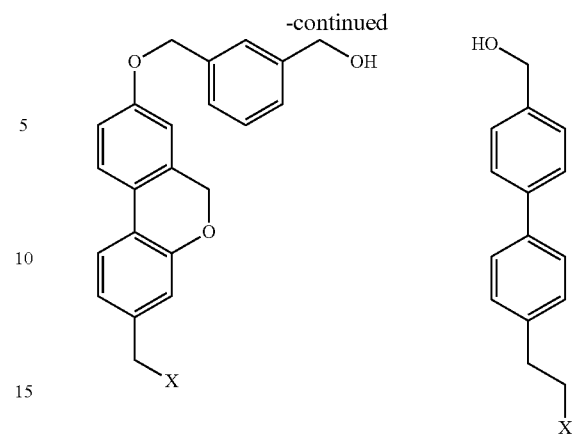
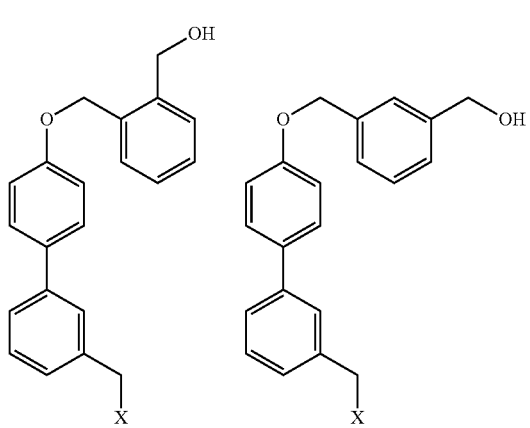
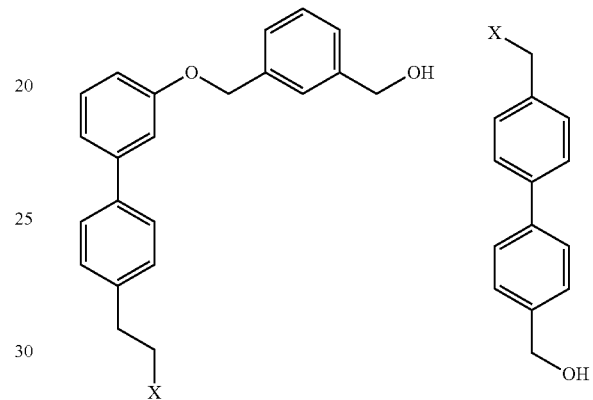
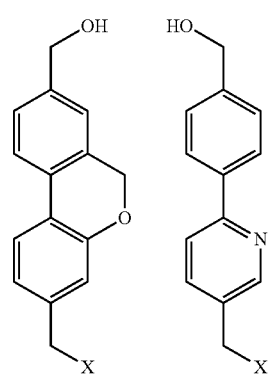
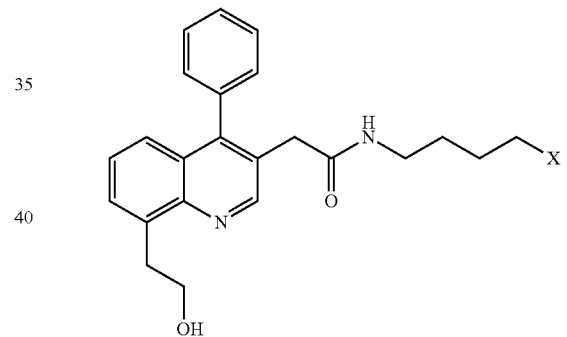
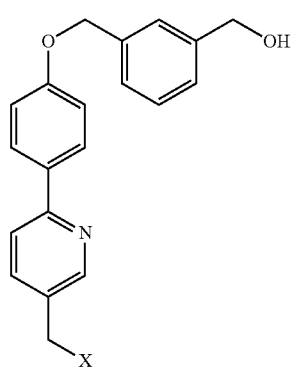
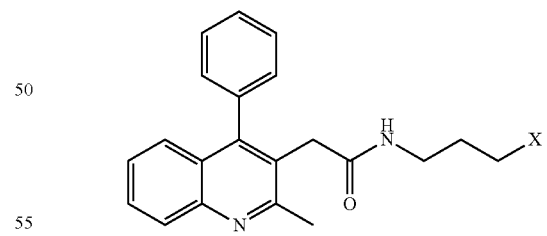
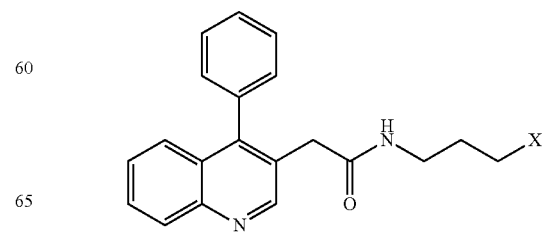

387
-continued
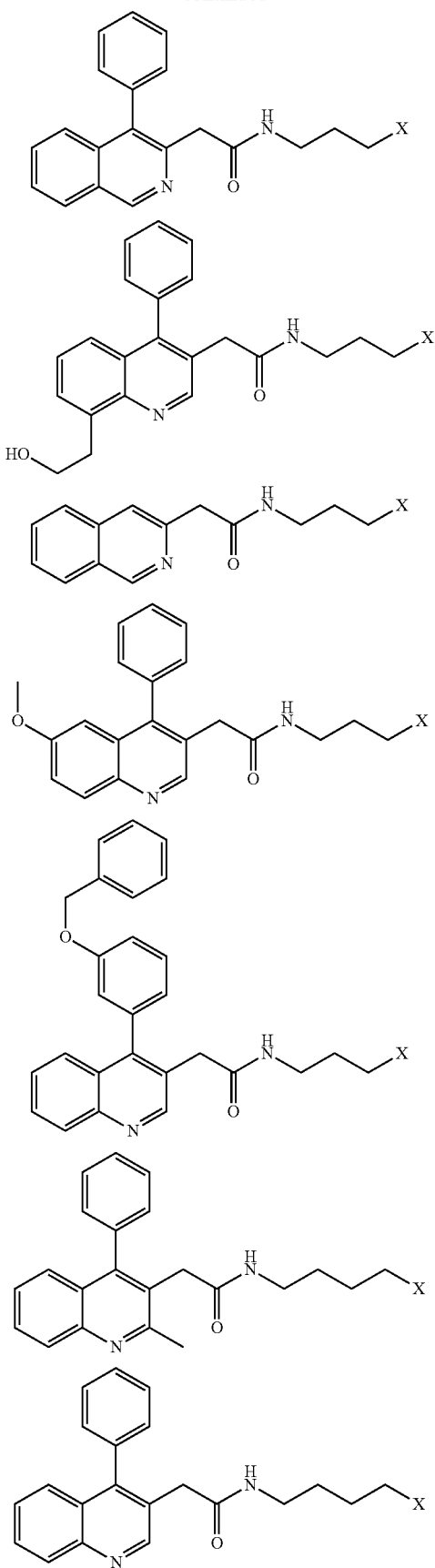
388
-continued
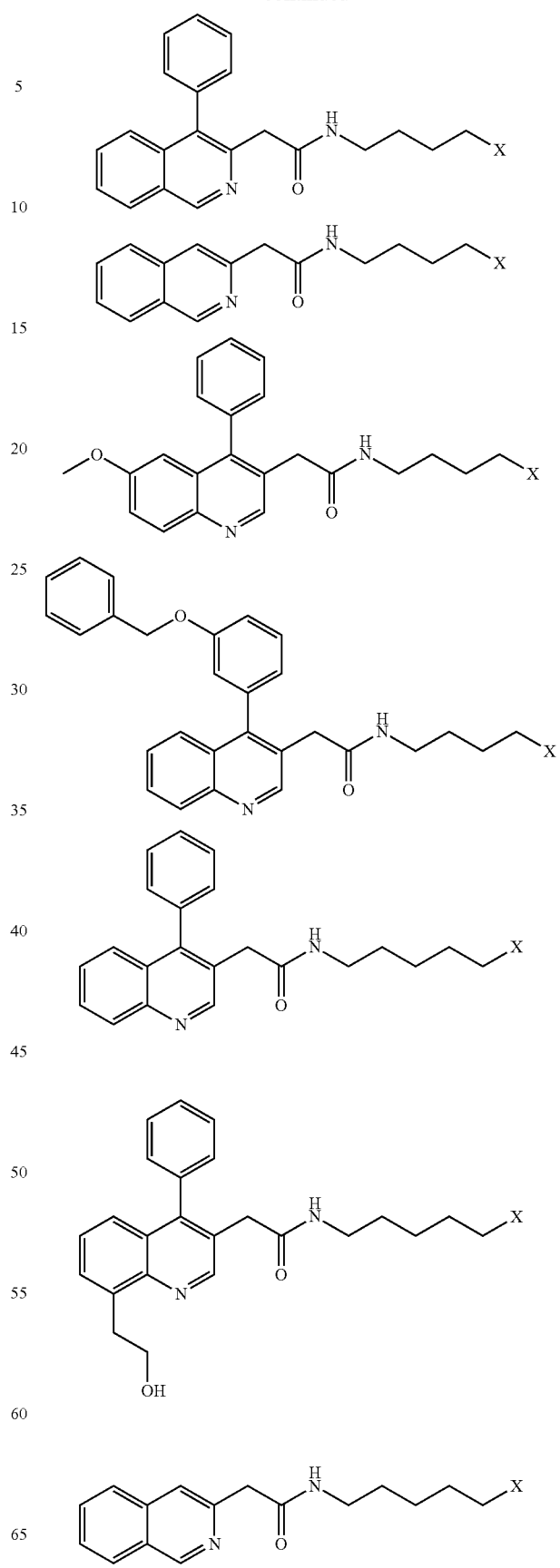

389
-continued
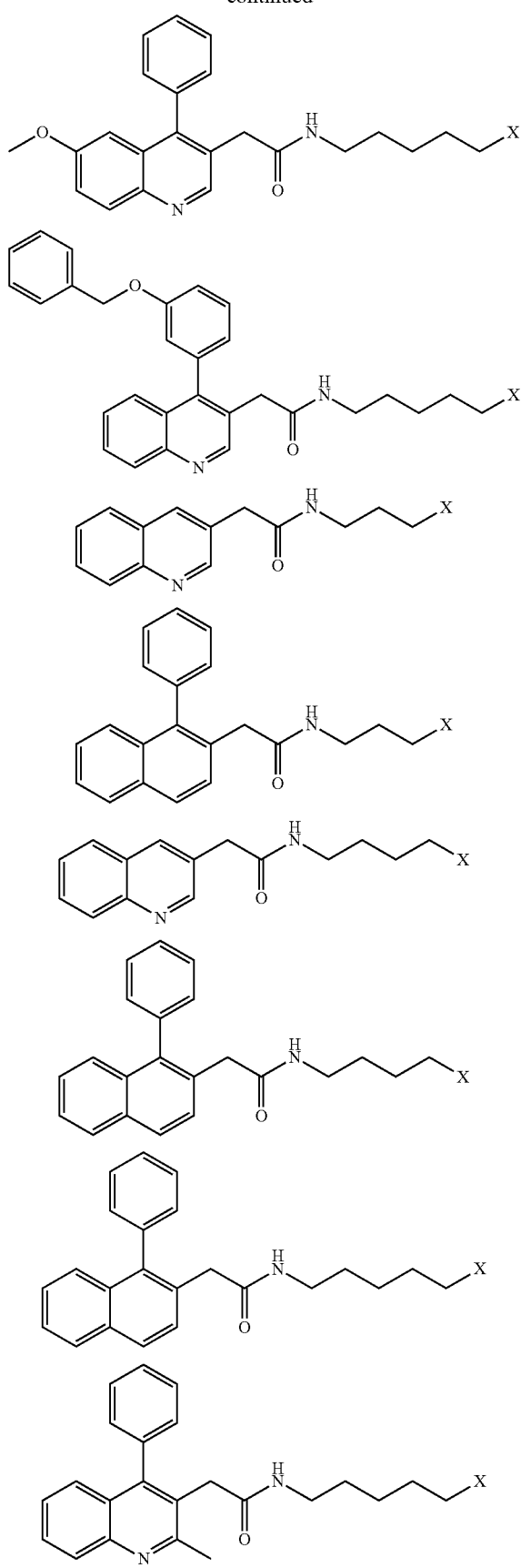
390
-continued
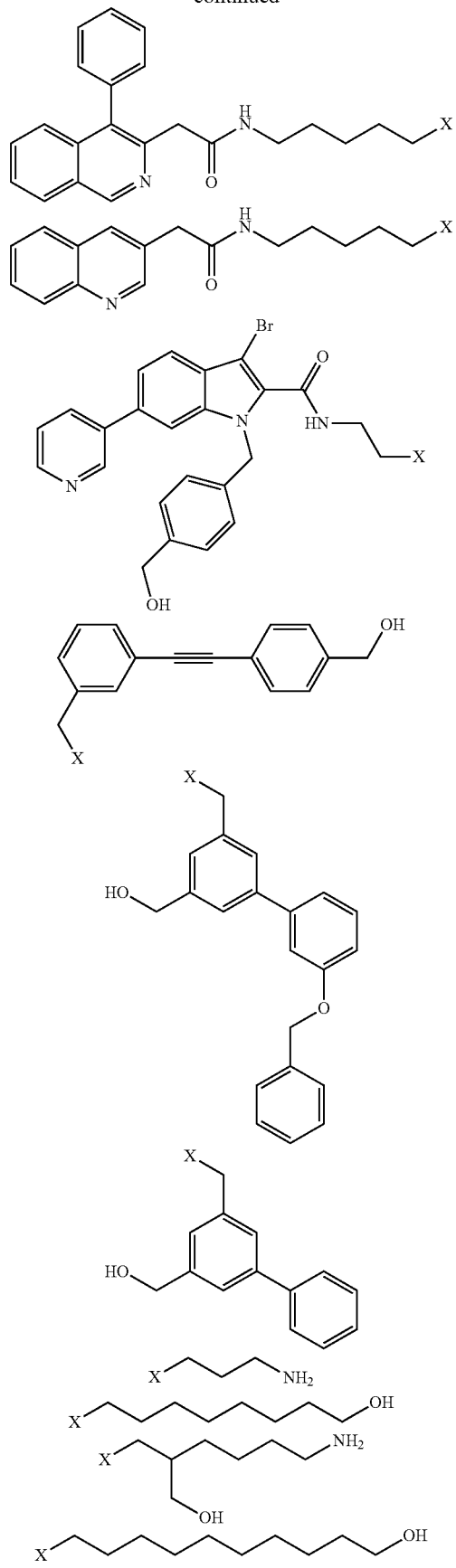

-continued

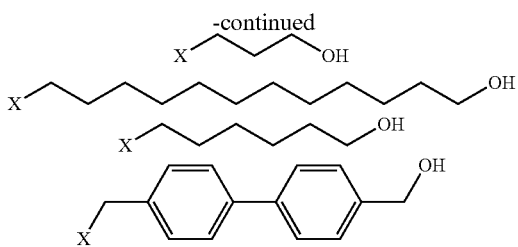

In which:
X is the attachment to the phosphate or modified internucleoside linker at the 3' end of the at least one of the first or second 18-mer strands, or
the attachment to the second phosphate or modified internucleoside linker of the at least one of the first or second 18-mer strands
q is selected from 1 and 2; or
wherein the first and/or second 3' end cap is selected from any of: triethylene glycol, cyclohexyl, phenyl, lithochol (lithocholic acid), or adamantane.

11. The RNAi agent of claim 1 wherein the first and second 3' end caps on the first and second strands are different.

12. The RNAi agent of claim 1 wherein one or more nucleotide are modified or substituted.

13. The RNAi agent of claim 1 wherein the RNAi agent comprises at least one non-natural nucleobase.

14. The RNAi agent of claim 13 wherein the non-natural nucleobase is difluorotolyl, nitroindolyl, nitropyrrolyl, or nitroimidazolyl.

15. The RNAi agent of claim 1 wherein the first two base-pairing nucleotides on the 3' end of the first and/or second strand are modified.

16. The RNAi agent of claim 1 wherein the first two base-pairing nucleotides on the 3' end of the first and/or second strand are 2'-MOE.

17. The RNAi agent of claim 1 wherein the 3' end of the first and/or second strands terminates in a modified internucleoside linker.

18. The RNAi agent of claim 1 wherein at least one 18-mer strand comprises 1-3 2'-deoxynucleotides.

19. The RNAi agent of claim 1 wherein the RNAi agent is modified on one or both 5' ends.

20. A pharmaceutical composition comprising the RNAi agent of claim 1 and a pharmaceutically acceptable carrier.

21. A method for reducing the level and/or activity of a target gene in a cell, comprising the step of introducing into the cell the RNAi agent of claim 1, wherein the RNAi agent targets the target gene.

* * * * *

SEQUENCE LISTING

```
<160> NUMBER OF SEQ ID NOS: 150

<210> SEQ ID NO 1
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(19)
<223> OTHER INFORMATION: a, c, u, g, unknown or other

<400> SEQUENCE: 1
```
nnnnnnnnnn nnnnnnnnn                                              19

<210> SEQ ID NO 2
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(19)
<223> OTHER INFORMATION: a, c, u, g, unknown or other

<400> SEQUENCE: 2
nnnnnnnnnn nnnnnnnnn                                              19

<210> SEQ ID NO 3
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
uuuaauugaa accaagaca                                              19

<210> SEQ ID NO 4
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
ugucuugguu ucaauuaaa                                              19

<210> SEQ ID NO 5
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 5
tattccaaga cctatgtt                                               18

<210> SEQ ID NO 6
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

-continued

<400> SEQUENCE: 6
tattccaaga cctatgtt                                           18

<210> SEQ ID NO 7
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 7
tattccaaga cctatgtt                                           18

<210> SEQ ID NO 8
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 8
tattccaaga cctatgtt                                           18

<210> SEQ ID NO 9
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 9
tattccaaga cctatgtt                                           18

<210> SEQ ID NO 10
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 10
tattccaaga cctatgtt                                           18

<210> SEQ ID NO 11

```
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 11
tttattccaa gacctatg                                                  18

<210> SEQ ID NO 12
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 12
tttattccaa gacctatg                                                  18

<210> SEQ ID NO 13
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 13
tttattccaa gacctatg                                                  18

<210> SEQ ID NO 14
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 14
tttattccaa gacctatg                                                  18

<210> SEQ ID NO 15
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 15
tttattccaa gacctatg                                                        18

<210> SEQ ID NO 16
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 16
tttattccaa gacctatg                                                        18

<210> SEQ ID NO 17
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 17
tattccaaga cctatgttcu u                                                    21

<210> SEQ ID NO 18
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 18
aacataggtc ttggaata                                                        18

<210> SEQ ID NO 19
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 19
```
aacataggtc ttggaata                                                    18

<210> SEQ ID NO 20
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 20
aacataggtc ttggaata                                                    18

<210> SEQ ID NO 21
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 21
aacataggtc ttggaata                                                    18

<210> SEQ ID NO 22
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 22
aacataggtc ttggaata                                                    18

<210> SEQ ID NO 23
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 23
aacataggtc ttggaata                                                    18

<210> SEQ ID NO 24
<211> LENGTH: 18
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 24
cataggtctt ggaataaa                                                 18

<210> SEQ ID NO 25
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 25
cataggtctt ggaataaa                                                 18

<210> SEQ ID NO 26
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 26
cataggtctt ggaataaa                                                 18

<210> SEQ ID NO 27
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 27
cataggtctt ggaataaa                                                 18

<210> SEQ ID NO 28
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

Molecule: Synthetic oligonucleotide"

<400> SEQUENCE: 28
cataggtctt ggaataaa                                                18

<210> SEQ ID NO 29
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 29
cataggtctt ggaataaa                                                18

<210> SEQ ID NO 30
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 30
gaacataggt cttggaatau u                                            21

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 34
tautccaaga ccuaugtt                                                  18

<210> SEQ ID NO 35
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 35
aacauagguc uuggaata                                                  18

<210> SEQ ID NO 36
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 36
ttuauuccaa gaccuatg                                                  18

<210> SEQ ID NO 37

<400> SEQUENCE: 37

000

<210> SEQ ID NO 38

<400> SEQUENCE: 38

000

<210> SEQ ID NO 39
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
uuaauuaucu auuccgua                                                  18

<210> SEQ ID NO 40
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
uacggaauag auaauuaa                                                  18

<210> SEQ ID NO 41
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 41
uuaauuaucu auccgua                                                  18

<210> SEQ ID NO 42
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 42
uuacauuaaa gucugutg                                                 18

<210> SEQ ID NO 43
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 43
aauguaauuu cagacaac                                                 18

<210> SEQ ID NO 44
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 44
uuaauuaucu auccgua                                                  18

<210> SEQ ID NO 45
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:

```
<221> NAME/KEY: modified_base
<222> LOCATION: (1)..(20)
<223> OTHER INFORMATION: a, c, u, g, unknown or other

<400> SEQUENCE: 45
nnnnnnnnnn nnnnnnnnnn                                                   20

<210> SEQ ID NO 46
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 46
nnnnnnnnnn nnnnnnnnnn                                                   20

<210> SEQ ID NO 47
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(18)
<223> OTHER INFORMATION: a, c, u, g, unknown or other

<400> SEQUENCE: 47
nnnnnnnnnn nnnnnnnn                                                     18

<210> SEQ ID NO 48
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(18)
<223> OTHER INFORMATION: a, c, u, g, unknown or other

<400> SEQUENCE: 48
nnnnnnnnnn nnnnnnnn                                                     18

<210> SEQ ID NO 49
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 49
tgttacagca tttacagc                                                     18
```

```
<210> SEQ ID NO 50
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
uuacauuaaa gucuguuguu u                                                   21

<210> SEQ ID NO 51
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
uuaauguaau uucagacaac a                                                   21

<210> SEQ ID NO 52
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
uuacauuaaa gucuguugu                                                      19

<210> SEQ ID NO 53
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
aauguaauuu cagacaaca                                                      19

<210> SEQ ID NO 54
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
uuacauuaaa gucuguug                                                       18

<210> SEQ ID NO 55
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

```
Synthetic oligonucleotide"

<400> SEQUENCE: 55
aauguaauuu cagacaac                                                 18

<210> SEQ ID NO 56
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
uuacauuaaa gucuguu                                                  17

<210> SEQ ID NO 57
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
aauguaauuu cagacaa                                                  17

<210> SEQ ID NO 58
<211> LENGTH: 16
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
uuacauuaaa gucugu                                                   16

<210> SEQ ID NO 59
<211> LENGTH: 16
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
aauguaauuu cagaca                                                   16

<210> SEQ ID NO 60
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
ugucuugguu ucaauuaaa                                                19

<210> SEQ ID NO 61
<211> LENGTH: 19
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61 ugcuugguu ucaauuaaa                                                  19

<210> SEQ ID NO 62
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62 ugcuugguu ucaauuaaa                                                  19

<210> SEQ ID NO 63
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63 ugcuugguu ucaauuaaa                                                  19

<210> SEQ ID NO 64
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64 ugcuugguu ucaauuaaa                                                  19

<210> SEQ ID NO 65
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65 ugcuugguu ucaauuaaa                                                  19

<210> SEQ ID NO 66
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
```
ugucuugguu ucaauuaaa                                            19

<210> SEQ ID NO 67
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
ugucuugguu ucaauuaaa                                            19

<210> SEQ ID NO 68
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
ugucuugguu ucaauuaaa                                            19

<210> SEQ ID NO 69
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
ugucuugguu ucaauuaaa                                            19

<210> SEQ ID NO 70
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 70
tcgaagtact cagcgtaagt t                                         21

<210> SEQ ID NO 71
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 71
ugucuugguu ucaauuaaat t                                         21

<210> SEQ ID NO 72
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
ugucuugguu ucaauuaaa                                              19

<210> SEQ ID NO 73
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
uuuaauugaa accaagaca                                              19

<210> SEQ ID NO 74
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
uuuaauugaa accaagaca                                              19

<210> SEQ ID NO 75
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
uuuaauugaa accaagaca                                              19

<210> SEQ ID NO 76
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
uuuaauugaa accaagaca                                              19

<210> SEQ ID NO 77
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 77
uuuaauugaa accaagaca                                                19

<210> SEQ ID NO 78
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
uuuaauugaa accaagaca                                                19

<210> SEQ ID NO 79
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
uuuaauugaa accaagaca                                                19

<210> SEQ ID NO 80
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
uuuaauugaa accaagaca                                                19

<210> SEQ ID NO 81
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
uuuaauugaa accaagaca                                                19

<210> SEQ ID NO 82
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
uuuaauugaa accaagaca                                                19

<210> SEQ ID NO 83
<211> LENGTH: 21

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 83
cttacgctga gtacttcgat t                                            21

<210> SEQ ID NO 84
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 84
uuuaauugaa accaagacat t                                            21

<210> SEQ ID NO 85
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85
uuuaauugaa accaagaca                                               19

<210> SEQ ID NO 86
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
uuuaauugaa accaagaca                                               19

<210> SEQ ID NO 87
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
uuuaauugaa accaagaca                                               19

<210> SEQ ID NO 88
<211> LENGTH: 19
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
uuuaauugaa accaagaca                                                  19

<210> SEQ ID NO 89
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
uuuaauugaa accaagaca                                                  19

<210> SEQ ID NO 90
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
uuuaauugaa accaagaca                                                  19

<210> SEQ ID NO 91
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
uuuaauugaa accaagaca                                                  19

<210> SEQ ID NO 92
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
uuuaauugaa accaagaca                                                  19

<210> SEQ ID NO 93
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
uuuaauugaa accaagaca                                                  19
```

-continued

```
<210> SEQ ID NO 94
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
uuuaauugaa accaagaca                                                      19

<210> SEQ ID NO 95
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 95
uuuaauugaa accaagacat t                                                   21

<210> SEQ ID NO 96
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 96
uuaauuaucu auccgua                                                        18

<210> SEQ ID NO 97
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
uuaauuaucu auccgua                                                        18

<210> SEQ ID NO 98
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
gacaguauuc ucagugcu                                                       18
```

```
<210> SEQ ID NO 99
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
gacaguauuc ucagugcu                                                       18

<210> SEQ ID NO 100
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
gacaguauuc ucagugcu                                                       18

<210> SEQ ID NO 101
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
gacaguauuc ucagugcu                                                       18

<210> SEQ ID NO 102
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
gacaguauuc ucagugcu                                                       18

<210> SEQ ID NO 103
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103
gacaguauuc ucagugcu                                                       18

<210> SEQ ID NO 104
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 104
gacaguauuc ucagugcu                                                    18

<210> SEQ ID NO 105
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
gacaguauuc ucagugcu                                                    18

<210> SEQ ID NO 106
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
gacaguauuc ucagugcu                                                    18

<210> SEQ ID NO 107
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
gacaguauuc ucagugcu                                                    18

<210> SEQ ID NO 108
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
gacaguauuc ucagugcu                                                    18

<210> SEQ ID NO 109
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
gacaguauuc ucagugcu                                                    18

<210> SEQ ID NO 110
<211> LENGTH: 18
<212> TYPE: RNA
```

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
gacaguauuc ucagugcu                                              18

<210> SEQ ID NO 111
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
gacaguauuc ucagugcu                                              18

<210> SEQ ID NO 112
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
gacaguauuc ucagugcu                                              18

<210> SEQ ID NO 113
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
gacaguauuc ucagugcu                                              18

<210> SEQ ID NO 114
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
gacaguauuc ucagugcu                                              18

<210> SEQ ID NO 115
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
gacaguauuc ucagugcu                                              18

```
<210> SEQ ID NO 116
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
gacaguauuc ucagugcu                                                        18

<210> SEQ ID NO 117
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
gacaguauuc ucagugcu                                                        18

<210> SEQ ID NO 118
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 118
ggacaguauu cucagugcuu u                                                    21

<210> SEQ ID NO 119
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
agcacugaga auacugu                                                         17

<210> SEQ ID NO 120
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
agcacugaga auacugc                                                         17

<210> SEQ ID NO 121
<211> LENGTH: 17
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
agcacugaga auacuuc                                                    17

<210> SEQ ID NO 122
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
agcacugaga auacguc                                                    17

<210> SEQ ID NO 123
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
agcacugaga auauguc                                                    17

<210> SEQ ID NO 124
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
agcacugaga aucuguc                                                    17

<210> SEQ ID NO 125
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
agcacugaga aacuguc                                                    17

<210> SEQ ID NO 126
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
agcacugaga uacuguc                                                    17
```

```
<210> SEQ ID NO 127
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
agcacugaga uacuguc                                                        17

<210> SEQ ID NO 128
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
agcacugaaa uacuguc                                                        17

<210> SEQ ID NO 129
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
agcacuggaa uacuguc                                                        17

<210> SEQ ID NO 130
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
agcacuagaa uacuguc                                                        17

<210> SEQ ID NO 131
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 131
agcacgagaa uacuguc                                                        17

<210> SEQ ID NO 132
<211> LENGTH: 17
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
agcaugagaa uacuguc                                                    17

<210> SEQ ID NO 133
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
agccugagaa uacuguc                                                    17

<210> SEQ ID NO 134
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
agacugagaa uacuguc                                                    17

<210> SEQ ID NO 135
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
acacugagaa uacuguc                                                    17

<210> SEQ ID NO 136
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
gcacugagaa uacuguc                                                    17

<210> SEQ ID NO 137
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
agcacugaga auacuguc                                                   18
```

```
<210> SEQ ID NO 138
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 138
agcacugaga auacuguc                                                 18

<210> SEQ ID NO 139
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 139
agcacugaga auacuguccu u                                             21

<210> SEQ ID NO 140
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
ugucuugguu ucaauuaaa                                                19

<210> SEQ ID NO 141
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
ugucuugguu ucaauuaaa                                                19

<210> SEQ ID NO 142
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
ugucuugguu ucaauuaaa                                                19
```

```
<210> SEQ ID NO 143
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
ugucuugguu ucaauuaaa                                                        19

<210> SEQ ID NO 144
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
ugucuugguu ucaauuaaa                                                        19

<210> SEQ ID NO 145
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
ugucuugguu ucaauuaaa                                                        19

<210> SEQ ID NO 146
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
ugucuugguu ucaauuaaa                                                        19

<210> SEQ ID NO 147
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
ugucuugguu ucaauuaaa                                                        19

<210> SEQ ID NO 148
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 148
ugucuugguu ucaauuaaa                                                  19

<210> SEQ ID NO 149
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 149
ugucuugguu ucaauuaaat t                                               21

<210> SEQ ID NO 150
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 150
cauaggucuu ggaauaaa                                                   18
```